US006420417B1

(12) United States Patent
Keller et al.

(10) Patent No.: US 6,420,417 B1
(45) **Date of Patent: *Jul. 16, 2002**

(54) COMBINATION THERAPY EMPLOYING ILEAL BILE ACID TRANSPORT INHIBITING BENZOTHIEPINES AND HMG CO-A REDUCTASE INHIBITORS

(75) Inventors: Bradley T. Keller, Chesterfield; Kevin C. Glenn, Maryland Heights; Robert E. Manning, St. Louis, all of MO (US)

(73) Assignee: G. D. Searle & Co., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/676,466

(22) Filed: Sep. 29, 2000

Related U.S. Application Data

(60) Division of application No. 09/037,308, filed on Mar. 9, 1998, now Pat. No. 6,268,392, which is a continuation-in-part of application No. 08/831,284, filed on Mar. 31, 1997, now abandoned, which is a continuation-in-part of application No. 08/816,065, filed on Mar. 11, 1997, now abandoned, which is a continuation of application No. 08/517,051, filed on Aug. 21, 1995, now abandoned, which is a continuation-in-part of application No. 08/305,526, filed on Sep. 13, 1994, now abandoned.

(60) Provisional application No. 60/040,660, filed on Mar. 11, 1997, and provisional application No. 60/013,119, filed on Mar. 11, 1996.

(51) Int. Cl.$^{7}$ .................... A61K 31/38; C07D 337/12; C07D 307/30

(52) U.S. Cl. ......................... 514/431; 549/12; 549/292

(58) Field of Search ............................... 514/431, 449, 514/451, 550

(56) References Cited

U.S. PATENT DOCUMENTS

| | | | |
|---|---|---|---|
| 3,262,850 | A | 7/1966 | Glynne |
| 3,287,370 | A | 11/1966 | Mohrbacher |
| 3,389,144 | A | 6/1968 | Mohrbacher |
| 3,520,891 | A | 7/1970 | Mohrbacher |
| 3,674,836 | A | 7/1972 | Creger |
| 3,692,895 | A | 9/1972 | Nelson |
| 3,714,190 | A | 1/1973 | Boissier |
| 3,781,328 | A | 12/1973 | Witte |
| 3,948,973 | A | 4/1976 | Phillips |
| 3,962,261 | A | 6/1976 | Zinnes |
| 3,972,878 | A | 8/1976 | Schirmann |
| 3,983,140 | A | 9/1976 | Endo |
| 4,002,750 | A | 1/1977 | Ambrogi |
| 4,058,552 | A | 11/1977 | Mieville |
| 4,185,109 | A | 1/1980 | Rosen |
| 4,231,938 | A | 11/1980 | Monaghan |
| 4,251,526 | A | 2/1981 | McCall |
| 4,346,227 | A | 8/1982 | Terahara |
| 4,410,629 | A | 10/1983 | Terahara et al. |
| 4,444,784 | A | 4/1984 | Hoffman |
| 4,448,979 | A | 5/1984 | Terahara et al. |
| 4,559,332 | A | 12/1985 | Grob |

(List continued on next page.)

FOREIGN PATENT DOCUMENTS

| | | | |
|---|---|---|---|
| AU | A-30209/92 | | 12/1992 |
| AU | A-61946/94 | | 6/1994 |
| AU | A-61948/94 | | 6/1994 |
| AU | A-61949/94 | | 6/1994 |
| CA | 2025294 | | 3/1991 |
| CA | 2078588 | | 3/1993 |
| CA | 2085782 | | 6/1993 |
| CA | 2085830 | | 6/1993 |
| DE | 1211258 | | 2/1968 |
| DE | 3 122 499 | A1 | 12/1981 |
| DE | 196 27 430 | A1 | 8/1996 |
| EP | 0 022 487 | A1 | 1/1981 |
| EP | 0 033 538 | B1 | 8/1981 |
| EP | 0 067 086 | | 10/1982 |
| EP | 0 129 748 | | 2/1985 |
| EP | 0 250 265 | | 6/1987 |
| EP | 0 244 364 | A2 | 11/1987 |
| EP | 0 338 331 | | 6/1989 |
| EP | 0 379 161 | | 1/1990 |
| EP | 0 409 281 | A1 | 1/1991 |
| EP | 0 531 901 | A2 | 2/1992 |
| EP | 0 508 425 | A1 | 9/1992 |
| EP | 0 549 967 | A1 | 12/1992 |
| EP | 0 526 402 | A1 | 2/1993 |
| EP | 0 559 064 | A2 | 2/1993 |
| EP | 0 563 731 | A1 | 3/1993 |
| EP | 0 568 898 | A1 | 4/1993 |
| EP | 0 818 197 | A1 | 6/1997 |
| EP | 0 818 448 | A1 | 6/1997 |
| EP | 0 796 846 | A1 | 7/1997 |
| EP | 0 801 060 | A1 | 10/1997 |
| FR | 2 661 676 | A1 | 2/1990 |
| GB | 1 211 258 | | 11/1970 |
| GB | 2 077 264 | A | 12/1981 |
| GB | 2 305 665 | | 4/1997 |
| GB | 2 329 334 | | 3/1999 |
| JP | 10-287662 | | 10/1998 |
| WO | 89/01477 | | 2/1989 |

(List continued on next page.)

OTHER PUBLICATIONS

US 3,694,445, 09/1972, Houlihan (withdrawn)

A. Barrett et al., “Total Synthesis and Stercochemical Assignment of the Quinquecyclopropane–Containing Cholesteryl Ester Transfer Protein Inhibitor U–106305”, J. Am Chem. Soc., 1996, 118, pp. .7863–7864.

P. Barter et al. “High Density Lipoproteins and Coronary Heart Disease”, Atherosclerosis, 121 1996, pp. 1–12.

(List continued on next page.)

*Primary Examiner*—Deborah C. Lambkin
(74) *Attorney, Agent, or Firm*—Banner & Witcoff Ltd.

(57) ABSTRACT

Provided are novel benzothiepines, derivatives, and analogs thereof; pharmaceutical compositions containing them; and methods of using these compounds and compositions in medicine, particularly in the prophylaxis and treatment of hyperlipidemic conditions such as those associated with atherosclerosis or hypercholesterolemia, in mammals. Also provided are compositions and methods for combination therapy employing ileal bile acid transport inhibitors and HMG Co-A reductase inhibitors for the treatment of hyperlipidemic conditions.

50 Claims, No Drawings

U.S. PATENT DOCUMENTS

| | | | | | |
|---|---|---|---|---|---|
| 5,075,293 | A | | 12/1991 | Reifschneider | |
| 5,153,184 | A | | 10/1992 | Reifschneider | |
| 5,158,943 | A | | 10/1992 | Sohda | |
| 5,244,887 | A | | 9/1993 | Straub | |
| 5,260,316 | A | | 11/1993 | Van Duzer | |
| 5,334,600 | A | | 8/1994 | Van Duzer | |
| 5,350,761 | A | | 9/1994 | Van Duzer | |
| 5,354,772 | A | | 10/1994 | Kathawala | |
| 5,430,116 | A | | 7/1995 | Kramer | |
| 5,502,045 | A | | 3/1996 | Miettinen | |
| 5,512,558 | A | | 4/1996 | Enhsen | |
| 5,519,001 | A | | 5/1996 | Rampratap | |
| 5,602,152 | A | | 2/1997 | Berthelon | |
| 5,610,151 | A | | 3/1997 | Glombik | |
| 5,663,165 | A | | 9/1997 | Brieaddy | |
| 5,703,188 | A | | 12/1997 | Mandeville | |
| 5,705,524 | A | | 1/1998 | McGee | |
| 5,723,458 | A | | 3/1998 | Brieaddy | |
| 5,767,115 | A | | 6/1998 | Rosenblum | |
| 5,929,062 | A | | 7/1999 | Haines | |
| 5,994,391 | A | | 11/1999 | Lee | |
| 6,020,330 | A | | 2/2000 | Enhsen | |
| 6,107,323 | A | * | 8/2000 | Tamura et al. | 514/401 |
| 6,143,755 | A | * | 11/2000 | Bocan | 514/277 |
| 6,180,660 | B1 | * | 1/2001 | Whitney et al. | 514/451 |
| 6,235,311 | B1 | * | 5/2001 | Ullah et al. | 424/472 |
| 6,245,797 | B1 | * | 6/2001 | Winokur | 514/406 |
| 6,251,852 | B1 | * | 6/2001 | Gould et al. | 514/2 |
| 6,264,938 | B1 | * | 7/2001 | Huval et al. | 424/78.35 |
| 6,277,831 | B1 | * | 8/2001 | Frick et al. | 514/43 |

FOREIGN PATENT DOCUMENTS

| | | |
|---|---|---|
| WO | 91/08205 | 6/1991 |
| WO | 92/17467 | 10/1992 |
| WO | 92/18115 | 10/1992 |
| WO | 92/18462 | 10/1992 |
| WO | 93/16055 | 8/1993 |
| WO | 93/21146 | 10/1993 |
| WO | 94/18183 | 8/1994 |
| WO | 94/18184 | 8/1994 |
| WO | 94/24087 | 10/1994 |
| WO | 95/21843 | 8/1995 |
| WO | 96/05188 | 2/1996 |
| WO | 96/08484 | 3/1996 |
| WO | 96/16051 | 5/1996 |
| WO | 96/40255 | 12/1996 |
| WO | 97/03953 | 2/1997 |
| WO | 97/33882 | 9/1997 |
| WO | 97/49387 | 12/1997 |
| WO | 97/49736 | 12/1997 |
| WO | 98/02432 | 1/1998 |
| WO | 98/06405 | 2/1998 |
| WO | 98/23593 | 6/1998 |
| WO | 98/35937 | 8/1998 |
| WO | WO 98/38182 | 9/1998 |
| WO | 98/38182 | 9/1998 |
| WO | 98/39299 | 9/1998 |
| WO | WO 98/40375 | 9/1998 |
| WO | 98/40375 | 9/1998 |
| WO | 98/56757 | 12/1998 |
| WO | 99/11259 | 3/1999 |
| WO | 99/11260 | 3/1999 |
| WO | 99/11263 | 3/1999 |
| WO | 99/14174 | 3/1999 |
| WO | 99/14204 | 3/1999 |
| WO | 99/14215 | 3/1999 |
| WO | 99/32478 | 7/1999 |
| WO | 99/35135 | 7/1999 |
| WO | 99/64409 | 12/1999 |
| WO | 00/35889 | 6/2000 |

OTHER PUBLICATIONS

A. Beckwith et al., "Iododediazoniation of Arenediazonium Salts Accompanied by Aryl Radical Ring Closure" J. Org. Chem. 1987, vol. 52, pp. 1922–1930.

D. Bilheimer et al., "Melvinolin and Colestipol Stimulate Receptor–Mediated Clearance of Low Density Lipoprotein From Plasma In Familial Hypercholesterolemia Heterzygotes", Proc. Natl. Acad. Sci. USA, vol. 80, Jul. 1983, pp. 4124–4128.

C. Bisgaier et al., Cholesteryl Ester Transfer Protein Inhibition By PD 140195, Lipids, vol. 29, No. 12, 1994, pp. 811–818.

D. Blankenhorn et al., "Beneficial Effects of Combined Colestipol–Niacin Therapy On Coronary Atherosclerosis and Coronary Venous Bypass Grafts", JAMA, Jun. 19, 1987, vol. 257, No. 23, pp. 3233–3240.

D. Blankenhorn et al., "Beneficial Effects of Colestipol–Niacin Therapy on the Common Carotid Artery" Circulation vol. 88, Jul. 1, 1993, pp. 20–28.

P. Bonin et al., "A Peptide Inhibitor Of Cholesteryl Ester Transfer Protein Identified By Screening a Bacteriophage Display Library", Journal of Peptide Research, 51, 1998, pp. 216–225.

G. Brown, et al., "Regression of Coronary Artery Disease As A Result of Intensive Lipid–Lowering Therapy in Men With High Levels of Apolipoprotein B", The New England Journal of Medicine, vol. 323, Nov. 8, 1990, No. 19, pp. 1289–1339.

M. Brown et al., Induction of 3–hydroxy–3Methylglutaryl Coenzyme A Reductase Activity in Human Fibroblasts Incubated with Compactin (ML–236B), A Competitive Inhibitor of the Reductase, The Journal of Biological Chemistry, vol. 253, No. 4, Feb. 22, 1978, pp. 1121–1128.

S. Busch et al., "Cholesteryl Ester Analogs Inhibit Cholesteryl Ester But Not Triglyceride Transfer Catalyzed By The Plasma Cholesteryl Ester–Triglyceride Transfer Protein", Lipids, vol. 25, No. 4 (1990), pp. 216–220.

C. Camoutsis et al., "N–Substituted 4,5–Dihydro–1, 2–Benzothiazepin–3–One 1, 1–Dioxide", J. Heterocyclic Chem. 17, pp. 1135–1136 (1980).

L. Cashin–Hemphill et al., "Beneficial Effects of Colestipol–Niacin on Coronary Atherosclerosis A 4–Year Follow–up", JAMA, Dec. 19, 1990, vol. 264, No. 23, pp. 3013–3017.

P. Catsoulacos et al., "Synthesis of Some N–Substituted 4,5–Dihydro–7,8–dimethoxybenzothiazepin–3–one 1, 1–Dioxides", J. Heterocyclic Chem., vol. 13 (1976), pp. 1309–1314.

P. Catsoulacos et al., "Thiazo Compounds. Derivatives of 4,5–Dihydro–7,8–Dimethoxybenzothiazepin–3 one 1, 1–Dioxides", Journal of Chemical and Engineering Data, vol. 22, No. 3, 1977, pp. 353–354.

K. Cho et al, "A Peptide From Hog Plasma that Inhibits Human Cholesteryl Ester Transfer Protein", Biochimica et Biophysica Acta, 1391, 1998, pp. 133–144.

D. Connolly et al., "Inactivation of Cholesteryl Ester Transfer Protein by Cysteine Modification", Biochemical and Biophysical Research Communications 223, pp. 42–47, 1996.

S. Coval et al., "Wiedendiol–A and–B, Cholesteryl Ester Transfer Protein Inhibitors From The Marine Sponge *Xestosponga Weidenmayeri",* Bioorganic & Medicinal Chemistry Letter, vol. 5, No. 6, pp. 605–610, 1995.

J. Davignon et al., "Apolipoprotein E and Atherosclerosis: Quest for an APO E Receptor Defect Leads to the Discovery of Pseudo Type III Dyslipoproteinemia in a Family", Atherosclerosis IX, pp. 199–203.

J. Davignon et al., "Comparative Efficacy and Safety of Pravastatin, Nicotinic Acid and The Two Combined in Patients with Hypercholesterolemia", The American Journal of Cardiology, Feb. 15, 1994, pp. 339–345.

C. East et al., "Combination Drug Therapy for Familial Combined Hyperlipidemia", Annals of Internal Medicine, Jul. 1, 1988, pp. 25–32.

J. Emmerich et al., "Efficacy and Safety of Simvastatin (Alone or in Association with Cholestyramine) A 1 yr. Study in 66 Patients with Type II Hyperlipoproteinaemia", European Heart Journal (1990), 11, pp. 149–155.

D. Erkelens, "Combination Drug Therapy with HMG Co A Reductase Inhibitors and Bile Acid Sequestrants for Hypercholesterolmia", Cardiology, 1990, 77, (suppl 4). pp. 33–38.

H. Ginsberg, "Update on the Treatment of Hypercholesterolemia, with a Focus on HMG–CoA Reductase Inhibitors and Combination Regimens", Clinical Cardiology 18, pp. 307–315, (1995).

C. Glueck et al., "Gemfibrozil–Lovastatin Therapy for Primary Hyperlipoproteinemias" The American Journal of Cardiology, Jul. 1, 1992, vol. 70, No. 1, pp. 1–9.

S. Grundy et al., "Influence of Combined Therapy with Mevinolin and Interruption of Bile–Acid Reabsorption on Low Density Lipoproteins in Heterozygous Familial Hypercholesterolemia", Annals of Internal Medicine, 1985, 103: pp. 339–343.

H. Gylling et al.,, "Effects Of Inhibiting Cholesterol Absorption And Synthesis On Cholesterol and Lipoprotein Metabolism In Hypercholesterolemic Non–Insulin–Dependent Diabetic Men", Journal of Lipid Research, vol. 37, 1996, pp. 1776–1785.

E. Haber, "Molecular Cardiovascular Medicine" Scientific American, pp. 35–40.

V. Hedge et al., "A Depsipeptide Fungal Metabolite Inhibitor Of Cholesteryl Ester Transfer Protein", Bioorganic & Medicinal Chemistry Letters 8, 1998, pp. 1277–1280.

L.Hellberg et al., "5a–Hydroxy–3a–Cholestanecarboxylic" The New Journal for Organic Synthesis, vol. 15, No. 1–2, Feb.–Apr. 1983, pp. 154–156.

J. Heubi et al., "Primary Bile Acid Malabsorption: Defective In Vitro Ileal Active Bile Acid Transport", Gastroenterology 1982, 83: pp. 804–811.

N. Hoogerbrugge et al.,"The Additional Effects of Acipimox To Simvastatin In The Treatment of Combined Hyperlipidaemia", Journal of Internal Medicine, 1997, 241:pp. 151–155.

N. Hoogerbrugge et al., "The Efficacy and Safety of Pravastatin, Compared To And In Combination With Bile Acid Binding Resins, In Familial Hypercholesterolaemia", Journal of Internal Medicine 1990, 228; pp. 261–266.

A. Hutchesson et al., "Dual Bezafibrate–Simvastatin Therapy For Combined Hyperlipidaemia", Journal of Clinical Pharmacy and Therapeutics 1994, 19, pp. 387–3898.

T. Ichihashi, "Metabolism of Hypercholesterolemic Action of S–8921 in Rats: S–8921 Inhibits Ileal Bile Acid Absorption", The Journal Of Pharmacology And Experimental Therapeutics, vol. 284, No. 1, pp. 43–50.

D. Illingworth, et al., "Influence of Lovstatin plus Gemfibrozil on Plasma Lipids and Lipoproteins in Patients With Heterozygous Familial Hypercholesterolemia", Circulation vol. 79, Nov. 3, Mar. 1989, 590–596.

D. Illingworth, "Mevinolin Plus Colestipol in Therapy for Severe Heterozygous Familial Hypercholesterolemia", Annalos of Internal Medicine, 1984; 101, pp. 598–604.

International Search Report mailed May 23, 2000 based on PCT/US 99/27942.

International Search Report mailed May 23, 2000 based on PCT/US 99/27943.

International Search Report mailed May 23, 2000 based on PCT US/99/27944.

International Search Report mailed May 23, 2000 based on PCT/US 99/27945.

International Search Report mailed May 18, 2000 based on PCT/US 99/27947.

International Search Report mailed May 15, 2000 based on PCT/US 99/27948.

International Search Report mailed May 17, 2000 based on PCT/US 99/27949.

J. Kane, et al., "Regression of Coronary Atherosclerosis During Treatment of Familial Hypercholesterolemia With Combined Drug Regimens", JAMA, Dec. 19, 1990, Chapter 26, vol. 264, No. 23, pp. 3007–3012.

A. Katritzky et al., "Preparation Of 6–7– And 8–Membered Sultams By Friedel–Crafts Cyclization Of w–Phenylalkanesulfamoyl Chlorides", Organic Preparations and Procedures Int., 24 (4), pp. 463–467 (1992).

T. Kazumi et al., "Effects of Niceritrol On Elevated Serum Lipoprotein LP (A) Levels in Diabetic Patients With Or Without Overt Proteinuria", Current Therapeutic Research, vol. 55, No. 5, May 1994, pp. 546–551.

W. Kramer, et al., "Intestinal Bile Acid Absorption", The Journal of Biological Chemistry, vol. 268, No. 24 Issue of Aug. 25, pp. 18035–18046, 1993.

Kuo, M.S. et al., "Discovery, Isolation, Structure Elucidation, and Biosynthesis of U–106305, a Choresteryl Ester Transfer Protein Inhibitor from UC 11136", J. Am. Chem. Soc. 117, pp. 10629–10634 (1995).

Kvis, K. et al., "Benzocycloheptenes and Heterocyclic Analogues as Potential Drugs. VII, 4–Phenyl–3,4, 5–Tetrahydro–1–Benzothiepins and Some Related Compounds", Chem. Commun./Vo.37/(1973) pp. 3808–3816.

Lee, J.C. et al.,"A Cholesteryl Ester Transfer Protein Inhibitor from an Insect–associated Fungus", The Journal of Antibiotics 49(7), pp. 693–696.

A.M. Lees et al., "Therapy of Hypercholesterolemia With Mevinolin And Other Lipid–Lowering Drugs", Arteriosclerosis 6, 1986, p. 544a.

T. Leren et al., "Effects of Lovastatin Alone and In Combination with Cholestyraminc on Serum Lipids and Apolipoproteins in Heterozygotes for Familial Hypercholesterolemia", International Journal for Research and Investigation on Atherosclerosis and Related Diseases, 73, (1988), pp. 135–141.

M. Lewis, et al., Effects Of 2164U90 on Ileal Bile Acid Absorption and Serum Cholesterol in Rats and Mice, Journal of Lipid Research, vol. 36, 1995,pp. 1098–1105.

R. Lewis, Hawley's Condensed Chemical Dictionary, p. 1238.
W. Ling et al., "Minireview Dietary Phytosterols A Review of Metabolism, Benefits and Side Effects", Life Sciences, vol. 57, No. 3, 1995, pp. 195–206.
H. Mabuchi et al., "Reduction of Serum Cholesterol In Heterozygous Patients with Familial Hypercholesterolemia", The New England Journal of Medicine, vol. 308 Mar. 17, 1983,pp. 609–613.
M. Malloy et al., "Complementarity of Colestipol, Niacin, and Lovastatin in Treatment of Severe Familial Hypercholesterolemia", Annals of Internal Medicine 1987; 107: pp. 616–623.
W. Mandeville et al., Bile Acid Sequestrants: Their Use in Combination With Other Lipid–Lowering Agents, Idrugs 1999 vol. 2., No. 3, pp. 237–242.
G. Marais et al., "Rhabdomyolysis and Acute Renal Failure Induced by Combination Lovastatin and Gemfibrozil Therapy", Annals of Internal Medicine, Feb. 1, 1990, vol. 112, No. 3, pp. 228–230.
P. McCarthy, "New Approaches to Atherosclerosis: An Overview", Medicinal Research Reviews, vol. 13, No. 2, 1993, pp. 139–159.
R. Morton, Regulation of Lipid Transfer Between Lipoproteins By An Endogenous Plasma Protein: Selective Inhibition Among Lipoprotein Classes, Journal of Lipid Research, vol. 35, 1994, pp. 836–847.
F. Nerdel et al., "Quartermay Salts of B–Amino Aldehydes and B–Iodoaldehydes", Chemische Berichte (Ed. H. Zahn), vol. 98 (1965), pp. 728–734.
M. Newman et al., "The Conversion of Phenols to Thiophenols via Dialkylthiocarbamates", The Journal Of Organic Chemistry, vol. 31, Sep.–Dec. 1966, pp. 3980–3984.
A. Orahovats et al., "A Ring Enlargement from Seven–to Ten–Membered–Ring Sulfonamide Derivatives", Helvetica Chimica Acta,vol. 79, (1996), pp. 1121–1128.
H. Pan et al., "Pharmacokinetics and Pharmacodynamics of Pravastatin Alone and With Cholestyramine in Hypercholesterolemia", Clin. Pharmacol. Ther. (1980) 9, 313, pp. 201–207.
N. Panagiotopoulos et al., "N(P–Bromophenyl)–4,5–Dihydro–7,8–Dimethoxy Benzothiazepine–One 1, 1–Dioxide C17 H16 brNO5S", Cryst. Struct. Comm. (1980) 9, pp. 313–319.
R. Pasternak et al., "Effect of Combination Therapy with Lipid–Reducing Drugs in Patients with Coronary Heart Disease and "Normal" Cholesterol Levels", Annals of Internal Medicine, Oct. 1, 1996, vol. 125, No. 7, pp. 529–538.
R. Patra et al., "Conformational and Steric Requirements Of The Side Chain For Sulphur Participation In Benzthiepin Derivatives", Tetrahedron Letters, vol. 30, No. 32, pp. 4279–4282, 1989.
R. Pierce et al., Myopathy and Rhabdomyolysis Associated With Lovastatin–Gemfibrozil Combination Therapy, JAMA, Jul. 4, 1990, vol. 264, No. 1, pp. 71–75.
W. Pirkle et al., "Trichlorosilane–Induced Cleavage. A Mild Method for Retrieving Carbinols From Carbamates", Jouranal Organic Chemistry, vol. 42, No. 15, 1977, pp. 2781–2782.
W. Pirkle et al., "Dynamic NMR Studies of Diastereomeric Carbamates: Implications toward the Determination of Relative Configuration by NMR" Journal of Organic Chemistry, vol. 44, No. 26, 1979, pp. 4891–4896.
W. Pirkle et al., "An Example of Automated Liquid Chromatography Synthesis of a Broad–Spectrum Resolving Agent and Resolution of 1–(Naphthyl) 2, 2, 2–Trifluroethanol", The Journal of Organic Chemistry vol. 39, No. 26, 1974, pp. 3904–3906.
T. Pietzonka et al., "Phosphonate–Containing Analogs Of Cholesteryl Ester As Novel Inhibitors Of Cholesteryl Ester Transfer Protein", Bioorganic & Medicinal Chemistry Letters, vol. 6, No. 16, pp. 1951–1954.
Pravastatin Multicenter Study Group II, "Comparative Efficacy and Safety of Pravastatin and Cholestyramine Alone And Combined in Patients With Hypercholesterolemia", Archives of Internal Medicine, vol. 153, Jun. 14, 1993, pp. 1321–1328.
E. Reihner et al., Regulation of Hepatic Cholesterol Metabolism In Humans: Stimulatory Effects of Cholestyramine on HMG–CoA Reductase Activity and Low Density Lipoprotein Receptor Expression In Gallstone Patients, Journal of Lipid Research, vol. 31, 1990, pp. 2219–2226.
R. Remick et al., "Comparison of Fluoxetine and Desipramine In Depressed Outpatients", Therapeutic Research, vol. 53, No. 5, May 1993, pp. 457–483.
S. Rosenblum et al., Discovery of 1–(4–Fluorophenyl)–(3R)–[3–)4–fluorophenyl)–(3S)–hydroxypropyl] –(4S)–(4–hydroxyphenyl)–2–azetidinone (SCH 58235): A Designed, Potent, Orally Active Inhibitor of Cholesterol Absorption, Journal of Medicinal Chemistry, 1998, vol. 41, No. 6, pp. 973–980.
G. Salem et al., "Benzothiazine and Benzothizepine Derivatives: Structures of N–p–Bromophenyl–6, 7–Dimethoxy–1, 2–Benzothiazin–3(4H)–One 1, 1–Dioxide (BBTZ) and 4,5–Dihydro–8,9–Dimethoxy–N–(5–Methyl–2–Pyridyl)–1, 2–Benzothiazepin–3–One 1, 1–Dioxide (MPTE)", Acta Cryst. (1986) C42, pp. 1581–1584.
J. Sasaki et al., "Effects of Fluvastatin, A New Inhibitor of HMG–CoA Reductase, and Niceritol on Serum Lipids, Lipoproteins and Cholesterol Ester Transfer Activity In Primary Hypercholesterolemic Patients", International Journal of Clinical Pharmacology and Therapeutics, vol. 33, No. 7, 1995, pp. 420–426.
K. Sindelar et al., Neurotropic and Psychotropic Compounds. XXIX. Derivatives Of 2,3,4, 5–Tetrahydro–1–Benzothiepin, Chemical Commun., vol. 33, 1968, pp. 4315–4327.
K. Sindelar et al., Benzocycloheptenes and Hetelrocyclic Analogues As Potential Drugs. III. Further Synthetic Experiments In The Series Of 1–Benzothiepin Derivatives, vol. 37, 1972, 1195–1206.
C. Sirtori, "New Targets For Lipid Lowering And Atherosclerosis Prevention", Pharmac. Ther. vol. 67, No. 3., pp. 433–447, 1995.
Y. Son, "Purification and Characterization of Human Plasma Proteins That Inhibit Lipid Transfer Activities" Biochimica et Biophysica Acta 795, 1984 pp. 473–480.
Activities, Biochimica et Biophysica Acta, 795, 1984, pp. 473–480.
D. Sprecher et al., "Low–Dose Combined Therapy with Fluvastin and Cholestyramine in Hyperlipidemic Patients", Ann Intern Med. 1994; 120: pp. 537–543.
C.I. Stassinopoulou, et al., "C NMR Spectra of Benzothiazepinones, Benzothiazinone and Benzosulphonamide N–Substituted Derivatives" Department of Biology, Nuclear Research Center.

E. Stedronsky et al., "Interaction of Bile Acids and Cholesterol with Non–Systemic Agents Having Hypocholesterolemic Properties", Biochimica et Biophysica Acta., 1210, 1994, pp. 255–287.

I. Stein, et al., "Effects of Simvastatin and Cholestyraminc in Familial and Nonfamilial Hypercholesterolemia", Arch Intern Med. vol. 150, Feb. 1990, pp. 341–345.

E. Stein, et al., "Lovastatin Alone And In Combination For Treatment Of Primary Hypercholesterolema", Alan R. Liss, Inc. 1988, pp. 281–293.

K. Suckling, et al., Cholesterol Lowering and Bile Acid Excretion in the Hamster with Cholestryramine Treatment, Atherosclerosis, 89, (1991) pp. 183–190.

T. Swenson, "Mechanism of Cholesteryl Ester Transfer Protein Inhibition by a Neutralizing Monoclonal Antibody and Mapping of the Monoclonal Antibody Epitope", The Journal of Biological Chemistry, vol. 264, No. 24, Aug. 25, pp. 14318–14326, 1989.

A. Tall, "Plasma Cholesteryl Ester Transfer Protein", Journal of Lipid Research, vol. 34, 1993, pp. 1255–1274.

Y. Tamura et al., Novel Conversions of Benzo [b] thiophen–3 (2–H)–ones into 1,2–Benzisothiazole and Tetrahydro–1, 2–Benzothiazepin–5–One Systems via Sulphimide Intermediates, J.C.S. Perkin I, pp. 2830–2834.

K. Thurmond et al., "Water–Soluble Knedel–like Structures: The Preparation of Shell–Cross–Linked Small Particles", Journal American Chemistry Soc. vol. 118, No. 30, 1996, pp. 7239–7240.

P. Tyle, "Iontophoretic Devices for Drug Delivery", Pharmaceutical Research, vol. 3, No. 6 1986, pp. 318–325.

M. Unc et al., Metabolism of 3a, 7a–Dihydroxy–7b–Methyl–5b–Cholanoic Acid and 3a, 7B–Dihydroxy–7a–Methyl–5B–Cholanoic Acid Hamsters, Biochimica et Biophysica Acta, 833 (1985), pp. 196–202.

J. Vacek et al., Comparison of Lavastatin (20 mg) and Nicotinic Acid (1.2g) With Either Drug Alone for Type II Hyperlipoproteinemia, The American Journal Of Cardiology, vol. 76, Jul. 15, 1995, pp. 182–184.

M. Van Heek et al., "In Vivo Metabolism–Based Discovery of a Potent Cholesterol Absorption Inhibitor, SCH58235, in the Rat and Rhesus Monkey Through the Identification of the Active Metabolites of SCH48461", The Journal of Pharmacology and Experimental Therapeutics, vol. 283, No. 1, pp. 157–754.

G. Vega et al., "Treatment of Primary Moderate Hypercholesterolemia With Lovastatin (Mevinolin) and Colestipol", JAMA, Jan. 2, 1987, vol. 257, No. 1, pp. 33–37.

G. Wess et al., "Synthesis and Biological Activity of Bile Acid–Derived HMG–CoA Reductase Inhibitors. The Role of 21–Methyl in Recognition of HMB–CoA Reductase and the Ileal Bile Acid Transport System", Journal Of Medicinal Chemistry 1994, 37, pp. 3240–3246.

J. Wetterau et al., "An MTP Inhibitor that Normalizes Atherogenic Lipoprotein Levels In WHHL Rabbits", Science vol. 282, Oct. 23, 1998, pp. 751–754.

O. Wiklund et al., "Pravastatin and Gemfibrozil Alone and in Combination for the Treatment of Hypercholesterolemia", The American Journal of Medicine vol. 94, Jan. 1993, pp. 13–19.

S. Wirebaugh et al., "A Retrospective Review of the Use of Lipid–Lowering Agents in Combination, Specifically, Gemfribrozil and Lovastatin", Pharmacotherapy vol. 12, No. 6, 1992, pp. 445–450.

J. Witztum, "Drugs Used In The Treatment of Hyperlipoproteinemias", The Pharmacological Basis of Therapeutics, $9^{th}$ Edition, pp. 875–894.

Yan Xia et al., "Substituted 1,3,5–Triazines As Cholesterol Ester Transfer Protein Inhibitors", Bioorganic & Medicinal Chemistry Letters, vol. 6, No. 7, 1996, pp. 919–922.

A. Yamamoto et al., "Effects of Probucol on Xanthomata Regression in Familial Hypercholesterolemia", Am Journal Cardiology, 1986, 57: pp. 29H–35H.

K. Ytre–Arne et al., "Simvastatin and Cholestyramine In The Long–Term Treatment of Hypercholesterolaemia", Journal of Internal Medicine (1989): 226, pp. 285–290.

Angelin, B., "Regulations of Hepatic Cholesterol Metabolism In Man," Ann. Med. 23, pp. 10–27 (1991).

Blum, C. B., "Comparison of Properties of Four Inhibitors of 3–Hydroxy–3–Methylglutaryl–Coenzyme A Reductase," Am. J. Cardiol., 73(14), 3D–11D, (1994).

Cayeń, M.N., "Disposition, Metabolism and Pharmacokinetics of Antihyperlipidemic Agents in Laboratory Animals and Man," Pharmac. & Ther., 29, pp. 157–204 (1985).

Da Col, et al., "Tolerability and Efficacy of Combination Therapy with Simvastatin Plus Gemfibroail in Type II Refractory Familial Combined Hyperlipidemia," Curr. Therap. Research, vol. 53, No. 5, pp. 473–483 (1993).

Davignon, et al. "HMG CoA Reductase Inhibitors: A look back and a look ahead," Can. J. Cardiol., 8(8), pp. 843–864 (1992).

Endo, A., "Chemistry, biochemistry and pharmacology of HMG–Co–A reductase inhibitors, " Klin. Wochemschr. 66, pp. 421–427 (1988).

Kramer et al., "Bile acid derived HMG–CoA reductase inhibitors," Biochimica et Biophysica Acta, 1227 pp. 137–154 (1994).

Marcus, A., "Role of the HMG–CoA Reductase Inhibitors in the Treatment of Dyslipidemia: An Evolutionary Review," CVR&R, pp. 13–27 (Jan. 1996).

* cited by examiner

COMBINATION THERAPY EMPLOYING ILEAL BILE ACID TRANSPORT INHIBITING BENZOTHIEPINES AND HMG CO-A REDUCTASE INHIBITORS

This application is a divisional of U.S. application Ser. No. 09/037,308 filed Mar. 9, 1998, U.S. Pat. No. 6,263,342, which claims priority from U.S. Provisional application Ser. No. 60/040,660 filed Mar. 11, 1997 which is also a continuation-in-part application of U.S. Ser. No. 08/831, 284, filed Mar. 31, 1997, ABN, which is a continuation application of U.S. Ser. No. 08/517,051, filed Aug. 21, 1995, ABN, which is a continuation-in-part application of U.S. Ser. No. 08/305,526 filed Sep. 13, 1994 ABN; and is a continuation-in-part application of U.S. Ser. No. 08/816, 065, filed Mar. 11, 1997, ABN, which claims priority from U.S. provisional application Ser. No. 60/013,119, filed Mar. 11, 1996.

BACKGROUND OF THE INVENTION

1. Field of the Invention

The present invention relates to novel benzothiepines, derivatives and analogs thereof, in combination with HMG Co-A reductase inhibitors, pharmaceutical compositions containing them, and use of these compositions in medicine, particularly in the prophylaxis and treatment of hyperlipidemic conditions such as is associated with atherosclerosis or hypercholesterolemia, in mammals.

2. Description of Related Art

It is well-settled that hyperlipidemic conditions associated with elevated concentrations of total cholesterol and low-density lipoprotein cholesterol are major risk factors for coronary heart disease and particularly atherosclerosis. Interfering with the circulation of bile acids within the lumen of the intestinal tract is found to reduce the levels of serum cholesterol in a causal relationship. Epidemiological data has accumulated which indicates such reduction leads to an improvement in the disease state of atherosclerosis. Stedronsky, in “Interaction of bile acids and cholesterol with nonsystemic agents having hypocholesterolemic properties,” *Biochimica et Biophysica Acta,* 1210 (1994) 255–287 discusses the biochemistry, physiology and known active agents surrounding bile acids and cholesterol.

Pathophysiologic alterations are shown to be consistent with interruption of the enterohepatic circulation of bile acids in humans by Heubi, J. E., et al. See “Primary Bile Acid Malabsorption: Defective in Vitro Ileal Active Bile Acid Transport”, *Gastroenterology,* 1982:83:804–11.

In fact, cholestyramine binds the bile acids in the intestinal tract, thereby interfering with their normal enterohepatic circulation (Reihnér, E. et al, in “Regulation of hepatic cholesterol metabolism in humans: stimulatory effects of cholestyramine on HMG-CoA reductase activity and low density lipoprotein receptor expression in gallstone patients”, *Journal of Lipid Research,* Volume 31, 1990, 2219–2226 and Suckling el al, “Cholesterol Lowering and bile acid excretion in the hamster with cholestyramine treatment”, *Atherosclerosis,* 89 (1991) 183–190). This results in an increase in liver bile acid synthesis by the liver using cholesterol as well as an upregulation of the liver LDL receptors which enhances clearance of cholesterol and decreases serum LDL cholesterol levels.

In another approach to the reduction of recirculation of bile acids, the ileal bile acid transport system is a putative pharmaceutical target for the treatment of hypercholesterolemia based on an interruption of the enterohepatic circulation with specific transport inhibitors (Kramer, et al, “Intestinal Bile Acid Absorption” *The Journal of Biological Chemistry,* Vol. 268, No. 24, Issue of Aug. 25, 1993, pp. 18035–18046.

In a series of patent applications, eg Canadian Patent Application Nos. 2,025,294; 2,078,588; 2,085,782; and 2,085,830; and EP Application Nos. 0 379 161; 0 549 967; 0 559 064; and 0 563 731, Hoechst Aktiengesellschaft discloses polymers of various naturally occurring constituents of the enterohepatic circulation system and their derivatives, including bile acid, which inhibit the physiological bile acid transport with the goal of reducing the LDL cholesterol level sufficiently to be effective as pharmaceuticals and; in particular for use as hypocholesterolemic agents.

In vitro bile acid transportinhibition is disclosed to show hypolipidemic activity in The Wellcome Foundation Limited disclosure of the world patent application number WO 93/16055 for “Hypolipidemic Benzothiazepine Compounds”

Selected benzothiepines are disclosed in world patent application number WO93/321146 for numerous uses including fatty acid metabolism and coronary vascular diseases.

Other selected benzothiepines are known for use as hypolipaemic and hypocholesterolaemic agents, especially for the treatment or prevention of atherosclerosis as disclosed by application Nos. EP 508425, FR 2661676, and WO 92/18462, each of which is limited by an amide bonded to the carbon adjacent the phenyl ring of the fused bicyclo benzothiepine ring.

The above references show continuing efforts to find safe, effective agents for the prophylaxis and treatment of hyperlipidemic diseases and their usefulness as hypocholesterolemic agents.

Additionally selected benzothiepines are disclosed for use in various disease states not within the present invention utility. These are EP 568 898A as abstracted by Derwent Abstract No. 93-351589; WO 89/1477/A as abstracted in Derwent Abstract No. 89-370688; U.S. Pat. No. 3,520,891 abstracted in Derwent 50701R-B; U.S. Pat. Nos. 3,287,370, 3,389,144; 3,694,446 abstracted in Derwent Abstr. No. 65860T-B and WO 92/18462.

HMG Co-A reductase inhibitors have been used as cholesterol-lowering agents. This class of compounds inhibits 3-hydroxy-3-methylglutaryl-coenzyme A (HMG Co-A) reductase. This enzyme catalyzes the conversion of HMG Co-A to mevalonate, which is an early and rate-limiting step in the biosynthesis of cholesterol.

Benzothiazepine anti-hyperlipidemic agents are disclosed in WO 94/18183, WO 94/18184, WO 96/05188, WO 96/16051, AU-A-30209/92, AU-A-61946/94, AU-A-61948/94, and AU-A-61949/94.

The present invention furthers such efforts by providing novel pharmaceutical compositions and methods for the treatment of hyperlipidemic conditions.

SUMMARY OF THE INVENTION

Accordingly, among its various apects, the present invention provides compounds of formula (I):

(I)

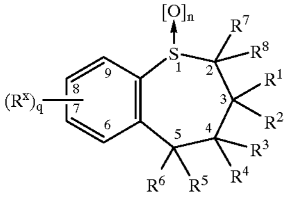

wherein:

q is an integer from 1 to 4;

n is an integer from 0 to 2;

$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^-R^9R^{10}R^wA^-$, $SR^9$, $S^+R^9R^{10}A^-$, $P^-R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, $SO_2$, $S^+R^9A^-$, $P^+R^9R^{10}A^-$, or phenylene, wherein $R^9$, $R^{10}$, and $R^w$ are independently selected from the group consisting of H, alkyl, alkenyl, alkynyl, cycloalkyl, aryl, acyl, heterocycle, heteroaryl, ammoniumalkyl, alkylammoniumalkyl, and arylalkyl; or $R^1$ and $R^2$ taken together with the carbon to which they are attached form $C_3$–$C_{10}$ cycloalkylidene;

$R^3$ and $R^4$ are independently selected from the group consisting of H, alkyl, alkenyl, alkynyl, acyloxy, aryl, heterocycle, heteroaryl, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together form $=O$, $=NOR^{11}$, $=S$, $=NNR^{11}R^{12}$, $=NR^9$, or $=CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, heteroaryl, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$ and SH, or $R^{11}$ and $R^{12}$ together with the nitrogen or carbon atom to which they are attached form a cyclic ring;

$R^5$ and $R^6$ are independently selected from the group consisting of H, alkyl, alkenyl, alkynyl, aryl, cycloalkyl, heterocycle, heteroaryl, quaternary heterocycle, quaternary heteroaryl, $SR^9$, $S(O)R^9$, $SO_2R^9$, and $SO_3R^9$, wherein alkyl, alkenyl, alkynyl, aryl, cycloalkyl, heterocycle, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, heteroaryl arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$,$NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}$ $R^{14}R^{15}A$–, $P(OR^{13})OR^{14}$, $S^+R^{13}R^{14}A$–, and $N^+R^9R^{11}R^{12}A^-$, wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, heterocycle and heteroaryl can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A$–, alkyl, alkenyl, alkynyl, aryl, cycloalkyl, heterocycle, heteroaryl, arylalkyl, quaternary heterocycle, quaternary heteroaryl, $P(O)R^7R^8$, $P^+R^7R^8R^9A^-$, and $P(O)(OR^7)OR^8$, and wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A$–, S, SO, $SO_2$, $S^+R^7A$–, $PR^7$, $P(O)R^7$, $P^+R^7R^8A$–, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl quaternary heterocycle, quaternary heteroaryl, and quaternary heteroarylalkyl, wherein alkyl, alkenyl, alkynyl, arylalkyl, heterocycle, heteroaryl, and polyalkyl optionally have one or more carbons replaced by O, $NR^9$, $N^+R^9R^{10}A$–, S, SO, $SO_2$, $S^{30}$ $R^9A^-$, $PR^9$, $P^+R^9R^{10}A$–, $P(O)R^9$, phenylene, carbohydrate, amino acid, peptide, or polypeptide, and $R^{13}$, $R^{14}$, and $R^{15}$ are optionally substituted with one or more groups selected from the group consisting of sulfoalkyl, heterocycle, heteroaryl, quanternary heterocycle, quaternary heteroaryl, $OR^9$, $NR^9R^{10}$, $N^+R^9R^{11}R^{12}A$–, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A$–, $S^+R^9R^{10}A$–, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring;

$R^7$ and $R^8$ are independently selected from the group consisting of hydrogen and alkyl; and one or more $R^X$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A$–, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, heteroaryl, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, or C(O)OM, and wherein $R^{18}$ is selected from the group consisting of acyl, arylalkoxycarbonyl, arylalkyl, heterocycle, heteroaryl, alkyl, quaternary heterocycle, and quaternary heteroaryl wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A-$, S, SO, $SO_2$, $S^+R^{13}A-$, $PR^{13}$, $P(O)R^{13}$ $P^+R^{13}R^{14}A-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A-$, S, SO, $SO_2$, $S^+R^9A-$, $PR^9$, $P^+R^9R^{10}A-$, or P(O)R';

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, heteroaryl, arylalkyl, halogen, oxo–, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A-$, $P(OR^{13})OR^{14}$, $S^+R$—$R^{14}A^-$, and $N^+R^9R^{11}R^{12}A^-$, provided that both $R^5$ and $R^6$ cannot be hydrogen, OH, or SH, and when $R^5$ is OH, $R^1$, $R^2$, $R^3$, $R^4$, $R^7$ and $R^8$ cannot be all hydrogen;

provided that when $R^5$ or $R^6$ is phenyl, only one of $R^1$ or $R^2$ is H;

provided that when q=1 and $R^x$ is styryl, anilido, or anilinocarbonyl, only one of $R^5$ or $R^6$ is alkyl; or a pharmaceutically acceptable salt, solvate, or prodrug thereof.

Preferably, $R^5$ and $R^6$ can independently be selected from the group consisting of H, aryl, heterocycle, heteroaryl, quaternary heterocycle, and quaternary heteroaryl, wherein said aryl, heterocycle, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heteocycle, heteroarly, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $p^+R^{13}R^{14}R^{15}A-$, $P(OR^{13})OR^{14}$, $S+R^{13}R^{14}A-$, and $N^+R^9R^{11}R^{12}A^-$, wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A-$, S, SO, $SO_2$, $S^+R^7A-$, $PR^7$, $P(O)R^7$ $P^+R^7R^8A-$, or phenylene, wherein said alkyl, alkenyl, alkynyl, polyalkyl, polyether, aryl, haloalkyl, cycloalkyl, heterocycle and heteroaryl can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A-$, alkyl, alkenyl, alkynyl, aryl, cycloalkyl, heterocycle, heteroaryl, arylalkyl, quanternary heterocycle, quaternary heteroaryl, $P(O)R^7R^8$, $P^+R^7R^8R^9A-$, and $P(O)(OR^7)OR^8$.

More preferably, $R^5$ or $R^6$ has the formula:

$$-Ar-(R^y)_t$$

wherein t is an integer from 0 to 5;

Ar is selected from the group consisting of phenyl, thiophenyl, pyridyl, piperazinyl, piperonyl, pyrrolyl, naphthyl, furanyl, anthracenyl, quinolinyl, isoquinolinyl, quinoxalinyl, imidazolyl, pyrazolyl, oxazolyl, isoxazolyl, pyrimidinyl, thiazolyl, triazolyl, isothiazolyl, indolyl, benzoimidazolyl, benzoxazolyl, benzothiazolyl, and benzoisothiazolyl; and one or more $R^y$ are independently selected from the group consisting of H, alkyl, alkenyl, alkynyl, aryl, cycloalkyl, heterocycle, heteroaryl, quaternary heterocycle, quaternary heteroaryl $OR^9$, $SR^9$, $S(O)R^9$, $SO_2R^9$, and $SO_3R^9$, wherein alkyl, alkenyl, alkynyl, aryl, cycloalkvl. heterocycle, and heteroaryl can be substituted with one or more substituent groups independently selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}$ $R^{14}R^{15}A-$, $P(OR^{13})OR^{14}$, $S^+R^{13}R^{14}A^-$, and $N^+R^9R^{11}R^{12}A^-$, wherein said alkyl, alkenyl, alkynyl, polyalkyl, polyether, aryl, haloalkyl, cycloalkyl, heterocycle, and heteroaryl can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A-$, alkyl, alkenyl, alkynyl, aryl, cycloalkyl, heterocycle, heteroaryl, arylalkyl, quaternary heterocycle, quaternary heteroaryl, $P(O)R^7R^8$, $P^+R^7R^8R^9A-$, and $P(O)(OR^7)OR^8$, and wherein said alkyl, alkenyl, alkynyl, polyalkyl, polyether, aryl, haloalkyl, cycloalky, heterocycle, hetercycle, and heteroarly can optionally have one or more carbons replaced by O, $NR^7$, $N^+R^7R^8A-$, S, SO, $SO_2$, $S^+R^7A-$, $PR^7$, $P(O)R^7$, $P^+R^7R^8A-$, or phenylene.

Most preferably, $R^5$ or $R^6$ has the formula (II):

(II)

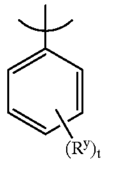

The invention is further directed to a compound selected from among:

(Formula DI)

$R^{20}—R^{19}—R^{21}$ (Formula DII)

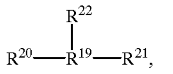

and (Formula DIII)

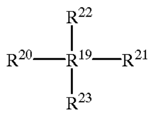

wherein $R^{19}$ is selected from the group consisting of alkane diyl, alkene diyl, alkyne diyl, polyalkane diyl, alkoxy diyl, polyether diyl, polyalkoxy diyl, carbohydrate, amino acid, peptide, and polypeptide, wherein alkane diyl, alkene diyl, alkyne diyl, polyalkane diyl, alkoxy diyl, polyether diyl, polyalkoxy diyl, carbohydrate, amino acid, peptide, and polypeptide can optionally have one or more carbon atoms replaced by O, $NR^7$, $N^+R^7R^8$, S, SO, $SO_2$, $S^+R^7R^8$, $PR^7$, $P^+P^7R^8$, phenylene, heterocycle, heteroaryl, quaternary heterocycle, quaternary heteroaryl, or aryl, wherein alkane diyl, alkene diyl, alkyne diyl, polyalkane diyl, alkoxy diyl, polyether diyl, polyalkoxy diyl, carbohydrate, amino acid, peptide, and polypeptide can be substituted with one or more substituent groups independently selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^+$, and $N^+R^9R^{11}R^{12}A^-$;

wherein $R^{19}$ further comprises functional linkages by which $R^{19}$ is bonded to $R^{20}$, $R^{21}$, or $R^{22}$ in the compounds of Fornulae DII and DIII, and $R^{23}$ in the compounds of Formula DIII. Each of $R^{20}$, $R^{21}$, or $R^{22}$ and $R^{23}$ comprises a benzothiepine moiety as described above that is therapeutically effective in inhibiting ileal bile acid transport.

The invention is also directed to a compound selected from among Formula DI, Formula DII and Formula DIII in which each of $R^{20}$, $R^{21}$, $R^{22}$ and $R^{23}$ comprises a benzothiepine moiety corresponding to the Formula:

(Formula DIV)

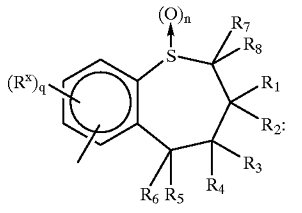

or

-continued (Formula DIVA)

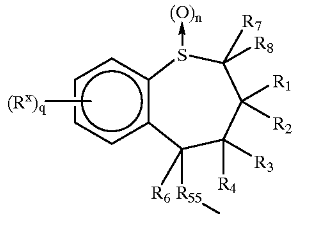

wherein $R^1$, $R^2$, $R^3$, $R^4$, $R^5$, $R^6$, $R^7$, $R^8$, $R^x$, q, and n are as defined in Formula I as described above, and $R^{55}$ is either a covalent bond or arylene.

In compounds of Formula DIV, it is particularly preferred that each of $R^{20}$, $R^{21}$, and $R^{22}$ in Formulae DII and DIII, and $R^{23}$ in Formula DIII, be bonded at its 7- or 8-position to $R^{19}$. In compounds of Formula DIVA, it is particularly preferred that $R^{55}$ comprise a phenylene moiety bonded at a m- or p-carbon thereof to $R^{19}$.

Examples of Formula DI include:

(III)

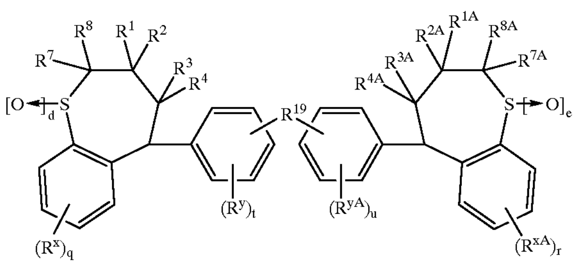

(IV)

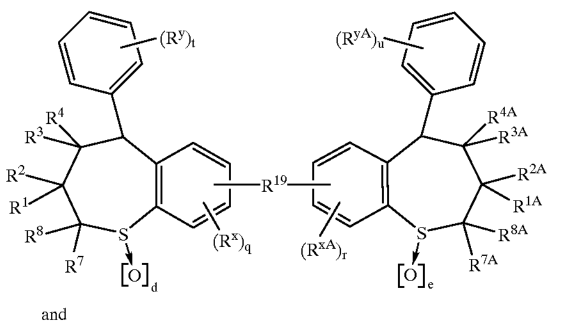

and (V)

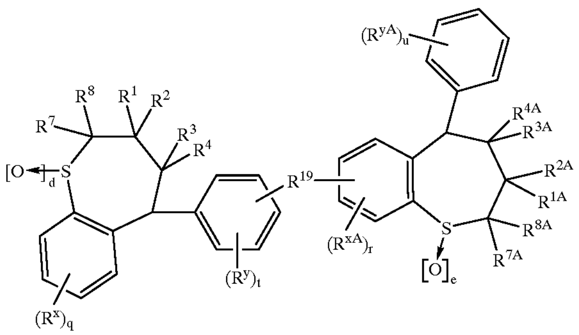

In any of the dimeric or multimeric structures discussed immediately above, benzothiepine compounds of the present invention can be used alone or in various combinations.

In any of the compounds of the present invention, $R^1$ and $R^2$ can be ethyl/butyl or butyl/butyl.

Other compounds useful in the present invention as ileal bile acid transport inhibitors are shown in Appendix A.

In another aspect, the present invention provides a pharmaceutical composition for the prophylaxis or treatment of a disease or condition for which a bile acid transport inhibitor is indicated, such as a hyperlipidemic condition, for example, atherosclerosis. Such compositions comprise any of the compounds disclosed above, alone or in combination, in an amount effective to reduce bile acid levels in the blood, or to reduce transport thereof across digestive system membranes, and a pharmaceutically acceptable carrier, excipient, or diluent.

In a further aspect, the present invention also provides a method of treating a disease or condition in mammals, including humans, for which a bile acid transport inhibitor is indicated, comprising administering to a patient in need thereof a compound of the present invention in an effective amount in unit dosage form or in divided doses.

In yet a further aspect, the present invention also provides processes for the preparation of compounds of the present invention.

In yet another aspect, the present invention provides a combination therapy comprising the use of a first amount of an ileal bile acid transport inhibitor and a second amount of a HMG Co-A reductase inhibitor useful to treat hyperlipidemic disorders, wherein said first and second amounts together comprise an anti-hyperlipidemic condition effective amount of said compounds.

HMG Co-A reductase inhibitor-compounds useful in the present invention are shown in Appendix B.

Further scope of the applicability of the present invention will become apparent from the detailed description provided below. However, it should be understood that the following detailed dscription and examples, while indicating preferred embodiments of the invention, are given by way of illustration only since various changes and modifications within the spirit and scope of the invention will beomce apparent to those skilled in the art from this detailed description.

DETAILED DESCRIPTION OF THE INVENTION

The following detailed description is provided to aid those skilled in the art in practicing the present invention. Even so, this detailed description should not be construed to unduly limit the present invention as modifications and variations in the emobodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

Definitions

In order to aid the reader in understanding the following detailed description, the following definitions are provided:

"Alkyl", "alkenyl," and "alkynyl" unless otherwise noted are each straight chain or branched chain hydrocarbons of from one to twenty carbons for alkyl or two to twenty carbons for alkenyl and alkynyl in the present invention and therefore mean, for example, methyl, ethyl, propyl, butyl, pentyl or hexyl and ethenyl, propenyl, butenyl, pentenyl, or hexenyl and ethynyl, propynyl, butynyl, pentynyl, or hexynyl respectively and isomers thereof.

"Aryl" means a fully unsaturated mono- or multi-ring carbocyle, including, but not limited to, substituted or unsubstituted phenyl, naphthyl, or anthracenyl.

"Heterocycle" means a saturated or unsaturated mono- or multi-ring carbocycle wherein one or more carbon atoms can be replaced by N, S, P, or O. This includes, for example, the following structures:

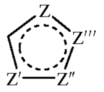
or
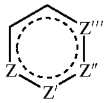

wherein Z, Z', Z" or Z"' is C, S, P, O, or N, with the proviso that one of Z, Z', Z" or Z"' is other than carbon, but is not O or S when attached to another Z atom by a double bond or when attached to another O or S atom. Furthermore, the optional substituents are understood to be attached to Z, Z', Z" or Z"' only when each is C.

The term "heteroaryl" means a fully unsaturated heterocycle.

In either "heterocycle" or "heteroaryl," the point of attachment to the molecule of interest can be at the heteroatom or elsewhere within the ring.

The term "quaternary heterocycle" means a heterocycle in which one or more of the heteroatoms, for example, O, N, S, or P, has such a number of bonds that it is positively charged. The point of attachment of the quaternary heterocycle to the molecule of interest can be at a heteroatom or elsewhere.

The term "quaternary heteroaryl" means a heteroaryl in which one or more of the heteroatoms, for example, O, N, S, or P, has such a number of bonds that it is positively charged. The point of attachment of the quaternary heteryaryl to the molecule of interest can be at a heteroatom or elsewhere.

The term "halogens" means a fluoro, chloro, bromo or iodo group.

The term "haloalkyl" means alkyl substituted with one or more halogens.

The term "cycloalkyl" means a mono- or multi-ringed carbocycle wherein each ring contains three to ten carbon atoms, and wherein any ring can contain one or more double or triple bonds.

The term "diyl" means a diradical moiety wherein said moiety has two points of attachment to molecules of interest.

The term "oxo" means a doubly bonded oxygen.

The term "polyalkyl" means a branched or straight hydrocarbon chain having a molecular weight up to about 20,000, more preferably up to about 10,000, most preferably up to about 5,000.

The term "polyether" means a polyalkyl wherein one or more carbons are replaced by oxygen, wherein the polyether has a molecular weight up to about 20,000, more preferably up to about 10,000, most preferably up to about 5,000.

The term "polyalkoxy" means a polymer of alkylene oxides, wherein the polyalkoxy has a molecular weight up to about 20,000, more preferably up to about 10,000, most preferably up to about 5,000.

The term "cycloaklylidene" means a mono- or multiringed carbocycle wherein a carbon within the ring structure is doubly bonded to an atom which is not within the ring structures.

The term "carbohydrate" means a mono-, di-, tri-, or polysaccharide wherein the polysaccharide can have a molecular weight of up to about 20,000, for example, hydroxypropyl-methylcellulose or chitosan.

The term "peptide" means polyamino acid containing up to about 100 amino acid units.

The term "polypeptide" means polyamino acid containing from about 100 amino acid units to about 1000 amino acid units, more preferably from about 100 amino acid units to about 750 amino acid untis, most preferably from about 100 amino acid units to about 500 amino acid units.

The term "alkylammoniumalkyl" means a $NH_2$ group or a mono-, di- or tri-substituted amino group, any of which is bonded to an alkyl wherein said alkyl is bonded to the molecule of interest.

The term "triazolyl" includes all positional isomers. In all other heterocycles and heteroaryls which contain more than one ring heteroatom and for which isomers are possible, such isomers are included in the definition of said heterocycles and heteroaryls.

The term "sulfoalkyl" means an alkyl group to which a sulfonate group is bonded, wherein said alkyl is bonded to the molecule of interest.

The term "active compound" means a compound of the present invention which inhibits transport of bile acids.

When used in combination, for example "alkylaryl" or "arylalkyl," the individual terms listed above have the meaning indicated above.

The term "a bile acid transport inhibitor" means a compound capable of inhibiting absorption of bile acids from the intestine into the circulatory system of a mammal, such as a human. This includes increasing the fecal excretion of bile acids, as well as reducing the blood plasma or serum concentrations of cholesterol and cholesterol ester, and more specifically, reducing LDL and VLDL cholesterol. Conditions or diseases which benefit from the prophylaxis or treatment by bile acid transport inhibition include, for example, a hyperlipidemic condition such as atherosclerosis.

The phrase "combination therapy" refers to the administration of an ileal bile acid transport inhibitor and a HMG Co-A reductase inhibitor to treat a hyperlipidemic condition, for example atherosclerosis and hypercholesterolemia. Such administration encompasses co-administration of these inhibitors in a substantially simultaneous manner, such as in a single capsule having a fixed ratio of active ingredients or in multiple, separate capsules for each inhibitor agent. In addition, such administration also encompasses use of each type of inhibitor in a sequential manner. In either case, the treatment regimen will provide beneficial effects of the drug combination in treating the hyperlipidemic condition.

The phrase "theraputically effective" is intended to qualify the combined amount of inhibitors in the combination therapy. This combined amount will achieve the goal of reducing or eliminating the hyperlipidemic condition.

Compounds

The compounds of the present invention can have at least two asymmetrical carbon atoms, and therefore include racemates and stereoisomers, such as diastereomers and enantiomers, in both pure form and in admixture. Such stereoisomers can be prepared using conventional techniques, either by reacting enantiomeric starting materials, or by separating isomers of compounds of the present invention.

Isomers may include geometric isomers, for example cis isomers or trans isomers across a double bond. All such isomers are contemplated among the compounds of the present invention.

The compounds of the present invention also include tautomers.

The compounds of the present invention as discussed below include their salts, solvates and prodrugs.

Compound Syntheses

The starting materials for use in the preparation of the compounds of the invention are known or can be prepared by conventional methods known to a skilled person or in an analogous manner to processes described in the art.

Generally, the compounds of the present invention can be prepared by the procedures described below.

For example, as shown in Scheme I, reaction of aldehyde II with formaldehyde and sodium hydroxide yields the hydroxyaldehyde III which is converted to mesylate IV with methanesulfonyl chloride and triethylamine similar to the procedure described in Chem. Ber. 98, 728–734 (1965). Reaction of mesylate IV with thiophenol V, prepared by the procedure described in WO 93/16055, in the presence of triethylamine yields keto-aldehyde VI which can be cyclized with the reagent, prepared from zinc and titanium trichloride in refluxing ethylene glycol dimethyl ether (DME), to give a mixture of 2,3-dihydrobenzothiepine VII and two racemic steroisomers of benzothiepin-(5H)-4-one VIII when $R^1$ and $R^2$ are nonequivalent. Oxidation of VII with 3 equivalents of m-chloro-perbenzoic acid (MCPBA) gives isomeric sulfone-epoxides IX which upon hydrogenation with palladium on carbon as the catalyst yield a mixture of four racemic stereoisomers of 4-hydroxy-2,3,4,5-tetrahydrobenzothiepine-1,1-dioxides X and two racemic stereoisomers of 2,3,4,5-tetrahydro-benzothiepine-1,1-dioxides XI when $R^1$ and $R^2$ are nonequivalent.

Optically active compounds of the present invention can be prepared by using optically active starting material III or by resolution of compounds X with optical resolution agents well known in the art as described in *J. Org. Chem.,* 39, 3904 (1974), ibid., 42, 2781 (1977), and ibid., 44, 4891 (1979).

Scheme 1

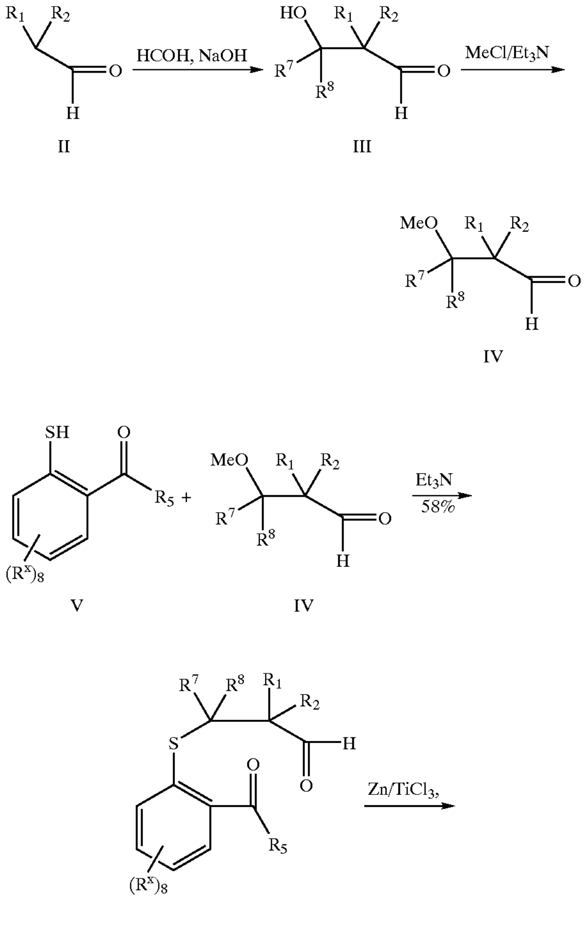

II III IV V IV

-continued

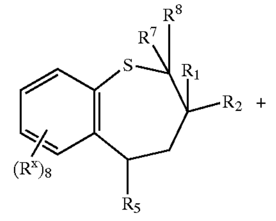

VII

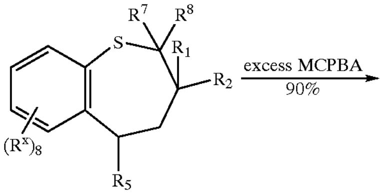

VIII

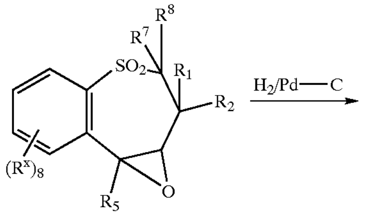

X

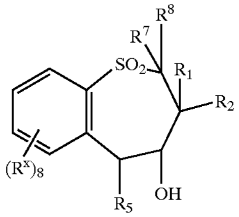

X

+

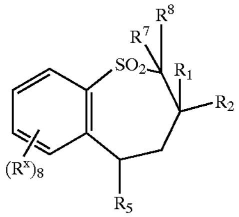

XI

Alternatively, keto-aldehyde VI where $R^2$ is H can be prepared by reaction of thiophenol V with a 2-substituted acrolein.

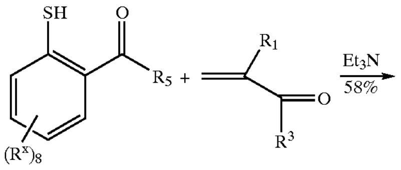

V

-continued

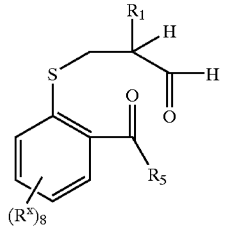

VI

Benzothiepin-(5H)-4-one VIII can be oxidized with MCPBA to give the benzothiepin-(5H)-4-one-1,1-dioxide XII which can be reduced with sodium borohydride to give four racemic stereoisomers of X. The two stereoisomers of X, Xa and Xb, having the OH group and $R^5$ on the opposite sides of the benzothiepine ring can be converted to the other two isomers of X, Xc and Xd, having the OH group and $R^5$ on the same side of the benzothiepine ring by reaction in methylene chloride with 40–50% sodium hydroxide in the presence of a phase transfer catalyst (PTC). The transformation can also be carried out with potassium t-butoxide in THF.

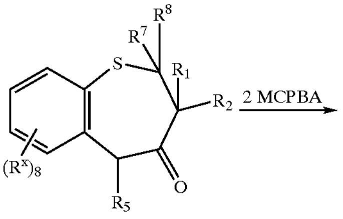

VIII

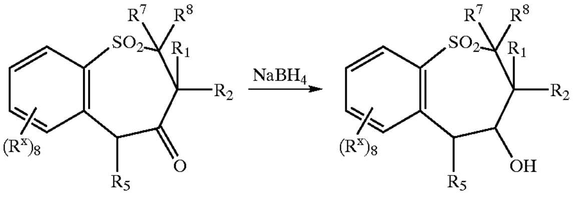

XI X

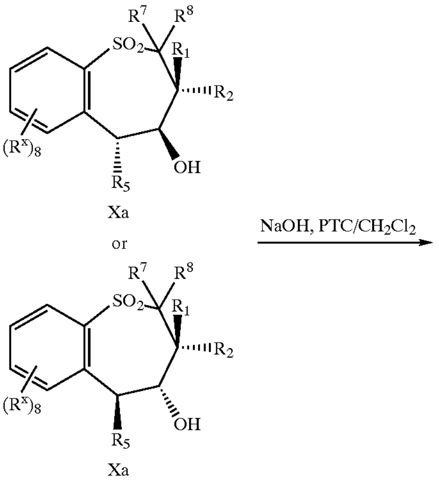

Xa or

Xa

-continued

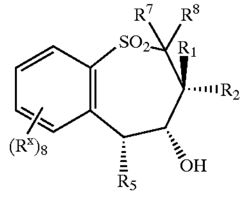

Xc

+

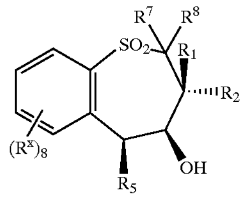

Xd

When $R_1$ = Bu, $R_2$ = Et, $R_5$ = Ph, X = H, q = 4
6a = Xa
6b = Xb
6c = Xc
6d = Xd The compounds of the present invention where $R^5$ is OR, NRR' or $S(O)_nR$ and $R^4$ is hydroxy can be prepared by reaction of epoxide IX where $R^5$ is H with thiol, alcohol, or amine in the presence of a base.

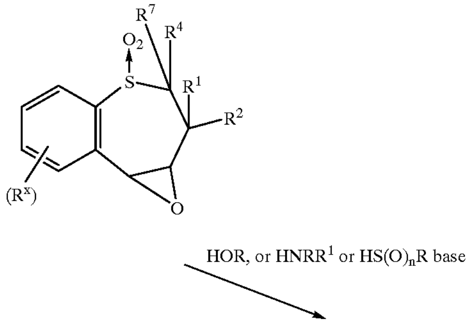

-continued

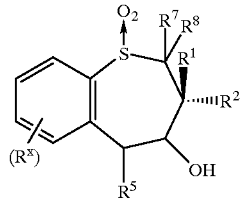

$R^5$ = OR, $NRR^1$, $S(O)_nR$

Another route to Xc and Xd of the present invention is shown in Scheme 2. Compound VI is oxidized to compound XIII with two equivalent of m-chloroperbenzoic acid. Hydrogenolysis of compound XIII with palladium on carbon yields compound XIV which can be cyclized with either potassium t-butoxide or sodium hydroxide under phase transfer conditions to a mixture of Xc and Xd. Separation of Xc and Xd can be accomplished by either HPLC or fractional crystallization.

The thiophenols XVIII and V used in the present invention can also be prepared according to the Scheme 3. Alkylation of phenol XV with an arylmethyl chloride in a nonpolar solvent according to the procedure in *J. Chem. Soc.*, 2431–2432 (1958) gives the ortho substituted phenol XVI. The phenol XVI can be converted to the thiophenol XVIII via the thiocarbamate XVII by the procedure described in *J. Org. Chem.*, 31, 3980 (1966). The phenol XVI is first reacted with dimethyl thiocarbamoyl chloride and triethylamine to give thiocarbamate XVII which is thermally rearranged at 200–300° C., and the rearranged product is hydrolyzed with sodium hydroxide to yield the thiophenol XVIII. Similarly, Thiophenol V can also be prepared from 2-acylphenol XIX via the intermediate thiocarbamate XX.

Scheme 2

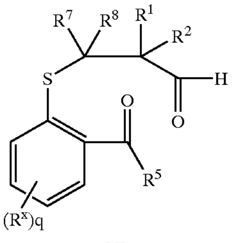

VI

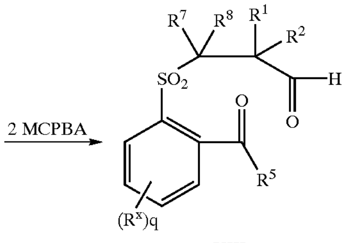

XIII

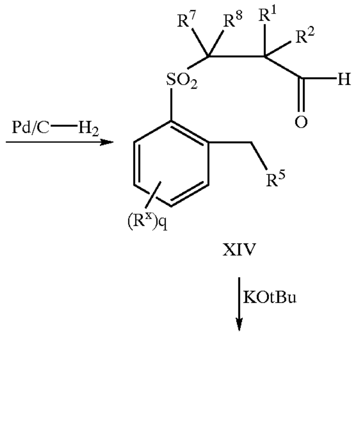

XIV

-continued

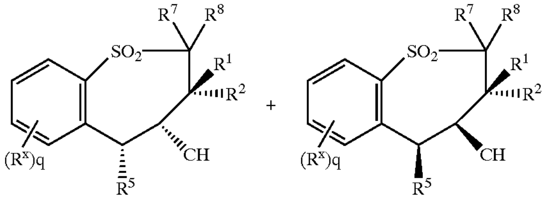

Xc Xd

Scheme 3

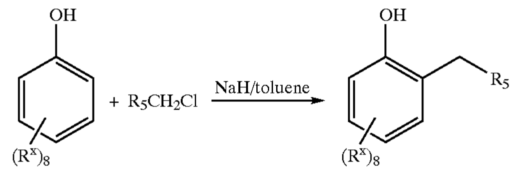

XV XVI

-continued

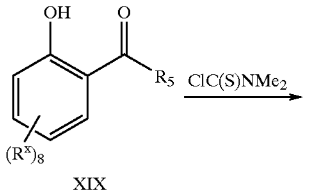

XIX

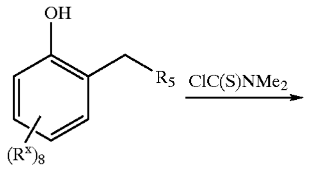

XVI

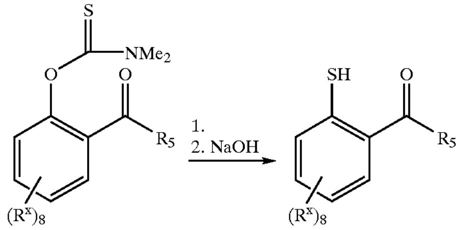

XX V

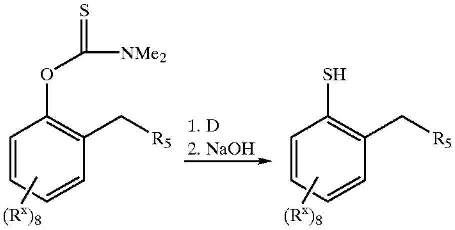

XVII XVIII

Scheme 4 shows another route to benzothiepine-1,1-dioxides Xc and Xd starting from the thiophenol XVIII. Compound XVIII can be reacted with mesylate IV to give the sulfide-aldehyde XXI. Oxidation of XXI with two equivalents of MCPBA yields the sulfone-aldehyde XIV which can be cyclized with potassium t-butoxide to a mixture of Xc and Xd. Cyclyzation of sulfide-aldehyde with potassium t-butoxide also gives a mixture of benzothiepine XXIIc and XXIId.

Scheme 4

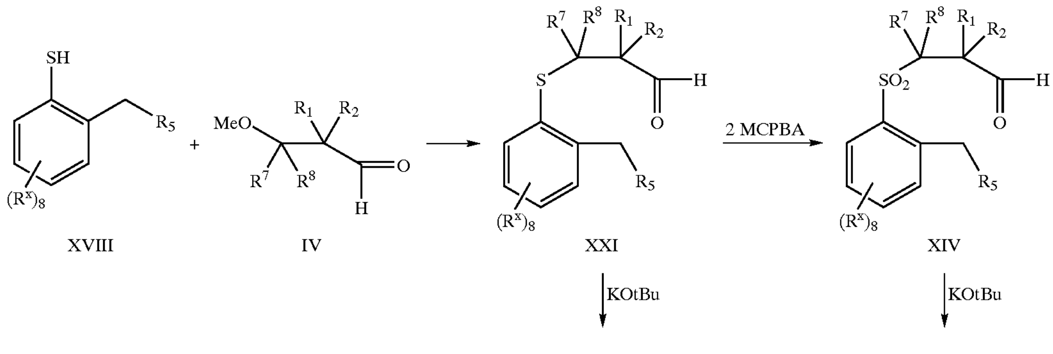

XVIII IV XXI XIV

-continued

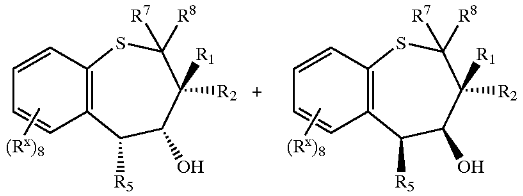

XXIIc

XXIId

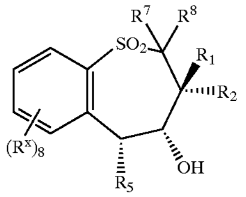

Xc

+

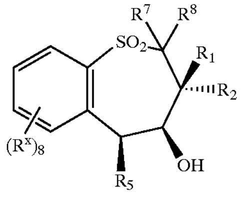

Xd

Examples of amine- and hydroxylamine-containing compounds of the present invention can be prepared as shown in Scheme 5 and Scheme 6. 2-Chloro-5-nitrobenzophenone is reduced with triethylsilane and trifluoromethane sulfonic acid to 2-chloro-5-nitrodiphenylmethane 32. Reaction of 32 with lithium sulfide followed by reacting the resulting sulfide with mesylate IV gives sulfide-aldehyde XXIII. Oxidation of XXIII with 2 equivalents of MCPBA yields sulfone-aldehyde XXIV which can be reduced by hydrogenation to the hydroxylamine XXV. Protecting the hydroxylamine XXV with di-t-butyldicarbonate gives the N,O-di-(t-butoxycarbonyl)hydroxylamino derivative XXVI. Cyclization of XXVI with potassium t-butoxide and removal of the t-butoxycarbonyl protecting group gives a mixture of hydroxylamino derivatives XXVIIc and XXVIId. The primary amine XXXIIIc and XXXIIId derivatives can also be prepared by further hydrogenation of XXIV or XXVIIc and XXVIId.

Scheme 5

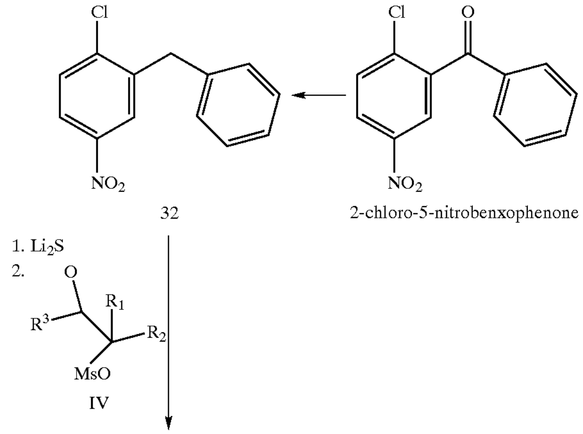

32

2-chloro-5-nitrobenxophenone

IV

-continued

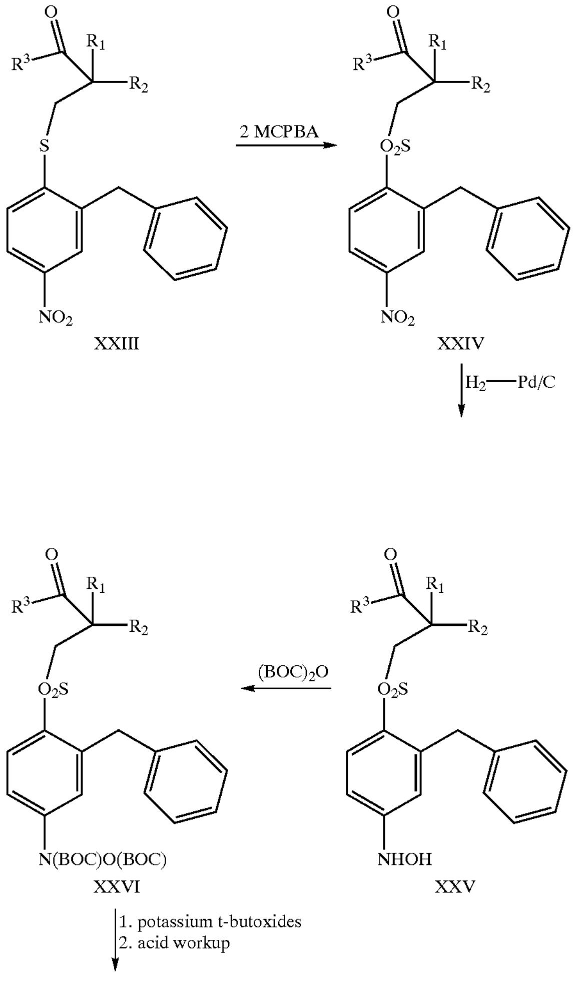

XXIII

XXIV

XXV

XXVI

-continued

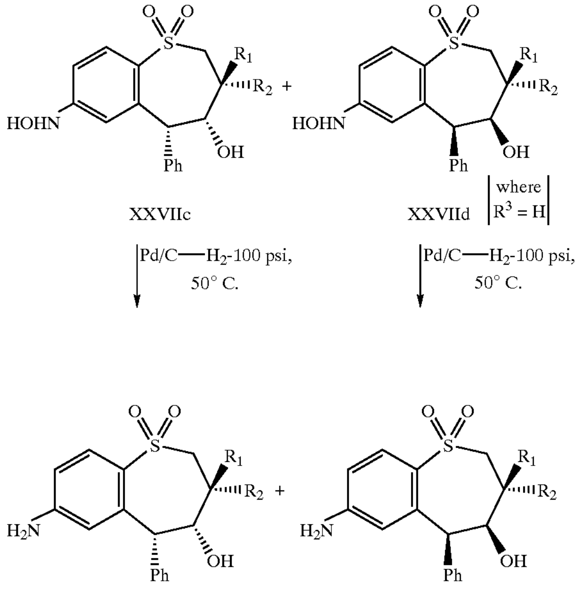

XXVIIc

XXVIId

XXXIIIc

XXXIIId

In Scheme 6, reduction of the sulfone-aldehyde XXV with hydrogen followed by reductive alkylation of the resulting amino derivative with hydrogen and an aldehyde catalyzed by palladium on carbon in the same reaction vessel yields the substituted amine derivative Scheme 6

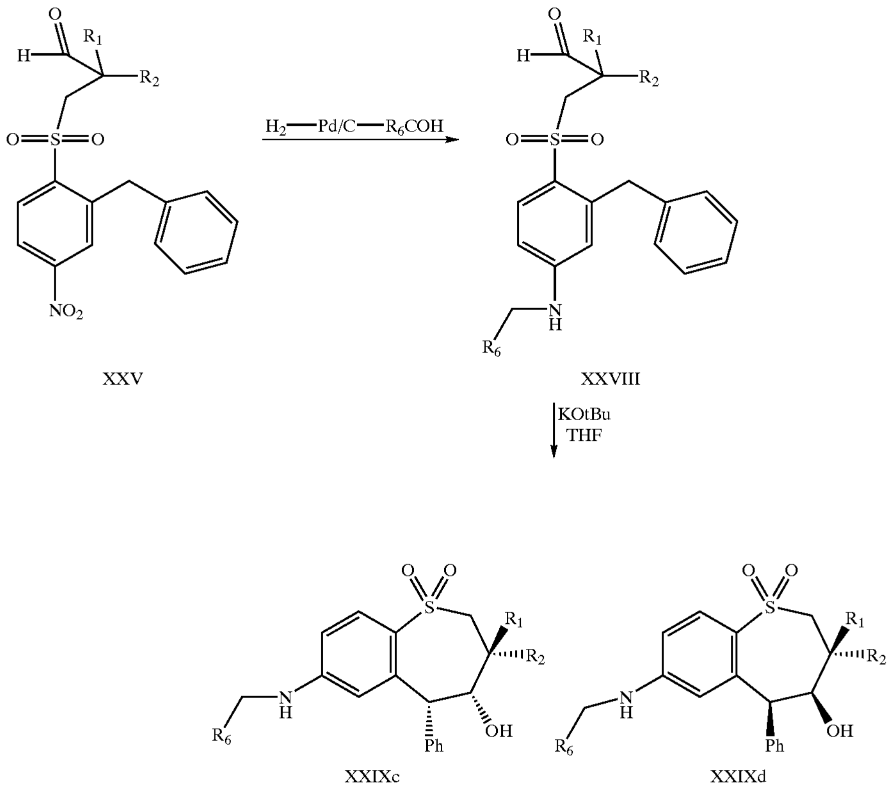

XXV

XXVIII

XXIXc

XXIXd

XXVIII. Cyclization of XXVIII with potassium t-butoxide yields a mixture of substituted amino derivatives of this invention XXIXc and XXIXd.

Scheme 7 describes one of the methods of introducing a substituent to the aryl ring at the 5-position of benzothiepine. Iodination of 5-phenyl derivative XXX with iodine catalyzed by mercuric triflate gives the iodo derivative XXXI, which upon palladium-catalyzed carbonylation in an alcohol yields the carboxylate XXXII. Hydrolysis of the carboxylate Scheme 7

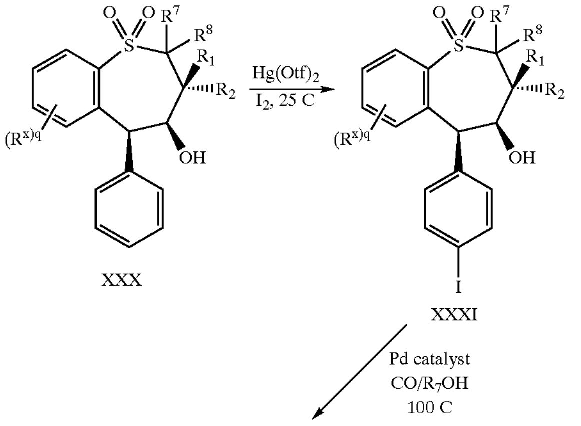

XXX

XXXI

-continued

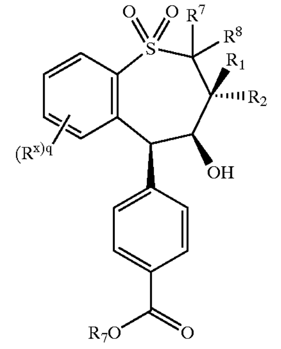

XXXII and derivatization of the resulting acid to acid derivatives are well known in the art.

Abbreviations used in the foregoing description have the following meanings:

THF—tetrahydrofuran
PTC—phase transfer catalyst
Aliquart 336—methyltricaprylylammonium chloride
MCPBA—m-chloroperbenzoic acid
Celite—a brand of diatomaceous earth filtering aid
DMF—dimethylformamide
DME—ethylene glycol dimethyl ether
BOC—t-butoxycarbonyl group $R^1$ and $R^2$ can be selected from among substituted and unsubstituted $C_1$ to $C_{10}$ alkyl wherein the substituent(s) can be selected from among alkylcarbonyl, alkoxy, hydroxy, and nitrogen-containing heterocycles joined to the $C_1$ to $C_{10}$ alkyl through an ether linkage. Substituents at the 3-carbon can include ethyl, n-propyl, n-butyl, n-pentyl, isobutyl, isopropyl, $—CH_2C(=O)C_2H_5$, $—CH_2OC_2H_5$, and $—CH_2O—$(4-picoline). Ethyl, n-propyl, n-butyl, and isobutyl are preferred. In certain particularly preferred compounds of the present invention, substituents $R^1$ and $R^2$ are identical, for example n-butyl/n-butyl, so that the compound is achiral at the 3-carbon. Eliminating optical isomerism at the 3-carbon simplifies the selection, synthesis, separation, and quality control of the compound used as an ileal bile acid transport inhibitor. In both compounds having a chiral 3-carbon and those having an achiral 3-carbon, substituents ($R^x$) on the benzo- ring can include hydrogen, aryl, alkyl, hydroxy, halo, alkoxy, alkylthio, alkylsulfinyl, alkylsulfonyl, haloalkyl, haloalkoxy, (N)-hydroxycarbonylalkyl amine, haloalkylthio, haloalkylsulfinyl, haloalkylsufonyl, amino, N-alkylamino, N,N-dialkylamino, (N)-alkoxycarbamoyl, (N)-aryloxycarbamoyl, (N)-aralkyloxycarbamoyl, trialkylammonium (especially with a halide counterion), (N)-amido, (N)-alkylamido, —N-alkylamido, —N,N-dialkylamido, (N)-haloalkylamido, (N)-sulfonamido, (N)-alkylsulfonamido, (N)-haloalkylsulfonamido, carboxyalkylamino, trialkyl-ammonium salt, (N)-carbamic acid, alkyl or benzyl ester, N-acylamine, hydroxylamine, haloacylamine, carbohydrate, thiophene a trialkyl ammonium salt having a carboxylic acid or hydroxy substituent on one or more of the alkyl substituents, an alkylene bridge having a quaternary ammonium salt substituted thereon, $—[O(CH_2)_w]_x$-X where x is 2 to 12, w is 2 or 3 and X is a halo or a quaternary ammonium salt, and (N)-nitrogen containing heterocycle wherein the nitrogen of said heterocycle is optionally quaternized. Among the preferred species which may constitute $R^x$ are methyl, ethyl, isopropyl, t-butyl$^-$, hydroxy, methoxy, ethoxy, isopropoxy, methylthio, iodo, bromo, fluoro, methylsulfinyl, methylsulfonyl, ethylthio, amino, hydroxylamine, N-methylamino, N,N-dimethylamino, N,N-diethylamino, (N)-benzyloxycarbamoyl, trimethylammonium, $A^-$, $—NHC(=O)CH_3$, $—NHC(=O)C_5H_{11}$, $—NHC(=O)C_6H_{13}$, carboxyethylamino, (N)-morpholinyl, (N)-azetidinyl, (N)-N-methylazetidinium $A^-$, (N)-pyrrolidinyl, pyrrolyl, (N)-N-methylpyridinium $A^-$, (N)-N-methylmorpholinium $A^-$, and N-N'-methylpiperazinyl, (N)-bromomethylamido, (N)-N-hexylamino, thiophene, $—N^+(CH_3)_2CO_2H$ $I^-$, $—NCH_3CH_2CO_2H$, —(N)-N'-dimethylpiperazinium $I^-$, (N)-t-butyloxycarbamoyl, (N)-methylsulfonamido, (N)N'-methylpyrrolidinium, and $—(OCH_2CH_2)_3I$, where $A^-$ is a pharmaceutically acceptable anion. The benzo ring can be mono-substituted at the 6, 7 or 8 position, or disubstituted at the 7- and -8 positions. Also included are the 6,7,8-trialkoxy compounds, for example the 6,7,8-trimethoxy compounds. A variety of other substituents can be advantageously present on the 6, 7, 8, and/or 9-positions of the benzo ring, including, for example, guanidinyl, cycloalkyl, carbohydrate (e.g., a 5 or 6 carbon monosaccharide), peptide, and quaternary ammonium salts linked to the ring via poly (oxyalkylene) linkages, e.g., $—(OCH_2CH_2)_x—N^+R^{13}R^{14}R^{15}A^-$, where x is 2 to 10. Exemplary compounds are those set forth below in Table 1.

TABLE 1

Alternative compounds #3 (Family F101.xxx.yyy)*

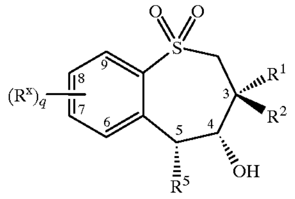

| Prefix (FFF.xxx. | Cpd# yyy) | $R^1$=$R^2$ | $R^5$ | ($R^x$)q |
|---|---|---|---|---|
| F101.001 | 01 | n-propyl | Ph— | 7-methyl |
| | 02 | n-propyl | Ph— | 7-ethyl |
| | 03 | n-propyl | Ph— | 7-iso-propyl |
| | 04 | n-propyl | Ph— | 7-tert-butyl |
| | 05 | n-propyl | Ph— | 7-OH |
| | 06 | n-propyl | Ph— | 7-$CCH_3$ |
| | 07 | n-propyl | Ph— | 7-O(iso-propyl) |
| | 08 | n-propyl | Ph— | 7-$SCH_3$ |
| | 09 | n-propyl | Ph— | 7-$SCCH_3$ |
| | 10 | n-propyl | Ph— | 7-$SO_2CH_3$ |
| | 11 | n-propyl | Ph— | 7-$SCH_2CH_3$ |
| | 12 | n-propyl | Ph— | 7-$NH_2$ |
| | 13 | n-propyl | Ph— | 7-NHOH |
| | 14 | n-propyl | Ph— | 7-$NHCH_3$ |
| | 15 | n-propyl | Ph— | 7-$N(CH_3)_2$ |
| | 16 | n-propyl | Ph— | 7-$N^+(CH_3)_3$, $I^-$ |
| | 17 | n-propyl | Ph— | 7-$NHC(=O)CH_3$ |
| | 18 | n-propyl | Ph— | 7-$N(CH_2CH_3)_2$ |
| | 19 | n-propyl | Ph— | 7-$NMeCH_2CO_2H$ |
| | 20 | n-propyl | Ph— | 7-$N^+(Me)_2CH_2CO_2H$, $I^-$ |
| | 21 | n-propyl | Ph— | 7-(N)-morpholine |
| | 22 | n-propyl | Ph— | 7-(N)-azetidine |
| | 23 | n-propyl | Ph— | 7-(N)-N-methylazetidinium, $I^-$ |
| | 24 | n-propyl | Ph— | 7-(N)-pyrrolidine |
| | 25 | n-propyl | Ph— | 7-(N)-N-methyl-pyrrolidinium, $I^-$ |
| | 26 | n-propyl | Ph— | 7-(N)-N-methyl-morpholinium, $I^-$ |
| | 27 | n-propyl | Ph— | 7-(N)-N'-methylpiperazine |
| | 28 | n-propyl | Ph— | 7-(N)-N'-dimethylpiperazinium, $I^-$ |
| | 29 | n-propyl | Ph— | 7-NH—CBZ |

TABLE 1-continued

Alternative compounds #3 (Family F101.xxx.yyy)*

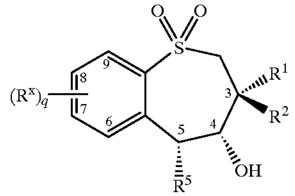

| Prefix (FFF.xxx. | Cpd# yyy) | $R^1$=$R^2$ | $R^5$ | $(R^x)q$ |
|---|---|---|---|---|
| | 30 | n-propyl | Ph— | 7-NHC(O)$C_5H_{11}$ |
| | 31 | n-propyl | Ph— | 7-NHC(O)$CH_2$Br |
| | 32 | n-propyl | Ph— | 7-NH—C(NH)$NH_2$ |
| | 33 | n-propyl | Ph— | 7-(2)-thiophene |
| | 34 | n-propyl | Ph— | 8-methyl |
| | 35 | n-propyl | Ph— | 8-ethyl |
| | 36 | n-propyl | Ph— | 8-iso-propyl |
| | 37 | n-propyl | Ph— | 8-tert-butyl |
| | 38 | n-propyl | Ph— | 8-OH |
| | 39 | n-propyl | Ph— | 8-$OCH_3$ |
| | 40 | n-propyl | Ph— | 8-O-(iso-propyl) |
| | 41 | n-propyl | Ph— | 8-$SCH_3$ |
| | 42 | n-propyl | Ph— | 8-$SOCH_3$ |
| | 43 | n-propyl | Ph— | 8-$SO_2CH_3$ |
| | 44 | n-propyl | Ph— | 8-$SCH_2CH_3$ |
| | 45 | n-propyl | Ph— | 8-$NH_2$ |
| | 46 | n-propyl | Ph— | 8-NHOH |
| | 47 | n-propyl | Ph— | 8-$NHCH_3$ |
| | 48 | n-propyl | Ph— | 8-$N(CH_3)_2$ |
| | 49 | n-propyl | Ph— | 8-$N^+(CH_3)_3$, $I^-$ |
| | 50 | n-propyl | Ph— | 8-NHC(=O)$CH_3$ |
| | 51 | n-propyl | Ph— | 8-$N(CH_2CH_3)_2$ |
| | 52 | n-propyl | Ph— | 8-$NMeCH_2CO_2H$ |
| | 53 | n-propyl | Ph— | 8-$N^+(Me)_2CH_2CO_2H$, $I^-$ |
| | 54 | n-propyl | Ph— | 8-(N)-morpholine |
| | 55 | n-propyl | Ph— | 8-(N)-azetidine |
| | 56 | n-propyl | Ph— | 8-(N)-N-methylazetidinium, $I^-$ |
| | 57 | n-propyl | Ph— | 8-(N)-pyrrolidine |
| | 58 | n-propyl | Ph— | 8-(N)-N-methyl-pyrrolidinium, $I^-$ |
| | 59 | n-propyl | Ph— | 8-(N)-N-methyl-morpholinium, $I^-$ |
| | 60 | n-propyl | Ph— | 8-(N)-N'-methylpiperazine |
| | 61 | n-propyl | Ph— | 8-(N)-N'-dimethylpiperazinium, $I^-$ |
| | 62 | n-propyl | Ph— | 8-NH—CBZ |
| | 63 | n-propyl | Ph— | 8-NHC(O)$C_5H_{11}$ |
| | 64 | n-propyl | Ph— | 8-NHC(O)$CH_2$Br |
| | 65 | n-propyl | Ph— | 8-NH-C(NH)$NH_2$ |
| | 66 | n-propyl | Ph— | 8-(2)-thiophene |
| | 67 | n-propyl | Ph— | 9-methyl |
| | 68 | n-propyl | Ph— | 9-ethyl |
| | 69 | n-propyl | Ph— | 9-iso-propyl |
| | 70 | n-propyl | Ph— | 9-tert-butyl |
| | 71 | n-propyl | Ph— | 9-OH |
| | 72 | n-propyl | Ph— | 9-$OCH_3$ |
| | 73 | n-propyl | Ph— | 9-O(iso-propyl) |
| | 74 | n-propyl | Ph— | 9-$SCH_3$ |
| | 75 | n-propyl | Ph— | 9-$SOCH_3$ |
| | 76 | n-propyl | Ph— | 9-$SO_2CH_3$ |
| | 77 | n-propyl | Ph— | 9-$SCH_2CH_3$ |
| | 78 | n-propyl | Ph— | 9-$NH_2$ |
| | 79 | n-propyl | Ph— | 9-NHOH |
| | 80 | n-propyl | Ph— | 9-$NHCH_3$ |
| | 81 | n-propyl | Ph— | 9-$N(CH_3)_2$ |
| | 82 | n-propyl | Ph— | 9-$N^+(CH_3)_3$, $I^-$ |
| | 83 | n-propyl | Ph— | 9-NHC(=O)$CH_3$ |
| | 84 | n-propyl | Ph— | 9-$N(CH_2CH_3)_2$ |
| | 85 | n-propyl | Ph— | 9-$NMeCH_2CO_2H$ |
| | 86 | n-propyl | Ph— | 9-$N^+(Me)_2CH_2CO_2H$, $I^-$ |
| | 87 | n-propyl | Ph— | 9-(N)-morpholine |
| | 88 | n-propyl | Ph— | 9-(N)-azetidine |

TABLE 1-continued

Alternative compounds #3 (Family F101.xxx.yyy)*

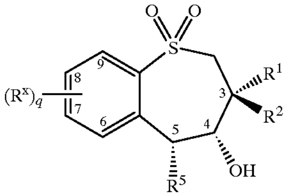

| Prefix (FFF.xxx. | Cpd# yyy) | $R^1$=$R^2$ | $R^5$ | $(R^x)q$ |
|---|---|---|---|---|
| | 89 | n-propyl | Ph— | 9-(N)-N-methylazetidinium, $I^-$ |
| | 90 | n-propyl | Ph— | 9-(N)-pyrrolidine |
| | 91 | n-propyl | Ph— | 9-(N)-N-methyl-pyrrolidinium, $I^-$ |
| | 92 | n-propyl | Ph— | 9-(N)-N-methyl-morpholinium, $I^-$ |
| | 93 | n-propyl | Ph— | 9-(N)-N'-methylpiperazine |
| | 94 | n-propyl | Ph— | 9-(N)-N'-dimethylpiperazinium, $I^-$ |
| | 95 | n-propyl | Ph— | 9-NH—CBZ |
| | 96 | n-propyl | Ph— | 9-NHC(O)$C_5H_{11}$ |
| | 97 | n-propyl | Ph— | 9-NHC(O)$CH_2$Br |
| | 98 | n-propyl | Ph— | 9-NH—C(NH)$NH_2$ |
| | 99 | n-propyl | Ph— | 9-(2)-thiophene |
| | 100 | n-propyl | Ph— | 7-$OCH_3$, 8-$OCH_3$ |
| | 101 | n-propyl | Ph— | 7-$SCH_3$, 8-$OCH_3$ |
| | 102 | n-propyl | Ph— | 7-$SCH_3$, 8-$SCH_3$ |
| | 103 | n-propyl | Ph— | 6-$OCH_3$, 7-$OCH_3$, 8-$OCH_3$ |
| F101.002 | 01 | n-butyl | Ph— | 7-methyl |
| | 02 | n-butyl | Ph— | 7-ethyl |
| | 03 | n-butyl | Ph— | 7-iso-propyl |
| | 04 | n-butyl | Ph— | 7-tert-butyl |
| | 05 | n-butyl | Ph— | 7-OH |
| | 06 | n-butyl | Ph— | 7-$OCH_3$ |
| | 07 | n-butyl | Ph— | 7-O(iso-propyl) |
| | 08 | n-butyl | Ph— | 7-$SCH_3$ |
| | 09 | n-butyl | Ph— | 7-$SOCH_3$ |
| | 10 | n-butyl | Ph— | 7-$SO_2CH_3$ |
| | 11 | n-butyl | Ph— | 7-$SCH_2CH_3$ |
| | 12 | n-butyl | Ph— | 7-$NH_2$ |
| | 13 | n-butyl | Ph— | 7-NHOH |
| | 14 | n-butyl | Ph— | 7-$NHCH_3$ |
| | 15 | n-butyl | Ph— | 7-$N(CH_3)_2$ |
| | 16 | n-butyl | Ph— | 7-$N^+(CH_3)_3$,$I^-$ |
| | 17 | n-butyl | Ph— | 7-NHC(=O)$CH_3$ |
| | 18 | n-butyl | Ph— | 7-$N(CH_2CH_3)_2$ |
| | 19 | n-butyl | Ph— | 7-$NMeCH_2CO_2H$ |
| | 20 | n-butyl | Ph— | 7-$N^+(Me)_2CH_2CO_2H$, $I^-$ |
| | 21 | n-butyl | Ph— | 7-(N)-morpholine |
| | 22 | n-butyl | Ph— | 7-(N)-azetidine |
| | 23 | n-butyl | Ph— | 7-(N)-N-methylazetidinium, $I^-$ |
| | 24 | n-butyl | Ph— | 7-(N)-pyrrolidine |
| | 25 | n-butyl | Ph— | 7-(N)-N-methyl-pyrrolidinium, $I^-$ |
| | 26 | n-butyl | Ph— | 7-(N)-N-methyl-morpholinium, $I^-$ |
| | 27 | n-butyl | Ph— | 7-(N)-N'-methylpiperazine |
| | 28 | n-butyl | Ph— | 7-(N)-N'-dimethylpiperazinium, $I^-$ |
| | 29 | n-butyl | Ph— | 7-NH—CBZ |
| | 30 | n-butyl | Ph— | 7-NHC(O)$C_5H_{11}$ |
| | 31 | n-butyl | Ph— | 7-NHC(O)$CH_2$Br |
| | 32 | n-butyl | Ph— | 7-NH—C(NH)$NH_2$ |
| | 33 | n-butyl | Ph— | 7-(2)-thiophene |
| | 34 | n-butyl | Ph— | 8-methyl |
| | 35 | n-butyl | Ph— | 8-ethyl |
| | 36 | n-butyl | Ph— | 8-iso-propyl |
| | 37 | n-butyl | Ph— | 8-tert-butyl |
| | 38 | n-butyl | Ph— | 8-OH |

TABLE 1-continued

Alternative compounds #3 (Family F101.xxx.yyy)*

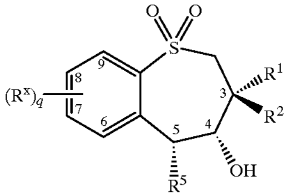

| Prefix (FFF.xxx. | Cpd# yyy) | $R^1$=$R^2$ | $R^5$ | $(R^x)q$ |
|---|---|---|---|---|
| | 39 | n-butyl | Ph— | 8-$OCH_3$ |
| | 40 | n-butyl | Ph— | 8-O-(iso-propyl) |
| | 41 | n-butyl | Ph— | 8-$SCH_3$ |
| | 42 | n-butyl | Ph— | 8-$SOCH_3$ |
| | 43 | n-butyl | Ph— | 8-$SO_2CH_3$ |
| | 44 | n-butyl | Ph— | 8-$SCH_2CH_3$ |
| | 45 | n-butyl | Ph— | 8-$NH_2$ |
| | 46 | n-butyl | Ph— | 8-NHOH |
| | 47 | n-butyl | Ph— | 8-$NHCH_3$ |
| | 48 | n-butyl | Ph— | 8-$N(CH_3)_2$ |
| | 49 | n-butyl | Ph— | 8-$N^+(CH_3)3$, $I^-$ |
| | 50 | n-butyl | Ph— | 8-$NHC(=O)CH_3$ |
| | 51 | n-butyl | Ph— | 8-$N(CH_2CH_3)_2$ |
| | 52 | n-butyl | Ph— | 8-$NMeCH_2CO_2H$ |
| | 53 | n-butyl | Ph— | 8-$N^+(Me)_2CH_2CO_2H$, $I^-$ |
| | 54 | n-butyl | Ph— | 8-(N)-morpholine |
| | 55 | n-butyl | Ph— | 8-(N)-azetidine |
| | 56 | n-butyl | Ph— | 8-(N)-N-methylazetidinium, $I^-$ |
| | 57 | n-butyl | Ph— | 8-(N)-pyrrolidine |
| | 58 | n-butyl | Ph— | 8-(N)-N-methyl-pyrrolidinium, $I^-$ |
| | 59 | n-butyl | Ph— | 8-(N)-N-methyl-morpholinium, $I^-$ |
| | 60 | n-butyl | Ph— | 8-(N)-N'-methylpiperazine |
| | 61 | n-butyl | Ph— | 8-(N)-N'-dimethylpiperazinium, $I^-$ |
| | 62 | n-butyl | Ph— | 8-NH—CBZ |
| | 63 | n-butyl | Ph— | 8-$NHC(O)C_5H_{11}$ |
| | 64 | n-butyl | Ph— | 8-$NHC(O)CH_2Br$ |
| | 65 | n-butyl | Ph— | 8-NH-$C(NH)NH_2$ |
| | 66 | n-butyl | Ph— | 8-(2)-thiophene |
| | 67 | n-butyl | Ph— | 9-methyl |
| | 68 | n-butyl | Ph— | 9-ethyl |
| | 69 | n-butyl | Ph— | 9-iso-propyl |
| | 70 | n-butyl | Ph— | 9-tert-butyl |
| | 71 | n-butyl | Ph— | 9-OH |
| | 72 | n-butyl | Ph— | 9-$OCH_3$ |
| | 73 | n-butyl | Ph— | 9-O(iso-propyl) |
| | 74 | n-butyl | Ph— | 9-$SCH_3$ |
| | 75 | n-butyl | Ph— | 9-$SOCH_3$ |
| | 76 | n-butyl | Ph— | 9-$SO_2CH_3$ |
| | 77 | n-butyl | Ph— | 9-$SCH_2CH_3$ |
| | 78 | n-butyl | Ph— | 9-$NH_2$ |
| | 79 | n-butyl | Ph— | 9-NHOH |
| | 80 | n-butyl | Ph— | 9-$NHCH_3$ |
| | 81 | n-butyl | Ph— | 9-$N(CH_3)_2$ |
| | 82 | n-butyl | Ph— | 9-$N^+(CH_3)_3$, $I^-$ |
| | 83 | n-butyl | Ph— | 9-$NHC(=O)CH_3$ |
| | 84 | n-butyl | Ph— | 9-$N(CH_2CH_3)_2$ |
| | 85 | n-butyl | Ph— | 9-$NMeCH_2CO_2H$ |
| | 86 | n-butyl | Ph— | 9-$N^+(Me)_2CH_2CO_2H$, $I^-$ |
| | 87 | n-butyl | Ph— | 9-(N)-morpholine |
| | 88 | n-butyl | Ph— | 9-(N)-azetidine |
| | 89 | n-butyl | Ph— | 9-(N)-N-methylazetidinium, $I^-$ |
| | 90 | n-butyl | Ph— | 9-(N)-pyrrolidine |
| | 91 | n-butyl | Ph— | 9-(N)-N-methyl-pyrrolidinium, $I^-$ |
| | 92 | n-butyl | Ph— | 9-(N)-N-methyl-morpholinium, $I^-$ |
| | 93 | n-butyl | Ph— | 9-(N)-N'-methylpiperazine |

TABLE 1-continued

Alternative compounds #3 (Family F101.xxx.yyy)*

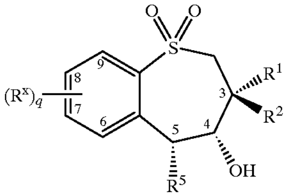

| Prefix (FFF.xxx. | Cpd# yyy) | $R^1$=$R^2$ | $R^5$ | $(R^x)q$ |
|---|---|---|---|---|
| | 94 | n-butyl | Ph— | 9-(N)-N'-dimethylpiperazinium, $I^-$ |
| | 95 | n-butyl | Ph— | 9-NH—CBZ |
| | 96 | n-butyl | Ph— | 9-$NHC(O)C_5H_{11}$ |
| | 97 | n-butyl | Ph— | 9-$NHC(O)CH_2Br$ |
| | 98 | n-butyl | Ph— | 9-NH—$C(NH)NH_2$ |
| | 99 | n-butyl | Ph— | 9-(2)-thiophene |
| | 100 | n-butyl | Ph— | 7-$OCH_3$, 8-$OCH_3$ |
| | 101 | n-butyl | Ph— | 7-$SCH_3$, 8-$OCH_3$ |
| | 102 | n-butyl | Ph— | 7-$SCH_3$, 8-$SCH_3$ |
| | 103 | n-butyl | Ph— | 6-$OCH_3$, 7-$OCH_3$, 8-$OCH_3$ |
| F101.003 | 01 | n-pentyl | Ph— | 7-methyl |
| | 02 | n-pentyl | Ph— | 7-ethyl |
| | 03 | n-pentyl | Ph— | 7-iso-propyl |
| | 04 | n-pentyl | Ph— | 7-tert-butyl |
| | 05 | n-pentyl | Ph— | 7-OH |
| | 06 | n-pentyl | Ph— | 7-$OCH_3$ |
| | 07 | n-pentyl | Ph— | 7-O(iso-propyl) |
| | 08 | n-pentyl | Ph— | 7-$SCH_3$ |
| | 09 | n-pentyl | Ph— | 7-$SOCH_3$ |
| | 10 | n-pentyl | Ph— | 7-$SO_2CH_3$ |
| | 11 | n-pentyl | Ph— | 7-$SCH_2CH_3$ |
| | 12 | n-pentyl | Ph— | 7-$NH_2$ |
| | 13 | n-pentyl | Ph— | 7-NHOH |
| | 14 | n-pentyl | Ph— | 7-$NHCH_3$ |
| | 15 | n-pentyl | Ph— | 7-$N(CH_3)_2$ |
| | 16 | n-pentyl | Ph— | 7-$N^+(CH_3)_3$, $I^-$ |
| | 17 | n-pentyl | Ph— | 7-$NHC(=O)CH_3$ |
| | 18 | n-pentyl | Ph— | 7-$N(CH_2CH_3)_2$ |
| | 19 | n-pentyl | Ph— | 7-$NMeCH_2CO_2H$ |
| | 20 | n-pentyl | Ph— | 7-$N^+(Me)_2CH_2CO_2H$, $I^-$ |
| | 21 | n-pentyl | Ph— | 7-(N)-morpholine |
| | 22 | n-pentyl | Ph— | 7-(N)-azetidine |
| | 23 | n-pentyl | Ph— | 7-(N)-N-methylazetidinium, $I^-$ |
| | 24 | n-pentyl | Ph— | 7-(N)-pyrrolidine |
| | 25 | n-pentyl | Ph— | 7-(N)-N-methyl-pyrrolidinium, $I^-$ |
| | 26 | n-pentyl | Ph— | 7-(N)-N-methyl-morpholinium, $I^-$ |
| | 27 | n-pentyl | Ph— | 7-(N)-N'-methylpiperazine |
| | 28 | n-pentyl | Ph— | 7-(N)-N'-dimethylpiperazinium, $I^-$ |
| | 29 | n-pentyl | Ph— | 7-NH—CBZ |
| | 30 | n-pentyl | Ph— | 7-$NHC(O)C_5H_{11}$ |
| | 31 | n-pentyl | Ph— | 7-$NHC(O)CH_2Br$ |
| | 32 | n-pentyl | Ph— | 7-NH—$C(NH)NH_2$ |
| | 33 | n-pentyl | Ph— | 7-(2)-thiophene |
| | 34 | n-pentyl | Ph— | 8-methyl |
| | 35 | n-pentyl | Ph— | 8-ethyl |
| | 36 | n-pentyl | Ph— | 8-iso-propyl |
| | 37 | n-pentyl | Ph— | 8-tert-butyl |
| | 38 | n-pentyl | Ph— | 8-OH |
| | 39 | n-pentyl | Ph— | 8-$OCH_3$ |
| | 40 | n-pentyl | Ph— | 8-O-(iso-propyl) |
| | 41 | n-pentyl | Ph— | 8-$SCH_3$ |
| | 42 | n-pentyl | Ph— | 8-$SOCH_3$ |
| | 43 | n-pentyl | Ph— | 8-$SO_2CH_3$ |
| | 44 | n-pentyl | Ph— | 8-$SCH_2CH_3$ |
| | 45 | n-pentyl | Ph— | 8-$NH_2$ |
| | 46 | n-pentyl | Ph— | 8-NHOH |
| | 47 | n-pentyl | Ph— | 8-$NHCH_3$ |

TABLE 1-continued

Alternative compounds #3 (Family F101.xxx.yyy)*

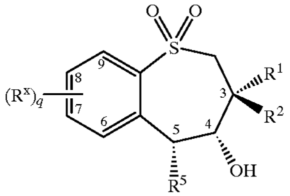

| Prefix (FFF.xxx. | Cpd# yyy) | $R^1$=$R^2$ | $R^5$ | $(R^x)q$ |
|---|---|---|---|---|
| | 48 | n-pentyl | Ph— | 8-$N(CH_3)_2$ |
| | 49 | n-pentyl | Ph— | 8-$N^+(CH_3)_3$, $I^-$ |
| | 50 | n-pentyl | Ph— | 8-NHC(=O)$CH_3$ |
| | 51 | n-pentyl | Ph— | 8-$N(CH_2CH_3)_2$ |
| | 52 | n-pentyl | Ph— | 8-$NMeCH_2CO_2H$ |
| | 53 | n-pentyl | Ph— | 8-$N^+(Me)_2CH_2CO_2H$, $I^-$ |
| | 54 | n-pentyl | Ph— | 8-(N)-morpholine |
| | 55 | n-pentyl | Ph— | 8-(N)-azetidine |
| | 56 | n-pentyl | Ph— | 8-(N)-N-methylazeti-dinium, $I^-$ |
| | 57 | n-pentyl | Ph— | 8-(N)-pyrrolidine |
| | 58 | n-pentyl | Ph— | 8-(N)-N-methyl-pyrroli-dinium, $I^-$ |
| | 59 | n-pentyl | Ph— | 8-(N)-N-methyl-morpho-linium, $I^-$ |
| | 60 | n-pentyl | Ph— | 8-(N)-N'-methylpiper-azine |
| | 61 | n-pentyl | Ph— | 8-(N)-N'-dimethylpiper-azinium, $I^-$ |
| | 62 | n-pentyl | Ph— | 8-NH—CBZ |
| | 63 | n-pentyl | Ph— | 8-NHC(O)$C_5H_{11}$ |
| | 64 | n-pentyl | Ph— | 8-NHC(O)$CH_2Br$ |
| | 65 | n-pentyl | Ph— | 8-NH-C(NH)$NH_2$ |
| | 66 | n-pentyl | Ph— | 8-(2)-thiophene |
| | 67 | n-pentyl | Ph— | 9-methyl |
| | 68 | n-pentyl | Ph— | 9-ethyl |
| | 69 | n-pentyl | Ph— | 9-iso-propyl |
| | 70 | n-pentyl | Ph— | 9-tert-butyl |
| | 71 | n-pentyl | Ph— | 9-OH |
| | 72 | n-pentyl | Ph— | 9-$OCH_3$ |
| | 73 | n-pentyl | Ph— | 9-O(iso-propyl) |
| | 74 | n-pentyl | Ph— | 9-$SCH_3$ |
| | 75 | n-pentyl | Ph— | 9-$SOCH_3$ |
| | 76 | n-pentyl | Ph— | 9-$SO_2CH_3$ |
| | 77 | n-pentyl | Ph— | 9-$SCH_2CH_3$ |
| | 78 | n-pentyl | Ph— | 9-$NH_2$ |
| | 79 | n-pentyl | Ph— | 9-NHOH |
| | 80 | n-pentyl | Ph— | 9-$NHCH_3$ |
| | 81 | n-pentyl | Ph— | 9-$N(CH_3)_2$ |
| | 82 | n-pentyl | Ph— | 9-$N^+(CH_3)_3$, $I^-$ |
| | 83 | n-pentyl | Ph— | 9-NHC(=O)$CH_3$ |
| | 84 | n-pentyl | Ph— | 9-$N(CH_2CH_3)_2$ |
| | 85 | n-pentyl | Ph— | 9-$NMeCH_2CO_2H$ |
| | 86 | n-pentyl | Ph— | 9-$N^+(Me)_2CH_2CO_2H$, $I^-$ |
| | 87 | n-pentyl | Ph— | 9-(N)-morpholine |
| | 88 | n-pentyl | Ph— | 9-(N)-azetidine |
| | 89 | n-pentyl | Ph— | 9-(N)-N-methylazeti-dinium, $I^-$ |
| | 90 | n-pentyl | Ph— | 9-(N)-pyrrolidine |
| | 91 | n-pentyl | Ph— | 9-(N)-N-methyl-pyrroli-dinium, $I^-$ |
| | 92 | n-pentyl | Ph— | 9-(N)-N-methyl-morpho-linium, $I^-$ |
| | 93 | n-pentyl | Ph— | 9-(N)-N'-methylpiper-azine |
| | 93 | n-pentyl | Ph— | 9-(N)-N'-dimethylpiper-azinium, $I^-$ |
| | 95 | n-pentyl | Ph— | 9-NH—CBZ |
| | 96 | n-pentyl | Ph— | 9-NHC(O)$C_5H_{11}$ |
| | 97 | n-pentyl | Ph— | 9-NHC(O)$CH_2Br$ |
| | 98 | n-pentyl | Ph— | 9-NH—C(NH)$NH_2$ |
| | 99 | n-pentyl | Ph— | 9-(2)-thiophene |
| | 100 | n-pentyl | Ph— | 7-$OCH_3$, 8-$OCH_3$ |
| | 101 | n-pentyl | Ph— | 7-$SCH_3$, 8-$OCH_3$ |

TABLE 1-continued

Alternative compounds #3 (Family F101.xxx.yyy)*

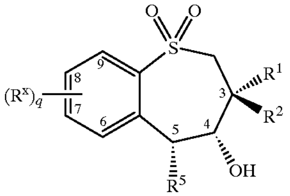

| Prefix (FFF.xxx. | Cpd# yyy) | $R^1$=$R^2$ | $R^5$ | $(R^x)q$ |
|---|---|---|---|---|
| | 102 | n-pentyl | Ph— | 7-$SCH_3$, 8-$SCH_3$ |
| | 103 | n-pentyl | Ph— | 6-$OCH_3$, 7-$OCH_3$, 8-$OCH_3$ |
| F101.004 | 01 | n-hexyl | Ph— | 7-methyl |
| | 02 | n-hexyl | Ph— | 7-ethyl |
| | 03 | n-hexyl | Ph— | 7-iso-propyl |
| | 04 | n-hexyl | Ph— | 7-tert-butyl |
| | 05 | n-hexyl | Ph— | 7-OH |
| | 06 | n-hexyl | Ph— | 7-$OCH_3$ |
| | 07 | n-hexyl | Ph— | 7-O(iso-propyl) |
| | 08 | n-hexyl | Ph— | 7-$SCH_3$ |
| | 09 | n-hexyl | Ph— | 7-$SOCH_3$ |
| | 10 | n-hexyl | Ph— | 7-$SO_2CH_3$ |
| | 11 | n-hexyl | Ph— | 7-$SCH_2CH_3$ |
| | 12 | n-hexyl | Ph— | 7-$NH_2$ |
| | 13 | n-hexyl | Ph— | 7-NHOH |
| | 14 | n-hexyl | Ph— | 7-$NHCH_3$ |
| | 15 | n-hexyl | Ph— | 7-$N(CH_3)_2$ |
| | 16 | n-hexyl | Ph— | 7-$N^+(CH_3)_3$,$I^-$ |
| | 17 | n-hexyl | Ph— | 7-NHC(=O)$CH_3$ |
| | 18 | n-hexyl | Ph— | 7-$N(CH_2CH_3)_2$ |
| | 19 | n-hexyl | Ph— | 7-$NMeCH_2CO_2H$ |
| | 20 | n-hexyl | Ph— | 7-$N^+(Me)_2CH_2CO_2H$, $I^-$ |
| | 21 | n-hexyl | Ph— | 7-(N)-morpholine |
| | 22 | n-hexyl | Ph— | 7-(N)-azetidine |
| | 23 | n-hexyl | Ph— | 7-(N)-N-methylazeti-dinium, $I^-$ |
| | 24 | n-hexyl | Ph— | 7-(N)-pyrrolidine |
| | 25 | n-hexyl | Ph— | 7-(N)-N-methyl-pyrroli-dinium, $I^-$ |
| | 26 | n-hexyl | Ph— | 7-(N)-N-methyl-morpho-linium, $I^-$ |
| | 27 | n-hexyl | Ph— | 7-(N)-N'-methylpiper-azine |
| | 28 | n-hexyl | Ph— | 7-(N)-N'-dimethylpiper-azinium, $I^-$ |
| | 29 | n-hexyl | Ph— | 7-NH—CBZ |
| | 30 | n-hexyl | Ph— | 7-NHC(O)$C_5H_{11}$ |
| | 31 | n-hexyl | Ph— | 7-NHC(O)$CH_2Br$ |
| | 32 | n-hexyl | Ph— | 7-NH—C(NH)$NH_2$ |
| | 33 | n-hexyl | Ph— | 7-(2)-thiophene |
| | 34 | n-hexyl | Ph— | 8-methyl |
| | 35 | n-hexyl | Ph— | 8-ethyl |
| | 36 | n-hexyl | Ph— | 8-iso-propyl |
| | 37 | n-hexyl | Ph— | 8-tert-butyl |
| | 38 | n-hexyl | Ph— | 8-OH |
| | 39 | n-hexyl | Ph— | 8-$OCH_3$ |
| | 40 | n-hexyl | Ph— | 8-O-(iso-propyl) |
| | 41 | n-hexyl | Ph— | 8-$SCH_3$ |
| | 42 | n-hexyl | Ph— | 8-$SOCH_3$ |
| | 43 | n-hexyl | Ph— | 8-$SO_2CH_3$ |
| | 44 | n-hexyl | Ph— | 8-$SCH_2CH_3$ |
| | 45 | n-hexyl | Ph— | 8-$NH_2$ |
| | 46 | n-hexyl | Ph— | 8-NHOH |
| | 47 | n-hexyl | Ph— | 8-$NHCH_3$ |
| | 48 | n-hexyl | Ph— | 8-$N(CH_3)_2$ |
| | 49 | n-hexyl | Ph— | 8-$N^+(CH_3)_3$, $I^-$ |
| | 50 | n-hexyl | Ph— | 8-NHC(=O)$CH_3$ |
| | 51 | n-hexyl | Ph— | 8-$N(CH_2CH_3)_2$ |
| | 52 | n-hexyl | Ph— | 8-$NMeCH_2CO_2H$ |
| | 53 | n-hexyl | Ph— | 8-$N^+(Me)_2CH_2CO_2H$, $I^-$ |
| | 54 | n-hexyl | Ph— | 8-(N)-morpholine |
| | 55 | n-hexyl | Ph— | 8-(N)-azetidine |

TABLE 1-continued

Alternative compounds #3 (Family F101.xxx.yyy)*

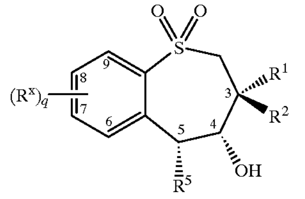

| Prefix (FFF.xxx. | Cpd# yyy) | $R^1$═$R^2$ | $R^5$ | $(R^x)q$ |
|---|---|---|---|---|
| | 56 | n-hexyl | Ph— | 8-(N)-N-methylazeti-dinium, $I^-$ |
| | 57 | n-hexyl | Ph— | 8-(N)-pyrrolidine |
| | 58 | n-hexyl | Ph— | 8-(N)-N-methyl-pyrroli-dinium, $I^-$ |
| | 59 | n-hexyl | Ph— | 8-(N)-N-methyl-morpho-linium, $I^-$ |
| | 60 | n-hexyl | Ph— | 8-(N)-N'-methylpiper-azine |
| | 61 | n-hexyl | Ph— | 8-(N)-N'-dimethylpiper-azinium, $I^-$ |
| | 62 | n-hexyl | Ph— | 8-NH—CBZ |
| | 63 | n-hexyl | Ph— | 8-NHC(O)$C_5H_{11}$ |
| | 64 | n-hexyl | Ph— | 8-NHC(O)$CH_2Br$ |
| | 65 | n-hexyl | Ph— | 8-NH-C(NH)$NH_2$ |
| | 66 | n-hexyl | Ph— | 8-(2)-thiophene |
| | 67 | n-hexyl | Ph— | 9-methyl |
| | 68 | n-hexyl | Ph— | 9-ethyl |
| | 69 | n-hexyl | Ph— | 9-iso-propyl |
| | 70 | n-hexyl | Ph— | 9-tert-butyl |
| | 71 | n-hexyl | Ph— | 9-OH |
| | 72 | n-hexyl | Ph— | 9-$OCH_3$ |
| | 73 | n-hexyl | Ph— | 9-O(iso-propyl) |
| | 74 | n-hexyl | Ph— | 9-$SCH_3$ |
| | 75 | n-hexyl | Ph— | 9-$SOCH_3$ |
| | 76 | n-hexyl | Ph— | 9-$SO_2CH_3$ |
| | 77 | n-hexyl | Ph— | 9-$SCH_2CH_3$ |
| | 78 | n-hexyl | Ph— | 9-$NH_2$ |
| | 79 | n-hexyl | Ph— | 9-NHOH |
| | 80 | n-hexyl | Ph— | 9-$NHCH_3$ |
| | 81 | n-hexyl | Ph— | 9-$N(CH_3)_2$ |
| | 82 | n-hexyl | Ph— | 9-$N^+(CH_3)_3$, $I^-$ |
| | 83 | n-hexyl | Ph— | 9-NHC(═O)$CH_3$ |
| | 84 | n-hexyl | Ph— | 9-$N(CH_2CH_3)_2$ |
| | 85 | n-hexyl | Ph— | 9-$NMeCH_2CO_2H$ |
| | 86 | n-hexyl | Ph— | 9-$N^+(Me)_2CH_2CO_2H$, $I^-$ |
| | 87 | n-hexyl | Ph— | 9-(N)-morpholine |
| | 88 | n-hexyl | Ph— | 9-(N)-azetidine |
| | 89 | n-hexyl | Ph— | 9-(N)-N-methylazeti-dinium, $I^-$ |
| | 90 | n-hexyl | Ph— | 9-(N)-pyrrolidine |
| | 91 | n-hexyl | Ph— | 9-(N)-N-methyl-pyrroli-dinium, $I^-$ |
| | 92 | n-hexyl | Ph— | 9-(N)-N-methyl-morpho-linium, $I^-$ |
| | 93 | n-hexyl | Ph— | 9-(N)-N'-methylpiper-azine |
| | 94 | n-hexyl | Ph— | 9-(N)-N'-dimethylpiper-azinium, $I^-$ |
| | 95 | n-hexyl | Ph— | 9-NH—CBZ |
| | 96 | n-hexyl | Ph— | 9-NHC(O)$C_5H_{11}$ |
| | 97 | n-hexyl | Ph— | 9-NHC(O)$CH_2Br$ |
| | 98 | n-hexyl | Ph— | 9-NH—C(NH)$NH_2$ |
| | 99 | n-hexyl | Ph— | 9-(2)-thiophene |
| | 100 | n-hexyl | Ph— | 7-$OCH_3$, 8-$OCH_3$ |
| | 101 | n-hexyl | Ph— | 7-$SCH_3$, 8-$OCH_3$ |
| | 102 | n-hexyl | Ph— | 7-$SCH_3$, 8-$SCH_3$ |
| | 103 | n-hexyl | Ph— | 6-$OCH_3$, 7-$OCH_3$, 8-$OCH_3$ |
| F101.005 | 01 | iso-propyl | Ph— | 7-methyl |
| | 02 | iso-propyl | Ph— | 7-ethyl |
| | 03 | iso-propyl | Ph— | 7-iso-propyl |
| | 04 | iso-propyl | Ph— | 7-tert-butyl |
| | 05 | iso-propyl | Ph— | 7-OH |

TABLE 1-continued

Alternative compounds #3 (Family F101.xxx.yyy)*

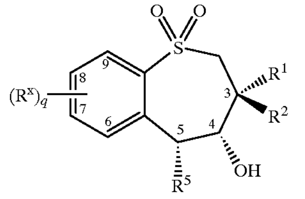

| Prefix (FFF.xxx. | Cpd# yyy) | $R^1$═$R^2$ | $R^5$ | $(R^x)q$ |
|---|---|---|---|---|
| | 06 | iso-propyl | Ph— | 7-$OCH_3$ |
| | 07 | iso-propyl | Ph— | 7-O(iso-propyl) |
| | 08 | iso-propyl | Ph— | 7-$SCH_3$ |
| | 09 | iso-propyl | Ph— | 7-$SOCH_3$ |
| | 10 | iso-propyl | Ph— | 7-$SO_2CH_3$ |
| | 11 | iso-propyl | Ph— | 7-$SCH_2CH_3$ |
| | 12 | iso-propyl | Ph— | 7-$NH_2$ |
| | 13 | iso-propyl | Ph— | 7-NHOH |
| | 14 | iso-propyl | Ph— | 7-$NHCH_3$ |
| | 15 | iso-propyl | Ph— | 7-$N(CH_3)_2$ |
| | 16 | iso-propyl | Ph— | 7-$N^+(CH_3)_3$, $I^-$ |
| | 17 | iso-propyl | Ph— | 7-NHC(═O)$CH_3$ |
| | 18 | iso-propyl | Ph— | 7-$N(CH_2CH_3)_2$ |
| | 19 | iso-propyl | Ph— | 7-$NMeCH_2CO_2H$ |
| | 20 | iso-propyl | Ph— | 7-$N^+(Me)_2CH_2CO_2H$, $I^-$ |
| | 21 | iso-propyl | Ph— | 7-(N)-morpholine |
| | 22 | iso-propyl | Ph— | 7-(N)-azetidine |
| | 23 | iso-propyl | Ph— | 7-(N)-N-methylazeti-dinium, $I^-$ |
| | 24 | iso-propyl | Ph— | 7-(N)-pyrrolidine |
| | 25 | iso-propyl | Ph— | 7-(N)-N-methyl-pyrroli-dinium, $I^-$ |
| | 26 | iso-propyl | Ph— | 7-(N)-N-methyl-morpho-linium, $I^-$ |
| | 27 | iso-propyl | Ph— | 7-(N)-N'-methylpiper-azine |
| | 28 | iso-propyl | Ph— | 7-(N)-N'-dimethylpiper-azinium, $I^-$ |
| | 29 | iso-propyl | Ph— | 7-NH—CBZ |
| | 30 | iso-propyl | Ph— | 7-NHC(O)$C_5H_{11}$ |
| | 31 | iso-propyl | Ph— | 7-NHC(O)$CH_2Br$ |
| | 32 | iso-propyl | Ph— | 7-NH—C(NH)$NH_2$ |
| | 33 | iso-propyl | Ph— | 7-(2)-thiophene |
| | 34 | iso-propyl | Ph— | 8-methyl |
| | 35 | iso-propyl | Ph— | 8-ethyl |
| | 36 | iso-propyl | Ph— | 8-iso-propyl |
| | 37 | iso-propyl | Ph— | 8-tert-butyl |
| | 38 | iso-propyl | Ph— | 8-OH |
| | 39 | iso-propyl | Ph— | 8-$OCH_3$ |
| | 40 | iso-propyl | Ph— | 8-O-(iso-propyl) |
| | 41 | iso-propyl | Ph— | 8-$SCH_3$ |
| | 42 | iso-propyl | Ph— | 8-$SOCH_3$ |
| | 43 | iso-propyl | Ph— | 8-$SO_2CH_3$ |
| | 44 | iso-propyl | Ph— | 8-$SCH_2CH_3$ |
| | 45 | iso-propyl | Ph— | 8-$NH_2$ |
| | 46 | iso-propyl | Ph— | 8-NHOH |
| | 47 | iso-propyl | Ph— | 8-$NHCH_3$ |
| | 48 | iso-propyl | Ph— | 8-$N(CH_3)_2$ |
| | 49 | iso-propyl | Ph— | 8-$N^+(CH_3)_3$, $I^-$ |
| | 50 | iso-propyl | Ph— | 8-NHC(═O)$CH_3$ |
| | 51 | iso-propyl | Ph— | 8-$N(CH_2CH_3)_2$ |
| | 52 | iso-propyl | Ph— | 8-$NMeCH_2CO_2H$ |
| | 53 | iso-propyl | Ph— | 8-$N^+(Me)_2CH_2CO_2H$, $I^-$ |
| | 54 | iso-propyl | Ph— | 8-(N)-morpholine |
| | 55 | iso-propyl | Ph— | 8-(N)-azetidine |
| | 56 | iso-propyl | Ph— | 8-(N)-N-methylazeti-dinium, $I^-$ |
| | 57 | iso-propyl | Ph— | 8-(N)-pyrrolidine |
| | 58 | iso-propyl | Ph— | 8-(N)-N-methyl-pyrroli-dinium, $I^-$ |
| | 59 | iso-propyl | Ph— | 8-(N)-N-methyl-morpho-linium, $I^-$ |
| | 60 | iso-propyl | Ph— | 8-(N)-N'-methylpiper-azine |

TABLE 1-continued

Alternative compounds #3 (Family F101.xxx.yyy)*

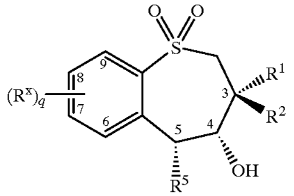

| Prefix (FFF.xxx. | Cpd# yyy) | $R^1$=$R^2$ | $R^5$ | $(R^x)q$ |
|---|---|---|---|---|
| | 61 | iso-propyl | Ph— | 8-(N)-N'-dimethylpiper-azinium, $I^-$ |
| | 62 | iso-propyl | Ph— | 8-NH—CBZ |
| | 63 | iso-propyl | Ph— | $8\text{-}NHC(O)C_5H_{11}$ |
| | 64 | iso-propyl | Ph— | $8\text{-}NHC(O)CH_2Br$ |
| | 65 | iso-propyl | Ph— | $8\text{-}NH\text{-}C(NH)NH_2$ |
| | 66 | iso-propyl | Ph— | 8-(2)-thiophene |
| | 67 | iso-propyl | Ph— | 9-methyl |
| | 68 | iso-propyl | Ph— | 9-ethyl |
| | 69 | iso-propyl | Ph— | 9-iso-propyl |
| | 70 | iso-propyl | Ph— | 9-tert-butyl |
| | 71 | iso-propyl | Ph— | 9-OH |
| | 72 | iso-propyl | Ph— | $9\text{-}OCH_3$ |
| | 73 | iso-propyl | Ph— | 9-O(iso-propyl) |
| | 74 | iso-propyl | Ph— | $9\text{-}SCH_3$ |
| | 75 | iso-propyl | Ph— | $9\text{-}SOCH_3$ |
| | 76 | iso-propyl | Ph— | $9\text{-}SO_2CH_3$ |
| | 77 | iso-propyl | Ph— | $9\text{-}SCH_2CH_3$ |
| | 78 | iso-propyl | Ph— | $9\text{-}NH_2$ |
| | 79 | iso-propyl | Ph— | 9-NHOH |
| | 80 | iso-propyl | Ph— | $9\text{-}NHCH_3$ |
| | 81 | iso-propyl | Ph— | $9\text{-}N(CH_3)_2$ |
| | 82 | iso-propyl | Ph— | $9\text{-}N^+(CH_3)_3$, $I^-$ |
| | 83 | iso-propyl | Ph— | $9\text{-}NHC(=O)CH_3$ |
| | 84 | iso-propyl | Ph— | $9\text{-}N(CH_2CH_3)_2$ |
| | 85 | iso-propyl | Ph— | $9\text{-}NMeCH_2CO_2H$ |
| | 86 | iso-propyl | Ph— | $9\text{-}N^+(Me)_2CH_2CO_2H$, $I^-$ |
| | 87 | iso-propyl | Ph— | 9-(N)-morpholine |
| | 88 | iso-propyl | Ph— | 9-(N)-azetidine |
| | 89 | iso-propyl | Ph— | 9-(N)-N-methylazeti-dinium, $I^-$ |
| | 90 | iso-propyl | Ph— | 9-(N)-pyrrolidine |
| | 91 | iso-propyl | Ph— | 9-(N)-N-methyl-pyrroli-dinium, $I^-$ |
| | 92 | iso-propyl | Ph— | 9-(N)-N-methyl-morpho-linium, $I^-$ |
| | 93 | iso-propyl | Ph— | 9-(N)-N'-methylpiper-azine |
| | 94 | iso-propyl | Ph— | 9-(N)-N'-dimethylpiper-azinium, $I^-$ |
| | 95 | iso-propyl | Ph— | 9-NH—CBZ |
| | 96 | iso-propyl | Ph— | $9\text{-}NHC(O)C_5H_{11}$ |
| | 97 | iso-propyl | Ph— | $9\text{-}NHC(O)CH_2Br$ |
| | 98 | iso-propyl | Ph— | $9\text{-}NH\text{—}C(NH)NH_2$ |
| | 99 | iso-propyl | Ph— | 9-(2)-thiophene |
| | 100 | iso-propyl | Ph— | $7\text{-}OCH_3$, $8\text{-}OCH_3$ |
| | 101 | iso-propyl | Ph— | $7\text{-}SCH_3$, $8\text{-}OCH_3$ |
| | 102 | iso-propyl | Ph— | $7\text{-}SCH_3$, $8\text{-}SCH_3$ |
| | 103 | iso-propyl | Ph— | $6\text{-}OCH_3$, $7\text{-}OCH_3$, $8\text{-}OCH_3$ |
| F101.006 | 01 | iso-butyl | Ph— | 7-methyl |
| | 02 | iso-butyl | Ph— | 7-ethyl |
| | 03 | iso-butyl | Ph— | 7-iso-butyl |
| | 04 | iso-butyl | Ph— | 7-tert-butyl |
| | 05 | iso-butyl | Ph— | 7-OH |
| | 06 | iso-butyl | Ph— | $7\text{-}OCH_3$ |
| | 07 | iso-butyl | Ph— | 7-O(iso-propyl) |
| | 08 | iso-butyl | Ph— | $7\text{-}SCH_3$ |
| | 09 | iso-butyl | Ph— | $7\text{-}SOCH_3$ |
| | 10 | iso-butyl | Ph— | $7\text{-}SO_2CH_3$ |
| | 11 | iso-butyl | Ph— | $7\text{-}SCH_2CH_3$ |
| | 12 | iso-butyl | Ph— | $7\text{-}NH_2$ |
| | 13 | iso-butyl | Ph— | 7-NHOH |
| | 14 | iso-butyl | Ph— | $7\text{-}NHCH_3$ |

TABLE 1-continued

Alternative compounds #3 (Family F101.xxx.yyy)*

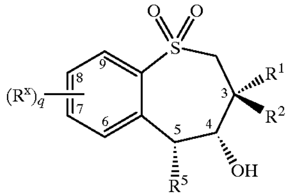

| Prefix (FFF.xxx. | Cpd# yyy) | $R^1$=$R^2$ | $R^5$ | $(R^x)q$ |
|---|---|---|---|---|
| | 15 | iso-butyl | Ph— | $7\text{-}N(CH_3)_2$ |
| | 16 | iso-butyl | Ph— | $7\text{-}N^+(CH_3)_3$, $I^-$ |
| | 17 | iso-butyl | Ph— | $7\text{-}NHC(=O)CH_3$ |
| | 18 | iso-butyl | Ph— | $7\text{-}N(CH_2CH_3)_2$ |
| | 19 | iso-butyl | Ph— | $7\text{-}NMeCH_2CO_2H$ |
| | 20 | iso-butyl | Ph— | $7\text{-}N^+(Me)_2CH_2CO_2H$, $I^-$ |
| | 21 | iso-butyl | Ph— | 7-(N)-morpholine |
| | 22 | iso-butyl | Ph— | 7-(N)-azetidine |
| | 23 | iso-butyl | Ph— | 7-(N)-N-methylazeti-dinium, $I^-$ |
| | 24 | iso-butyl | Ph— | 7-(N)-pyrrolidine |
| | 25 | iso-butyl | Ph— | 7-(N)-N-methyl-pyrroli-dinium, $I^-$ |
| | 26 | iso-butyl | Ph— | 7-(N)-N-methyl-morpho-linium, $I^-$ |
| | 27 | iso-butyl | Ph— | 7-(N)-N'-methylpiper-azine |
| | 28 | iso-butyl | Ph— | 7-(N)-N'-dimethylpiper-azinium, $I^-$ |
| | 29 | iso-butyl | Ph— | 7-NH—CBZ |
| | 30 | iso-butyl | Ph— | $7\text{-}NHC(O)C_5H_{11}$ |
| | 31 | iso-butyl | Ph— | $7\text{-}NHC(O)CH_2Br$ |
| | 32 | iso-butyl | Ph— | $7\text{-}NH\text{—}C(NH)NH_2$ |
| | 33 | iso-butyl | Ph— | 7-(2)-thiophene |
| | 34 | iso-butyl | Ph— | 8-methyl |
| | 35 | iso-butyl | Ph— | 8-ethyl |
| | 36 | iso-butyl | Ph— | 8-iso-propyl |
| | 37 | iso-butyl | Ph— | 8-tert-butyl |
| | 38 | iso-butyl | Ph— | 8-OH |
| | 39 | iso-butyl | Ph— | $8\text{-}OCH_3$ |
| | 40 | iso-butyl | Ph— | 8-O-(iso-propyl) |
| | 41 | iso-butyl | Ph— | $8\text{-}SCH_3$ |
| | 42 | iso-butyl | Ph— | $8\text{-}SOCH_3$ |
| | 43 | iso-butyl | Ph— | $8\text{-}SO_2CH_3$ |
| | 44 | iso-butyl | Ph— | $8\text{-}SCH_2CH_3$ |
| | 45 | iso-butyl | Ph— | $8\text{-}NH_2$ |
| | 46 | iso-butyl | Ph— | 8-NHOH |
| | 47 | iso-butyl | Ph— | $8\text{-}NHCH_3$ |
| | 48 | iso-butyl | Ph— | $8\text{-}N(CH_3)_2$ |
| | 49 | iso-butyl | Ph— | $8\text{-}N^+(CH_3)_3$, $I^-$ |
| | 50 | iso-butyl | Ph— | $8\text{-}NHC(=O)CH_3$ |
| | 51 | iso-butyl | Ph— | $8\text{-}N(CH_2CH_3)_2$ |
| | 52 | iso-butyl | Ph— | $8\text{-}NMeCH_2CO_2H$ |
| | 53 | iso-butyl | Ph— | $8\text{-}N^+(Me)_2CH_2CO_2H$, $I^-$ |
| | 54 | iso-butyl | Ph— | 8-(N)-morpholine |
| | 55 | iso-butyl | Ph— | 8-(N)-azetidine |
| | 56 | iso-butyl | Ph— | 8-(N)-N-methylazeti-dinium, $I^-$ |
| | 57 | iso-butyl | Ph— | 8-(N)-pyrrolidine |
| | 58 | iso-butyl | Ph— | 8-(N)-N-methyl-pyrroli-dinium, $I^-$ |
| | 59 | iso-butyl | Ph— | 8-(N)-N-methyl-morpho-linium, $I^-$ |
| | 60 | iso-butyl | Ph— | 8-(N)-N'-methylpiper-azine |
| | 61 | iso-butyl | Ph— | 8-(N)-N'-dimethylpiper-azinium, $I^-$ |
| | 62 | iso-butyl | Ph— | 8-NH—CBZ |
| | 63 | iso-butyl | Ph— | $8\text{-}NHC(O)C_5H_{11}$ |
| | 64 | iso-butyl | Ph— | $8\text{-}NHC(O)CH_2Br$ |
| | 65 | iso-butyl | Ph— | $8\text{-}NH\text{-}C(NH)NH_2$ |
| | 66 | iso-butyl | Ph— | 8-(2)-thiophene |
| | 67 | iso-butyl | Ph— | 9-methyl |
| | 68 | iso-butyl | Ph— | 9-ethyl |

TABLE 1-continued

Alternative compounds #3 (Family F101.xxx.yyy)*

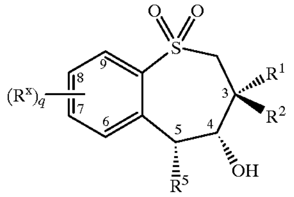

| Prefix (FFF.xxx. | Cpd# yyy) | $R^1$=$R^2$ | $R^5$ | $(R^x)q$ |
|---|---|---|---|---|
| | 69 | iso-butyl | Ph— | 9-iso-propyl |
| | 70 | iso-butyl | Ph— | 9-tert-butyl |
| | 71 | iso-butyl | Ph— | 9-OH |
| | 72 | iso-butyl | Ph— | 9-$OCH_3$ |
| | 73 | iso-butyl | Ph— | 9-O(iso-propyl) |
| | 74 | iso-butyl | Ph— | 9-$SCH_3$ |
| | 75 | iso-butyl | Ph— | 9-$SOCH_3$ |
| | 76 | iso-butyl | Ph— | 9-$SO_2CH_3$ |
| | 77 | iso-butyl | Ph— | 9-$SCH_2CH_3$ |
| | 78 | iso-butyl | Ph— | 9-$NH_2$ |
| | 79 | iso-butyl | Ph— | 9-NHOH |
| | 80 | iso-butyl | Ph— | 9-$NHCH_3$ |
| | 81 | iso-butyl | Ph— | 9-$N(CH_3)_2$ |
| | 82 | iso-butyl | Ph— | 9-$N^+(CH_3)_3$, $I^-$ |
| | 83 | iso-butyl | Ph— | 9-NHC(=O)$CH_3$ |
| | 84 | iso-butyl | Ph— | 9-$N(CH_2CH_3)_2$ |
| | 85 | iso-butyl | Ph— | 9-$NMeCH_2CO_2H$ |
| | 86 | iso-butyl | Ph— | 9-$N^+(Me)_2CH_2CO_2H$, $I^-$ |
| | 87 | iso-butyl | Ph— | 9-(N)-morpholine |
| | 88 | iso-butyl | Ph— | 9-(N)-azetidine |
| | 89 | iso-butyl | Ph— | 9-(N)-N-methylazetidinium, $I^-$ |
| | 90 | iso-butyl | Ph— | 9-(N)-pyrrolidine |
| | 91 | iso-butyl | Ph— | 9-(N)-N-methyl-pyrrolidinium, $I^-$ |
| | 92 | iso-butyl | Ph— | 9-(N)-N-methyl-morpholinium, $I^-$ |
| | 93 | iso-butyl | Ph— | 9-(N)-N'-methylpiperazine |
| | 94 | iso-butyl | Ph— | 9-(N)-N'-dimethylpiperazinium, $I^-$ |
| | 95 | iso-butyl | Ph— | 9-NH—CBZ |
| | 96 | iso-butyl | Ph— | 9-NHC(O)$C_5H_{11}$ |
| | 97 | iso-butyl | Ph— | 9-NHC(O)$CH_2Br$ |
| | 98 | iso-butyl | Ph— | 9-NH—C(NH)$NH_2$ |
| | 99 | iso-butyl | Ph— | 9-(2)-thiophene |
| | 100 | iso-butyl | Ph— | 7-$OCH_3$, 8-$OCH_3$ |
| | 101 | iso-butyl | Ph— | 7-$SCH_3$, 8-$OCH_3$ |
| | 102 | iso-butyl | Ph— | 7-$SCH_3$, 8-$SCH_3$ |
| | 103 | iso-butyl | Ph— | 6-$OCH_3$, 7-$OCH_3$, 8-$OCH_3$ |
| F101.007 | 01 | iso-pentyl | Ph— | 7-methyl |
| | 02 | iso-pentyl | Ph— | 7-ethyl |
| | 03 | iso-pentyl | Ph— | 7-iso-propyl |
| | 04 | iso-pentyl | Ph— | 7-tert-butyl |
| | 05 | iso-pentyl | Ph— | 7-OH |
| | 06 | iso-pentyl | Ph— | 7-$OCH_3$ |
| | 07 | iso-pentyl | Ph— | 7-O(iso-propyl) |
| | 08 | iso-pentyl | Ph— | 7-$SCH_3$ |
| | 09 | iso-pentyl | Ph— | 7-$SOCH_3$ |
| | 10 | iso-pentyl | Ph— | 7-$SO_2CH_3$ |
| | 11 | iso-pentyl | Ph— | 7-$SCH_2CH_3$ |
| | 12 | iso-pentyl | Ph— | 7-$NH_2$ |
| | 13 | iso-pentyl | Ph— | 7-NHOH |
| | 14 | iso-pentyl | Ph— | 7-$NHCH_3$ |
| | 15 | iso-pentyl | Ph— | 7-$N(CH_3)_2$ |
| | 16 | iso-pentyl | Ph— | 7-$N^+(CH_3)_3$, $I^-$ |
| | 17 | iso-pentyl | Ph— | 7-NHC(=O)$CH_3$ |
| | 18 | iso-pentyl | Ph— | 7-$N(CH_2CH_3)_2$ |
| | 19 | iso-pentyl | Ph— | 7-$NMeCH_2CO_2H$ |
| | 20 | iso-pentyl | Ph— | 7-$N^+(Me)_2CH_2CO_2H$, $I^-$ |
| | 21 | iso-pentyl | Ph— | 7-(N)-morpholine |
| | 22 | iso-pentyl | Ph— | 7-(N)-azetidine |

TABLE 1-continued

Alternative compounds #3 (Family F101.xxx.yyy)*

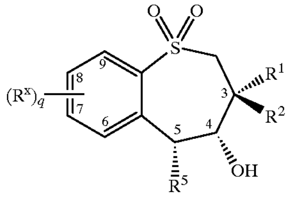

| Prefix (FFF.xxx. | Cpd# yyy) | $R^1$=$R^2$ | $R^5$ | $(R^x)q$ |
|---|---|---|---|---|
| | 23 | iso-pentyl | Ph— | 7-(N)-N-methylazetidinium, $I^-$ |
| | 24 | iso-pentyl | Ph— | 7-(N)-pyrrolidine |
| | 25 | iso-pentyl | Ph— | 7-(N)-N-methyl-pyrrolidinium, $I^-$ |
| | 26 | iso-pentyl | Ph— | 7-(N)-N-methyl-morpholinium, $I^-$ |
| | 27 | iso-pentyl | Ph— | 7-(N)-N'-methylpiperazine |
| | 28 | iso-pentyl | Ph— | 7-(N)-N'-dimethylpiperazinium, $I^-$ |
| | 29 | iso-pentyl | Ph— | 7-NH—CBZ |
| | 30 | iso-pentyl | Ph— | 7-NHC(O)$C_5H_{11}$ |
| | 31 | iso-pentyl | Ph— | 7-NHC(O)$CH_2Br$ |
| | 32 | iso-pentyl | Ph— | 7-NH—C(NH)$NH_2$ |
| | 33 | iso-pentyl | Ph— | 7-(2)-thiophene |
| | 34 | iso-pentyl | Ph— | 8-methyl |
| | 35 | iso-pentyl | Ph— | 8-ethyl |
| | 36 | iso-pentyl | Ph— | 8-iso-propyl |
| | 37 | iso-pentyl | Ph— | 8-tert-butyl |
| | 38 | iso-pentyl | Ph— | 8-OH |
| | 39 | iso-pentyl | Ph— | 8-$OCH_3$ |
| | 40 | iso-pentyl | Ph— | 8-O-(iso-propyl) |
| | 41 | iso-pentyl | Ph— | 8-$SCH_3$ |
| | 42 | iso-pentyl | Ph— | 8-$SOCH_3$ |
| | 43 | iso-pentyl | Ph— | 8-$SO_2CH_3$ |
| | 44 | iso-pentyl | Ph— | 8-$SCH_2CH_3$ |
| | 45 | iso-pentyl | Ph— | 8-$NH_2$ |
| | 46 | iso-pentyl | Ph— | 8-NHOH |
| | 47 | iso-pentyl | Ph— | 8-$NHCH_3$ |
| | 48 | iso-pentyl | Ph— | 8-$N(CH_3)_2$ |
| | 49 | iso-pentyl | Ph— | 8-$N^+(CH_3)_3$, $I^-$ |
| | 50 | iso-pentyl | Ph— | 8-NHC(=O)$CH_3$ |
| | 51 | iso-pentyl | Ph— | 8-$N(CH_2CH_3)_2$ |
| | 52 | iso-pentyl | Ph— | 8-$NMeCH_2CO_2H$ |
| | 53 | iso-pentyl | Ph— | 8-$N^+(Me)_2CH_2CO_2H$, $I^-$ |
| | 54 | iso-pentyl | Ph— | 8-(N)-morpholine |
| | 55 | iso-pentyl | Ph— | 8-(N)-azetidine |
| | 56 | iso-pentyl | Ph— | 8-(N)-N-methylazetidinium, $I^-$ |
| | 57 | iso-pentyl | Ph— | 8-(N)-pyrrolidine |
| | 58 | iso-pentyl | Ph— | 8-(N)-N-methyl-pyrrolidinium, $I^-$ |
| | 59 | iso-pentyl | Ph— | 8-(N)-N-methyl-morpholinium, $I^-$ |
| | 60 | iso-pentyl | Ph— | 8-(N)-N'-methylpiperazine |
| | 61 | iso-pentyl | Ph— | 8-(N)-N'-dimethylpiperazinium, $I^-$ |
| | 62 | iso-pentyl | Ph— | 8-NH—CBZ |
| | 63 | iso-pentyl | Ph— | 8-NHC(O)$C_5H_{11}$ |
| | 64 | iso-pentyl | Ph— | 8-NHC(O)$CH_2Br$ |
| | 65 | iso-pentyl | Ph— | 8-NH-C(NH)$NH_2$ |
| | 66 | iso-pentyl | Ph— | 8-(2)-thiophene |
| | 67 | iso-pentyl | Ph— | 9-methyl |
| | 68 | iso-pentyl | Ph— | 9-ethyl |
| | 69 | iso-pentyl | Ph— | 9-iso-propyl |
| | 70 | iso-pentyl | Ph— | 9-tert-butyl |
| | 71 | iso-pentyl | Ph— | 9-OH |
| | 72 | iso-pentyl | Ph— | 9-$OCH_3$ |
| | 73 | iso-pentyl | Ph— | 9-O(iso-propyl) |
| | 74 | iso-pentyl | Ph— | 9-$SCH_3$ |
| | 75 | iso-pentyl | Ph— | 9-$SOCH_3$ |
| | 76 | iso-pentyl | Ph— | 9-$SO_2CH_3$ |

TABLE 1-continued

Alternative compounds #3 (Family F101.xxx.yyy)*

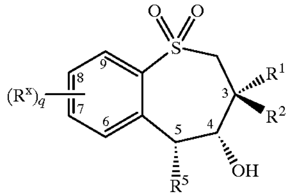

| Prefix (FFF.xxx. | Cpd# yyy) | $R^1$=$R^2$ | $R^5$ | $(R^x)q$ |
|---|---|---|---|---|
| | 77 | iso-pentyl | Ph— | 9-$SCH_2CH_3$ |
| | 78 | iso-pentyl | Ph— | 9-$NH_2$ |
| | 79 | iso-pentyl | Ph— | 9-NHOH |
| | 80 | iso-pentyl | Ph— | 9-$NHCH_3$ |
| | 81 | iso-pentyl | Ph— | 9-$N(CH_3)_2$ |
| | 82 | iso-pentyl | Ph— | 9-$N^+(CH_3)_3$, $I^-$ |
| | 83 | iso-pentyl | Ph— | 9-$NHC(=O)CH_3$ |
| | 84 | iso-pentyl | Ph— | 9-$N(CH_2CH_3)_2$ |
| | 85 | iso-pentyl | Ph— | 9-$NMeCH_2CO_2H$ |
| | 86 | iso-pentyl | Ph— | 9-$N^+(Me)_2CH_2CO_2H$, $I^-$ |
| | 87 | iso-pentyl | Ph— | 9-(N)-morpholine |
| | 88 | iso-pentyl | Ph— | 9-(N)-azetidine |
| | 89 | iso-pentyl | Ph— | 9-(N)-N-methylazeti-dinium, $I^-$ |
| | 90 | iso-pentyl | Ph— | 9-(N)-pyrrolidine |
| | 91 | iso-pentyl | Ph— | 9-(N)-N-methyl-pyrroli-dinium, $I^-$ |
| | 92 | iso-pentyl | Ph— | 9-(N)-N-methyl-morpho-linium, $I^-$ |
| | 93 | iso-pentyl | Ph— | 9-(N)-N'-methylpiper-azine |
| | 94 | iso-pentyl | Ph— | 9-(N)-N'-dimethylpiper-azinium, $I^-$ |
| | 95 | iso-pentyl | Ph— | 9-NH—CBZ |
| | 96 | iso-pentyl | Ph— | 9-$NHC(O)C_5H_{11}$ |
| | 97 | iso-pentyl | Ph— | 9-$NHC(O)CH_2Br$ |
| | 98 | iso-pentyl | Ph— | 9-NH—C(NH)$NH_2$ |
| | 99 | iso-pentyl | Ph— | 9-(2)-thiophene |
| | 100 | iso-pentyl | Ph— | 7-$OCH_3$, 8-$OCH_3$ |
| | 101 | iso-pentyl | Ph— | 7-$SCH_3$, 8-$OCH_3$ |
| | 102 | iso-pentyl | Ph— | 7-$SCH_3$, 8-$SCH_3$ |
| | 103 | iso-pentyl | Ph— | 6-$OCH_3$, 7-$OCH_3$, 8-$OCH_3$ |
| F101.008 | 01 | $CH_2C(=O)C_2H_5$ | Ph— | 7-methyl |
| | 02 | $CH_2C(=O)C_2H_5$ | Ph— | 7-ethyl |
| | 03 | $CH_2C(=O)C_2H_5$ | Ph— | 7-iso-propyl |
| | 04 | $CH_2C(=O)C_2H_5$ | Ph— | 7-tert-butyl |
| | 05 | $CH_2C(=O)C_2H_5$ | Ph— | 7-OH |
| | 06 | $CH_2C(=O)C_2H_5$ | Ph— | 7-$OCH_3$ |
| | 07 | $CH_2C(=O)C_2H_5$ | Ph— | 7-O(iso-propyl) |
| | 08 | $CH_2C(=O)C_2H_5$ | Ph— | 7-$SCH_3$ |
| | 09 | $CH_2C(=O)C_2H_5$ | Ph— | 7-$SOCH_3$ |
| | 10 | $CH_2C(=O)C_2H_5$ | Ph— | 7-$SO_2CH_3$ |
| | 11 | $CH_2C(=O)C_2H_5$ | Ph— | 7-$SCH_2CH_3$ |
| | 12 | $CH_2C(=O)C_2H_5$ | Ph— | 7-$NH_2$ |
| | 13 | $CH_2C(=O)C_2H_5$ | Ph— | 7-NHOH |
| | 14 | $CH_2C(=O)C_2H_5$ | Ph— | 7-$NHCH_3$ |
| | 15 | $CH_2C(=O)C_2H_5$ | Ph— | 7-$N(CH_3)_2$ |
| | 16 | $CH_2C(=O)C_2H_5$ | Ph— | 7-$N^+(CH_3)_3$, $I^-$ |
| | 17 | $CH_2C(=O)C_2H_5$ | Ph— | 7-$NHC(=O)CH_3$ |
| | 18 | $CH_2C(=O)C_2H_5$ | Ph— | 7-$N(CH_2CH_3)_2$ |
| | 19 | $CH_2C(=O)C_2H_5$ | Ph— | 7-$NMeCH_2CO_2H$ |
| | 20 | $CH_2C(=O)C_2H_5$ | Ph— | 7-$N^+(Me)_2CH_2CO_2H$, $I^-$ |
| | 21 | $CH_2C(=O)C_2H_5$ | Ph— | 7-(N)-morpholine |
| | 22 | $CH_2C(=O)C_2H_5$ | Ph— | 7-(N)-azetidine |
| | 23 | $CH_2C(=O)C_2H_5$ | Ph— | 7-(N)-N-methylazeti-dinium, $I^-$ |
| | 24 | $CH_2C(=O)C_2H_5$ | Ph— | 7-(N)-pyrrolidine |
| | 25 | $CH_2C(=O)C_2H_5$ | Ph— | 7-(N)-N-methyl-pyrroli-dinium, $I^-$ |
| | 26 | $CH_2C(=O)C_2H_5$ | Ph— | 7-(N)-N-methyl-morpho-linium, $I^-$ |
| | 27 | $CH_2C(=O)C_2H_5$ | Ph— | 7-(N)-N'-methylpiper-azine |

TABLE 1-continued

Alternative compounds #3 (Family F101.xxx.yyy)*

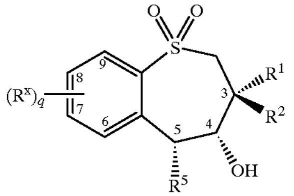

| Prefix (FFF.xxx. | Cpd# yyy) | $R^1$=$R^2$ | $R^5$ | $(R^x)q$ |
|---|---|---|---|---|
| | 28 | $CH_2C(=O)C_2H_5$ | Ph— | 7-(N)-N'-dimethylpiper-azinium, $I^-$ |
| | 29 | $CH_2C(=O)C_2H_5$ | Ph— | 7-NH—CBZ |
| | 30 | $CH_2C(=O)C_2H_5$ | Ph— | 7-$NHC(O)C_5H_{11}$ |
| | 31 | $CH_2C(=O)C_2H_5$ | Ph— | 7-$NHC(O)CH_2Br$ |
| | 32 | $CH_2C(=O)C_2H_5$ | Ph— | 7-NH—C(NH)$NH_2$ |
| | 33 | $CH_2C(=O)C_2H_5$ | Ph— | 7-(2)-thiophene |
| | 34 | $CH_2C(=O)C_2H_5$ | Ph— | 8-methyl |
| | 35 | $CH_2C(=O)C_2H_5$ | Ph— | 8-ethyl |
| | 36 | $CH_2C(=O)C_2H_5$ | Ph— | 8-iso-propyl |
| | 37 | $CH_2C(=O)C_2H_5$ | Ph— | 8-tert-butyl |
| | 38 | $CH_2C(=O)C_2H_5$ | Ph— | 8-OH |
| | 39 | $CH_2C(=O)C_2H_5$ | Ph— | 8-$OCH_3$ |
| | 40 | $CH_2C(=O)C_2H_5$ | Ph— | 8-O-(iso-propyl) |
| | 41 | $CH_2C(=O)C_2H_5$ | Ph— | 8-$SCH_3$ |
| | 42 | $CH_2C(=O)C_2H_5$ | Ph— | 8-$SOCH_3$ |
| | 43 | $CH_2C(=O)C_2H_5$ | Ph— | 8-$SO_2CH_3$ |
| | 44 | $CH_2C(=O)C_2H_5$ | Ph— | 8-$SCH_2CH_3$ |
| | 45 | $CH_2C(=O)C_2H_5$ | Ph— | 8-$NH_2$ |
| | 46 | $CH_2C(=O)C_2H_5$ | Ph— | 8-NHOH |
| | 47 | $CH_2C(=O)C_2H_5$ | Ph— | 8-$NHCH_3$ |
| | 48 | $CH_2C(=O)C_2H_5$ | Ph— | 8-$N(CH_3)_2$ |
| | 49 | $CH_2C(=O)C_2H_5$ | Ph— | 8-$N^+(CH_3)_3$, $I^-$ |
| | 50 | $CH_2C(=O)C_2H_5$ | Ph— | 8-$NHC(=O)CH_3$ |
| | 51 | $CH_2C(=O)C_2H_5$ | Ph— | 8-$N(CH_2CH_3)_2$ |
| | 52 | $CH_2C(=O)C_2H_5$ | Ph— | 8-$NMeCH_2CO_2H$ |
| | 53 | $CH_2C(=O)C_2H_5$ | Ph— | 8-$N^+(Me)_2CH_2CO_2H$, $I^-$ |
| | 54 | $CH_2C(=O)C_2H_5$ | Ph— | 8-(N)-morpholine |
| | 55 | $CH_2C(=O)C_2H_5$ | Ph— | 8-(N)-azetidine |
| | 56 | $CH_2C(=O)C_2H_5$ | Ph— | 8-(N)-N-methylazeti-dinium, $I^-$ |
| | 57 | $CH_2C(=O)C_2H_5$ | Ph— | 8-(N)-pyrrolidine |
| | 58 | $CH_2C(=O)C_2H_5$ | Ph— | 8-(N)-N-methyl-pyrroli-dinium, $I^-$ |
| | 59 | $CH_2C(=O)C_2H_5$ | Ph— | 8-(N)-N-methyl-morpho-linium, $I^-$ |
| | 60 | $CH_2C(=O)C_2H_5$ | Ph— | 8-(N)-N'-methylpiper-azine |
| | 61 | $CH_2C(=O)C_2H_5$ | Ph— | 8-(N)-N'-dimethylpiper-azinium, $I^-$ |
| | 62 | $CH_2C(=O)C_2H_5$ | Ph— | 8-NH—CBZ |
| | 63 | $CH_2C(=O)C_2H_5$ | Ph— | 8-$NHC(O)C_5H_{11}$ |
| | 64 | $CH_2C(=O)C_2H_5$ | Ph— | 8-$NHC(O)CH_2Br$ |
| | 65 | $CH_2C(=O)C_2H_5$ | Ph— | 8-NH-C(NH)$NH_2$ |
| | 66 | $CH_2C(=O)C_2H_5$ | Ph— | 8-(2)-thiophene |
| | 67 | $CH_2C(=O)C_2H_5$ | Ph— | 9-methyl |
| | 68 | $CH_2C(=O)C_2H_5$ | Ph— | 9-ethyl |
| | 69 | $CH_2C(=O)C_2H_5$ | Ph— | 9-iso-propyl |
| | 70 | $CH_2C(=O)C_2H_5$ | Ph— | 9-tert-butyl |
| | 71 | $CH_2C(=O)C_2H_5$ | Ph— | 9-OH |
| | 72 | $CH_2C(=O)C_2H_5$ | Ph— | 9-$OCH_3$ |
| | 73 | $CH_2C(=O)C_2H_5$ | Ph— | 9-O(iso-propyl) |
| | 74 | $CH_2C(=O)C_2H_5$ | Ph— | 9-$SCH_3$ |
| | 75 | $CH_2C(=O)C_2H_5$ | Ph— | 9-$SOCH_3$ |
| | 76 | $CH_2C(=O)C_2H_5$ | Ph— | 9-$SO_2CH_3$ |
| | 77 | $CH_2C(=O)C_2H_5$ | Ph— | 9-$SCH_2CH_3$ |
| | 78 | $CH_2C(=O)C_2H_5$ | Ph— | 9-$NH_2$ |
| | 79 | $CH_2C(=O)C_2H_5$ | Ph— | 9-NHOH |
| | 80 | $CH_2C(=O)C_2H_5$ | Ph— | 9-$NHCH_3$ |
| | 81 | $CH_2C(=O)C_2H_5$ | Ph— | 9-$N(CH_3)_2$ |
| | 82 | $CH_2C(=O)C_2H_5$ | Ph— | 9-$N^+(CH_3)_3$, $I^-$ |
| | 83 | $CH_2C(=O)C_2H_5$ | Ph— | 9-$NHC(=O)CH_3$ |
| | 84 | $CH_2C(=O)C_2H_5$ | Ph— | 9-$N(CH_2CH_3)_2$ |
| | 85 | $CH_2C(=O)C_2H_5$ | Ph— | 9-$NMeCH_2CO_2H$ |

TABLE 1-continued

Alternative compounds #3 (Family F101.xxx.yyy)*

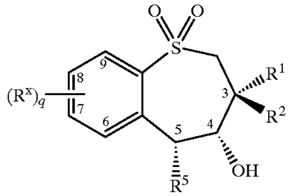

| Prefix (FFF.xxx. | Cpd# yyy) | $R^1$═$R^2$ | $R^5$ | $(R^x)q$ |
|---|---|---|---|---|
| | 86 | $CH_2C(═O)C_2H_5$ | Ph— | $9-N^+(Me)_2CH_2CO_2H, I^-$ |
| | 87 | $CH_2C(═O)C_2H_5$ | Ph— | 9-(N)-morpholine |
| | 88 | $CH_2C(═O)C_2H_5$ | Ph— | 9-(N)-azetidine |
| | 89 | $CH_2C(═O)C_2H_5$ | Ph— | 9-(N)-N-methylazeti-dinium, $I^-$ |
| | 90 | $CH_2C(═O)C_2H_5$ | Ph— | 9-(N)-pyrrolidine |
| | 91 | $CH_2C(═O)C_2H_5$ | Ph— | 9-(N)-N-methyl-pyrroli-dinium, $I^-$ |
| | 92 | $CH_2C(═O)C_2H_5$ | Ph— | 9-(N)-N-methyl-morpho-linium, $I^-$ |
| | 93 | $CH_2C(═O)C_2H_5$ | Ph— | 9-(N)-N'-methylpiper-azine |
| | 94 | $CH_2C(═O)C_2H_5$ | Ph— | 9-(N)-N'-dimethylpiper-azinium, $I^-$ |
| | 95 | $CH_2C(═O)C_2H_5$ | Ph— | 9-NH—CBZ |
| | 96 | $CH_2C(═O)C_2H_5$ | Ph— | $9-NHC(O)C_5H_{11}$ |
| | 97 | $CH_2C(═O)C_2H_5$ | Ph— | $9-NHC(O)CH_2Br$ |
| | 98 | $CH_2C(═O)C_2H_5$ | Ph— | $9-NH—C(NH)NH_2$ |
| | 99 | $CH_2C(═O)C_2H_5$ | Ph— | 9-(2)-thiophene |
| | 100 | $CH_2C(═O)C_2H_5$ | Ph— | $7-OCH_3$, $8-OCH_3$ |
| | 101 | $CH_2C(═O)C_2H_5$ | Ph— | $7-SCH_3$, $8-OCH_3$ |
| | 102 | $CH_2C(═O)C_2H_5$ | Ph— | $7-SCH_3$, $8-SCH_3$ |
| | 103 | $CH_2C(═O)C_2H_5$ | Ph— | $6-OCH_3$, $7-OCH_3$, $8-OCH_3$ |
| F101.009 | 01 | $CH_2OC_2H_5$ | Ph— | 7-methyl |
| | 02 | $CH_2OC_2H_5$ | Ph— | 7-ethyl |
| | 03 | $CH_2OC_2H_5$ | Ph— | 7-iso-propyl |
| | 04 | $CH_2OC_2H_5$ | Ph— | 7-tert-butyl |
| | 05 | $CH_2OC_2H_5$ | Ph— | 7-OH |
| | 06 | $CH_2OC_2H_5$ | Ph— | $7-OCH_3$ |
| | 07 | $CH_2OC_2H_5$ | Ph— | 7-O(iso-propyl) |
| | 08 | $CH_2OC_2H_5$ | Ph— | $7-SCH_3$ |
| | 09 | $CH_2OC_2H_5$ | Ph— | $7-SOCH_3$ |
| | 10 | $CH_2OC_2H_5$ | Ph— | $7-SO_2CH_3$ |
| | 11 | $CH_2OC_2H_5$ | Ph— | $7-SCH_2CH_3$ |
| | 12 | $CH_2OC_2H_5$ | Ph— | $7-NH_2$ |
| | 13 | $CH_2OC_2H_5$ | Ph— | 7-NHOH |
| | 14 | $CH_2OC_2H_5$ | Ph— | $7-NHCH_3$ |
| | 15 | $CH_2OC_2H_5$ | Ph— | $7-N(CH_3)_2$ |
| | 16 | $CH_2OC_2H_5$ | Ph— | $7-N^+(CH_3)_3, I^-$ |
| | 17 | $CH_2OC_2H_5$ | Ph— | $7-NHC(═O)CH_3$ |
| | 18 | $CH_2OC_2H_5$ | Ph— | $7-N(CH_2CH_3)_2$ |
| | 19 | $CH_2OC_2H_5$ | Ph— | $7-NMeCH_2CO_2H$ |
| | 20 | $CH_2OC_2H_5$ | Ph— | $7-N^+(Me)_2CH_2CO_2H, I^-$ |
| | 21 | $CH_2OC_2H_5$ | Ph— | 7-(N)-morpholine |
| | 22 | $CH_2OC_2H_5$ | Ph— | 7-(N)-azetidine |
| | 23 | $CH_2OC_2H_5$ | Ph— | 7-(N)-N-methylazeti-dinium, $I^-$ |
| | 24 | $CH_2OC_2H_5$ | Ph— | 7-(N)-pyrrolidine |
| | 25 | $CH_2OC_2H_5$ | Ph— | 7-(N)-N-methyl-pyrroli-dinium, $I^-$ |
| | 26 | $CH_2OC_2H_5$ | Ph— | 7-(N)-N-methyl-morpho-linium, $I^-$ |
| | 27 | $CH_2OC_2H_5$ | Ph— | 7-(N)-N'-methylpiper-azine |
| | 28 | $CH_2OC_2H_5$ | Ph— | 7-(N)-N'-dimethylpiper-azinium, $I^-$ |
| | 29 | $CH_2OC_2H_5$ | Ph— | 7-NH—CBZ |
| | 30 | $CH_2OC_2H_5$ | Ph— | $7-NHC(O)C_5H_{11}$ |
| | 31 | $CH_2OC_2H_5$ | Ph— | $7-NHC(O)CH_2Br$ |
| | 32 | $CH_2OC_2H_5$ | Ph— | $7-NH—C(NH)NH_2$ |
| | 33 | $CH_2OC_2H_5$ | Ph— | 7-(2)-thiophene |
| | 34 | $CH_2OC_2H_5$ | Ph— | 8-methyl |
| | 35 | $CH_2OC_2H_5$ | Ph— | 8-ethyl |

TABLE 1-continued

Alternative compounds #3 (Family F101.xxx.yyy)*

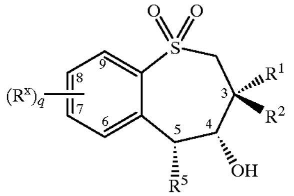

| Prefix (FFF.xxx. | Cpd# yyy) | $R^1$═$R^2$ | $R^5$ | $(R^x)q$ |
|---|---|---|---|---|
| | 36 | $CH_2OC_2H_5$ | Ph— | 8-iso-propyl |
| | 37 | $CH_2OC_2H_5$ | Ph— | 8-tert-butyl |
| | 38 | $CH_2OC_2H_5$ | Ph— | 8-OH |
| | 39 | $CH_2OC_2H_5$ | Ph— | $8-OCH_3$ |
| | 40 | $CH_2OC_2H_5$ | Ph— | 8-O-(iso-propyl) |
| | 41 | $CH_2OC_2H_5$ | Ph— | $8-SCH_3$ |
| | 42 | $CH_2OC_2H_5$ | Ph— | $8-SOCH_3$ |
| | 43 | $CH_2OC_2H_5$ | Ph— | $8-SO_2CH_3$ |
| | 44 | $CH_2OC_2H_5$ | Ph— | $8-SCH_2CH_3$ |
| | 45 | $CH_2OC_2H_5$ | Ph— | $8-NH_2$ |
| | 46 | $CH_2OC_2H_5$ | Ph— | 8-NHOH |
| | 47 | $CH_2OC_2H_5$ | Ph— | $8-NHCH_3$ |
| | 48 | $CH_2OC_2H_5$ | Ph— | $8-N(CH_3)_2$ |
| | 49 | $CH_2OC_2H_5$ | Ph— | $8-N^+(CH_3)_3, I^-$ |
| | 50 | $CH_2OC_2H_5$ | Ph— | $8-NHC(═O)CH_3$ |
| | 51 | $CH_2OC_2H_5$ | Ph— | $8-N(CH_2CH_3)_2$ |
| | 52 | $CH_2OC_2H_5$ | Ph— | $8-NMeCH_2CO_2H$ |
| | 53 | $CH_2OC_2H_5$ | Ph— | $8-N^+(Me)_2CH_2CO_2H, I^-$ |
| | 54 | $CH_2OC_2H_5$ | Ph— | 8-(N)-morpholine |
| | 55 | $CH_2OC_2H_5$ | Ph— | 8-(N)-azetidine |
| | 56 | $CH_2OC_2H_5$ | Ph— | 8-(N)-N-methylazeti-dinium, $I^-$ |
| | 57 | $CH_2OC_2H_5$ | Ph— | 8-(N)-pyrrolidine |
| | 58 | $CH_2OC_2H_5$ | Ph— | 8-(N)-N-methyl-pyrroli-dinium, $I^-$ |
| | 59 | $CH_2OC_2H_5$ | Ph— | 8-(N)-N-methyl-morpho-linium, $I^-$ |
| | 60 | $CH_2OC_2H_5$ | Ph— | 8-(N)-N'-methylpiper-azine |
| | 61 | $CH_2OC_2H_5$ | Ph— | 8-(N)-N'-dimethylpiper-azinium, $I^-$ |
| | 62 | $CH_2OC_2H_5$ | Ph— | 8-NH—CBZ |
| | 63 | $CH_2OC_2H_5$ | Ph— | $8-NHC(O)C_5H_{11}$ |
| | 64 | $CH_2OC_2H_5$ | Ph— | $8-NHC(O)CH_2Br$ |
| | 65 | $CH_2OC_2H_5$ | Ph— | $8-NH-C(NH)NH_2$ |
| | 66 | $CH_2OC_2H_5$ | Ph— | 8-(2)-thiophene |
| | 67 | $CH_2OC_2H_5$ | Ph— | 9-methyl |
| | 68 | $CH_2OC_2H_5$ | Ph— | 9-ethyl |
| | 69 | $CH_2OC_2H_5$ | Ph— | 9-iso-propyl |
| | 70 | $CH_2OC_2H_5$ | Ph— | 9-tert-butyl |
| | 71 | $CH_2OC_2H_5$ | Ph— | 9-OH |
| | 72 | $CH_2OC_2H_5$ | Ph— | $9-OCH_3$ |
| | 73 | $CH_2OC_2H_5$ | Ph— | 9-O(iso-propyl) |
| | 74 | $CH_2OC_2H_5$ | Ph— | $9-SCH_3$ |
| | 75 | $CH_2OC_2H_5$ | Ph— | $9-SOCH_3$ |
| | 76 | $CH_2OC_2H_5$ | Ph— | $9-SO_2CH_3$ |
| | 77 | $CH_2OC_2H_5$ | Ph— | $9-SCH_2CH_3$ |
| | 78 | $CH_2OC_2H_5$ | Ph— | $9-NH_2$ |
| | 79 | $CH_2OC_2H_5$ | Ph— | 9-NHOH |
| | 80 | $CH_2OC_2H_5$ | Ph— | $9-NHCH_3$ |
| | 81 | $CH_2OC_2H_5$ | Ph— | $9-N(CH_3)_2$ |
| | 82 | $CH_2OC_2H_5$ | Ph— | $9-N^+(CH_3)_3, I^-$ |
| | 83 | $CH_2OC_2H_5$ | Ph— | $9-NCH(═O)CH_3$ |
| | 84 | $CH_2OC_2H_5$ | Ph— | $9-N(CH_2CH_3)_2$ |
| | 85 | $CH_2OC_2H_5$ | Ph— | $9-NMeCH_2CO_2H$ |
| | 86 | $CH_2OC_2H_5$ | Ph— | $9-N^+(Me)_2CH_2CO_2H, I^-$ |
| | 87 | $CH_2OC_2H_5$ | Ph— | 9-(N)-morpholine |
| | 88 | $CH_2OC_2H_5$ | Ph— | 9-(N)-azetidine |
| | 89 | $CH_2OC_2H_5$ | Ph— | 9-(N)-N-methylazeti dinium, $I^-$ |
| | 90 | $CH_2OC_2H_5$ | Ph— | 9-(N)-pyrrolidine |
| | 91 | $CH_2OC_2H_5$ | Ph— | 9-(N)-N-methyl-pyrroli-dinium, $I^-$ |

TABLE 1-continued

Alternative compounds #3 (Family F101.xxx.yyy)*

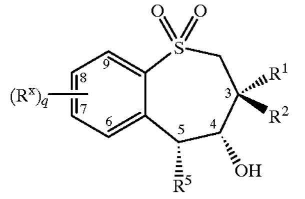

| Prefix (FFF.xxx. | Cpd# yyy) | $R^1$=$R^2$ | $R^5$ | $(R^x)q$ |
|---|---|---|---|---|
| | 92 | $CH_2OC_2H_5$ | Ph— | 9-(N)-N-methyl-morpholinium, $I^-$ |
| | 93 | $CH_2OC_2H_5$ | Ph— | 9-(N)-N'-methylpiperazine |
| | 94 | $CH_2OC_2H_5$ | Ph— | 9-(N)-N'-dimethylpiperazinium, $I^-$ |
| | 95 | $CH_2OC_2H_5$ | Ph— | 9-NH—CBZ |
| | 96 | $CH_2OC_2H_5$ | Ph— | 9-NHC(O)$C_5H_{11}$ |
| | 97 | $CH_2OC_2H_5$ | Ph— | 9-NHC(O)$CH_2Br$ |
| | 98 | $CH_2OC_2H_5$ | Ph— | 9-NH—C(NH)$NH_2$ |
| | 99 | $CH_2OC_2H_5$ | Ph— | 9-(2)-thiophene |
| | 100 | $CH_2OC_2H_5$ | Ph— | 7-$OCH_3$, 8-$OCH_3$ |
| | 101 | $CH_2OC_2H_5$ | Ph— | 7-$SCH_3$, 8-$OCH_3$ |
| | 102 | $CH_2OC_2H_5$ | Ph— | 7-$SCH_3$, 8-$SCH_3$ |
| | 103 | $CH_2OC_2H_5$ | Ph— | 6-$OCH_3$, 7-$OCH_3$, 8-$OCH_3$ |
| F101.010 | 01 | $CH_2CH(OH)C_2H_5$ | Ph— | 7-methyl |
| | 02 | $CH_2CH(OH)C_2H_5$ | Ph— | 7-ethyl |
| | 03 | $CH_2CH(OH)C_2H_5$ | Ph— | 7-iso-propyl |
| | 04 | $CH_2CH(OH)C_2H_5$ | Ph— | 7-tert-butyl |
| | 05 | $CH_2CH(OH)C_2H_5$ | Ph— | 7-OH |
| | 06 | $CH_2CH(OH)C_2H_5$ | Ph— | 7-$OCH_3$ |
| | 07 | $CH_2CH(OH)C_2H_5$ | Ph— | 7-O(iso-propyl) |
| | 08 | $CH_2CH(OH)C_2H_5$ | Ph— | 7-$SCH_3$ |
| | 09 | $CH_2CH(OH)C_2H_5$ | Ph— | 7-$SOCH_3$ |
| | 10 | $CH_2CH(OH)C_2H_5$ | Ph— | 7-$SO_2CH_3$ |
| | 11 | $CH_2CH(OH)C_2H_5$ | Ph— | 7-$SCH_2CH_3$ |
| | 12 | $CH_2CH(OH)C_2H_5$ | Ph— | 7-$NH_2$ |
| | 13 | $CH_2CH(OH)C_2H_5$ | Ph— | 7-NHOH |
| | 14 | $CH_2CH(OH)C_2H_5$ | Ph— | 7-$NHCH_3$ |
| | 15 | $CH_2CH(OH)C_2H_5$ | Ph— | 7-$N(CH_3)_2$ |
| | 16 | $CH_2CH(OH)C_2H_5$ | Ph— | 7-$N^+(CH_3)_3$, $I^-$ |
| | 17 | $CH_2CH(OH)C_2H_5$ | Ph— | 7-NHC(=O)$CH_3$ |
| | 18 | $CH_2CH(OH)C_2H_5$ | Ph— | 7-$N(CH_2CH_3)_2$ |
| | 19 | $CH_2CH(OH)C_2H_5$ | Ph— | 7-$NMeCH_2CO_2H$ |
| | 20 | $CH_2CH(OH)C_2H_5$ | Ph— | 7-$N^+(Me)_2CH_2CO_2H$, $I^-$ |
| | 21 | $CH_2CH(OH)C_2H_5$ | Ph— | 7-(N)-morpholine |
| | 22 | $CH_2CH(OH)C_2H_5$ | Ph— | 7-(N)-azetidine |
| | 23 | $CH_2CH(OH)C_2H_5$ | Ph— | 7-(N)-N-methylazetidinium, $I^-$ |
| | 24 | $CH_2CH(OH)C_2H_5$ | Ph— | 7-(N)-pyrrolidine |
| | 25 | $CH_2CH(OH)C_2H_5$ | Ph— | 7-(N)-N-methyl-pyrrolidinium, $I^-$ |
| | 26 | $CH_2CH(OH)C_2H_5$ | Ph— | 7-(N)-N-methyl-morpholinium, $I^-$ |
| | 27 | $CH_2CH(OH)C_2H_5$ | Ph— | 7-(N)-N'-methylpiperazine |
| | 28 | $CH_2CH(OH)C_2H_5$ | Ph— | 7-(N)-N'-dimethylpiperazinium, $I^-$ |
| | 29 | $CH_2CH(OH)C_2H_5$ | Ph— | 7-NH—CBZ |
| | 30 | $CH_2CH(OH)C_2H_5$ | Ph— | 7-NHC(O)$C_5H_{11}$ |
| | 31 | $CH_2CH(OH)C_2H_5$ | Ph— | 7-NHC(O)$CH_2Br$ |
| | 32 | $CH_2CH(OH)C_2H_5$ | Ph— | 7-NH—C(NH)$NH_2$ |
| | 33 | $CH_2CH(OH)C_2H_5$ | Ph— | 7-(2)-thiophene |
| | 34 | $CH_2CH(OH)C_2H_5$ | Ph— | 8-methyl |
| | 35 | $CH_2CH(OH)C_2H_5$ | Ph— | 8-ethyl |
| | 36 | $CH_2CH(OH)C_2H_5$ | Ph— | 8-iso-propyl |
| | 37 | $CH_2CH(OH)C_2H_5$ | Ph— | 8-tert-butyl |
| | 38 | $CH_2CH(OH)C_2H_5$ | Ph— | 8-OH |
| | 39 | $CH_2CH(OH)C_2H_5$ | Ph— | 8-$OCH_3$ |
| | 40 | $CH_2CH(OH)C_2H_5$ | Ph— | 8-O-(iso-propyl) |
| | 41 | $CH_2CH(OH)C_2H_5$ | Ph— | 8-$SCH_3$ |
| | 42 | $CH_2CH(OH)C_2H_5$ | Ph— | 8-$SOCH_3$ |
| | 43 | $CH_2CH(OH)C_2H_5$ | Ph— | 8-$SO_2CH_3$ |

TABLE 1-continued

Alternative compounds #3 (Family F101.xxx.yyy)*

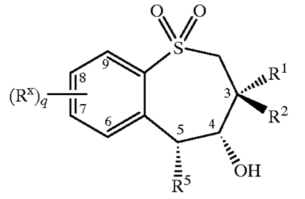

| Prefix (FFF.xxx. | Cpd# yyy) | $R^1$=$R^2$ | $R^5$ | $(R^x)q$ |
|---|---|---|---|---|
| | 44 | $CH_2CH(OH)C_2H_5$ | Ph— | 8-$SCH_2CH_3$ |
| | 45 | $CH_2CH(OH)C_2H_5$ | Ph— | 8-$NH_2$ |
| | 46 | $CH_2CH(OH)C_2H_5$ | Ph— | 8-NHOH |
| | 47 | $CH_2CH(OH)C_2H_5$ | Ph— | 8-$NHCH_3$ |
| | 48 | $CH_2CH(OH)C_2H_5$ | Ph— | 8-$N(CH_3)_2$ |
| | 49 | $CH_2CH(OH)C_2H_5$ | Ph— | 8-$N^+(CH_3)3$, $I^-$ |
| | 50 | $CH_2CH(OH)C_2H_5$ | Ph— | 8-NHC(=O)$CH_3$ |
| | 51 | $CH_2CH(OH)C_2H_5$ | Ph— | 8-$N(CH_2CH_3)_2$ |
| | 52 | $CH_2CH(OH)C_2H_5$ | Ph— | 8-$NMeCH_2CO_2H$ |
| | 53 | $CH_2CH(OH)C_2H_5$ | Ph— | 8-$N^+(Me)_2CH_2CO_2H$, $I^-$ |
| | 54 | $CH_2CH(OH)C_2H_5$ | Ph— | 8-(N)-morpholine |
| | 55 | $CH_2CH(OH)C_2H_5$ | Ph— | 8-(N)-azetidine |
| | 56 | $CH_2CH(OH)C_2H_5$ | Ph— | 8-(N)-N-methylazetidinium, $I^-$ |
| | 57 | $CH_2CH(OH)C_2H_5$ | Ph— | 8-(N)-pyrrolidine |
| | 58 | $CH_2CH(OH)C_2H_5$ | Ph— | 8-(N)-N-methyl-pyrrolidinium, $I^-$ |
| | 59 | $CH_2CH(OH)C_2H_5$ | Ph— | 8-(N)-N-methyl-morpholinium, $I^-$ |
| | 60 | $CH_2CH(OH)C_2H_5$ | Ph— | 8-(N)-N'-methylpiperazine |
| | 61 | $CH_2CH(OH)C_2H_5$ | Ph— | 8-(N)-N'-dimethylpiperazinium, $I^-$ |
| | 62 | $CH_2CH(OH)C_2H_5$ | Ph— | 8-NH—CBZ |
| | 63 | $CH_2CH(OH)C_2H_5$ | Ph— | 8-NHC(O)$C_5H_{11}$ |
| | 64 | $CH_2CH(OH)C_2H_5$ | Ph— | 8-NHC(O)$CH_2Br$ |
| | 65 | $CH_2CH(OH)C_2H_5$ | Ph— | 8-NH-C(NH)$NH_2$ |
| | 66 | $CH_2CH(OH)C_2H_5$ | Ph— | 8-(2)-thiophene |
| | 67 | $CH_2CH(OH)C_2H_5$ | Ph— | 9-methyl |
| | 68 | $CH_2CH(OH)C_2H_5$ | Ph— | 9-ethyl |
| | 69 | $CH_2CH(OH)C_2H_5$ | Ph— | 9-isopropyl |
| | 70 | $CH_2CH(OH)C_2H_5$ | Ph— | 9-tert-butyl |
| | 71 | $CH_2CH(OH)C_2H_5$ | Ph— | 9-OH |
| | 72 | $CH_2CH(OH)C_2H_5$ | Ph— | 9-$OCH_3$ |
| | 73 | $CH_2CH(OH)C_2H_5$ | Ph— | 9-O(iso-propyl) |
| | 74 | $CH_2CH(OH)C_2H_5$ | Ph— | 9-$SCH_3$ |
| | 75 | $CH_2CH(OH)C_2H_5$ | Ph— | 9-$SOCH_3$ |
| | 76 | $CH_2CH(OH)C_2H_5$ | Ph— | 9-$SO_2CH_3$ |
| | 77 | $CH_2CH(OH)C_2H_5$ | Ph— | 9-$SCH_2CH_3$ |
| | 78 | $CH_2CH(OH)C_2H_5$ | Ph— | 9-$NH_2$ |
| | 79 | $CH_2CH(OH)C_2H_5$ | Ph— | 9-NHOH |
| | 80 | $CH_2CH(OH)C_2H_5$ | Ph— | 9-$NHCH_3$ |
| | 81 | $CH_2CH(OH)C_2H_5$ | Ph— | 9-$N(CH_3)_2$ |
| | 82 | $CH_2CH(OH)C_2H_5$ | Ph— | 9-$N^+(CH_3)_3$, $I^-$ |
| | 83 | $CH_2CH(OH)C_2H_5$ | Ph— | 9-NHC(=O)$CH_3$ |
| | 84 | $CH_2CH(OH)C_2H_5$ | Ph— | 9-$N(CH_2CH_3)_2$ |
| | 85 | $CH_2CH(OH)C_2H_5$ | Ph— | 9-$NMeCH_2CO_2H$ |
| | 86 | $CH_2CH(OH)C_2H_5$ | Ph— | 9-$N^+(Me)_2CH_2CO_2H$, $I^-$ |
| | 87 | $CH_2CH(OH)C_2H_5$ | Ph— | 9-(N)-morpholine |
| | 88 | $CH_2CH(OH)C_2H_5$ | Ph— | 9-(N)-azetidine |
| | 89 | $CH_2CH(OH)C_2H_5$ | Ph— | 9-(N)-N-methylazetidinium, $I^-$ |
| | 90 | $CH_2CH(OH)C_2H_5$ | Ph— | 9-(N)-pyrrolidine |
| | 91 | $CH_2CH(OH)C_2H_5$ | Ph— | 9-(N)-N-methyl-pyrrolidinium, $I^-$ |
| | 92 | $CH_2CH(OH)C_2H_5$ | Ph— | 9-(N)-N-methyl-morpholinium, $I^-$ |
| | 93 | $CH_2CH(OH)C_2H_5$ | Ph— | 9-(N)-N'-methylpiperazine |
| | 94 | $CH_2CH(OH)C_2H_5$ | Ph— | 9-(N)-N'-dimethylpiperazinium, $I^-$ |
| | 95 | $CH_2CH(OH)C_2H_5$ | Ph— | 9-NH—CBZ |
| | 96 | $CH_2CH(OH)C_2H_5$ | Ph— | 9-NHC(O)$C_5H_{11}$ |
| | 97 | $CH_2CH(OH)C_2H_5$ | Ph— | 9-NHC(O)$CH_2Br$ |

TABLE 1-continued

Alternative compounds #3 (Family F101.xxx.yyy)*

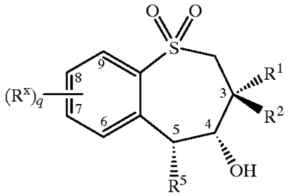

| Prefix (FFF.xxx. | Cpd# yyy) | $R^1$=$R^2$ | $R^5$ | $(R^x)q$ |
|---|---|---|---|---|
| | 98 | $CH_2CH(OH)C_2H_5$ | Ph— | 9-NH—C(NH)$NH_2$ |
| | 99 | $CH_2CH(OH)C_2H_5$ | Ph— | 9-(2)-thiophene |
| | 100 | $CH_2CH(OH)C_2H_5$ | Ph— | 7-$OCH_3$, 8-$OCH_3$ |
| | 101 | $CH_2CH(OH)C_2H_5$ | Ph— | 7-$SCH_3$, 8-$OCH_3$ |
| | 102 | $CH_2CH(OH)C_2H_5$ | Ph— | 7-$SCH_3$, 8-$SCH_3$ |
| | 103 | $CH_2CH(OH)C_2H_5$ | Ph— | 6-$OCH_3$, 7-$OCH_3$, 8-$OCH_3$ |
| F101.011 | 01 | $CH_2O$-(4-picoline) | Ph— | 7-methyl |
| | 02 | $CH_2O$-(4-picoline) | Ph— | 7-ethyl |
| | 03 | $CH_2O$-(4-picoline) | Ph— | 7-iso-propyl |
| | 04 | $CH_2O$-(4-picoline) | Ph— | 7-tert-butyl |
| | 05 | $CH_2O$-(4-picoline) | Ph— | 7-OH |
| | 06 | $CH_2O$-(4-picoline) | Ph— | 7-$OCH_3$ |
| | 07 | $CH_2O$-(4-picoline) | Ph— | 7-O(iso-propyl) |
| | 08 | $CH_2O$-(4-picoline) | Ph— | 7-$SCH_3$ |
| | 09 | $CH_2O$-(4-picoline) | Ph— | 7-$SOCH_3$ |
| | 10 | $CH_2O$-(4-picoline) | Ph— | 7-$SO_2CH_3$ |
| | 11 | $CH_2O$-(4-picoline) | Ph— | 7-$SCH_2CH_3$ |
| | 12 | $CH_2O$-(4-picoline) | Ph— | 7-$NH_2$ |
| | 13 | $CH_2O$-(4-picoline) | Ph— | 7-NHOH |
| | 14 | $CH_2O$-(4-picoline) | Ph— | 7-$NHCH_3$ |
| | 15 | $CH_2O$-(4-picoline) | Ph— | 7-$N(CH_3)_2$ |
| | 16 | $CH_2O$-(4-picoline) | Ph— | 7-$N^+(CH_3)_3$, $I^-$ |
| | 17 | $CH_2O$-(4-picoline) | Ph— | 7-NHC(=O)$CH_3$ |
| | 18 | $CH_2O$-(4-picoline) | Ph— | 7-$N(CH_2CH_3)_2$ |
| | 19 | $CH_2O$-(4-picoline) | Ph— | 7-$NMeCH_2CO_2H$ |
| | 20 | $CH_2O$-(4-picoline) | Ph— | 7-$N^+(Me)_2CH_2CO_2H$, $I^-$ |
| | 21 | $CH_2O$-(4-picoline) | Ph— | 7-(N)-morpholine |
| | 22 | $CH_2O$-(4-picoline) | Ph— | 7-(N)-azetidine |
| | 23 | $CH_2O$-(4-picoline) | Ph— | 7-(N)-N-methylazetidinium, $I^-$ |
| | 24 | $CH_2O$-(4-picoline) | Ph— | 7-(N)-pyrrolidine |
| | 25 | $CH_2O$-(4-picoline) | Ph— | 7-(N)-N-methyl-pyrrolidinium, $I^-$ |
| | 26 | $CH_2O$-(4-picoline) | Ph— | 7-(N)-N-methyl-morpholinium, $I^-$ |
| | 27 | $CH_2O$-(4-picoline) | Ph— | 7-(N)-N'-methylpiperazine |
| | 28 | $CH_2O$-(4-picoline) | Ph— | 7-(N)-N'-dimethylpiperazinium, $I^-$ |
| | 29 | $CH_2O$-(4-picoline) | Ph— | 7-NH—CBZ |
| | 30 | $CH_2O$-(4-picoline) | Ph— | 7-NHC(O)$C_5H_{11}$ |
| | 31 | $CH_2O$-(4-picoline) | Ph— | 7-NHC(O)$CH_2Br$ |
| | 32 | $CH_2O$-(4-picoline) | Ph— | 7-NH—C(NH)$NH_2$ |
| | 33 | $CH_2O$-(4-picoline) | Ph— | 7-(2)-thiophene |
| | 34 | $CH_2O$-(4-picoline) | Ph— | 8-methyl |
| | 35 | $CH_2O$-(4-picoline) | Ph— | 8-ethyl |
| | 36 | $CH_2O$-(4-picoline) | Ph— | 8-iso-propyl |
| | 37 | $CH_2O$-(4-picoline) | Ph— | 8-tert-butyl |
| | 38 | $CH_2O$-(4-picoline) | Ph— | 8-OH |
| | 39 | $CH_2O$-(4-picoline) | Ph— | 8-$OCH_3$ |
| | 40 | $CH_2O$-(4-picoline) | Ph— | 8-O-(iso-propyl) |
| | 41 | $CH_2O$-(4-picoline) | Ph— | 8-$SCH_3$ |
| | 42 | $CH_2O$-(4-picoline) | Ph— | 8-$SOCH_3$ |
| | 43 | $CH_2O$-(4-picoline) | Ph— | 8-$SO_2CH_3$ |
| | 44 | $CH_2O$-(4-picoline) | Ph— | 8-$SCH_2CH_3$ |
| | 45 | $CH_2O$-(4-picoline) | Ph— | 8-$NH_2$ |
| | 46 | $CH_2O$-(4-picoline) | Ph— | 8-NHOH |
| | 47 | $CH_2O$-(4-picoline) | Ph— | 8-$NHCH_3$ |
| | 48 | $CH_2O$-(4-picoline) | Ph— | 8-$N(CH_3)_2$ |
| | 49 | $CH_2O$-(4-picoline) | Ph— | 8-$N^+(CH_3)3$, $I^-$ |
| | 50 | $CH_2O$-(4-picoline) | Ph— | 8-NHC(=O)$CH_3$ |
| | 51 | $CH_2O$-(4-picoline) | Ph— | 8-$N(CH_2CH_3)_2$ |
| | 52 | $CH_2O$-(4-picoline) | Ph— | 8-$NMeCH_2CO_2H$ |

TABLE 1-continued

Alternative compounds #3 (Family F101.xxx.yyy)*

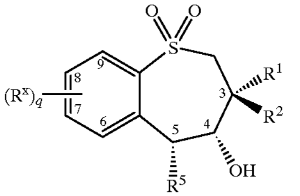

| Prefix (FFF.xxx. | Cpd# yyy) | $R^1$=$R^2$ | $R^5$ | $(R^x)q$ |
|---|---|---|---|---|
| | 53 | $CH_2O$-(4-picoline) | Ph— | 8-$N^+(Me)_2CH_2CO_2H$, $I^-$ |
| | 54 | $CH_2O$-(4-picoline) | Ph— | 8-(N)-morpholine |
| | 55 | $CH_2O$-(4-picoline) | Ph— | 8-(N)-azetidine |
| | 56 | $CH_2O$-(4-picoline) | Ph— | 8-(N)-N-methylazetidinium, $I^-$ |
| | 57 | $CH_2O$-(4-picoline) | Ph— | 8-(N)-pyrrolidine |
| | 58 | $CH_2O$-(4-picoline) | Ph— | 8-(N)-N-methyl-pyrrolidinium, $I^-$ |
| | 59 | $CH_2O$-(4-picoline) | Ph— | 8-(N)-N-methyl-morpholinium, $I^-$ |
| | 60 | $CH_2O$-(4-picoline) | Ph— | 8-(N)-N'-methylpiperazine |
| | 61 | $CH_2O$-(4-picoline) | Ph— | 8-(N)-N'-dimethylpiperazinium, $I^-$ |
| | 62 | $CH_2O$-(4-picoline) | Ph— | 8-NH—CBZ |
| | 63 | $CH_2O$-(4-picoline) | Ph— | 8-NHC(O)$C_5H_{11}$ |
| | 64 | $CH_2O$-(4-picoline) | Ph— | 8-NHC(O)$CH_2Br$ |
| | 65 | $CH_2O$-(4-picoline) | Ph— | 8-NH-C(NH)$NH_2$ |
| | 66 | $CH_2O$-(4-picoline) | Ph— | 8-(2)-thiophene |
| | 67 | $CH_2O$-(4-picoline) | Ph— | 9-methyl |
| | 68 | $CH_2O$-(4-picoline) | Ph— | 9-ethyl |
| | 69 | $CH_2O$-(4-picoline) | Ph— | 9-iso-propyl |
| | 70 | $CH_2O$-(4-picoline) | Ph— | 9-tert-butyl |
| | 71 | $CH_2O$-(4-picoline) | Ph— | 9-OH |
| | 72 | $CH_2O$-(4-picoline) | Ph— | 9-$OCH_3$ |
| | 73 | $CH_2O$-(4-picoline) | Ph— | 9-O(iso-propyl) |
| | 74 | $CH_2O$-(4-picoline) | Ph— | 9-$SCH_3$ |
| | 75 | $CH_2O$-(4-picoline) | Ph— | 9-$SOCH_3$ |
| | 76 | $CH_2O$-(4-picoline) | Ph— | 9-$SO_2CH_3$ |
| | 77 | $CH_2O$-(4-picoline) | Ph— | 9-$SCH_2CH_3$ |
| | 78 | $CH_2O$-(4-picoline) | Ph— | 9-$NH_2$ |
| | 79 | $CH_2O$-(4-picoline) | Ph— | 9-NHOH |
| | 80 | $CH_2O$-(4-picoline) | Ph— | 9-$NHCH_3$ |
| | 81 | $CH_2O$-(4-picoline) | Ph— | 9-$N(CH_3)_2$ |
| | 82 | $CH_2O$-(4-picoline) | Ph— | 9-$N^+(CH_3)_3$, $I^-$ |
| | 83 | $CH_2O$-(4-picoline) | Ph— | 9-NCH(=O)$CH_3$ |
| | 84 | $CH_2O$-(4-picoline) | Ph— | 9-$N(CH_2CH_3)_2$ |
| | 85 | $CH_2O$-(4-picoline) | Ph— | 9-$NMeCH_2CO_2H$ |
| | 86 | $CH_2O$-(4-picoline) | Ph— | 9-$N^+(Me)_2CH_2CO_2H$, $I^-$ |
| | 87 | $CH_2O$-(4-picoline) | Ph— | 9-(N)-morpholine |
| | 88 | $CH_2O$-(4-picoline) | Ph— | 9-(N)-azetidine |
| | 89 | $CH_2O$-(4-picoline) | Ph— | 9-(N)-N-methylazetidinium, $I^-$ |
| | 90 | $CH_2O$-(4-picoline) | Ph— | 9-(N)-pyrrolidine |
| | 91 | $CH_2O$-(4-picoline) | Ph— | 9-(N)-N-methyl-pyrrolidinium, $I^-$ |
| | 92 | $CH_2O$-(4-picoline) | Ph— | 9-(N)-N-methyl-morpholinium, $I^-$ |
| | 93 | $CH_2O$-(4-picoline) | Ph— | 9-(N)-N'-methylpiperazine |
| | 94 | $CH_2O$-(4-picoline) | Ph— | 9-(N)-N'-dimethylpiperazinium, $I^-$ |
| | 95 | $CH_2O$-(4-picoline) | Ph— | 9-NH—CBZ |
| | 96 | $CH_2O$-(4-picoline) | Ph— | 9-NHC(O)$C_5H_{11}$ |
| | 97 | $CH_2O$-(4-picoline) | Ph— | 9-NHC(O)$CH_2Br$ |
| | 98 | $CH_2O$-(4-picoline) | Ph— | 9-NH—C(NH)$NH_2$ |
| | 99 | $CH_2O$-(4-picoline) | Ph— | 9-(2)-thiophene |
| | 100 | $CH_2O$-(4-picoline) | Ph— | 7-$OCH_3$, 8-$OCH_3$ |
| | 101 | $CH_2O$-(4-picoline) | Ph— | 7-$SCH_3$, 8-$OCH_3$ |
| | 102 | $CH_2O$-(4-picoline) | Ph— | 7-$SCH_3$, 8-$SCH_3$ |
| | 103 | $CH_2O$-(4-picoline) | Ph— | 6-$OCH_3$, 7-$OCH_3$, 8-$OCH_3$ |

Additional Structures of the Present Invention

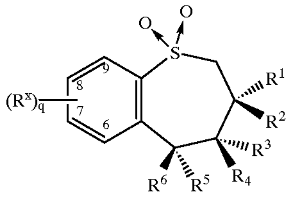

| Compound Number | $R^1$ | $R^2$ | $R^3$ | $R^4$ | $R^5$ | $R^6$ | $(R^x)_q$ |
|---|---|---|---|---|---|---|---|
| 101 | ethyl | n-butyl | OH | H | phenyl | H | 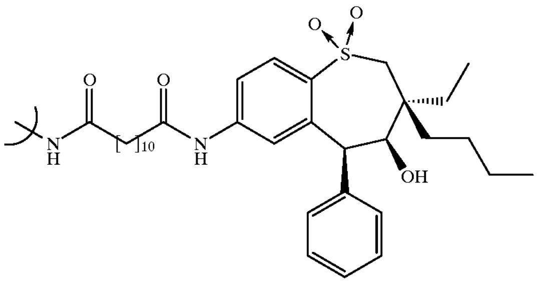 at the 7-position |
| 102 | ethyl | n-butyl | OH | H | phenyl | H | 7-trimethylammonium iodide |
| 103 | n-butyl | ethyl | OH | H | phenyl | H | 7-trimethylammonium iodide |
| 104 | ethyl | n-butyl | OH | H | phenyl | H | 7-dimethylamino |
| 105 | ethyl | n-butyl | OH | H | phenyl | H | 7-methanesulfonamido |
| 106 | ethyl | n-butyl | OH | H | phenyl | H | 7-(2'-bromoacetamido) |
| 107 | n-butyl | ethyl | OH | H | 4-(decyloxy)phenyl | H | 7-amino |
| 108 | ethyl | n-butyl | OH | H | phenyl | H | 7-(hexylamido) |
| 109 | ethyl | n-butyl | OH | H | 4-(decylocy)phenyl | H | 7-amino |
| 110 | ethyl | n-butyl | OH | H | phenyl | H | 7-acetamido |
| 111 | n-butyl | ethyl | OH | H | 4-hydroxyphenyl | H | 7-amino |

-continued

Additional Structures of the Present Invention

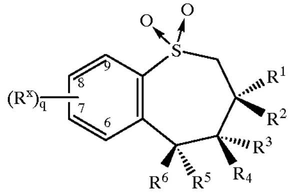

| Compound Number | $R^1$ | $R^2$ | $R^3$ | $R^4$ | $R^5$ | $R^6$ | $(R^x)_q$ |
|---|---|---|---|---|---|---|---|
| 112 | ethyl | n-butyl | OH | H | 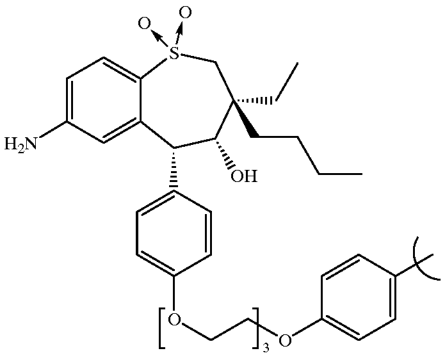 | H | 7-amino |
| 113 | ethyl | n-butyl | OH | H | 4-hydroxyphenyl | H | 7-amino |
| 114 | ethyl | n-butyl | OH | H | 4-methoxyphenyl | H | 7-amino |
| 115 | n-butyl | ethyl | OH | H | 4-methoxyphenyl | H | 7-(O-benzylcarbamato) |
| 116 | ethyl | n-butyl | OH | H | 4-methoxyphenyl | H | 7-(O-benzylcarbamato) |
| 117 | n-butyl | ethyl | OH | H | phenyl | H | 7-(O-benzylcarbamato) |
| 118 | ethyl | n-butyl | OH | H | phenyl | H | 7-(O-benzylcarbamato) |
| 119 | ethyl | n-butyl | OH | H | phenyl | H | 7-(O-tert-butylcarbamato) |
| 120 | n-butyl | ethyl | OH | H | phenyl | H | 7-(O-benzylcarbamato) |
| 121 | ethyl | n-butyl | OH | H | phenyl | H | 7-amino |
| 122 | n-butyl | ethyl | OH | H | phenyl | H | 7-amino |
| 123 | ethyl | n-butyl | OH | H | phenyl | H | 7-hexylamino |
| 124 | n-butyl | ethyl | OH | H | phenyl | H | 7-(hexylamino) |
| 125 | ethyl | n-butyl | OH | H | phenyl | H | 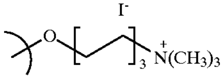 at the 8-position |

-continued

Additional Structures of the Present Invention

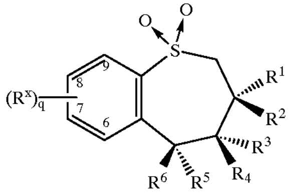

| Compound Number | $R^1$ | $R^2$ | $R^3$ | $R^4$ | $R^5$ | $R^6$ | $(R^x)_q$ |
|---|---|---|---|---|---|---|---|
| 126 | n-butyl | ethyl | OH | H | 4-fluorophenyl | H | 7-(O-benzylcarbamato) |
| 127 | n-butyl | ethyl | OH | H | 4-fluorophenyl | H | 7-amino |
| 128 | ethyl | n-butyl | OH | H | 4-fluorophenyl | H | 7-(O-benzylcarbamato) |
| 129 | ethyl | n-butyl | OH | H | 4-fluorophenyl | H | 7-amino |
| 131 | ethyl | n-butyl | OH | H | 4-fluorophenyl | H | 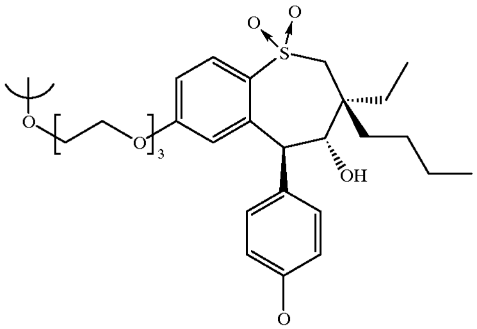 at the 7-position |
| 132 | ethyl | n-butyl | OH | H | phenyl | H | 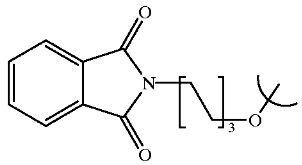 at the 8-position |
| 133 | ethyl | n-butyl | OH | H | phenyl | H | 8-(hexyloxy) |

-continued
Additional Structures of the Present Invention
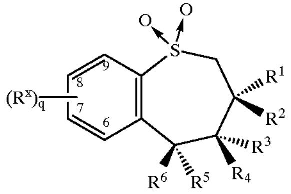
| Compound Number | $R^1$ | $R^2$ | $R^3$ | $R^4$ | $R^5$ | $R^6$ | $(R^x)_q$ |
|---|---|---|---|---|---|---|---|
| 134 | ethyl | n-butyl | OH | H | phenyl | H | 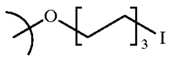 at the 8-position |
| 135 | ethyl | n-butyl | OH | H | phenyl | H | 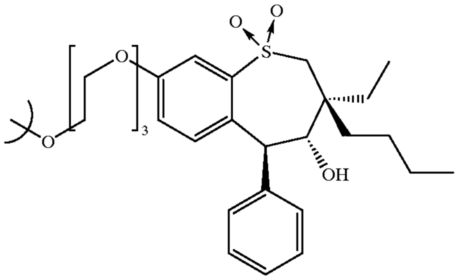 at the 8-position |
| 136 | ethyl | n-butyl | OH | H | phenyl | H | 8-hydroxy |
| 137 | n-butyl | ethyl | OH | H | phenyl | H | 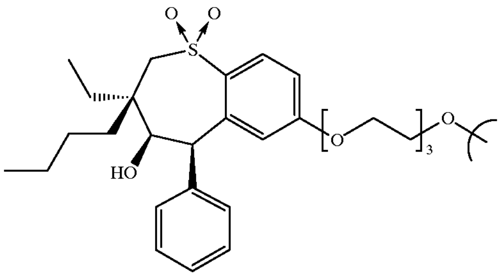 at the 7-position |

-continued

Additional Structures of the Present Invention

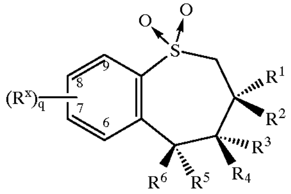

| Compound Number | $R^1$ | $R^2$ | $R^3$ | $R^4$ | $R^5$ | $R^6$ | $(R^x)_q$ |
|---|---|---|---|---|---|---|---|
| 138 | n-butyl | ethyl | OH | H | phenyl | H | 8-acetoxy |
| 139 | n-butyl | ethyl | OH | H | phenyl | H | 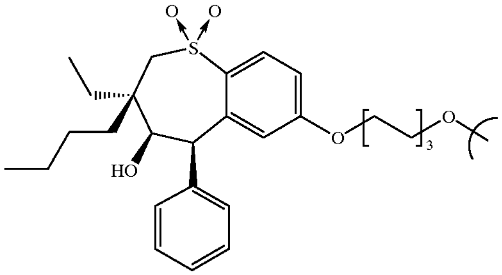 at the 7-position |
| 142 | ethyl | n-butyl | H | OH | H | 3-methoxy-phenyl | 7-methylmercapto |
| 143 | ethyl | n-butyl | OH | H | 3-methoxyphenyl | H | 7-methylmercapto |
| 144 | ethyl | n-butyl | OH | H | 4-fluorophenyl | H | 7-(N-azetidinyl) |
| 262 | ethyl | n-butyl | OH | H | 3-methoxyphenyl | H | 7-methoxy |
| 263 | ethyl | n-butyl | H | OH | H | 3-methoxy phenyl | 7-methoxy |
| 264 | ethyl | n-butyl | OH | H | 3-triflouromethylphenyl | H | 7-methoxy |
| 265 | ethyl | n-butyl | H | OH | H | 3-trifluoro-methyl-phenyl | 7-methoxy |
| 266 | ethyl | n-butyl | OH | H | 3-hydroxyphenyl | H | 7-hydroxy |
| 267 | ethyl | n-butyl | OH | H | 3-hydroxyphenyl | H | 7-methoxy |
| 268 | ethyl | n-butyl | OH | H | 4-fluorophenyl | H | 7-methoxy |
| 269 | ethyl | n-butyl | H | OH | H | 4-fluoro-phenyl | 7-methoxy |
| 270 | ethyl | n-butyl | OH | H | 4-fluorophenyl | H | 7-hydroxy |
| 271 | ethyl | n-butyl | OH | H | 3-methoxyphenyl | H | 7-bromo |
| 272 | ethyl | n-butyl | H | OH | H | 3-methoxy- | 7-bromo |

-continued

Additional Structures of the Present Invention

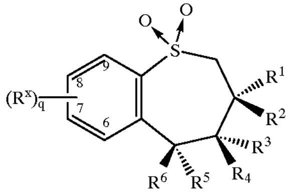

| Compound Number | R¹ | R² | R³ | R⁴ | R⁵ | R⁶ | $(R^x)_q$ |
|---|---|---|---|---|---|---|---|
| | | | | | | phenyl | |
| 273 | ethyl | n-butyl | H | OH | H | 4-fluoro-phenyl | 7-fluoro |
| 274 | ethyl | n-butyl | OH | H | 4-fluorophenyl | H | 7-fluoro |
| 275 | ethyl | n-butyl | H | OH | H | 3-methoxy-phenyl | 7-fluoro |
| 276 | ethyl | n-butyl | OH | H | 3-methoxyphenyl | H | 7-fluoro |
| 277 | ethyl | n-butyl | OH | H | 3-fluorophenyl | H | 7-methoxy |
| 278 | ethyl | n-butyl | H | OH | 2-fluorophenyl | H | 7-methoxy |
| 279 | ethyl | n-butyl | H | OH | 3-fluorophenyl | H | 7-methoxy |
| 280 | ethyl | n-butyl | OH | H | 2-fluorophenyl | H | 7-methoxy |
| 281 | ethyl | n-butyl | OH | H | 4-fluorophenyl | H | 7-methylmercapto |
| 282 | ethyl | n-butyl | OH | H | 4-fluorophenyl | H | 7-methyl |
| 283 | ethyl | n-butyl | H | OH | H | 4-fluoro-phenyl | 7-methyl |
| 284 | ethyl | n-butyl | OH | H | 4-fluorophenyl | H | 7-(4'-morpholino) |
| 285 | | | | | MISSING | | |
| 286 | ethyl | ethyl | OH | H | phenyl | H | 7-(o-benzylcarbamato) |
| 287 | ethyl | ethyl | OH | H | phenyl | H | 7-amino |
| 288 | methyl | methyl | OH | H | phenyl | H | 7-amino |
| 289 | n-butyl | n-butyl | OH | H | phenyl | H | 7-amino |
| 290 | n-butyl | n-butyl | OH | H | phenyl | H | 7-amino |
| 291 | n-butyl | n-butyl | OH | H | phenyl | H | 7-(O-benzylcarbamato) |
| 292 | n-butyl | n-butyl | OH | H | 4-fluorophenyl | H | 7-amino |
| 293 | n-butyl | n-butyl | OH | H | phenyl | H | 7-benzylamino |
| 294 | n-butyl | n-butyl | OH | H | phenyl | H | 7-dimethylamino |
| 295 | ethyl | n-butyl | OH | H | 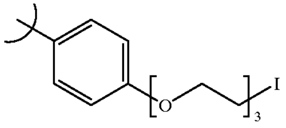 | H | 7-amino |

-continued
Additional Structures of the Present Invention
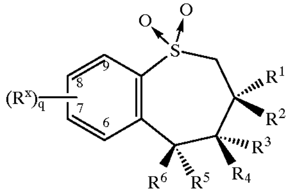
| Compound Number | $R^1$ | $R^2$ | $R^3$ | $R^4$ | $R^5$ | $R^6$ | $(R^x)_q$ |
|---|---|---|---|---|---|---|---|
| 296 | ethyl | n-butyl | OH | H | 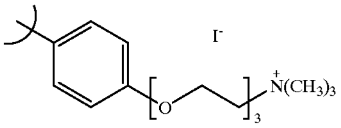 | H | 7-amino |
| 1000 | ethyl | n-butyl | OH | H | 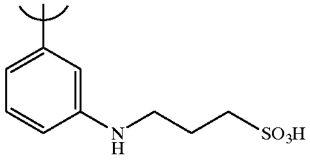 | H | 7-dimethylamino |
| 1001 | ethyl | n-butyl | OH | H | 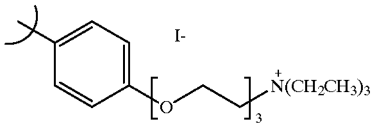 | H | 7-dimethylamino |
| 1002 | ethyl | n-butyl | OH | H | 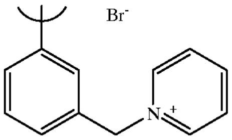 | H | 7-dimethylamino |

-continued
Additional Structures of the Present Invention
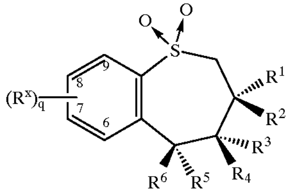
| Compound Number | $R^1$ | $R^2$ | $R^3$ | $R^4$ | $R^5$ | $R^6$ | $(R^x)_q$ |
|---|---|---|---|---|---|---|---|
| 1003 | ethyl | n-butyl | OH | H | 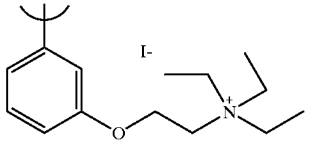 | H | 7-dimethylamino |
| 1004 | ethyl | n-butyl | OH | H | 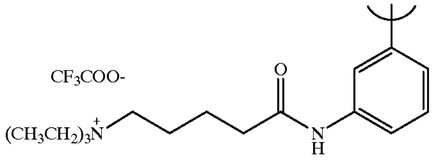 | H | 7-dimethylamino |
| 1005 | n-butyl | n-butyl | OH | H | 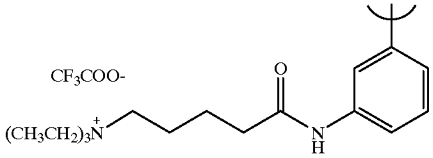 | H | 7-dimethylamino |
| 1006 | n-butyl | n-butyl | OH | H | 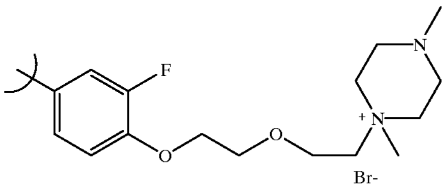 | H | 7-dimethylamino |

-continued

Additional Structures of the Present Invention

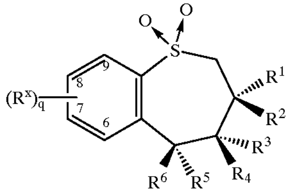

| Compound Number | $R^1$ | $R^2$ | $R^3$ | $R^4$ | $R^5$ | $R^6$ | $(R^x)_q$ |
|---|---|---|---|---|---|---|---|
| 1007 | n-butyl | n-butyl | OH | H | 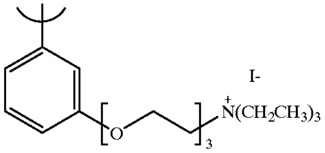 | H | 7-dimethylamino |
| 1008 | n-butyl | n-butyl | OH | H | 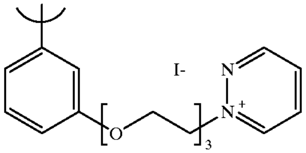 | H | 7-dimethylamino |
| 1009 | n-butyl | n-butyl | OH | H | 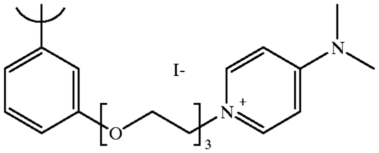 | H | 7-dimethylamino |
| 1010 | n-butyl | n-butyl | OH | H | 3-fluoro-4-methoxyphenyl | H | 7-dimethylamino |
| 1011 | n-butyl | n-butyl | OH | H | 3-fluoro-4-(5-triethylammoniumpentyloxy)phenyl, trifluoroacetate salt | H | 7-dimethylamino |
| 1012 | n-butyl | n-butyl | OH | H | 4-hydroxyphenyl | H | 7-dimethylamino; 9-methoxy |
| 1013 | n-butyl | n-butyl | OH | H | 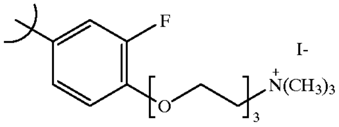 | H | 7-dimethylamino |

-continued
Additional Structures of the Present Invention
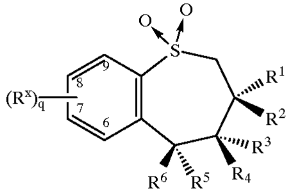
| Compound Number | $R^1$ | $R^2$ | $R^3$ | $R^4$ | $R^5$ | $R^6$ | $(R^x)_q$ |
|---|---|---|---|---|---|---|---|
| 1014 | n-butyl | n-butyl | OH | H | 4-methoxyphenyl | H | 7-dimethylamino; 9-methoxy |
| 1015 | n-butyl | n-butyl | OH | H | 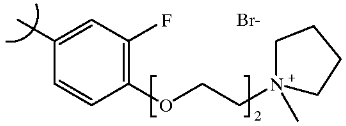 | H | 7-dimethylamino |
| 1016 | n-butyl | n-butyl | OH | H | 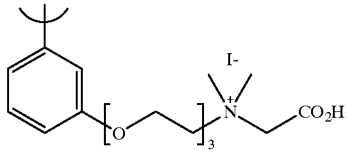 | H | 7-dimethylamino |
| 1017 | n-butyl | n-butyl | OH | H | 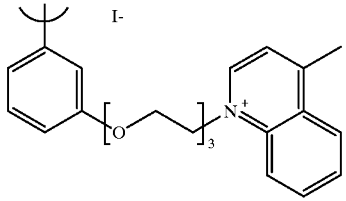 | H | 7-dimethylamino |

-continued
Additional Structures of the Present Invention
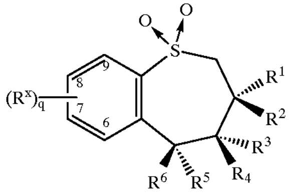
| Compound Number | $R^1$ | $R^2$ | $R^3$ | $R^4$ | $R^5$ | $R^6$ | $(R^x)_q$ |
|---|---|---|---|---|---|---|---|
| 1018 | n-butyl | n-butyl | OH | H | 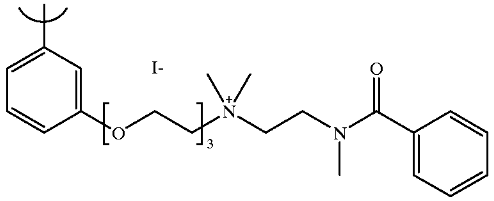 | H | 7-dimethylamino |
| 1019 | n-butyl | n-butyl | OH | H | 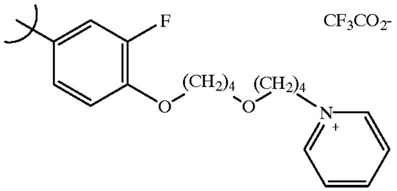 | H | 7-dimethylamino |
| 1020 | n-butyl | n-butyl | OH | H | 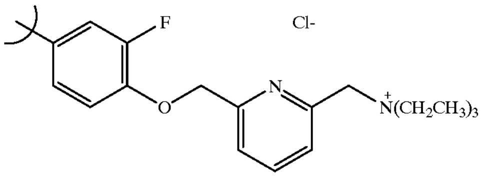 | H | 7-dimethylamino |

-continued
Additional Structures of the Present Invention
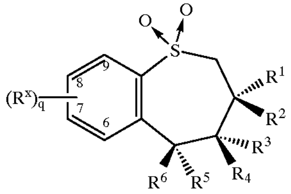
| Compound Number | $R^1$ | $R^2$ | $R^3$ | $R^4$ | $R^5$ | $R^6$ | $(R^x)_q$ |
|---|---|---|---|---|---|---|---|
| 1021 | n-butyl | n-butyl | OH | H | 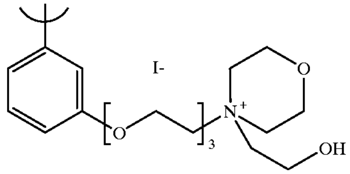 | H | 7-dimethylamino |
| 1022 | n-butyl | n-butyl | OH | H | 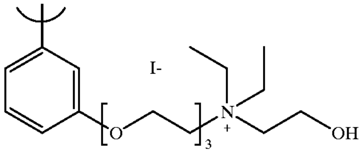 | H | 7-dimethylamino |
| 1023 | n-butyl | n-butyl | OH | H | 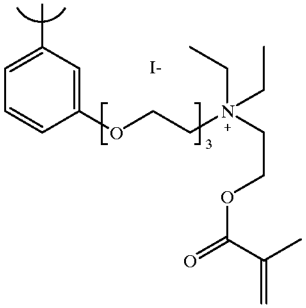 | H | 7-dimethylamino |

-continued
Additional Structures of the Present Invention
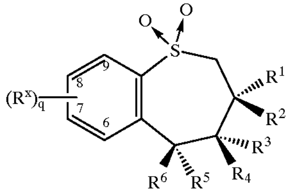
| Compound Number | $R^1$ | $R^2$ | $R^3$ | $R^4$ | $R^5$ | $R^6$ | $(R^x)_q$ |
|---|---|---|---|---|---|---|---|
| 1024 | n-butyl | n-butyl | OH | H | 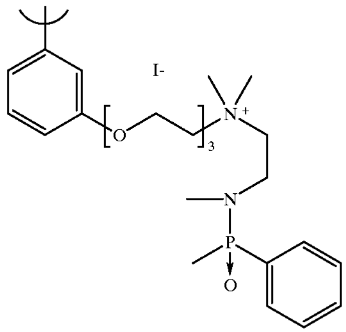 | H | 7-dimethylamino |
| 1025 | n-butyl | n-butyl | OH | H | 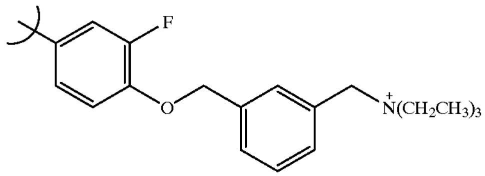 | H | 7-dimethylamino |
| 1026 | n-butyl | n-butyl | OH | H | 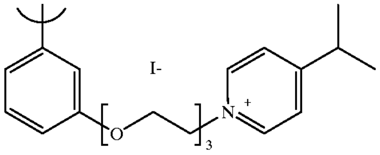 | H | 7-dimethylamino |

-continued
Additional Structures of the Present Invention
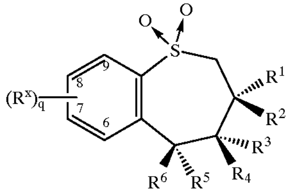
| Compound Number | $R^1$ | $R^2$ | $R^3$ | $R^4$ | $R^5$ | $R^6$ | $(R^x)_q$ |
|---|---|---|---|---|---|---|---|
| 1027 | n-butyl | n-butyl | OH | H | 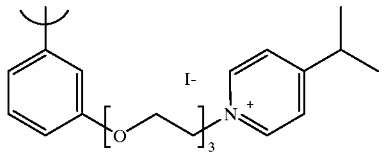 | H | 7-dimethylamino |
| 1028 | n-butyl | n-butyl | OH | H | 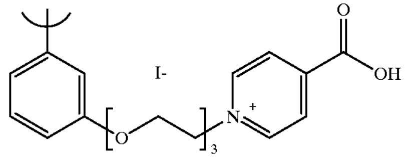 | H | 7-dimethylamino |
| 1029 | n-butyl | n-butyl | OH | H | 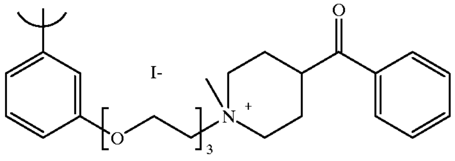 | H | 7-dimethylamino |
| 1030 | n-butyl | n-butyl | OH | H | 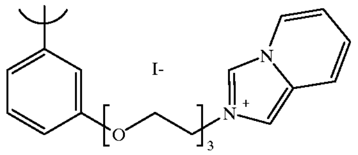 | H | 7-dimethylamino |

-continued
Additional Structures of the Present Invention
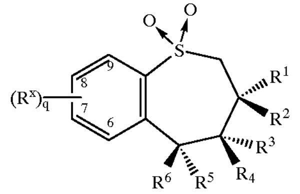
| Compound Number | $R^1$ | $R^2$ | $R^3$ | $R^4$ | $R^5$ | $R^6$ | $(R^x)_q$ |
|---|---|---|---|---|---|---|---|
| 1031 | n-butyl | n-butyl | OH | H | 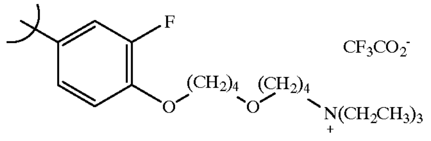 | H | 7-dimethylamino |
| 1032 | n-butyl | n-butyl | OH | H | 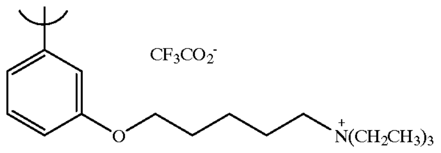 | H | 7-dimethylamino |
| 1033 | n-butyl | n-butyl | OH | H | 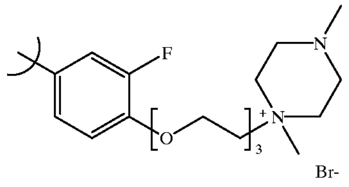 | H | 7-dimethylamino |

-continued
Additional Structures of the Present Invention
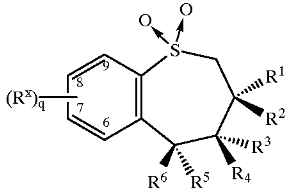
| Compound Number | $R^1$ | $R^2$ | $R^3$ | $R^4$ | $R^5$ | $R^6$ | $(R^x)_q$ |
|---|---|---|---|---|---|---|---|
| 1034 | n-butyl | n-butyl | OH | H | 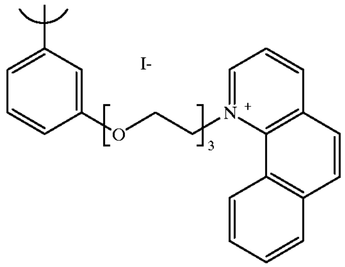 | H | 7-dimethylamino |
| 1035 | n-butyl | n-butyl | OH | H | 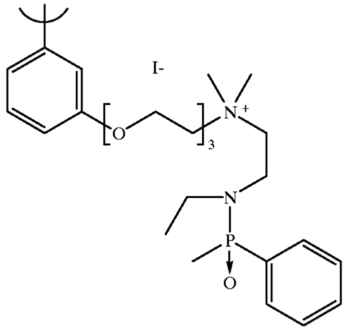 | H | 7-dimethylamino |

-continued
Additional Structures of the Present Invention
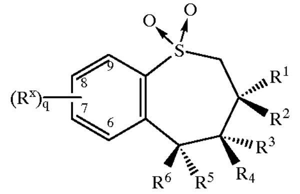
| Compound Number | $R^1$ | $R^2$ | $R^3$ | $R^4$ | $R^5$ | $R^6$ | $(R^x)_q$ |
|---|---|---|---|---|---|---|---|
| 1036 | n-butyl | n-butyl | OH | H | 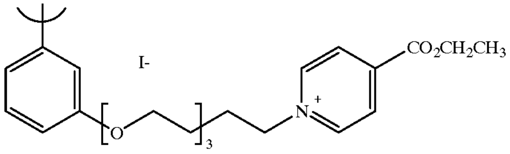 | H | 7-dimethylamino |
| 1037 | n-butyl | n-butyl | OH | H | 4-hydroxyphenyl | H | 7-dimethylamino |
| 1038 | n-butyl | n-butyl | OH | H | 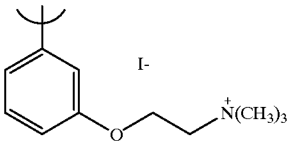 | H | 7-dimethylamino |
| 1039 | n-butyl | n-butyl | OH | H | phenyl | H | 7-dimethylamino |
| 1040 | n-butyl | n-butyl | OH | H | 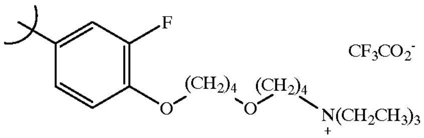 ???How does this differ from 73281? | H | 7-dimethylamino |

-continued
Additional Structures of the Present Invention
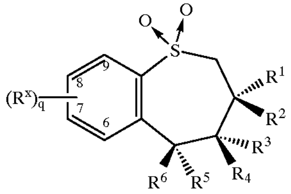
| Compound Number | $R^1$ | $R^2$ | $R^3$ | $R^4$ | $R^5$ | $R^6$ | $(R^x)_q$ |
|---|---|---|---|---|---|---|---|
| 1041 | n-butyl | n-butyl | OH | H | 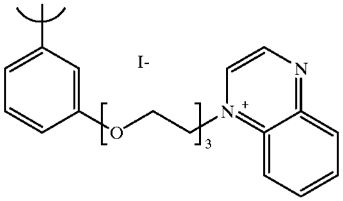 | H | 7-dimethylamino |
| 1042 | n-butyl | n-butyl | OH | H | 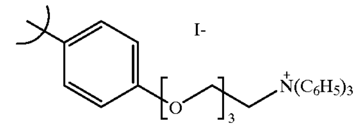 | H | 7-dimethylamino |
| 1043 | n-butyl | n-butyl | OH | H | 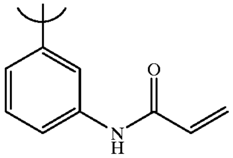 | H | 7-dimethylamino |
| 1044 | n-butyl | n-butyl | OH | H | 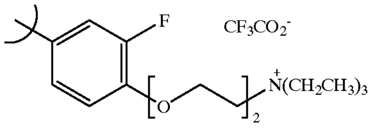 | H | 7-dimethylamino |

-continued
Additional Structures of the Present Invention
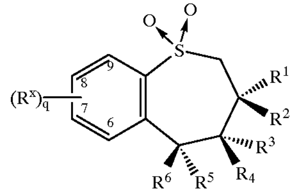
| Compound Number | R¹ | R² | R³ | R⁴ | R⁵ | R⁶ | $(R^x)_q$ |
|---|---|---|---|---|---|---|---|
| 1045 | n-butyl | n-butyl | OH | H | 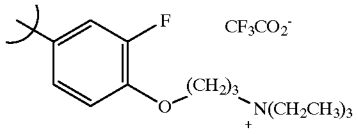 | H | 7-dimethylamino |
| 1046 | n-butyl | n-butyl | OH | H | 3-aminophenyl | H | 7-dimethylamino |
| 1047 | n-butyl | n-butyl | OH | H | 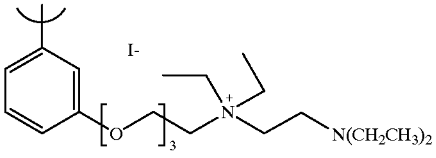 | H | 7-dimethylamino |
| 1048 | n-butyl | n-butyl | OH | H | 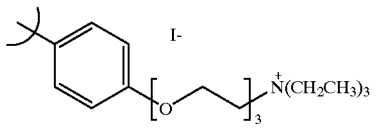 | H | 7-dimethylamino |
| 1049 | n-butyl | n-butyl | OH | H | 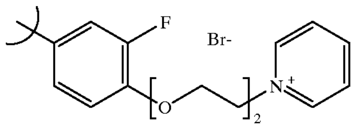 | H | 7-dimethylamino |

-continued
Additional Structures of the Present Invention
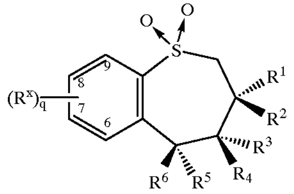
| Compound Number | $R^1$ | $R^2$ | $R^3$ | $R^4$ | $R^5$ | $R^6$ | $(R^x)_q$ |
|---|---|---|---|---|---|---|---|
| 1050 | n-butyl | n-butyl | OH | H | 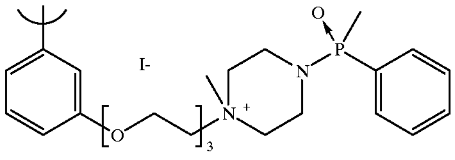 | H | 7-dimethylamino |
| 1051 | n-butyl | n-butyl | OH | H | 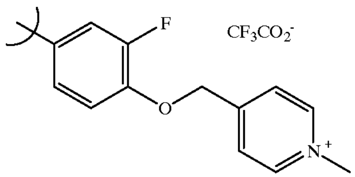 | H | 7-dimethylamino |
| 1052 | n-butyl | n-butyl | OH | H | 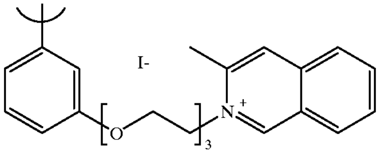 | H | 7-dimethylamino |

-continued
Additional Structures of the Present Invention
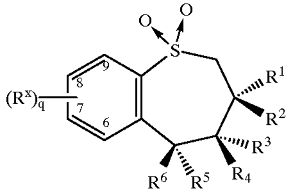
| Compound Number | $R^1$ | $R^2$ | $R^3$ | $R^4$ | $R^5$ | $R^6$ | $(R^x)_q$ |
|---|---|---|---|---|---|---|---|
| 1053 | n-butyl | n-butyl | OH | H | 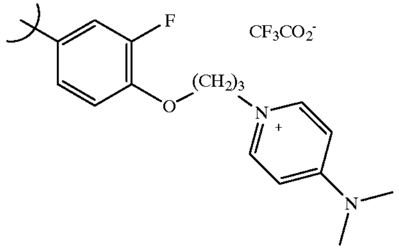 | H | 7-dimethylamino |
| 1054 | n-butyl | n-butyl | OH | H | 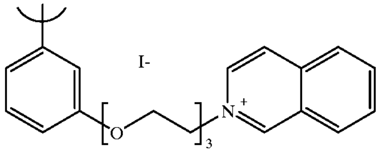 | H | 7-dimethylamino |
| 1055 | n-butyl | n-butyl | OH | H | 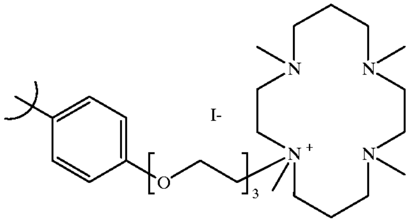 | H | 7-dimethylamino |

-continued
Additional Structures of the Present Invention
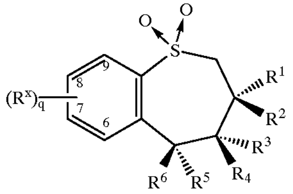
| Compound Number | $R^1$ | $R^2$ | $R^3$ | $R^4$ | $R^5$ | $R^6$ | $(R^x)_q$ |
|---|---|---|---|---|---|---|---|
| 1056 | n-butyl | n-butyl | OH | H | 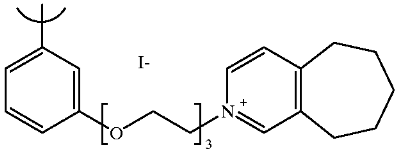 | H | 7-dimethylamino |
| 1057 | n-butyl | n-butyl | OH | H | 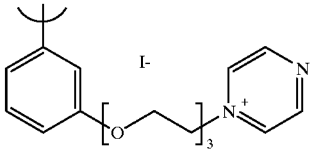 | H | 7-dimethylamino |
| 1058 | n-butyl | n-butyl | OH | H | 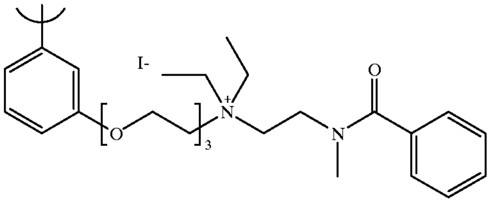 | H | 7-dimethylamino |
| 1059 | n-butyl | n-butyl | OH | H | 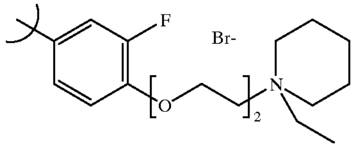 | H | 7-dimethylamino |
| 1060 | ethyl | n-butyl | OH | H | 3-fluoro-4-methoxyphenyl | H | 7-methylamino |

-continued
Additional Structures of the Present Invention
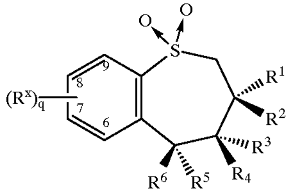
| Compound Number | $R^1$ | $R^2$ | $R^3$ | $R^4$ | $R^5$ | $R^6$ | $(R^x)_q$ |
|---|---|---|---|---|---|---|---|
| 1061 | n-butyl | n-butyl | OH | H | 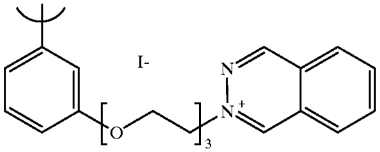 | H | 7-methylamino |
| 1062 | n-butyl | n-butyl | OH | H | 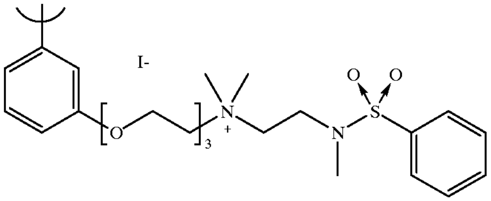 | H | 7-methylamino |
| 1063 | n-butyl | n-butyl | OH | H | 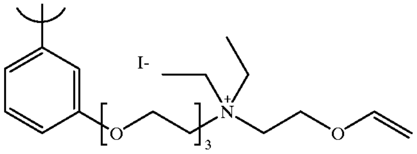 | H | 7-methylamino |

-continued
Additional Structures of the Present Invention
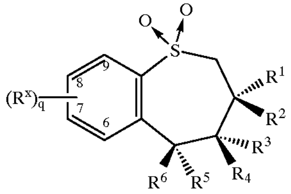
| Compound Number | $R^1$ | $R^2$ | $R^3$ | $R^4$ | $R^5$ | $R^6$ | $(R^x)_q$ |
|---|---|---|---|---|---|---|---|
| 1064 | n-butyl | n-butyl | OH | H | 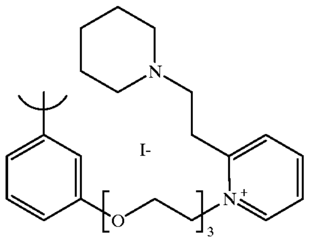 | H | 7-methylamino |
| 1065 | n-butyl | n-butyl | OH | H | 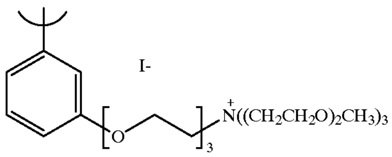 | H | 7-dimethylamino |
| 1066 | n-butyl | n-butyl | OH | H | 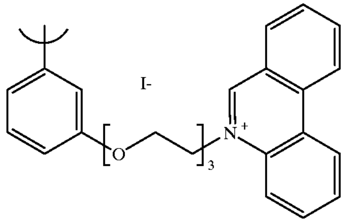 | H | 7-dimethylamino |
| 1067 | n-butyl | n-butyl | OH | H | thiophen-3-yl | H | 9-dimethylamino |

-continued
Additional Structures of the Present Invention
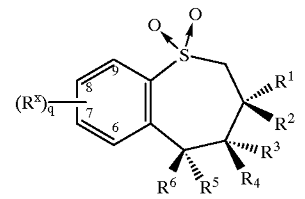
| Compound Number | $R^1$ | $R^2$ | $R^3$ | $R^4$ | $R^5$ | $R^6$ | $(R^x)_q$ |
|---|---|---|---|---|---|---|---|
| 1068 | n-butyl | n-butyl | OH | H | 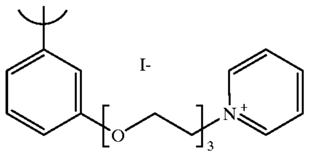 | H | 7-dimethylamino |
| 1069 | n-butyl | n-butyl | OH | H | phenyl | H | 7-dimethylamino; 9-dimethylamino |
| 1070 | n-butyl | n-butyl | OH | H | 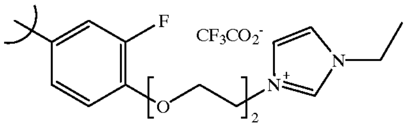 | H | 7-dimethylamino |
| 1071 | n-butyl | n-butyl | OH | H | 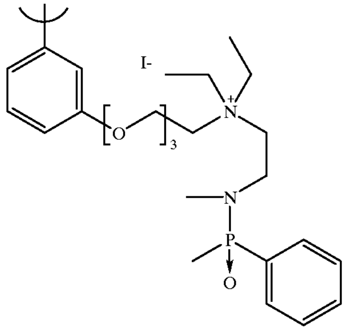 | H | 7-dimethylamino |

-continued

Additional Structures of the Present Invention

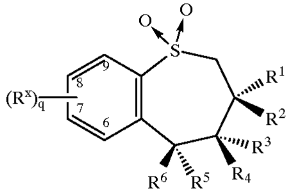

| Compound Number | $R^1$ | $R^2$ | $R^3$ | $R^4$ | $R^5$ | $R^6$ | $(R^x)_q$ |
|---|---|---|---|---|---|---|---|
| 1072 | n-butyl | n-butyl | OH | H | 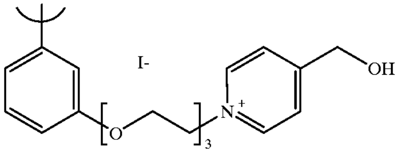 | H | 7-dimethylamino |
| 1073 | n-butyl | n-butyl | OH | H | 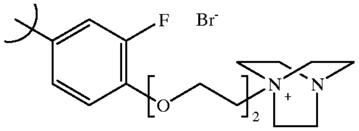 | H | 7-dimethylamino |
| 1074 | ethyl | n-butyl | OH | H | 3-fluoro-4-methoxyphenyl | H | 7-dimethylamino |
| 1075 | n-butyl | n-butyl | OH | H | 4-fluorophenyl | H | 7-dimethylamino; 9-dimethylamino |
| 1076 | n-butyl | n-butyl | OH | H | 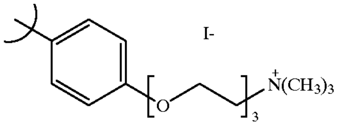 | H | 7-dimethylamino |
| 1077 | n-butyl | n-butyl | OH | H | 3-hydroxymethylphenyl | H | 7-dimethylamino |
| 1078 | ethyl | n-butyl | OH | H | 4-hydroxyphenyl | H | 7-dimethylamino |

-continued
Additional Structures of the Present Invention
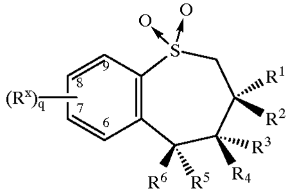
| Compound Number | $R^1$ | $R^2$ | $R^3$ | $R^4$ | $R^5$ | $R^6$ | $(R^x)_q$ |
|---|---|---|---|---|---|---|---|
| 1079 | ethyl | n-butyl | OH | H | 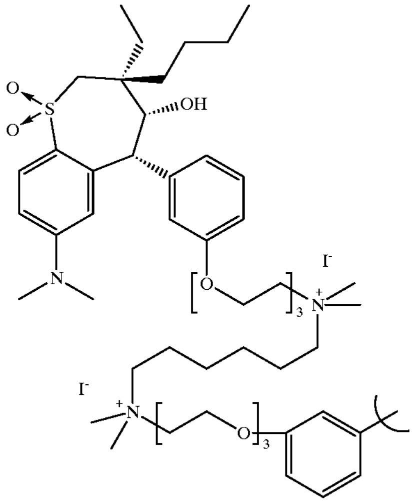 | H | 7-dimethylamino |
| 1080 | n-butyl | n-butyl | OH | H | 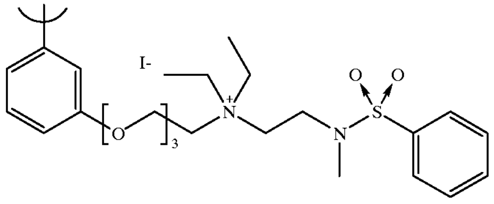 | H | 7-dimethylamino |

-continued
Additional Structures of the Present Invention
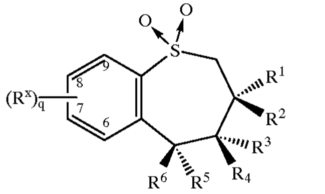
| Compound Number | $R^1$ | $R^2$ | $R^3$ | $R^4$ | $R^5$ | $R^6$ | $(R^x)_q$ |
|---|---|---|---|---|---|---|---|
| 1081 | n-butyl | n-butyl | OH | H | 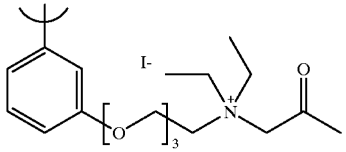 | H | 7-dimethylamino |
| 1082 | n-butyl | n-butyl | OH | H | 2-pyridyl | H | 7-dimethylamino |
| 1083 | n-butyl | n-butyl | OH | H | 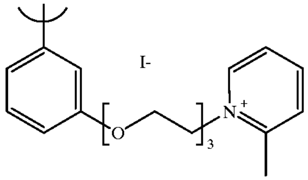 | H | 7-dimethylamino |
| 1084 | n-butyl | n-butyl | OH | H | 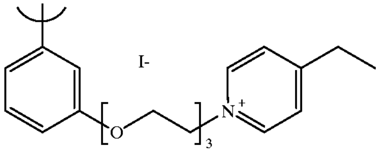 | H | 7-dimethylamino |
| 1085 | n-butyl | n-butyl | OH | H | thiophen-3-yl | H | 7-dimethylamino |

-continued
Additional Structures of the Present Invention
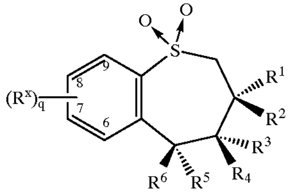
| Compound Number | $R^1$ | $R^2$ | $R^3$ | $R^4$ | $R^5$ | $R^6$ | $(R^x)_q$ |
|---|---|---|---|---|---|---|---|
| 1086 | n-butyl | n-butyl | OH | H | 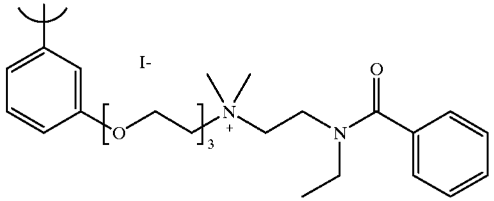 | H | 7-dimethylamino |
| 1087 | n-butyl | n-butyl | OH | H | 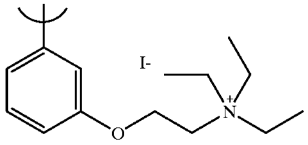 | H | 7-dimethylamino |
| 1088 | ethyl | n-butyl | OH | H | 3,4-methylenedioxyphenyl | H | 7-dimethylamino |
| 1089 | ethyl | n-butyl | OH | H | 4-methoxyphenyl | H | 7-dimethylamino |
| 1090 | n-butyl | n-butyl | OH | H | 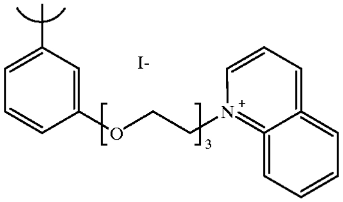 | H | 7-dimethylamino |

-continued
Additional Structures of the Present Invention
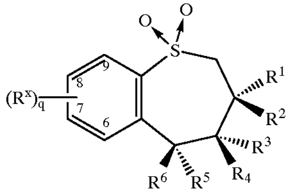
| Compound Number | $R^1$ | $R^2$ | $R^3$ | $R^4$ | $R^5$ | $R^6$ | $(R^x)_q$ |
|---|---|---|---|---|---|---|---|
| 1091 | n-butyl | n-butyl | OH | H | 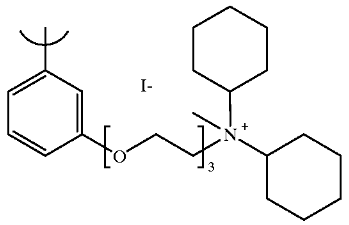 | H | 7-dimethylamino |
| 1092 | n-butyl | n-butyl | OH | H | 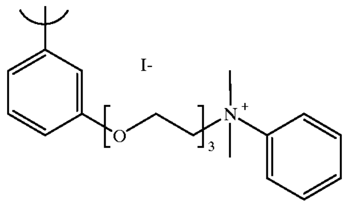 | H | 7-dimethylamino |
| 1093 | n-butyl | n-butyl | OH | H | 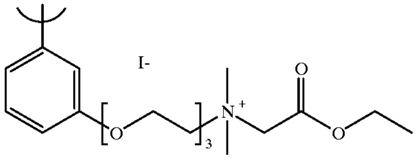 | H | 7-dimethylamino |

-continued
Additional Structures of the Present Invention
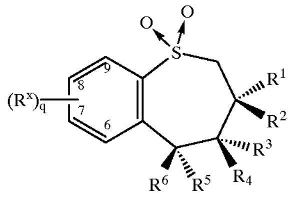
| Compound Number | $R^1$ | $R^2$ | $R^3$ | $R^4$ | $R^5$ | $R^6$ | $(R^x)_q$ |
|---|---|---|---|---|---|---|---|
| 1094 | n-butyl | n-butyl | OH | H | 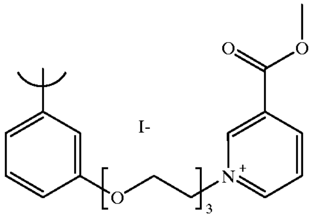 | H | 7-dimethylamino |
| 1095 | n-butyl | n-butyl | OH | H | 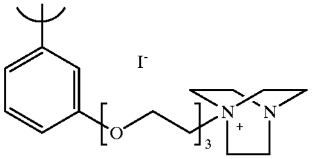 | H | 7-dimethylamino |
| 1096 | n-butyl | n-butyl | OH | H | 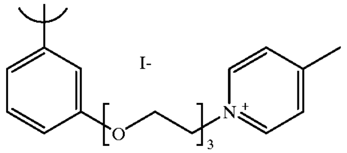 | H | 7-dimethylamino |
| 1097 | n-butyl | n-butyl | OH | H | 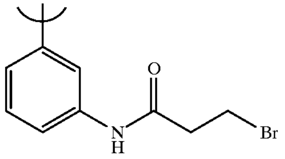 | H | 7-dimethylamino |

-continued

Additional Structures of the Present Invention

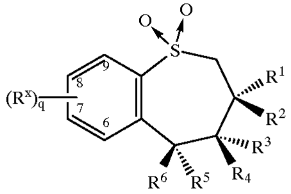

| Compound Number | $R^1$ | $R^2$ | $R^3$ | $R^4$ | $R^5$ | $R^6$ | $(R^x)_q$ |
|---|---|---|---|---|---|---|---|
| 1098 | n-butyl | n-butyl | OH | H | 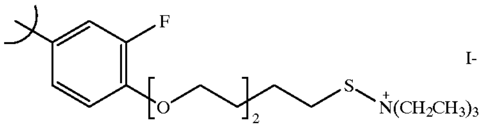 | H | 7-dimethylamino |
| 1099 | ethyl | n-butyl | OH | H | 4-methoxyphenyl | H | 7-dimethylamino |
| 1100 | n-butyl | n-butyl | OH | H | 4-methoxyphenyl | H | 7-dimethylamino |
| 1101 | n-butyl | n-butyl | OH | H | 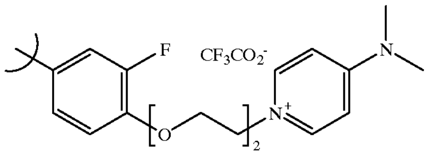 | H | 7-dimethylamino |
| 1102 | n-butyl | n-butyl | OH | H | 3-carboxymethylphenyl | H | 7-dimethylamino |
| 1103 | n-butyl | n-butyl | OH | H | 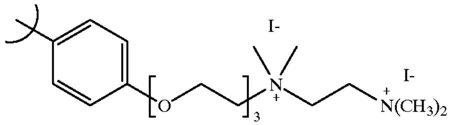 | H | 7-dimethylamino |

-continued
Additional Structures of the Present Invention
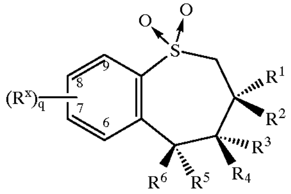
| Compound Number | $R^1$ | $R^2$ | $R^3$ | $R^4$ | $R^5$ | $R^6$ | $(R^x)_q$ |
|---|---|---|---|---|---|---|---|
| 1104 | n-butyl | n-butyl | OH | H | 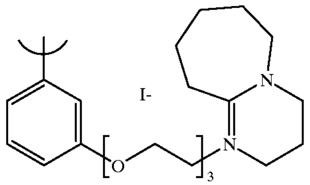 | H | 7-dimethylamino |
| 1105 | n-butyl | n-butyl | OH | H | 5-piperonyl | H | 7-dimethylamino |
| 1106 | n-butyl | n-butyl | OH | H | 3-hydroxyphenyl | H | 7-dimethylamino |
| 1107 | n-butyl | n-butyl | OH | H | 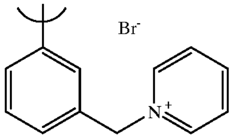 | H | 7-dimethylamino |
| 1108 | n-butyl | n-butyl | OH | H | 3-pyridyl | H | 7-dimethylamino |
| 1109 | n-butyl | n-butyl | OH | H | 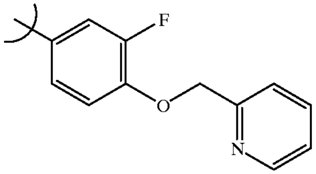 | H | 7-dimethylamino |

-continued

Additional Structures of the Present Invention

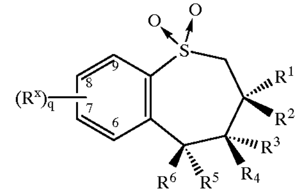

| Compound Number | $R^1$ | $R^2$ | $R^3$ | $R^4$ | $R^5$ | $R^6$ | $(R^x)_q$ |
|---|---|---|---|---|---|---|---|
| 1110 | n-butyl | n-butyl | OH | H | 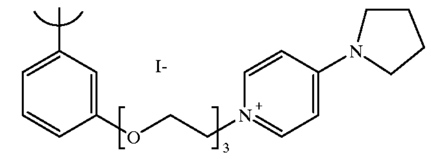 | H | 7-dimethylamino |
| 1111 | n-butyl | n-butyl | OH | H | 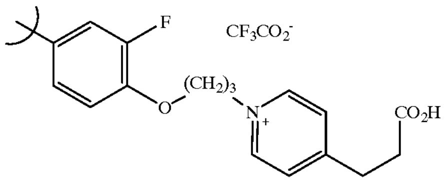 | H | 7-dimethylamino |
| 1112 | n-butyl | n-butyl | OH | H | 4-pyridyl | H | 7-dimethylamino |
| 1113 | n-butyl | n-butyl | OH | H | 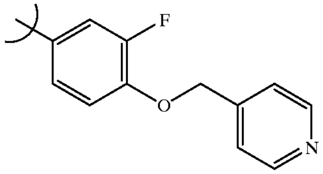 | H | 7-dimethylamino |
| 1114 | n-butyl | n-butyl | OH | H | 3-methoxyphenyl | H | 7-methylamino |
| 1115 | n-butyl | n-butyl | OH | H | 4-fluorophenyl | H | 7-dimethylamino |
| 1116 | ethyl | n-butyl | OH | H | 3-tolyl | H | 7-dimethylamino |

-continued
Additional Structures of the Present Invention
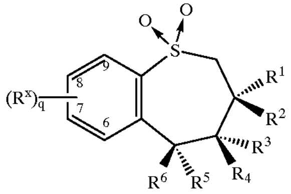
| Compound Number | $R^1$ | $R^2$ | $R^3$ | $R^4$ | $R^5$ | $R^6$ | $(R^x)_q$ |
|---|---|---|---|---|---|---|---|
| 1117 | ethyl | n-butyl | OH | H | 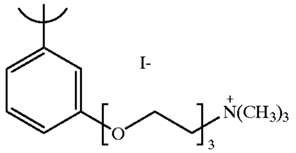 | H | 7-dimethylamino |
| 1118 | ethyl | n-butyl | OH | H | 3-fluoro-4-hydroxyphenyl | H | 7-dimethylamino |
| 1119 | n-butyl | n-butyl | OH | H | 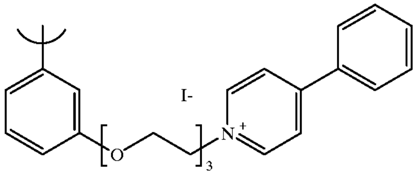 | H | 7-dimethylamino |
| 1120 | n-butyl | n-butyl | OH | H | 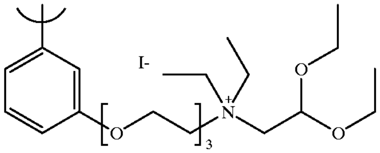 | H | 7-dimethylamino |
| 1121 | n-butyl | n-butyl | OH | H | 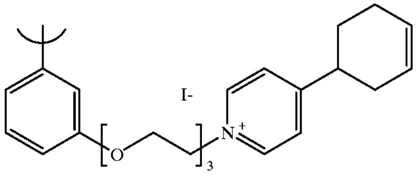 | H | 7-dimethylamino |

-continued

Additional Structures of the Present Invention

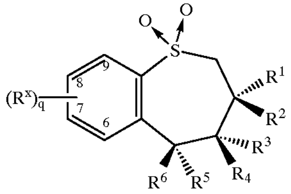

| Compound Number | $R^1$ | $R^2$ | $R^3$ | $R^4$ | $R^5$ | $R^6$ | $(R^x)_q$ |
|---|---|---|---|---|---|---|---|
| 1122 | n-butyl | n-butyl | OH | H | 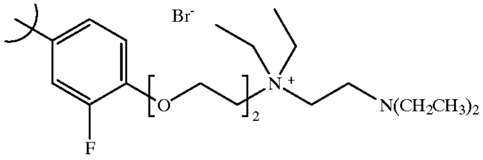 | H | 7-dimethylamino |
| 1123 | n-butyl | n-butyl | OH | H | phenyl | H | 7-dimethylamino |
| 1124 | n-butyl | n-butyl | OH | H | 3-methoxyphenyl | H | 7-dimethylamino |
| 1125 | n-butyl | n-butyl | OH | H | 3-chloro-4-methoxyphenyl | H | 7-dimethylamino |
| 1126 | ethyl | n-butyl | OH | H | 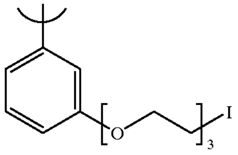 | H | 7-dimethylamino |
| 1127 | n-butyl | n-butyl | OH | H | 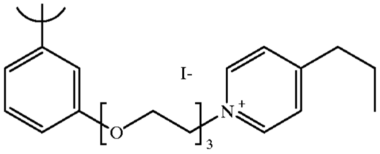 | H | 7-dimethylamino |
| 1128 | n-butyl | n-butyl | OH | H | 3-fluoro-4-hydroxyphenyl | H | 7-dimethylamino |
| 1129 | n-butyl | n-butyl | OH | H | 4-fluorophenyl | H | 9-dimethylamino |
| 1130 | n-butyl | n-butyl | OH | H | 3-chloro-4-fluorophenyl | H | 7-dimethylamino |
| 1131 | ethyl | n-butyl | OH | H | 4-methoxyphenyl | H | 7-dimethylamino |

-continued

Additional Structures of the Present Invention

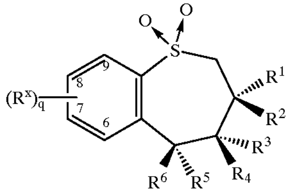

| Compound Number | $R^1$ | $R^2$ | $R^3$ | $R^4$ | $R^5$ | $R^6$ | $(R^x)_q$ |
|---|---|---|---|---|---|---|---|
| 1132 | n-butyl | n-butyl | OH | H | 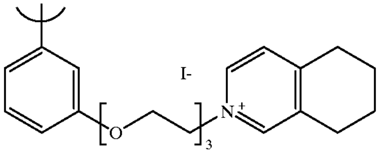 | H | 7-dimethylamino |
| 1133 | n-butyl | n-butyl | OH | H | 4-cyanomethylphenyl | H | 7-dimethylamino |
| 1134 | ethyl | n-butyl | OH | H | 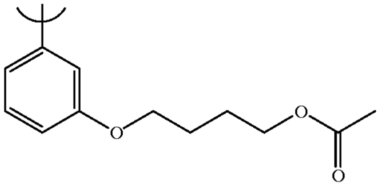 | H | 7-dimethylamino |
| 1135 | n-butyl | n-butyl | OH | H | 3,4-dimethoxyphenyl | H | 7-dimethylamino |
| 1136 | n-butyl | n-butyl | OH | H | 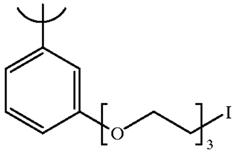 | H | 7-dimethylamino |
| 1137 | n-butyl | n-butyl | OH | H | 4-fluorophenyl | H | 9-(2',1'-dimethylhydrazino) |

-continued

Additional Structures of the Present Invention

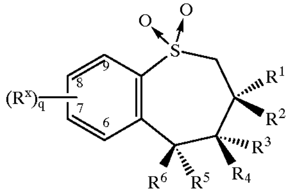

| Compound Number | $R^1$ | $R^2$ | $R^3$ | $R^4$ | $R^5$ | $R^6$ | $(R^x)_q$ |
|---|---|---|---|---|---|---|---|
| 1138 | n-butyl | n-butyl | OH | H | 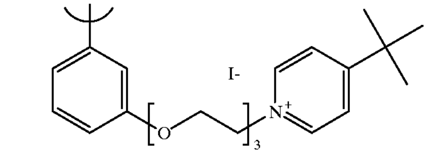 | H | 7-dimethylamino |
| 1139 | n-butyl | n-butyl | OH | H | 3,4-difluorophenyl | H | 7-dimethylamino |
| 1140 | n-butyl | n-butyl | OH | H | 3-methoxyphenyl | H | 7-(2',2'-dimethylhydrazino) |
| 1141 | n-butyl | n-butyl | OH | H | 4-fluorophenyl | H | 7-ethylmethylamino |
| 1142 | n-butyl | n-butyl | OH | H | 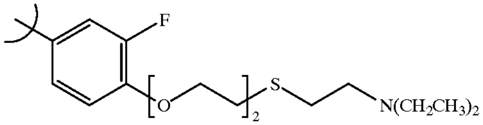 | H | 7-dimethylamino |
| 1143 | n-butyl | n-butyl | H | OH | H | 3-fluoro-4-methoxy-phenyl | 7-dimethylamino |
| 1144 | n-butyl | n-butyl | OH | H | 5-piperonyl | H | 7-dimethylamino |
| 1145 | n-butyl | n-butyl | OH | H | 4-methoxyphenyl | H | 9-dimethylamino |
| 1146 | n-butyl | n-butyl | OH | H | 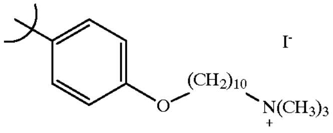 | H | 7-dimethylamino |
| 1147 | n-butyl | n-butyl | OH | H | 3-methoxyphenyl | H | 7-dimethylamino |
| 1148 | n-butyl | n-butyl | OH | H | 4-fluorophenyl | H | 7-dimethylamino, fluoride salt |
| 1149 | n-butyl | n-butyl | OH | H | 4-fluorophenyl | H | 7-ethylamino |
| 1150 | n-butyl | n-butyl | OH | H | 3-methoxyphenyl | H | 7-ethymethylamino |

-continued

Additional Structures of the Present Invention

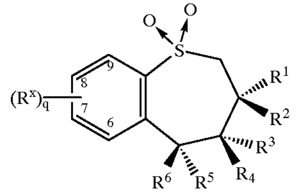

| Compound Number | $R^1$ | $R^2$ | $R^3$ | $R^4$ | $R^5$ | $R^6$ | $(R^x)_q$ |
|---|---|---|---|---|---|---|---|
| 1151 | n-butyl | ethyl | OH | H | 3-fluoro-4-methoxyphenyl | H | 7-dimethylamino |
| 1152 | n-butyl | n-butyl | OH | H | phenyl | H | 7-(ethoxymethyl) methylamino |
| 1153 | n-butyl | n-butyl | OH | H | 4-fluorophenyl | H | 7-methylamino |
| 1154 | n-butyl | n-butyl | OH | H | 3-methoxyphenyl | H | 9-methoxy |
| 1155 | n-butyl | n-butyl | OH | H | 4-fluorophenyl | H | 7-methyl |
| 1156 | n-butyl | n-butyl | OH | H | 4-fluorophenyl | H | 7-methylmercapto |
| 1157 | n-butyl | n-butyl | OH | H | 4-fluorophenyl | H | 7-fluoro; 9-dimethylamino |
| 1158 | n-butyl | n-butyl | OH | H | 4-pyridinyl, hydrochloride salt | H | 7-methoxy |
| 1159 | n-butyl | ethyl | OH | H | phenyl | H | 7-dimethylamino |
| 1160 | n-butyl | n-butyl | OH | H | 4-fluorophenyl | H | 7-diethylamino |
| 1161 | n-butyl | n-butyl | OH | H | 3,5-dichloro-4-methoxyphenyl | H | 7-dimethylamino |
| 1162 | n-butyl | n-butyl | OH | H | phenyl | H | 7-dimethylamino |
| 1163 | n-butyl | n-butyl | OH | H | 3-(dimethylamino)phenyl | H | 7-methoxy |
| 1164 | n-butyl | n-butyl | OH | H | 4-pyridinyl | H | 7-methoxy |
| 1165 | n-butyl | n-butyl | OH | H | 3-fluoro-4-methoxyphenyl | H | 7-trimethylammonium iodide |
| 1166 | n-butyl | n-butyl | OH | H | 3-hydroxyphenyl | H | 7-trimethylammonium iodide |
| 1167 | n-butyl | n-butyl | OH | H | 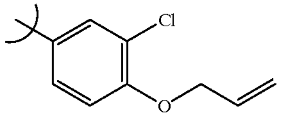 | H | 7-dimethylamino |
| 1168 | n-butyl | n-butyl | OH | H | 4-hydroxyphenyl | H | 7-trimethylammonium iodide |
| 1169 | n-butyl | n-butyl | OH | H | phenyl | H | 8-dimethylamino |
| 1170 | n-butyl | n-butyl | OH | H | 3-methoxyphenyl | H | 7-ethylpropylamino |
| 1171 | n-butyl | n-butyl | OH | H | 4-(trifluoromethysulfonyloxy)phenyl | H | 7-dimethylamino |
| 1172 | n-butyl | n-butyl | OH | H | 4-pyridinyl | H | 7-methoxy |
| 1173 | n-butyl | n-butyl | OH | H | 4-fluorophenyl | H | 7-ethylpropylamino |
| 1174 | ethyl | n-butyl | OH | H | 3-methoxyphenyl | H | 7-phenyl |
| 1175 | ethyl | n-butyl | OH | H | 3-methoxyphenyl | H | 7-methylsulfonyl |
| 1176 | n-butyl | n-butyl | OH | H | 4-fluorophenyl | H | 9-fluoro |
| 1177 | n-butyl | n-butyl | OH | H | 3-methoxyphenyl | H | 7-butylmethylamino |
| 1178 | n-butyl | n-butyl | OH | H | 3-(trifluoromethylsulfonyloxy)phenyl | H | 7-dimethylamino |
| 1179 | n-butyl | n-butyl | OH | H | phenyl | H | 8-methoxy |
| 1180 | n-butyl | n-butyl | OH | H | phenyl | H | 7-trimethylammonium iodide |

-continued

Additional Structures of the Present Invention

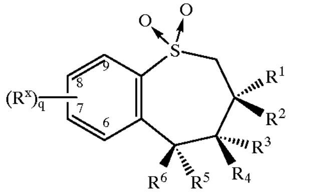

| Compound Number | $R^1$ | $R^2$ | $R^3$ | $R^4$ | $R^5$ | $R^6$ | $(R^x)_q$ |
|---|---|---|---|---|---|---|---|
| 1181 | n-butyl | n-butyl | OH | H | 4-fluorophenyl | H | 7-butylmethylamino |
| 1182 | n-butyl | n-butyl | OH | H | 4-(dimethylamino)phenyl | H | 7-methoxy |
| 1183 | n-butyl | n-butyl | OH | H | 3-methoxyphenyl | H | 7-fluoro |
| 1184 | n-butyl | n-butyl | OH | H | 4-fluorophenyl | H | 7-fluoro; 9-fluoro |
| 1185 | n-butyl | n-butyl | OH | H | 4-fluorophenyl | H | 7-fluoro |
| 1186 | n-butyl | n-butyl | OH | H | phenyl | H | 7-fluoro; 9-fluoro |
| 1187 | n-butyl | n-butyl | OH | H | 4-fluorophenyl | H | 7-methyl |
| 1188 | n-butyl | n-butyl | OH | H | 4-methoxyphenyl | H | 7-trimethylammonium iodide |
| 1189 | n-butyl | n-butyl | OH | H | 3,4-difluorophenyl | H | 7-trimethylammonium iodide |
| 1190 | n-butyl | n-butyl | OH | H | 2-bromophenyl | H | 7-bromo |
| 1191 | n-butyl | n-butyl | OH | H | 4-(dimethylamino)phenyl | H | 7-hydroxy |
| 1192 | n-butyl | n-butyl | OH | H | 3-(dimethylamino)phenyl | H | 7-hydroxy |
| 1193 | n-butyl | n-butyl | OH | H | 4-(2-(2-methylpropyl))phenyl | H | 7-dimethylamino |
| 1194 | n-butyl | n-butyl | OH | H | 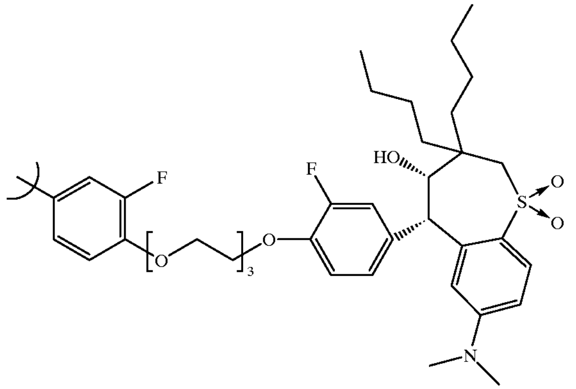 | H | 7-dimethylamino |
| 1195 | n-butyl | n-butyl | OH | H | 4-methoxyphenyl | H | 7-(4'-methylpiperazin-l-yl) |

-continued
Additional Structures of the Present Invention
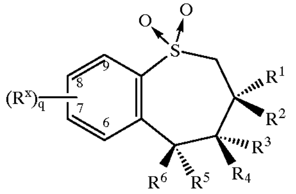
| Compound Number | $R^1$ | $R^2$ | $R^3$ | $R^4$ | $R^5$ | $R^6$ | $(R^x)_q$ |
|---|---|---|---|---|---|---|---|
| 1196 | n-butyl | n-butyl | OH | H | 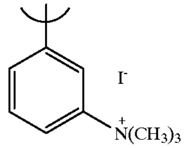 | H | 7-methoxy |
| 1197 | n-butyl | ethyl | R3 + R4 = oxo | R3 + R4 = oxo | phenyl | H | 7-(N-methylformamido) |
| 1198 | n-butyl | n-butyl | OH | H | 4-(pyridinyl-N-oxide) | H | 7-methoxy |
| 1199 | n-butyl | n-butyl | OH | H | 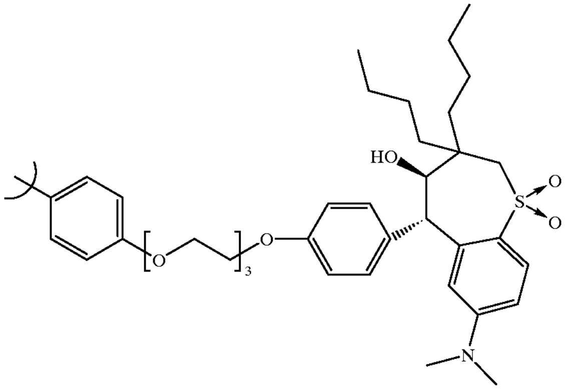 | H | 7-dimethylamino |
| 1200 | n-butyl | n-butyl | H | OH | H | phenyl | 7-dimethylamino |
| 1201 | n-butyl | n-butyl | OH | H | H | H | 7-methyl |

-continued

Additional Structures of the Present Invention

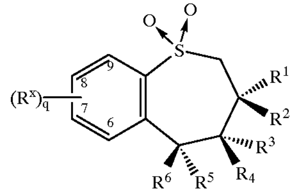

| Compound Number | $R^1$ | $R^2$ | $R^3$ | $R^4$ | $R^5$ | $R^6$ | $(R^x)_q$ |
| --- | --- | --- | --- | --- | --- | --- | --- |
| 1202 | n-butyl | n-butyl | OH | H | 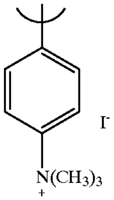 | H | 7-methoxy |
| 1203 | n-butyl | n-butyl | OH | H | 5-piperazinyl | H | 7-(4'-tert-butylphenyl) |
| 1204 | n-butyl | n-butyl | OH | H | 4-fluorophenyl | H | 7-methoxy |
| 1205 | n-butyl | n-butyl | OH | H | 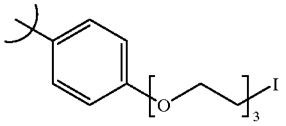 | H | 7-dimethylamino |
| 1206 | n-butyl | n-butyl | OH | H | 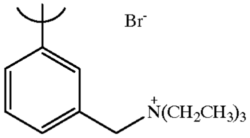 | H | 7-dimethylamino |
| 1207 | n-butyl | n-butyl | OH | H | 3,5-dichlorophenyl | H | 7-dimethylamino |
| 1208 | n-butyl | n-butyl | OH | H | 4-methoxyphenyl | H | 7-dimethylamino |
| 1209 | n-butyl | n-butyl | acetoxy | H | phenyl | H | 7-dimethylphenyl |
| 1210 | n-butyl | n-butyl | OH | H | 2-(dimethylamino)phenyl | H | 7-dimethylamino |

-continued

Additional Structures of the Present Invention

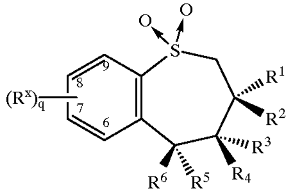

| Compound Number | $R^1$ | $R^2$ | $R^3$ | $R^4$ | $R^5$ | $R^6$ | $(R^x)_q$ |
|---|---|---|---|---|---|---|---|
| 1211 | ethyl | n-butyl | OH | H | 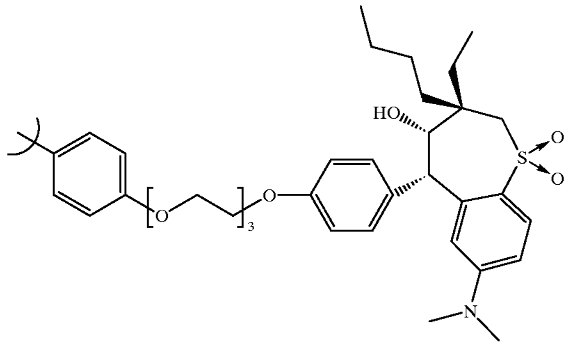 | H | 7-dimethylamino |
| 1212 | n-butyl | n-butyl | OH | H | 4-methoxyphenyl | H | 9-(4'-morpholino) |
| 1213 | n-butyl | ethyl | H | OH | H | 3-fluoro-4-methoxy-phenyl | 7-dimethylamino |
| 1214 | n-butyl | ethyl | OH | H | phenyl | H | 7-(N-methylformamido) |
| 1215 | n-butyl | n-butyl | OH | H | 4-methoxyphenyl | H | 9-methylmercapto |
| 1216 | ethyl | n-butyl | OH | H | 5-piperonyl | H | 7-bromo |
| 1217 | n-butyl | n-butyl | OH | H | 4-caroxyphenyl | H | 7-dimethylamino |
| 1218 | n-butyl | n-butyl | OH | H | 4-methoxyphenyl | H | 9-methylsulfonyl |
| 1219 | n-butyl | n-butyl | OH | H | 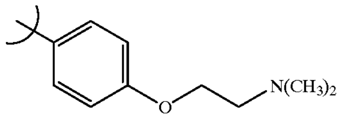 | H | 7-dimethylamino |
| 1220 | n-butyl | n-butyl | OH | H | 3-methoxyphenyl | H | 7-isopropylamino |

-continued

Additional Structures of the Present Invention

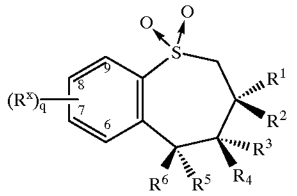

| Compound Number | $R^1$ | $R^2$ | $R^3$ | $R^4$ | $R^5$ | $R^6$ | $(R^x)_q$ |
|---|---|---|---|---|---|---|---|
| 1221 | n-butyl | n-butyl | OH | H | 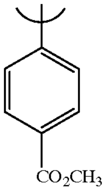 | H | 7-dimethylamino |
| 1222 | n-butyl | n-butyl | OH | H | 3-methoxyphenyl | H | 7-ethylamino |
| 1223 | n-butyl | n-butyl | OH | H | phenyl | H | 8-bromo; 7-methylamino |
| 1224 | n-butyl | n-butyl | OH | H | 3-nitrophenyl | H | 7-fluoro |
| 1225 | n-butyl | ethyl | OH | H | 3-methylphenyl | H | 7-dimethylamino |
| 1226 | ethyl | n-butyl | OH | H | 5-piperonyl | H | 7-bromo |
| 1227 | n-butyl | n-butyl | OH | H | 4-fluorophenyl | H | 7-(tert-butylamino |
| 1228 | n-butyl | n-butyl | OH | H | 2-pyrrolyl | H | 8-bromo; 7-dimethylamino |
| 1229 | n-butyl | n-butyl | OH | H | 3-chloro-4-hydroxyphenyl | H | 7-dimethylamino |
| 1230 | n-butyl | n-butyl | OH | H | phenyl | H | 9-dimethylamino; 7-fluoro |
| 1231 | n-butyl | n-butyl | OH | H | 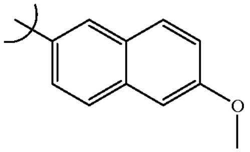 | H | 7-dimethylamino |
| 1232 | n-butyl | n-butyl | H | OH | 3-triophenyl | H | 9-dimethylamino |

-continued
Additional Structures of the Present Invention
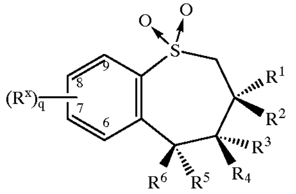
| Compound Number | $R^1$ | $R^2$ | $R^3$ | $R^4$ | $R^5$ | $R^6$ | $(R^x)_q$ |
|---|---|---|---|---|---|---|---|
| 1233 | n-butyl | n-butyl | OH | H | 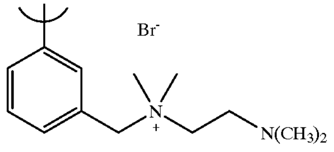 | H | 7-dimethylamino |
| 1234 | n-butyl | n-butyl | OH | H | 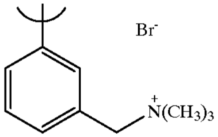 | H | 7-dimethylamino |
| 1235 | n-butyl | n-butyl | OH | H | 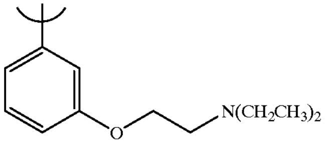 | H | 7-dimethylamino |
| 1236 | n-butyl | n-butyl | OH | H | 4-(bromomethyl)phenyl | H | 7-dimethylamino |
| 1237 | n-butyl | n-butyl | OH | H | 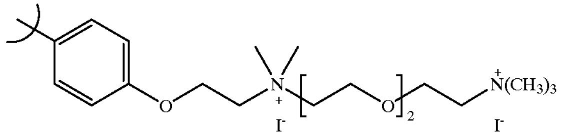 | H | 7-dimethylamino |

-continued

Additional Structures of the Present Invention

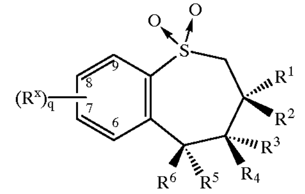

| Compound Number | $R^1$ | $R^2$ | $R^3$ | $R^4$ | $R^5$ | $R^6$ | $(R^x)_q$ |
|---|---|---|---|---|---|---|---|
| 1238 | n-butyl | n-butyl | OH | H | 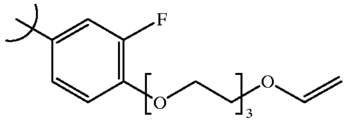 | H | 7-dimethylamino |
| 1239 | n-butyl | n-butyl | OH | H | 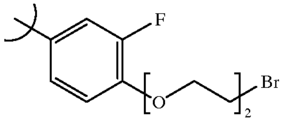 | H | 7-dimethylamino |
| 1240 | n-butyl | n-butyl | OH | H | 4-methoxy-3-methylphenyl | H | 7-dimethylamino |
| 1241 | n-butyl | n-butyl | OH | H | 3-(dimethylaminomethyl)phenyl | H | 7-dimethylamino |
| 1242 | n-butyl | n-butyl | OH | H | 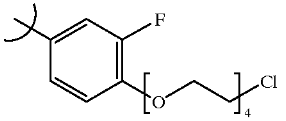 | H | 7-dimethylamino |
| 1243 | n-butyl | n-butyl | OH | H | 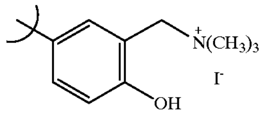 | H | 7-dimethylamino |
| 1244 | n-butyl | n-butyl | OH | H | 3-methoxyphenyl | H | 7-(1'-methylhydrazido) |

-continued

Additional Structures of the Present Invention

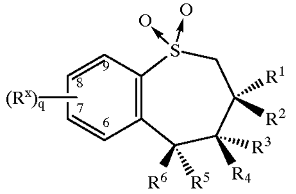

| Compound Number | $R^1$ | $R^2$ | $R^3$ | $R^4$ | $R^5$ | $R^6$ | $(R^x)_q$ |
|---|---|---|---|---|---|---|---|
| 1245 | n-butyl | n-butyl | OH | H | 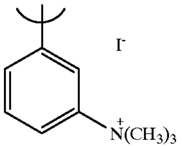 | H | 7-dimethylamino |
| 1246 | n-butyl | n-butyl | OH | H | 3-(bromomethyl)phenyl | H | 7-dimethylamino |
| 1247 | n-butyl | n-butyl | OH | H | 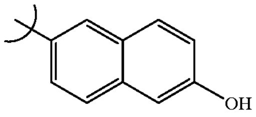 | H | 7-dimethylamino |
| 1248 | n-butyl | n-butyl | OH | H | 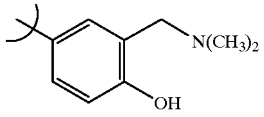 | H | 7-dimethylamino |
| 1249 | n-butyl | n-butyl | OH | H | 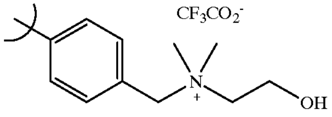 | H | 7-dimethylamino |
| 1250 | n-butyl | n-butyl | OH | H | 3-(dimethylamino)phenyl | H | 7-dimethylamino |
| 1251 | n-butyl | n-butyl | OH | H | 1-naphthyl | H | 7-dimethylamino |

-continued

Additional Structures of the Present Invention

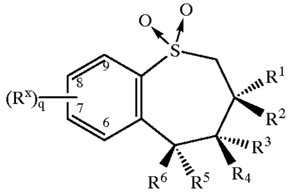

| Compound Number | $R^1$ | $R^2$ | $R^3$ | $R^4$ | $R^5$ | $R^6$ | $(R^x)_q$ |
|---|---|---|---|---|---|---|---|
| 1252 | n-butyl | n-butyl | OH | H | 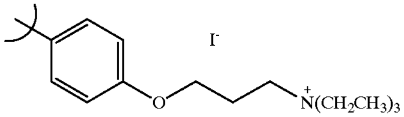 | H | 7-dimethylamino |
| 1253 | n-butyl | n-butyl | OH | H | 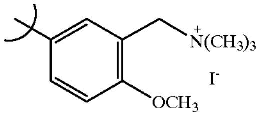 | H | 7-dimethylamino |
| 1254 | n-butyl | n-butyl | OH | H | 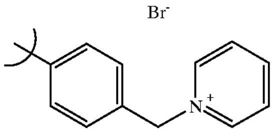 | H | 7-dimethylamino |
| 1255 | n-butyl | n-butyl | OH | H | 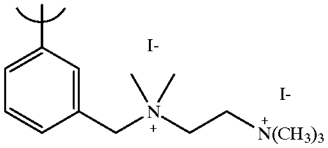 | H | 7-dimethylamino |
| 1256 | n-butyl | n-butyl | OH | H | 3-nitrophenyl | H | 7-dimethylamino |
| 1257 | n-butyl | n-butyl | OH | H | phenyl | H | 8-bromo; 7-dimethylamino |
| 1258 | n-butyl | n-butyl | OH | H | 4-fluorophenyl | H | 9-(tert-butylamino) |
| 1259 | ethyl | n-butyl | H | OH | H | phenyl | 7-dimethylamino |
| 1260 | ethyl | n-butyl | OH | H | 3-hydroxyphenyl | H | 7-dimethylamino |

-continued

Additional Structures of the Present Invention

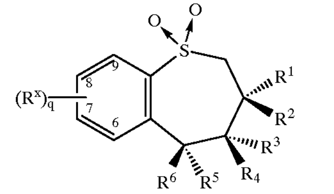

| Compound Number | $R^1$ | $R^2$ | $R^3$ | $R^4$ | $R^5$ | $R^6$ | $(R^x)_q$ |
|---|---|---|---|---|---|---|---|
| 1261 | n-butyl | n-butyl | OH | H | 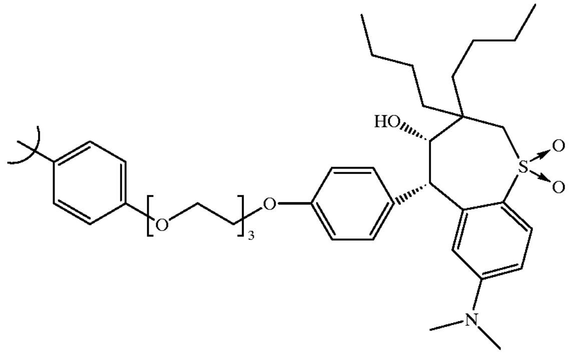 | H | 7-dimethylamino |
| 1262 | n-butyl | n-butyl | OH | H | 2-thiophenyl | H | 7-dimethylamino |
| 1263 | n-butyl | n-butyl | OH | H | 5-piperonyl | H | 7-bromo |
| 1264 | n-butyl | n-butyl | OH | H | 4-fluorophenyl | H | 7-isopropylamino |
| 1265 | n-butyl | n-butyl | OH | H | 4-fluorophenyl | H | 9-osopropylamino |
| 1266 | n-butyl | n-butyl | OH | H | 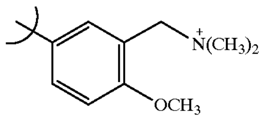 | H | 7-dimethylamino |
| 1267 | n-butyl | ethyl | OH | H | 5-piperonyl | H | 7-carboxy, methyl ester |

-continued
Additional Structures of the Present Invention
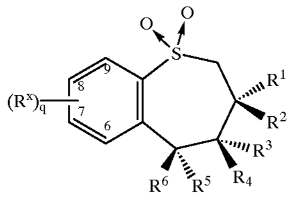
| Compound Number | $R^1$ | $R^2$ | $R^3$ | $R^4$ | $R^5$ | $R^6$ | $(R^x)_q$ |
|---|---|---|---|---|---|---|---|
| 1268 | n-butyl | n-butyl | OH | H | 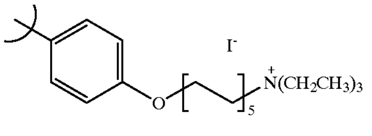 | H | 7-dimethylamino |
| 1269 | n-butyl | n-butyl | OH | H | 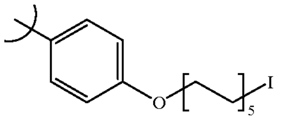 | H | 7-dimethylamino |
| 1270 | n-butyl | n-butyl | OH | H | 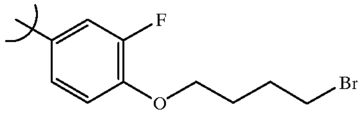 | H | 7-dimethylamino |
| 1271 | n-butyl | n-butyl | OH | H | 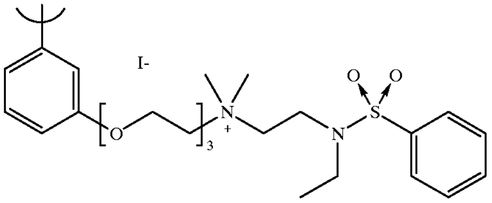 | H | 7-dimethylamino |

-continued
Additional Structures of the Present Invention
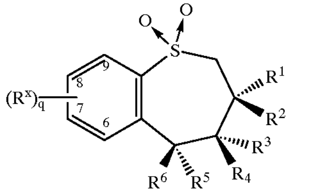
| Compound Number | $R^1$ | $R^2$ | $R^3$ | $R^4$ | $R^5$ | $R^6$ | $(R^x)_q$ |
|---|---|---|---|---|---|---|---|
| 1272 | n-butyl | n-butyl | OH | H | 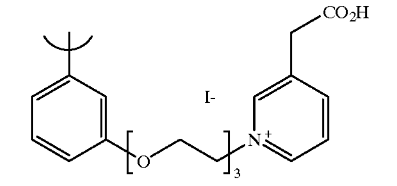 | H | 7-dimethylamino |
| 1273 | n-butyl | n-butyl | OH | H | 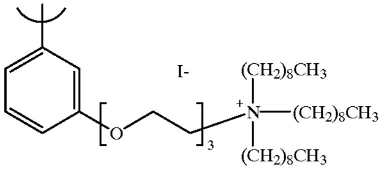 | H | 7-dimethylamino |
| 1274 | n-butyl | n-butyl | OH | H | 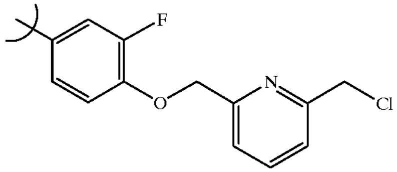 | H | 7-dimethylamino |
| 1275 | n-butyl | n-butyl | OH | H | 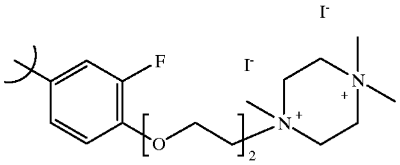 | H | 7-dimethylamino |

-continued
Additional Structures of the Present Invention
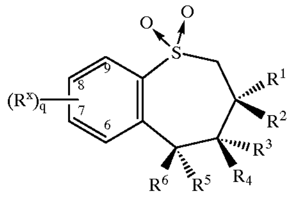
| Compound Number | $R^1$ | $R^2$ | $R^3$ | $R^4$ | $R^5$ | $R^6$ | $(R^x)_q$ |
|---|---|---|---|---|---|---|---|
| 1276 | n-butyl | n-butyl | OH | H | 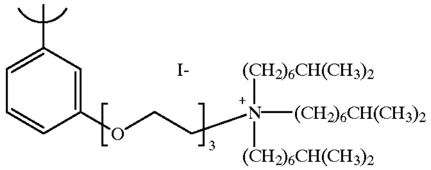 | H | 7-dimethylamino |
| 1277 | n-butyl | n-butyl | OH | H | 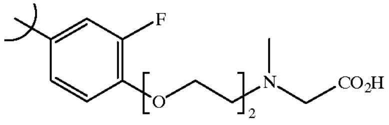 | H | 7-dimethylamino |
| 1278 | n-butyl | n-butyl | OH | H | 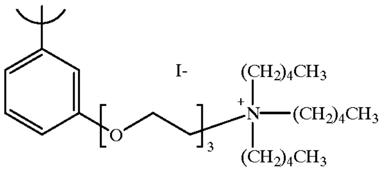 | H | 7-dimethylamino |
| 1279 | n-butyl | n-butyl | OH | H | 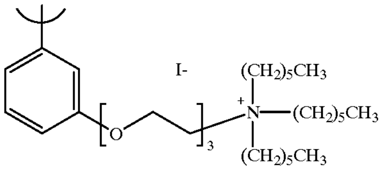 | H | 7-dimethylamino |

-continued

Additional Structures of the Present Invention

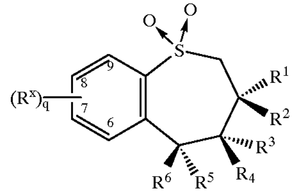

| Compound Number | $R^1$ | $R^2$ | $R^3$ | $R^4$ | $R^5$ | $R^6$ | $(R^x)_q$ |
|---|---|---|---|---|---|---|---|
| 1280 | n-butyl | n-butyl | OH | H | 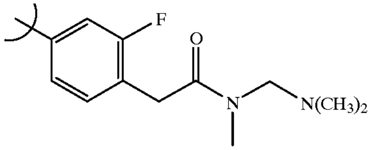 | H | 7-dimethylamino |
| 1281 | n-butyl | n-butyl | OH | H | 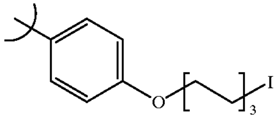 | H | 7-dimethylamino |
| 1282 | ethyl | n-butyl | OH | H | 3-fluoro-4-methoxyphenyl | H | 7-trimethylammonium iodide |
| 1283 | n-butyl | n-butyl | OH | H | 4-hydroxymethylphenyl | H | 7-dimethylamino |
| 1284 | n-butyl | n-butyl | OH | H | 4-fluorophenyl | H | 9-ethylamino |
| 1285 | n-butyl | ethyl | OH | H | phenyl | H | 7-dimethylamino |
| 1286 | n-butyl | n-butyl | OH | H | 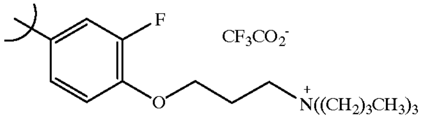 | H | 7-dimethylamino |
| 1287 | n-butyl | ethyl | OH | H | 4-hydroxyphenyl | H | 7-dimethylamino |
| 1288 | n-butyl | n-butyl | OH | H | 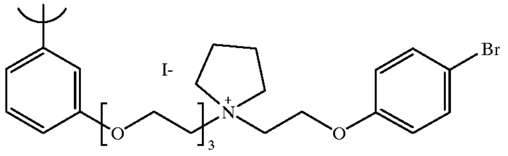 | H | 7-dimethylamino |

-continued
Additional Structures of the Present Invention
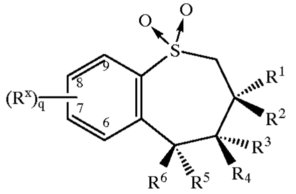
| Compound Number | $R^1$ | $R^2$ | $R^3$ | $R^4$ | $R^5$ | $R^6$ | $(R^x)_q$ |
|---|---|---|---|---|---|---|---|
| 1289 | n-butyl | n-butyl | OH | H | 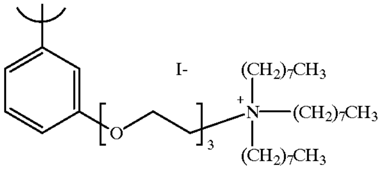 | H | 7-dimethylamino |
| 1290 | n-butyl | n-butyl | OH | H | 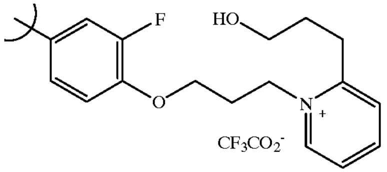 | H | 7-dimethylamino |
| 1291 | n-butyl | n-butyl | OH | H | 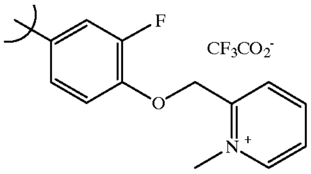 | H | 7-dimethylamino |
| 1292 | n-butyl | n-butyl | OH | H | 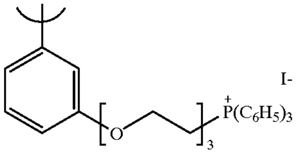 | H | 7-dimethylamino |

-continued
Additional Structures of the Present Invention
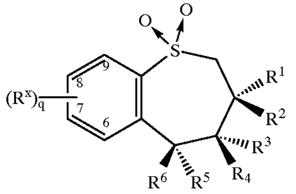
| Compound Number | $R^1$ | $R^2$ | $R^3$ | $R^4$ | $R^5$ | $R^6$ | $(R^x)_q$ |
|---|---|---|---|---|---|---|---|
| 1293 | n-butyl | n-butyl | OH | H | 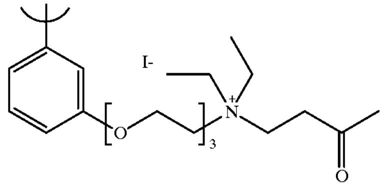 | H | 7-dimethylamino |
| 1294 | n-butyl | n-butyl | OH | H | 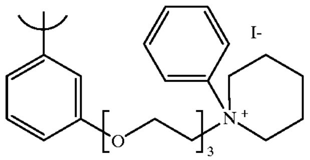 | H | 7-dimethylamino |
| 1295 | n-butyl | n-butyl | OH | H | 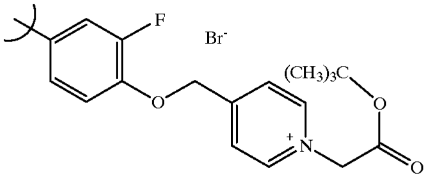 | H | 7-dimethylamino |

-continued
Additional Structures of the Present Invention
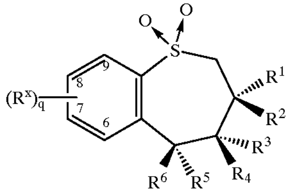
| Compound Number | $R^1$ | $R^2$ | $R^3$ | $R^4$ | $R^5$ | $R^6$ | $(R^x)_q$ |
|---|---|---|---|---|---|---|---|
| 1296 | n-butyl | n-butyl | OH | H | 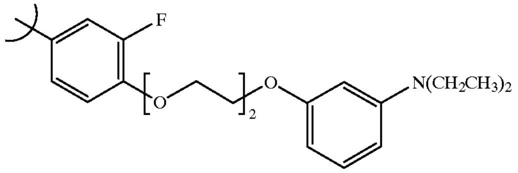 | H | 7-dimethylamino |
| 1297 | n-butyl | n-butyl | OH | H | 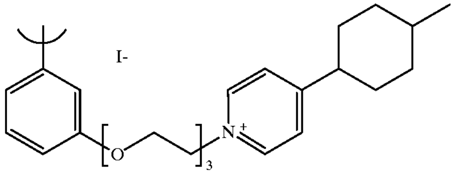 | H | 7-dimethylamino |
| 1298 | n-butyl | n-butyl | OH | H | 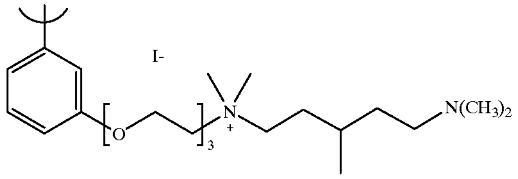 | H | 7-dimethylamino |
| 1299 | n-butyl | n-butyl | OH | H | 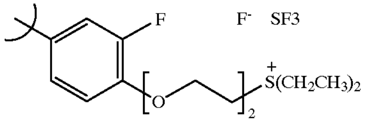 | H | 7-dimethylamino |
| 1300 | n-butyl | ethyl | H | OH | H | phenyl | 7-dimethylamino |

-continued

Additional Structures of the Present Invention

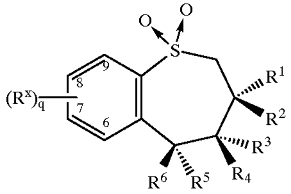

| Compound Number | $R^1$ | $R^2$ | $R^3$ | $R^4$ | $R^5$ | $R^6$ | $(R^x)_q$ |
|---|---|---|---|---|---|---|---|
| 1301 | n-butyl | n-butyl | OH | H | 3-methoxyphenyl | H | 7-trimethylammonium iodide |
| 1302 | n-butyl | n-butyl | OH | H | 3-hydroxyphenyl | H | 9-hydroxy |
| 1303 | n-butyl | n-butyl | OH | H | 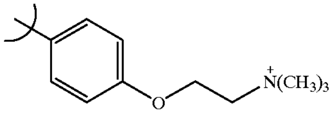 | H | 7-dimethylamino |
| 1304 | n-butyl | n-butyl | OH | H | 3-methoxyphenyl | H | 7-tert-butylamino |
| 1305 | n-butyl | n-butyl | OH | H | 4-fluorophenyl | H | 9-methylamino |
| 1306 | n-butyl | n-butyl | OH | H | 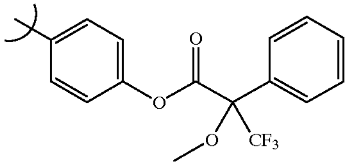 | H | 7-dimethylamino |
| 1307 | n-butyl | n-butyl | OH | H | H | 4-methoxy-phenyl | 9-(4'-morpholino) |
| 1308 | ethyl | n-butyl | OH | H | 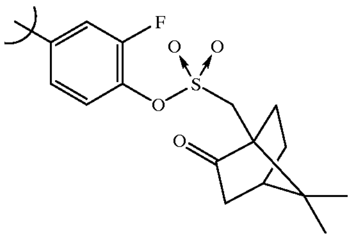 | H | 7-dimethylamino |

-continued

Additional Structures of the Present Invention

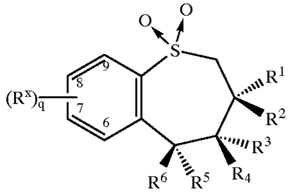

| Compound Number | $R^1$ | $R^2$ | $R^3$ | $R^4$ | $R^5$ | $R^6$ | $(R^x)_q$ |
|---|---|---|---|---|---|---|---|
| 1309 | n-butyl | n-butyl | OH | H | 4-methoxyphenyl | H | 9-fluoro |
| 1310 | ethyl | n-butyl | OH | H | phenyl | H | 7-amino |
| 1311 | n-butyl | ethyl | OH | H | phenyl | H | 7-(hydroxylamino) |
| 1312 | n-butyl | ethyl | OH | H | phenyl | H | 8-hexyloxy |
| 1313 | n-butyl | ethyl | OH | H | phenyl | H | 8-ethoxy |
| 1314 | ethyl | n-butyl | OH | H | phenyl | H | 7-(hydroxylamino) |
| 1315 | ethyl | n-butyl | OH | H | phenyl | H | 7-(hexyloxy) |
| 1316 | n-butyl | ethyl | OH | H | phenyl | H | 8-hydroxy |
| 1317 | n-butyl | ethyl | OH | H | phenyl | H | 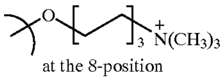 at the 8-position |
| 1318 | ethyl | n-butyl | OH | H | phenyl | H | 7-dimethylamino |
| 1319 | ethyl | n-butyl | OH | H | 3-methoxyphenyl | H | 7-fluoro |
| 1320 | ethyl | n-butyl | OH | H | phenyl | H | 7-amino |
| 1321 | n-butyl | ethyl | OH | H | phenyl | H | 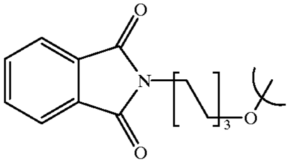 at the 8-position |
| 1322 | n-butyl | n-butyl | OH | H | 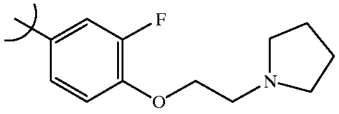 | H | 7-dimethylamino |

-continued
Additional Structures of the Present Invention
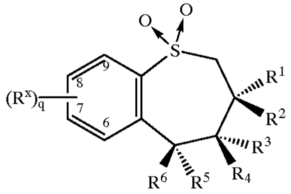
| Compound Number | $R^1$ | $R^2$ | $R^3$ | $R^4$ | $R^5$ | $R^6$ | $(R^x)_q$ |
|---|---|---|---|---|---|---|---|
| 1323 | n-butyl | n-butyl | OH | H | 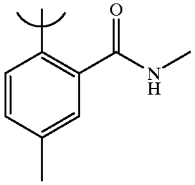 | H | 7-dimethylamino |
| 1324 | n-butyl | n-butyl | OH | H | 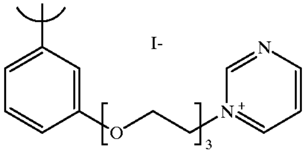 | H | 7-dimethylamino |
| 1325 | n-butyl | n-butyl | OH | H | 4-((diethylamino)methyl)phenyl | H | 7-dimethylamino |
| 1326 | n-butyl | n-butyl | OH | H | 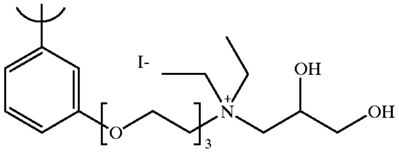 | H | 7-dimethylamino |
| 1327 | n-butyl | n-butyl | OH | H | 3-fluoro-4-hydroxy-5-iodophenyl | H | 7-dimethylamino |

-continued
Additional Structures of the Present Invention
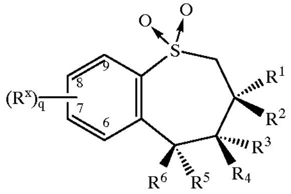
| Compound Number | $R^1$ | $R^2$ | $R^3$ | $R^4$ | $R^5$ | $R^6$ | $(R^x)_q$ |
|---|---|---|---|---|---|---|---|
| 1328 | n-butyl | n-butyl | OH | H | 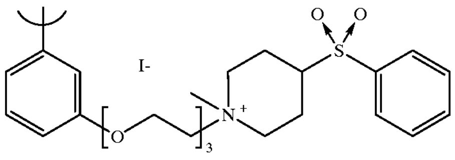 | H | 7-dimethylamino |
| 1329 | n-butyl | n-butyl | OH | H | 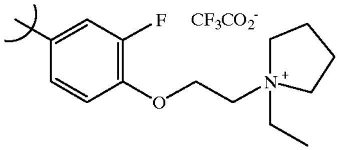 | H | 7-dimethylamino |
| 1330 | n-butyl | n-butyl | OH | H | 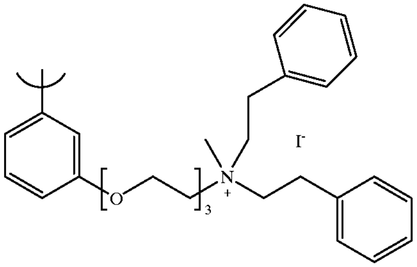 | H | 7-dimethylamino |

-continued
Additional Structures of the Present Invention
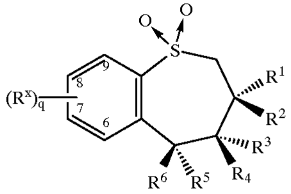
| Compound Number | $R^1$ | $R^2$ | $R^3$ | $R^4$ | $R^5$ | $R^6$ | $(R^x)_q$ |
|---|---|---|---|---|---|---|---|
| 1331 | n-butyl | n-butyl | OH | H | 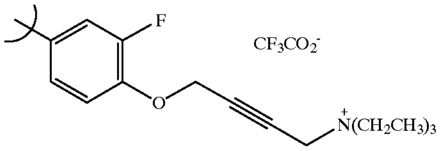 | H | 7-dimethylamino |
| 1332 | n-butyl | n-butyl | OH | H | 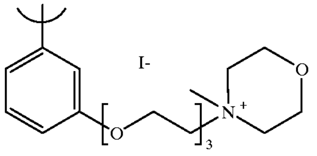 | H | 7-dimethylamino |
| 1333 | n-butyl | n-butyl | OH | H | 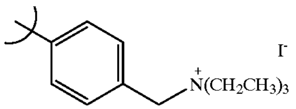 | H | 7-dimethylamino |
| 1334 | n-butyl | n-butyl | OH | H | 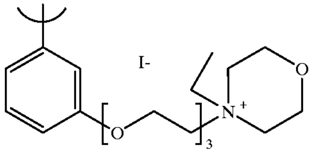 | H | 7-dimethylamino |

-continued
Additional Structures of the Present Invention
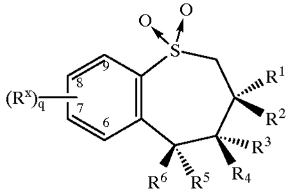
| Compound Number | $R^1$ | $R^2$ | $R^3$ | $R^4$ | $R^5$ | $R^6$ | $(R^x)_q$ |
|---|---|---|---|---|---|---|---|
| 1335 | n-butyl | n-butyl | OH | H | 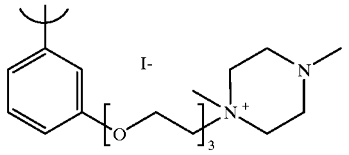 | H | 7-dimethylamino |
| 1336 | n-butyl | n-butyl | OH | H | 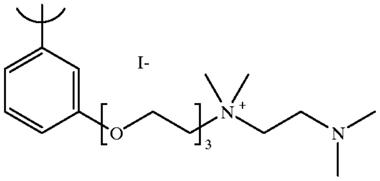 | H | 7-dimethylamino |
| 1337 | n-butyl | n-butyl | OH | H | 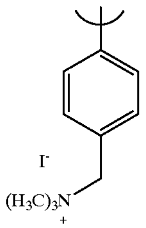 | H | 7-dimethylamino |
| 1338 | n-butyl | n-butyl | OH | H | 4-methoxyphenyl | H | 7-(4'-methylpiperazinyl) |

-continued

Additional Structures of the Present Invention

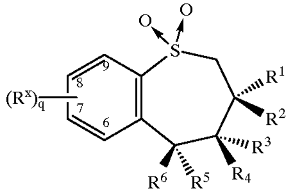

| Compound Number | $R^1$ | $R^2$ | $R^3$ | $R^4$ | $R^5$ | $R^6$ | $(R^x)_q$ |
|---|---|---|---|---|---|---|---|
| 1339 | n-butyl | n-butyl | OH | H | 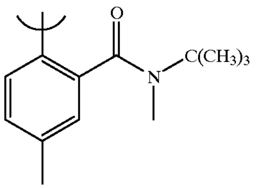 | H | 7-dimethylamino |
| 1340 | n-butyl | ethyl | OH | H | 5-piperonyl | H | 7-methyl |
| 1341 | n-butyl | n-butyl | acetoxy | H | 3-methoxyphenyl | H | 7-dimethylamino |
| 1342 | n-butyl | n-butyl | OH | H | 5-piperonyl | H | 7-(4'-fluorophenyl) |
| 1343 | ethyl | n-butyl | OH | H | phenyl | H | 7-amino |
| 1344 | n-butyl | n-butyl | OH | H | 3-fluoro-4-methoxyphenyl | H | 7-dimethylamino |
| 1345 | ethyl | n-butyl | OH | H | phenyl | H | 7-trimethylammonium iodide |
| 1346 | ethyl | n-butyl | OH | H | phenyl | H | 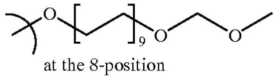 at the 8-position |
| 1347 | n-butyl | n-butyl | OH | H | 3-fluoro-4-methoxyphenyl | H | 7-dimethylamino |
| 1348 | isobutyl | isobutyl | OH | H | phenyl | H | 7-dimethylamino |
| 1349 | ethyl | n-butyl | OH | H | phenyl | H | 7-dimethylamino |
| 1350 | n-butyl | n-butyl | OH | H | 3-fluoro-4-methoxyphenyl | H | 7-trimethylammonium iodide |
| 1351 | n-butyl | n-butyl | OH | H | 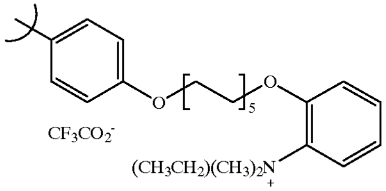 | H | 7-dimethylamino |

-continued
Additional Structures of the Present Invention
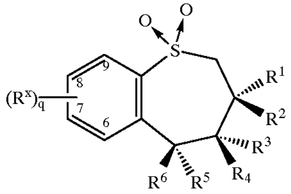
| Compound Number | $R^1$ | $R^2$ | $R^3$ | $R^4$ | $R^5$ | $R^6$ | $(R^x)_q$ |
|---|---|---|---|---|---|---|---|
| 1352 | n-butyl | n-butyl | OH | H | 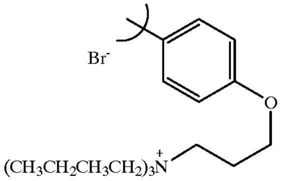 | H | 7-dimethylamino |
| 1353 | n-butyl | n-butyl | OH | H | 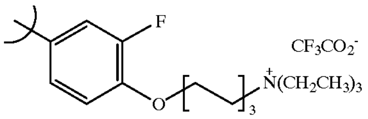 | H | 7-dimethylamino |
| 1354 | n-butyl | n-butyl | OH | H | 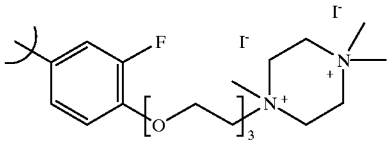 | H | 7-dimethylamino |
| 1355 | n-butyl | n-butyl | OH | H | 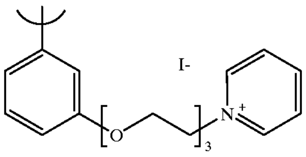 | H | 7-dimethylamino |

-continued
Additional Structures of the Present Invention
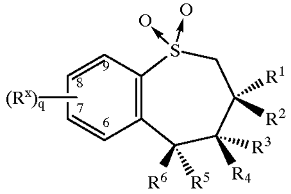
| Compound Number | $R^1$ | $R^2$ | $R^3$ | $R^4$ | $R^5$ | $R^6$ | $(R^x)_q$ |
|---|---|---|---|---|---|---|---|
| 1356 | n-butyl | n-butyl | OH | H | 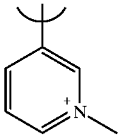 | H | 7-dimethylamino |
| 1357 | n-butyl | n-butyl | OH | H | 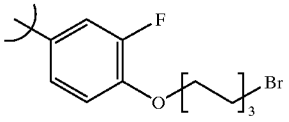 | H | 7-dimethylamino |
| 1358 | n-butyl | n-butyl | OH | H | 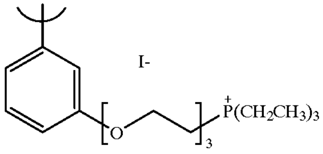 | H | 7-dimethylamino |
| 1359 | n-butyl | n-butyl | OH | H | 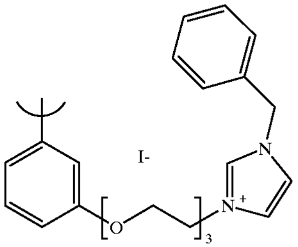 | H | 7-dimethylamino |

-continued
Additional Structures of the Present Invention
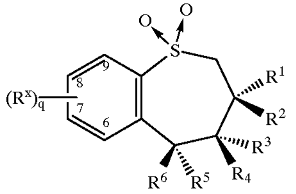
| Compound Number | $R^1$ | $R^2$ | $R^3$ | $R^4$ | $R^5$ | $R^6$ | $(R^x)_q$ |
|---|---|---|---|---|---|---|---|
| 1360 | n-butyl | n-butyl | OH | H | 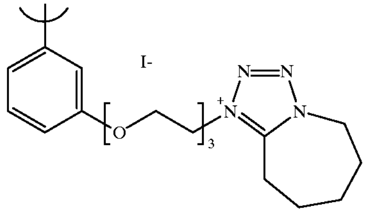 | H | 7-dimethylamino |
| 1361 | n-butyl | n-butyl | OH | H | 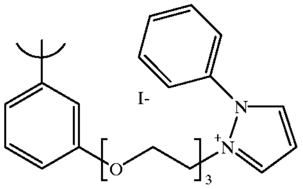 | H | 7-dimethylamino |
| 1362 | n-butyl | n-butyl | OH | H | 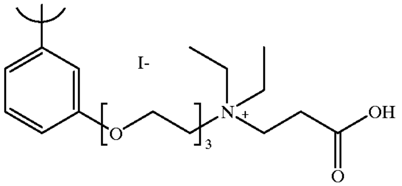 | H | 7-dimethylamino |

-continued
Additional Structures of the Present Invention
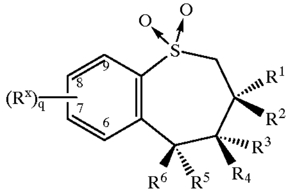
| Compound Number | $R^1$ | $R^2$ | $R^3$ | $R^4$ | $R^5$ | $R^6$ | $(R^x)_q$ |
|---|---|---|---|---|---|---|---|
| 1363 | n-butyl | n-butyl | OH | H | 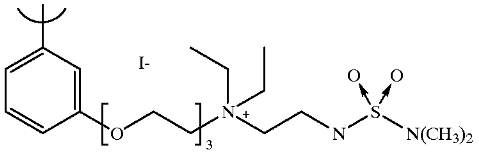 | H | 7-dimethylamino |
| 1364 | n-butyl | n-butyl | OH | H | 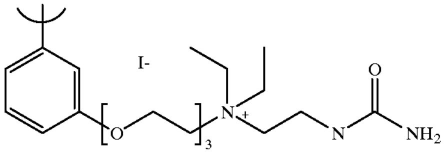 | H | 7-dimethylamino |
| 1365 | n-butyl | n-butyl | OH | H | 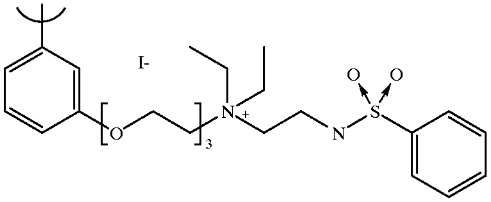 | H | 7-dimethylamino |
| 1366 | n-butyl | n-butyl | OH | H | 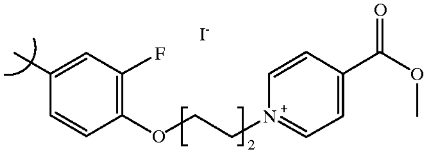 | H | 7-dimethylamino |

-continued
Additional Structures of the Present Invention
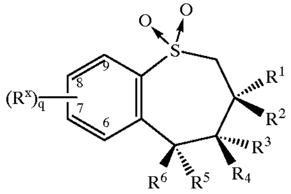
| Compound Number | $R^1$ | $R^2$ | $R^3$ | $R^4$ | $R^5$ | $R^6$ | $(R^x)_q$ |
|---|---|---|---|---|---|---|---|
| 1367 | n-butyl | n-butyl | OH | H | 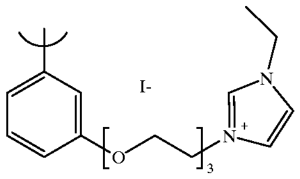 | H | 7-dimethylamino |
| 1368 | n-butyl | n-butyl | OH | H | 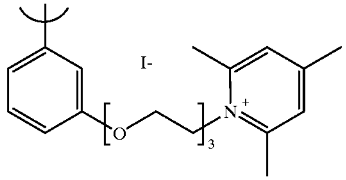 | H | 7-dimethylamino |
| 1369 | n-butyl | n-butyl | OH | H | 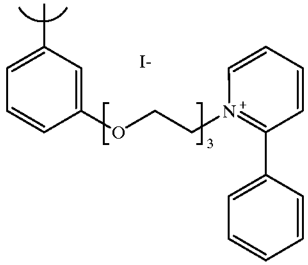 | H | 7-dimethylamino |

-continued
Additional Structures of the Present Invention
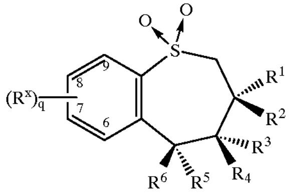
| Compound Number | $R^1$ | $R^2$ | $R^3$ | $R^4$ | $R^5$ | $R^6$ | $(R^x)_q$ |
|---|---|---|---|---|---|---|---|
| 1370 | n-butyl | n-butyl | OH | H | 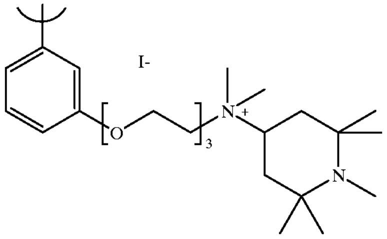 | H | 7-dimethylamino |
| 1371 | n-butyl | n-butyl | OH | H | 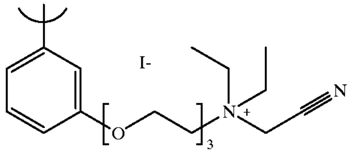 | H | 7-dimethylamino |
| 1372 | n-butyl | n-butyl | OH | H | 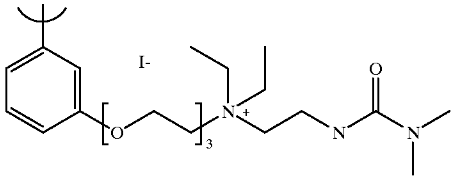 | H | 7-dimethylamino |

-continued
Additional Structures of the Present Invention
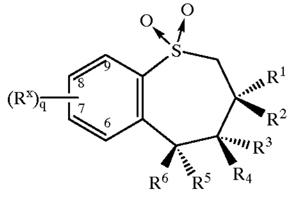
| Compound Number | $R^1$ | $R^2$ | $R^3$ | $R^4$ | $R^5$ | $R^6$ | $(R^x)_q$ |
|---|---|---|---|---|---|---|---|
| 1373 | n-butyl | n-butyl | OH | H | 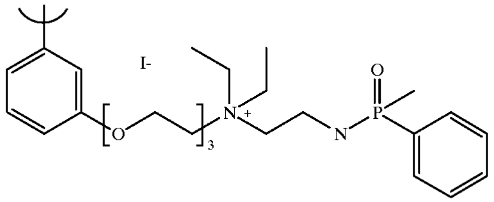 | H | 7-dimethylamino |
| 1374 | n-butyl | n-butyl | OH | H | 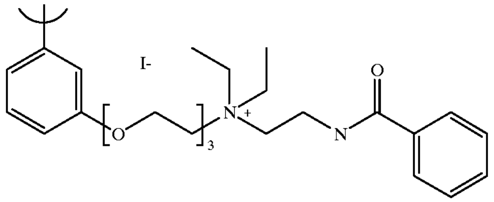 | H | 7-dimethylamino |
| 1375 | n-butyl | n-butyl | OH | H | 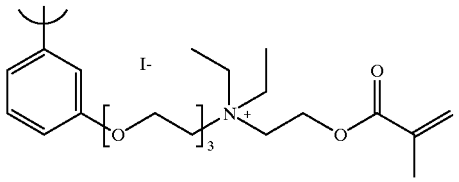 | H | 7-dimethylamino |

-continued
Additional Structures of the Present Invention
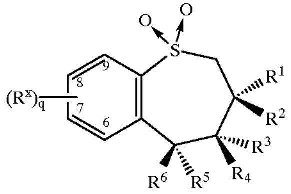
| Compound Number | $R^1$ | $R^2$ | $R^3$ | $R^4$ | $R^5$ | $R^6$ | $(R^x)_q$ |
|---|---|---|---|---|---|---|---|
| 1376 | n-butyl | n-butyl | OH | H | 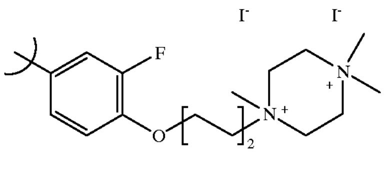 | H | 7-dimethylamino |
| 1377 | n-butyl | n-butyl | OH | H | 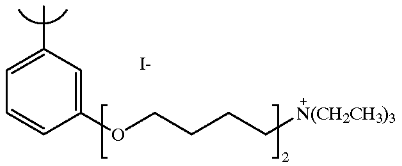 | H | 7-dimethylamino |
| 1378 | n-butyl | n-butyl | OH | H | 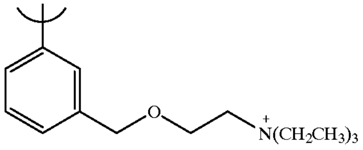 | H | 7-dimethylamino |
| 1379 | n-butyl | n-butyl | OH | H | 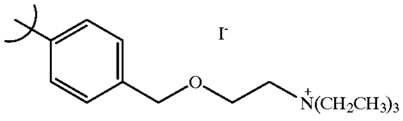 | H | 7-dimethylamino |

-continued
Additional Structures of the Present Invention
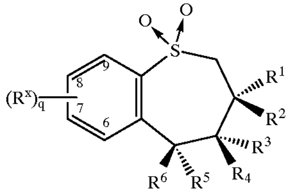
| Compound Number | $R^1$ | $R^2$ | $R^3$ | $R^4$ | $R^5$ | $R^6$ | $(R^x)_q$ |
|---|---|---|---|---|---|---|---|
| 1380 | n-butyl | n-butyl | OH | H | 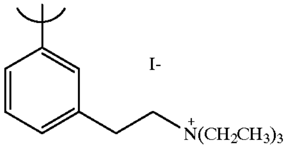 | H | 7-dimethylamino |
| 1381 | n-butyl | n-butyl | OH | H | 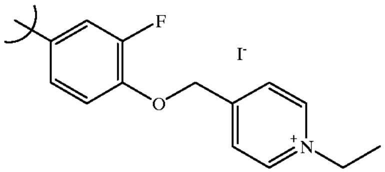 | H | 7-dimethylamino |
| 1382 | n-butyl | n-butyl | OH | H | 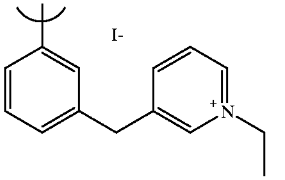 | H | 7-dimethylamino |
| 1383 | n-butyl | n-butyl | OH | H | 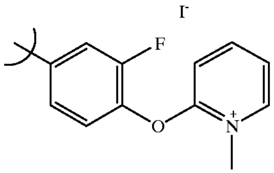 | H | 7-dimethylamino |

-continued
Additional Structures of the Present Invention
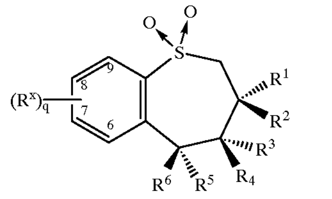
| Compound Number | $R^1$ | $R^2$ | $R^3$ | $R^4$ | $R^5$ | $R^6$ | $(R^x)_q$ |
|---|---|---|---|---|---|---|---|
| 1384 | n-butyl | n-butyl | OH | H | 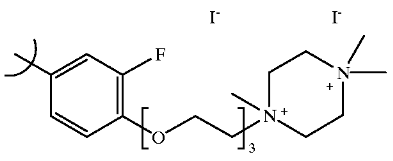 | H | 7-dimethylamino |
| 1385 | n-butyl | n-butyl | OH | H | 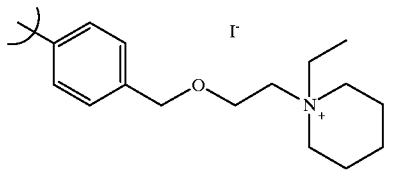 | H | 7-dimethylamino |
| 1386 | n-butyl | n-butyl | OH | H | 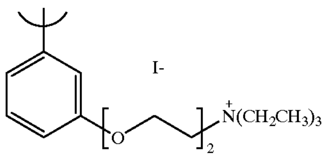 | H | 7-dimethylamino |
| 1387 | n-butyl | n-butyl | OH | H | 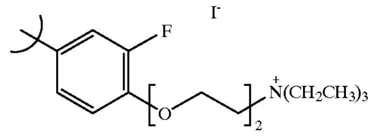 | H | 7-dimethylamino |

-continued
Additional Structures of the Present Invention
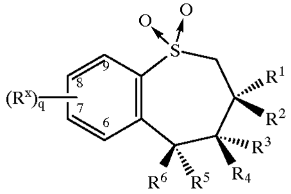
| Compound Number | $R^1$ | $R^2$ | $R^3$ | $R^4$ | $R^5$ | $R^6$ | $(R^x)_q$ |
|---|---|---|---|---|---|---|---|
| 1388 | n-butyl | n-butyl | OH | H | 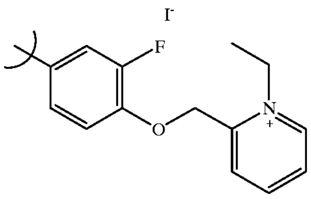 | H | 7-dimethylamino |
| 1389 | n-butyl | n-butyl | OH | H | 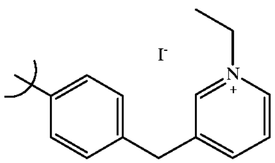 | H | 7-dimethylamino |
| 1390 | n-butyl | n-butyl | OH | H | 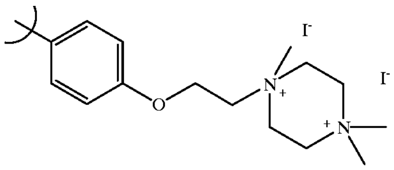 | H | 7-dimethylamino |

-continued
Additional Structures of the Present Invention
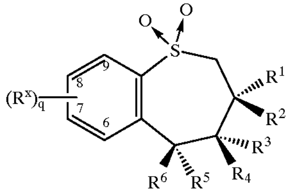
| Compound Number | $R^1$ | $R^2$ | $R^3$ | $R^4$ | $R^5$ | $R^6$ | $(R^x)_q$ |
|---|---|---|---|---|---|---|---|
| 1391 | n-butyl | n-butyl | OH | H | 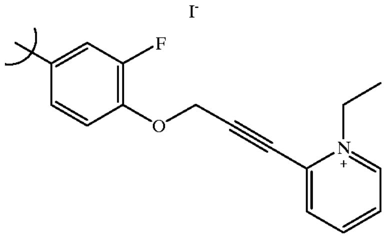 | H | 7-dimethylamino |
| 1392 | n-butyl | n-butyl | OH | H | 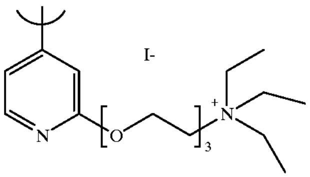 | H | 7-dimethylamino |
| 1393 | n-butyl | n-butyl | OH | H | 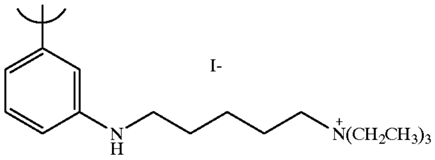 | H | 7-dimethylamino |

-continued
| Additional Structures of the Present Invention | | | | | | | |
|---|---|---|---|---|---|---|---|
| 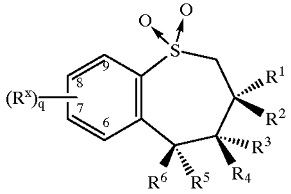 | | | | | | | |
| Compound Number | $R^1$ | $R^2$ | $R^3$ | $R^4$ | $R^5$ | $R^6$ | $(R^x)_q$ |
| 1394 | n-butyl | n-butyl | OH | H | $I^-$ 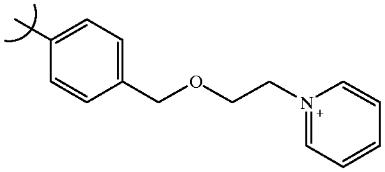 | H | 7-dimethylamino |
| 1395 | n-butyl | n-butyl | OH | H | 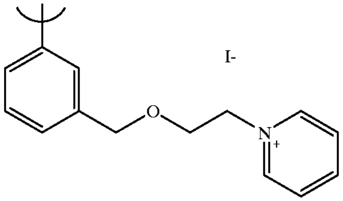 I- | H | 7-dimethylamino |
| 1396 | n-butyl | n-butyl | OH | H | 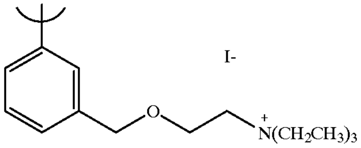 I- | H | 7-dimethylamino |

-continued
Additional Structures of the Present Invention
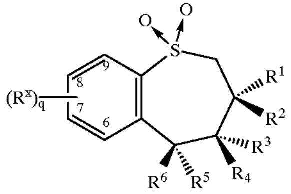
| Compound Number | $R^1$ | $R^2$ | $R^3$ | $R^4$ | $R^5$ | $R^6$ | $(R^x)_q$ |
|---|---|---|---|---|---|---|---|
| 1397 | n-butyl | n-butyl | OH | H | I- 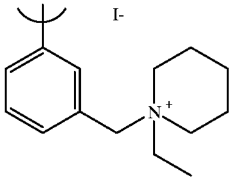 | H | 7-dimethylamino |
| 1398 | n-butyl | n-butyl | OH | H | I- 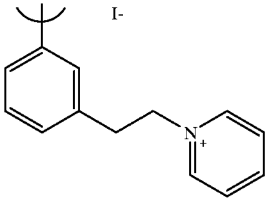 | H | 7-dimethylamino |
| 1399 | n-butyl | n-butyl | OH | H | $I^-$ $I^-$ 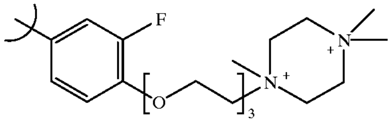 | H | 7-dimethylamino |
| 1400 | n-butyl | n-butyl | OH | H | $I^-$ 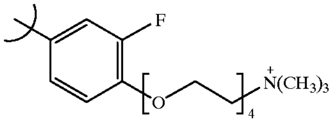 | H | 7-dimethylamino |

-continued
Additional Structures of the Present Invention
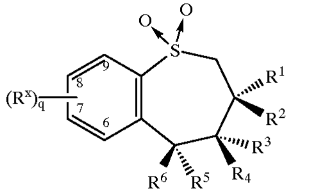
| Compound Number | $R^1$ | $R^2$ | $R^3$ | $R^4$ | $R^5$ | $R^6$ | $(R^x)_q$ |
|---|---|---|---|---|---|---|---|
| 1401 | n-butyl | n-butyl | OH | H | 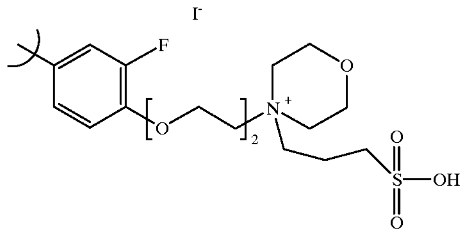 | H | 7-dimethylamino |
| 1402 | n-butyl | n-butyl | OH | H | 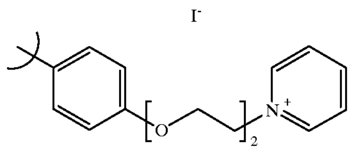 | H | 7-dimethylamino |
| 1403 | n-butyl | n-butyl | OH | H | 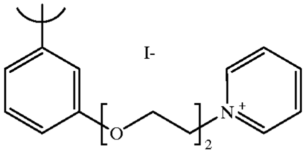 | H | 7-dimethylamino |

-continued
Additional Structures of the Present Invention
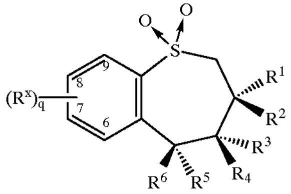
| Compound Number | $R^1$ | $R^2$ | $R^3$ | $R^4$ | $R^5$ | $R^6$ | $(R^x)_q$ |
|---|---|---|---|---|---|---|---|
| 1404 | n-butyl | n-butyl | OH | H | 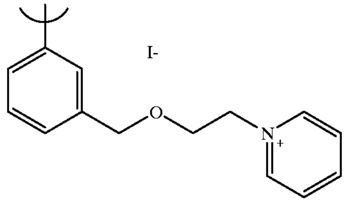 | H | 7-dimethylamino |
| 1405 | n-butyl | n-butyl | OH | H | 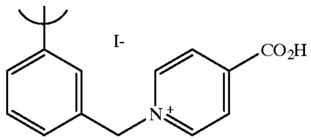 | H | 7-dimethylamino |
| 1406 | n-butyl | n-butyl | OH | H | 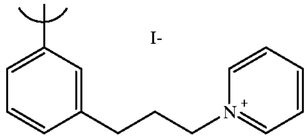 | H | 7-dimethylamino |
| 1407 | n-butyl | n-butyl | OH | H | 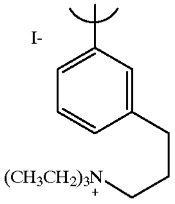 | H | 7-dimethylamino |

-continued
Additional Structures of the Present Invention
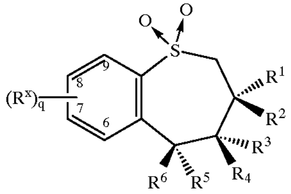
| Compound Number | $R^1$ | $R^2$ | $R^3$ | $R^4$ | $R^5$ | $R^6$ | $(R^x)_q$ |
|---|---|---|---|---|---|---|---|
| 1408 | n-butyl | n-butyl | OH | H | 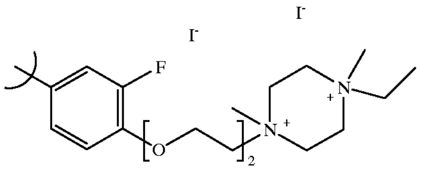 | H | 7-dimethylamino |
| 1409 | n-butyl | n-butyl | OH | H | 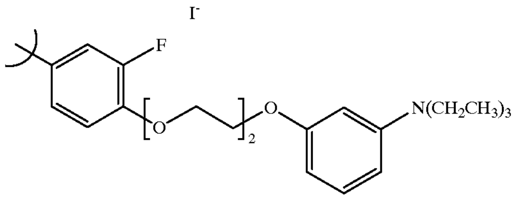 | H | 7-dimethylamino |
| 1410 | n-butyl | n-butyl | OH | H | 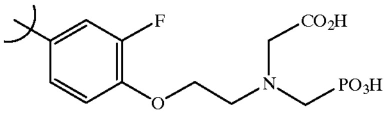 | H | 7-dimethylamino |
| 1411 | n-butyl | n-butyl | OH | H | 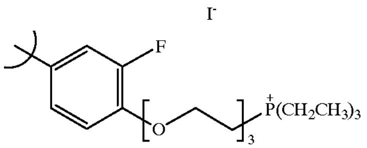 | H | 7-dimethylamino |

-continued
Additional Structures of the Present Invention
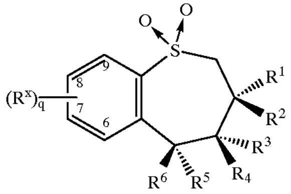
| Compound Number | $R^1$ | $R^2$ | $R^3$ | $R^4$ | $R^5$ | $R^6$ | $(R^x)_q$ |
|---|---|---|---|---|---|---|---|
| 1412 | n-butyl | n-butyl | OH | H | 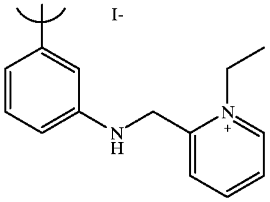 | H | 7-dimethylamino |
| 1413 | n-butyl | n-butyl | OH | H | 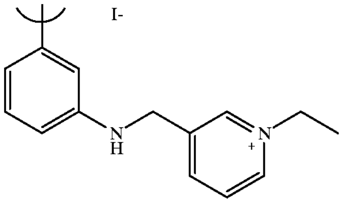 | H | 7-dimethylamino |
| 1414 | n-butyl | n-butyl | OH | H | 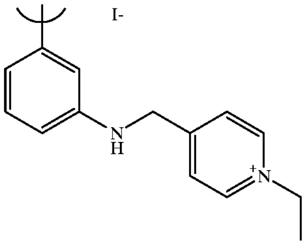 | H | 7-dimethylamino |

-continued
Additional Structures of the Present Invention
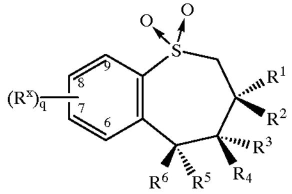
| Compound Number | $R^1$ | $R^2$ | $R^3$ | $R^4$ | $R^5$ | $R^6$ | $(R^x)_q$ |
|---|---|---|---|---|---|---|---|
| 1415 | n-butyl | n-butyl | OH | H | 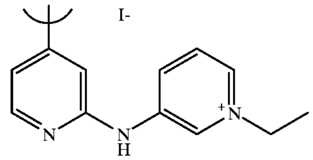 | H | 7-dimethylamino |
| 1416 | n-butyl | n-butyl | OH | H | 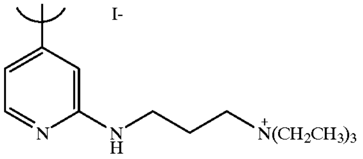 | H | 7-dimethylamino |
| 1417 | n-butyl | n-butyl | OH | H | 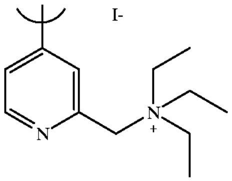 | H | 7-dimethylamino |
| 1418 | n-butyl | n-butyl | OH | H | 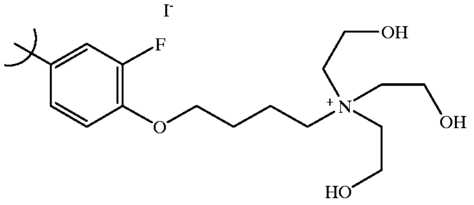 | H | 7-dimethylamino |

-continued
Additional Structures of the Present Invention
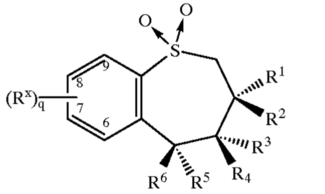
| Compound Number | $R^1$ | $R^2$ | $R^3$ | $R^4$ | $R^5$ | $R^6$ | $(R^x)_q$ |
|---|---|---|---|---|---|---|---|
| 1419 | n-butyl | n-butyl | OH | H | 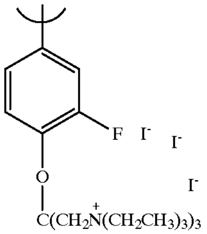 | H | 7-dimethylamino |
| 1420 | n-butyl | n-butyl | OH | H | 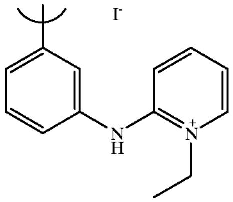 | H | 7-dimethylamino |
| 1421 | n-butyl | n-butyl | OH | H | 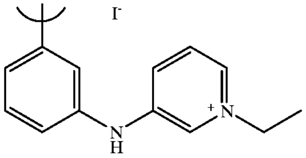 | H | 7-dimethylamino |

-continued
Additional Structures of the Present Invention
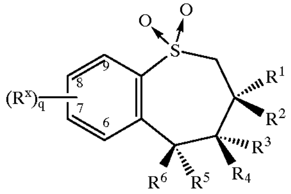
| Compound Number | $R^1$ | $R^2$ | $R^3$ | $R^4$ | $R^5$ | $R^6$ | $(R^x)_q$ |
|---|---|---|---|---|---|---|---|
| 1422 | n-butyl | n-butyl | OH | H | 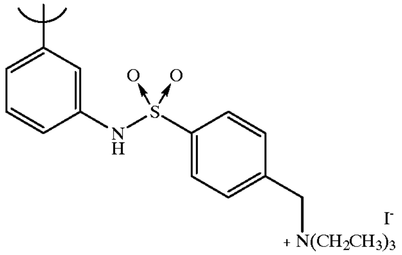 | H | 7-dimethylamino |
| 1423 | n-butyl | n-butyl | OH | H | 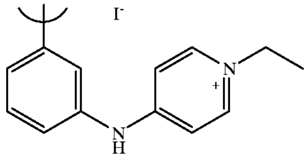 | H | 7-dimethylamino |
| 1424 | n-butyl | n-butyl | OH | H | 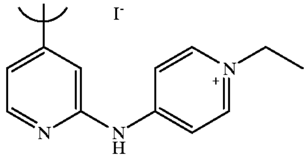 | H | 7-dimethylamino |

-continued
Additional Structures of the Present Invention
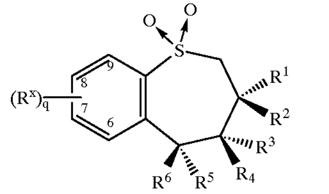
| Compound Number | $R^1$ | $R^2$ | $R^3$ | $R^4$ | $R^5$ | $R^6$ | $(R^x)_q$ |
| --- | --- | --- | --- | --- | --- | --- | --- |
| 1425 | n-butyl | n-butyl | OH | H | 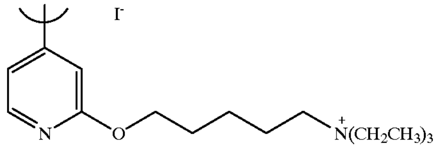 | H | 7-dimethylamino |
| 1426 | n-butyl | n-butyl | OH | H | 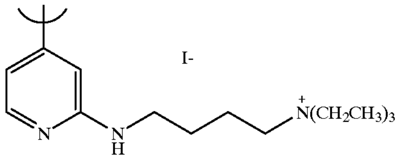 | H | 7-dimethylamino |
| 1427 | n-butyl | n-butyl | OH | H | 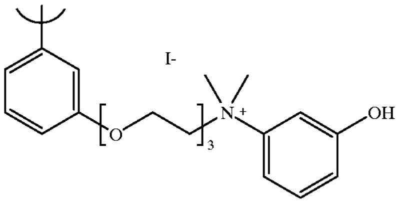 | H | 7-dimethylamino |
| 1428 | n-butyl | n-butyl | OH | H | 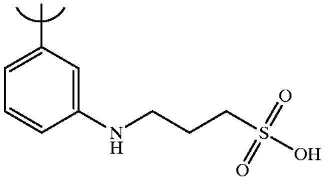 | H | 7-dimethylamino |

-continued
Additional Structures of the Present Invention
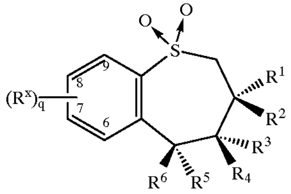
| Compound Number | $R^1$ | $R^2$ | $R^3$ | $R^4$ | $R^5$ | $R^6$ | $(R^x)_q$ |
|---|---|---|---|---|---|---|---|
| 1429 | n-butyl | n-butyl | OH | H | 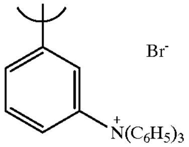 | H | 7-dimethylamino |
| 1430 | n-butyl | n-butyl | OH | H | 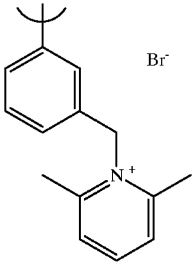 | H | 7-dimethylamino |
| 1431 | n-butyl | n-butyl | OH | H | 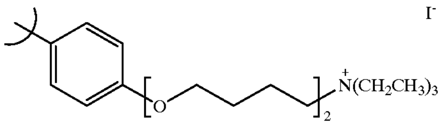 | H | 7-dimethylamino |
| 1432 | n-butyl | n-butyl | OH | H | 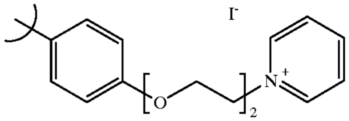 | H | 7-dimethylamino |

-continued
Additional Structures of the Present Invention
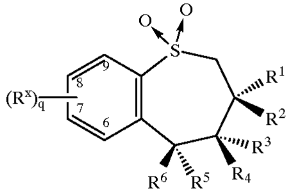
| Compound Number | $R^1$ | $R^2$ | $R^3$ | $R^4$ | $R^5$ | $R^6$ | $(R^x)_q$ |
|---|---|---|---|---|---|---|---|
| 1433 | n-butyl | n-butyl | OH | H | 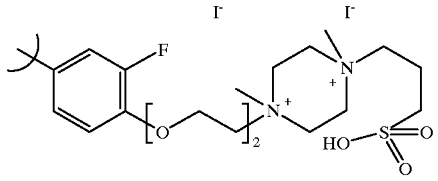 | H | 7-dimethylamino |
| 1434 | n-butyl | n-butyl | OH | H | 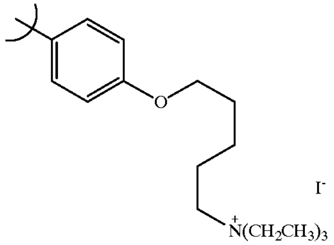 | H | 7-dimethylamino |
| 1435 | n-butyl | n-butyl | OH | H | 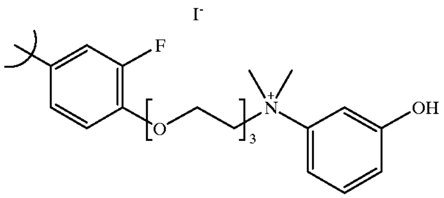 | H | 7-dimethylamino |

-continued
Additional Structures of the Present Invention
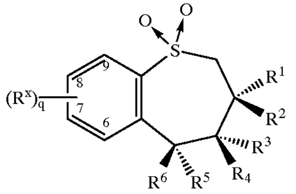
| Compound Number | $R^1$ | $R^2$ | $R^3$ | $R^4$ | $R^5$ | $R^6$ | $(R^x)_q$ |
|---|---|---|---|---|---|---|---|
| 1436 | n-butyl | n-butyl | OH | H | 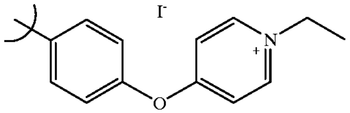 | H | 7-dimethylamino |
| 1437 | n-butyl | n-butyl | OH | H | 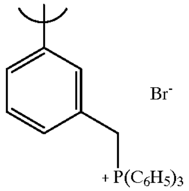 | H | 7-dimethylamino |
| 1438 | n-butyl | n-butyl | OH | H | 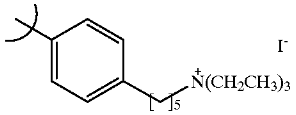 | H | 7-dimethylamino |
| 1439 | n-butyl | n-butyl | OH | H | 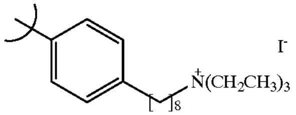 | H | 7-dimethylamino |

-continued
Additional Structures of the Present Invention
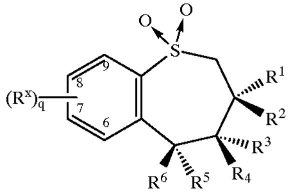
| Compound Number | $R^1$ | $R^2$ | $R^3$ | $R^4$ | $R^5$ | $R^6$ | $(R^x)_q$ |
|---|---|---|---|---|---|---|---|
| 1440 | n-butyl | n-butyl | OH | H | 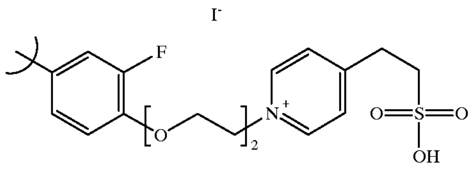 | H | 7-dimethylamino |
| 1441 | n-butyl | n-butyl | OH | H | 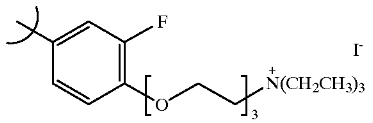 | H | 7-dimethylamino |
| 1442 | n-butyl | n-butyl | OH | H | 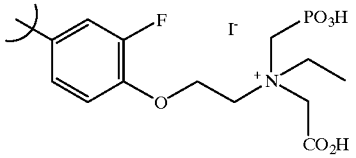 | H | 7-dimethylamino |
| 1443 | n-butyl | n-butyl | OH | H | 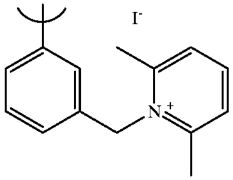 | H | 7-dimethylamino |

-continued
Additional Structures of the Present Invention
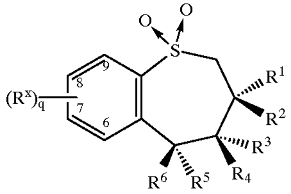
| Compound Number | $R^1$ | $R^2$ | $R^3$ | $R^4$ | $R^5$ | $R^6$ | $(R^x)_q$ |
|---|---|---|---|---|---|---|---|
| 1444 | n-butyl | n-butyl | OH | H | 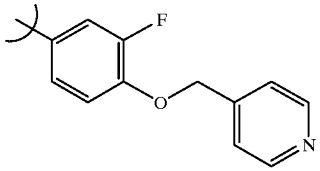 | H | 7-dimethylamino |
| 1445 | n-butyl | n-butyl | OH | H | 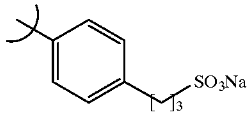 | H | 7-dimethylamino |
| 1446 | n-butyl | n-butyl | OH | H | 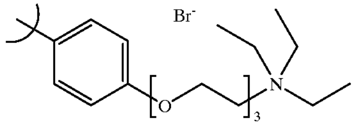 | H | 7-methoxy; 8-methoxy |
| 1447 | n-butyl | n-butyl | OH | H | 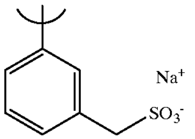 | H | 7-dimethylamino |
| 1448 | n-butyl | n-butyl | OH | H | 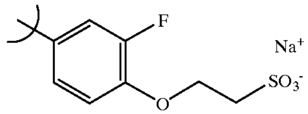 | H | 7-dimethylamino |

-continued
Additional Structures of the Present Invention
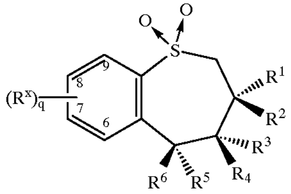
| Compound Number | $R^1$ | $R^2$ | $R^3$ | $R^4$ | $R^5$ | $R^6$ | $(R^x)_q$ |
|---|---|---|---|---|---|---|---|
| 1449 | n-butyl | n-butyl | OH | H | 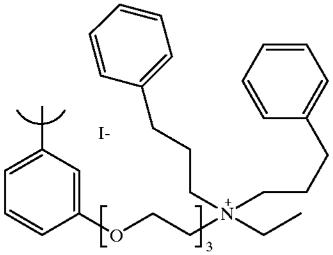 | H | 7-dimethylamino |
| 1450 | n-butyl | n-butyl | OH | H | phenyl | H | 7-dimethylamino |
| 1451 | n-butyl | n-butyl | OH | H | 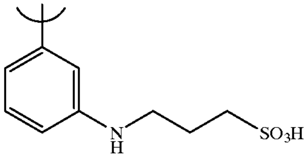 | H | 7-dimethylamino |

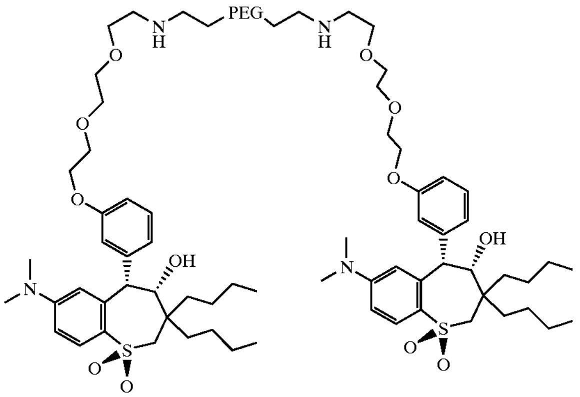
PEG=3400 molecular weight polyethylene glycol polymer chain
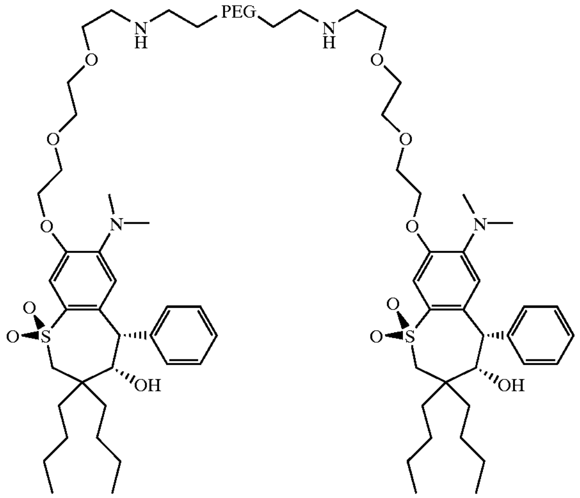
PEG=3400 molecular weight polyethylene glycol polymer chain
PEG=3400 molecular weight polyethylene glycol polymer chain
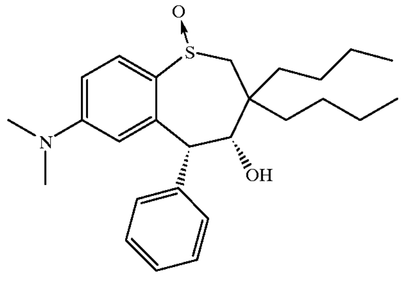
C22 H23 N 03 S
387.543
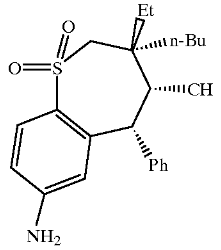
C22 H25 N 03 S
387.543
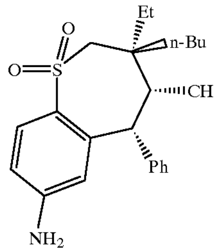
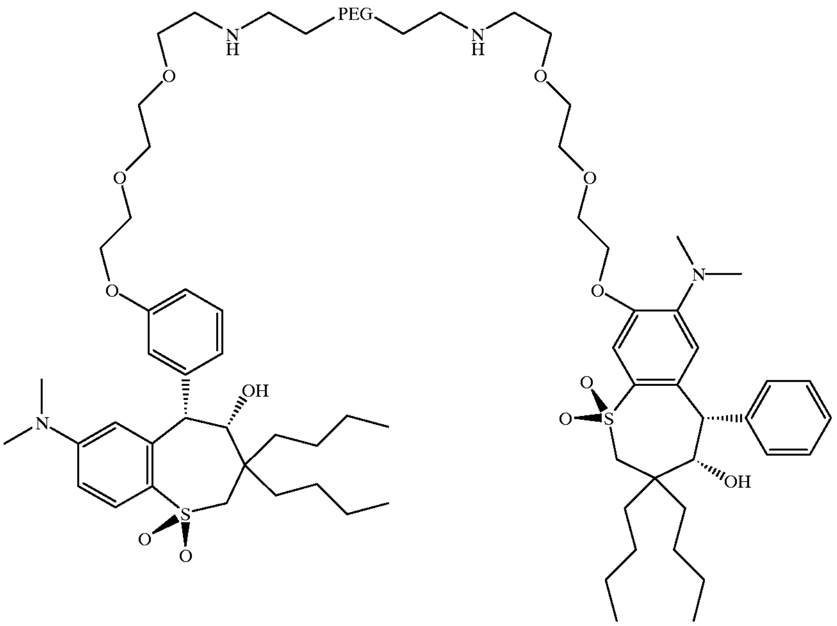

-continued
C22 H28 03 S
372.529
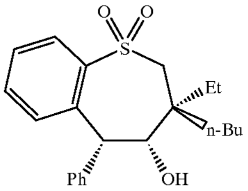
C21 H24 03 S
356.486
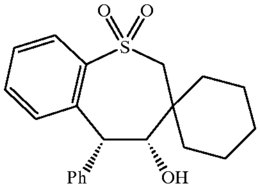
C22 H28 0 S
340.53
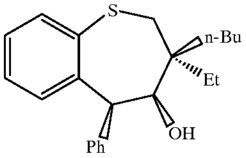
C22 H28 0 S
340.53
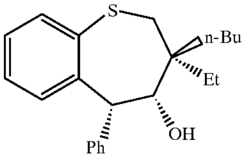
C22 H28 04 S
388.528
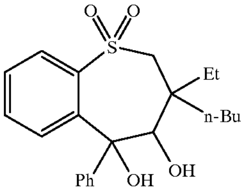
C22 H32 03 S • C22 H25 03 S
749.085
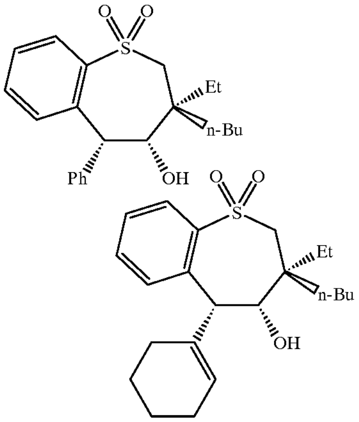
-continued
C22 H28 02 S
356.529
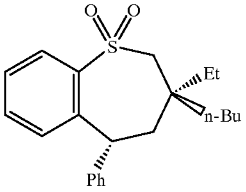
C28 H41 H 03 S
471.704
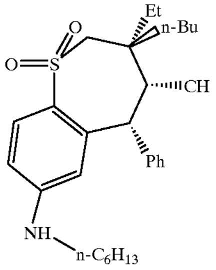
C22 H27 I 03 S
498.425
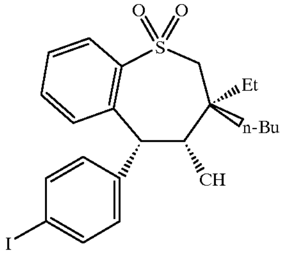
C24 H30 05 S
430.565
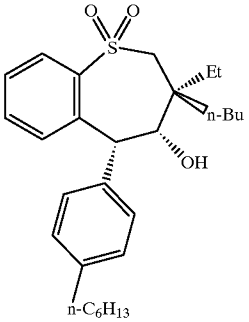
C22 H25 N 04 S
403.543
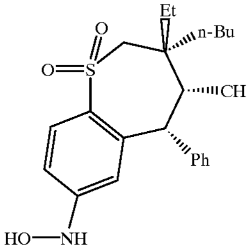

-continued
C28 H41 N 03 S
471.704
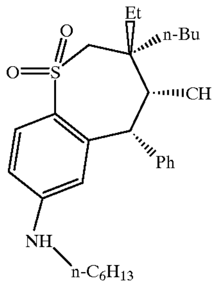
C28 H40 04 S
472.685
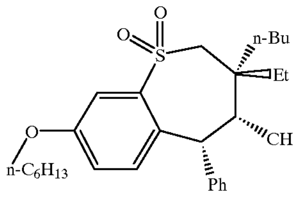
C24 H30 05 S
430.565
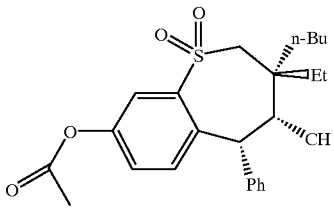
C36 H43 N 06 S
617.807
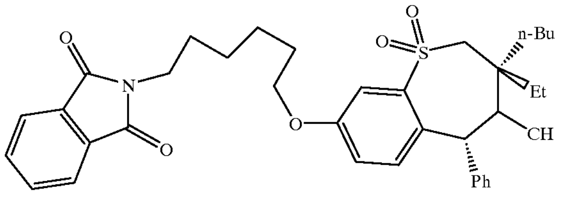
C23 H30 04 S
402.555
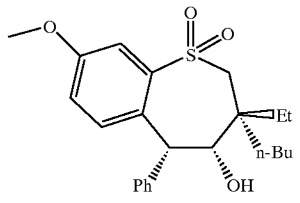
C22 H29 04 S
388.528
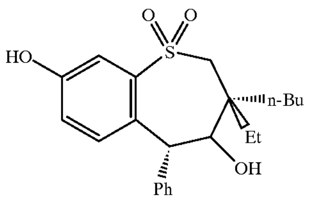
-continued
C24 H32 04 S
416.582
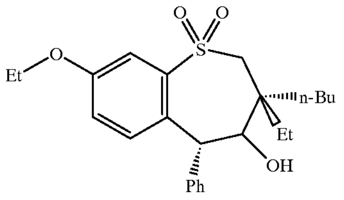
C22 H28 03 S
372.525
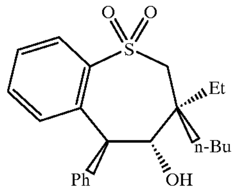
C22 H28 03 S
372.525
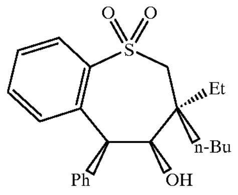
C23 H30 04 S
402.555
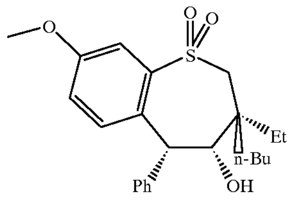
C22 H28 04 S • C22 H28 03 S
761.056
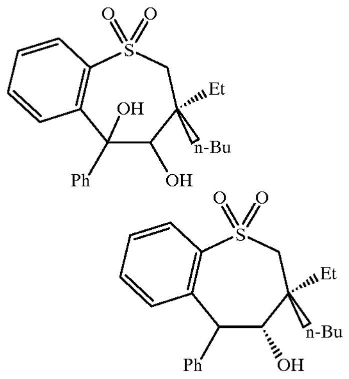
2 C22 H28 03 S2
434.595
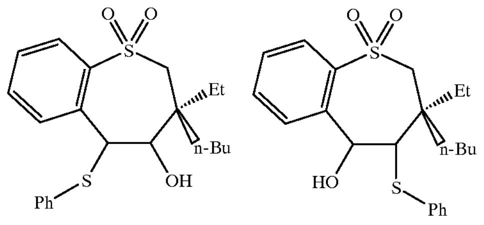

-continued

C22 H26 I2 03 S
624.322

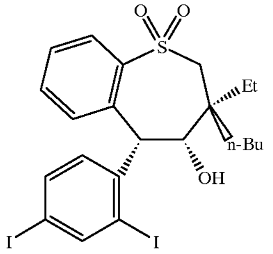

C21 H24 03 S
356.486

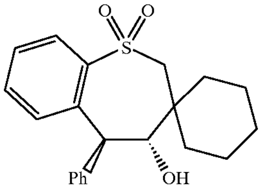

C23 H30 04 S
402.555

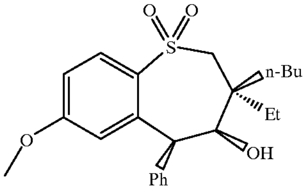

C23 H30 04 S
432.555

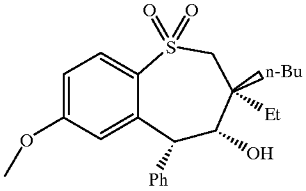

C18 H20 03 S
316.421

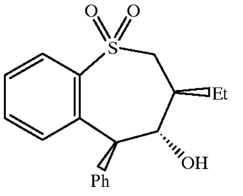

C18 H20 03 S
316.421

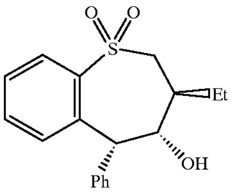

-continued

C22 H28 02 S
356.529

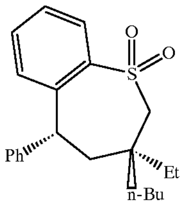

C18 H20 02 S
300.422

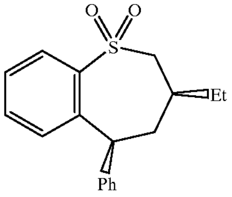

C22 H28 03 S
372.529

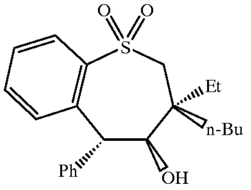

In further compounds of the present invention, $R^5$ and $R^6$ are independently selected from among hydrogen and ring-carbon substituted or unsubstituted aryl, thiophene, pyridine, pyrrole, thiazole, imidazole, pyrazole, pyrimidine, morpholine, N-alkylpyridinium, N-alkyl-piperazinium, N-alkylmorpholinium, or furan in which the substituent(s) are selected from among halo, hydroxyl, trihaloalkyl, alkoxy, amino, N-alkylamino, N,N-dialkylamino, quaternary ammonium salts, a $C_1$ to $C_4$ alkylene bridge having a quaternary ammonium salt substituted thereon, alkoxycarbonyl, aryloxycarbonyl, alkylcarbonyloxy and arylcarbonyloxy, (O,O)-dioxyalkylene, —$[O(CH_2)_w]_x$X where x is 2 to 12, w is 2 or 3 and X comprises halo or a quaternary ammonium salt, thiophene, pyridine, pyrrole, thiazole, imidazole, pyrazole, or furan. The aryl group of $R^5$ or $R^6$ is preferably phenyl, phenylene, or benzene triyl, i.e., may be unsubstituted, mono-substituted, or di-substituted. Among the species which may constitute the substituents on the aryl ring of $R^5$ or $R^6$ are fluoro, chloro, bromo, methoxy, ethoxy, isopropoxy, trimethylammonium (preferably with an iodide or chloride counterion), methoxycarbonyl, ethoxycarbonyl, formyl, acetyl, propanoyl, (N)-hexyldimethylammonium, hexylenetrimethylammonium, tri(oxyethylene)iodide, and tetra(oxyethylene)trimethylammonium iodide, each substituted at the p-position, the m-position, or both of the aryl ring. Other substituents that can be present on a phenylene, benzene triyl or other aromatic ring include 3,4-dioxymethylene (5-membered ring) and 3,4-dioxyethylene (6-membered ring). Among compounds which have been or can be demonstrated to have desirable ileal bile acid transport inhibiting properties are those in which $R^5$ or $R^6$ is selected from phenyl, p-fluorophenyl, m-fluorophenyl, p-hydroxyphenyl, m-hydroxyphenyl, p-methoxyphenyl, m-methoxyphenyl, p-N,N-dimethylaminophenyl, m-N,N-dimethylaminophenyl, $I^-$ p-$(CH_3)_3$—$N^+$-phenyl, $I^-$ m-$(CH_3)_3$—$N^+$-phenyl, $I^-$ m-$(CH_3)_3$—$N^+$—$CH_2CH_2$—$(OCH_2CH_2)_2$—O-phenyl, $I^-$ p-$(CH_3)_3$—$N^+$—$CH_2CH_2$—$(OCH_2CH_2)_2$—O-phenyl, $I^-$ m-(N,N-dimethyl-piperazinium)—(N')—$CH_2$—$(OCH_2CH_2)_2$—O-phenyl, 3-methoxy-4-fluorophenyl, thienyl-2-yl, 5-cholorothienyl-2-yl, 3,4-difluorophenyl, $I^-$ p-(N,N-dimethylpiperazinium)-(N')—$CH_2$—$(OCH_2CH_2)_2$—O-phenyl, 3-fluoro-4-methoxyphenyl, 4-pyridinyl, 2-pyridinyl, 3-pyridinyl, N-methyl-4-pyridinium, $I^-$ N-methyl-3-pyridinium, 3,4-dioxethylenephenyl, 3,4-dioxyethylenephenyl, and p-methoxycarbonylphenyl. Preferred compounds include 3-ethyl-3-butyl and 3-butyl-3-butyl compounds having each of the above preferred $R^5$ substituents in combination with the $R^X$ substituents shown in Table 1. It is particularly preferred that one but not both of $R^5$ and $R^6$ is hydrogen.

It is especially preferred that $R^4$ and $R^6$ be hydrogen, that $R^3$ and $R^5$ not be hydrogen, and that $R^3$ and $R^5$ be oriented in the same direction relative to the plane of the molecule, i.e., both in α- or both in β-configuration. It is further preferred that, where $R^2$ is butyl and $R^1$ is ethyl, then $R^1$ has the same orientation relative to the plane of the molecule as $R^3$ and $R^5$.

Set forth in Table 1A are lists of species of $R^1/R^2$, $R^5/R^6$ and $R^X$.

TABLE 1A

Alternative R groups

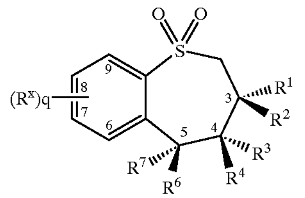

| $R^1$, $R^2$ | $R^3$, $R^4$ | $R^5$ | $(R^x)_q$ |
|---|---|---|---|
| ethyl | HO— | Ph— | 7-methyl |
| n-propyl | H— | p-F—Ph— | 7-ethyl |
| n-butyl | | m-F—Ph— | 7-iso-propyl |
| n-pentyl | | p-$CH_3O$—Ph— | 7-tert-butyl |
| n-hexyl | | | 7-OH |
| iso-propyl | | m-$CH_3O$—Ph— | 7-$OCH_3$ |
| iso-butyl | | p-$(CH_3)_2N$—Ph— | 7-O(iso-propyl) |
| iso-pentyl | | m-$(CH_3)_2N$—Ph— | 7-$SCH_3$ |
| $CH_2C(=O)C_2H_5$ | | $I^-$, p-$(CH_3)_3$—$N^+$—Ph— | 7-$SOCH_3$ |
| $CH_2OC_2H_5$ | | $I^-$, m-$(CH_3)_3$—$N^+$—Ph— | 7-$SO_2Ch_3$ |
| $CH_2CH(OH)C_2H_5$ | | $I^-$, p-$(CH_3)_3$—$N^+$—$CH_2CH_2$— | 7-$SCH_2CH_3$ |
| $CH_2O$—(4-picoline) | | $(CCH_2CH_2)_2$—O—Ph— | 7-$NH_2$ |
| | | $I^-$, m-$CH_3)_3$—$N^+$—$CH_2CH_2$— | 7-NHCH |
| | | $(CCH_2CH_2)_2$—C—Ph— | 7-$NHCH_3$ |
| | | $I^-$, p-(N,N- | 7-$N(CH_2)_2$ |
| | | dimethylpiperazine)- | 7-$N^+(CH_3)_3$, $I^-$ |
| | | (N')—$CH_2$—$(CCH_2CH_2)_2$—O— | 7-$NHC(=O)CH_3$ |
| | | Ph— | 7-$N(CH_2CH_3)_2$ |
| | | $I^-$, m-(N,N- | 7-$NMeCH_2CO_2H$ |
| | | dimethylpiperazine)- | 7-$N^+(Me)_2CH_2CO_2H$, $I^-$ |
| | | (N')—$CH_2$—$(CCH_2CH_2)_2$—O— | 7-(N)-morpholine |
| | | Ph— | 7-(N)-azezidine |
| | | m-F, p-$CH_3O$—Ph— | 7-(N)-N-methylazetidinium, $I^-$ |
| | | 3,4,dioxymethylene-Ph | 7-(N)-pyrrolidine |
| | | m-$CH_3O$—, p-F—Ph— | 7-(N)-N-methyl-pyrrolidinium, $I^-$ |
| | | 4-pyridine | 7-(N)-N-methyl-morpholinium, $I^-$ |
| | | N-methyl-4-pyridinium, $I^-$ | 7-(N)-N'-methylpiperazine |
| | | 3-pyridine | 7-(N)-N'-dimethylpiperazinium, $I^-$ |
| | | N-methyl-3-pyridinium, $I^-$ | 7-NH—CBZ |
| | | 2-pyridine | 7-$NHC(=O)C_5H_{11}$ |
| | | p-$CH_3O_2C$—Ph— | 7-$NHC(=O)CH_2Br$ |
| | | thienyl-2-yl | 7-NH—$C(NH)NH_2$ |
| | | 5-Cl-thienyl-2-yl | 7-(2)-thiophene |
| | | 3,4-difluoro | 8-methyl |
| | | m-F, P—$CH_3O$—Ph | 8-ethyl |
| | | | 8-iso-propyl |
| | | | 8-tert-butyl |
| | | | 8-OH |
| | | | 8-$CCH_3$ |
| | | | 8-O(iso-propyl) |
| | | | 8-$SCH_3$ |
| | | | 8-$SCCH_3$ |
| | | | 8-$SO_2CH_3$ |
| | | | 8-$SCH_2CH_3$ |
| | | | 8-$NH_2$ |
| | | | 8-NHOH |

TABLE 1A-continued

Alternative R groups

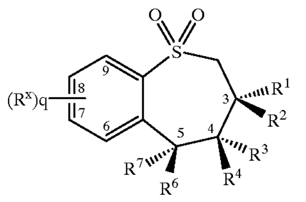

| $R^1$, $R^2$ | $R^3$, $R^4$ | $R^5$ | $(R^x)_q$ |
|---|---|---|---|
| | | | 8-$NHCH_3$ |
| | | | 8-$N(CH_3)_2$ |
| | | | 8-$N^+(CH_3)_3$, $I^-$ |
| | | | 8-$NHC(=O)CH_3$ |
| | | | 8-$N(CH_2CH_3)_2$ |
| | | | 8-$NMeCH_2CO_2H$ |
| | | | 8-$N^+(Me)_2CH_2CO_2H$, $I^-$ |
| | | | 8-(N)-morpholine |
| | | | 8-(N)-azetidine |
| | | | 8-(N)-N-methylazetidinium, $I^-$ |
| | | | 8-(N)-pyrrolidine |
| | | | 8-(N)-N-methyl-pyrrolidinium, $I^-$ |
| | | | 8-(N)-N-methyl-morpholinium, $I^-$ |
| | | | 8-(N)-N'-methylpiperazine |
| | | | 8-(N)-N'-dimethylpiperazinium, $I^-$ |
| | | | 8-NH—CBZ |
| | | | 8-$NHC(O)C_5H_{11}$ |
| | | | 8-$NHC(O)CH_2Br$ |
| | | | 8-NH—$C(NH)NH_2$ |
| | | | 8-(2)-thiophene |
| | | | 9-methyl |
| | | | 9-ethyl |
| | | | 9-iso-propyl |
| | | | 9-tert-butyl |
| | | | 9-OH |
| | | | 9-$CCH_3$ |
| | | | 9-O(iso-propyl) |
| | | | 9-$SCH_3$ |
| | | | 9-$SCCH_3$ |
| | | | 9-$SO_2CH_3$ |
| | | | 9-$SCH_2CH_3$ |
| | | | 9-$NH_2$ |
| | | | 9-NHOH |
| | | | 9-$NHCH_3$ |
| | | | 9-$N(CH_3)_2$ |
| | | | 9-$N^+(CH_3)_3$, $I^-$ |
| | | | 9-$NHC(=O)CH_3$ |
| | | | 9-$N(CH_2CH_3)_2$ |
| | | | 9-$NMeCH_2CO_2H$ |
| | | | 9-$N^+(Me)_2CH_2CO_2H$, $I^-$ |
| | | | 9-(N)-morpholine |
| | | | 9-(N)-azetidine |
| | | | 9-(N)-N-methylazetidinium, $I^-$ |
| | | | 9-(N)-pyrrolidine |
| | | | 9-(N)-N-methyl-pyrrolidinium, $I^-$ |
| | | | 9-(N)-N-methyl-morpholinium, $I^-$ |
| | | | 9-(N)-N'-methylpiperazine |
| | | | 9-(N)-N'-dimethylpiperazinium, $I^-$ |
| | | | 9-NH—CBZ |
| | | | 9-$NHC(O)C_5H_{11}$ |
| | | | 9-$NHC(O)CH_2Br$ |
| | | | 9-NH—$C(NH)NH_2$ |
| | | | 9-(2)-thiophene |
| | | | 7-$CCH_3$, 8-$CCH_3$ |
| | | | 7-$SCH_3$, 8-$CCH_3$ |
| | | | 7-$SCH_3$, 8-$SCH_3$ |
| | | | 6-$CCH_3$, 7-$CCH_3$, 8-$CCH_3$ |

Further preferred compounds of the present invention comprise a core structure having two or more pharmaceutically active benzothiepine structures as described above, covalently bonded to the core moiety via functional linkages. Such active benzothiepine structures preferably comprise:

(Formula DIV)

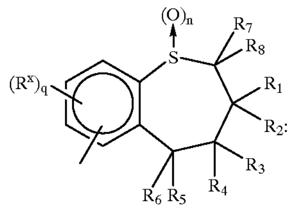

or (Formula DIVA)

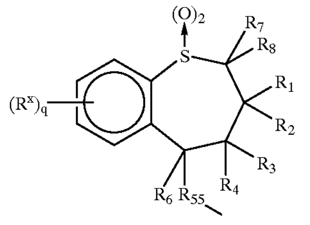

where $R^1$, $R^2$, $R^3$, $R^4$, $R^6$, $R^5$, $R^6$, $R^7$, $R^8$, X, q and n are as defined above, and $R^{55}$ is either a covalent bond or arylene.

The core moiety can comprise alkane diyl, alkene diyl, alkyne diyl, polyalkane diyl, alkoxy diyl, polyether diyl, polyalkoxy diyl, carbohydrate, amino acid, and peptide, polypeptide, wherein alkane diyl, alkene diyl, alkyne diyl, polyalkane diyl, alkoxy diyl, polyether diyl, polyalkoxy diyl, carbohydrate, amino acid, and peptide polypeptide, can optionally have one or more carbon replaced by O, $NR^7$, $N^+R^7R^8$, S, SO, $SO_2$ $S^+R^7R^8$, $PR^7$, $P^+R^7R^8$, phenylene, heterocycle, quatarnary heterocycle, quaternary heteroaryl, or aryl, wherein alkane diyl, alkene diyl, alkyne diyl, polyalkane diyl, alkoxy diyl, polyether diyl, polyalkoxy diyl, carbohydrate, amino acid, peptide, and polypeptide can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A-$, $P(OR^{13})OR^{14}$, $S^+R^{13}R^{14}A^-$, and $N^+R^9R^{11}R^{12}A^-$;

wherein said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A-$, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A-$, S, SO, $SO_2$, $S^+R^7A-$, $PR^7$, $P(O)R^7$, $P^+R^7R^8A-$, or phenylene.

Exemplary core moieties include:

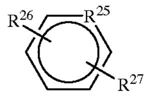

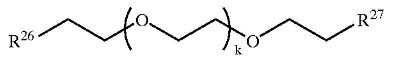

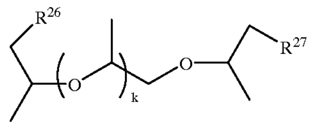

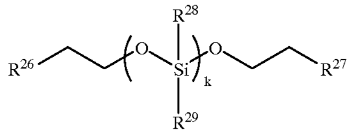

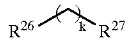

wherein:

$R^{25}$ is selected from the group consisting of C and N, and $R^{26}$ and $R^{27}$ are independently selected from the group consisting of:

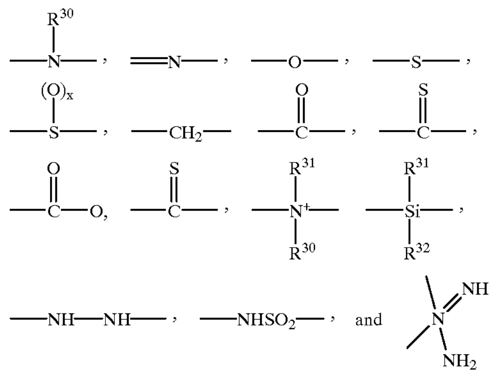

wherein $R^{26}$, $R^{29}$, $R^{30}$ and $R^{31}$ are independently selected from alkyl, alkenyl, alkylaryl, aryl, arylalkyl, cycloalkyl, heterocycle, and heterocycloalkyl, $A^-$ is a pharmaceutically acceptable anion, and k=1 to 10.

In compounds of Formula DIV, R20, $R^{21}$, $R^{22}$ in Formulae DII and DIII, and $R^{23}$ in Formula DIII can be bonded at any of their 6-, 7-, 8-, or 9-positions to $R^{19}$. In compounds of Formula DIVA, it is preferred that $R^{55}$ comprises a phenylene moiety bonded at a m- or p-position thereof to $R^{19}$.

In another embodiment, a core moiety backbone, $R^{19}$, as discussed herein in Formulas DII and DIII can be multiply substituted with more than four pendant active benzothiepine units, i.e., $R^{20}$, $R^{21}$, $R^{22}$ and $R^{23}$ as discussed above, through multiple functional groups within the core moiety backbone. The core moiety backbone unit, $R^{19}$, can comprise a single core moiety unit, multimers thereof, and multimeric mixtures of the different core moiety units discussed herein, i.e., alone or in combination. The number of individual core moiety backbone units can range from about one to about 100, preferably about one to about 80, more preferably about one to about 50, and even more preferably about one to about 25. The number of points of attachment of similar or different pendant active benzothiepine units within a single core moiety backbone unit can be in the range from about one to about 100, preferably about one to about 80, more preferably about one to about 50, and even more preferably about one to about 25. Such points of attachment can include bonds to C, S, O, N, or P within any of the groups encompassed by the definition of $R^{19}$.

The more preferred benzothiepine moieties comprising $R^{20}$, $R^{21}$, $R^{22}$ and/or $R^{23}$ conform to the preferred structures as outlined above for Formula I. The 3-carbon on each benzothiepine moiety can be achiral, and the substituents $R^1$, $R^2$, $R^3$, $R^4$, $R^5$ and $R^X$ can be selected from the preferred groups and combinations of substituents as discussed above. The core structures can comprise, for example, Poly (oxyalkylene) or oligo(oxyalkylene), especially poly- or oligo(oxyethylene) or poly- or oligo(oxypropylene).

Dosages, Formulations, and Routes of Administration

The ileal bile acid transport inhibitor compounds of the present invention can be administered for the prophylaxis and treatment of hyperlipidemic diseases or conditions by any means, preferably oral, that produce contact of these compounds with their site of action in the body, for example in the ileum of a mammal, e.g., a human.

For the prophylaxis or treatment of the conditions referred to above, the compounds of the present invention can be used as the compound per se.

Pharmaceutically acceptable salts are particularly suitable for medical applications because of their greater aqueous solubility relative to the parent compound. Such salts must clearly have a pharmaceutically acceptable anion or cation. Suitable pharmaceutically acceptable acid addition salts of the compounds of the present invention when possible include those derived from inorganic acids, such as hydrochloric, hydrobromic, phosphoric, metaphosphoric, nitric, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, succinic, toluenesulfonic, tartaric, and trifluoroacetic acids. The chloride salt is particularly preferred for medical purposes. Suitable pharmaceutically acceptable base salts include ammonium salts, alkali metal salts such as sodium and potassium salts, and alkaline earth salts such as magnesium and calcium salts.

The anions of the definition of $A^-$ in the present invention are, of course, also required to be pharmaceutically acceptable and are also selected from the above list.

The compounds of the present invention can be presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present, including other compounds of the present invention. The pharmaceutical compositions of the invention can be prepared by any of the well known techniques of pharmacy, consisting essentially of admixing the components.

These compounds can be administered by any conventional means available for use in conjunction with pharmaceuticals, either as individual therapeutic compounds or as a combination of therapeutic compounds.

The amount of compound which is required to achieve the desired biological effect will, of course, depend on a number of factors such as the specific compound chosen, the use for which it is intended, the mode of administration, and the clinical condition of the recipient.

In general, a daily dose can be in the range of from about 0.3 to about 100 mg/kg bodyweight/day, preferably from about 1 mg to about 50 mg/kg bodyweight/day, more preferably from about 3 to about 10 mg/kg bodyweight/day. This total daily dose can be administered to the patient in a single dose, or in proportionate multiple subdoses. Subdoses can be administered 2 to 6 times per day. Doses can be in sustained release form effective to obtain desired results.

Orally administrable unit dose formulations, such as tablets or capsules, can contain, for example, from about 0.1 to about 100 mg of benzothiepine compound, preferably about 1 to about 75 mg of compound, more preferably from about 10 to about 50 mg of compound. In the case of pharmaceutically acceptable salts, the weights indicated above refer to the weight of the benzothiepine ion derived from the salt.

Oral delivery of an ileal bile acid transport inhibitor of the present invention can include formulations, as are well known in the art, to provide prolonged or sustained delivery of the drug to the gastrointestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. The intended effect is to extend the time period over which the active drug molecule is delivered to the site of action (the ileum) by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester.

When administered intravenously, the dose can, for example, be in the range of from about 0.1 mg/kg body weight to about 1.0 mg/kg body weight, preferably from about 0.25 mg/kg body weight to about 0.75 mg/kg body weight, more preferably from about 0.4 mg/kg body weight to about 0.6 mg/kg body weight. This dose can be conveniently administered as an infusion of from about 10 ng/kg body weight to about 100 ng/kg body weight per minute. Infusion fluids suitable for this purpose can contain, for example, from about 0.1 ng to about 10 mg, preferably from about 1 ng to about 10 mg per milliliter. Unit doses can contain, for example, from about 1 mg to about 10 g of the compound of the present invention. Thus, ampoules for injection can contain, for example, from about 1 mg to about 100 mg.

Pharmaceutical compositions according to the present invention include those suitable for oral, rectal, topical, buccal (e.g., sublingual), and parenteral (e.g., subcutaneous, intramuscular; intradermal, or intravenous) administration, although the most suitable route in any given case will depend on the nature and severity of the condition being treated and on the nature of the particular compound which is being used. In most cases, the preferred route of administration is oral.

Pharmaceutical compositions suitable for oral administration can be presented in discrete units, such as capsules, cachets, lozenges, or tablets, each containing a predetermined amount of at least one compound of the present invention; as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active compound(s) and the carrier (which can constitute one or more accessory ingredients). In general, the compositions are prepared by uniformly and intimately admixing the active compound with a liquid or finely divided solid carrier, or both, and then, if necessary, shaping the product. For example, a tablet can be prepared by compressing or molding a powder or granules of the compound, optionally with one or more assessory ingredients. Compressed tablets can be prepared by compressing, in a suitable machine, the compound in a free-flowing form, such as a powder or granules optionally mixed with a binder, lubricant, inert diluent and/or surface active/dispersing agent (s). Molded tablets can be made by molding, in a suitable machine, the powdered compound moistened with an inert liquid diluent.

Pharmaceutical compositions suitable for buccal (sublingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration conveniently comprise sterile aqueous preparations of a compound of the present invention. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of a compound disclosed herein.

Pharmaceutical compositions suitable for rectal administration are preferably presented as unit-dose suppositories. These can be prepared by admixing a compound of the present invention with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include vaseline, lanoline, polyethylene glycols, alcohols, and combinations of two or more thereof. The active compound is generally present at a concentration of from 0.1 to 15% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for a prolonged period of time. Such patches suitably contain a compound of the present invention in an optionally buffered, aqueous solution, dissolved and/or dispersed in an adhesive, or dispersed in a polymer. A suitable concentration of the active compound is about 1% to 35%, preferably about 3% to 15%. As one particular possibility, the compound can be delivered from the patch by electrotransport or iontophoresis, for example, as described in *Pharmaceutical Research,* 3(6), 318 (1986).

In any case, the amount of active ingredient that can be combined with carrier materials to produce a single dosage form to be administered will vary depending upon the host treated and the particular mode of administration.

The solid dosage forms for oral administration including capsules, tablets, pills, powders, and granules noted above comprise one or more compounds of the present invention admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Injectable preparations, for example, sterile injectable aqueous or oleaginous suspensions may be formulated according to the known art using suitable dispersing or setting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutically acceptable carriers encompass all the foregoing and the like.

In combination therapy, administration of the ileal bile acid transport inhibitor and HMG Co-A reductase inhibitor may take place sequentially in separate formulations, or may be accomplished by simultaneous administration in a single formulation or separate formulations. Administration may be accomplished by oral route, or by intravenous, intramuscular, or subcutaneous injections. The formulation may be in the form of a bolus, or in the form of aaqueous or non-aqueous isotonic sterile injection solutions or suspensions. These solutions and suspensions may be prepared from sterile powders or granules having one or more pharmaceutically-acceptable carriers or diluents, or a binder such as gelatin or hydroxypropylmethyl cellulose, together with one or more of a lubricant, preservative, surface active or dispersing agent.

For oral administration, the pharmaceutical composition may be in the form of, for example, a tablet, capsule, suspension, or liquid. Capsules, tablets, etc., can be prepared by conventional methods well known in the art. The pharmaceutical composition is preferably made in the form of a dosage unit containing a particular amount of the active ingredient or ingredients. Examples of dosage units are tablets or capsules. These may with advantage contain one or more ileal bile acid transport inhibitors in an amount described above. In the case of HMG Co-A reductase inhibitors, the dose range may be from about 0.01 mg to about 500 mg or any other dose, dependent upon the specific inhibitor, as is known in the art.

The active ingredients may also be administered by injection as a composition wherein, for example, saline, dextrose, or water may be used as a suitable carrier. A suitable daily dose of each active inhibitor is one that achieves the same blood serum level as produced by oral administration as described above.

The active inhibitors may further be administered by any dual combination of oral/oral, oral/parenteral, or parenteral/parenteral route.

Pharmaceutical compositions for use in the treatment methods of the present invention may be administered in oral form or by intravenous administration. Oral administration of the combination therapy is preferred. Dosing for oral administration may be with a regimen calling for single daily dose, or for a single dose every other day, or for multiple, spaced doses throughout the day. The inhibitors which make up the combination therapy may be administered simultaneously, either in a combined dosage form or in separate dosage forms intended for substantially simultaneous oral administration. The inhibitors which make up the combination therapy may also be administered sequentially, with either inhibitor being administered by a regimen calling for two-step ingestion. Thus, a regimen may call for sequential administration of the inhibitors with spaced-apart ingestion of the separate, active agents. The time period between the multiple ingestion steps may range from a few minutes to several hours, depending upon the properties of each inhibitor such as potency, solubility, bioavailability, plasma half-life and kinetic profile of the inhibitor, as well as depending upon the age and condition of the patient. The inhibitors of the combined therapy whether administered simultaneously, substantially simultaneously, or sequentially, may involve a regimen calling for administration of one inhibitor by oral route and the other inhibitor by intravenous route. Whether the inhibitors of the combined therapy are administered by oral or intravenous route, separately or together, each such inhibitor will be contained in a suitable pharmaceutical formulation of pharmaceutically-acceptable excipients, diluents or other formulations components. Examples of suitable pharmaceutically-acceptable formulations containing the inhibitors for oral administration are given above.

Treatment Regimen

The dosage regimen to prevent, give relief from, or ameliorate a disease condition having hyperlipemia as an element of the disease, e.g., atherosclerosis, or to protect against or treat further high cholesterol plasma or blood levels with the compounds and/or compositions of the present invention is selected in accordance with a variety of factors. These include the type, age, weight, sex, diet, and medical condition of the patient, the severity of the disease, the route of administration, pharmacological considerations such as the activity, efficacy, pharmacokinetics and toxicology profiles of the particular compound employed, whether a drug delivery system is utilized, and whether the compound is administered as part of a drug combination. Thus, the dosage regimen actually employed may vary widely and therefore deviate from the preferred dosage regimen set forth above.

Initial treatment of a patient suffering from a hyperlipidemic condition can begin with the dosages indicated above. Treatment should generally be continued as necessary over a period of several weeks to several months or years until the hyperlipidemic disease condition has been controlled or eliminated. Patients undergoing treatment with the compounds or compositions disclosed herein can be routinely monitored by, for example, measuring serum LDL and total cholesterol levels by any of the methods well known in the art, to determine the effectiveness of the combination therapy. Continuous analysis of such data permits modification of the treatment regimen during therapy so that optimal effective amounts of each type of inhibitor are administered at any point in time, and so that the duration of treatment can be determined as well. In this way, the treatment regimen/dosing schedule can be rationally modified over the course of therapy so that the lowest amount of ileal bile acid transport inhibitor and HMG Co-A reductase inhibitor which together exhibit satisfactory effectiveness is administered, and so that administration is continued only so long as is necessary to successfully treat the hyperlipidemic condition.

A potential advantage of the combination therapy disclosed herein may be reduction of the amount of ileal bile acid transport inhibitor, HMG Co-A reductase inhibitor, or both, effective in treating hyperlipidemic conditions such as atherosclerosis and hypercholesterolemia.

The following non-limiting examples serve to illustrate various aspects of the present invention.

EXAMPLES OF SYNTHETIC PROCEDURES

Preparation 1

2-Ethyl-2-(mesyloxymethyl)hexanal (1)

(1)

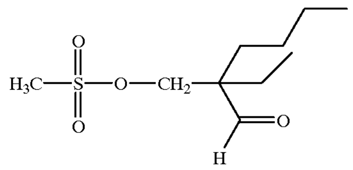

To a cold (10° C.) solution of 12.6 g (0.11 mole) of methanesulfonyl chloride and 10.3 g (0.13 mole) of triethylemine was added dropwise 15.8 g of 2-ethyl-2-(hydroxymethyl)hexanal, prepared according to the procedure described in Chem. Ber. 98, 728–734 (1965), while maintaining the reaction temperature below 30° C. The reaction mixture was stirred at room temperature for 18 h, quenched with dilute HCl and extracted with methlyene chloride. The methylene chloride extract was dried over $MgSO_4$ and concentrated in vacuo to give 24.4 g of brown oil.

Preparation 2

2-((2-Benzoylphenylthio)methyl)-2-ethylhexanal (2)

(2)

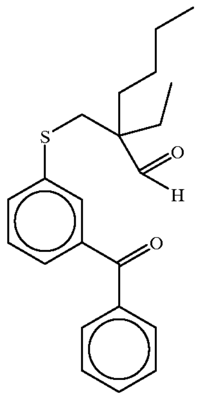

A mixture of 31 g (0.144 mol) of 2-mercaptobenzophenone, prepared according to the procedure described in WO 93/16055, 24.4 g (0.1 mole) of 2-ethyl-2-(mesyloxymethyl)-hexanal (1), 14.8 g (0.146 mole) of triethylamine, and 80 mL of 2-methoxyethyl ether was held at reflux for 24 h. The reaction mixture was poured into 3N HCl and extracted with 300 mL of methylene chloride. The methylene chloride layer was washed with 300 mL of 10% NaOH, dried over $MgSO_4$, and concentrated in vacuo to remove 2-methoxyethyl ether. The residue was purified by HPLC (10% EtOAc-hexane) to give 20.5 g (58%) of 2 as an oil.

Example 1

3-Butyl-3-ethyl-5-phenyl-2,3-dihydrobenzothiepine (3), cis-3-Butyl-3-ethyl-5-phenyl-2,3-dihydrobenzothiepin-(5H)4-one (4a) and trans-3-Butyl-3-ethyl-5-phenyl-2,3-dihydro-benzothiepin-(5H)4-one (4b)

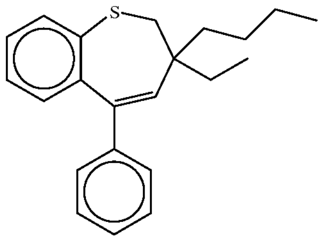

4a,4b

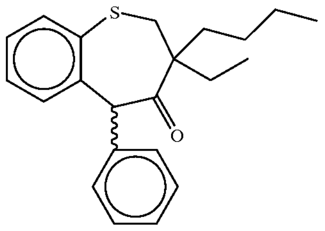

A mixture of 2.6 g (0.04 mole) of zinc dust, 7.2 g (0.047 mole) of TiCl, and 80 mL of anhydrous ethylene glycol dimethyl ether (DME) was held at reflux for 2 h. The reaction mixture was cooled to 5° C. To the reaction mixture was added dropwise a solution of 3.54 g (0.01 mole) of 2 in 30 mL of DME in 40 min. The reaction mixture was stirred at room temperature for 16 h and then was held at reflux for 2 h and cooled before being poured into brine. The organic was extract into methylene chloride. The methylene chloride extract was dried over $MgSO_4$ and concentrated in vacuo. The residue was purified by HPLC (hexane) to give 1.7 g (43%) of 3 as an oil in the first fraction. The second fraction was discarded and the third fraction was further purified by HPLC (hexane) to give 0.07 g (2%) of 4a in the earlier fraction and 0.1 g (3%) of 4b in the later fraction.

Example 2 cis-3-Butyl-3-ethyl-5-phenyl-2,3-dihydrobenzothiepin-(5H) 4-one-1,1-dioxide (5a) and trans-3-Butyl-3-ethyl-5-phenyl-2,3-dihydro-benzothiepin-(5H)4-one-1,1-dioxide (5b)

5a,5b

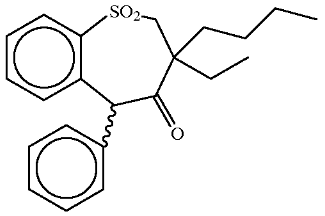

To a solution of 1.2 g (3.5 mmole) of 50–60% MCPBA in 20 mL of methylene chloride was added 0.59 g (1.75 mmole) of a mixture of 4a and 4b in 10 mL of methylene chloride. The reaction mixture was stirred for 20 h. An additional 1.2 g (1.75 mmole) of 50–60% MAPBA was added and the reaction mixture was stirred for an additional 3 h then was triturated with 50 mL of 10% NaOH. The insoluble solid was filtered. The methylene chloride layer of the filtrate was washed with brine, dried over $MgSO_4$, and concentrated in vacuo. The residual syrup was purified by HPLC (5% EtOAc-hexane) to give 0.2 g (30%) of 5a as an oil in the first fraction and 0.17 g (26%) of 5b as an oil in the second fraction.

Example 3

(3a,4a,5b) 3-Butyl-3-ethyl-4-hydroxy-5-phenyl-2,3,4,5-tetrahydrobenzothiepine-1,1-dioxide (6a), (3a,4b,5a)-3-Butyl-3-ethyl-4-hydroxy-5-phenyl-2,3,4,5-tetrahydro-benzothiepine-1,1-dioxide (6b), (3a,4a,5a) 3-Butyl-3-ethyl-4-hydroxy-5-phenyl-2,3,4,5-tetrahydrobenzothiepine-1,1-dioxide (6c), and (3a,4b,5b) 3-Butyl-3-ethyl-4-hydroxy-5-phenyl-2,3,4,5-tetrahydrobenzothiepine-1,1-dioxide (6d)

(6a)

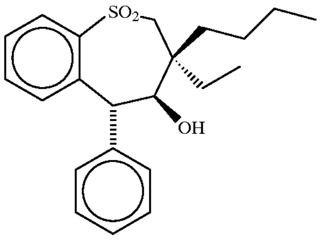

(6b)

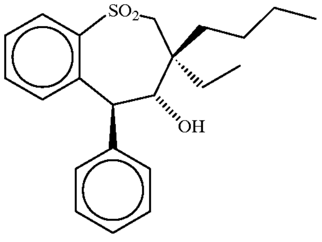

(6c)

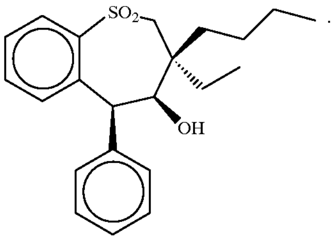

(6d)

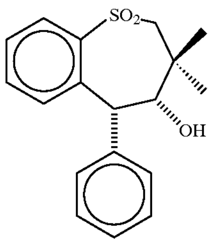

A. Reduction of 5a and 5b With Sodium Borohydride

To a solution of 0.22 g (0.59 mmole) of 5b in 10 mL of ethanol was added 0.24 g (6.4 mmole) of sodium borohydride. The reaction mixture was stirred at room temperature for 18 h and concentrated in vacuo to remove ethanol. The residue was triturated with water and extracted with methylene chloride. The methylene chloride extract was dried over $MgSO_4$ and concentrated in vacuo to give 0.2 g of syrup. In a separate experiment, 0.45 g of 5a was treated with 0.44 g of sodium borohydride in 10 mL of ethanol and was worked up as described above to give 0.5 g of syrup which was identical to the 0.2 g of syrup obtained above. These two materials were combined and purified by HPLC using 10% EtOAc-hexane as eluant. The first fraction was 0.18 g (27%) of 6a as a syrup. The second fraction was 0.2 g (30%) of 6b also as a syrup. The column was then eluted with 20% EtOAc-hexane to give 0.077 g (11%) of 6c in the third fraction as a solid. Recrystallization from hexane gave a solid, mp 179–181° C. Finally, the column was eluted with 30% EtOAc-hexane to give 0.08 g (12%) of 6d in the fourth fraction as a solid.

Recrystallization from hexane gave a solid, mp 160–161° C.

B. Conversion of 6a to 6c and 6d With NaOH and PTC

To a solution of 0.29 g (0.78 mmole) of 6a in 10 mL $CH_2Cl_2$, was added 9 g of 40% NaCH. The reaction mixture was stirred for 0.5 h at room temperature and was added one drop of Aliquat-336 (methyltricaprylylammonium chloride) phase transfer catalyst (PTC). The mixture was stirred for 0.5 h at room temperature before being treated with 25 mL of ice-crystals then was extracted with $CH_2Cl_2$ (3x10 ml), dried over $MgSO_4$ and concentrated in vacuo to recover 0.17 g of a colorless film. The components of this mixture were separated using an HPLC and eluted with EtOAc-hexane to give 12.8 mg (4%) of 2-(2-benzylphenylsulfonylmethyl)-2-ethylhexenal in the first fraction, 30.9 mg (11%) of 6c in the second fraction and 90.0 mg (31%) of 6d in the third fraction.

Oxidation of 6a to 5b

To a solution of 0.20 g (0.52 mmole) of 6a in 5 mL of $CH_2Cl_2$ was added 0.23 g (1.0 mmole) of pyridinium chlorochromate. The reaction mixture was stirred for 2 h then was treated with additional 0.23 g of pyridinium chlorochromate and stirred overnight. The dark reaction mixture was poured into a ceramic filterfrit containing silica gel and was eluted with $CH_2Cl_2$. The filtrate was concentrated in vacuo to recover 167 mg (87%) of 5b as a colorless oil.

Example 4

3-Butyl-3-ethyl-2,3-dihydrobenzothiepine-1,1-dioxide (7)

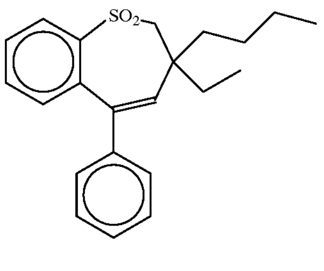

To a solution of 5.13 g (15.9 mmole) of 3 in 50 mL of $CH_2Cl_2$ was added 10 g (31.9 mmole) of 50–60% MCPBA (m-chloroperoxybenzoic acid) portionwise causing a mild reflux and formation of a white solid. The reaction mixture was allowed to stir overnight under $N_2$ and was triturated with 25 mL of water followed by 50 mL of 10% NaOH solution. The organic was extracted into $CH_2Cl_2$ (4x20 mL). The $CH_2Cl_2$ extract was dried over $MgSO_4$ and evaporated to dryness to recover 4.9 g (87%) of an opaque viscous oil.

Example 5

(1aa,2b,8ba ) 2-Butyl-2-ethyl-8b-phenyl-1a,2,3,8b-tetrahydro-benzothiepino[4,5-b]-oxirene-4,4-dioxide (8a) (1aa,2a,8ba) 2-Butyl-2-ethyl-8b-phenyl-1a,2,3,8b-tetrahydro-benzothiepino [4,5-b]oxirene-4,4-dioxide (8b)

(8b)

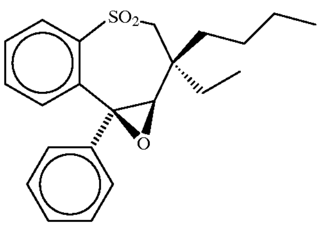

(8a)

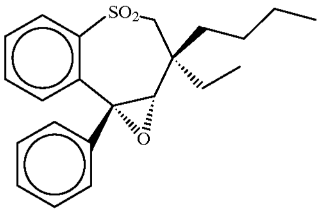

To 1.3 g (4.03 mole) of 3 in 25 mL of $CHCl_3$ was added portionwise 5 g (14.1 mmole) of 50–60% MCPBA causing a mild exotherm. The reaction mixture was stirred under $N_2$ overnight and was then held at reflux for 3 h. The insoluble white slurry was filtered. The filtrate was extracted with 10% potassium carbonate (3x50 mL), once with brine, dried over $MgSO_4$, and concentrated in vacuo to give 1.37 g of a light yellow oil. Purification by HPLC gave 0.65 g of crystalline product. This product is a mixture of two isomers. Trituration of this crystalline product in hexane recovered 141.7 mg (10%) of a white crystalline product. This isomer was characterized by NMR and mass spectra to be the (1aa,2b, 8ba) isomer 8a. The hexane filtrate was concentrated in vacuo to give 206 mg of white film which is a mixture of 30% 8a and 70% 8b by $^1H$ NMR.

Example 6 cis-3-Butyl-3-ethyl-5-phenyl-2,3,4,5-tetrahydro-benzothiepine-1,1-dioxide (9a), trans-3-Butyl-3-ethyl-5-phenyl-2,3,4,5-tetrahydrobenzothiepine-1,1-dioxide (9b), and 3-Butyl-3-ethyl-4-hydroxy-5-cyclohexylidine-2,3,4,5-tetrahydrobenzothiepine-1,1-dioxide (10)

(9a)

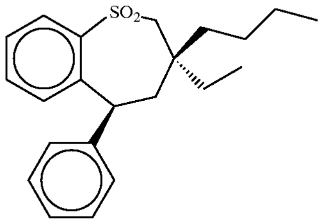

-continued (9b)

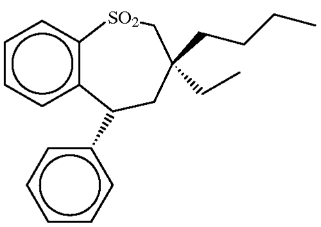

(10)

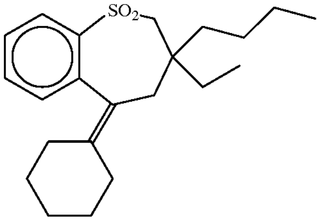

A mixture of 0.15 g (0.4 mmole) of a 3:7 mixture of 8a and 8b was dissolved in 15 ml MeOH in a 3 oz. Fisher/Porter vessel, then was added 0.1 g of 10% Pd/C catalyst. This mixture was hydrogenated at 70 psi $H_2$ for 5 h and filtered. The filtrate was evaporated to dryness in vacuo to recover 0.117 g of a colorless oil. This material was purified by HPLC eluting with EtOAc-hexane. The first fraction was 4.2 mg (3%) of 9b. The second fraction, 5.0 mg (4%), was a 50/50 mixture of 9a and 9b. The third fraction was 8.8 mg (6%) of 6a. The fourth fraction was 25.5 mg (18%) of 6b. The fifth fraction was 9.6 mg (7%) of a mixture of 6b and a product believed to be 3-butyl-3-ethyl-4,5-dihydroxy-5-phenyl-2,3,4,5-tetrahydrobenzothiepine-1,1-dioxide based on mass spectrum. The sixth fraction was 7.5 mg (5%) of a mixture of 6d and one of the isomers of 10, 10a.

Example 7

In another experiment, a product (3.7 g) from epoxidation of 3 with excess MCPBA in refluxing $CHCl_3$ under air was hydrogenated in 100 mL of methanol using 1 g of 10% Pd/C catalyst and 70 psi hydrogen. The product was purified by HPLC to give 0.9 g (25%) of 9b, 0.45 g (13%) of 9a, 0.27 g (7%) of 6a, 0.51 g (14%) of 6b, 0.02 g (1%) of 6c, 0.06 g (2%) of one isomer of 10, 10a and 0.03 g (1%) of another isomer of 10, 10b.

Example 8

2-((2-Benzoylphenylthio)methyl)butyraldehyde (11)

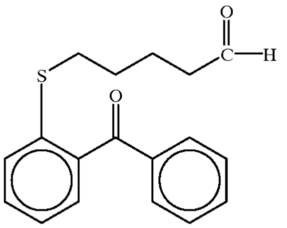

To an ice bath cooled solution of 9.76 g (0.116 mole) of 2-ethylacrolein in 40 mL of dry THF was added 24.6 g (0.116 mole) of 2-mercaptobenzophenone in 40 mL of THF followed by 13 g (0.128 mole) of triethylamine. The reaction mixture was stirred at room temperature for 3 days, diluted with ether, and was washed successively with dilute HCl, brine, and 1 M potassium carbonate. The ether layer was dried over $MgSO_4$ and concentrated in vacuo. The residue was purified by HPLC (10% EtOAc-hexane) to give 22 g (64%) of 11 in the second fraction. An attempt to further purifiy this material by kugelrohr distillation at 0.5 torr (160–190° C.) gave a fraction (12.2 g) which contained starting material indicating a reversed reaction during distillation. This material was dissolved in ether (100 mL) and was washed with 50 mL of 1 M potassium carbonate three times to give 6.0 g of a syrup which was purified by HPLC (10% EtOAc-hexane) to give 5.6 g of pure 11.

Example 9

3-Ethyl-5-phenyl-2,3-dihydrobenzothiepine (12)

(12)

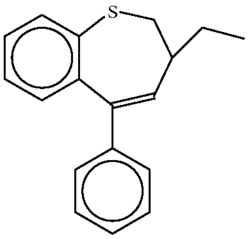

To a mixture of 2.61 g (0.04 mole) of zinc dust and 60 mL of DME was added 7.5 g (0.048 mole) of $TiCl_3$. The reaction mixture was held at reflux for 2 h. A solution of 2.98 g (0.01 mole) of 11 was added dropwise in 1 h. The reaction mixture was held at reflux for 18 h, cooled and poured into water. The organic was extracted into ether. The ether layer was washed with brine and filtered through Celite. The filtrate was dried over $MgSO_4$ and concentrated. The residual oil (2.5 g) was purified by HPLC to give 2.06 g (77%) of 12 as an oil in the second fraction.

Example 10

(1aa,2a,8ba) 2-Ethyl-8b-phenyl-1a,2,3,8b-tetrahydro-benzothiepino-[4,5-b]oxirene-4,4-dioxide (13)

(13)

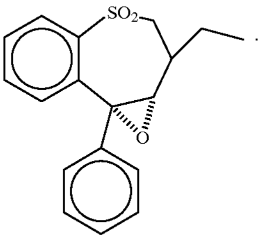

To a solution of 1.5 g (5.64 mmole) of 12 in 25 ml of CHCl, was added 6.8 g (19.4 mmole) of 50–60% MCPB portionwise causing an exothem and formation of a white solid. The mixture was stirred at room temperature overnight diluted with 100 ml methylene chloride and washed successively with 10% $K_2CO_3$ (4×50 ml), water (twice with 25 ml) and brine. The organic layer was then dried over $MgSO_4$ and evaporated to dryness to recover 1.47 g of an off white solid. $^1H$ NMR indicated that only one isomer is present. This solid was slurried in 200 ml of warm $Et_2O$ and filtered to give 0.82 g (46%) of 13 as a white solid, mp 185–186.5° C.

Example 11

(3a,4b,5a)-3-Ethyl-4-hydroxy-5-phenyl-2,3,4,5-tetrahydro-benzothiepine-1,1-dioxide (14a), (3a,4b,5b) 3-Ethyl-4- hydroxy-5-phenyl-2,3,4,5-tetrahydrobenzothiepine-1,1-dioxide (14b), and cis-3-Ethyl-5-phenyl-2,3,4,5-tetrahydrobenzothiepine-1,1-dioxide (15)

(14a)

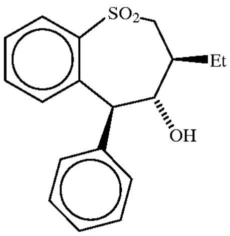

(14b)

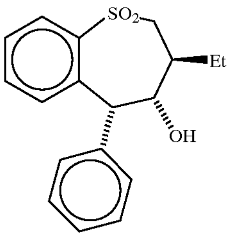

(15)

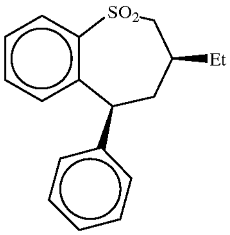

A mixture of 0.5 g (1.6 mole) of 13, 50 ml of acetic acid and 0.5 g of 10% Pd/C catalyst was hydrogenated with 70 psi hydrogen for 4 h. The crude reaction slurry was filtered and the filtrate was stirred with 150 ml of a saturated $NaHCO_3$ solution followed by 89 g of $NaHCO_3$ powder portionwise to neutralize the rest of acetic acid. The mixture was extracted with methylene chloride (4×25 ml), then the organic layer was dried over $MgSO_4$ and concentrated in vacuo to give 0.44 g (87%) of a voluminous white solid which was purified by HPLC (EtOAc-Hexane) to give 26.8 mg (6%) of 15 in the first fraction, 272 mg (54%) of 14a as a solid, mp 142– 143.5° C., in the second fraction, and 35 mg (7%) of impure 14b in the third fraction.

Example 12

2-Ethyl-2-((2-Hydroxethylphenyl)thiomethyl)hexenal (16)

(16)

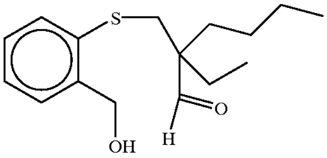

A mixture of 5.0 g (0.036 mole) of 2-mercaptobenzyl alcohol, 6.4 g (0.032 mole) of 1, 3.6 g (0.036 mole) of triethylamine and 25 mL of 2-methoxyethyl ether was held at reflux for 7 h. Additional 1.1 g of mercaptobenzyl alcohol and 0.72 g of triethylamine was added to the reaction mixture and the mixture was held at reflux for additional 16 h. The reaction mixture was cooled and poured into 6N HCl and extracted with methylene chloride. The methylene chloride extract was washed twice with 10% NaOH, dried over $MgSO_4$ and concentrated in vacuo to give 9.6 g of residue. Purification by HPLC (20% EtOAc-hexane) gave 3.7 g (41%)of 16 as an oil.

Example 13

2-Ethyl-2-((2-formylphenyl)thiomethyl)hexena (17)

(17)

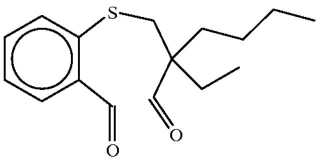

A mixture of 3.7 g of 16, 5.6 g (0.026 mole) of pyridinium chlorochromate, 2 g of Celite and 30 mL of methylene chloride was stirred for 18 h and filtered through a bed of silica gel. The silica gel was eluted with methylene chloride. The combined methylene chloride eluant was purified by HPLC (20% ETOAc-hexane) to give 2.4 g (66%) of an oil.

Example 14

3-Butyl-3-ethyl-2,3-dihydrobenzothiepine (18)

(18)

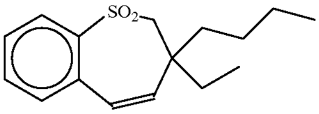

A mixture of 2.6 g (0.04 mole) of zinc dust, 7.2 g (0.047 mole) of $TiCl_3$, and 50 mL of DME was held at reflux for 2 h and cooled to room temperature. To this mixture was added 2.4 g (8.6 mmole) of 17 in 20 mL of DME in 10 min. The reaction mixture was stirred at room temperature for 2 h and held at reflux for 1 h then was let standing at room temperature over weekend. The reaction mixture was poured into dilute HCl and was stirred with methylene chloride. The methylene chloride-water mixture was filtered through Celite. The methylene chloride layer was washed with brine, dried over $MgSO_4$, and concentrated in vacuo to give 3.0 g of a residue. Purification by HPLC gave 0.41 g (20%) of 18 as an oil in the early fraction.

Example 15

(1aa,2a,8ba) 2-Butyl-2-ethyl-1a,2,3,8b-tetrahydrobenzothiepino[4,5-b]oxirene-4,4-dioxide (19a) and (1aa,2b,8ba) 2-Butyl-2-ethyl-8b-phenyl-1a,2,3,8b-tetrahydrobenzothiepino[4,5-b]oxirene-4,4-dioxide (19b)

(19a)

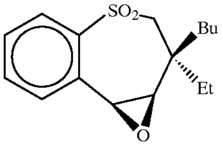

-continued (19b)

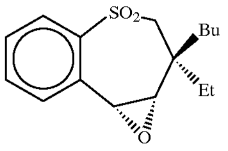

To a solution of 0.4 g of 0.4 g (1.6 mmole) of 18 in 30 mL of methylene chloride was added 2.2 g (3.2 mmole) of 50–60% MCPBA. The reaction mixture was stirred for 2 h and concentrated in vacuo. The residue was dissolved in 30 mL of $CHCl_3$ and was held at reflux for 18 h under $N_2$. The reaction mixture was stirred with 100 mL of 10% NaOH and 5 g of sodium sulfite. The methylene chloride layer was washed with brine, dried over $MgSO_4$ and concentrated in vacuo. The residue was purified by HPLC (20% EtOAc-hexane) to give a third fraction which was further purified by HPLC (10% EtOAc-hexane) to give 0.12 g of syrup in the first fraction.

Recrystallization from hexane gave 0.08 g (17%) of 19a, mp 89.5–105.5° C. The mother liquor from the first fraction was combined with the second fraction and was further purified by HPLC to give additional 19a in the first fraction and 60 mg of 19b in the second fraction.

Crystallization from hexane gave 56 mg of a white solid.

Example 16

3-Butyl-3-ethyl-4,5-dihydroxy-5-phenyl-2,3,4,5-tetrahydro-benzothiepine-1,1-dioxide (20)

(20)

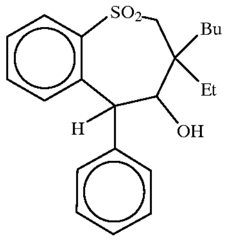

This product was isolated along with 6b from hydrogenation of a mixture of 8a and 8b.

Example 17

3-Butyl-3-ethyl-4-hydroxy-5-phenylthio-2,3,4,5-tetrahydro-benzothiepine-1,1-dioxide (21)

(21)

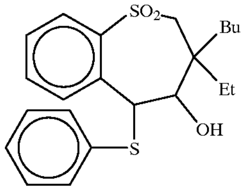

A mixture of 25 mg (0.085 mmole) of 19b, 0.27 g (2.7 mmole) of thiophenol, 0.37 g (2.7 mmole) of potassium carbonate, and 4 mL of DMF was stirred at room temperature under $N_2$ for 19 h. The reaction mixture was poured into water and extracted with methylene chloride. The methylene chloride layer was washed successively with 10% NaOH and brine, dried over $MgSO_4$, and concentrated in vacuo to give 0.19 g of semisolid which contain substantial amounts of diphenyl disulfide. This material was purified by HPLC (5% EtOAc-hexane) to remove diphenyl disulfide in the first fraction. The column was then eluted with 20% EtOAc-hexane to give 17 mg of a first fraction, 4 mg of a second fraction and 11 mg of a third fraction which were three different isomers of 21, i.e. 21a, 21b, and 21c, respectively, by $^{1}H$ NMR and mass spectra.

Example 18

Alternative Synthesis of 6c and 6d

A. Preparation from 2-((2-Benzoylphenylthio)methyl)-2-ethylhexanal (2)

Step 1

2-((2-Benzoylphenylsulfonyl)methyl)-2-ethylhexanal (44)

(44)

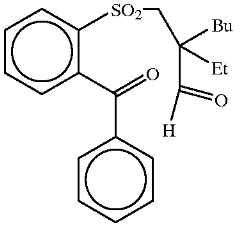

To a solution of 9.0 g (0.025 mole) of compound 2 in 100 ml of methylene chloride was added 14.6 g (0.025 mol) of 50–60% MCPBA portionwise. The reaction mixture was stirred at room temperature for 64 h then was stirred with 200 ml of 1 M potassium carbonate and filtered through Celite. The methylene chloride layer was washed twice with 300 ml of 1 M potassium carbonate, once with 10% sodium hydroxide and once with brine. The insoluble solid formed during washing was removed by filtration through Celite. The methylene chloride solution was dried and concentrated in vacuo to give 9.2 g (95%) of semisolid. A portion (2.6 g) of this solid was purified by HPLC(10% ethyl acetate-hexane) to give 1.9 g of crystals, mp 135–136° C.

Step 2

2-((2-Benzylphenylsulfonyl)methyl)-2-ethylhexanal (45)

(45)

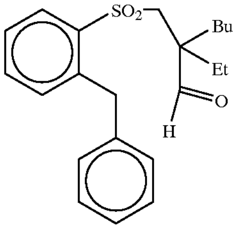

A solution of 50 g (0.13 mole) of crude 44 in 250 ml of methylene chloride was divided in two portions and charged to two Fisher-Porter bottles. To each bottle was charged 125 ml of methanol and 5 g of 10% Pd/C. The bottles were pressurized with 70 psi of hydrogen and the reaction mixture was stirred at room temperature for 7 h before being charged with an additional 5 g of 10% Pd/C. The reaction mixture was again hydrogenated with 70 psi of hydrogen for 7 h. This procedure was repeated one more time but only 1 g of Pd/C was charged to the reaction mixture. The combined reaction mixture was filtered and concentrated in vacuo to give 46.8 g of 45 as brown oil.

Step 3

(3a,4a,5a) 3-Butyl-3-ethyl-4-hydroxy-5-phenyl-2,3,4,5-tetrahydrobenzothiepine-1,1-dioxide (6c), and (3a,4b,5b) 3-Butyl-3-ethyl-4-hydroxy-5-phenyl-2,3,4,5-tetrahydrobenzothiepine-1,1-dioxide (6d)

To a solution of 27.3 g (73.4 mmole) of 45 in 300 ml of anhydrous THF cooled to 2° C. with an ice bath was added 9.7 g (73.4 mmole) of 95% potassium t-butoxide. The reaction mixture was stirred for 20 min, quenched with 300 ml of 10% HCl and extracted with methylene chloride. The methylene chloride layer was dried over magnesium sulfate and concentrated in vacuo to give 24.7 g of yellow oil. Purification by HPLC (ethyl acetate-hexane) yielded 9.4 g of recovered 45 in the first fraction, 5.5 g (20%) of 6c in the second fraction and 6.5 g (24%) of 6d in the third fraction.

B. Preparation From 2-hydroxydiphenylmethane

Step 1

2-mercaptodiphenylmethane (46)

(46)

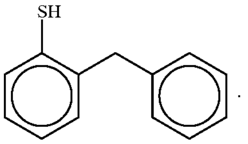

To a 500 ml flask was charged 16 g (0.33 mol) of 60% sodium hydride oil dispersion. The sodium hydride was washed twice with 50 ml of hexane. To the reaction flask was charged 100 ml of DMF. To this mixture was added a solution of 55.2 g (0.3 mol) of 2-hydroxydiphenylmethane in 200 ml of DMF in 1 h while temperature was maintained below 30° C. by an ice-water bath. After complete addition of the reagent, the mixture was stirred at room temperature for 30 min then cooled with an ice bath. To the reaction mixture was added 49.4 g (0.4 mole) of dimethyl thiocarbamoyl chloride at once. The ice bath was removed and the reaction mixture was stirred at room temperature for 18 h before being poured into 300 ml of water. The organic was extracted into 500 ml of toluene. The toluene layer was washed successively with 10% sodium hydroxide and brine and was concentrated in vacuo to give 78.6 g of a yellow oil which was 95% pure dimethyl O-2-benzylphenyl thiocarbamate. This oil was heated at 280–300° C. in a kugelrohhr pot under house vacuum for 30 min. The residue was kugelrohr distilled at 1 torr (180–280° C.). The distillate (56.3 g) was crystallized from methanol to give 37.3 g (46%) of the rearranged product dimethyl S-2-benzylphenyl thiocarbamate as a yellow solid. A mixture of 57 g (0.21 mole) of this yellow solid, 30 g of potassium hydroxide and 150 ml of methanol was stirred overnight then was concentrated in vacuo. The residue was diluted with 200 ml of water and extracted with ether. The aqueous layer was made acidic with concentrate HCl, The oily suspension was extracted into ether. The ether extract was dried over magnesium sulfate and concentrated in vacuo. The residue was crystallized from hexane to give 37.1 g (88%) of 2-mercaptodiphenylmethane as a yellow solid.

Step 2

2-((2-Benzylphenylthio)methyl)-2-ethylhexanal (47)

(47)

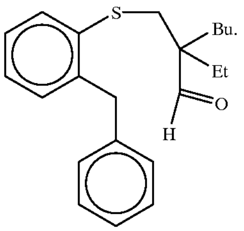

A mixture of 60 g (03 mole) of yellow solid from step 1, 70 g (0.3 mole) of compound 1 from preparation 1, 32.4 g (0.32 mole) of triethylamine, 120 ml of 2-methoxyethyl ether was held at reflux for 6 hr and concentrated in vacuo. The residue was triturated with 500 ml of water and 30 ml of concentrate HCl. The organic was extracted into 400 ml of ether. The ether layer was washed successively with brine, 10% sodium hydroxide and brine and was dried over magnesium sulfate and concentrated in vacuo. The residue (98.3 g) was purified by HPLC with 2–5% ethyl acetate-hexane as eluent to give 2-((2-benzylphenylthio)methyl)-2-ethylhexanal 47 as a yellow syrup.

Step 3

2-((2-Benzylphenylsulfonyl)methyl)-2-ethylhexanal (45)

(45)

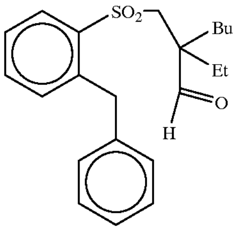

To a solution of 72.8 g (0.21 mole) of yellow syrup from step 2 in 1 liter of methylene chloride cooled to 10° C. was added 132 g of 50–60% MCPBA in 40 min. The reaction mixture was stirred for 2 h. An additional 13 g of 50–60% MCPBA was added to the reaction mixture. The reaction mixture was stirred for 2 h and filtered through Celite. The methylene chloride solution was washed twice with 1 liter of 1 M potassium carbonate then with 1 liter of brine. The methylene chloride layer was dried over magnesium sulfate and concentrated to 76 g of 2-((2-benzylphenylsulfonyl)methyl)-2-ethylhexanal 45 as a syrup.

Step 4

(3a,4a,5a) 3-Butyl-3-ethyl-4-hydroxy-5-phenyl-2,3,4,5-tetrahydrobenzothiepine-1,1-dioxide (6c), and (3a,4b,5b) 3-Butyl-3-ethyl-4-hydroxy-5-phenyl-2,3,4,5-tetrahydrobenzothiepine-1,1-dioxide (6d)

Reaction of 45 with potassium t-butoxide according to the procedure in step 3 of procedure A gave pure 6c and 6d after HPLC.

Example 19

(3a,4b,5b) 3-Butyl-3-ethyl-4-hydroxy-8-methoxy-5-phenyl-2,3,4,5-tetrahydrobenzothiepine-1,1-dioxide (25) and (3a,4a,5a) 3-Butyl-3-ethyl-4-hydroxy-8-methoxy-5-phenyl-2,3,4,5-tetrahydrobenzothiepine-1,1-dioxide (26)

Step 1

Preparation of 2-((2-benzoyl-4-methoxyphenylthio) methyl)-2-ethylhexanal (22)

(22)

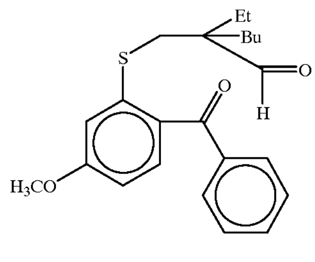

2-Hydroxy-4-methoxybenzophenone was converted to the dimethyl O-2-benzoyphenyl thiocarbamate by methods previously described in example 18. The product can be isolated by recrystallization from ethanol. Using this improved isolation procedure no chromatography was needed. The thermal rearrangement was performed by reacting the thiocarbamate(5 g) in diphenyl ether at 260° C. as previously described. The improved isolation procedure which avoided a chromatography step was described below.

The crude pyrolysis product was then heated at 65° C. in 100 ml of methanol and 100 ml of THF in the presence of 3.5 g of KOH for 4 h. After removing THF and methanol by rotary evaporation the solution was extracted with 5% NaOH and ether. The base layer was acidified and extracted with ether to obtain a 2.9 g of crude thiophenol product. The product was further purified by titrating the desired mercaptan into base with limited KOH. After acidification and extraction with ether pure 2-mercapto-4-methoxybenzophenone (2.3 g) was isolated.

2-mercapto-4-methoxybenzophenone can readily be converted to the 2-((2-benzoyl-4-methoxyphenylthio)methyl)-2-ethylhexanal (22) by reaction with 2-ethyl-2-(mesyloxethyl)hexanal (1) as previously described.

Step 2

2-((2-Benzoyl-5-methoxyphenylsulfonyl)methyl)-2-ethylhexanal (23)

(23)

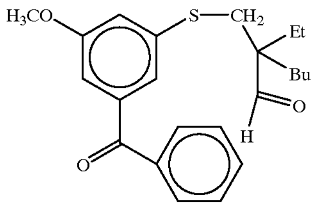

Substrate 22 was readily oxidized to 2-((2-benzoyl-5-methoxyphenyl-sulfonyl)methyl-2-ethylhexanal (23) as described in example 18.

(24)

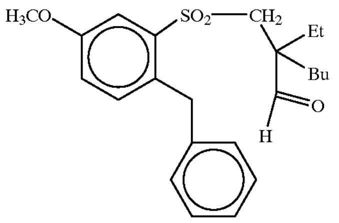

Step 3

2-((2-benzyl-5-methoxyphenylsulfonyl)methyl)-2-ethylhexanal (24)

Sulfone 23 was then reduced to 2-((2-benzyl-5-methoxyphenyl-sulfonyl)methyl)-2-ethylhexanal (24) as described in example 18.

(25)

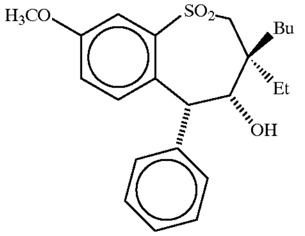

Step 4

(3a,4b,5b) 3-Butyl-3-ethyl-4-hydroxy-8-methoxy-5-phenyl-2,3,4,5-tetrahydrobenzothiepine-1,1-dioxide (25) and (3a,4a,5a) 3-Butyl-3-ethyl-4-hydroxy-8-methoxy-5-phenyl-2,3,4,5-tetrahydrobenzothiepine-1,1-dioxide (26)

(26)

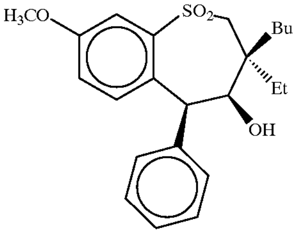

A 3-neck flask equipped with a powder addition funnel, thermocouple and nitrogen bubbler was charged with 19.8 g (0.05 mole) of sulfone 24 in 100 ml dry THF. The reaction was cooled to −1.6° C. internal temperature by means of ice/salt bath. Slowly add 5.61 g (0.05 mole) of potassium t-butoxide by means of the powder addition funnel. The resulting light yellow solution was maintained at −1.6° C. After 30 min reaction 400 ml of cold ether was added and this solution was extracted with cold 10% HCl. The acid layer was extracted with 300 ml of methylene chloride. The organic layers were combined and dried over magnesium sulfate and after filtration stripped to dryness to obtain 19.9 g of product. $^1H$ nmr and glpc indicated a 96% conversion to a 50/50 mixture of 25 and 26. The only other observable compound was 4% starting sulfone 24.

The product was then dissolved in 250 ml of 90/10 hexane/ethyl acetate by warming to 50° C. The solution was allowed to cool to room temperature and in this way pure 26 can be isolated. The crystallization can be enhanced by addition of a seed crystal of 26. After 2 crystallizations the mother liquor which was now 85.4% 25 and has a dry weight of 8.7 g. This material was dissolved in 100 ml of 90/10 hexane/ethyl acetate and 10 ml of pure ethyl acetate at 40 C. Pure 25 can be isolated by seeding this solution with a seed crystal of 25 after storing it overnight at 0 C.

Example 20

(3a,4a,5a) 3-Butyl-3-ethyl-4,8-dihydroxy-5-phenyl-2,3,4,5-tetrahydrobenzothiepine-1,1-dioxide (27)

(27)

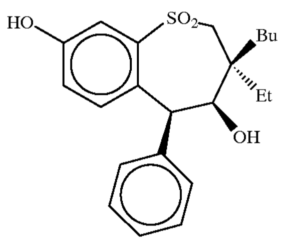

In a 25 ml round bottomed flask, 1 g of 26(2.5 mmoles) and 10 ml methylene chloride were cooled to −78° C. with stirring. Next 0.7 ml of boron tribromide(7.5 mmole) was added via syringe. The reaction was allowed to slowly warm to room temperature and stirred for 6 h. The reaction was then diluted with 50 ml methylene chloride and washed with saturated NaCl and then water. The organic layer was dried over magnesium sulfate. The product (0.88 g) 27 was characterized by NMR and mass spectra.

Example 21

General Alkylation of phenol 27

A 25 ml flask was charged with 0.15 g of 27(0.38 mmole), 5 ml anhydrous DMF, 54 mg of potassium carbonate(0.38 mmole) and 140 mg ethyl iodide (0.9 mmole). The reaction was stirred at room temperature overnight. The reaction was diluted with 50 ml ethyl ether and washed with water (25 ml) then 5% NaOH (20 ml) and then sat. NaCl. After stripping off the solvent the ethoxylated product 28 was obtained in high yield. The product was characterized by NMR and mass spectra. This same procedure was used to prepare products listed in table 1 from the corresponding iodides or bromides. For higher boiling alkyl iodides and bromides only one equivalent of the alkyl halide was used.

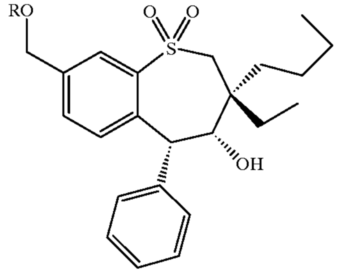

TABLE 1

| Compound No. | R |
|---|---|
| 27 | H |
| 26 | Me |
| 28 | Et |
| 29 | hexyl |
| 30 | Ac |
| 31 | (CH2) 6-N-pthalimide |

Example 22

(3a,4a,5a) 3-Butyl-3-ethyl-4-hydroxy-7-hydroxyamino-5-phenyl-2,3,4,5-tetrahydrobenzothiepine-1,1-dioxide (37) and (3a,4b,5b) 3-Butyl-3-ethyl-4-hydroxy-7-hydroxyamino-5-phenyl-2,3,4,5-tetrahydrobenzothiepine-1,1-dioxide (38)

Step 1

Preparation of 2-chloro-5-nitrodiphenylmethane (32)

(32)

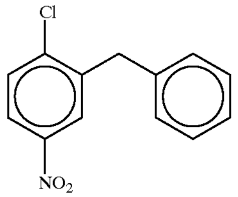

Procedure adapted from reference :Synthesis-Stuttgart 9 770–772 (1986) Olah G. Et al.

Under nitrogen, a 3 neck flask was charged with 45 g (0.172 mole ) of 2-chloro-5-nitrobenzophenone in 345 ml methylene chloride and the solution was cooled to ice/water temperature. By means of an additional funnel, 150 g(0.172 mole) of trifluoromethane sulfonic acid in 345 ml methylene chloride was added slowly. Next 30 g of triethylsilane (0.172 mole) in 345 ml methylene chloride was added dropwise to the chilled solution. Both addition steps(trifluoromethane sulfonic acid and triethylsilane) were repeated. After the additions were completed the reaction was allowed to slowly warm up to room temperature and stirred for 12 h under nitrogen. The reaction mixture was then poured into a chilled stirred solution of 1600 ml of saturated sodium bicarbonate. Gas evolution occurred. Poured into a 4 liter separatory funnel and separated layers. The methylene chloride layer was isolated and combined with two 500 ml methylene chloride extractions of the aqueous layer. The methylene chloride solution was dried over magnesium sulfate and concentrated in vacuo. The residue was recrystallized from hexane to give 39 g product. Structure 32 was confirmed by mass spectra and proton and carbon NMR.

Step 2

Preparation of 2-((2-benzyl-4-nitrophenylthio)methyl)-2-ethylhexanal (33)

(33)

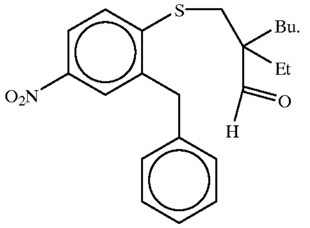

The 2-chloro-5-nitrodiphenylmethane product 32 (40 g, 0.156 mole) from above was placed in a 2 liter 2 neck flask with water condenser. Next 150 ml DMSO and 7.18 g (0.156 mole) of lithium sulfide was added and the solution was stirred at 75° C. for 12 h. The reaction was cooled to room temperature and then 51.7 g of mesylate IV was added in 90 ml DMSO. The reaction mixture was heated to 80° C. under nitrogen. After 12 h monitored by TLC and added more mysylate if necessary. Continued the reaction until the reaction was completed. Next the reaction mixture was slowly poured into a 1900 ml of 5% acetic aqueous solution with stirring, extracted with 4×700 ml of ether, and dried over MgSO4. After removal of ether, 82.7 g of product was isolated. The material can be further purified by silica gel chromatography using 95% hexane and 5% ethyl acetate. If pure mysylate was used in this step there was no need for further purification. The product 33 was characterized by mass spectra and NMR.

Step 3

Oxidation of the Nitro Product 33 to the Sulfone 2-((2-benzyl-4-nitrophenylsulfonyl)methyl)-2-ethylhexanal (34)

The procedure used to oxidize the sulfide 33 to the sulfone 34 has been previously described.

(34)

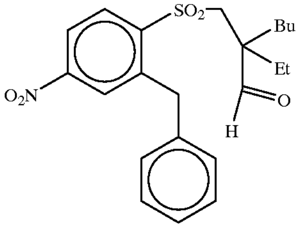

Step 4

Reduction of 34 to 2-((2-benzyl-4-hydroxyaminophenylsulfonyl)methyl)-2-ethylhexanal (35)

(35)

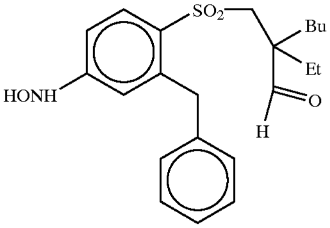

A 15 g sample of 34 was dissolved in 230 ml of ethanol and placed in a 500 ml rb flask under nitrogen. Next 1.5 g of 10 wt. % Pd/C was added and hydrogen gas was bubbled through the solution at room temperature until the nitro substrate 34 was consumed. The reaction could be readily monitored by silica gel TLC using 80/20 hexane/EtOAc. Product 35 was isolated by filtering off the Pd/C and then stripping off the EtOH solvent. The product was characterized by NMR and mass spectra.

Step 5

Preparation of the 2-((2-benzyl-4-N,O-di-(t-butoxycarbonyl) hydroxyaminophenylsulfonyl)methyl)-2-ethylhexanal (36).

(36)

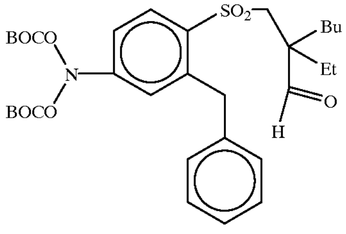

A 13.35 g sample of 35 (0.0344 mole) in 40 ml of dry THF was stirred in a 250 ml round bottomed flask. Next added 7.52 g (0.0344 mole) of di-t-butyl dicarbonate in 7 ml THF. Heated at 60° C. overnight. Striped off THF and redissolved in methylene chloride. Extracted with 1% HCl; and then 5% sodium bicarbonate.

The product was further purified by column chromatography using 90/10 hexane/ethyl acetate and then 70/30 hexane/ethyl acetate. The product 36 was obtained (4.12 g) which appeared to be mainly the di-(t-butoxycarbonyl) derivatives by proton NMR.

Step 6

(3a,4a,5a) 3-Butyl-3-ethyl-4-hydroxy-7-hydroxyamino-5-phenyl-2,3,4,5-tetrahydrobenzothiepine-1,1-dioxide (37) and (3a,4b,5b) 3-Butyl-3-ethyl-4-hydroxy-7-hydroxyamino-5-phenyl-2,3,4,5-tetrahydrobenzothiepine-1,1-dioxide (38)

(37)

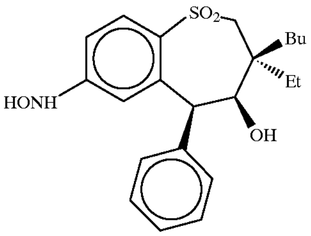

(38)

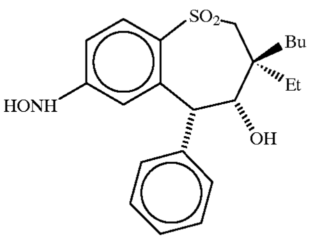

A 250 ml 3-neck round bottomed flask was charged with 4 g of 36 (6.8 mmoles), and 100 ml of anhydrous THF and cooled to −78° C. under a nitrogen atmosphere. Slowly add 2.29 g potassium tert-butoxide(20.4 mmoles) with stirring and maintaining a −78° C. reaction temperature. After 1 h at −78° C. the addition of base was completed and the temperature was brought to −10° C. by means of a ice/salt bath. After 3 h at −10° C., only trace 36 remained by TLC. Next add 35 ml of deionized water to the reaction mixture at −10° C. and stirred for 5 min. Striped off most of the THF and added to separatory funnel and extracted with ether until all of the organic was removed from the water phase. The combined ether phases were washed with saturated NaCl and then dried over sodium sulfate. The only products by TLC and NMR were the two BOC protected isomers of 37 and 38. The isomers were separated by silica gel chromatography using 85% hexane and 15% ethyl acetate; BOC-37 (0.71 g) and BOC-38 (0.78 g).

Next the BOC protecting group was removed by reacting 0.87 g of BOC-38 (1.78 mmoles) with 8.7 ml of 4 M HCl (34.8 mmoles) in dioxane for 30 min. Next added 4.74 g of sodium acetate (34.8 mmoles) to the reaction mixture and 16.5 ml ether and stirred until clear. After transferring to a separatory funnel extracted with ether and water and then dried the ether layer with sodium sulfate. After removing the ether, 0.665 g of 38 was isolated. Isomer 37 could be obtained in a similar procedure.

Example 23

(3a,4a,5a) 3-Butyl-3-ethyl-7-(n-hexylamino)-4-hydroxy-5-phenyl-2,3,4,5-tetrahydrobenzothiepine-1,1-dioxide (40) and (3a,4b,5b) 3-Butyl-3-ethyl-7-(n-hexylamino)-4-hydroxy-5-phenyl-2,3,4,5-tetrahydrobenzothiepine-1,1-dioxide (41)

Step 1

2-((2-Benzyl-4-(n-hexylamino)phenylsulfonyl)methyl)-2-ethylhexanal (39)

(39)

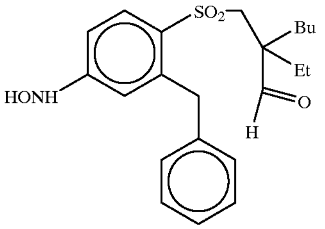

In a Fischer porter bottle weighed out 0.5 g of 34 (1.2 mmoles) and dissolved in 3.8 ml of ethanol under nitrogen. Next added 0.1 g of Pd/C and 3.8 ml of hexanal. Seal and pressure to 50 psi of hydrogen gas. Stirred for 48 h. After filtering off the catalyst and removing the solvent by rotary evaporation 39 was isolated by column chromatography (0.16 g) using 90/10 hexane ethyl acetate and gradually increasing the mobile phase to 70/30 hexane/ethyl acetate. The product was characterized by NMR and mass spectra.

Step 2

(3a,4a,5a) 3-Butyl-3-ethyl-7-(n-hexylamino)-4-hydroxy-5-phenyl-2,3,4,5-tetrahydrobenzothiepine-1,1-dioxide (40) and (3a,4b,5b) 3-Butyl-3-ethyl-7-(n-hexylamino)-4-hydroxy-5-phenyl-2,3,4,5-tetrahydrobenzothiepine-1,1-dioxide (41)

(40)

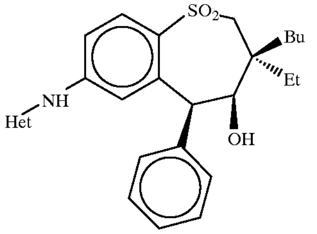

A 2-neck, 25 ml round bottomed flask with stir bar was charged with 0.158 g 39 (0.335 mmole) and 5 ml anhydrous THF under nitrogen. Cool to −10° C. by means of a salt/water bath. Slowly add 0.113 g of potassium tert butoxide (0.335 mmole). After 15 min at −10° C. all of the starting material was consumed by TLC and only the two isomers 40 and 41 were observed. Next added 5 ml of chilled 10% HCl and stirred at −10° C. for 5 min. Transferred to a separatory funnel and extract with ether. Dried over sodium sulfate. Proton NMR of the dried product (0.143 g) indicated only the presence of the two isomers 40 and 41. The two isomers were separated by silica gel chromatography using 90/10 hexane ethyl acetate and gradually increasing the mobile phase to 70/30 hexane/ethyl acetate. 40 (53.2 mg); 41(58.9 mg).

Example 24

Quaternization of Amine Substrates 40 and 41

(41)

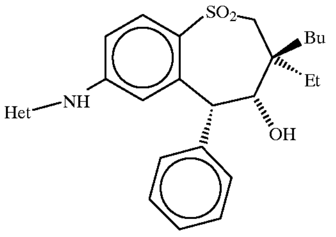

Amine products such as 40 and 41 can be readily alkylated to quaternary salts by reaction with alkyl halides. For example 40 in DMF with 5 equivalents of methyl iodide in the presence of 2,6 dimethyl lutidine produces the dimethylhexylamino quaternary salt.

Example 25

(3a,4b,5b) 3-Butyl-3-ethyl-4-hydroxy-5-(4-iodophenyl)-2,3,4,5-tetrahydrobenzothiepine-1,1-dioxide (42)

(42)

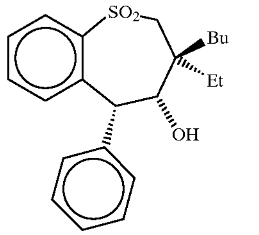

In a 25 ml round bottomed flask 0.5 g (1.3 mmole) of 6d, 0.67 g of mercuric triflate were dissolved in 20 ml of dry methylene chloride with stirring. Next 0.34 g of Iodine was added and the solution was stirred at room temperature for 30 h. The reaction was then diluted with 50 ml methylene chloride and washed with 10 ml of 1 M sodium thiosulfate; 10 ml of saturated KI; and dried over sodium sulfate. See Tetrahedron, Vol.50; No. 17, pp 5139–5146 (1994) Bachki, F. Et al. Mass spectrum indicated a mixture of 6d , mono iodide 42 and a diiodide adduct. The mixture was separated by column chromatography and 42 was characterized bt NMR and mass spectra.

Example 26

(3a,4b,5b) 3-Butyl-5-(4-carbomethoxypheny-3-ethyl-4-hydroxy-2,3,4,5-tetrahydrobenzothiepine-1,1-dioxide (43)

(43)

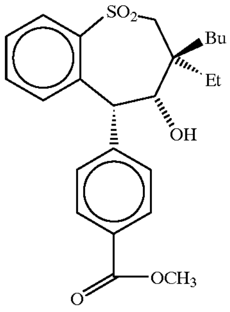

A 0.1 g sample of 42 (0.212 mmole), 2.5 ml dry methanol, 38 μl triethylamine (0.275 mmole), 0.3 ml toluene and 37 mg of palladium chloride (0.21 mmole) was charged to a glass lined mini reactor at 300 psi carbon monoxide. The reaction was heated at 100° C. overnight. The catalyst was filtered and a high yield of product was isolated. The product was characterized by NMR and mass spectra.

Note the ester functionalized product 43 can be converted to the free acid by hydrolysis.

Example 27

(3a,4a,5a) 3-Butyl-3-ethyl-4-hydroxy-7-methoxy-5-phenyl-2,3,4,5-tetrahydrobenzothiepine-1,1-dioxide (48), and (3a,4b,5b) 3-Butyl-3-ethyl-4-hydroxy-7-methoxy-5-phenyl-2,3,4,5-tetrahydrobenzothiepine-1,1-dioxide (49)

Step 1

2-Mercapto-5-methoxybenzophenone (50)

(50)

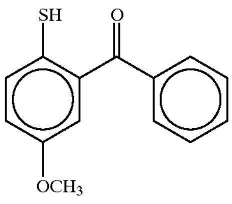

Reaction of 66.2 g of 4-methoxythiophenol with 360 ml of 2.5 N n-butyllithium, 105 g of tetramethylethylenediamine and 66.7 g of benzonitrile in 600 ml cyclohexane according to the procedure in WO 93/16055 gave 73.2 g of brown oil which was kugelrohr distilled to remove 4-methoxythiophenol and gave 43.86 g of crude 50 in the pot residue.

Step 2

2-((2-Benzoyl-4-methoxyphenylthio)methyl)-2-ethylhexanal (51)

(51)

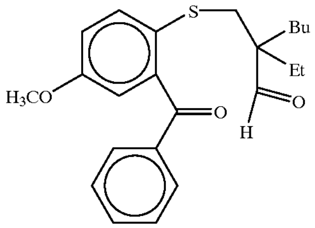

Reaction of 10 g (0.04 mole) of crude 50 with 4.8 g (0.02 mole) of mesylate 1 and 3.2 ml (0.23 mole) of triethylamine in 50 ml of diglyme according to the procedure for the preparation of 2 gave 10.5 g of crude product which was purified by HPLC (5% ethyl acetate-hexane) to give 1.7 g (22%) of 51.

Step 3

2-((2-Benzoyl-4-methoxyphenylsulfonyl)methyl)-2-ethylhexanal (52)

(52)

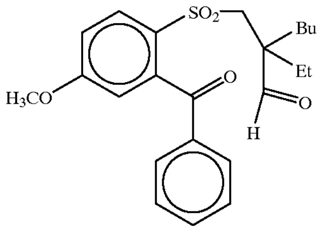

A solution of 1.2 g (3.1 mmoles) of 51 in 25 ml of methylene chloride was reacted with 2.0 g (6.2 mmoles) of 50–60% MCPBA according to the procedure of step 2 of procedure A in example 18 gave 1.16 g (90%) of 52 as a yellow oil.

Step 4

2-((2-Benzyl-4-methoxyphenylsulfonyl)methyl)-2-ethylhexanal (53)

(53)

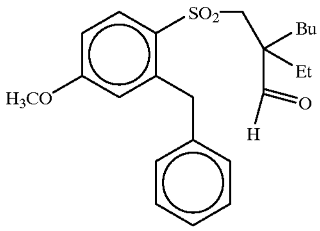

Hydrogenation of 1.1 g of 52 according to the procedure of step 3 of procedure A of example 18 gave 53 as a yellow oil (1.1 g). Step 5

(3a,4a,5a) 3-Butyl-3-ethyl-4-hydroxy-7-methoxy-5-phenyl-2,3,4,5-tetrahydrobenzothiepine-1,1-dioxide (48), and (3a,4b,5b) 3-Butyl-3-ethyl-4-hydroxy-7-methoxy-5-phenyl-2,3,4,5-tetrahydrobenzothiepine-1,1-dioxide (49)

(48)

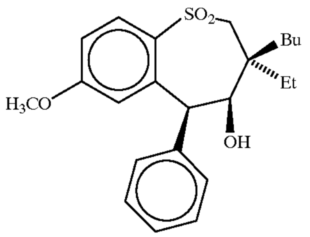

(49)

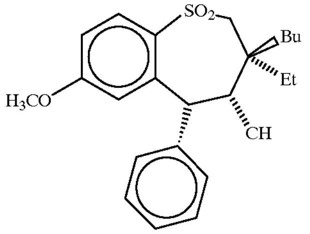

A solution of 1.1 g of 53, 0.36 g potassium t-butoxide and 25 ml of anhydrous THF was held at reflux for 2 h and worked up as in step 4 of procedure A of example 18 to give 1.07 g of a crude product which was purified by HPLC to give 40 mg (4%) of 48 as crystals, mp 153–154° C. and 90 mg (8%) of 49 as solid, mp 136–140° C.

Example 28

5-Phenyl-2,3-dihydrospirobenzothiepine-3,1'-cyclohexane (57)

Step 1

1-(Hydroxymethyl)-cyclohexanecarboxaldehyde (54)

(57)

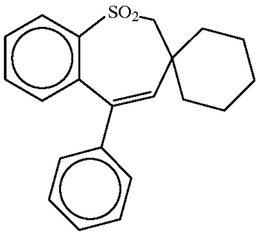

(54)

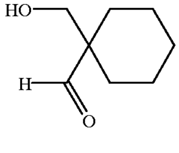

To a cold (0° C.) mixture of 100 g (0.891 mole) of cyclohexanecarboxaldehyde, 76.5 g of 37% of formaldehyde in 225 ml of methanol was added dropwise 90 ml of 1 N Sodium hydroxide in 1 h. The reaction mixture was stirred at room temperature over 48 then was evaporated to remove methanol. The reaction mixture was diluted with water and extracted with methylene chloride. The organic layer was washed with water, brine, and dried over sodium sulfate and concentrated under vacuum to give 75 g (59.7%) of thick oil. Proton NMR and mass spectra were consistent with the product.

Step 2

1-(mesyloxymethyl)cyclohexanecarboxaldehyde (55)

(55)

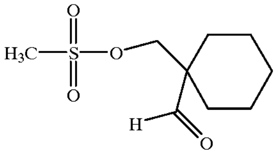

To a cold (0° C.) mixture of alcohol 54 (75 g, 0.54 mole) and 65.29 g (0.57 mole) of methanesulfonyl chloride in 80 ml of methylene chloride was added a solution of pyridine (47.96 g, 0.57 mole) in 40 ml of methylene chloride. The reaction mixture was stirred at room temperature for 18 h then quenched with water, acidified with conc. HCl and extracted with methylene chloride. The organic layer was washed with water, brine, and dried over sodium sulfate and concentrated under vacuum to give 91.63 g (77.8%) of thick oil. Proton NMR and mass spectra were consistent with the product.

Step 3

1-((2-Benzoylphenylthio)methyl) cyclohexanecarboxaldehyde (56)

(56)

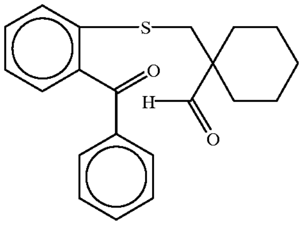

A mixture of 69 g (0.303 mole) of 2-mercaptobenzophenone, 82 g (0.303 mole) of mesylate 55, 32 g of triethylamine, and 150 ml of diglyme was stirred and held at reflux for 24 h. The mixture was cooled, poured into dil. HCl and extracted with methylene chloride. The organic layer was washed with 10% NaOH, water, brine, and dried over sodium sulfate and concentrated under vacuum to remove excess diglyme. This was purified by silica gel flush column (5% EtOAc:Hexane) and gave 18.6 g (75.9%) of yellow oil. Proton NMR and mass spectra were consistent with the product.

Step 4

5-Phenyl-2,3-dihydrospirobenzothiepine-3,1'-cyclohexane (57)

(57)

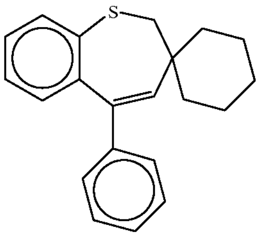

To a mixture of 6.19 g of zinc dust and 100 ml of dry DME was added TiCl,(16.8 g, 0.108 mole). The reaction mixture was heated to reflux for 2 h. A solution of compound 56 (8.3 g, 0.023 mole) in 50 ml of DME was added dropwise to the reaction mixture in 1 h and the mixture was held at reflux for 18 h. The mixture was cooled, poured into water and extracted with ether. The organic layer was washed with water, brine, and dried over sodium sulfate, filtered through celite and concentrated under vacuum. The residue was purified by HPLC (10% EtOAc:Hexane) to give 4.6 g (64%) of white solid, mp 90–91° C. Proton and carbon NMR and mass spectra were consistent with the product.

Example 29

8b-Phenyl-1a,2,3,8b-tetrahydrospiro(benzothiepino[4,5-b]oxirene-2,1'-cyclohexane)-4,4-dioxide (58)

(58)

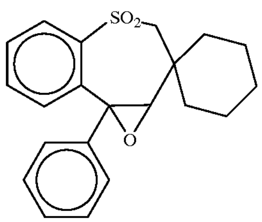

To a solution of 57 (4.6 g, 15 mmole) in 50 ml chloroform under nitrogen was added 55% MCPBA (16.5 g, 52.6 mmole) portionwise with spatula. The reaction was held at reflux for 18 h and washed with 10% NaOH(3x), water, brine, and dried over sodium sulfate and concentrated under vacuum to give 5 g of crude product. This was recrystallized from Hexane/EtOAc to give 4.31 g (81%) of yellow solid, mp 154–155° C. Proton and carbon NMR and mass spectra were consistent with the product.

Example 30 trans-4-Hydroxy-5-phenyl-2,3,4,5-tetrahydrospiro(benzothiepine-3,1'-cyclohexane)-1,1-dioxide (59)

(59)

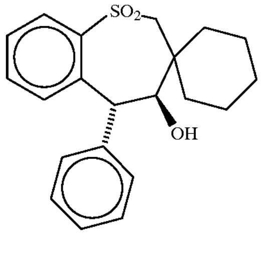

A mixture of 0.5 g (1.4 mmoles) of 58, 20 ml of ethanol, 10 ml of methylene chloride and 0.4 g of 10% Pd/C catalyst was hydrogenated with 70 psi hydrogen for 3 h at room temperature. The crude reaction slurry was filtered through Celite and evaporated to dryness. The residue was purified by HPLC (10% EtOAc-Hexane, 25% EtOAc-Hexane). The first fraction was 300 mg (60%) as a white solid, mp 99–100° C. Proton NMR showed this was a trans isomer. The second fraction gave 200 mg of solid which was impure cis isomer.

Example 31 cis-4-Hydroxy-5-phenyl-2,3,4,5-tetrahydrospiro(benzothiepine-3,1'-cyclohexane)-1,1-dioxide (60)

(60)

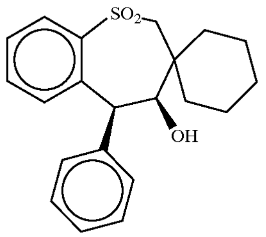

To a solution of 0.2 g (0.56 mmole) of 59 in 20 ml of $CH_2Cl_2$, was added 8 g of 50% NAOH and one drop of Aliquat-336 (methyltricaprylylammonium chloride) phase transfer catalyst. The reaction mixture was stirred for 10 h at room temperature. Twenty g of ice was added to the mixture and the mixture was extracted with $CH_2Cl_2$ (3x10 ml) washed with water, brine and dried over $MgSO_4$ and concentrated in vacuo to recover 0.15 g of crude product. This was recrystallized from Hexane/EtOAc to give 125 mg of white crystal, mp 209–210° C. Proton and carbon NMR and mass spectra were consistent with the product.

Example 32

(3a,4a,5a) 3-Butyl-3-ethyl-4-hydroxy-5-phenyl-2,3,4,5-tetrahydrobenzothiepine (61), and (3a,4b,5b) 3-Butyl3-ethyl-4-hydroxy-5-phenyl-2,3,4,5-tetrahydrobenzothiepine (62)

(61)

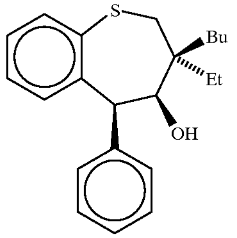

(62)

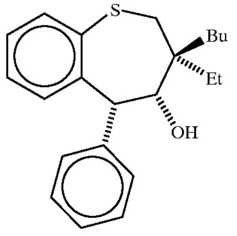

To a solution of 0.5 g (1.47 mmole) of compound 47 in 5 ml of anhydrous THF was added 0.17 g (1.47 mmole) of 95% potassium t-butoxide. The reaction mixture was stirred at room temperature for 18 h and quenched with 10 ml of 10% HCl. The organic was extracted into methylene chloride. The methylene chloride extract was dried over magnesium sulfate and concentrated in vacuo. The residue was purified by HPLC (2% EtOAc-hexane) to give 47 mg of 61 in the second fraction and 38 mg of 62 in the third fraction. Proton NMR and mass spectra were consistent with the assigned structures.

Example 33

(3a,4a,5a) 3-Butyl-3ethyl-4-hydroxy-7-amino-5-phenyl-2,3,4,5-tetrahydrobenzothiepine-1,1-dioxide (63) and (3a,4b,5b) 3-Butyl-3-ethyl-4-hydroxy-7-amino-5-phenyl-2,3,4,5-tetrahydrobenzothiepine-1,1-dioxide (64)

(63)

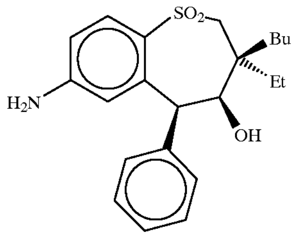

(64)

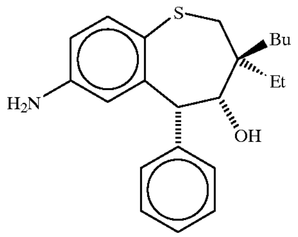

An autoclave was charged with 200 mg of 37 in 40 cc ethanol and 0.02 g 10% Pd/C. After purging with nitrogen the clave was charged with 100 psi hydrogen and heated to 55 C. The reaction was monitored by TLC and mass spec and allowed to proceed until all of 37 was consumed. After the reaction was complete the catalyst was filtered and the solvent was removed in vacuo and the only observable product was amine 63. This same procedure was used to produce 64 from 38.

Example 34

(3a,4a,5a) 3-Butyl-3-etyl-4-hydroxy-7-methoxy-5-(3'-methoxyphenyl)-2,3,4,5-tetrahydrobenzothiepine-1,1-dioxide (65), and (3a,4b,5b) 3-Butyl-3-ethyl-4-hydroxy-7-methoxy-5-(3'-methoxyphenyl)-2,3,4,5-tetrahydrobenzothiepine-1,1-dioxide (66).

(65)

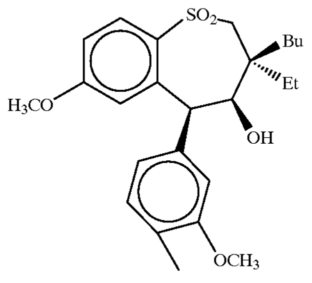

(66)

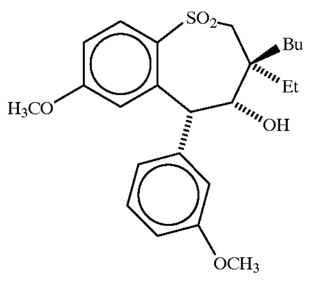

Alkylation of e-methoxyphenol with 3-methoxybenzyl chloride according to the procedure described in J. Chem. Soc, 2431 (1958) gave 4-methoxy-2-(3'-methoxybenzyl) phenol in 35% yield. This material was converted to compound 65, mp 138.5–141.5° C., and compound 66, mp 115.5–117.5° C., by the procedure similar to that in Example 18 method B.

Example 35

(3a,4a,5a) 3-Butyl-3-ethyl-4-hydroxy-7-methoxy-5-(3'-(trifluoromethyl)phenyl)-2,3,4,5-tetrahydrobenzothiepine-1,1-dioxide (67), and (3a,4b,5b) 3-Butyl-3-ethyl-4-hydroxy-7-methoxy 5-(3'-(trifluoromethyl)phenyl)-2,3,4,5-tetrahydrobenzothiepine-1,1-dioxide (68).

(67)

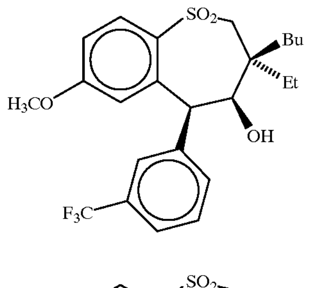

(68)

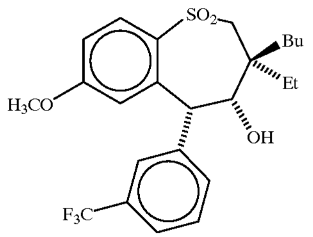

Alkylation of 4-methoxyphenol with 3-(trifluoromethyl) benzyl chloride according to the procedure described in J. Chem. Soc. 2431 (1958) gave 4-methoxy-2-(3'-(trifluoromethyl)benzyl)phenol. This material was converted to compound 67, mp 226.5–228° C., and compound 68, mp 188–190° C., byu the procedure similar to that in Example 18 method B.

Example 36

(3a,4a,5a) 3-Butyl-3-ethyl-5-(4'-fluorophenyl)-4-hydroxy-7-methoxy-2,3,4,5-tetrahydrobenzothiepine-1,1-dioxide (69), and (3a,4b,5b) 3-Butyl-3-ethyl-5-(4'-fluorophenyl)-4-hydroxy-7-methoxy-2,3,4,5-tetrahydrobenzothiepine-1,1-dioxide (70).

(69)

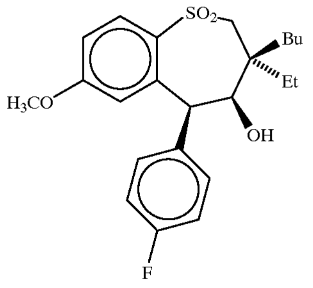

-continued (70)

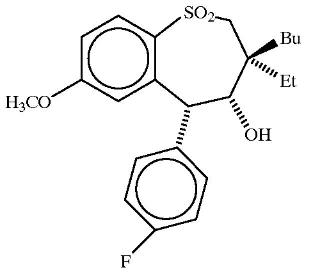

Alkylation of 4-methoxyphenol with 4-fluorobenzyl chloride according to the procedure described in J. Chem. Soc, 2431 (1958) gave 4-methoxy-2-(4'-fluorobenzyl)phenol. This material was converted to compound 69 and compound 70 by the procedure similar to that in Example 18 method B.

Example 37

(3a,4a,5a) 3-Butyl-3-ethyl-5-(3'-fluorophenyl)-4-hydroxy-7-methoxy-2,3,4,5-tetrahydrobenzothiepine-1,1-dioxide (71), and (3a,4b,5b) 3-Butyl-3-ethyl-5-(3'-fluorophenyl)-4-hydroxy-7-methoxy-2,3,4,5-tetrahydrobenzothiepine-1,1-dioxide (72).

(71)

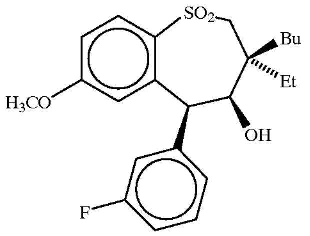

(72)

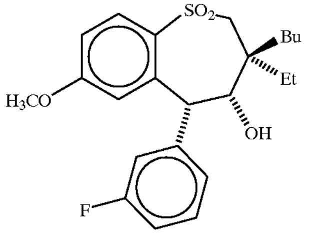

Alkylation of 4-methoxyphenol with 3-fluorobenzyl chloride according to the procedure described in J. Chem. Soc, 2431 (1958) gave 4-methoxy-2-(3'-fluorobenzyl)phenol. This material was converted to compound 71 and compound 72 by the procedure similar to that in Example 18 method B.

Example 38

(3a,4a,5a) 3-Butyl-3-ethyl-5-(2,-fluorophenyl)-4-hydroxy-7-methoxy-2,3,4,5-tetrahydrobenzothiepine-1,1-dioxide (73), and (3a,4b,5b) 3-Butyl-3-ethyl-5-(2'-fluorophenyl)-4-hydroxy-7-methoxy-2,3,4,5-tetrahydrobenzothiepine-1,1-dioxide (74).

(73)

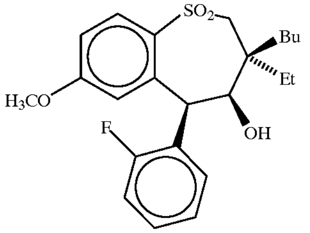

(74)

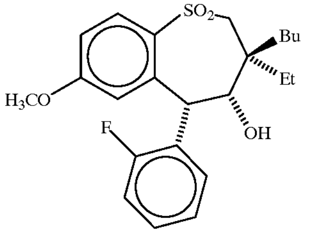

Alkylation of 4-methoxyphenol with 2-fluorobenzyl chloride according to the procedure described in J. Chem. Soc, 2431 (1958) gave 4-methoxy-2-(2'-fluorobenzyl)phenol. This material was converted to compound 73 and compound 74 by the procedure similar to that in Example 18 method B.

Example 39

(3a,4a,5a) 3-Butyl-7-bromo-3-ethyl-4-hydroxy-5-(3'-methoxyphenyl)-2,3,4,5-tetrahydrobenzothiepine-1,1-dioxide (75), and (3a,4b,5b) 3-Butyl-7-bromo-3-ethyl-4-hydroxy-5-(3'-methoxyphenyl)-2,3,4,5-tetrahydrobenzothiepine-1,1-dioxide (76).

(75)

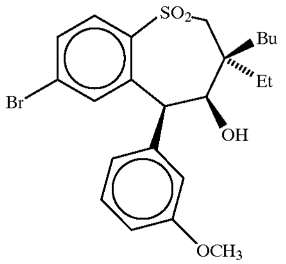

(76)

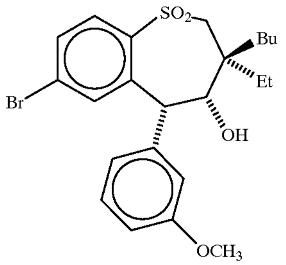

Alkylation of 4-bromophenol with 3-methoxybenzyl chloride according to the procedure described in J. Chem.Soc, 2431 (1958) gave 4-bromo-2-(3'-methoxybenzyl)phenol. This material was converted to compound 75, mp 97–101.5° C., and compound 76, mp 102–106° C., by the procedure similar to that in Example 18 method B.

Example 40

(3a,4a,5a) 3-Butyl-3-ethyl-7-fluoro-5-(4'-fluorophenyl)-4-hydroxy-2,3,4,5-tetrahydrobenzothiepine-1,1-dioxide (77), and (3a,4b,5b) 3-Butyl-3-ethyl-7-fluoro-5-(4'-fluorophenyl)-4-hydroxy-2,3,4,5-tetrahydrobenzothiepine-1,1-dioxide (78).

(77)

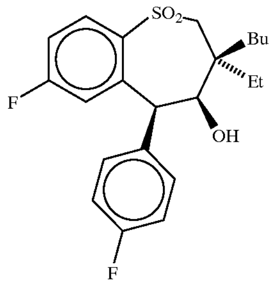

(78)

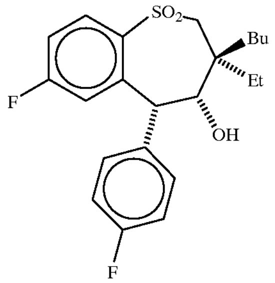

Alkylation of 4-fluorophenol with 4-fluorobenzyl chloride according to the procedure described in J. Chem. Soc, 2431 (1958) gave 4-fluoro-2-(4'-fluorobenzyl)phenol. This material was converted to compound 77, mp 228–230° C., and compound 78, mp 134.5–139° C., by the procedure similar to that in Example 18 method B.

Example 41

(3a,4a,5a) 3-Butyl-3-ethyl-7-fluoro-4-hydroxy-5-(3'-methoxyphenyl)-2,3,4,5-tetrahydrobenzothiepine-1,1-dioxide (79), and (3a,4b,5b) 3-Butyl-3-ethyl-7-fluoro-4-hydroxy-5-(3'-methoxyphenyl)-2,3,4,5-tetrahydrobenzothiepine-1,1-dioxide (80).

(79)

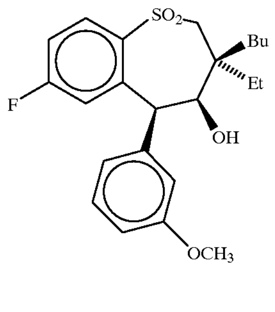

-continued (80)

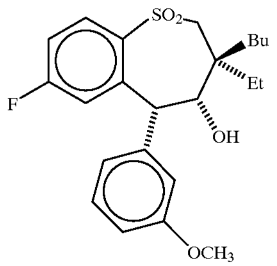

Alkylation of 4-fluorophenol with 3-methoxybenzyl chloride according to the procedure described in J. Chem. Soc, 2431 (1958) gave 4-fluoro-2-(3'-methoxybenzyl)phenol. This material was converted to compound 79, as a solid and compound 80, mp 153–155° C., by the procedure similar to that in Example 18 method B.

Example 42

(3a,4b,5b) 3-Butyl-3-ethyl-5-(4'-fluorophenyl)-4-hydroxy-7-methylthio-2,3,4,5-tetrahydrobenzothiepine-1,1-dioxide (81).

(81)

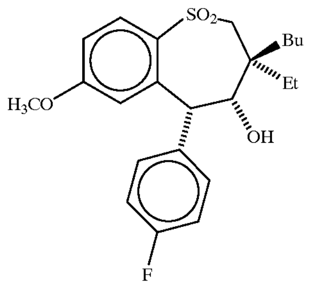

A mixture of 0.68 (1.66 mmol) of compound 77, 0.2 g (5 mmol) of sodium methanethiolate and 15 ml of anhydrous DMF was stirred at room temperature for 16 days. The reaction mixture was dilute with ether and washed with water and brine and dried over $M_gSO_4$. The ether solution was concentrated in vacuo. The residue was purified by HPLC (20% ethyl acetate in hexanes). The first fraction was impure (3a,4a,5a) 3-butyl-3-ethyl-4-hydroxy-7-methylthio-5-(4'-fluorophenyl)-2,3,4,5-tetrahydrobenzothiepine-1,1-dioxide. The second fraction was compound 81, mp 185–186.5° C.

Example 43

(3a,4b,5b) 3-Butyl-3-ethyl-5-(4'-fluorophenyl)-4-hydroxy-7-(1-pyrrolidinyl)-2,3,4,5-tetrahydrobenzothiepine-1,1-dioxide (82).

(82)

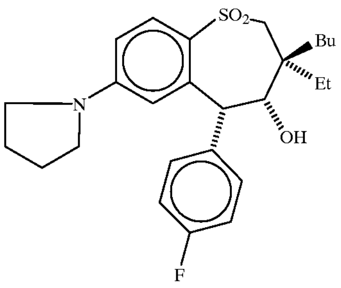

A mixture of 0.53 g (1.30 mmol) of compound 78 and 5 ml of pyrrolidine was held at reflux for 1 h. The reaction mixture was diluted with ether and washed with water and brine and dried over $M_gSO_4$. The ether solution was concentrated in vacuo. The residue was crystallized from ether-hexanes to give compound 82, mp 174.5–177° C.

Example 44

(3a,4b,5b) 3-Butyl-3-ethyl-5-(4'-fluoropheny)-4-hydroxy-7-(1-morpholinyl)-2,3,4,5-tetrahydrobenzothiepine-1,1-dioxide (83).

(83)

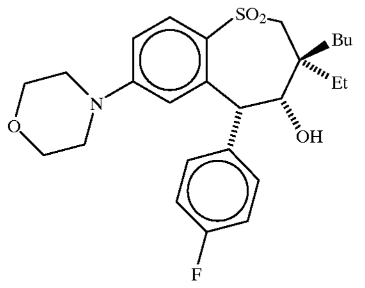

A mixture of 0.4 g (0.98 mmol) of compound 78 and 5.0 g (56 mmol) of morpholine was held at reflux for 2 h and concentrated in vacuo. The residue was diluted with ether (30 ml) and washed with water and brine and dried over $M_gSO_4$. The ether solution was concentrated in vacuo. The residue was recrystallized from ether-hexanes to give compound 83, mp 176.5–187.5° C.

Example 45

(3a,4a,5a) 3-Butyl-3-ethyl-5-(4'-fluorophenyl)-4-hydroxy-7-methyl-2,3,4,5-tetrahydrobenzothiepine-1,1-dioxide (84), and (3a,4b,5b) 3-Butyl-3-ethyl-5-(4'-fluorophenyl)-4-hydroxy-7-methyl-2,3,4,5-tetrahydrobenzothiepine-1,1-dioxide (85).

(84)

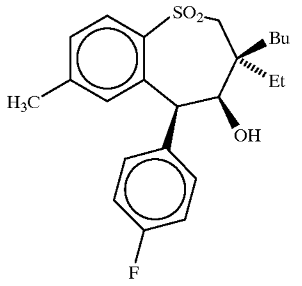

(85)

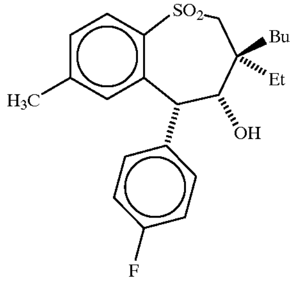

Alkylation of 4-methylphenol with 4-fluorobenzyl chloride according to the procedure described in J. Chem. Soc, 2431 (1958) gave 4-methyl-2-(4'-fluorobenzyl)phenol). This material was converted to compound 84 and compound 85 by the procedure similar to that in Example 18 method B.

Example 46

(3a,4b,5b) 3-Butyl-3-ethyl-4-hydroxy-5-(4'-hydroxyphenyl)-7-methoxy-2,3,4,5-tetrahydrobenzothiepine-1,1-dioxide (86), and (3a,4b,5b) 3-Butyl-3-ethyl-4,7-dihydroxy-5-(4'-hydroxyphenyl)-2,3,4,5-tetrahydrobenzothiepine-1,1-dioxide (87).

(86)

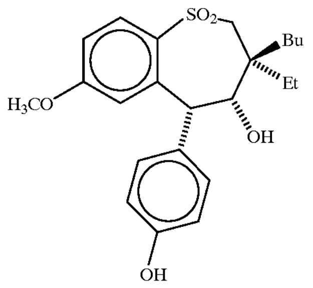

(87)

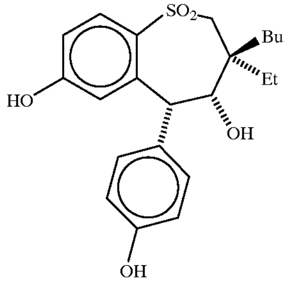

To a solution of 0.52 (1.2 mmol) of compound 66 in 20 ml of methylene chloride was added 1.7 g (6.78 mmol) of born tribromide. The reaction mixture was cooled to –78° C. and was stirred for 4 min. An additional 0.3 ml of boron tribromide was added to the reaction mixture and the reaction mixture was stirred at –78° C. for 1 h and quenced with 2 N HCl. The organic was extracted into ether. The ether layer was washed with brine, dried over $M_gSO_4$, and concentrated in vacuo. The residue (0.48 g) was purified by HPLC (30% ethyl acetate in hexanes). The first fraction was 0.11 g of compound 86 as a white solid, mp 171.5–173° C. The second fraction was crystallized from chloroform to give 0.04 g of compound 87 as a white solid, mp 264° C. (dec).

Example 47

(3a,4b,5b) 3-Butyl-3-ethyl-4,7-dihydroxy-5-(4'-fluorophenyl)-2,3,4,5-tetrahydrobenzothiepine-1,1-dioxide (88).

(88)

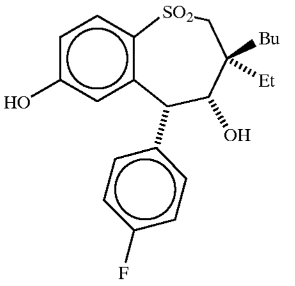

Reaction of compound 70 with excess boron tribromide at room temperature and worked up as in Example 46 gave compound 88 after an HPLC purification.

Example 48

(3a,4b,5b) 3-Butyl-3-ethyl-5-(4'-fluorophenyl)-4-hydroxy-7-(1-azetidinyl)-2,3,4,5-tetrahydrobenzothiepine-1,1-dioxide (89).

(89)

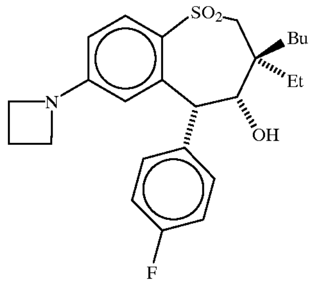

A mixture of 0.20 g (0.49 mmol) of compound 78, and 2.0 g (35 mmol) of aztidine was held at reflux for 3 h and concentrated in vacuo. The residue was diluted with ether (30 ml) and washed with water and brine and dried over MgSO4. The ether solution was concentrated on a steam bath. The separated crystals were filtered to give 0.136 g of 89 as prisms, mp 196.5–199.5° C.

Example 49

(3a,4a,5a) 3-Butyl-3-ethyl-5-(3'-methoxyphenyl )-4-hydroxy-7-methylthio-2,3,4,5-tetrahydrobenzothiepine-1,1-dioxide (90). (3a,4b,5b) 3-Butyl-3-ethyl-5-(3'-methoxyphenyl)-4-hydroxy-7-methylthio-2,3,4,5-tetrahydrobenzothiepine-1,1-dioxide (91).

(90)

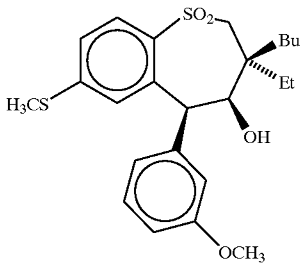

-continued (91)

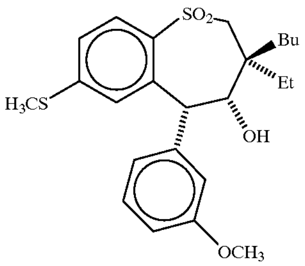

A mixture of 0.4 g (0.95 mmol) of compound 79, 0.08 g (1.14 mmol) of sodium methanethiolate and 15 ml of anhydrous DMF was stirred at 60° C. for 2 h. An additional 1.4 mmol of sodium methanethiolate was added to the reaction mixture and the mixture was stirred at 60° C. for an additional 2 h. The reaction mixture was triturated with 100 ml of water and extracted methylene chloride. The methylene chloride water mixture was filtered through Celite and the methylene chloride layer was dried over $M_gSO_4$ and concentrated in vacuo. The first fraction (0.1 g) was compound 90, mp 117–121° C. The second fraction (0.16 g) was compound 91, mp 68–76° C.

Example 50

Preparation of polyethyleneglycol functionalized benzothiepine A.

NO.141

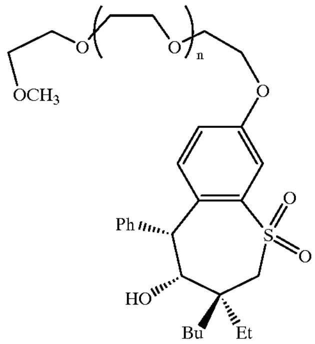

NO. 136

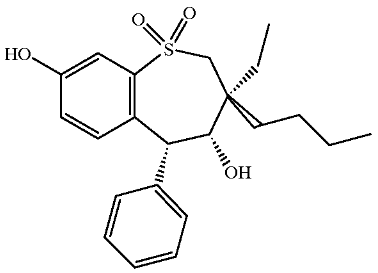

A 50 ml rb flash under a nitrogen atmosphere was charged with 0.54 g of M-Tres-5000 (Polyethyleneglycol Tresylate [methoxy-PEG-Tres,MW 5000] purchased from Shearwater Polymers Inc., 2130 Memorial Parkway, SW, Huntsville, Ala. 35801), 0.055 g Compound No. 136, 0.326 $C_sCO_3$ and 2 cc anhydrous acetonitrile. The reaction was stirred at 30 C. for 5 days and then the solution was filtered to remove salts. Next, the acetonitrile was removed under vacuum and the product was dissolved in THF and then precipitated by addition of hexane. The polymer precipitate was isolate by filtration from the solvent mixture (THF/hexane). This precipitation procedure was continued until no Compound No. 136 was detected in the precipitated product (by TLC SiO2). Next, the polymer precipitate was dissolved in water and filtered and the water soluble polymer was dialyzed for 48 hours through a cellulose dialysis tube (spectrum® 7 ,45 mm×0.5 ft, cutoff 1,000 MW). The polymer solution was then removed from the dialysis tube and lyophilized until dried. The NMR was consistent with the desired product A and gel permeation chromatography indicated the presence of a 4500 MW polymer and also verified that no free Compound No. 136 was present. This material was active in the IBAT in vitro cell assay.

Example 51

Preparation of Compound 140

No. 140

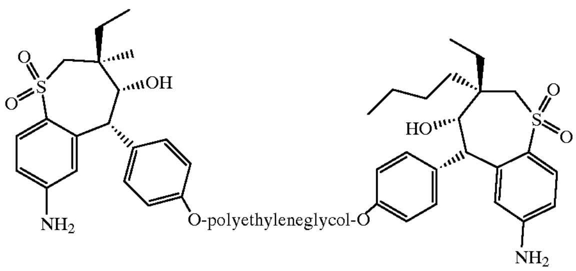

No.111

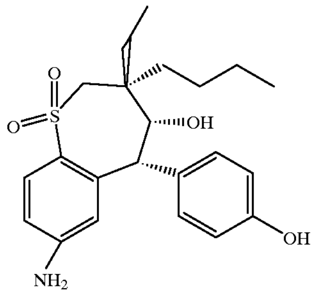

A 2-necked 50 ml round bottom Flask was charged with 0.42 g of Tres-3400 (Polyethyleneglycol Tresylate [Tres-PEG-Tres,MW 3400] purchased from Shearwater Polymers Inc., 2130 Memorial Parkway, SW, Huntsville, Ala. 35801), 0.1 potassium carbonate, 0.100 g of Compound No. 111 and 5 ml anhydrous DMF. Stir for 6 days at 27° C. TLC indicated the disappearance of the starting Compound No. 111. The solution was transferred to a separatory funnel and diluted with 50 cc methylene chloride and then extracted with water. The organic layer was evaporated to dryness by means of a rotary evaporator. Dry wgt. 0.4875 g. Next, the polymer was dissolved in water and then dialyzed for 48 hours at 40° C. through a cellulose dialysis tube (spectrum® 7 ,45 mm ×0.5 ft, cutoff 1,000 MW). The polymer solution was then removed from the dialysis tube and lyophilized until dried 0.341 g). NMR was consistent with the desired product B.

Example 52

No. 134

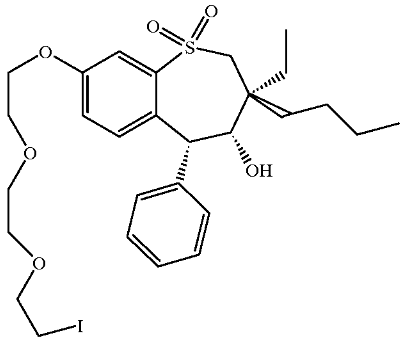

A 10 cc vial was charged with 0.21 g of Compound No. 136 (0.5 mmoles), 0.17 g (1.3 mmoles)potassium carbonate, 0.6 g (1.5 mmoles) of 1,2-bis-(2-iodoethoxy)-ethane and 10 cc DMF. The reaction was stirred for 4 days at room temperature and then worked up by washing with ether/water. The ether layer was stripped to dryness and the desired product Compound No. 134 was isolated on a silica gel column using 80/20 hexane ethyl acetate.

Example 53

No. 112

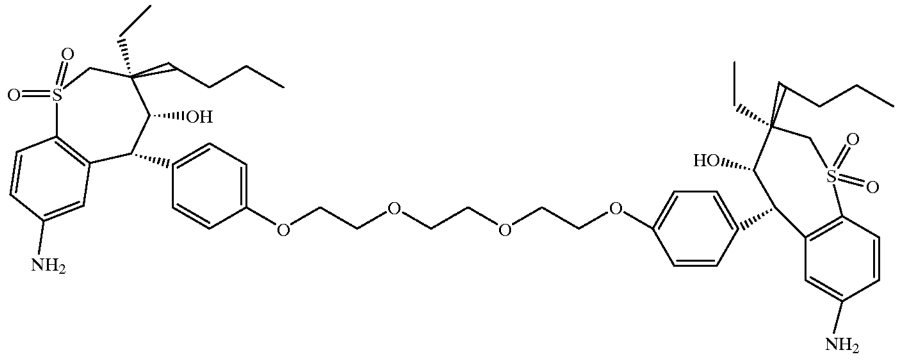

Example 54

No. 113

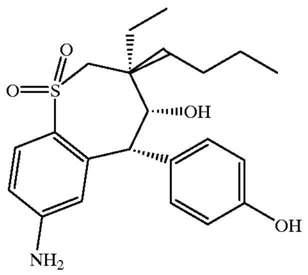

A two necked 25 ml round bottom Flask was charged with 0.5 g (1.24 mmoles) of 69462, 13 mls of anhydrous DMF, 0.055 g of 60% NaH dispersion and 0.230 g (0.62 mmoles) of 1,2-Bis [2-iodoethoxylethane] at 10° C. under nitrogen. Next, the reaction was slowly heated to 40° C. After 14 hours all of the Compound No. 113 was consumed and the reaction was cooled to room temperature and extracted with ether/water. The ether layer was evaporated to dryness and then chromatographed on Silicage (80/20 ethyl acetate/hexane). Isolated Compound No. 112 (0.28 g) was characterized by NMR and mass spec.

Example 55

No. 135

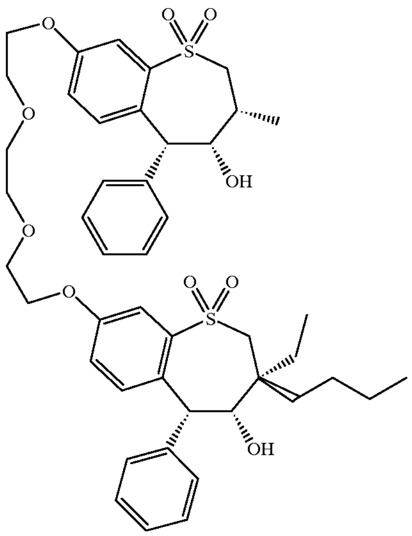

-continued

No. 136

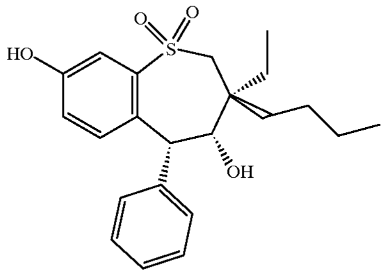

In a 50 ml round bottom Flask, add 0.7 g (1.8 mmoles) of Compound No. 136, 0.621 g of potassium carbonate, 6 ml DMF, and 0.33 g of 1,2-Bis [2-iodoethoxylethane]. Stir at 40° C. under nitrogen for 12 hours. The workup and isolation was the same procedure for Compound No. 112.

Examples 56 and 57

(Compound Nos. 131 and 137)

The compositions of these compounds are shown in Table 3.

The same procedure as for Example 55 except appropriate benzothiepine was used.

Example 58

(Compound No. 139)

The composition of this compound is shown in Table 3. Same procedure as for Example 55 with appropriate benzothiepine 1,6 diiodohexane was used instead of 1,2-Bis [2-iodoethoxylethane].

Example 59

(Compound No. 101)

No. 101

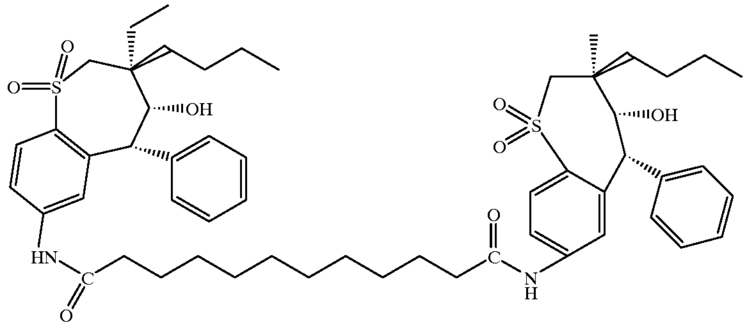

This compound is prepared by condensing the 7-$NH_2$ benzothiepine with the 1,12-dodecane dicarboxylic acid or acid halide.

Example 60

(Compound No. 104)

No. 104

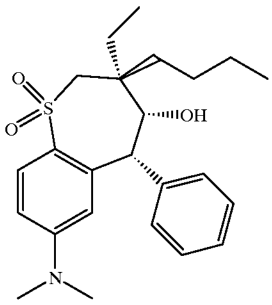

2-Chloro-4-nitrobenzophenone is reduced with triethylsilane and trifluoromethane sulfonic acid to .2-chloro-4-nitrodiphenylmethane 32. Reaction of 32 with lithium sulfide followed by reacting the resulting sulfide with mesylate IV gives sulfide-aldlehyde XXIII. Oxidation of XXIII with 2 equivalents of MCPBA yields sulfone-aldehyde XXIV (see Scheme 5). Reduction of the sulfone-aldehyde XXV formaldehyde and 100 psi hydrogen and 55 C. for 12 hours catalyzed by palladium on carbon in the same reaction vessel yields the substituted dimethylamine derivative XXVIII. Cyclization of XXVII with potassium t-butoxide yields a mixture of substituted amino derivatives of this invention Compound No. 104.

Example 61

No. 102

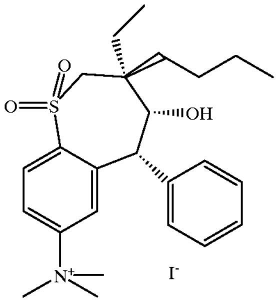

A 1 oz. Fisher-porter bottle was charged with 0.14 g (0.34 mmoles) of 70112, 0.97 gms (6.8 mmoles) of methyl iodide, and 7 ml of anhydrous acetonitrile. Heat to 50° C. for 4 days. The quat. Salt Compound No. 192 was isolated by concentrating to 1 cc acetonitrile and then precipitating with diethyl ether.

Example 62

No. 125

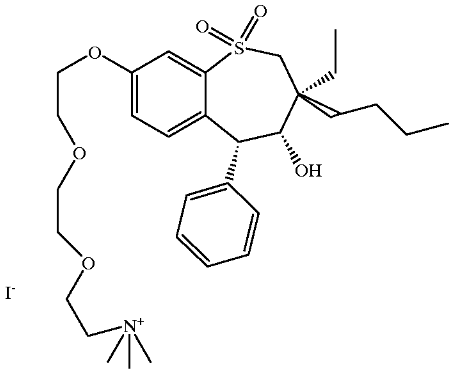

Scheme 6

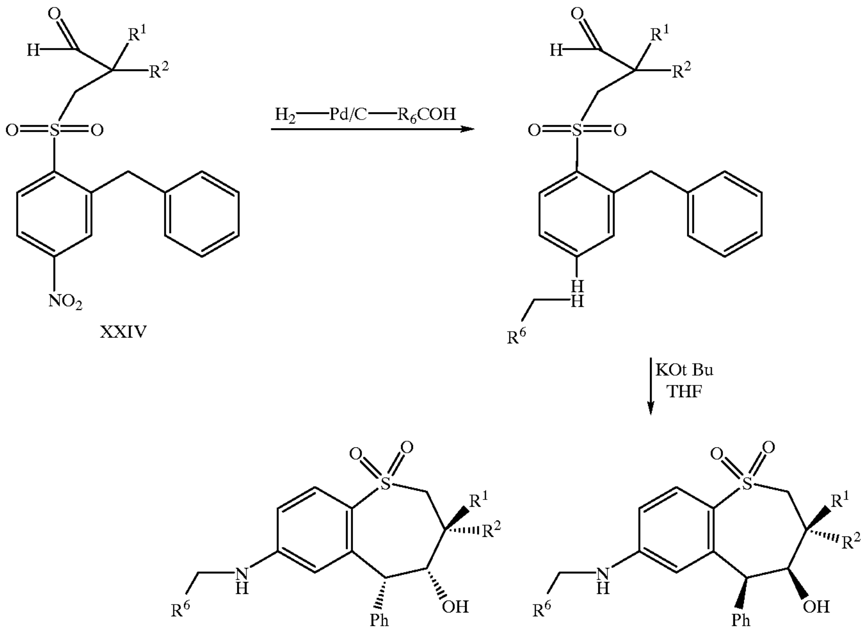

XXIV

XXI Xc

XXI Xd

A 0.1 g (0.159 mmoles) sample of Compound No. 134 was dissolved in 15 ml of anhydrous acetonitrile in a Fischer-porter bottle and then trimethylamine was bubbled through the solution for 5 minutes at 0° C. and then capped and warmed to room temperature. The reaction was stirred overnight and the desired product was isolated by removing solvent by rotary evaporation.

Example 63

(Compound No. 295)

No. 295

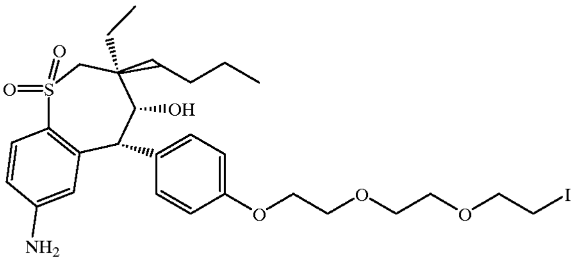

No. 113

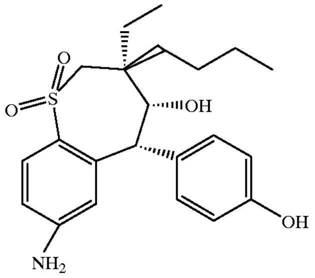

Sodium Hydride 60% (11 mg, 0.27 mmoles) in 1 cc of acetonitrile at 0° C. was reacted with 0.248 mmoles (.10 g) of Compound No. 54 in 2.5 cc of acetonitrile at 0° C. Next, 0.(980 g 2.48 mmoles) of 1,2-Bis [2-iodoethoxylethane]. After warming to room temperature, stir for 14 hours. The product was isolated by column chromatography.

Example 64

(Compound No. 286)

No. 286

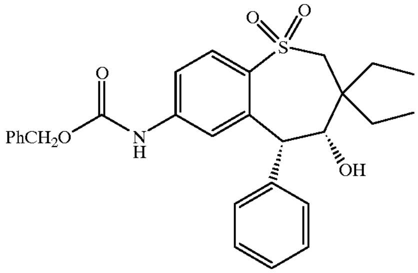

Following a procedure similar to the one described in Example 86, infra (see Compound No. 11.8), the title compound was prepared and purified as a colorless 20 solid; mp 180–181° C.; $^1$H NMR ($CHCl_3$) δ0.85 (t, J=6 Hz, 3H_, 0.92 (t, J=6 Hz, 3H), 1.24–1.42 (m, 2H), 1.46–1.56 (m, 1H), 1.64–1.80 (m, 1H), 2.24–2.38 (m, 1H), 3.15 (AB, $J_{AB}$=15 Hz, Δv=42 Hz, 2H), 4.20 (d, J=8 Hz, 1H), 5.13 (s, 2H), 5.53 (s, 1H), 6.46 (s, 1H), 6.68 (s, 1H), 7.29–7.51 (m, 10H), 7.74 (d, J=8 Hz, 1H), 8.06 (d, J=8 Hz, 1H). FABMS m/z 494 (M+H), HRMS calcd for (M+H) 494.2001, found 494.1993. Anal. Calcd. for $C_{28}H_{31}NO_5S$: C, 68.13; H, 6.33; N, 2.84. Found: C, 68.19; H, 6.56; N, 2.74.

Example 65

(Compound No. 287)

No. 287

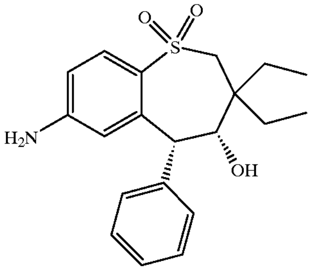

Following a procedure similar to the one described in Example 89, infra (see Compound No. 121), the title compound was prepared and purified as a colorless solid: mp 245–246° C., $^1$H NMR ($CDCl_3$) δ0.84 (t, J=6 Hz, 3H), 0.92 (t, J=6 Hz, 3H), 1.28, (d, J=8 Hz, 1H), 1.32–1.42 (m, 1H), 1.48–1.60 (m, 1H), 1.64–1.80 (m, 1H), 2.20–2.36 (m, 1H), 3.09 (AB, $J_{AB}$=15 Hz, Δv=42 Hz, 2H), 3.97 (bs, 2H), 4.15 (d, J=8 Hz, 1H), 5.49 (s, 1H), 5.95 (s, 1H), 6.54 (d, J=7 Hz, 1H), 7.29–7.53 (m, 5H), 7.88 (d, J=8 Hz, 1H); ESMS 366 (M+Li). Anal. Calcd. for $C_{20}H_{25}NO_3S$: C, 66.82; H, 7.01; N, 3.90. Found: C, 66.54; H, 7.20; N, 3.69.

Examples 66

(Compound No. 288)

No. 288

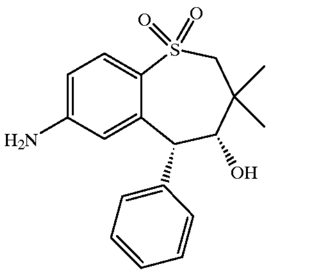

Following a procedure similar to the one described in Example 89, infra (see Compound No. 121), the title compound was prepared and purified by silica gel chromatography to give the desired product as a colorless solid: mp 185–186° C.; $^1$H NMR ($CDCl_3$) δ1.12 (S, 3H), 1.49 (s, 3H), 3.00 (d, J=15 Hz, 1H), 3.28 (d, J=15 Hz, 1H), 4.00 (s, 1H), 5.30 (s, 1H), 5.51 (s, 1H), 5.97 (s, 1H), 6.56 (dd, J=2.1, 8.4 Hz, 1H), 7.31–7.52 (m, 5H), 7.89 (d, J=8.4 Hz, 1H). MS (FAB+) (M+H) m/z 332.

Example 67

(Compound No. 289)

No. 289

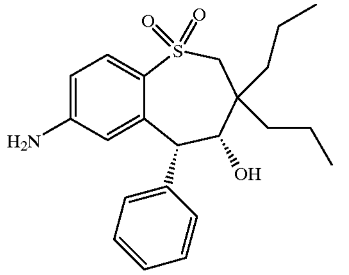

Following a procedure similar to the one described in Example 89 (see Compound No. 121), the title compound was prepared and purified by silica gel chromatography to give the desired product as a white solid: mp 205–206° C.; $^1$H NMR ($CDCl_3$) δ0.80–0.95 (m, 6H), 1.10–1.70 (m, 7H), 2.15 (m, 1H), 3.02 (d, J=15.3 Hz, 2H), 3.15 (d, J=15.1 Hz, 2H), 3.96 (s, br, 2H), 4.14 (d, J=7.8 Hz, 1H), 5.51 (s, 1H), 5.94 (d, J=2.2, 1H), 6.54 (dd, J=8.5, 2.2 Hz, 1H), 7.28–7.50 (m, 6H), 7.87 (d, J=8.5 Hz, 1H). MS (FAB): m/z 388 (M+H). cl Example 68

(Compound No. 290)

No. 290

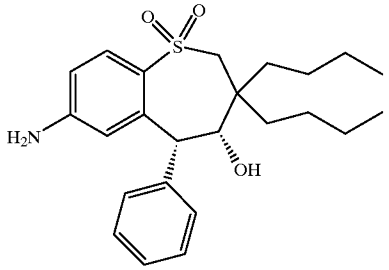

Following a procedure similar to the one described in Example 89, infra (see Compound No. 121), the title compound was prepared and purified as a colorless solid: mp=96–98° C., $^1$H NMR ($CDCl_3$) δ0.92 (t, J=7 Hz, 6H), 1.03–1.70 (m, 11H), 2.21 (t, J=8 Hz, 1H), 3.09 (AB, $J_{AB}$=−18 Hz, Δv=38 Hz, 2H), 3.96 (bs, 2H), 4.14 (d, J=7 Hz, 1H), 5.51 (s, 1H), 5.94 (s, 1H), 6.56 (d, J=9 Hz, 1H), 7.41–7.53 (m, 6H), 7.87 (d, J=8 Hz, 1H); FABMS m/z 416 (M+H).

Example 69

No. 291

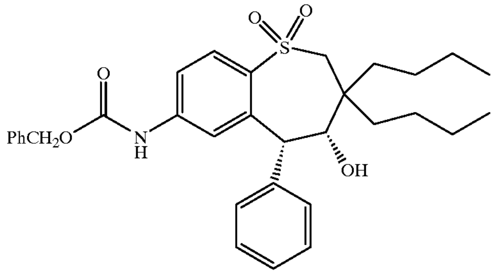

Following a procedure similar to the one described in Example 86, infra (see Compound No. 118), the title compound was prepared and purified as a colorless solid: $^1$H NMR ($CDCl_3$) δ0.91 (t, J=7 Hz, 6H), 1.02–1.52 (m, 11H), 1.60–1.70 (m, 1H), 2.23 (t, J=8 Hz, 1H), 3.12 (AB, $J_{AB}$=18 Hz, Δv=36 Hz, 2H), 4.18 (d, J=7 Hz, 1H), 5.13 (s, 2H), 5.53 (s, 1H), 6.43 (s, 1H), 6.65 (s, 1H), 7.29–7.52 (m, 10H), 7.74 (d, J=9 Hz, 1H), 8.03 (d, J=8 Hz, 1H); ESMS m/z 556 (M+Li).

Example 70

(Compound No. 292)

No. 292

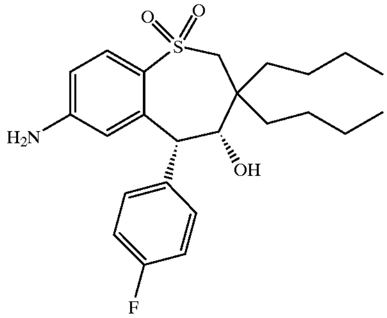

Following a procedure similar to the one descried in Example 89, infra (see Compound No. 121), the title compound was prepared and purified as a colorless solid: mp=111–112.5° C., $^1$H NMR ($CDCl_3$) δ0.90 (t, J=8 Hz, 6H), 1.03–1.50 (m, 10H), 1.55–1.70 (m, 2H), 2.18 (t, J=12 Hz, 2H), 3.07 (AB, $J_{AB}$=15 Hz, Δv=45 Hz, 2H), 4.09 (bs, 2H), 5.49 (s, 1H), 5.91 (s, 1H), 6.55 (d, J=9 Hz, 1H), 7.10 (t, J=7 Hz, 2H), 7.46 (t, J=6 Hz, 2H), 7.87 (d, J=9 Hz, 1H).

Example 71

(Compound No. 293)

No. 293

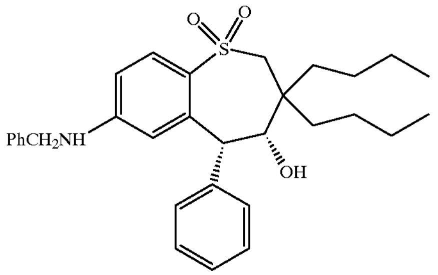

During the preparation of Compound No. 290 from Compound No. 291 using $BBr_3$, the title compound was isolated: $^1H$ NMR ($CDCl_3$) δ0.85 (t, J=6 Hz, 6H), 0.98–1.60 (m, 10H), 1.50–1.66 (m, 2H), 2.16 (t, J=8 Hz, 1H), 3.04 (AB, $J_{AB}$=15 Hz, Δv=41 Hz, 2H), 4.08 (s, 1H), 4.12 (s, 1H), 5.44 (s, 1H), 5.84 (s, 1H), 6.42 (d, J=9 Hz, 1H), 7.12 (d, J=8 Hz, 2H), 7.1–7.26 (m, 10H), 7.83 (d, J=8 Hz, 1H); ESMS m/z 512 (M+Li).

Example 72

(Compound No. 294)

Following a procedure similar to the one described in Example 60 (Compound No. 104), the title compound was prepared and purified as a colorless solid: $^1H$ NMR ($CDCl_3$) δ0.90 (t, J=6 Hz, 6H), 1.05–1.54 (m, 9H), 1.60–1.70 (m, 1H), 2.24 (t, J=8 Hz, 1H), 2.80 (s, 6H), 3.05 (AB, $J_{AB}$=15 Hz, Δv=42 Hz, 2H), 4.05–4.18 (m, 2H), 5.53 (s, 1H), 5.93 (s, 1H), 6.94 (d, J=9 Hz, 1H), 7.27–7.42 (m, 4H), 7.45 (d, J=8 Hz, 2H), 7.87 (d, J=9 Hz, 1H); ESMS m/z 444 (M+H).

Structures of the compounds of Examples 33 to 72 are shown in Tables 3 and 3A.

Examples 73–79, 87, 88 and 91–102

Using in each instance a method generally described in those of Examples 1 to 72 appropriate to the substituents to be introduced, compounds were prepared having the structures set forth in Table 3. The starting materials illustrated in the reaction schemes shown above were varied in accordance with principles of organic synthesis well known to the art to introduce the indicated substituents in the 4- and 5-positions ($R^3$, $R^4$, $R^5$, $R^6$) and in the indicated position on the benzo ring ($R^x$).

Structures of the the compounds produced in Examples 73–102 are set forth in Tables 3 and 3A.

Examples 80–84

Preparation of 115, 116, 111, 113

Preparation of 4-chloro-3-[4-methoxy-phenylmethyl]-nitrobenzene.

In a 500 ml 2-necked rb flask weigh out 68.3 gms phosphorus pentachloride (0.328 mole 1.1 eq). Add 50 mls chlorobenzene. Slowly add 60 gms 2-chloro-5-nitrobenzoic acid (0.298 mole). Stir at room temp overnight under N2 then heat 1 hr at 50 C.

Remove chlorobenzene by high vacuum. Wash residue with hexane. Dry wt=55.5 gms.

In the same rb flask, dissolve acid chloride (55.5 g 0.25 mole) from above with 100 mls anisole (about 3.4 eq). Chill solution with ice bath while purging with N2. Slowly add 40.3 g aluminum chloride (1,2 eq 0.3 mole). Stir under $N_2$ for 24 hrs.

After 24 hrs, the solution was poured into 300 mls 1N HCl soln. (cold). Stir this for 15 min Extract several times with diethyl ether. Extract organic layer once with 2% aqueous NaOH then twice with water. Dry organic layer with MgSO4, dry on vac line. Solid is washed well with ether and then ethanol before drying. Wt=34.57 g (mixture of meta, ortho and para).

| Elemental | theory | found |
|---|---|---|
| C | 57.65 | 57.45 |
| H | 3.46 | 5.51 |
| N | 4.8 | 4.8 |
| Cl | 12.15 | 12.16 |

With the next step of the reduction of the ketone with trifluoromethane sulfonic aid and trie(thyl silane, crystallization with ethyl acetate/hexane affords pure 4-chloro-3-[4-methoxy-phenylmethyl]-nitrobenzene.

4-Chloro-3-[4-methoxy-phenylmethyl]-nitrobenzene was then reacted as specified in the synthesis of 117 and 118 from 2-chloro-4-nitrophenylmethane. From these procedures 115 and 116 can be synthesized. Compounds 111 and 113 can be synthesized from the procedure used to prepare compound 121.

Compound 114 can be prepared by reaction of 116 with ethyl mercaptan and aluminum trichloride.

Examples 85 and 86

Preparation of 117 and 118

2-Chloro-4-nitrobenzophenone is reduced with triethylsilane and trifluoromethane sulfonic acid to 2-chloro-4-nitrodiphenylmethane 32. Reaction of 32 with lithium sulfide followed by reacting the resulting sulfide with mesylate IV gives sulfide-aldehyde XXIII. Oxidation of XXIII with 2 equivalents of MCPBA yields sulfone-aldehyde XXIII. Oxidation of XXIII with 2 equivalents of MCPBA yields sulfone-aldehyde XXIV (see Scheme 5).

The sulfone-aldehyde (31.8 g) was dissolved in ethanol/toluene and placed in a parr reactor with 100 ml toluene and 100 ml of ethanol and 3.2 g of 10% Pd/C and heated to 55 C. and 100 psi of hydrogen gas for 14 hours. The reaction was then filtered to remove the catalyst. The amine product (0.076 moles, 29.5 g) from this reaction was then reacted with benzyl chloroformate (27.4 g) in toluene in the presence of 35 g of potassium carbonate and stirred at room temperature overnight. After work up by extraction with water, the CBZ protected amine product was further purified by precipitation from toluene/hexane.

The CBZ protected amine product was then reacted with 3 equivalents of potassium t-butoxide in THF at 0 C. to yield compounds 117 and 118 which were separated by silica gel column chromatography.

Examples 89 and 90

Preparation of 121 or 122

Compound 118 (0.013 moles, 6.79 g) is dissolved in 135 ml of dry chloroform and cooled to −78 C., next 1.85 ml of boron tribromide (4.9 g) was added and the reaction is allowed to warm to room temperature. Reaction is complete after 1.5 hours. The reaction is quenched by addition of 10% potassium carbonate at 0 C. and extract with ether. Removal of ether yields compound 121. A similar procedure can be used to produce 122 from 117.

Examples 93–96

Compounds 126, 127, 128 and 129 as set forth in Table 3 were prepared substantially in the manner described above for compounds 115, 116, 111 and 113, respectively, except that fluorobenzene was, used as a starting material in place of anisole.

TABLE 3

Specific compounds (#102–111, 113–130, 132–134, 136, 138, 142–144, 262–296)

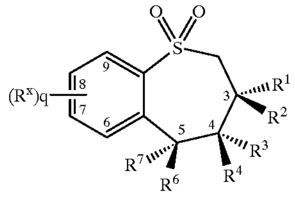

| Ex. | Cp# | $R^1$ | $R^2$ | $R^3$ | $R^4$ | $R^5$ | $R^6$ | $(R^x)_q$ |
|---|---|---|---|---|---|---|---|---|
| 61 | 102 | Et— | n-Bu— | HO— | H— | Ph— | H— | $I^-$, 7-$(CH_3)_3N^+$— |
| 73 | 103 | n-Bu— | Et— | HO— | H— | Ph— | H— $(CH_3)_3N^+$— | $I^-$, 7- |
| 60 | 104 | Et— | n-Bu— | HO— | H— | Ph— | H— | 7-$(CH_3)_2N$— |
| 74 | 105 | Et— | n-Bu— | HO— | H— | Ph— | H— | 7-$CH_3SO_2NH$— |
| 75 | 106 | Et— | n-Bu— | HO— | H— | Ph— | H— | 7-Br—$CH_2$—CONH— |
| 76 | 107 | n-Bu— | Et— | HO— | H— | p-n-$C_{10}H_{21}$—O—Ph— | H— | 7-$NH_2$— |
| 77 | 108 | Et— | n-Bu— | HO— | H— | Ph— | H— | 7-$C_5H_{11}$CONH— |
| 78 | 109 | Et— | n-Bu— | HO— | H— | p-n-$C_{10}H_{21}$—O—Ph— | H— | 7-$NH_2$— |
| 79 | 110 | Et— | n-Bu— | HO— | H— | Ph— | H— | 7-$CH_3$CONH— |
| 80 | 111 | n-Bu— | Et— | HO— | H— | p-EO—Ph— | H— | 7-$NH_2$ |
| 81 | 113 | Et— | n-Bu— | HO— | H— | p-HO—Ph— | H— | 7-$NH_2$— |
| 82 | 114 | Et— | n-Bu— | HO— | H— | p-$CH_3O$—Ph— | H— | 7-$NH_2$— |
| 83 | 115 | n-Bu— | Et— | HO— | H— | p-$CH_3O$—Ph— | H— | 7-NH—CBZ |
| 84 | 116 | Et— | n-Bu— | HO— | H— | p-$CH_3O$—Ph— | H— | 7-NH—CBZ |
| 85 | 117 | n-Bu— | Et— | HO— | H— | Ph— | H— | 7-NH—CBZ |
| 86 | 118 | n-Bu— | n-Bu— | HO— | H— | Ph— | H— | 7-NH—CBZ |
| 87 | 119 | n-Bu— | n-Bu— | HO— | H— | Ph— | H— | 7-$NHCO_2$-t-Bu |
| 88 | 120 | n-Bu— | Et— | HO— | H— | Ph— | H— | 7-$NHCO_2$-t-Bu |
| 89 | 121 | Et— | n-Bu— | HO— | H— | Ph— | H— | 7-$NH_2$— |
| 90 | 122 | n-Bu— | Et— | HO— | H— | Ph— | H— | 7-$NH_2$— |
| 91 | 123 | Et— | n-Bu— | HO— | H— | Ph— | H— | 7-n-$C_6H_{13}$—NH— |
| 92 | 124 | n-Bu— | Et— | HO— | H— | Ph— | H— | 7-n-$C_6H_{13}$—NH— |
| 62 | 125 | Et— | n-Bu— | HO— | H— | Ph— | H— | $I^-$, 8-$(CH_3)_3N^+(CH_2CH_2O)_3$— |
| 93 | 126 | n-Bu— | Et— | HO— | H— | p-F—Ph— | H— | 7-NH—CBZ |
| 94 | 127 | n-Bu— | Et— | HO— | H— | p-F—Ph— | H— | 7-$NH_2$— |
| 95 | 128 | Et— | n-Bu— | HO— | H— | p-F—Ph— | H— | 7-NH—CBZ |
| 96 | 129 | Et— | n-Bu— | HO— | H— | p-F—NH | H— | 7-$NH_2$— |
| 97 | 130 | Et— | n-Bu— | HO— | H— | Ph— | H— | $I^-$, 8-$(CH_3)_3N^+C_6H_{12}O$— |
| 98 | 132 | Et— | n-Bu— | HO— | H— | Ph— | H— | 8-phthal-imidyl-$C_6H_{12}O$— |
| 99 | 133 | Et— | n-Bu— | HO— | H— | Ph— | H— | 8-n-$C_{10}H_{21}$— |
| 52 | 134 | Et— | n-Bu— | HO— | H— | Ph— | H— | 8-I—$(C_2H_4O)_3$— |
| 100 | 136 | Et— | n-Bu— | HO— | H— | Ph— | H— | 8-HO— |
| 101 | 138 | n-Bu— | Et— | HO— | Ph— | H— | Ph— | 8-$CH_3CO_2$— |
| 49 | 90 | Et— | n-Bu— | H— | HO— | H— | m-$CH_3O$—Ph— | 7-$CH_3S$— |
| 49 | 91 | Et— | n-Bu— | HO— | H— | m-$CH_3O$—Ph— | H— | 7-$CH_3S$— |
| 48 | 89 | Et— | n-Bu— | HO— | H— | p-F—Ph— | H | 7-(N)-azetidine |
| 34 | 66 | Et— | n-Bu— | HO— | H | m-$CH_3O$—Ph— | H— | 7-$CH_3O$— |
| 34 | 65 | Et— | n-Bu— | H— | HO— | H— | m-$CH_3O$—Ph— | 7-$CH_3O$— |
| 35 | 68 | Et— | n-Bu— | HO— | H— | m-$CF_3$—Ph— | H— | 7-$CH_3O$— |
| 35 | 67 | Et— | n-Bu— | H— | HO— | H | m-$CF_3$—Ph— | 7-$CH_3O$— |
| 46 | 87 | Et— | n-Bu— | HO— | H— | m-HO—Ph— | H— | 7-HO— |
| 46 | 86 | Et— | n-Bu— | HO— | H— | m-HO—Ph— | H— | 7-$CH_3O$— |
| 36 | 70 | Et— | n-Bu— | HO— | H— | p-F—Ph— | H— | 7-$CH_3O$— |
| 36 | 69 | Et— | n-Bu— | H— | HO— | H— | p-F—Ph— | 7-$CH_3O$— |

TABLE 3-continued

Specific compounds (#102–111, 113–130, 132–134, 136, 138, 142–144, 262–296)

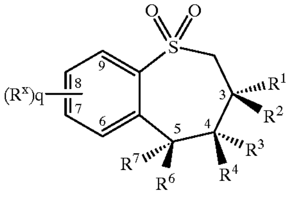

| Ex. | Cp# | $R^1$ | $R^2$ | $R^3$ | $R^4$ | $R^5$ | $R^6$ | $(R^x)_q$ |
|---|---|---|---|---|---|---|---|---|
| 47 | 88 | Et— | n-Bu— | HO— | H— | p-F—Ph— | H— | 7-HO— |
| 39 | 76 | Et— | n-Bu— | HO— | H— | m-$CH_3O$—Ph— | H— | 7-Br— |
| 39 | 75 | Et— | n-Bu— | H— | HO— | H— | m-$CH_3O$—Ph— | 7-Br— |
| 40 | 77 | Et— | n-Bu— | H— | HO— | H— | p-F—Ph— | 7-F— |
| 40 | 78 | Et— | n-Bu— | HO— | H— | p-F—Ph— | H— | 7-F— |
| 41 | 79 | Et— | n-Bu— | H— | HO— | H— | m-$CH_3O$—Ph— | 7-F— |
| 41 | 80 | Et— | n-Bu— | HO— | H— | m-$CH_3O$—Ph— | H— | 7-F— |
| 37 | 72 | Et— | n-Bu— | HO— | H— | m-F—Ph— | H— | 7-$CH_3O$— |
| 38 | 73 | Et— | n-Bu— | H— | HO— | H— | o-F—Ph— | 7-$CH_3O$— |
| 37 | 71 | Et— | n-Bu— | H— | HO— | H— | m-F—Ph— | 7-$CH_3O$— |
| 38 | 74 | Et— | n-Bu— | HO— | H— | o-F—Ph— | H— | 7-$CH_3O$— |
| 42 | 81 | Et— | n-Bu— | HO— | H— | p-F—Ph— | H— | 7-$CH_3S$ |
| 45 | 85 | Et— | n-Bu— | HO— | H— | p-F—Ph— | H— | 7-$CH_3$— |
| 45 | 84 | Et— | n-Bu— | H— | HO— | H— | p-F—Ph— | 7-$CH_3$— |
| 44 | 83 | Et— | n-Bu— | HO— | H— | p-F—Ph— | H— | 7-(N)-morpholine |
| 43 | 82 | Et— | n-Bu— | HO— | H— | p-F—Ph— | H— | 7-(N)-pyrroli-dine |
| 64 | 286 | Et— | Et— | HO— | H— | Ph— | H— | 7-NH—CBZ |
| 65 | 287 | Et— | Et— | HO— | H— | Ph— | H— | 7-$NH_2$— |
| 66 | 288 | $CH_3$— | $CH_3$— | HO— | H— | Ph— | H— | 7-$NH_2$— |
| 67 | 289 | n-$C_3H_7$— | n-$C_3H_7$— | HO— | H— | Ph— | H— | 7-$NH_2$— |
| 68 | 290 | n-Bu— | n-Bu— | HO— | H— | Ph— | H— | 7-$NH_2$— |
| 69 | 291 | n-Bu— | n-Bu— | HO— | H— | Ph— | H— | 7-NH—CBZ |
| 70 | 292 | n-Bu— | n-Bu— | HO— | H— | p-F—Ph— | H— | 7-$NH_2$— |
| 71 | 293 | n-Bu— | n-Bu— | HO— | H— | Ph— | H— | 7-$PhCH_2N$— |
| 72 | 294 | n-Bu— | n-Bu— | HO— | H— | Ph— | H— | 7-$(CH_3)_2N$— |
| 63 | 295 | Et— | n-Bu— | HO— | H— | p-I—$(C_2H_4O)_3$ Ph— | H— | 7-$NH_2$— |
| 102 | 296 | Et— | n-Bu— | HO— | H— | $I^-$, p-$(CH_3)_3N^+$$(C_2H_4O)_3$—Ph— | H— | 7-$NH_2$— |

TABLE 3A

Bridged Benzothiephenes (#101, 112, 131, 135, 137, 139–141)

CPD #101 (Ex. 59)

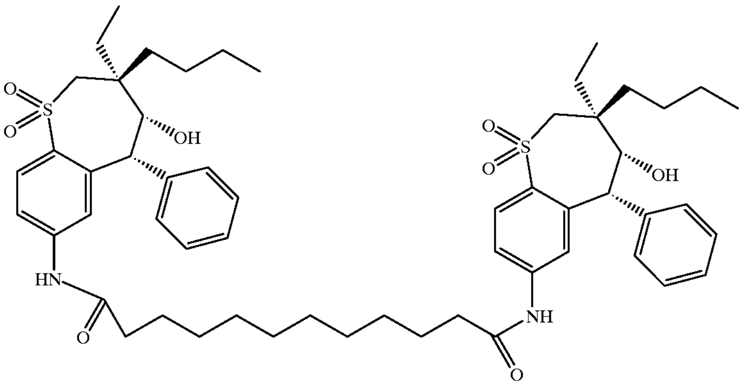

TABLE 3A-continued
Bridged Benzothiephenes (#101, 112, 131, 135, 137, 139–141)
CPD #112 (Ex. 53)
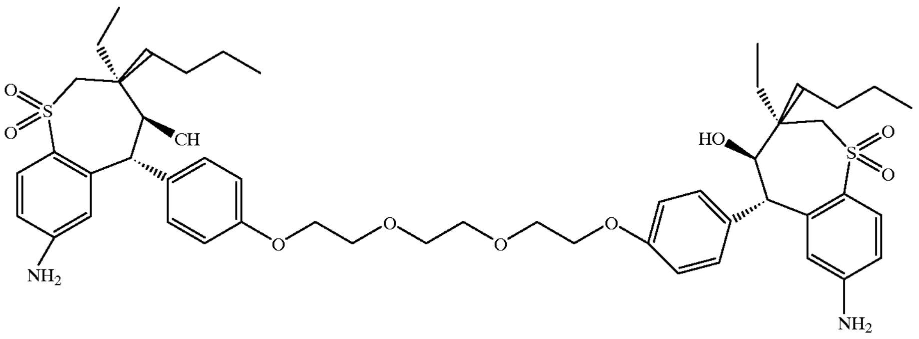
CPD #131 (Ex. 56)
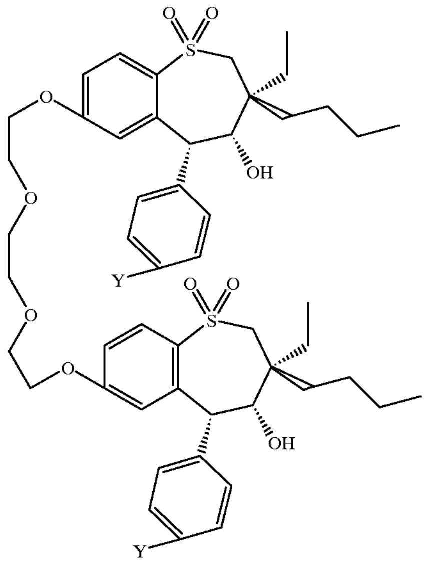
CPD #135 (Ex. 55)
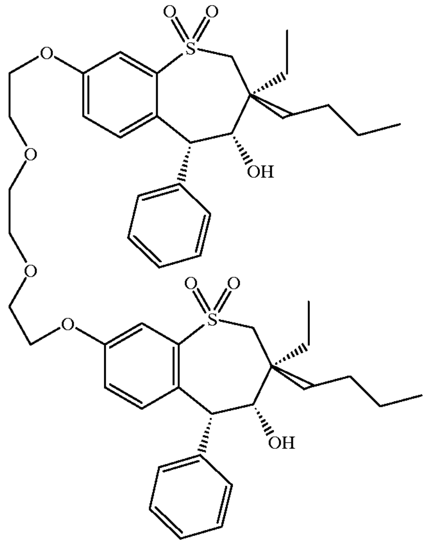

TABLE 3A-continued

Bridged Benzothiephenes (#101, 112, 131, 135, 137, 139–141)

| | |
|---|---|
| 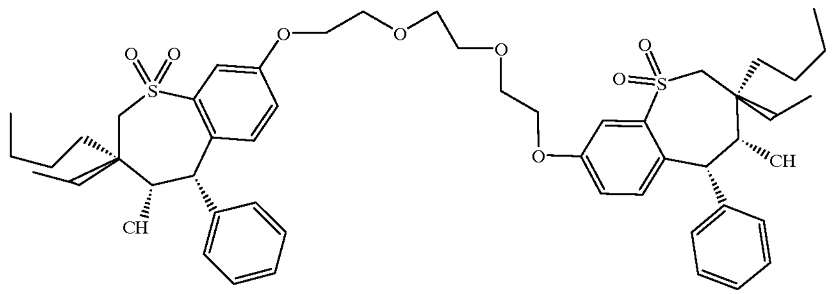 | CPD #137 (Ex. 57) |
| 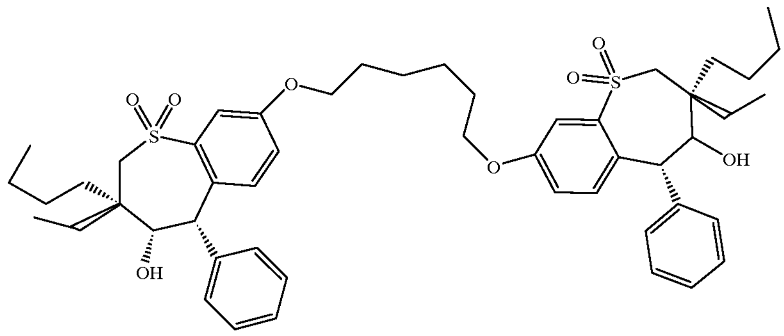 | CPD #139 (Ex. 58) |
| 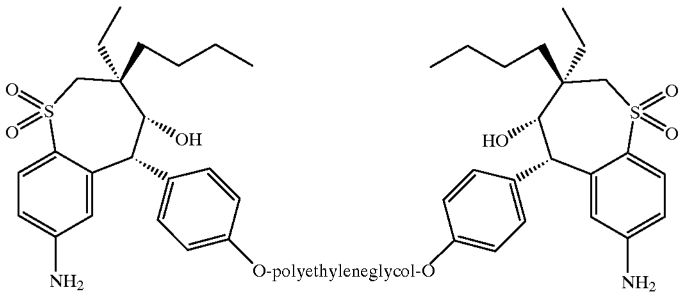<br>3400 MW polyethyleneglycol bridge | CPD #140 (Ex. 51) |
| 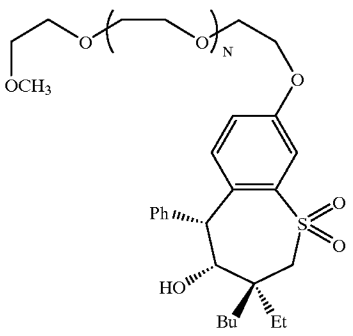 | CPD #141 (Ex. 50) |

Example 104–231

Using in each instance a method generally described in those of Examples 1 to 72 appropriate to the substituents to be introduced, including where necessary other common synthesis expedients well known to the art, compounds are prepared having the structures set forth in Table 4. The starting materials illustrated in the reaction schemes shown above are varied in accordance with principles of organic synthesis well known to the art in order to introduce the indicated substituents in the 4- and 5-positions ($R^3$, $R^4$, $R^5$, $R^6$) and in the indicated position on the benzo ring ($R^x$).

TABLE 4

Alternative compounds #1 (#302–312, 314–430)

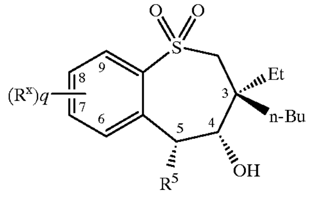

| Cpd# | $R^5$ | $(R^x)q$ |
|---|---|---|
| 302 | p-F—Ph— | 7-(1-aziridine) |
| 303 | p-F—Ph— | 7-EtS— |
| 304 | p-F—Ph— | 7-$CH_3S(O)$— |
| 305 | p-F—Ph— | 7-$CH_3S(O)_2$— |
| 306 | p-F—Ph— | 7-PhS— |
| 307 | p-F—Ph— | 7-$CH_3S$—<br>9-$CH_3S$— |
| 308 | p-F—Ph— | 7-$CH_3O$—<br>9-$CH_3O$— |
| 309 | p-F—Ph— | 7-Et— |
| 310 | p-F—Ph— | 7-iPr— |
| 311 | p-F—Ph— | 7-t-Bu— |
| 312 | p-F—Ph— | 7-(1-pyrazole)- |
| 314 | m-$CH_3O$—Ph | 7-(1-azetidine) |
| 315 | m-$CH_3O$—Ph— | 7-(1-aziridine) |
| 316 | m-$CH_3O$—Ph— | 7-EtS— |
| 317 | m-$CH_3O$—Ph— | 7-$CH_3S(O)$— |
| 318 | m-$CH_3O$—Ph— | 7-$CH_3S(O)_2$— |
| 319 | m-$CH_3O$—Ph— | 7-PhS— |
| 320 | m-$CH_3O$—Ph | 7-$CH_3S$—<br>9-$CH_3S$— |
| 321 | m-$CH_3O$—Ph | 7-$CH_3O$—<br>9-$CH_3O$— |
| 322 | m-$CH_3O$—Ph | 7-Et— |
| 323 | m-$CH_3O$—Ph | 7-iPr— |
| 324 | m-$CH_3O$—Ph | 7-t-Bu— |
| 325 | p-F—Ph— | 6-$CH_3O$—<br>7-$CH_3O$—<br>8-$CH_3O$— |
| 326 | p-F—Ph— | 7-(1-azetidine)<br>9-$CH_3$— |
| 327 | p-F—Ph— | 7-EtS—<br>9-$CH_3$— |
| 328 | p-F—Ph— | 7-$CH_3S(O)$—<br>9-$CH_3$— |
| 329 | p-F—Ph— | 7-$CH_3S(O)_2$—<br>9-$CH_3$— |
| 330 | p-F—Ph— | 7-PhS—<br>9-$CH_3$— |
| 331 | p-F—Ph— | 7-$CH_3S$—<br>9-$CH_3$— |
| 332 | p-F—Ph— | 7-$CH_3O$—<br>9-$CH_3$— |
| 333 | p-F—Ph— | 7-$CH_3$—<br>9-$CH_3$— |
| 334 | p-F—Ph— | 7-$CH_3O$—<br>9-$CH_3O$— |
| 335 | p-F—Ph— | 7-(1-pyrrole) |
| 336 | p-F—Ph— | 7-(N)-N'-methylpiperazine |
| 337 | p-F—Ph— | Ph— |
| 338 | p-F—Ph— | 7-$CH_3C(=CH_2)$— |
| 339 | p-F—Ph— | 7-cyclopropyl |
| 340 | p-F—Ph— | 7-$(CH_3)_2NH$— |
| 341 | p-F—Ph— | 7-(N)-azetidine<br>9-$CH_3S$— |
| 342 | p-F—Ph— | 7-(N-pyrrolidine)<br>9-$CH_3S$— |
| 343 | p-F—Ph— | 7-$(CH_3)_2N$—<br>9-$CH_3S$— |

TABLE 4-continued

Alternative compounds #1 (#302–312, 314–430)

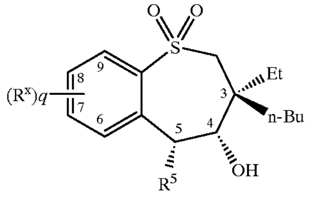

| Cpd# | $R^5$ | $(R^x)q$ |
|---|---|---|
| 344 | m-$CH_3O$—Ph— | 7-(1-pyrazole) |
| 345 | m-$CH_3O$—Ph— | 7-(N)-N'-methylpiperazine |
| 346 | m-$CH_3O$—Ph— | Ph— |
| 347 | m-$CH_3O$—Ph— | 7-$CH_3C(=CH_2)$— |
| 348 | m-$CH_3O$—Ph— | 7-cyclopropyl |
| 349 | m-$CH_3O$—Ph— | 7-$(CH_3)_2NH$— |
| 350 | m-$CH_3O$—Ph— | 7-(N)-azetidine<br>9-$CH_3S$— |
| 351 | m-$CH_3O$—Ph— | 7-(N-pyrrolidine)-<br>9-$CH_3S$— |
| 352 | m-$CH_3O$—Ph— | 7-$(CH_3)_2N$—<br>9-$CH_3S$— |
| 353 | m-$CH_3O$—Ph— | 6-$CH_3O$—<br>7-$CH_3O$—<br>8-$CH_3O$— |
| 354 | m-$CH_3O$—Ph— | 7-(1-azetidine)<br>9-$CH_3$— |
| 355 | m-$CH_3O$—Ph— | 7-EtS—<br>9-$CH_3$— |
| 356 | m-$CH_3O$—Ph— | 7-$CH_3S(O)$—<br>9-$CH_3$— |
| 357 | m-$CH_3O$—Ph— | 7-$CH_3S(O)_2$—<br>9-$CH_3$— |
| 358 | m-$CH_3O$—Ph— | 7-PhS—<br>9-$CH_3$— |
| 359 | m-$CH_3O$—Ph— | 7-$CH_3S$—<br>9-$CH_3$— |
| 360 | m-$CH_3O$—Ph— | 7-$CH_3O$—<br>9-$CH_3$— |
| 361 | m-$CH_3O$—Ph— | 7-$CH_3$—<br>9-$CH_3$— |
| 362 | m-$CH_3O$—Ph— | 7-$CH_3O$—<br>9-$CH_3O$— |
| 363 | thien-2-yl | 7-(1-aziridine) |
| 364 | thien-2-yl | 7-EtS— |
| 365 | thien-2-yl | 7-$CH_3S(O)$— |
| 366 | thien-2-yl | 7-$CH_3S(O)_2$— |
| 367 | thien-2-yl | 7-PhS— |
| 368 | thien-2-yl | 7-$CH_3S$—<br>9-$CH_3S$— |
| 369 | thien-2-yl | 7-$CH_3O$—<br>9-$CH_3O$— |
| 370 | thien-2-yl | 7-Et— |
| 371 | thien-2-yl | 7-iPr— |
| 372 | thien-2-yl | 7-t-Bu— |
| 373 | thien-2-yl | 7-(1-pyrrole)- |
| 374 | thien-2-yl | 7-$CH_3O$— |
| 375 | thien-2-yl | 7-$CH_3S$— |
| 376 | thien-2-yl | 7-(1-azetidine) |
| 377 | thien-2-yl | 7-Me— |
| 378 | 5-Cl-thien-2-yl | 7-(1-azetidine) |
| 379 | 5-Cl-thien-2-yl | 7-(1-aziridine) |
| 380 | 5-Cl-thien-2-yl | 7-EtS— |
| 381 | 5-Cl-thien-2-yl | 7-$CH_3S(O)$— |
| 382 | 5-Cl-thien-2-yl | 7-$CH_3S(O)_2$— |
| 383 | 5-Cl-thien-2-yl | 7-PhS— |
| 384 | 5-Cl-thien-2-yl | 7-$CH_3S$—<br>9-$CH_3S$— |
| 385 | 5-Cl-thien-2-yl | 7-$CH_3O$—<br>9-$CH_3O$— |
| 386 | 5-Cl-thien-2-yl | 7-Et— |
| 387 | 5-Cl-thien-2-yl | 7-iPr— |
| 388 | 5-Cl-thien-2-yl | 7-t-Bu— |
| 389 | 5-Cl-thien-2-yl | 7-$CH_3O$— |
| 390 | 5-Cl-thien-2-yl | 7-$CH_3S$— |

TABLE 4-continued

Alternative compounds #1 (#302–312, 314–430)

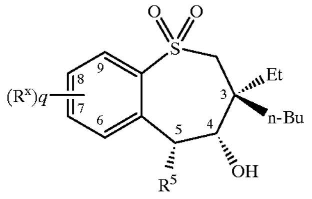

| Cpd# | $R^5$ | $(R^x)q$ |
|---|---|---|
| 391 | 5-Cl-thien-2-yl | 7-Me |
| 392 | thien-2-yl | 7-(1-azetidine)<br>9-$CH_3$— |
| 393 | thien-2-yl | 7-EtS—<br>9-$CH_3$— |
| 394 | thien-2-yl | 7-$CH_3S(O)$—<br>9-$CH_3$— |
| 395 | thien-2-yl | 7-$CH_3S(O)_2$—<br>9-$CH_3$— |
| 396 | thien-2-yl | 7-PhS—<br>9-$CH_3$— |
| 397 | thien-2-yl | 7-$CH_3S$—<br>9-$CH_3$— |
| 398 | thien-2-yl | 7-$CH_3O$—<br>9-$CH_3$— |
| 399 | thien-2-yl | 7-$CH_3$—<br>9-$CH_3$— |
| 400 | thien-2-yl | 7-$CH_3O$—<br>9-$CH_3O$— |
| 401 | thien-2-yl | 7-(1-pyrazrole) |
| 402 | thien-2-yl | 7-(N)-N'-methylpiperazine |
| 403 | thien-2-yl | Ph— |
| 404 | thien-2-yl | 7-$CH_3C(=CH_2)$— |
| 405 | thien-2-yl | 7-cyclpropyl |
| 406 | thien-2-yl | 7-$(CH_3)_2NH$— |
| 407 | thien-2-yl | 7-(N)-azetidine<br>9-$CH_3S$— |
| 408 | thien-2-yl | 7-(N-pyrrolidine)<br>9-$CH_3S$— |
| 409 | thien-2-yl | 7-$(CH_3)_2N$—<br>9-$CH_3S$— |
| 411 | 5-Cl-thien-2-yl | 7-(1-pyrazrole) |
| 412 | 5-Cl-thien-2-yl | 7-(N)-N'-methylpiperazine |
| 413 | 5-Cl-thien-2-yl | Ph— |
| 414 | 5-Cl-thien-2-yl | 7-$CH_3C(=CH_2)$— |
| 415 | 5-Cl-thien-2-yl | 7-cyclopropyl |
| 416 | 5-Cl-thien-2-yl | 7-$(CH_3)_2NH$— |
| 417 | 5-Cl-thien-2-yl | 7-(N)-azetidine<br>9-$CH_3S$— |
| 418 | 5-Cl-thien-2-yl | 7-(N-pyrrolidine)-<br>9-$CH_3S$— |
| 419 | 5-Cl-thien-2-yl | 7-$(CH_3)_2N$—<br>9-$CH_3S$— |
| 420 | 5-Cl-thien-2-yl | 7-(1-azetidine)<br>9-$CH_3$— |
| 421 | 5-Cl-thien-2-yl | 7-EtS—<br>9-$CH_3$— |
| 422 | 5-Cl-thien-2-yl | 7-$CH_3S(O)$—<br>9-$CH_3$— |
| 423 | 5-Cl-thien-2-yl | 7-$CH_3S(O)_2$—<br>9-$CH_3$— |
| 424 | 5-Cl-thien-2-yl | 7-PhS—<br>9-$CH_3$— |
| 425 | 5-Cl-thien-2-yl | 7-$CH_3S$—<br>9-$CH_3$— |
| 426 | 5-Cl-thien-2-yl | 7-$CH_3O$—<br>9-$CH_3$— |
| 427 | 5-Cl-thien-2-yl | 7-$CH_3$—<br>9-$CH_3$— |
| 428 | 5-Cl-thien-2-yl | 7-$CH_3O$—<br>9-$CH_3O$— |
| 429 | thien-2-yl | 6-$CH_3O$—<br>7-$CH_3O$—<br>8-$CH_3O$— |

TABLE 4-continued

Alternative compounds #1 (#302–312, 314–430)

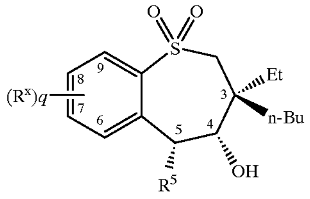

| Cpd# | $R^5$ | $(R^x)q$ |
|---|---|---|
| 430 | 5-Cl-thien-2-yl | 6-$CH_3O$—<br>7-$CH_3O$—<br>8-$CH_3O$— |

Examples 232–1394

Using in each instance a method generally described in those of Examples 1 to 72 appropriate to the substituents to be introduced, including where necessary other common synthesis expedients well known to the art, compounds are prepared having the structures set forth in Table 1. The starting materials illustrated in the reaction schemes shown above are varied in accordance with principles of organic synthesis well known to the art in order to introduce the indicated substituents in the 4- and 5-positions ($R^3$, $R^4$, $R^5$, $R^6$) and in the indicated position on the benzo ring ($R^x$).

Example 1395

Dibutyl 4-fluorobenzene Dialdehyde

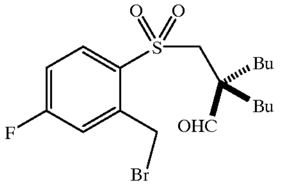

Step 1

Preparation of Dibutyl 4-fluorobenzene Dialdehyde

To a stirred solution of 17.5 g (123 mmol) of 2,5-difluorobenzaldehyde (Aldrich) in 615 mL of DMSO at ambient temperature was added 6.2 g (135 mmol) of lithium sulfide (Aldrich). The dark red solution was stirred at 75 C. for 1.5 hours, or until the starting material was completely consumed, and then 34 g (135 mmol) of dibutyl mesylate aldehyde was added at about 50 C. The reaction mixture was stirred at 75 C. for three hours or until the reaction was completed. The cooled solution was poured into water and extracted with ethyl acetate. The combined extracts were washed with water several times, dried ($MgSO_4$) and concentrated in vacuo. Silica gel chromatographic purification of the crude product gave 23.6 g (59%) of fluorobenzene dialdehyde as a yellow oil: $^1H$ NMR ($CDCl_3$) d 0.87 (t, J=7.05 Hz, 6H), 1.0–1.4 (m, 8H), 1.5–1.78 (m, 4H), 3.09 (s, 2H), 7.2–7.35 (m, 1H), 7.5–7.6 (m, 2H), 9.43 (s, 1H), 10.50 (d, J=2.62 Hz, 1H).

Step 2

Preparation of Dibutyl 4-fluorobenzyl Alcohol

To a solution of 22.6 g (69.8 mmol) of the dialdehyde obtained from Step 1 in 650 mL of THF at −60 C. was added 69.8 mL (69.8 mmol) of DIBAL (1M in THF) via a syringe. The reaction mixture was stirred at −40 C. for 20 hours. To the cooled solution at −40 C. was added sufficient amount of ethyl acetae to quench the excess is of DIBAL, followed by 3 N HCl. The mixture was extracted with ethyl acetate, washed with water, dried ($MgSO_4$), and concentrated in vacuo. Silica gel chromatographic purification of the crude product gave 13.5 g (58%) of recovered starting material, and 8.1 g (36%) of the desired fluorobenzyl alcohol as a colorless oil: $^1H$ NMR ($CDCl_3$) d 0.88 (t, J=7.05 Hz, 6H), 1.0–1.4 (m, 8H), 1.5–1.72 (m, 4H), 1.94 (br s, 1H), 3.03 (s, 2H), 4.79 (s, 2H), 6.96 (dt, J=8.46, 3.02 Hz, 1H), 7.20 (dd, J=9.47, 2.82 Hz, 1H), 7.42 (dd, J=8.67, 5.64, 1H), 9.40 (s, 1H).

Step 3

Preparation of dibutyl 4-fluorobenzyl Bromide

To a solution of 8.1 g (25 mmol) of benzyl alcohol obtained from Step 2 in 100 mL of DMF at −40 C. was added 47 g (50 mmol) of bromotriphenyphosphonium bromide (Aldrich). The resulting solution was stirred cold for 30 min, then was allowed to warm to 0 C. To the mixture was added 10% solution of sodium sulfite and ethyl acetate. The extract was washed a few times with water, dried (MgSO4), and concentrated in vacuo. The mixture Was stirred in small amount of ethyl acetate/hexane mixture (1:4 ratio) and filtered through a pad of silica gel, eluting with same solvent mixture. The combined filtrate was concentrated in vacuo to give 9.5 g (98%) of the desired product as a colorless oil: $^1H$ NMR ($CDCl_3$) d 0.88 (t, J=7.05 Hz, 6H), 1.0–1.4 (m, 8H), 1.55–1.78 (m, 4H), 3.11 (s, 2H), 4.67 (s, 2H), 7.02 (dt, J=8.46, 3.02 Hz, 1H), 7.15 (dd, J=9.47, 2.82 Hz, 1H), 7.46 (dd, J=8.67, 5.64, 1H), 9.45 (s, 1H).

Step 4

Preparation of Sulfonyl 4-fluorobenzyl Bromide

To a solution of 8.5 g (25 mmol) of sulfide obtained from Step 3 in 200 mL of $CH_2Cl_2$ at 0° C. was added 15.9 g (60 mmol) of mCPBA (64% peracid). The resulting solution was stirred cold for 10 min, then was allowed to stirred ambient temperature for 5 hours. To the mixture was added 10% solution of sodium sulfite and ethyl acetate. The extract was washed several times with saturated $Na_2CO_3$, dried ($MgSO_4$), and concentrated in vacuo to give 10.2 g (98%) of the desired product as a colorless oil: $^1H$ NMR ($CDCl_3$) d 0.91 (t, J=7.05 Hz, 6H), 1.03–1.4 (m, 8H), 1.65–1.82 (m, 2H), 1.90–2.05 (m, 2H), 3.54 (s, 2H), 5.01 (s, 2H), 7.04–7.23 (m, 1H), 7.30 (dd, J=8.87, 2.42 Hz, 1H), 8.03 (dd, J=8.86, 5.64, 1H), 9.49 (s, 1H).

Example 1396

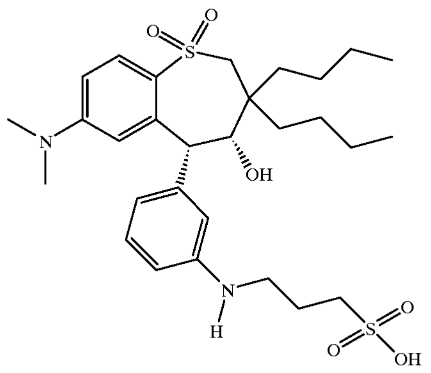

Generic Scheme X

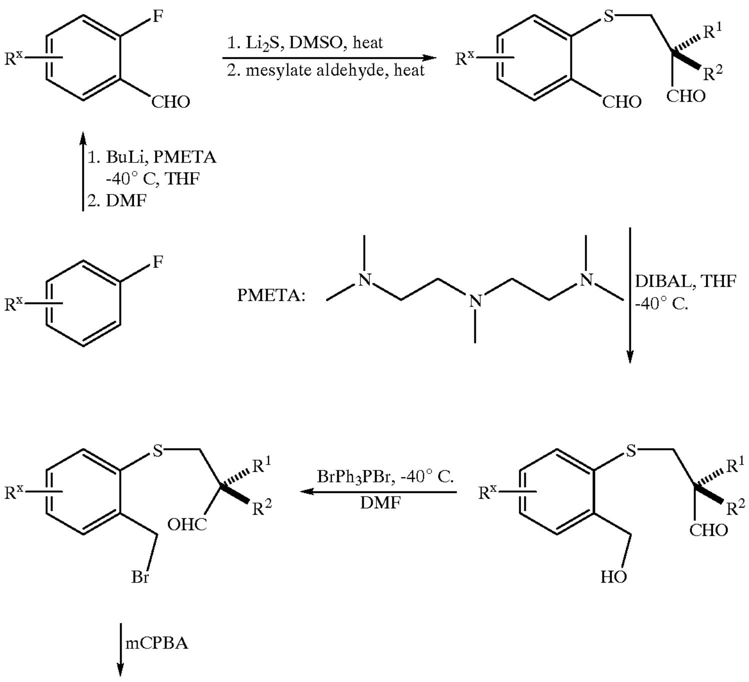

-continued

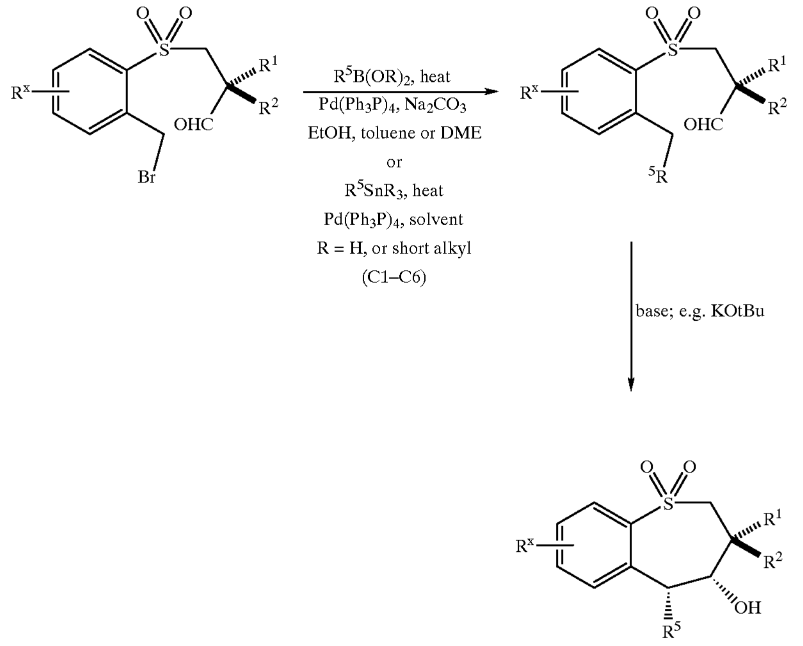

Generic Scheme X: The nucleophilic substitution of an appropriately substituted 2-fluorobenzaldehyde with lithium sulfide or other nucleophilic sulfide anion in polar solvent (such as DMF, DMA, DMSO, etc), followed by the addition of dialkyl mesylate aldehyde (X), provided a dialkyl benzene dialdehyde Y. DIBAL reduction of the dialdehyde at low temperature yielded benzyl alcohol monoaldehyde Z. Conversion of benzyl alcohol to benzyl bromide, followed by oxidation of sulfide to sulfone yielded the key intermediate W.

Preparation of N-propylsulfonic Acid

To a solution of 51 mg (111 μm) Compound X in ethanol (400 μl) was added 1,3 propane sultone (19.5 μl, 222 μm). The reaction was stirred in a sealed vial at 55° C. for 25 hr. Sample was concentrated under a nitrogen stream and purified by reversed phase chromatography using acetonitrile/water as eluent (30–45%) and afforded the desired material as an off-white solid (28.4 mg, 44%): $^1H$ NMR ($CDCL_3$) d 0.82–0.96 (m, 6H), 1.11–1.52 (m of m, 10H), 1.58–1.72 (m, 1H), 2.08–2.21 (m, 1H), 2.36–2.50 (m, 2H), 2.93 (s, 6H), 3.02–3.22 (m of m, 5H), 3.58–3.76 (m, 2H), 4.15 (s, 1H), 5.51 (s, 1H), 6.45–6.58 (m, 1H), 6.92–7.02 (m, 1H), 7.35–7.41 (m, 1H), 7.41–7.51 (m, 2H), 8.08 (d, J=8.1 Hz, 1H), 8.12–8.25 (m, 1H); MS ES- M-H m/z 579.

Example 1397

The 7-fluoro, 9-fluoro and 7,9-difluoro analogs of benzothiepine compounds of this invention can be reacted with sulfur and nitrogen nucleophiles to give the corresponding sulfur and nitrogen substituted analogs. The following example demonstrates the synthesis of these analogs.

3,3-Dibutyl-5a-(4'-fluorophenyl)-4a-hydroxy-7-methylthio-2,3,4,5-tetrahydrobenzothiepine-1,1-dioxide

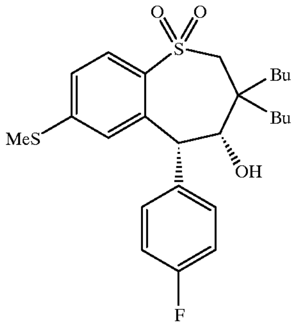

A mixture of 0.4 g Of 3,3-dibutyl-7-fluoro-5a-(4'-fluorophenyl)-4a-hydroxy-2,3,4,5-tetrahydrobenzothiepine-1,1-dioxide, prepared by previously described method, 0.12 g of sodium methanethiolate and 20 ml of DMF was stirred at 50 C., for 3 days. An additional 0.1 g of sodium methanethiolate was added to the reaction mixture and the mixture was stirred for additional 20 h at 50 C. then was concentrated in vacuo. The residue was triturated with water and extracte wiith ether. The ether extract was dried over $MgSO_4$ and concentrated in vacuo to 0.44 g of an oil. Purification by HPLC (10% EtOAc in hexane) gave 0.26 g of needles, mp 164–165.5%C.

3,3-Dibutyl-9-dimethylamino-7-fluoro-5a-(4'-fluorophenyl)-4a-hydroxy-2,3,4,5-tetrahydrobenzothiepine-1-dioxide and 7,9-1,1dioxide and 7,9-Bis (dimethylamino)-3,3-dibutyl-5a-(4'-fluorophenyl)-4a-hydroxy-2,3,4,5-tetrahydrobenzothiepine-1-dioxide

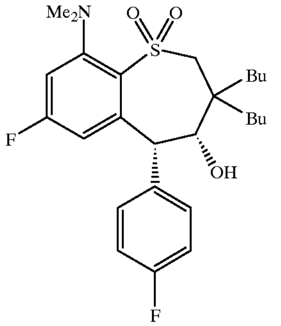

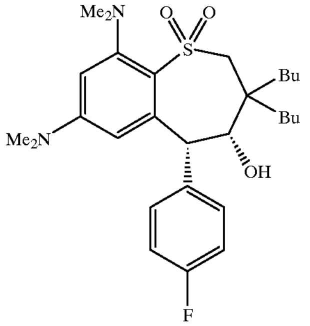

A solution of 0.105 g of 3,3-dibutyl-7,9-difluoro-5a-(4'-fluorophenyl)-4a-hydroxy-2,3,4,5-tetrahydrobenzothiepine-1,1-dioxide, prepared by the method described previously, in 20 ml of 2 N dimethylamine in THF was heated at 160 C. in a sealed Parr reactor overnight. The reaction mixture was cooled and concentrated in vacuo. The residue was triturated with 25 ml of water and extracted with ether. The ether extract was dried over $MgSO_4$ and concentrated in vacuo. The resdue was purified by HPLC (10% EtOAc in hexane) to give 35 mg of an earlier fraction which was identified as 3,3-dibutyl-9-dimethylamino-7-fluoro-5a-(4'-fluorophenyl)-4a-hydroxy-2,3,4,5-tetrahydrobenzothiepine-1,1-dioxide, MS (CI) m/e 480 ($M^+$+1), and 29 mg of a later fraction which was identified as 7,9-bis(dimethylamino)-3,3-dibutyl-5a-(4'-fluorophenyl)-4a-hydroxy-2,3,4,5-tetrahydrobenzothiepine-1,1-dioxide, MS (CI) m/e 505 ($M^+$+1).

The compounds of this invention can also be synthesized using cyclic sulfate (A, below) as the reagent as shown in the following scheme. The following example describes a procedure for using the cyclic sulfate as the reagent.

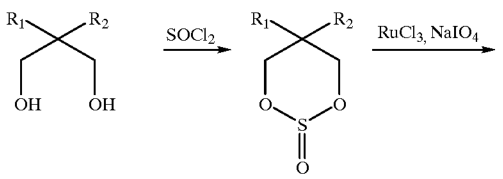

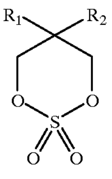

A

-continued

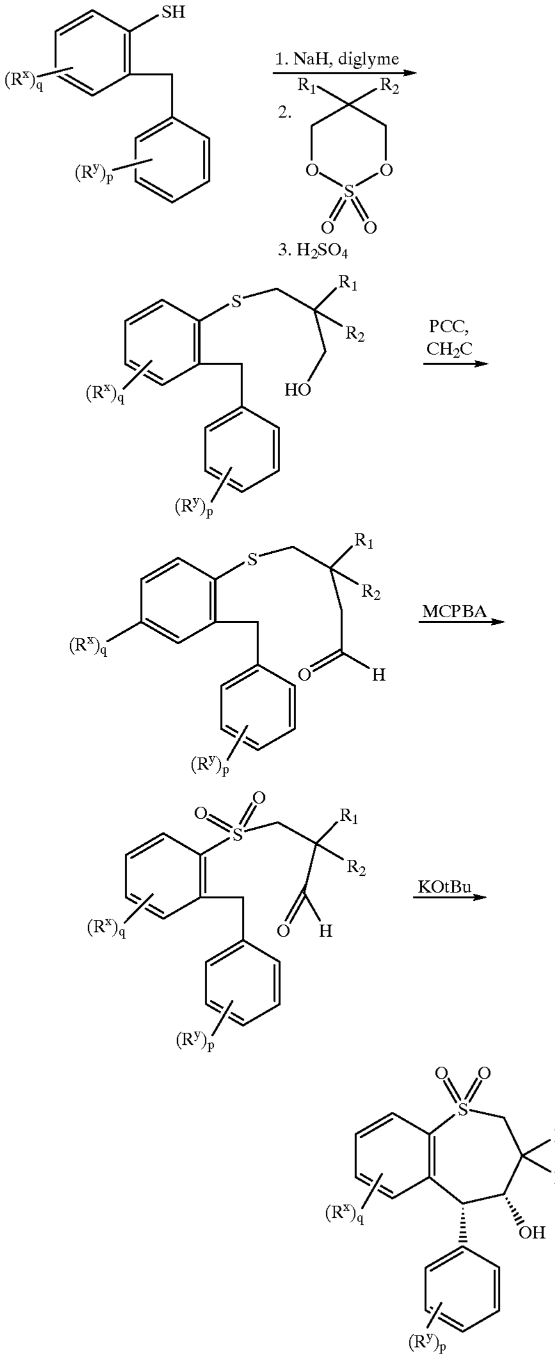

Dibutyl Cyclic Sulfite

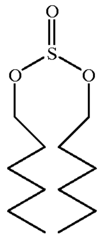

A solution of 2,2-dibutyl-1,3-propandiol (103 g, 0.548 mol) and triethylamine (221 g, 2.19 mol) in anhydrous methylene chloride (500 ml) and was stirred at 0 degrees C. under nitrogen. To the mixture, thionyl chloride (97.8 g, 0.82 mol) was added dropwise and within 5 min the solution turned yellow and then turned black when the addition was completed within half an hour. The reaction mixture was stirred for 3 hrs. GC showed that there was no starting material left. The mixture was washed with ice water twice then with brine twice. The organic phase was dried over magnesium sulfate and concentrated under vacuum to give the cyclic sulfite 128 g (100%) as a black oil. Mass spectrum (MS) was consistent with the product.

To a solution of the above compound (127.5 g , 0.54 mol) in 600 ml acetonitrile and 500 ml of water cooled in an ice bath under nitrogen was added ruthenium (III) chloride (1 g) and sodium periodate (233 g, 1.08 mol). The reaction was stirred overnight and the color of the solution turned black. GC showed that there was no starting material left. The mixture was extracted with 300 ml of ether and the ether extract was washed three times with brine. The organic phase was dried over magnesium sulfate and passed through celite. The filtrate was concentrated under vacuum and gave the cyclic sulfate 133 g (97.8%) as an oil. Proton, carbon NMR and MS were consistent with the product.

2-[(2-(4'-Fluorobenzyl)-4-methylphenylthio) methyl]-2-butylhexanol

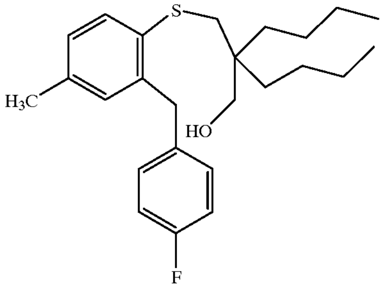

Sodium hydride (60% oil dispersion), 0.27 g (6.68 mmole), was washed with hexane and the hexane wash was decanted. To the washed sodium hydride was added 20 ml of 2-methoxyethyl ether (diglyme) and the mixture was cooled in an ice bath. A solution of 1.55 g (6.68 mmole) of 2-(4'-fluorobenzyl)-4-methylbenzenethiol in 10 ml of 2-methoxyethyl ether was added dropwise to the reaction mixture in 15 min. A mixture of 2.17 g (8.68 mmole) of the dibutyl cyclic sulfate in 10 ml of 2-methoxyethyl ether was added once and stirred for 30 min at 0 C. then at room temperature for 1 hr under nitrogen. GC showed that there was no thiol left. The solvent was evaporated and triturated wth water then was extracted with ether twice. The water layer was separated, treated with 20 ml of 10% NaOH then was boiled for 30 min and cooled, acidified with 6N HCl and boiled for 10 min. The reaction mixture was cooled and extracted with ether. The organic layer was washed successively with water and brine, dried over magnesium sulfate and concentrated under vacuum to give 2.47 g (92.5%) of an oil. Proton NMR , $^{13}C$. NMR and MS were consistent with the product.

2-[(2-(4'-Fluorobenzyl)-4-methylphenylthio) methyl]-2-butylhexanal

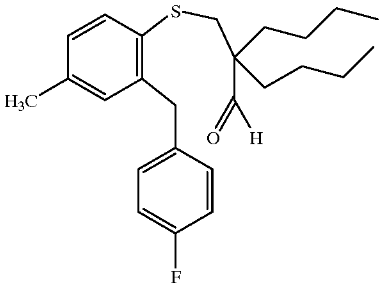

To a solution of the above product (2 g , 4.9 mmol) in 40 ml methylene chloride cooled in an ice bath under nitrogen was added pyridinium chlorochromate (2.18 g, 9.9 mmol) at once. The reaction was stirred with 3 hrs and filtered through a bed of silica gel. The filtrate was concentrated under vacuum to give 1.39 g (70%) of an oil. Proton, carbon NMR and MS were consistent with the product.

2-[(2-(4'-Fluorobenzyl)-4-methylphenylsulfonyl)methyl]-2-butylhexanal

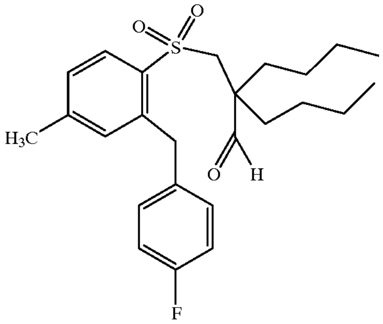

To a solution of the above product (0.44 g ,1.1 mmole) in 20 ml methylene chloride solution cooled in an ice bath under nitrogen was added 70% m-chloroperbenzoic acid (0.54 g, 2.2 mmol) at once. The reaction mixture was stirred for 18 hrs and filtered. The filtrate was washed successively with 10% NaOH (3X), water and brine, dried over magnesium sulfate and concentrated under vacum to give 0.42 g (90%) of an oil. Proton, carbon NMR and MS were consistent with the product.

3,3-Dibutyl-7-methyl-5a-(4'-fluorophenyl)-4a-hydroxy-2,3,4,5-tetrahydrobenzothiepine-1,1-dioxide

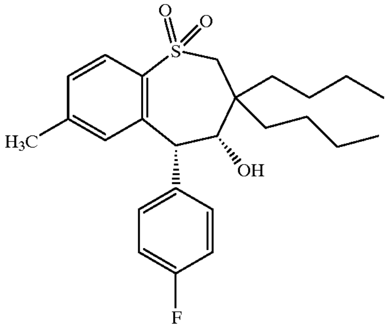

A mixture of 0.37 g (0.85 mmol) of the above product in 30 ml of anhydrous THF was stirred at 0%C. Then potassium t-butoxide (102 mg, 0.85 mmol) was added. After 3 hrs, TLC showed that there was a product and some starting material left. The crude reaction mixture was acidified with 10% HCl and extracted with ether. The ether extract was washed successively with water and brine, dried with $MgSO_4$ and concentrated under vacuum. The residue was purified by HPLC (10% EtOAc-Hexane). The first fraction was 0.1 g of starting material as an oil and the second fraction was a white solid, 0.27 g (75%). Proton NMR and carbon NMR were consistent with the desired product. Mass spectrum (CI) also confirmed the product, m/e 433 ($M^{+}1$).

Example 1398

Step 1

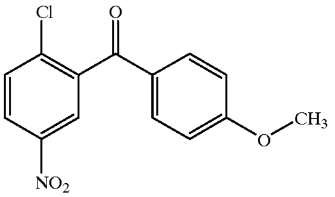

$C_{14}H_{10}ClNO_4$ fw = 291.69

In an inert atmosphere, weigh out 68.3 gms phosphorus pentachloride (0.328 mole Aldrich 15,777-5) into a 2-necked 500ml round bottom flask. Fit flask with a $N_2$ inlet adapter and suba seal. Remove from inert atmosphere and begin $N_2$ purge. Add 50 mls anhydrous chlorobenzene (Aldrich 28,451-3) to the $PCl_5$ via syringe and begin stirring with magnetic stir bar.

Weigh out 60 gms 2-chloro-5-nitrobenzoic acid (0.298 mole Aldrich 12,511-3). Slowly add to the chlorobenzene solution while under $N_2$ purge. Stir at room temperature overnight. After stirring at room temperature for ~20 hrs, place in oil bath and heat at 50 C. for 1 hr. Remove chlorobenzene by high vacuum. Wash residue with anhydrous hexane. Dry acid chloride wt=61.95 gms. Store in inert and dry atmosphere.

In inert atmosphere, dissolve acid chloride with 105 mls anhydrous anisole (0.97 mole Aldrich 29,629-5). Place solution in a 2-necked 500 ml round bottom flask.

Weigh out 45.1 gms aluminum chloride (0.34 moles Aldrich 29,471-3) and place in a solid addition funnel. Fit reaction flask with addition funnel and a $N_2$ inlet adapter. Remove from inert atmosphere. Chill reaction solution with ice bath and begin $N_2$ purge. Slowly add $AlCl_3$ to chilled solution. After addition is complete, allow to warm to room temperature. Stir overnight.

Quench reaction by pouring into a solution of 300 mls 1N HCl and ice. Stir 15 min. Extract twice with ether. Combine organic layers and extract twice with 2% NaOH, then twice with deionized $H_2O$. Dry with $MgSO_4$, filter and rotovap to dryness. Remove anisole by high vacuum. Crystalize product from 90% ethanol 10% ethyl acetate. Dry on vacuum line. Wt=35.2 gms. Yield 41%. Obtain NMR and mass spec (m/z=292).

Step 2

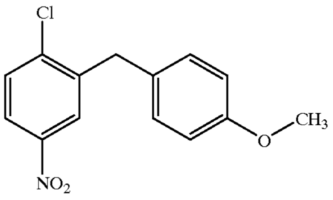

$C_{14}H_{12}ClNO_3$ fw = 277.71

Dissolve 38.10 gms (0.131 moles) of the benzophenone from step 1 in 250mls anhydrous methylene chloride. Place in a 3 liter flask fitted with $N_2$ inlet, addition funnel and stopper. Stir with magnetic stir bar. Chill solution with ice bath.

Prepare a solution of 39.32 gms trifluoromethane sulfonic acid (0.262 mole Aldrich 15,853-4) and 170 mls anhydrous methylene chloride. Place in addition funnel and add dropwise to chilled solution under $N_2$. Stir 5 minutes after addition is complete.

Prepare a solution of 22.85 gms triethyl silane (0.197 mole Aldrich 23,019-7) and 170 mls anhydrous methylene chloride. Place in addition funnel and add dropwise to chilled solution under $N_2$. Stir 5 minutes after addition is complete.

Prepare a second solution of 39.32 gms trifluoromethane sulfonic acid and 170 mls anhydrous methylene chloride. Place in addition funnel and add dropwise to chilled solution under $N_2$. Stir 5 minutes after addition is complete.

Prepare a second solution of 22.85 gms triethyl silane and 170 mls anhydrous methylene chloride. Place in addition funnel and add dropwise to chilled solution under $N_2$. After all additions are made allow to slowly warm to room temperature overnight. Stir under $N_2$ overnight.

Prepare 1300 mls saturated $NaHCO_3$ in a 4 liter beaker. Chill with ice bath. While stirring vigorously, slowly add reaction mixture. Stir at chilled temperature for 30 min. Pour into a separatory funnel and allow separation. Remove organic layer and extract aqueous layer 2 times with methylene chloride. Dry organic layers with $MgSO_4$. Crystallize from ethanol. Dry on vacuum line. Dry wt=28.8 gms. Confirm by NMR and mass spec (m/z=278).

Step 3

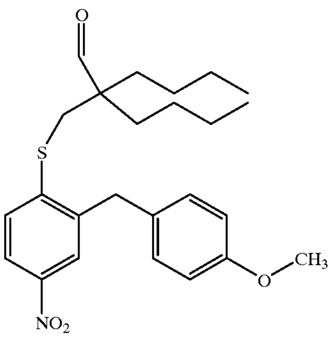

$C_{25}H_{33}NO_4S$ fw = 443.61

Dissolve 10.12 gms (0.036 moles) of product 2 with 200 mls anhydrous DMSO. Place in a 500 ml round bottom flask with magnetic stir bar. Fit flask with water condenser, $N_2$ inlet, and stopper. Add 1.84 gms $Li_2s$ (0.040 moles Aldrich 21,324-1). Place flask in oil bath and heat at 75° C. under $N_2$ overnight then cool to room temperature.

Weigh out 10.59 gms dibutyl mesylate (0.040 moles). Dissolve with anhydrous DMSO and add to reaction solution. Purge well with $N_2$, heat overnight at 80° C.

Cool to room temperature. Prepare 500 mls of 5% acetic acid in a 2 liter beaker. While stirring, slowly add reaction mixture. Stir 30 min. Extract with ether 3 times. Combine organic layers and extract with water and sat'd NaCl. Dry organic layer with $MgSO_4$, filter and rotovap to dryness. Dry oil on vacuum line. Obtain pure product by column chromatography using 95% hexane and 5% ethyl acetate as the mobile phase. Dry wt=7.8 gms. Obtain NMR and mass spec (m/z=444).

Step 4

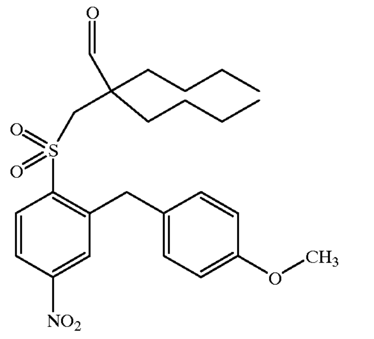

$C_{25}H_{33}NO_6S$ fw = 475.61

Dissolve 9.33 gms (0.021 moles) of product 3 with 120 mls anhydrous methylene chloride. Place in a 250 ml round bottom flask with magnetic stir bar. Fit flask with $N_2$ inlet and stopper. Chill solution with ice bath under $N_2$ purge. Slowly add 11.54 gms 3-chloroperbenzoic acid (0.0435 moles, Fluka 25800, ~65%). After addition is complete warm to room temperature and monitor reaction by TLC. Reaction goes quickly to the sulphoxide intermediate but takes 8 hrs to convert to the sulphone. Chill solution over night in freezer. Filter solid from reaction, extract filtrate with 10% $K_2CO_3$. Extract aqueous layer twice with methylene choride. Combine organic layers and dry with $MgSO_4$. Filter and rotovap to dryness. Obtain pure product by crystallizing from ethanol or isolating by column chromatography. Obtain NMR and mass spec (m/z=476).

Step 5

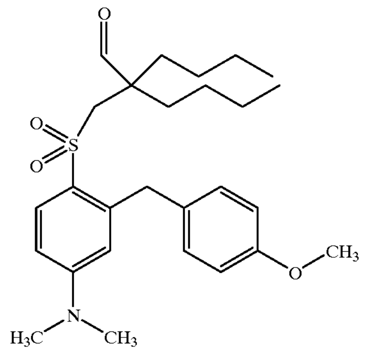

$C_{27}H_{39}NO_4S$ fw = 473.68

Reaction is done in a 300 ml stainless steel Parr stirred mini reactor. Place 9.68 gms (0.0204 moles) of product 4 in reactor base. Add 160 mls ethanol. For safety reasons next two compounds are added in a $N_2$ atmosphere glove bag. In glove bag, add 15.3 mls formaldehyde (0.204 moles, Aldrich 25,254-9, about 37 wt % in water) and 1.45 gms 10% Pd/Carbon (Aldrich 20,569-9). Seal reactor before removing from glove bag. Purge reactor three times with $H_2$. Heat to 55° C. under $H_2$. Run reaction at 200 psig $H_2$, 55° C., and a stir rate of 250 rpm. Run overnight under these conditions.

Cool reactor and vent $H_2$. Purge with $N_2$. Check progress of run by TLC. Reaction is a mixture of desired product and intermediate. Filter reaction mixture over a bed of celite washing well with ether. Rotovap and redissolve with ether. Extract with water. Dry organic layer with $MgSO_4$, filter and rotovap to dryness. Dry on vacuum line.

Charge reactor again with same amounts, seal reactor and run overnight under same conditions. After second run all of the material has been converted to the desired product. Cool and vent $H_2$ pressure. Purge with $N_2$. Filter over a bed of celite, washing well with ether. Rotovap to dryness. Dissolve with ether and extract with water. Dry organic layer with $MgSO_4$, filter and rotovap to dryness. Dry on vacuum line. Obtain NMR and mass spec (m/z=474).

Step 6

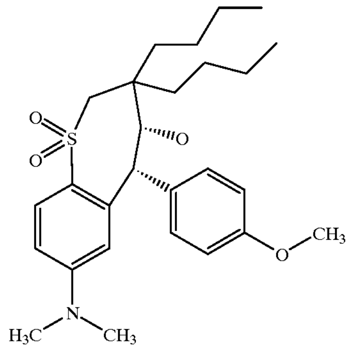

$C_{27}H_{39}NO_4S$ fw = 473.68

Dissolve 8.97 gms (0.0189 mole) of product 5 with 135 mls anhydrous THF. Place in a 250 ml round bottom flask with magnetic stir bar. Fit flask with $N_2$ inlet and stopper. Chill solution with ice/salt bath under $N_2$ purge. Slowly add 2.55 gms potassium t-butoxide (0.227 mole Aldrich 15,667-1)–After addition is complete, continue to stir at −10° C. monitoring by TLC. Once reaction is complete, quench by adding 135 mls 10% HCl stirring 10 min. Extract three times with ether. Dry organic layer with $MgSO_4$, filter and rotovap to dryness. Crystallize from ether. Obtain NMR and mass spec (m/z=474).

Step 7

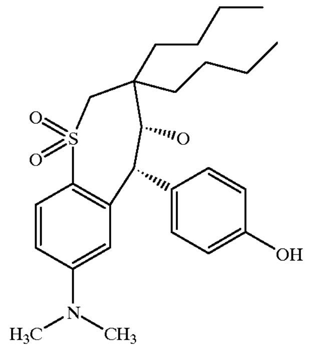

$C_{24}H_{37}NO_4S$ fw = 459.65

Dissolve 4.67 gms (0.01 moles) of product 6 with 100 mls anhydrous chloroform. Place in a 250 ml round bottom flask with magnetic stir bar. Fit flask with $N_2$ inlet adapter and suba seal. Chill solution with dry ice/acetone bath under a $N_2$ purge. Slowly add, via syringe, 2.84 mls boron tribromide (0.03 moles Aldrich 20,220-7). Stir at cold temperature for 15 min after addition then allow to warm to room temperature. Monitor reaction progress by TLC. Reaction is usually complete in 3 hrs.

Chill solution with ice bath. Quench with 100 mls 10% $K_2CO_3$ while stirring rapidly. Stir 10 min. then transfer to sep funnel and allow separation. Remove aqueous layer. Extract organic layer once with 10% HCl, once $H_2O$, and once with saturated NaCl solution. Dry organic layer with $MgSO_4$, filter and rotovap to dryness. Crystallize product from ether. Obtain NMR and mass spec (m/z=460).

Step 8

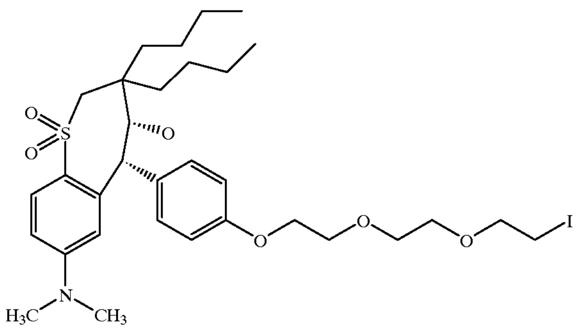

$C_{32}H_{48}NO_4SI$ fw = 701.71

Weigh 0.38 gms NaH (9.57 mmoles Aldrich 19,923-0 60% disp. in mineral oil) in a 250 ml round bottom flask with magnetic stir bar. Fit flask with $N_2$ inlet and stopper. Chill NaH with ice bath and begin $N_2$ purge.

Dissolve 4.0 gms (8.7 mmoles) of product 7 with 60 mls anhydrous DMF. Add to the cold NaH. Stir at cold temperature for 30 min. Add 1.33 gms $K_2CO_3$ (9.57 mmoles Fisher P-208).

Dissolve 16.1 gms 1,2-bis-(2-iodoethoxy)ethane (43.5 mmoles Aldrich 33,343-3) with 60 mls anhydrous DMF. Add to cold reaction mixture. Warm to room temperature then heat to 40° C. overnight under $N_2$.

Cleanup by diluting with ether and extracting sequentially with 5% NaOH, $H_2O$, and saturated NaCl. Dry organic layer with $MgSO_4$, filter and dry. Obtain pure product by column chromatography using 75% hexane 25% ethyl acetate as the mobile phase. Obtain NMR and mass spec (m/z=702).

Step 9

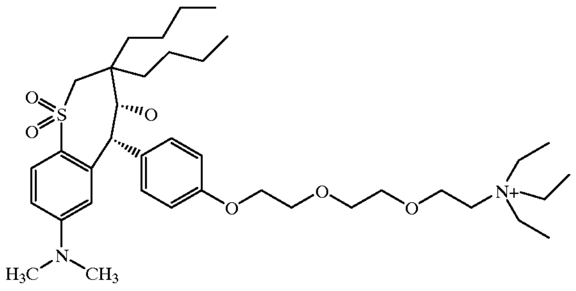

$C_{38}H_{43}N_2O_6SI$ fw = 802.90

Dissolve 1.0 gms (1.43 moles) of product 8 with 10 mls anhydrous acetonitrile. Place in a 3 ounce Fischer-Porter pressure reaction vessel with magnetic stir bar. Add 2.9 gms triethyl amine (28.6 mmoles Aldrich 23,962-3) dissolved in 10 mls anhydrous acetonitrile. Purge well with $N_2$ then close system Heat at 45° C. Monitor reaction by TLC. Reaction is usually complete in 48 hrs.

Perform cleanup by removing acetonitrile under vacuum. Redissolve with anhydrous chloroform and precipitate quaternary ammonium salt with ether. Repeat several times. Dry to obtain crystalline product. Obtain NMR and mass spec (m/z=675).

Example 1399

Step 1

Preparation of 1

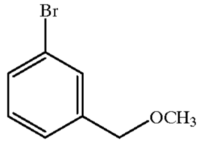

To a solution of 144 g of KOH (2560 mmol) in 1.1 L of DMSO was added 120 g of 2-bromobenzyl alcohol (641 mmol) slowly via addition funnel. Then was added 182 g of methyliodide (80 mL, 1282 mmol) via addition funnel. Stirred at ambient temperature for fifteen minutes. Poured reaction contents into 1.0 L of water and extracted three times with ethyl acetate. The organic layer was dried over $MgSO_4$ and concentrated in vacuo. Purified by silica-gel chromatography through a 200 mL plug using hexanes (100%) as elutant yielded. 103.2 g (80%) of 1 as a clear colorless liquid. $^1H$ NMR ($CDCl_3$) d 3.39 (s, 3H), 4.42 (s, 2H), 7.18–7.27 (m, 2H), 7.12 (d, J=7.45, 1H), 7.50 (s, 1H).

Step 2

Preparation of 2

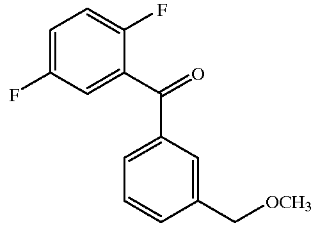

To a cooled (−78° C.) solution of 95 g (472 mmol) of 1 in 1.5 L THF was added 240 mL of 2.5 M n-butyl lithium (576 mmol). The mixture was stirred for one hour, and then to it was added 180 g of zinc iodide (566 mmol) dissolved in 500 ml THF. The mixture was stirred thirty minutes, allowed to warm to 5 C., cooled to −10° C. and to it was added 6 g of $Pd(PPh_3)_4$ (5.2 mmol) and 125 g 2,5-difluorobenzoyl chloride (708 mmol). The mixture was stirred at ambient temperature for 18 hoursand then cooled to 10° C., quenched with water, partitioned between ethyl acetate and water, and washed organic layer with 1N HCL and with 1N NaOH. The organic layer was dried over $MgSO_4$ and concentrated in vacuo. Purification by silica gel chromatography (Waters Prep-500) using 5% ethyl acetate/hexanes as elutant gave 53.6 g (43%) of 2 as an orange oil. $^1$H NMR ($CDCl_3$) d 3.40 (s, 3H), 4.51 (s, 2H), 7.12–7.26 (m,3H), 7.47 (t, J=7.50, 1H), 7.57 (d, J=7.45, 1H), 7.73 (d, J=7.45, 1H), 7.80 (s, 1H).

Step 3

Preparation of 3

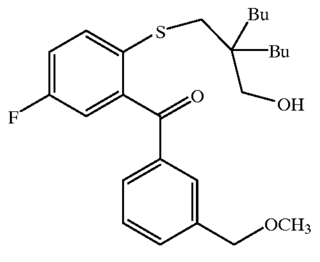

A solution of 53 g (202.3 mmol) of 2 and 11.2 g Li2S (242.8 mmol) in 250 mL DMF was heated to 100° C. for 18 hours. The reaction was cooled (0° C.) and 60.7 g of X (the cyclic sulfate compound of example 1397) (242.8 mmol) in 50 mL DMF was added. Stirred at ambient temperature for 18 hours then condensed in vacuo. Added 1 L water to organic residue and extracted twice with diethyl ether. Aqueous layer acidified (pH 1) and refluxed 2 days. Cooled to ambient temperature and extracted with methylene chloride, dried organic layer over $MgSO_4$ and condensed in vacuo. Purification by silica gel chromatography (Waters Prep-500) using 10% ethyl acetate/hexanes as elutant gave 42.9 g (48%) of 3 as a yellow oil. $^1$H NMR ($CDCl_3$) d 0.86 (t, J=7.25 Hz, 6H), 1.10–1.26 (m, 12H), 2.83 (s, 2H), 3.32 (s, 2H), 3.40 (s, 3H), 4.48 (s, 3H), 7.02 (dd, J=8.26 Hz and 2.82 Hz, 1H), 7.16 (dt, J=8.19 Hz and 2.82 Hz, 1H), 7.45 (t, J=7.65 Hz, 1H), 7.56–7.61 (m, 2H), 7.69 (d, J=7.85 Hz, 1H), 7.74 (s, 1H)

Step 4

Preparation of 4

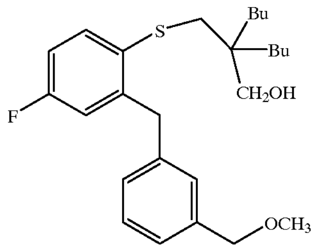

To a cooled (−40° C.) solution of 42.9 g (96.2 mmol) of 3 in 200 mL of methylene chloride was added 21.6 g trifluoromethane sulfonic acid (12.8 mL, 144 mmol) followed by the addition of 22.4 g triethyl silane (30.7 mL, 192.4 mmol). Stirred at −20° C. for two hours, quenched with water and warmed to ambient temperature. Partitioned between methylene chloride and water, dried the organic layer over $MgSO_4$ and condensed in vacuo. Purification by silica gel chromatography (Waters Prep-500) using 10% ethyl acetate/hexanes as elutant gave 24.2 g (60%)of 4 as a oil. $^1$H NMR ($CDCl_3$) d 0.89 (t, J=7.05 Hz, 6H), 1.17–1.40 (m, 12H), 1.46 (t, J=5.84 Hz, 1H), 2.81 (s, 2H), 3.38 (s, 3H), 3.43 (d, J=5.23 Hz, 2H), 4.16 (s, 2H), 4.42 (s, 2H), 6.80 (d, J=9.67 Hz, 1H), 6.90 (t, J=8.46 Hz, 1H), 7.09 (d, J=7.45 Hz, 1H), 7.15–7.21 (m, 2H), 7.25–7.32 (m, 2H), 7.42 (m, 1H).

Step 5

Preparation of 5

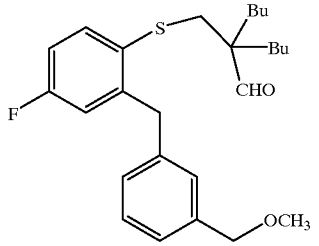

To a cooled (15–18° C.) solution of 24.2 g (55.8 mmol) of 4 in 100 mL DMSO was added 31.2 g sulfur trioxide pyridine complex (195 mmol). Stirred at ambient temperature for thirty minutes. Poured into cold water and extracted three times with ethyl acetate. Washed organics with 5% HCl (300 mL) and then with brine (300 mL), dired organics over $MgSO_4$ and condensed in vacuo to give 23.1 g (96%) of 5 as a light brown oil. $^1$H NMR ($CDCl_3$) d 0.87 (t, J=7.05 Hz, 6H), 1.01–1.32 (m, 8H), 1.53–1.65 (m, 4H), 2.98 (s, 2H), 3.38 (s, 3H), 4.15 (s, 2H), 4.43 (s, 2H), 6.81 (dd, J=9.66 Hz and 2.82 Hz, 1H), 6.91 (t, J=8.62 Hz, 1H), 7.07 (d, J=7.46 Hz, 1H), 7.14 (s, 1H), 7.19 (d, J=7.65 Hz, 1H), 7.26–7.32 (m, 1H), 7.42 (dd, J=8.66 Hz and 5.64 Hz, 1H), 9.40 (s, 1H).

Step 6

Preparation of 6

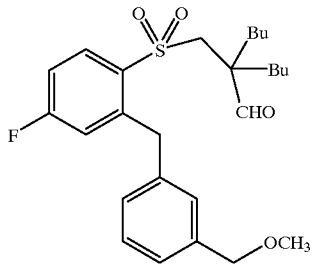

To a cooled (0° C.) solution of 23.1 g (53.6 mmol) of 5 in 200 mL methylene chloride was added 28.6 g meta cholorperoxy-benzoic acid (112.6 mmol). Stirred at ambient temperature for 24 hours. Quenched with 100 mL 10% $Na_2SO_3$, partitioned between water and methylene chloride. Dried organic layer over $MgSO_4$ and condensed in vacuo to give 24.5 g (98%) of 6 as a light yellow oil. $^1$H NMR ($CDCl_3$) d 0.86–1.29 (m, 14H), 1.58–1.63 (m, 2H), 1.82–1.91 (m, 2H), 3.13 (s, 2H), 3.39 (s, 3H), 4.44 (s, 2H), 4.50 (s, 2H), 6.93 (d, J=9.07 Hz, 1H), 7.10–7.33 (m, 5H), 8.05 (s, 1H), 9.38 (s, 1H).

Step 7

Preparartion of 7

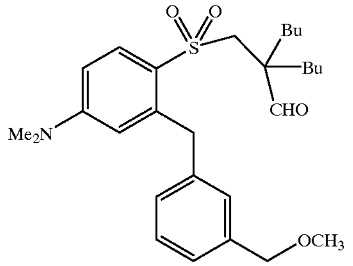

To a solution of 24.5 g (52.9 mmol) of 6 in 20 mL of THF contained in a stainless steel reaction vessel was added 100 mL of a 2.0 M solution of dimethyl amine and 20 mL of neat dimethyl amine. The vessel was sealed and heated to 110° C. for 16 hours. The reaction vessel was cooled to ambient temperature and the contents concentrated in vacuo. Purification by silica gel chromatography (Waters Prep-500) using 15% ethyl acetate/hexanes gave 21.8 g (84%) of 7 as a clear colorless oil. $^1$H NMR ($CDCl_3$) d 0.85 (t, J=7.25 Hz, 6H), 0.93–1.29 (m, 8H), 1.49–1.59 (m, 2H), 1.70–1.80 (m, 2H), 2.98 (s, 8H), 3.37 (s, 3H), 4.41 (s, 2H), 4.44 (s, 2H), 6.42 (s, 1H), 6.58 (dd, J=9.0 Hz and 2.61 Hz, 1H), 7.13 (d, J=7.45 Hz, 1H), 7.21 (s, 1H), 7.28 (t, J=7.85 Hz, 1H), 7.82 (d, J=9.06 Hz, 1H), 9.36 (s, 1H).

Step 8

Preparation of 8

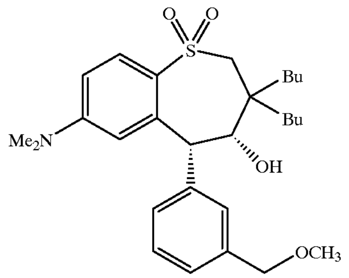

A solution of 21.8 g (44.8 mmol) of 7 in 600 mL of THF was cooled to 0° C. 58.2 mL of a 1 M solution of potassium t-butoxide was added slowly, maintaining the temperature at <5° C. Stirred for 30 minutes, then quenched with 50 mL of saturated ammonium chloride. The organic layer was partitioned between ethyl acetate and water, dried over MgSO4 and concentrated in vacuo. Purification by recrystalization from ~10% ethyl acetate/hexanes gave 15.1 g of 8 as a white solid. The mother liquor was purified by silica gel chromatography (Waters Prep-500) using 30% ethyl acetate/hexanes as the elutant to give 3.0 g of 8 as a white solid. MS (FABLi$^-$) m/e 494.6. HRMS (EI$^-$) calculated for M+H 487.2756. Found 487.2746.

Step 9
Preparation of 9

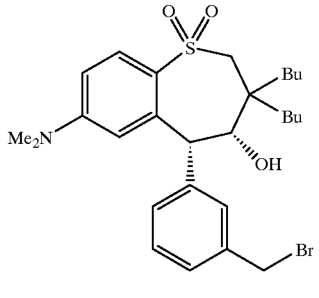

A solution of 2.0 g (4.1 mmol) of 8 in 20 mL of methylene chloride was cooled to −60° C. 4.1 mL of a 1M solution of boron tribromide was added. Stirred at ambient temperature for thirty minutes. Cooled reaction to ~10° C. and quenched with 50 mL of water. The organic layer was partitioned between methylene chloride and water, dried over $MgSO_4$ and concentrated in vacuo. Purification by recrystalization from 50% ethyl acetate/methylene chloride gave 1.95 g (89%) of 9 as a white solid. MS (FABH$^-$) m/e 537. HRMS (FAB) calculated for M 536.1834. Found 536.1822.

Step 10
Preparation of 10

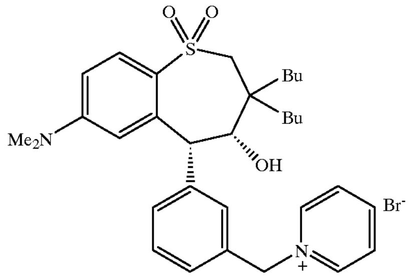

A solution of 1.09 g (2.0 mmol) of 9 and 4.9 g (62 mmol) of pyridine in 30 mL of acetonitrile was stirred at ambient temperature for 18 hours. The reaction was concentrated in vacuo. Purification by recrystallization from methanol/diethyl ether gave 1.19 g (96%) of 10 as an off white solid. MS (FAB$^-$) m/e 535.5.

Example 1398

Step 1
Preparation of 2

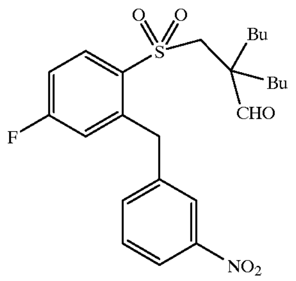

To a solution of 6.0 g of dibutyl 4-fluorobenzene dialdehyde of Example 1395 (14.3 mmol) in 72 mL of toluene and 54 mL of ethanol was added 4.7 g 3-nitrobenzeneboronic acid (28.6 mmol), 0.8 g of tetrakis (triphenylphosphine) palladium(0) (0.7 mmol) and 45 mL of a 2 M solution of sodium carbonate in water. This heterogeneous mixture was refluxed for three hours, then cooled to ambient temperature and partitioned between ethyl acetate and water. The organic layer was dried over $MgSO_4$ and concentrated in vacuo. Purification by silica gel chromatography (Waters Prep-2000) using ethyl acetate/hexanes (25/75) gave 4.8 g (73%) of the title compound as a yellow solid. $^1H$ NMR ($CDCl_3$) d 0.88 (t, J=7.45 Hz, 6H), 0.99–1.38 (m, 8H), 1.62–1.75 (m, 2H), 1.85–2.00 (m, 2H), 3.20 (s, 2H), 4.59 (s, 2H), 6.93 (dd, J=10.5 and 2.4 Hz, 1H), 7.15 (dt, J=8.4 and 2.85 Hz, 1H), 7.46–7.59 (m, 2H), 8.05–8.16 (m, 3H), 9.40 (s, 1H).

Step 3

Preparation of 3

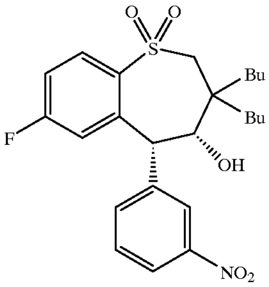

A solution of 4.8 g (10.4 mmol) of 2 in 500 mL THF was cooled to 0° C. in an ice bath. 20 mL of a 1 M solution of potassium t-butoxide was added slowly, maintaining the temperature at <5° C. Stirring was continued for 30 minutes, then the reaction was quenched with 100 mL of saturated ammonium chloride. The mixture was partitioned between ethyl acetate and water; the organic layer was washed with brine, then dried ($MgSO_4$) and concentrated in vacuo. Purification by silica gel chromatography through a 100 ml plug using $CH_2Cl_2$ as eluent yielded 4.3 g (90%) of 3 as a pale yellow foam. $^1H$ NMR ($CDCl_3$) d 0.93 (t, J=7.25 Hz, 6H), 1.00–1.55 (m, 8H), 1.59–1.74 (m, 3H), 2.15–2.95 (m, 1H), 3.16 ($q_{AB}$, $J_{AB}$=15.0 Hz, ΔV=33.2 Hz, 2H), 4.17 (d, J=6.0 Hz, 1H), 5.67 (s, 1H), 6.34 (dd, J=9.6 and 3.0 Hz, 1H), 7.08 (dt, J=8.5 and 2.9 Hz, 1H), 7.64 (t, J=8.1 Hz, 1H), 7.81 (d, J=8.7 Hz, 1H), 8.13 (dd, J=9.9 and 3.6 Hz, 1H), 8.23–8.30 (m, 1H), 8.44 (s, 1H). MS(FABH$^+$) m/e (relative intensity) 464.5 (100), 446.6 (65). HRMS calculated for M+H 464.1907. Found 464.1905.

Step 4

Preparation of 4

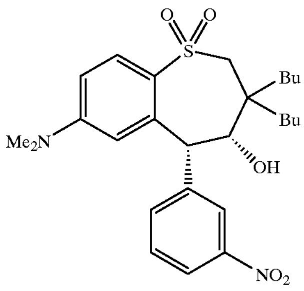

To a cooled (0° C.) solution of 4.3 g (9.3 mmol) of 3 in 30 ml THF contained in a stainless steel reaction vessel was added 8.2 g dimethyl amine (182 mmol). The vessel was sealed and heated to 110° C. for 16 hours. The reaction vessel was cooled to ambient temperature and the contents concentrated in vacuo. Purification by silica gel chromatography (Waters Prep-2000) using an ethyl acetate/hexanes gradient (10–40% ethyl acetate) gave 4.0 g (88%) of 4 as a yellow solid. $^1H$ NMR ($CDCl_3$) d 0.80–0.95 (m, 6H), 0.96–1.53 (m, 8H), 1.60–1.69 (m, 3H), 2.11–2.28 (m, 1H), 2.79 (s, 6H), 3.09 ($q_{AB}$, $J_{AB}$=15.0 Hz, DV=45.6 Hz, 2H), 4.90 (d, J=9.0 Hz, 1H), 5.65 (s, 1H), 5.75 (d, J=2.1 Hz, 1H), 6.52 (dd, J=9.6 and 2.7 Hz, 1H), 7.59 (t, J=8.4 Hz, 1H), 7.85 (d, J=7.80 Hz, 1H), 7.89 (d, J=9.0 Hz, 1H), 8.20 (dd, J=8.4 and 1.2 Hz, 1H), 8.43 (s, 1H). MS(FABH$^+$) m/e (relative intensity) 489.6 (100), 471.5 (25). HRMS calculated for M+H 489.2423. Found 489.2456.

Step 5

Preparation of 5

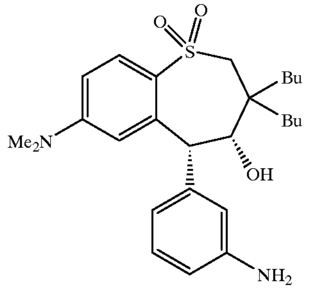

To a suspension of 1.0 g (2.1 mmol) of 4 in 100 ml ethanol in a stainless steel Parr reactor was added 1 g 10% palladium on carbon. The reaction vessel was sealed, purged twice with $H_2$, then charged with $H_2$ (100 psi) and heated to 45° C. for six hours. The reaction vessel was cooled to ambient temperature and the contents filtered to remove the catalyst. The filtrate was concentrated in vacuo to give 0.9 g (96%) of 5. $^1H$ NMR ($CDCl_3$) d 0.80–0.98 (m, 6H), 1.00–1.52 (m, 10H), 1.52–1.69 (m, 1H), 2.15–2.29 (m, 1H), 2.83 (s, 6H), 3.07 ($q_{AB}$, $J_{AB}$=15.1 Hz, DV=44.2 Hz, 2H), 3.70 (s, 2H), 4.14 (s, 1H), 5.43 (s, 1H), 6.09 (d, J=2.4 Hz, 1H), 6.52 (dd, J=12.2 and 2.6 Hz, 1H), 6.65 (dd, J=7.8 and 1.8 Hz, 1H), 6.83 (s, 1H), 6.93 (d, J=7.50 Hz, 1H), 7.19 (t, J=7.6 Hz, 1H), 7.89 (d, J=8.9 Hz, 1H). MS(FABH$^+$) m/e (relative intensity) 459.7 (100). HRMS calculated for M+H 459.2681. Found 459.2670.

Step 6

Preparation of 6

To a solution of 914 mg (2.0 mmol) of 5 in 50 ml THF was added 800 mg (4.0 mmol) 5-bromovaleroyl chloride. Next was added 4 g (39.6 mmol) TEA. The reaction was stirred 10 minutes, then partitioned between ethyl acetate and brine. The organic layer was dried ($MgSO_4$) and concentrated in vacuo. Purification by silica gel chromatography through a 70 ml MPLC column using a gradient of ethyl acetate (20–50%) in hexane as eluent yielded 0.9 g (73%) of 6 as a pale yellow oil. $^1H$ NMR ($CDCl_3$) d 0.84–0.95 (m, 6H), 1.02–1.53 (m, 10H), 1.53–1.68 (m, 1H), 1.80–2.00 (m, 4H), 2.12–2.26 (m, 4H), 2.38 (t, J=6.9 Hz, 2H), 2.80 (s, 6H), 3.07 ($q_{AB}$, $J_{AB}$=15.6 Hz, DV=40.4 Hz, 2H), 3.43 (t, J=6.9 Hz, 2H), 4.10 (s, 1H), 5.51 (s, 1H), 5.95 (d, J=2.4 Hz, 1H), 6.51 (dd, J=9.3 and 2.7 Hz, 1H), 7.28 (s, 1H), 7.32–7.41 (m, 2H), 7.78 (d, J=8.1 Hz, 1H), 7.90 (d, J=9.0 Hz, 1H).

Step 7
Preparation of 7

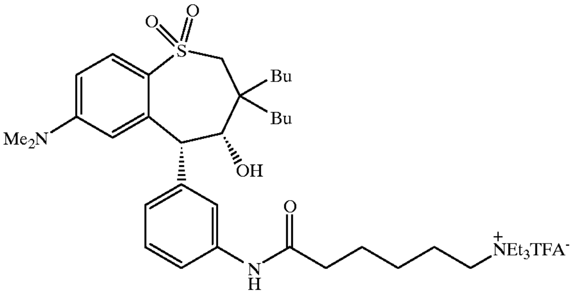

To a solution of 0.9 g (1.45 mmol) of 6 in 25 ml acetonitrile add 18 g (178 mmol) TEA. Heat at 55° C. for 16 hours. The reaction mixture was cooled to ambient temperature and concentrated in vacuo. Purification by reverse-phase silica gel chromatography (Waters Delta Prep 3000) using an acetonitrile/water gradient containing 0.05% TFA (20–65% acetonitrile) gave 0.8 g (73%) of 7 as a white foam. $^1$H NMR ($CDCl_3$) d 0.80–0.96 (m, 6H), 0.99–1.54 (m, 19H), 1.59–1.84 (m, 3H), 2.09–2.24 (m, 1H), 2.45–2.58 (m, 2H), 2.81 (s, 6H), 3.09 ($q_{AB}$, $J_{AB}$=15.6 Hz, DV=18.5 Hz, 2H), 3.13–3.31 (m, 8H), 4.16 (s, 1H), 5.44 (s, 1H), 6.08 (d, J=1.8 Hz, 1H), 6.57 (dd, J=9.3 and 2.7 Hz, 1H), 7.24 (t, J=7.5 Hz, 1H), 7.34 (t, J=8.4 Hz, 1H), 7.56 (d, J=8.4 Hz, 1H), 7.74 (s, 1H), 7.88 (d, J=9.0 Hz, 1H), 9.22 (s, 1H). HRMS calcd 642.4304; observed 10 642.4343.

Example 1400

Step 1

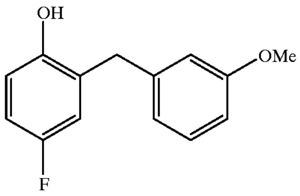

$C_{14}H_{13}O_2F$ fw = 232.25

A 12-liter, 4-neck round-bottom flask was equipped with reflux condenser, $N_2$ gas adaptor, mechanical stirrer, and an addition funnel. The system was purged with $N_2$.

A slurry of sodium hydride (126.0 g/4.988 mol) in toluene (2.5 L) was added, and the mixture was cooled to 6 C. A solution of 4-fluorophenol (560.5 g/5.000 mol) in toluene (2.5 L) was added via addition funnel over a period of 2.5 h. The reaction mixture was heated to reflux (100 C.) for 1h. A solution of 3-methoxybenzyl chloride (783.0 g/5.000 mol) in toluene (750 mL) was added via addition funnel while maintaining reflux. After 15 h. refluxing, the mixture was cooled to room temperature and poured into $H_2O$ (2.5 L). After 20 min. stirring, the layers were separated, and the organic layer was extracted with a solution of potassium hydroxide (720 g) in MeOH (2.5 L). The MeOH layer was added to 20% aqueous potassium hydroxide, and the mixture was stirred for 30 min. The mixture was then washed 5 times with toluene. The toluene washes were extracted with 20% aq. KOH. All 20% ag. KOH solutions were combined and acidified with concentrated HCl. The acidic solution was extracted three times with ethyl ether, dried ($MgSO_4$), filtered and concentrated in vacuo. The crude product was purified by Kugelrohr distillation to give a clear, colorless oil (449.0 g/39% yield). b.p.: 120–130 C./50mtorrHg. $^1$H NMR and MS $[(M+H)^+=233]$ confirmed desired structure.

Step 2

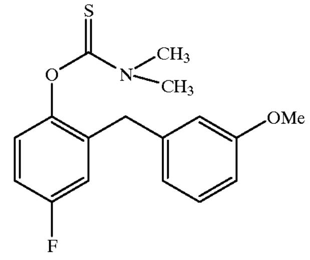

$C_{17}H_{18}NO_2FS$ fw = 319.39

A 12-liter, 3-neck round-bottom flask was fitted with mechanical stirrer and $N_2$ gas adaptor. The system was purged with $N_2$. 4-Fluoro-2-(3-methoxybenzyl)-phenol (455.5 g/1.961 mol) and dimethylformamide were added. The solution was cooled to 6 C., and sodium hydride (55.5 g/2.197 mol) was added slowly. After warming to room temperature, dimethylthiocarbamoyl chloride (242.4 g/1.961 mol) was added. After 15 h, the reaction mixture was poured into $H_2O$ (4.0 L), and extracted two times with ethyl ether. The combined organic layers were washed with $H_2O$ and saturated aqueous NaCl, dried ($MgSO_4$), filtered, and concentrated in vacuo to give the product (605.3 g, 97% yield). $^1$H NMR and MS $[(M+H)^+=320]$ confirm desired structure.

Step 3

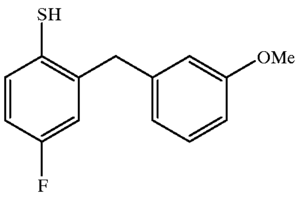

$C_{14}H_{13}OFS$ fw = 248.32

A 12-liter, round-bottom flask was equipped with $N_2$ gas adaptor, mechanical stirrer, and reflux condenser. The system was purged with $N_2$. 4-Fluoro-2-(3-methoxybenzyl)-phenyldimethylthiocarbamate (605.3 g/1.895 mol) and phenyl ether (2.0 kg) were added, and the solution was heated to reflux for 2 h. The mixture was stirred for 64 h. at room temparature and then heated to reflux for 2 h. After cooling to room temperature, MeOH (2.0 L) and THF (2.0 L) were added, and the solution was stirred for 15 h. Potassium hydroxide (425.9 g/7.590 mol) was added, and the mixture was heated to reflux for 4 h. After cooling to room temparature, the mixture was concentrated by rotavap, dissolved in ethyl ether (1.0 L), and extracted with $H_2O$. The aqueous extracts were combined, acidified with concentrated HCl, and extracted with ethyl ether. The ether extracts were dried ($MgSO_4$), filtered, and concentrated in vacuo to give an amber oil (463.0 g, 98% yield). $^1$H NMR confirmed desired structure.

Step 4

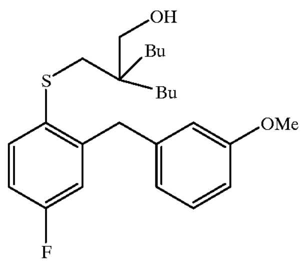

$C_{25}H_{35}O_2FS$ fw = 418.61

A 5-liter, 3-neck, round-bottom flask was equipped with $N_2$ gas adaptor and mechanical stirrer. The system was purged with $N_2$. 4-Fluoro-2-(3-methoxybenzyl)- thiophenol (100.0 g/403.2 mmol) and 2-methoxyethyl ether (1.0 L) were added and the solution was cooled to 0 C. Sodium hydride (9.68 g/383.2 mmol) was added slowly, and the mixture was allowed to warm to room temparature, 2,2-Dibutylpropylene sulfate (110.89 g/443.6 mmol) was added, and the mixture was stirred for 64 h. The reaction mixture was concentrated by rotavap and dissolved in $H_2O$. The aqueous solution was washed with ethyl ether, and concentrated $H_2SO_4$ was added. The aqueous solution was heated to reflux for 30 min, cooled to room temperature, and extracted with ethyl ether. The ether solution was dried ($MgSO_4$), filtered, and conc'd in vacuo to give an amber oil (143.94 g/85% yield). $^1H$ NMR and MS $[(M+H)^+=419]$ confirm the desired structure.

Step 5

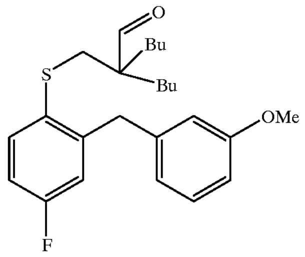

$C_{25}H_{33}O_2FS$ fw = 416.59

A 2-liter, 4-neck, round-bottom flask was equipped with $N_2$ gas adaptor, and mechanical stirrer. The system was purged with $N_2$. The corresponding alcohol (143.94 g/343.8 mmol) and $CH_2Cl_2$ (1.0 L) were added and cooled to 0° C. Pyridinium chlorochromate (140.53 g/651.6 mmol) was added. After 6 h., $CH_2Cl_2$ was added. After 20 min, the mixture was filtered through silica gel, washing with $CH_2Cl_2$. The filtrate was concentrated in vacuo to give a dark yellow-red oil (110.6 g, 77% yield). $^1H$ NMR and MS $[(M+H)^+=417]$ confirm the desired structure.

Step 6

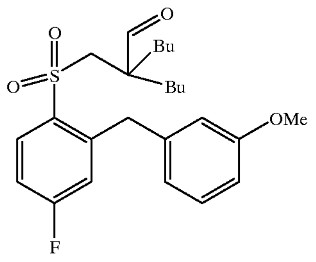

$C_{25}H_{33}O_4FS$ fw = 448.59

A 2-liter, 4-neck, round-bottom flask was equipped with $N_2$ gas adaptor and mechanical stirrer. The system was purged with $N_2$. The corresponding sulfide (110.6 g/265.5 mmol) and $CH_2Cl_2$ (1.0 L) were added. The solution was cooled to 0° C., and 3-chloroperbenzoic acid (158.21 g/531.7 mmol) was added portionwise. After 30 min, the reaction mixture was allowed to warm to room temperature After 3.5 h, the reaction mixture was cooled to 0° C. and filtered through a fine fritted funnel. The filtrate was washed with 10% aqueous $K_2CO_3$. An emulsion formed which was extracted with ethyl ether. The organic layers were combined, dried ($MgSO_4$), filtered, and concentrated in vacuo to give the product (93.2 g, 78% yield). $^1H$ NMR confirmed the desired structure.

Step 7

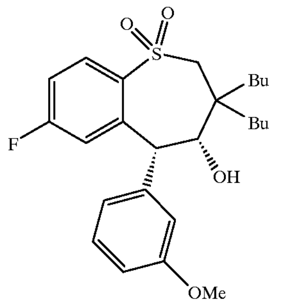

$C_{25}H_{33}O_4FS$ fw = 448.59

A 2-liter, 4-neck, round-bottom flask was equipped with $N_2$ gas adaptor, mechanical stirrer, and a powder addition funnel. The system was purged with $N_2$. The corresponding aldehyde (93.2 g/208 mmol) and THF (1.0 L) were added, and the mixture was cooled to 0° C. Potassium tert-butoxide (23.35 g/208.1 mmol) was added via addition funnel. After 1h, 10% aq/HCl (1.0 L) was added. After 1 h, the mixture was extracted three times with ethyl ether, dried ($MgSO_4$), filtered, and concentrated in vacuo. The crude product was purified by recryst. from 80/20 hexane/ethyl acetate to give a white solid (32.18 g). The mother liquor was concentrated in vacuo and recrystelized from 95/5 toluene/ethyl acetate to give a white solid (33.60 g/combined yield: 71%). $^1H$ NMR confirmed the desired product.

Step 8

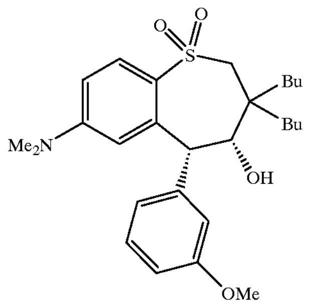

$C_{27}H_{39}O_4NS$ fw = 473.67

A Fisher porter bottle was fitted with $N_2$ line and magnetic stirrer. The system was purged with $N_2$. The corresponding fluoro-compound (28.1 g/62.6 mmol) was added, and the vessel was sealed and cooled to −78 C. Dimethylamine (17.1 g/379 mmol) was condensed via a $CO_2$/acetone bath and added to the reaction vessel. The mixture was allowed to warm to room temperature and was heated to 60° C. After 20 h, the reaction mixture was allowed to cool and was dissolved in ethyl ether. The ether solution was washed with $H_2O$, saturated aqueous NaCl, dried ($MgSO_4$), filtered, and concentrated in vacuo to give a white solid (28.5 g/96% yield). $^1$H NMR confirmed the desired structure.

Step 9

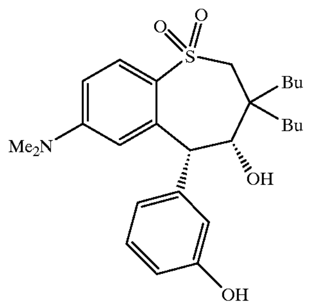

$C_{26}H_{37}O_4NS$ fw = 459.64

A 250-mL, 3-neck, round-bottom flask was equipped with $N_2$ gas adaptor and magnetic stirrer. The system was purged with $N_2$. The corresponding methoxy-compound (6.62 g/14.0 mmol) and $CHCl_3$ (150 mL) were added. The reaction mixture was cooled to −78 C., and boron tribromide (10.50 g/41.9 mmol) was added. The mixture was allowed to warm to room temperature After 4 h, the reaction mixture was cooled to 0° C. and was quenched with 10% $K_2CO_3$ (100 mL). After 10 min, the layers were separated, and the aqueous layer was extracted two times with ethyl ether. The $CHCl_3$ and ether extracts were combined, washed with saturated aqueous NaCl, dried ($MgSO_4$), filtered, and concentrated in vacuo to give the product (6.27 g/98% yield). $^1$H NMR confirmed the desired structure.

Step 10

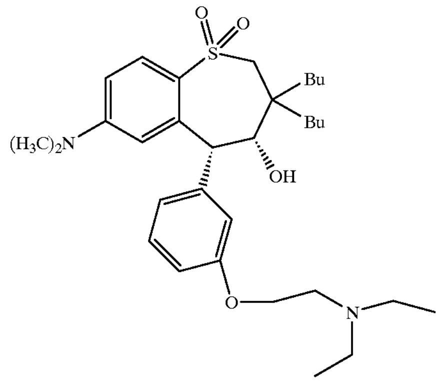

In a 250 ml single neck round bottom Flask with stir bar place 2-diethylamineoethyl chloride hydochloride (fw 172.10 g/mole) Aldrich D8, 720-1 (2.4 mmol,4.12 g), 34 ml dry ether and 34 ml of 1N KOH(aqueous). Stir 15 minutes and then separate by ether extraction and dry over anhydrous potassium carbonate.

In a separate 2-necked 250 ml round bottom flask with stir bar add sodium hydride (60% dispersion in mineral oil, 100 mg , 2.6 mmol) and 34 ml of DMF. Cool to ice temperature. Next add phenol product(previous step) 1.1 g (2.4 mmilomoles in 5 ml DMF and the ether solution prepared above. Heat to 40 C. for 3 days. The product which contained no starting material by TLC was diluted with ether and extracted with 1 portion of 5% NaOH, followed by water and then brine. The ether layer was dried over magnesium sulfate and isolated by removing ether by rotary evaporation (1.3 gms). The product may be further purified by chromatography (SiO2 99% ethyl acetate/1% NH4OH at 5 ml/min.). Isolated yield: 0.78 g (mass spec , and H1 NMR)

step 11

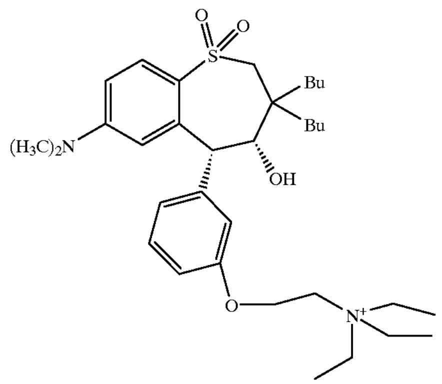

The product from step 10 (0.57 gms, 1.02 millimole fw 558.83 g/mole) and 1.6 gms iodoethane (10.02 mmol) was placed in 5 ml acetonitrile in a fischer-porter bottle and heated to 45 C. for 3 days. The solution was evaporated to dryness and redissolved in 5 mls of chloroform. Next ether was added to the chloroform solution and the resulting mixture was chilled. The desired product is isolated as a precipitate 0.7272 gms. Mass spec M-I=587.9, H NMR).

Example 1401

Step 1

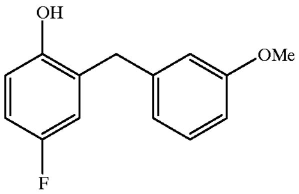

$C_{14}H_{13}O_2F$ fw = 232.25

A 12-liter, 4-neck round-bottom flask was equipped with reflux condenser, $N_2$ gas adaptor, mechanical stirrer, and an addition funnel. The system was purged with $N_2$. A slurry of sodium hydride (126.0 g/4.988 mol) in toluene (2.5 L) was added, and the mixture was cooled to 6 C. A solution of 4-fluorophenol (560.5 g/5.000 mol) in toluene (2.5 L) was added via addition funnel over a period of 2.5 h. The reaction mixture was heated to reflux (100 C.) for 1 h. A solution of 3-methoxybenzyl chloride (783.0 g/5.000 mol) in toluene (750 mL) was added via addition funnel while maintaining reflux. After 15 h. refluxing, the mixture was cooled to room temperature and poured into $H_2O$ (2.5 L). After 20 min. stirring, the layers were separated, and the organic layer was extracted with a solution of potassium hydroxide (720 g) in MeOH (2.5 L). The MeOH layer was added to 20% aqueous potassium hydroxide, and the mixture was stirred for 30 min. The mixture was then washed 5 times with toluene. The toluene washes were extracted with 20% aq. KOH. All 20% aqueous KOH solutions were combined and acidified with concentrated HCl. The acidic solution was extracted three times with ethyl ether, dried over $MgSO_4$, filtered and concentrated in vacuo. The crude product was purified by Kugelrohr distillation to give a clear, colorless oil (449.0 g/39% yield). b.p.: 120–130 C./50mtorrHg. $^1H$ NMR and MS $[(M+H)^+=2331]$ confirmed desired structure.

Step 2

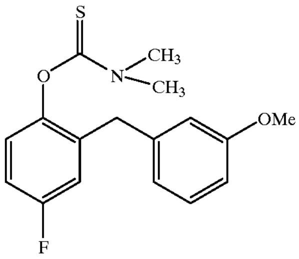

$C_{17}H_{18}NO_2FS$ fw = 319.39

A 12-liter, 3-neck round-bottom flask was fitted with mechanical stirrer and $N_2$ gas adaptor. The system was purged with $N_2$. 4-Fluoro-2-(3-methoxybenzyl)-phenol (455.5 g/1.961 mol) and dimethylformamide were added. The solution was cooled to 6 C., and sodium hydride (55.5 g/2.197 mol) was added slowly. After warming to room temperature, dimethylthiocarbamoyl chloride (242.4 g/1.961 mol) was added. After 15 h, the reaction mixture was poured into $H_2O$ (4.0 L), and extracted two times with ethyl ether. The combined organic layers were washed with $H_2O$ and saturated aqueous NaCl, dried over $MgSO_4$, filtered, and concentrated in vacuo to give the product (605.3 g, 97% yield). $^1H$ NMR and MS $[(M+H)^+=320]$ Confirm desired structure.

Step 3

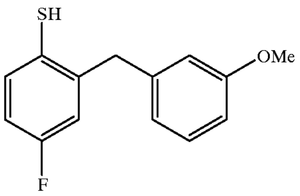

$C_{14}H_{13}OFS$ fw = 248.32

A 12-liter, round-bottom flask was equipped with $N_2$ gas adaptor, mechanical stirrer, and reflux condenser. The system was purged with $N_2$. 4-Fluoro-2-(3-methoxybenzyl)-phenyldimethylthiocarbamate (605.3 g/1.895 mol) and phenyl ether (2.0 kg) were added, and the solution was heated to reflux for 2 h. The mixture was stirred for 64 h. at room temperature and then heated to reflux for 2 h. After cooling to room temperature, MeOH (2.0 L) and THF (2.0 L) were added, and the solution was stirred for 15 h. Potassium hydroxide (425.9 g/7.590 mol) was added, and the mixture was heated to reflux for 4 h. After cooling to room temperature, the mixture was concentrated by rotavap, dissolved in ethyl ether (1.0 L), and extracted with $H_2O$. The aqueous extracts were combined, acidified with conc. HCl, and extracted with ethyl ether. The ether extracts were dried ($MgSO_4$), filtered, and concentrated in vacuo to give an amber oil (463.0 g, 98% yield). $^1H$ NDR confirmed desired structure.

Step 4

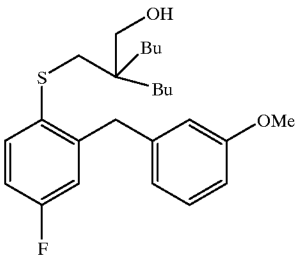

$C_{25}H_{35}O_2FS$ fw = 418.61

A 5-liter, 3-neck, round-bottom flask was equipped with $N_2$ gas adaptor and mechanical stirrer. The system was purged with $N_2$. 4-Fluoro-2-(3-methoxybenzyl)-thiophenol (100 .0 g/403.2 mmol) and 2-methoxyethyl ether (1.0 L) were added and the solution was cooled to 0° C. Sodium hydride (9.68 g/383.2 mmol) was added slowly, and the mixture was allowed to warm to room temperature 2,2-Dibutylpropylene sulfate (110.89 g/443.6 mmol) was added, and the mixture was stirred for 64 h. The reaction mixture was concentrated by rotavap and dissolved in $H_2O$. The aqueous solution was washed with ethyl ether, and conc. $H_2SO_4$ was added. The aqueous solution was heated to reflux for 30 min, cooled to room temperature, and extracted with ethyl ether. The ether solution was dried (MgSO4), filtered, and concentrated in vacuo to give an amber oil (143.94 g/85% yield). $^1H$ NMR and MS $[(M+H)^+=419]$ confirm the desired structure.

Step 5

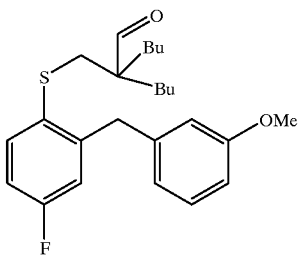

$C_{25}H_{33}O_2FS$ fw=416.59

A 2-liter, 4-neck, round-bottom flask was equipped with $N_2$ gas adaptor, and mechanical stirrer. The system was purged with $N_2$. The corresponding alcohol (143.94 g/343.8 mmol) and $CH_2Cl_2$ (1.0 L) were added and cooled to 0° C. Pyridinium chlorochromate (140.53 g/1651.6 mmol) was added. After 6 h., $CH_2Cl_2$ was added. After 20 min, the mixture was filtered through silica gel, washing with $CH_2Cl_2$. The filtrate was concentrated in vacuo to give a dark yellow-red oil (110.6 g, 77% yield). $^1H$ NMR and MS $[(M+H)^+=417]$ confirm the desired structure.

Step 6

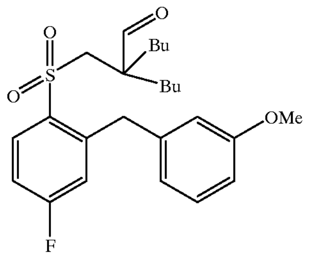

$C_{25}H_{33}O_4FS$ fw=448.59

A 2-liter, 4-neck, round-bottom flask was equipped with $N_2$ gas adaptor and mechanical stirrer. The system was purged with $N_2$. The corresponding sulfide (110.6 g/265.5 mmol) and $CH_2Cl_2$ (1.0 L) were added. The solution was cooled to 0 C., and 3-chloroperbenzoic acid (158.21 g/531.7 mmol) was added portionwise. After 30 min, the reaction mixture was allowed to warm to room temperature After 3.5 h, the reaction mixture was cooled to 0 C. and filtered through a fine fritted funnel. The filtrate was washed with 10% aqueous $K_2CO_3$. An emulsion formed which was extracted with ethyl ether. The organic layers were combined, dried ($MgSO_4$), filtered, and concentrated in vacuo to give the product (93.2 g, 78% yield). $^1H$ NMR confirmed the desired structure.

Step 7

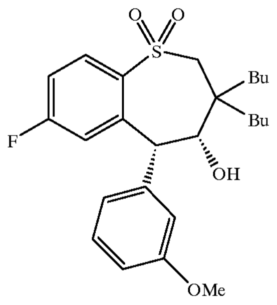

$C_{25}H_{33}O_4FS$ fw=448.59

A 2-liter, 4-neck, round-bottom flask was equipped with $N_2$ gas adaptor, mechanical stirrer, and a powder addition funnel. The system was purged with $N_2$. The corresponding aldehyde (93.2 g/208 mmol) and THF (1.0 L) were added, and the mixture was cooled to 0° C. Potassium tert-butoxide (23.35 g/208.1 mmol) was added via addition funnel. After 1 h, 10% aq/HCl (1.0 L) was added. After 1 h, the mixture was extracted three times with ethyl ether, dried ($MgSO_4$), filtered, and concentrated in vacuo. The crude product was purified by recrystallized from 80/20 hexane/ethyl acetate to give a white solid (32.18 g). The mother liquor was concentrated in vacuo and recrystallized from 95/5 toluene/ethyl acetate to give a white solid (33.60 g, combined yield: 71%). $^1H$ NMR confirmed the desired product.

Step 8

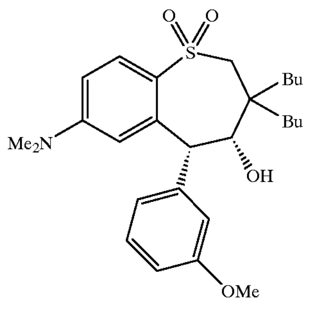

$C_{27}H_{39}O_4NS$ fw=473.67

A Fisher porter bottle was fitted with $N_2$ line and magnetic stirrer. The system was purged with $N_2$. The corresponding fluoro-compound (28.1 g/62.6 mmol) was added, and the vessel was sealed and cooled to −78 C. Dimethylamine (17.1 g/379 mmol) was condensed via a $CO_2$/acetone bath and added to the reaction vessel. The mixture was allowed to warm to room temperature and was heated to 60 C. After 20 h, the reaction mixture was allowed to cool and was dissolved in ethyl ether. The ether solution was washed with $H_2O$, saturated aqueous NaCl, dried over $MgSO_4$, filtered, and concentrated in vacuo to give a white solid (28.5 g/96% yield). $^1H$ NMR confirmed the desired structure.

Step 9

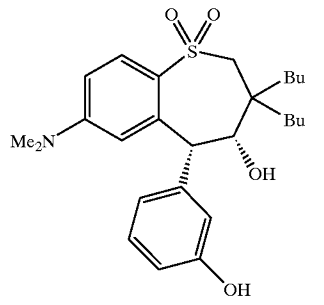

$C_{26}H_{37}O_4NS$ fw=459.64

A 250-mL, 3-neck, round-bottom flask was equipped with $N_2$ gas adaptor and magnetic stirrer. The system was purged with $N_2$. The corresponding methoxy-compound (6.62 g/14.0 mmol) and $CHCl_3$ (150 mL) were added. The reaction mixture was cooled to −78 C., and boron tribromide (10.50 g/41.9 mmol) was added. The mixture was allowed to warm to room temperature After 4 h, the reaction mixture was cooled to 0 C. and was quenched with 10% $K_2CO_3$ (100 mL). After 10 min, the layers were separated, and the aqueous layer was extracted two times with ethyl ether. The $CHCl_3$ and ether extracts were combined, washed with saturated aqueous NaCl, dried over $MgSO_4$, filtered, and concentrated in vacuo to give the product (6.27 g/98% yield). $^1$H NMR confirmed the desired structure.

Step 10

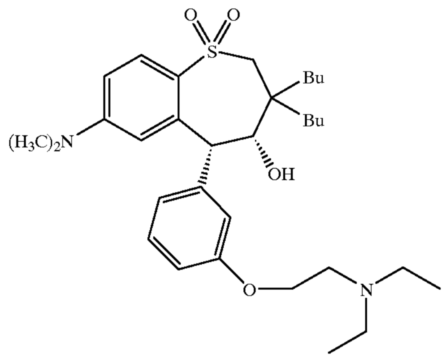

In a 250 ml single neck round bottom flask with stir bar place 2-diethylamineoethyl chloride hydochloride (fw 172.10 g/mole) Aldrich D8, 720-1 (2.4 millimoles, 4.12 g), 34 ml dry ether and 34 ml of 1N KOH (aqueous). Stir 15 minutes and then separate by ether extraction and dry over anhydrous potassium carbonate.

In a separate 2-necked 250 ml round bottom flask with stir bar add sodium hydride (60% dispersion in mineral oil, 100 mg, (2.6 mmol) and 34 ml of DMF. Cool to ice temperature. Next add phenol product (previous step) 1.1 g (2.4 mmol in 5 ml DMF and the ether solution prepared above. Heat to 40 C. for 3 days. The product which contained no starting material by TLC was diluted with ether and extracted with 1 portion of 5% NaOH, followed by water and then brine. The ether layer was dried over Magnesium sulfate and isolated by removing ether by rotary evaporation (1.3 gms). The product may be further purified by chromatography (silica 99% ethyl acetate/1% NH4OH at 5 ml/min.). Isolated yield: 0.78 g (mass spec , and H1 NMR)

Step 11

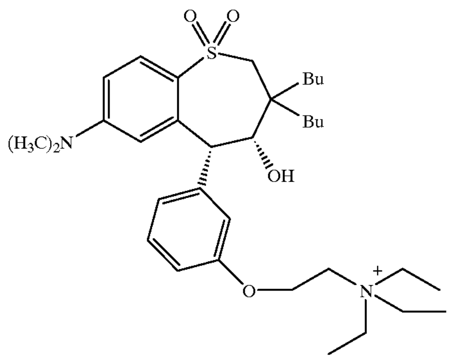

The product from step 10 (0.57 gms, 1.02 millimole fw 558.83 g/mole) and iodoethane (1.6 gms (10.02 mmol) was place in 5 ml acetonitrile in a Fischer-Porter bottle and heated to 45 C. for 3 days. The solution was evaporated to dryness and redissolved in 5 mls of chloroform. Next ether was added to the chloroform solution and the resulting mixture was chilled. The desired product is isolated as a precipitate 0.7272 gms. Mass spec M−I=587.9, $^1$H NMR)

BIOLOGICAL ASSAYS

The utility of the compounds of the present invention is shown by the following assays. These assays are performed in vitro and in animal models essentially using a procedure recognized to show the utility of the present invention.

In Vitro Assay of Compounds That Inhibit IBAT-mediated Uptake of [$^{14}$C]-Taurocholate (TC) in H14 Cells Baby hamster kidney cells (BHK) transfected with the cDNA of human IBAT (H14 cells) are seeded at 60,000 cells/well in 96 well Top-Count tissue culture plates for assays run within in 24 hours of seeding, 30,000 cells/well for assays run within 48 hours, and 10,000 cells/well for assays run within 72 hours.

On the day of assay, the cell monolayer is gently washed once with 100 ml assay buffer (Dulbecco's Modified Eagle's medium with 4.5 g/L glucose+0.2% (w/v) fatty acid free bovine serum albumin—(FAF)BSA). To each well 50 ml of a two-fold concentrate of test compound in assay buffer is added along with 50 ml of 6 mM [$^{14}$C]-taurocholate in assay buffer (final concentration of 3 mM [$^{14}$C]-taurocholate). The cell culture plates are incubated 2 hours at 37° C. prior to gently washing each well twice with 100 ml 4° C. Dulbecco's phosphate-buffered saline (PBS) containing 0.2% (w/v) (FAF)BSA. The wells are then gently washed once with 100 ml 4° C. PBS without (FAF)BSA. To each 200 ml of liquid scintillation counting fluid is added, the plates are heat sealed and shaken for 30 minutes at room temperature prior to measuring the amount of radioactivity in each well on a Packard Top-Count instrument.

In Vitro Assay of Compounds That Inhibit Uptake of [$^{14}$C]-Alanine

The alanine uptake assay is performed in an identical fashion to the taurocholate assay, with the exception that labeled alanine is substituted for the labeled taurocholate.

In Vivo Assay of Compounds That Inhibit Rat Ileal Uptake of [$^{14}$C]-Taurocholate into Bile (See "Metabolism of 3a,7b-dihydroxy-7a-methyl-5b-cholanoic acid and 3a,7b-dihydroxy-7a-methyl-5b-cholanoic acid in hamsters" in Biochimica et Biophysica Acta 833 (1985) 196–202 by Une et al.)

Male wistar rats (200–300 g) are anesthetized with inactin @100 mg/kg. Bile ducts are cannulated with a 10" length of PE10 tubing. The small intestine is exposed and laid out on a gauze pad. A canulae (⅛ luer lock, tapered female adapter) is inserted at 12 cm from the junction of the small intestine and the cecum. A slit is cut at 4 cm from this same junction (utilizing a 8 cm length of ileum). 20 ml of warm Dulbecco's phosphate buffered saline, pH 6.5 (PBS) is used to flush out the intestine segment. The distal opening is cannulated with a 20 cm length of silicone tubing (0.02" I.D.×0.037" O.D.). The proximal cannulae is hooked up to a peristaltic pump and the intestine is washed for 20 min with warm PBS at 0.25 ml/min. Temperature of the gut segment is monitored continuously. At the start of the experiment, 2.0 ml of control sample ([$^{14}$C]-taurocholate @ 0.05 mi/ml with 5 mM cold taurocholate) is loaded into the gut segment with a 3 ml syringe and bile sample collection is begun. Control sample is infused at a rate of 0.25 ml/min for 21 min. Bile samples fractions are collected every 3 minute for the first 27 minutes of the procedure. After the 21 min of sample infusion, the ileal loop is washed out with 20 ml of warm PBS (using a 30 ml syringe), and then the loop is washed out for 21 min with warm PBS at 0.25 ml/min. A second perfusion is initiated as described above but this with test compound being administered as well (21 min administration followed by 21 min of wash out) and bile sampled every 3 min for the first 27 min. If necessary, a third perfusion is performed as above that typically contains the control sample.

Measurement of Hepatic Cholesterol Concentration (HEPATIC CHOL)

Liver tissue was weighed and homogenized in chloroform:methanol (2:1). After homogenization and centrifugation the supernatant was separated and dried under nitrogen. The residue was dissolved in isopropanol and the cholesterol content was measured enzymatically, using a combination of cholesterol oxidase and peroxidase, as described by Allain, C. A., et al. (1974) *Clin. Chem.* 20, 470.

Measurement of Hepatic HMG CoA-Reductase Activity (HMG COA)

Hepatic microsomes were prepared by homogenizing liver samples in a phosphate/sucrose buffer, followed by centrifugal separation. The final pelleted material was resuspended in buffer and an aliquot was assayed for HMG CoA reductase activity by incubating for 60 minutes at 37° C. in the presence of $^{14}$C-HMG-CoA (Dupont-NEN). The reaction was stopped by adding 6N HCl followed by centrifugation. An aliquot of the supernatant was separated, by thin-layer chromatography, and the spot corresponding to the enzyme product was scraped off the plate, extracted and radioactivity was determined by scintillation counting. (Reference: Akerlund, J. and Bjorkhem, I. (1990) *J. Lipid Res.* 31, 2159).

Determination of Serum Cholesterol (SER.CHOL, HDL-CHOL, TGI and VLDL+LDL)

Total serum cholesterol (SER.CHOL) was measured enzymatically using a commercial kit from Wako Fine Chemicals (Richmond, Va.); Cholesterol C11, Catalog No. 276-64909. HDL cholesterol (HDL-CHOL) was assayed using this same kit after precipitation of VLDL and LDL with Sigma Chemical Co. HDL Cholesterol reagent, Catalog No. 352-3 (dextran sulfate method). Total serum triglycerides (blanked) (TGI) were assayed enzymatically with Sigma Chemical Co. GPO-Trinder, Catalog No. 337-B. VLDL and LDL (VLDL+LDL) cholesterol concentrations were calculated as the difference between total and HDL cholesterol.

Measurement of Hepatic Cholesterol 7-a-Hydroxylase Activity (7a-OHase)

Hepatic microsomes were prepared by homogenizing liver samples in a phosphate/sucrose buffer, followed by centrifugal separation. The final pelleted material was resuspended in buffer and an aliquot was assayed for cholesterol 7-a-hydroxylase activity by incubating for 5 minutes at 37° C. in the presence of NADPH. Following extraction into petroleum ether, the organic solvent was evaporated and the residue was dissolved in acetonitrile/methanol. The enzymatic product was separated by injecting an aliquot of the extract onto a $C_{18}$ reversed phase HPLC column and quantitating the eluted material using UV detection at 240 nm. (Reference: Horton, J. D., et al. (1994) *J. Clin. Invest.* 93, 2084).

Measurement of Fecal Bile Acid Concentration (FBA)

Total fecal output from individually housed hamsters was collected for 24 or 48 hours, dried under a stream of nitrogen, pulverized and weighed. Approximately 0.1 gram was weighed out and extracted into an organic solvent (butanol/water). Following separation and drying, the residue was dissolved in methanol and the amount of bile acid present was measured enzymatically using the 3a-hydroxysteroid steroid dehydrogenase reaction with bile acids to reduce NAD. (Reference: Mashige, F., et al. (1981) *Clin. Chem.* 27, 1352).

[$^{3}$H]taurocholate Uptake in Rabbit Brush Border Membrane Vesicles (BBMV)

Rabbit ileal brush border membranes were prepared from frozen ileal mucosa by the calcium precipitation method describe by Malathi et al. (Reference: (1979) *Biochimica Biophysica Acta,* 554, 259). The method for measuring taurocholate was essentially as described by Kramer et al. (Reference: (1992) *Biochimica Biophysica Acta,* 1111, 93) except the assay volume was 200 μl instead of 100 μl. Briefly, at room temperature a 190 μl solution containing 2 μM [$^{3}$H]-taurocholate(0.75 μCi), 20 mM tris, 100 mM NaCl, 100 mM mannitol pH 7.4 was incubated for 5 sec with 10 μl of brush border membrane vesicles (60–120 μg protein). The incubation was initiated by the addition of the BBMV while vortexing and the reaction was stopped by the addition of 5 ml of ice cold buffer (20 mm Hepes-tris, 150 mM KCl) followed immediately by filtration through a nylon filter (0.2 μm pore) and an additional 5 ml wash with stop buffer.

Acyl-CoA; Cholesterol Acyl Transferase (ACAT)

Hamster liver and rat intestinal microsomes were prepared from tissue as described previously (Reference: (1980) *J. Biol. Chem.* 255, 9098) and used as a source of ACAT enzyme. The assay consisted of a 2.0 ml incubation containing 24 μM Oleoyl-CoA (0.05 μCi) in a 50 mM sodium phosphate, 2 mM DTT ph 7.4 buffer containing 0.25% BSA and 200 μg of microsomal protein. The assay was initiated by the addition of oleoyl-CoA. The reaction went for 5 min at 37° C. and was terminated by the addition of 8.0 ml of chloroform/methanol (2:1). To the extraction was added 125 μg of cholesterol oleate in chloroform methanol to act as a carrier and the organic and aqueous phases of the extraction were separated by centrifugation after thorough vortexing. The chloroform phase was taken to dryness and then spotted on a silica gel 60 TLC plate and developed in hexane/ethyl ether (9:1). The amount of cholesterol ester formed was determined by measuring the amount of radioactivity incorporated into the cholesterol oleate spot on the TLC plate with a Packard instaimager.

Data from each of the noted compounds in the assays described above is as set forth in TABLES 5, 6, 7, and 8 as follows:

TABLE 5

| COMPOUND | IC50 uM* | In vitro % Inhibition of TC Uptake @ 100 uM # | % Inhibition of Alanine Uptake @ 100 uM # | % of Control Transport of TC in Rat Ileum @ 0.1 mM # |
|---|---|---|---|---|
| Benzothiazepine= | 2 | | 0 | 45.4 +/−0.7 |
| 12 | | 25 | | |
| 3 | | 0 | | |
| 4a | | 3 | | |
| 5a | | 34 | | |
| 5b | 40 | | 0 | 72.9 ± 5.4 @ 0.5 mM |
| 4b | | 9 | | |
| 18 | | 6 | | |
| 14b | | 18 | | |
| 14a | | 13 | | |
| 13 | | 23 | | |
| 15 | 60 | | | |
| 19a | | 0 | | |
| 19b | | 15 | | |
| 8a | | 41 | | |
| Mixture of 8a and 8b | | 69 | | |
| Mixture of 9a and 9b | 6 | | | |
| 6a | 5 | | | |
| 6b | | 85 | | |
| 9a | 5 | | 0% @ 25 mM | 53.7 +/− 3.9 |
| Mixture of 6a and 20 | 13 | | | |
| Mixture of 6d and 10a | 0.8 | | 14% @ 25 mM | |
| 21a | | 37 | | |
| 21c | | 52 | | |
| 21b | | 45 | | |
| 6c | 2 | | 58.5 | 68.8 +/− 5.7 at 0.4 mM |
| 6d | 0.6 | | 77.7 | 16.1 +/− 1.1 @ 0.5 mM 30.2 +/− 0.9 @ 0.15 mM |
| 17 | | 10 | | |
| 7 | 50 | | 49.3 | |
| 10a | 7 | | 77.6 | 62.4 =/− 2.5 @ 0.2 mM |
| 10b | 15 | | 68.6 | |
| 25 | 0.1 | | 4% @ 10 mM | 26.0 +/− 3.3 |
| 26 | 2 | | 31% @ 25 mM | 87.9 +/− 1.5 |
| 27 | 5 | | 7% @ 20 mM | |
| 28 | 8 | | 31% @ 20 mM | |
| 29 | | 88 @ 50 mM | | |
| 30 | | 96 @ 50 mM | | |
| 31 | | 41 @ 50 mM | | |
| 37 | 3 | | 0% @ 5 mM | |
| 38 | 0.3 | | 11% @ 5 mM | 20.6 +/− 5.7 |
| 40 | | 49 @ 50 mM | | |
| 41 | 2 | | 0% @ 20 mM | |
| 42 | 1.5 | | | |
| 43 | 1.5 | | 16% @ 25 mM | |
| 48 | 2 | | 22% @ 20 mM | |
| 49 | 0.15 | | 21% @ 200 mM | 21.2 +/− 2.7 |
| 57 | | 51 @ 50 mM | | |
| 58 | | 20 @ 50 mM | | |
| 59 | 70 | | | |
| 60 | 9 | | 59 | |
| 61 | 30 | | 175 | |
| 62 | 10 | | | |
| 63 | | 90 @ 6 mM | | |
| 64 | | 100 @ 6 mM | | |

*In vitro Taurocholate Cell Uptake
Unless otherwise noted
=Comparative Example is Example No. 1 in WO 93/16055

TABLE 6

| Compound | TC-uptake (H14 cells) IC(50) | TC-uptake Ileal Loop EC(50) | TC-uptake (BBMV) IC(50) | ACAT (liver) IC(50) | ACAT intestine IC(50) |
|---|---|---|---|---|---|
| COMP. EXAMPLE | 1 mM | 74 mM | 3 mM | 20 mM | 20 mM |
| 6d | 0.6 mM | 31 mM | 1.5 mM | 25 mM | 20 mM |
| * 38 | 0.3 mM | 12 mM | 2 mM | 15 mM | N.D. |
| 49 | 0.1 mM | 12 mM | N.D. | 6 mM | N.D. |
| 25 | 0.1 mM | 20 mM | 0.8 mM | 8 mM | 8 mM |

Comparative Example is Example No. 1 in WO 93/16055

TABLE 7

EFFICACY OF COMPOUND NO. 25 IN CHOLESTEROL-FED HAMSTERS

| PARAMETER WEIGHT (G) | CONTROL | 4% CHOLES-TYRAMINE | 0.2% CPD. NO. 25 |
|---|---|---|---|
| | (mean ± SEM, *p < 0.05, A-Student's t, B-Dunnett's) | | |
| day 1 | 117 (2) | 114 (6) | 117 (5) |
| day 14 | 127 (3) | 127 (3) | 132 (4) |
| LIVER WEIGHT (G) | 5.4 (0.3) | 4.9 (0.4) | 5.8 (0.2) |
| SER. CHOL (mg %) | 143 (7) | 119 (4) *A,B | 126 (2) *A,B |
| HDL-CHOL (mg %) | 89 (4) | 76 (3) *A,B | 76 (1) *A,B |
| VLDL + LDL | 54 (7) | 42 (3) *A | 50 (3) |
| TGI (mg %) | 203 (32) | 190 (15) | 175 (11) |
| HEPATIC CHOL (mg/g) | 2.5 (0.3) | 1.9 (0.1) *A,B | 1.9 (0.1) *A,B |
| HMG COA (pm/mg/min.) | 15.8 (7.6) | 448.8 (21.6) *A,B | 312.9 (37.5) *A,B |
| 7a-OHase (pm/mg/min.) | 235.3 (25.1) | 357.2 (28.3) *A,B | 291.0 (6.0) *A |
| 24 HR. FECAL Wt (G) | | | |
| FBA (mM/24 H/100 g) | 2.3 (0.1) | 2.7 (0.1) *A,B | 2.4 (0.04) |
| | 6.2 (0.8) | 12.3 (1.5) *A,B | 11.9 (0.5) *A,B |

TABLE 8

EFFICACY OF COMPOUND NO. 25 IN RAT ALZET MINIPUMP MODEL

| PARAMETER WEIGHT (G) | CONTROL | 20 MPL/DAY CPD. NO. 25 |
|---|---|---|
| | (mean ± SEM, *p < 0.05, A-Student's t, B-Dunnett's) | |
| day 1 | 307 (4) | 307 (3) |
| day 8 | 330 (4) | 310 (4) *A,B |
| LIVER WEIGHT (G) | 15.5 (0.6) | 14.6 (0.4) |
| SER. CHOL (mg %) | 85 (3) | 84 (3) |
| HEPATIC CHOL (mg/g) | 21 (0.03) | 2.0 (0.03) |
| HMG COA pm/mg/min | 75.1 (6.4) | 318.0 (40.7) *A,B |
| 7a-OHase (pm/mg/min) | 281.9 (13.9) | 535.2 (35.7) *A,B |
| 24 HR. FECAL WT (G) | 5.8 (0.1) | 5.7 (0.4) |
| FBA (mM/24 H/100 g) | 17.9 (0.9) | 39.1 (4.5) *A,B |

Additional taurocholate uptake tests were conducted in the following compounds listed in Table 9.

TABLE 9

Biological Assay Data for Some Compounds of the Present Invention

| Compound Number | Human TC $IC_{50}$ ($\mu$M) | Alanine Uptake Percent Inhibition @ $\mu$M |
|---|---|---|
| 101 | | 0 @ 1.0 |
| 102 | 0.083 | |

TABLE 9-continued

Biological Assay Data for Some Compounds of the Present Invention

| Compound Number | Human TC $IC_{50}$ ($\mu$M) | Alanine Uptake Percent Inhibition @ $\mu$M |
|---|---|---|
| 103 | | 13 @ 0.25 |
| 104 | 0.0056 | |
| 105 | 0.6 | |
| 106 | 0.8 | |
| 107 | | 14.0 @ 0.063 |

TABLE 9-continued

Biological Assay Data for Some Compounds of the Present Invention

| Compound Number | Human TC $IC_{50}$ ($\mu$M) | Alanine Uptake Percent Inhibition @ $\mu$M |
|---|---|---|
| 108 | 0.3 | |
| 109 | | 2.0 @ 0.063 |
| 110 | 0.09 | |
| 111 | 2.5 | |
| 112 | 3.0 | |
| 113 | 0.1 | |
| 114 | 0.19 | |
| 115 | 8.0 | |
| 116 | 0.3 | |
| 117 | | 12.0 @ 0.625 |
| 118 | 0.4 | |
| 119 | 1.3 | |
| 120 | | 34.0 @ 5.0 |
| 121 | 0.068 | |
| 122 | 1.07 | |
| 123 | 1.67 | |
| 124 | | 14.0 @ 6.25 |
| 125 | 18.0 | |
| 126 | | 18 @ 1.25 |
| 127 | 0.55 | |
| 128 | 0.7 | |
| 129 | 0.035 | |
| 131 | 1.28 | |
| 132 | | 5.4 @ 0.063 |
| 133 | 16.0 | |
| 134 | 0.3 | |
| 135 | 22.0 | |

TABLE 9-continued

Biological Assay Data for Some Compounds of the Present Invention

| Compound Number | Human TC $IC_{50}$ ($\mu$M) | Alanine Uptake Percent Inhibition @ $\mu$M |
|---|---|---|
| 136 | 0.09 | |
| 137 | 2.4 | |
| 138 | 3.0 | |
| 139 | >25.0 | |
| 142 | 0.5 | |
| 143 | 0.03 | |
| 144 | 0.053 | |
| 262 | 0.07 | |
| 263 | 0.7 | |
| 264 | 0.2 | |
| 265 | 2.0 | |
| 266 | 0.5 | |
| 267 | 0.073 | |
| 268 | 0.029 | |
| 269 | 0.08 | |
| 270 | 0.12 | |
| 271 | 0.07 | |
| 272 | 0.7 | |
| 273 | 1.9 | |
| 274 | 0.18 | |
| 275 | | 5.0 @ 0.25 |
| 276 | 0.23 | |
| 277 | 0.04 | |
| 278 | 3.0 | |
| 279 | 0.4 | |
| 280 | 0.18 | |
| 281 | 0.019 | |
| 282 | 0.021 | |
| 283 | 0.35 | |
| 284 | 0.08 | |
| 286 | 19.0 | |
| 287 | 4.0 | |
| 288 | | 10.0 @ 6.25 |
| 289 | 0.23 | |
| 290 | 0.054 | |
| 291 | 0.6 | |
| 292 | 0.046 | |
| 293 | 1.9 | |
| 294 | 0.013 | |
| 295 | 1.3 | |
| 296 | 1.6 | |
| 1005 | 0.0004 | |
| 1006 | 0.001 | |
| 1007 | 0.001 | |
| 1008 | 0.001 | |
| 1009 | 0.001 | |
| 1010 | 0.001 | |
| 1011 | 0.001 | |
| 1012 | 0.0015 | |
| 1013 | 0.002 | |
| 1014 | 0.002 | |
| 1015 | 0.002 | |
| 1016 | 0.002 | |
| 1017 | 0.002 | |
| 1018 | 0.002 | |
| 1019 | 0.002 | |
| 1020 | 0.002 | |
| 1021 | 0.002 | |
| 1022 | 0.002 | |
| 1023 | 0.002 | |
| 1024 | 0.002 | |
| 1025 | 0.002 | |
| 1026 | 0.002 | |
| 1027 | 0.002 | |
| 1028 | 0.002 | |
| 1029 | 0.002 | |
| 1030 | 0.002 | |
| 1031 | 0.002 | |
| 1032 | 0.002 | |
| 1033 | 0.002 | |
| 1034 | 0.002 | |
| 1035 | 0.002 | |

TABLE 9-continued

Biological Assay Data for Some Compounds of the Present Invention

| Compound Number | Human TC $IC_{50}$ ($\mu$M) | Alanine Uptake Percent Inhibition @ $\mu$M |
|---|---|---|
| 1036 | 0.002 | |
| 1037 | 0.0022 | |
| 1038 | 0.0025 | |
| 1039 | 0.0026 | |
| 1040 | 0.003 | |
| 1041 | 0.003 | |
| 1042 | 0.003 | |
| 1043 | 0.003 | |
| 1044 | 0.003 | |
| 1045 | 0.003 | |
| 1046 | 0.003 | |
| 1047 | 0.003 | |
| 1048 | 0.003 | |
| 1049 | 0.003 | |
| 1050 | 0.003 | |
| 1051 | 0.003 | |
| 1052 | 0.003 | |
| 1053 | 0.003 | |
| 1054 | 0.003 | |
| 1055 | 0.003 | |
| 1056 | 0.003 | |
| 1057 | 0.003 | |
| 1058 | 0.003 | |
| 1059 | 0.003 | |
| 1060 | 0.0036 | |
| 1061 | 0.004 | |
| 1062 | 0.004 | |
| 1063 | 0.004 | |
| 1064 | 0.004 | |
| 1065 | 0.004 | |
| 1066 | 0.004 | |
| 1067 | 0.004 | |
| 1068 | 0.004 | |
| 1069 | 0.004 | |
| 1070 | 0.004 | |
| 1071 | 0.004 | |
| 1072 | 0.004 | |
| 1073 | 0.004 | |
| 1074 | 0.004 | |
| 1075 | 0.0043 | |
| 1076 | 0.0045 | |
| 1077 | 0.0045 | |
| 1078 | 0.0045 | |
| 1079 | 0.005 | |
| 1080 | 0.005 | |
| 1081 | 0.005 | |
| 1082 | 0.005 | |
| 1083 | 0.005 | |
| 1084 | 0.005 | |
| 1085 | 0.005 | |
| 1086 | 0.005 | |
| 1087 | 0.005 | |
| 1088 | 0.0055 | |
| 1089 | 0.0057 | |
| 1090 | 0.006 | |
| 1091 | 0.006 | |
| 1092 | 0.006 | |
| 1093 | 0.006 | |
| 1094 | 0.006 | |
| 1095 | 0.006 | |
| 1096 | 0.006 | |
| 1097 | 0.006 | |
| 1098 | 0.006 | |
| 1099 | 0.0063 | |
| 1100 | 0.0068 | |
| 1101 | 0.007 | |
| 1102 | 0.007 | |
| 1103 | 0.007 | |
| 1104 | 0.007 | |
| 1105 | 0.007 | |
| 1106 | 0.0073 | |
| 1107 | 0.0075 | |

TABLE 9-continued

Biological Assay Data for Some Compounds of the Present Invention

| Compound Number | Human TC $IC_{50}$ ($\mu$M) | Alanine Uptake Percent Inhibition @ $\mu$M |
|---|---|---|
| 1108 | 0.0075 | |
| 1109 | 0.008 | |
| 1110 | 0.008 | |
| 1111 | 0.008 | |
| 1112 | 0.008 | |
| 1113 | 0.009 | |
| 1114 | 0.009 | |
| 1115 | 0.0098 | |
| 1116 | 0.0093 | |
| 1117 | 0.01 | |
| 1118 | 0.01 | |
| 1119 | 0.01 | |
| 1120 | 0.01 | |
| 1121 | 0.01 | |
| 1122 | 0.011 | |
| 1123 | 0.011 | |
| 1124 | 0.011 | |
| 1125 | 0.012 | |
| 1126 | 0.013 | |
| 1127 | 0.013 | |
| 1128 | 0.017 | |
| 1129 | 0.018 | |
| 1130 | 0.018 | |
| 1131 | 0.02 | |
| 1132 | 0.02 | |
| 1133 | 0.02 | |
| 1134 | 0.02 | |
| 1135 | 0.021 | |
| 1136 | 0.021 | |
| 1137 | 0.021 | |
| 1138 | 0.022 | |
| 1139 | 0.022 | |
| 1140 | 0.023 | |
| 1141 | 0.023 | |
| 1142 | 0.024 | |
| 1143 | 0.027 | |
| 1144 | 0.028 | |
| 1145 | 0.029 | |
| 1146 | 0.029 | |
| 1147 | 0.029 | |
| 1148 | 0.03 | |
| 1149 | 0.03 | |
| 1150 | 0.03 | |
| 1151 | 0.031 | |
| 1152 | 0.036 | |
| 1153 | 0.037 | |
| 1154 | 0.037 | |
| 1155 | 0.039 | |
| 1156 | 0.039 | |
| 1157 | 0.04 | |
| 1158 | 0.06 | |
| 1159 | 0.06 | |
| 1160 | 0.062 | |
| 1161 | 0.063 | |
| 1162 | 0.063 | |
| 1163 | 0.09 | |
| 1164 | 0.093 | |
| 1165 | 0.11 | |
| 1166 | 0.11 | |
| 1167 | 0.12 | |
| 1168 | 0.12 | |
| 1169 | 0.12 | |
| 1170 | 0.13 | |
| 1171 | 0.14 | |
| 1172 | 0.14 | |
| 1173 | 0.15 | |
| 1174 | 0.15 | |
| 1175 | 0.17 | |
| 1176 | 0.18 | |
| 1177 | 0.18 | |
| 1178 | 0.19 | |
| 1179 | 0.19 | |

TABLE 9-continued

Biological Assay Data for Some Compounds of the Present Invention

| Compound Number | Human TC $IC_{50}$ ($\mu$M) | Alanine Uptake Percent Inhibition @ $\mu$M |
|---|---|---|
| 1180 | 0.2 | |
| 1181 | 0.22 | |
| 1182 | 0.25 | |
| 1183 | 0.28 | |
| 1184 | 0.28 | |
| 1185 | 0.28 | |
| 1186 | 0.3 | |
| 1187 | 0.32 | |
| 1188 | 0.35 | |
| 1189 | 0.35 | |
| 1190 | 0.55 | |
| 1191 | 0.65 | |
| 1192 | 1.0 | |
| 1193 | 1.0 | |
| 1194 | 1.6 | |
| 1195 | 1.7 | |
| 1196 | 2.0 | |
| 1197 | 2.2 | |
| 1198 | 2.5 | |
| 1199 | 4.0 | |
| 1200 | 6.1 | |
| 1201 | 8.3 | |
| 1202 | 40.0 | |
| 1203 | | 0 @ 0.063 |
| 1204 | 0.05 | |
| 1205 | 0.034 | |
| 1206 | 0.035 | |
| 1207 | 0.068 | |
| 1208 | 0.042 | |
| 1209 | | 0 @ 0.063 |
| 1210 | 0.14 | |
| 1211 | 0.28 | |
| 1212 | 0.39 | |
| 1213 | 1.7 | |
| 1214 | 0.75 | |
| 1215 | 0.19 | |
| 1216 | 0.39 | |
| 1217 | 0.32 | |
| 1218 | 0.19 | |
| 1219 | 0.34 | |
| 1220 | 0.2 | |
| 1221 | 0.041 | |
| 1222 | 0.065 | |
| 1223 | 0.28 | |
| 1224 | 0.33 | |
| 1225 | 0.12 | |
| 1226 | 0.046 | |
| 1227 | 0.25 | |
| 1228 | 0.038 | |
| 1229 | 0.049 | |
| 1230 | 0.062 | |
| 1231 | 0.075 | |
| 1232 | 1.2 | |
| 1233 | 0.15 | |
| 1234 | 0.067 | |
| 1235 | 0.045 | |
| 1236 | 0.05 | |
| 1237 | 0.07 | |
| 1238 | 0.8 | |
| 1239 | 0.035 | |
| 1240 | 0.016 | |
| 1241 | 0.047 | |
| 1242 | 0.029 | |
| 1243 | 0.63 | |
| 1244 | 0.062 | |
| 1245 | 0.32 | |
| 1246 | 0.018 | |
| 1247 | 0.017 | |
| 1248 | 0.33 | |
| 1249 | 10.2 | |
| 1250 | 0.013 | |
| 1251 | 0.62 | |

TABLE 9-continued

| Biological Assay Data for Some Compounds of the Present Invention | | |
|---|---|---|
| Compound Number | Human TC $IC_{50}$ ($\mu$M) | Alanine Uptake Percent Inhibition @ $\mu$M |
| 1252 | 29. | |
| 1253 | 0.3 | |
| 1254 | 0.85 | |
| 1255 | 0.69 | |
| 1256 | 0.011 | |
| 1257 | 0.1 | |
| 1258 | 0.12 | |
| 1259 | 16.5 | |
| 1260 | 0.012 | |
| 1261 | 0.019 | |
| 1262 | 0.03 | |
| 1263 | 0.079 | |
| 1264 | 0.21 | |
| 1265 | 0.24 | |
| 1266 | 0.2 | |
| 1267 | 0.29 | |
| 1268 | 0.035 | |
| 1269 | 0.024 | |
| 1270 | 0.024 | |
| 1271 | 0.011 | |
| 1272 | 0.047 | |
| 1273 | 0.029 | |
| 1274 | 0.028 | |
| 1275 | 0.024 | |
| 1276 | 0.029 | |
| 1277 | 0.018 | |
| 1278 | 0.017 | |
| 1279 | 0.028 | |
| 1280 | 0.76 | |
| 1281 | 0.055 | |
| 1282 | 0.17 | |
| 1283 | 0.17 | |
| 1284 | 0.011 | |
| 1285 | 0.027 | |
| 1286 | 0.068 | |
| 1287 | 0.071 | |
| 1288 | 0.013 | |
| 1289 | 0.026 | |
| 1290 | 0.017 | |
| 1291 | 0.013 | |
| 1292 | 0.025 | |
| 1293 | 0.019 | |
| 1294 | 0.011 | |
| 1295 | 0.014 | |
| 1296 | 0.063 | |
| 1297 | 0.029 | |
| 1298 | 0.018 | |
| 1299 | 0.012 | |
| 1300 | 1.0 | |
| 1301 | 0.15 | |
| 1302 | 1.4 | |
| 1303 | 0.26 | |
| 1304 | 0.25 | |
| 1305 | 0.25 | |
| 1306 | 1.2 | |
| 1307 | 3.1 | |
| 1308 | 0.04 | |
| 1309 | 0.24 | |
| 1310 | 1.16 | |
| 1311 | 3.27 | |
| 1312 | 5.0 | |
| 1313 | 6.1 | |
| 1314 | 0.26 | |
| 1315 | 1.67 | |
| 1316 | 3.9 | |
| 1317 | 21.0 | |
| 1319 | | 11.0 @ 0.25 |
| 1321 | | 11.1 @ 5.0 |
| 1322 | | 3.0 @ 0.0063 |
| 1323 | | 4.0 @ 0.0063 |
| 1324 | | 43.0 @ 0.0008 |
| 1325 | | 1.0 @ 0.0063 |
| 1326 | | 36.0 @ 0.0008 |
| 1327 | | 3.0 @ 0.0063 |
| 1328 | | 68.0 @ 0.0063 |
| 1329 | | 2.0 @ 0.0063 |
| 1330 | | 9.0 @ 0.0063 |
| 1331 | | 57.0 @ 0.0008 |
| 1332 | | 43.0 @ 0.0008 |
| 1333 | | 0 @ 0.0063 |
| 1334 | | 50.0 @ 0.0008 |
| 1335 | | 38.0 @ 0.0008 |
| 1336 | | 45.0 @ 0.0008 |
| 1337 | | 0 @ 0.0063 |
| 1338 | | 1.0 @ 0.25 |
| 1339 | | 0 @ 0.063 |
| 1340 | | 9.0 @ 0.063 |
| 1341 | | 1.0 @ 0.063 |
| 1342 | | 1.0 @ 0.063 |
| 1345 | | 13.0 @ 0.25 |
| 1347 | | 0.0036 |
| 1351 | 0.44 | |
| 1352 | 0.10 | |
| 1353 | 0.0015 | |
| 1354 | 0.006 | |
| 1355 | 0.0015 | |
| 1356 | 0.22 | |
| 1357 | 0.023 | |
| 1358 | 0.008 | |
| 1359 | 0.014 | |
| 1360 | 0.003 | |
| 1361 | 0.004 | |
| 1362 | 0.019 | |
| 1363 | 0.008 | |
| 1364 | 0.006 | |
| 1365 | 0.008 | |
| 1366 | 0.015 | |
| 1367 | 0.002 | |
| 1368 | 0.005 | |
| 1369 | 0.005 | |
| 1370 | 0.002 | |
| 1371 | 0.004 | |
| 1372 | 0.004 | |
| 1373 | 0.008 | |
| 1374 | 0.007 | |
| 1375 | 0.002 | |
| 1449 | 0.052 | |
| 1450 | 0.039 | |
| 1451 | 0.014 | |

The examples herein can be repeated with similar success by substituting the generically or specifically described reactants and/or operating conditions of this invention for those used in the preceding examples.

Novel compositions of the invention are further illustrated in attached Exhibits A and B.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

TABLE C2

Alternative compounds #2 (Families F101–F123)

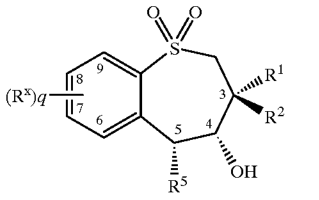

| Family Cpd# | $R^1 = R^2$ | $R^5$ | $(R^x)q$ |
|---|---|---|---|
| F101 | CHOSEN FROM TABLE D* | Ph— | CHOSEN FROM TABLE D |
| F102 | CHOSEN FROM TABLE D | p-F—Ph— | CHOSEN FROM TABLE D |
| F103 | CHOSEN FROM TABLE D | m-F—Ph— | CHOSEN FROM TABLE D |
| F104 | CHOSEN FROM TABLE D | p-$CH_3O$—Ph— | CHOSEN FROM TABLE D |
| F105 | CHOSEN FROM TABLE D | m-$CH_3O$—Ph— | CHOSEN FROM TABLE D |
| F106 | CHOSEN FROM TABLE D | p-$(CH_3)_2N$—Ph— | CHOSEN FROM TABLE D |
| F107 | CHOSEN FROM TABLE D | m-$(CH_3)_2N$—Ph | CHOSEN FROM TABLE D |
| F108 | CHOSEN FROM TABLE D | $I^-$, p-$(CH_3)_3$—$N^+$—Ph— | CHOSEN FROM TABLE D |
| F109 | CHOSEN FROM TABLE D | $I^-$, m-$(CH_3)_3$—$N^+$—Ph— | CHOSEN FROM TABLE D |
| F110 | CHOSEN FROM TABLE D | $I^-$, p-$(CH_3)_3$—$N^+$—$CH_2CH_2$—$(OCH_2CH_2)_2$—O—Ph— | CHOSEN FROM TABLE D |
| F111 | CHOSEN FROM TABLE D | $I^-$, m-$(CH_3)_3$—$N^+$—$CH_2CH_2$—$(OCH_2CH_2)_2$—O—Ph— | CHOSEN FROM TABLE D |
| F112 | CHOSEN FROM TABLE D | $I^-$, p-(N,N-dimethylpiperazine)-(N')-$CH_2$—$(OCH_2CH_2)_2$—O—Ph— | CHOSEN FROM TABLE D |
| F113 | CHOSEN FROM TABLE D | $I^-$, m-(N,N-dimethylpiperazine)-(N')-$CH_2$—$(OCH_2CH_2)_2$—O—Ph— | CHOSEN FROM TABLE D |
| F114 | CHOSEN FROM TABLE D | m-F—Ph— p-$CH_3O$— | CHOSEN FROM TABLE D |

TABLE C2-continued

Alternative compounds #2 (Families F101–F123)

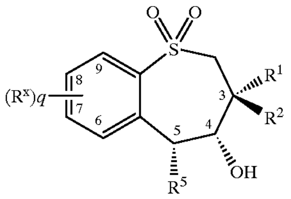

| Family Cpd# | $R^1 = R^2$ | $R^5$ | $(R^x)q$ |
|---|---|---|---|
| F115 | CHOSEN FROM TABLE D | 3,4,dioxy-methylene-Ph— | CHOSEN FROM TABLE D |
| F116 | CHOSEN FROM TABLE D | m-F—Ph— p-F—Ph— | CHOSEN FROM TABLE D |
| F117 | CHOSEN FROM TABLE D | m-$CH_3O$— p-F—Ph— | CHOSEN FROM TABLE D |
| F118 | CHOSEN FROM TABLE D | 4-pyridine | CHOSEN FROM TABLE D |
| F119 | CHOSEN FROM TABLE D | N-methyl-4-pyridinium | CHOSEN FROM TABLE D |
| F120 | CHOSEN FROM TABLE D | 3-pyridine | CHOSEN FROM TABLE D |
| F121 | CHOSEN FROM TABLE D | N-methyl-3-pyridinium | CHOSEN FROM TABLE D |
| F122 | CHOSEN FROM TABLE D | 2-pyridine | CHOSEN FROM TABLE D |
| F123 | CHOSEN FROM TABLE D | p-$CH_3O_2C$—Ph— | CHOSEN FROM TABLE D |

Similar families can be generated where $R^1<>R^2$, such as $R^1$=Et and $R^2$=n-Bu, but $(R^x)$q is chosen from table C1.

Exhibit B

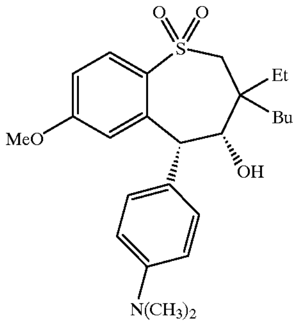

-continued
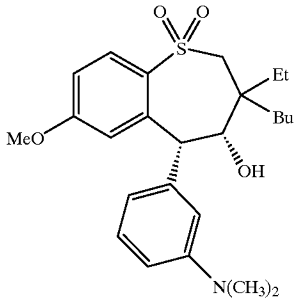
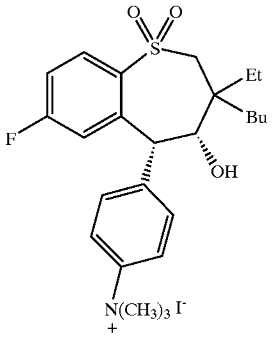
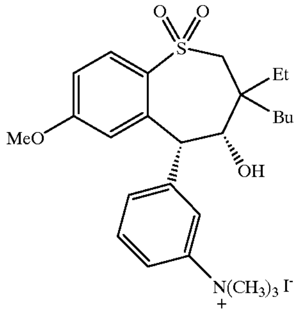
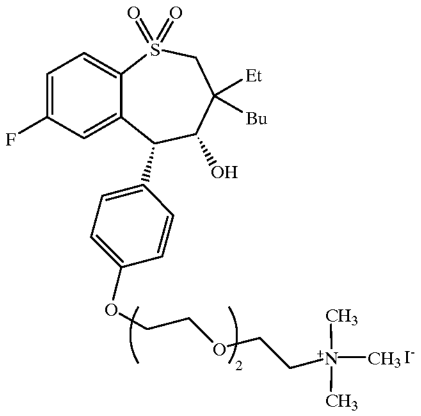
-continued
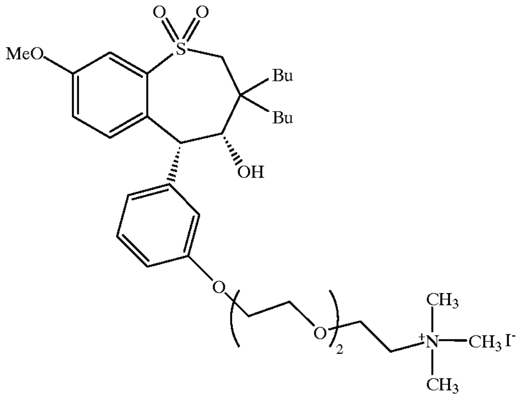
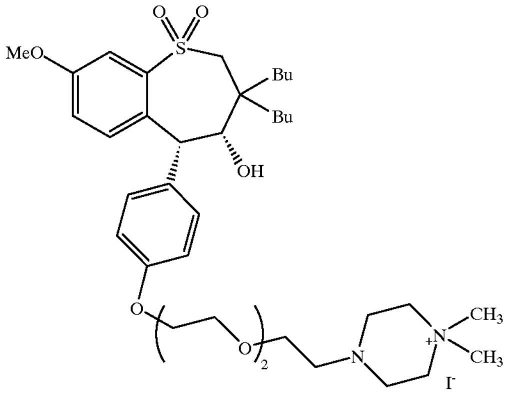
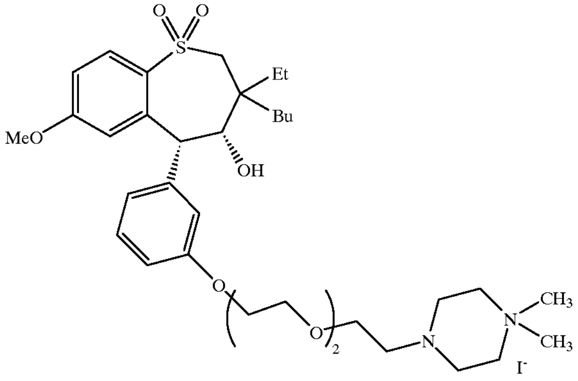
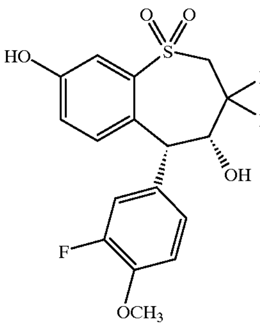

-continued
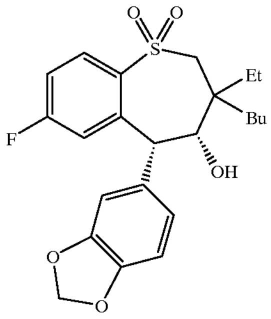
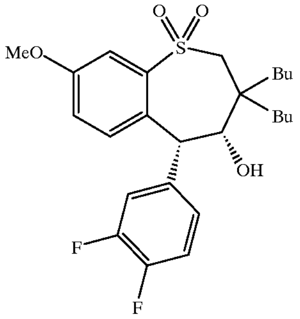
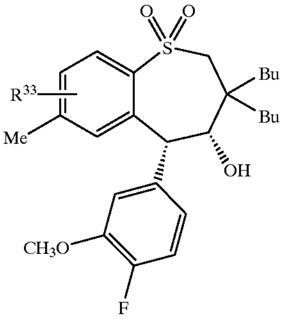
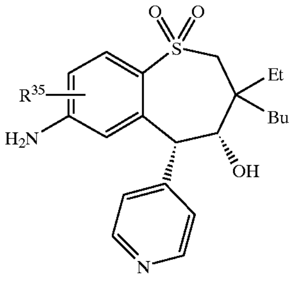
-continued
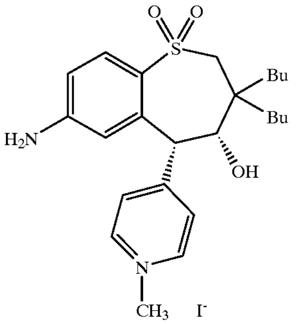
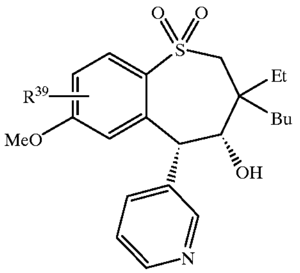
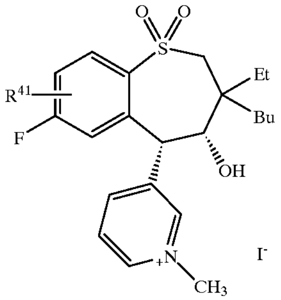
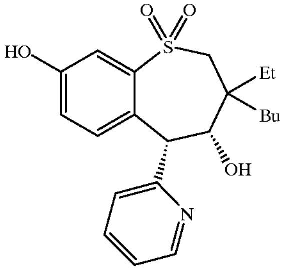

APPENDIX A

The ileal bile acid transport inhibitors used in the present invention include, for example, those compounds disclosed in this Appendix A.

1) The compounds of the formula (I)

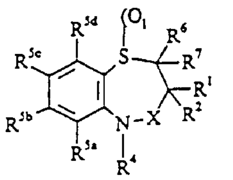

(I)

wherein $R^1$ and $R^2$ are the same or different and each is optionally substituted $C_{1-6}$ alkyl, $C_{3-6}$ cycloalkyl, or $R^1$ and $R^2$ together with the carbon atom to which they are attached form an optionally substituted $C_{3-6}$ spiro-cycloalkyl group;

$R^4$ is a $C_{6-14}$ aryl, or a $C_{3-13}$ heteroaryl group each optionally substituted with one to eight substituents which are the same or different and are each selected from halogen, hydroxy, nitro, phenyl-$C_{1-6}$ alkoxy, $C_{1-6}$ alkoxy, optionally substituted $C_{1-6}$ alkyl, $S(O)_nR^8$, $SO_2NR^8R^9$, $CO_2R^8$, $O(CH_2CH_2O)_nR^8$, $OSO_2R^8$, $O(CH_2)_pSO_3R^8$, $O(CH_2)_pNR^9R^{10}$ and $O(CH_2)_pN^+R^9R^{10}R^{11}$ wherein $R^8$ to $R^{11}$ are the same or different and are independently selected from hydrogen or optionally substituted $C_{1-6}$ alkyl, and wherein p is an integer from 1-4 and n is an integer from 0-3;

$R^{5a}$, $R^{5b}$, $R^{5c}$, and $R^{5d}$ each represent atoms or groups which are the same or different and each is hydrogen, halogen, cyano, $R^8$-acetylide, $OR^8$, optionally substituted $C_{1-6}$ alkyl, $COR^8$, $CH(OH)R^8$, $S(O)_nR^8$, $SO_2NR^8R^9$, $P(O)(OR^8)_2$, $OCOR^8$, $OCF_3$, OCN, SCN, NHCN, $CH_2OR^8$, CHO, $(CH_2)_pCN$, $CONR^9R^{10}$, $(CH_2)_pCO_2R^8$, $(CH_2)_pNR^9R^{10}$, $CO_2R^8$, $NHCOCF_3$, $NHSO_2R^8$, $OCH_2OR^8$, $OCH{=}CHR^8$, $O(CH_2CH_2O)_nR^8$, $OSO_2R^8$, $O(CH_2)_pSO_3R^8$, $O(CH_2)_pNR^9R^{10}$ and $O(CH_2)_pN^+R^9R^{10}R^{11}$ wherein $R^8$ to $R^{11}$, n, and p are as hereinbefore defined; or $R^{5a}$ and $R^{5b}$, $R^{5b}$ and $R^{5c}$, or $R^{5c}$ and $R^{5d}$ together with the ring to which they are attached form a cyclic group $-O(CR^9R^{10})_mO-$ wherein $R^9$ and $R^{10}$ are as hereinbefore defined and m is 1 or 2;

$R^6$ and $R^7$ are the same or different and each is hydrogen, optionally substituted $C_{1-6}$ alkyl, $C_{3-6}$ cycloalkyl, or $R^6$ and $R^7$ together with the carbon atom to which they are attached form an optionally substituted $C_{3-6}$ spiro-cycloalkyl group;
X is $CH_2$, C=O, C=S, or C=$NR^8$ wherein $R^8$ is as hereinbefore defined; and
l is an integer from 0-2;
and salts, solvates or a physiologically functional derivatives thereof.

2) A compound of formula (I) according to claim 1 wherein
$R^1$ is methyl or ethyl;

$R^2$ is methyl, ethyl or n-butyl;

$R^4$ is phenyl;

$R^{5a}$ and $R^{5d}$ are hydrogen;

$R^{5b}$ and $R^{5c}$ are the same or different and are each hydrogen, methyl, methoxy, hydroxy, trifluoromethyl or halo;

$R^6$ and $R^7$ are the same or different and are each hydrogen, methyl, ethyl or i-butyl;

X is $CH_2$ or C=O;

l is 2;
or a salt, solvate, or physiologically functional derivative thereof.

3) A compound of formula (I) selected from the group consisting of
(±)-3-n-Butyl-3-ethyl-2,3-dihydro-5-phenyl-1,5-benzothiazepin-4-one;
(±)-3-n-Butyl-3-ethyl-2,3-dihydro-5-phenyl-1,5-benzothiazepin-4-one-1,1-dioxide;
(±)-3-n-Butyl-3-ethyl-2,3,4,5-tetrahydro-5-phenyl-1,5-benzothiazepine;
(±)-3-n-Butyl-3-ethyl-2,3,4,5-tetrahydro-5-phenyl-1,5-benzothiazepine-1,1-dioxide;
(±)-3-n-Butyl-2-isobutyl-3-ethyl-2,3,4,5-tetrahydro-5-phenyl-1,5-benzothiazepine-1,1-dioxide;
3,3-Diethyl-2,3-dihydro-5-phenyl-1,5-benzothiazepin-4-one;
3,3-Diethyl-2,3-dihydro-5-phenyl-1,5-benzothiazepin-4-one 1,1-dioxide;
3,3-Diethyl-2,3,4,5-tetrahydro-5-phenyl-1,5-benzothiazepine;
3,3-Diethyl-2,3,4,5-tetrahydro-5-phenyl-1,5-benzothiazepine-1,1-dioxide;

3,3-Dimethyl-2,3-dihydro-5-phenyl-1,5-benzothiazepin-4-one;
3,3-Dimethyl-2,3-dihydro-5-phenyl-1,5-benzothiazepin-4-one-1,1-dioxide;
3,3-Dimethyl-2,3,4,5-tetrahydro-5-phenyl-1,5-benzothiazepine;
3,3-Dimethyl-2,3,4,5-tetrahydro-5-phenyl-1,5-benzothiazepine-1,1-dioxide;
(±)-3-n-Butyl-3-ethyl-2,3,4,5-tetrahydro-7,8-dimethoxy-5-phenyl-1,5-benzothiazepine-1,1-dioxide;
3,3-Diethyl-2,3,4,5-tetrahydro-7,8-dimethoxy-5-phenyl-1,5-benzothiazepine-1,1-dioxide;
(±)-3-n-Butyl-3-ethyl-2,3,4,5-tetrahydro-8-methoxy-5-phenyl-1,5-benzothiazepine-1,1-dioxide;
3,3-Diethyl-2,3,4,5-tetrahydro-8-methoxy-5-phenyl-1,5-benzothiazepine-1,1-dioxide;
(±)-3-n-Butyl-3-ethyl-2,3,4,5-tetrahydro-5-phenyl-1,5-benzothiazepin-8-ol-1,1-dioxide;
3,3-Diethyl-2,3,4,5-tetrahydro-5-phenyl-1,5-benzothiazepin-8-ol-1,1-dioxide;
(±)-3-n-Butyl-3-ethyl-2,3,4,5-tetrahydro-7-methoxy-5-phenyl-1,5-benzothiazepin-8-ol-1,1-dioxide;
3,3-Diethyl-2,3,4,5-tetrahydro-7-methoxy-5-phenyl-1,5-benzothiazepin-8-ol-1,1-dioxide;
(±)-7-bromo-3-n-Butyl-3-ethyl-2,3,4,5-tetrahydro-8-methoxy-5-phenyl-1,5-benzothiazepine-1,1-dioxide;
7-bromo-3,3-Diethyl-2,3,4,5-tetrahydro-8-methoxy-5-phenyl-1,5-benzothiazepine-1,1-dioxide;
(±)-3-n-Butyl-3-ethyl-2,3,4,5-tetrahydro-5-phenyl-1,5-benzothiazepin-7,8-diol-1,1-dioxide;
3,3-Diethyl-2,3,4,5-tetrahydro-5-phenyl-1,5-benzothiazepin-7,8-diol-1,1-dioxide;
(±)-3-n-Butyl-3-ethyl-2,3,4,5-tetrahydro-8-methoxy-5-phenyl-1,5-benzothiazepine-1-monoxide;
3,3-Diethyl-2,3,4,5-tetrahydro-8-methoxy-5-phenyl-1,5-benzothiazepine-1-monoxide;
(±)-3-n-Butyl-3-ethyl-2,3,4,5-tetrahydro-5-phenyl-1,5-benzothiazepin-8-ol-1-monoxide;
3,3-Diethyl-2,3,4,5-tetrahydro-5-phenyl-1,5-benzothiazepin-8-ol-1-monoxide;
(±)-3-n-Butyl-3-ethyl-2,3-dihydro-8-methoxy-5-phenyl-1,5-benzothiazepin-4-one;
(±)-3-n-Butyl-3-ethyl-2,3,4,5-tetrahydro-8-methoxy-5-phenyl-1,5-benzothiazepine;
(±)-3-n-Butyl-3-ethyl-2,3,4,5-tetrahydro-8-methoxy-5-phenyl-1,5-benzothiazepine-1,1-dioxide;
(±)-3-n-Butyl-3-ethyl-2,3,4,5-tetrahydro-8-hydroxy-5-phenyl-1,5-benzothiazepine-1,1-dioxide;

(±)-7-Bromo-3-n-butyl-3-ethyl-2,3-dihydro-8-methoxy-5-phenyl-1,5-benzothiazepin-4-one;

(±)-7-Bromo-3-n-butyl-3-ethyl-2,3,4,5-tetrahydro-8-methoxy-5-phenyl-1,5-benzothiazepine 1,1-dioxide;

(±)-7-Bromo-3-n-butyl-3-ethyl-2,3,4,5-tetrahydro-5-phenyl-1,5-benzothiazepin-8-ol 1,1-dioxide;

(±)-3-n-butyl-3-ethyl-2,3,4,5-tetrahydro-7-methoxy-5-phenyl-1,5-benzothiazepin-8-ol 1,1-dioxide;

(±)-3-n-butyl-3-ethyl-2,3,4,5-tetrahydro-7,8-dimethoxy-5-phenyl-1,5-benzothiazepine 1,1-dioxide;

(±)-3-n-butyl-3-ethyl-2,3,4,5-tetrahydro-5-phenyl-1,5-benzothiazepine-7,8-diol 1,1-dioxide;

(±)-7-Bromo-3-n-butyl-3-ethyl-2,3-dihydro-5-phenyl-1,5-benzothiazepin-4-one;

(±)-3-n-butyl-3-ethyl-2,3,4,5-tetrahydro-7-methoxy-5-phenyl-1,5-benzothiazepine 1,1-dioxide; and (±)-3-n-butyl-3-ethyl-2,3,4,5-tetrahydro-5-phenyl-1,5-benzothiazepin-7-ol 1,1-dioxide.

4) A compound of formula (I) selected from:

(±)-3-n-butyl-3-ethyl-2,3,4,5-tetrahydro-7-methoxy-5-phenyl-1,5-benzothiazepin-8-ol 1,1-dioxide; and (±)-3-n-Butyl-3-ethyl-2,3,4,5-tetrahydro-8-hydroxy-5-phenyl-1,5-benzothiazepine-1,1-dioxide or a salt, solvate, or physiologically functional derivative thereof.

(±)-3-n-Butyl-3-ethyl-2,3-dihydro-5-phenyl-1,5-benzothiazepin-4-one-1,1-dioxide;
(±)-3-n-Butyl-3-ethyl-2,3,4,5-tetrahydro-5-phenyl-1,5-benzothiazepine;
(±)-3-n-Butyl-3-ethyl-2,3,4,5-tetrahydro-5-phenyl-1,5-benzothiazepine-1,1-dioxide;
(±)-3-n-Butyl-2-isobutyl-3-ethyl-2,3,4,5-tetrahydro-5-phenyl-1,5-benzothiazepine-1,1-dioxide;
3,3-Diethyl-2,3-dihydro-5-phenyl-1,5-benzothiazepin-4-one;
3,3-Diethyl-2,3-dihydro-5-phenyl-1,5-benzothiazepin-4-one 1,1-dioxide;
3,3-Diethyl-2,3,4,5-tetrahydro-5-phenyl-1,5-benzothiazepine;
3,3-Diethyl-2,3,4,5-tetrahydro-5-phenyl-1,5-benzothiazepine-1,1-dioxide;
3,3-Dimethyl-2,3-dihydro-5-phenyl-1,5-benzothiazepin-4-one;
3,3-Dimethyl-2,3-dihydro-5-phenyl-1,5-benzothiazepin-4-one-1,1-dioxide;
3,3-Dimethyl-2,3,4,5-tetrahydro-5-phenyl-1,5-benzothiazepine;
3,3-Dimethyl-2,3,4,5-tetrahydro-5-phenyl-1,5-benzothiazepine-1,1-dioxide;
(±)-3-n-Butyl-3-ethyl-2,3,4,5-tetrahydro-7,8-dimethoxy-5-phenyl-1,5-benzothiazepine-1,1-dioxide;
3,3-Diethyl-2,3,4,5-tetrahydro-7,8-dimethoxy-5-phenyl-1,5-benzothiazepine-1,1-dioxide;
(±)-3-n-Butyl-3-ethyl-2,3,4,5-tetrahydro-8-methoxy-5-phenyl-1,5-benzothiazepine-1,1-dioxide;
3,3-Diethyl-2,3,4,5-tetrahydro-8-methoxy-5-phenyl-1,5-benzothiazepine-1,1-dioxide;
(±)-3-n-Butyl-3-ethyl-2,3,4,5-tetrahydro-5-phenyl-1,5-benzothiazepin-8-ol-1,1-dioxide;
3,3-Diethyl-2,3,4,5-tetrahydro-5-phenyl-1,5-benzothiazepin-8-ol-1,1-dioxide;
(±)-3-n-Butyl-3-ethyl-2,3,4,5-tetrahydro-7-methoxy-5-phenyl-1,5-benzothiazepin-8-ol-1,1-dioxide;
3,3-Diethyl-2,3,4,5-tetrahydro-7-methoxy-5-phenyl-1,5-benzothiazepin-8-ol-1,1-dioxide;
(±)-7-bromo-3-n-Butyl-3-ethyl-2,3,4,5-tetrahydro-8-methoxy-5-phenyl-1,5-benzothiazepine-1,1-dioxide;
7-bromo-3,3-Diethyl-2,3,4,5-tetrahydro-8-methoxy-5-phenyl-1,5-benzothiazepine-1,1-dioxide;
(±)-3-n-Butyl-3-ethyl-2,3,4,5-tetrahydro-5-phenyl-1,5-benzothiazepin-7,8-diol-1,1-dioxide;
3,3-Diethyl-2,3,4,5-tetrahydro-5-phenyl-1,5-benzothiazepin-7,8-diol-1,1-dioxide;
(±)-3-n-Butyl-3-ethyl-2,3,4,5-tetrahydro-8-methoxy-5-phenyl-1,5-benzothiazepine-1-monoxide;
3, 3-Diethyl-2,3,4,5-tetrahydro-8-methoxy-5-phenyl-1,5-benzothiazepine-1-monoxide;
(±)-3-n-Butyl-3-ethyl-2,3,4,5-tetrahydro-5-phenyl-1,5-benzothiazepin-8-ol-1-monoxide;
3,3-Diethyl-2,3,4,5-tetrahydro-5-phenyl-1,5-benzothiazepin-8-ol-1-monoxide;
(±)-3-n-Butyl-3-ethyl-2,3-dihydro-8-methoxy-5-phenyl-1,5-benzothiazepin-4-one;
(±)-3-n-Butyl-3-ethyl-2,3,4,5-tetrahydro-8-methoxy-5-phenyl-1,5-benzothiazepine;

(±)-3-n-Butyl-3-ethyl-2,3,4,5-tetrahydro-8-methoxy-5-phenyl-1,5-benzothiazepine-1,1-dioxide;
(±)-3-n-Butyl-3-ethyl-2,3,4,5-tetrahydro-8-hydroxy-5-phenyl-1,5-benzothiazepine-1,1-dioxide;
(±)-7-Bromo-3-n-butyl-3-ethyl-2,3-dihydro-8-methoxy-5-phenyl-1,5-benzothiazepin-4-one;
(±)-7-Bromo-3-n-butyl-3-ethyl-2,3,4,5-tetrahydro-8-methoxy-5-phenyl-1,5-benzothiazepine 1,1-dioxide;
(±)-7-Bromo-3-n-butyl-3-ethyl-2,3,4,5-tetrahydro-5-phenyl-1,5-benzothiazepin-8-ol 1,1-dioxide;
(±)-3-n-butyl-3-ethyl-2,3,4,5-tetrahydro-7-methoxy-5-phenyl-1,5-benzothiazepin-8-ol 1,1-dioxide;
(±)-3-n-butyl-3-ethyl-2,3,4,5-tetrahydro-7,8-dimethoxy-5-phenyl-1,5-benzothiazepine 1,1-dioxide;
(±)-3-n-butyl-3-ethyl-2,3,4,5-tetrahydro-5-phenyl-1,5-benzothiazepine-7,8-diol 1,1-dioxide;
(±)-7-Bromo-3-n-butyl-3-ethyl-2,3-dihydro-5-phenyl-1,5-benzothiazepin-4-one;
(±)-3-n-butyl-3-ethyl-2,3,4,5-tetrahydro-7-methoxy-5-phenyl-1,5-benzothiazepine 1,1-dioxide; and
(±)-3-n-butyl-3-ethyl-2,3,4,5-tetrahydro-5-phenyl-1,5-benzothiazepin-7-ol 1,1-dioxide.

Particularly preferred compounds include:
(±)-3-n-butyl-3-ethyl-2,3,4,5-tetrahydro-7-methoxy-5-phenyl-1,5-benzothiazepin-8-ol 1,1-dioxide; and
(±)-3-n-Butyl-3-ethyl-2,3,4,5-tetrahydro-8-hydroxy-5-phenyl-1,5-benzothiazepine-1,1-dioxide.

3,3-Diethyl-2,3,4,5-tetrahydro-1,1-dioxo-5-phenyl-1,4-benzothiazepin-8-yl aspartate.

(3R,5R)-3-Butyl-3-ethyl-2,3,4,5-tetradhydro-7,8-dimethoxy-5-phenyl-1,4-benzothiazepine-1,1-dioxide;

(3R,5R)-3-Butyl-3-ethyl-2,3,4,5-tetrahydro-7,8-dimethoxy-5-phenyl-1,4-benzothiazepin-4-ol 1,1-dioxide;

(+-)-Trans-3-butyl-3-ethyl-2,3,4,5-tetrahydro-7,8-dimethoxy-5-phenyl-1,4-benzothiazepine-1,1-dioxide;

(+-)-Trans-3-butyl-3-ethyl-2,3,4,5-tetrahydro-7,8-dimethoxy-5-phenyl-1,4,-benzothiazepin-4-ol 1,1-dioxide;

(3R,5R)-7-Bromo-3-butyl-3-ethyl-2,3,4,5-tetrahydro-8-methoxy-5-phenyl-1,4-benzothiazepine 1,1-dioxide;

(3R,5R)-7-Bromo-3-butyl-3-ethyl-2,3,4,5-tetrahydro-8-methoxy-5-phenyl-1,4-benzothiazepin-4-ol 1,1-dioxide;

(3R,5R)-3-Butyl-3-ethyl-2,3,4,5-tetrahydro-5-phenyl-1,4-benzothiazepine-7,8-diol1,1-dioxide;

(3R,5R)-3-Butyl-3-ethyl-2,3,4,5-tetrahydro-8-methoxy-5-phenyl-1,4-benzothiazepin-7-ol 1,1-dioxide;

(3R,5R)-3-Butyl-3-ethyl-2,3,4,5-tetrahydro-7-methoxy-5-phenyl-1,4-benzothiazepin-8-ol 1,1-dioxide;

(+-)-Trans-3-butyl-3-ethyl-2,3,4,5-tetrahydro-8-methoxy-5-phenyl-1,4-benzothiazepine 1,1-dioxide;

(+-)-Trans-3-butyl-3-ethyl-2,3,4,5-tetrahydro-5-phenyl-1,4-benzothiazepin-8-ol1,1-dioxide;

(+-)-Trans-3-butyl-3-ethyl-2,3,4,5-tetrahydro-5-phenyl-1,4-benzothiazepine-4,8-diol;

(+-)-Trans-3-butyl-3-ethyl-2,3,4,5-tetrahydro-8-methoxy-5-phenyl-1,4-benzothiazepine-7-carbaldehyde 1,1-dioxide;

(+-)-Trans-2-((3-butyl-3-ethyl-2,3,4,5-tetrahydro-8-methoxy-5-phenyl-1,4-benzothiazepin-7-yl)methoxy) ethanol S,S-dioxide;

(+-)-Trans-3-butyl-3-ethyl-2,3,4,5-tetrahydro-8-hydroxy-5-phenyl-1,4-benzothiazepine-7-carbaldehyde 1,1-dioxide;

(+-)-Trans-3-butyl-3-ethyl-2,3,4,5-tetrahydro-5-phenyl-1,4-benzothiazepin-8-thiol1,1-dioxide;

(+-)-Trans-3-butyl-3-ethyl-2,3,4,5-tetrahydro-5-phenyl-1,4-benzothiazepin-8-sulfonic acid-1,1-dioxide;

(7R,9R)-7-Butyl-7-ethyl-6,7,8,9-tetrahydro-9-phenyl-1,3-dioxolo(4,5-H)(1,4)-benzothiazepine 5,5-dioxide;

(+-)-Trans-3-butyl-3-ethyl-2,3,4,5-tetrahydro-8,9-dimethoxy-5-phenyl-1,4-benzothiazepine-1,1-dioxide;

(3R,5R)-3-butyl-3-ethyl-5-(4-fluorophenyl)-2,3,4,5-tetrahydro-7,8-dimethoxy-1,4-benzothiazpin-4-ol 1,1-dioxide;

(+-)-Trans-3-butyl-3-ethyl-2,3,4,5-tetrahydro-8-methoxy-5-phenyl-1,4-benzothiazepine-7-methanol S,S-dioxide;

(3R,5R)-3-butyl-3-ethyl-2,3,4,5-tetrahydro-8-methoxy-7-nitro-5-phenyl-1,4-benzothiazepine-1,1-dioxide;

(+-)-Trans-3-butyl-3-ethyl-2,3,4,5-tetrahydro-8-methoxy-7-(methoxymethyl)-5-phenyl-1,4-benzothiazepine 1,1-dioxide;

(3R,5R)-3-butyl-3-ethyl-2,3,4,5-tetrahydro-5-phenyl-1,4-benzothiazepin-7,8-diyl diacetate-1,1-dioxide;

(8R,10R)-8-Butyl-8-ethyl-2,3,7,8,9,10-hexahydro-10-1,4-dioxono(2,3-H)(1,4)-benzothiazepine 6,6-dioxide;

(3R,5R)-3-butyl-7,8-diethoxy-2,3,4,5-tetrahydro-5-phenyl-1,4-benzothiazepine 1,1-dioxide;

(+-)-Trans-3-butyl-8-ethoxy-3-ethyl-2,3,4,5-tetrahydro-5-phenyl-1,4-benzothiazepine-1,1-dioxide;

(+-)-Trans-3-butyl-3-ethyl-2,3,4,5-tetrahydro-8-isopropoxy-5-phenyl-1,4-benzothiazepine1,1-dioxide hydrochloride;

(+-)-Trans-3-butyl-3-ethyl-2,3,4,5-tetrahydro-5-phenyl-1,4-benzothiazepin-8-carbaldehyde-1,1-dioxide;

3,3-Diethyl-2,3,4,5-tetrahydro-7,8-dimethoxy-5-phenyl-1,4-benzothiazepine 1,1-dioxide;

3,3-Diethyl-5-(4-fluorophenyl)-2,3,4,5-tetrahydro-8-methoxy-1,4-benzothiazepine 1,1-dioxide;

3,3-Diethyl-2,3,4,5-tetrahydro-8-methoxy-5-phenyl-1,4-benzothiazepine1,1-dioxide;

3,3-Diethyl-2,3,4,5-tetrahydro-5-phenyl-1,4-benzothiazpin-4,8-diol1,1-dioxide;

(RS)-3,3-Diethyl-2,3,4,5-tetrahydro-4-hydroxy-7,8-dimethoxy-5-phenyl-1,4-benzothiazepine 1,1-dioxide;

(+-)-Trans-3-butyl-8-ethoxy-3-ethyl-2,3,4,5-tetrahydro-5-phenyl-1,4-benzothiazepin-4-ol-1,1-dioxide;

(+-)-Trans-3-butyl-3-ethyl-2,3,4,5-tetrahydro-8-isopropoxy-5-phenyl-1,4-benzothiazepin-4-ol 1,1-dioxide;

(+-)-Trans-3-butyl-3-ethyl-2,3,4,5-tetrahydro-7,8,9-trimethoxy-5-phenyl-1,4-benzothiazepin-4-ol 1,1-dioxide;

(3R,5R)-3-butyl-3-ethyl-2,3,4,5-tetrahydro-5-phenyl-1,4-benzothiazpin-4,7,8-triol 1,1-dioxide;

(+-)-Trans-3-butyl-3-ethyl-2,3,4,5-tetrahydro-4,7,8-trimethoxy-5-phenyl-1,4-benzothiazepine 1,1-dioxide;

(+-)-Trans-3-butyl-3-ethyl-5-phenyl-2,3,4,5-tetrahydro-7,8-dimethoxy-1,4-benzothiazepin-4-yl acetate S,S-dioxide;

3,3-Diethyl-2,3,4,5-tetrahydro-5-phenyl-1,4-benzothiazepin-8-ol 1,1-dioxide;

3,3-Diethyl-2,3,4,5-tetrahydro-7-methoxy-5-phenyl-1,4-benzothiazepin-8-ol 1,1-dioxide;

3,3-Dibutyl-2,3,4,5-tetrahydro-5-phenyl-1,4-benzothiazepin-8-ol 1,1-dioxide;

(+-)-Trans-3-Butyl-3-ethyl-2,3,4,5-tetrahydro-1,1-dioxo-5-phenyl-1,4-benzothiazepin-8-yl hydrogen sulfate;

(+-)-Trans-3-Butyl-3-ethyl-2,3,4,5-tetrahydro-1,1-dioxo-5-phenyl-1,4-benzothiazepin-8-yl dihydrogen phosphate;

3,3-Diethyl-2,3,4,5-tetrahydro-1,1-dioxo-5-phenyl-1,4-benzothiazepin-8-yl hydrogen sulfate;

3,3-Diethyl-2,3,4,5-tetrahydro-1,1-dioxo-5-phenyl-1,4-benzothiazepin-8-yl-dihydrogen phosphate;

(+-)-Trans-3-Butyl-3-ethyl-2,3,4,5-tetrahydro-1,1-dioxo-5-phenyl-1,4-benzothiazepin-8-yl aspartate; and ..

(22) (+-)-Trans-3-butyl-3-ethyl-2,3,4,5-tetrahydro-8-methoxy-5-phenyl-1,4-benzothiazepine-7-methanol S,S-dioxide, mp 122-123° C

(23) (3R,5R)-3-butyl-3-ethyl-2,3,4,5-tetrahydro-8-methoxy-7-nitro-5-phenyl-1,4-benzothiazepine 1,1-dioxide 0.40 hydrate, mp 122-123° C

(24) (+-)-Trans-3-butyl-3-ethyl-2,3,4,5-tetrahydro-8-methoxy-7-(methoxymethyl)-5-phenyl-1,4-benzothiazepine 1,1-dioxide, mp 118-119° C

(25) (+-)-Trans-7-bromo-3-butyl-3-ethyl-2,3,4,5-tetrahydro-5-phenyl-1,4-benzothiazepin-8-ol 1,1-dioxide 0.40 hydrate, mp 137-138° C

(26) (+-)-Trans-3-butyl-3-ethyl-2,3,4,5-tetrahydro-7,8,9-trimethoxy-5-phenyl-1,4-benzothiazepine 1,1-dioxide, mp 169-170° C

(27) (3R,5R)-3-butyl-3-ethyl-2,3,4,5-tetrahydro-5-phenyl-1,4-benzothiazepin-7,8-diyl diacetate 1,1-dioxide, mp 79-81° C

(28) (8R,10R)-8-Butyl-8-ethyl-2,3,7,8,9,10-hexahydro-10-1,4-dioxono(2,3-H)(1,4)-benzothiazepine 6,6-dioxide, mp 82° C

(29) (3R,5R)-3-butyl-7,8-diethoxy-2,3,4,5-tetrahydro-5-phenyl-1,4-benzothiazepine 1,1 dioxide 0.20 hydrate, mp 110-111° C

(30) (+-)-Trans-3-butyl-8-ethoxy-3-ethyl-2,3,4,5-tetrahydro-5-phenyl-1,4-benzothiazepine 1,1-dioxide, mp 45-54° C

(31) (+-)-Trans-3-butyl-3-ethyl-2,3,4,5-tetrahydro-8-(methylthio)-5-phenyl-1,4-benzothiazepine1,1-dioxide hydrochloride, mp 194-197° C

(32) (+-)-Trans-3-butyl-3-ethyl-2,3,4,5-tetrahydro-8-isopropoxy-5-phenyl-1,4-benzothiazepine 1,1-dioxide hydrochloride, mp 178-181° C

(33) (+-)-Trans-3-butyl-3-ethyl-2,3,4,5-tetrahydro-5-phenyl-1,4-benzothiazepin-8-carbaldehyde 1,1-dioxide, mp 165-170° C

(34) 3,3-Diethyl-2,3,4,5-tetrahydro-1,1-dioxo-5-phenyl-1,4-benzothiazepin-8-yl aspartate

(35) 3,3-Diethyl-2,3,4,5-tetrahydro-7,8-dimethoxy-5-phenyl-1,4-benzothiazepine-1,1-dioxide, mp 163-164° C

(36) 3,3-Diethyl-5-(4-fluorophenyl)-2,3,4,5-tetrahydro-8-methoxy-1,4-benzothiazepine-1,1-dioxide mp 101-103° C

(37) 3,3-Diethyl-2,3,4,5-tetrahydro-8-methoxy-5-phenyl-1,4-benzothiazepine-1,1-dioxide, mp 132-133° C

(38) 3,3-Diethyl-2,3,4,5-tetrahydro-5-phenyl-1,4-benzothiazepin-4,8-diol-1,1-dioxide, mp 225-227° C

(39) (RS)-3,3-Diethyl-2,3,4,5-tetrahydro-4-hydroxy-7,8-dimethoxy-5-phenyl-1,4-benzothiazepine 1,1-dioxide, mp 205-206° C

(40) (+-)-Trans-3-butyl-8-ethoxy-3-ethyl-2,3,4,5-tetrahydro-5-phenyl-1,4-benzothiazepin-4-ol 1,1-dioxide, mp 149-150° C

(41) (+-)-Trans-3-butyl-3-ethyl-2,3,4,5-tetrahydro-8-isopropoxy-5-phenyl-1,4-benzothiazepin-4-ol 1,1-dioxide, mp 109-115° C

(42) (+-)-Trans-3-butyl-3-ethyl-2,3,4,5-tetrahydro-7,8,9-trimethoxy-5-phenyl-1,4-benzothiazepin-4-ol 1,1-dioxide, mp 84-96° C

(43) (3R,5R)-3-butyl-3-ethyl-2,3,4,5-tetrahydro-5-phenyl-1,4-benzothiazpin-4,7,8-triol-1,1-dioxide, mp 215-220° C

(44) (+-)-Trans-3-butyl-3-ethyl-2,3,4,5-tetrahydro-4,7,8-trimethoxy-5-phenyl-1,4-benzothiazepine 1,1-dioxide, mp 169-187° C

(45) (+-)-Trans-3-butyl-3-ethyl-5-phenyl-2,3,4,5-tetrahydro-7,8-dimethoxy-1,4-benzothiazepin-4-yl acetate S,S-dioxide, mp 154-156° C

(46) 3,3-Diethyl-2,3,4,5-tetrahydro-5-phenyl-1,4-benzothiazepin-8-ol1,1-dioxide, mp 177-178° C

(47) 3,3-Diethyl-2,3,4,5-tetrahydro-7-methoxy-5-phenyl-1,4-benzothiazepin-8-ol 1,1-dioxide

(48) 3,3-Dibutyl-2,3,4,5-tetrahydro-5-phenyl-1,4-benzothiazepin-8-ol1,1-dioxide

(49) (+-)-Trans-3-Butyl-3-ethyl-2,3,4,5-tetrahydro-1,1-dioxo-5-phenyl-1,4-benzothiazepin-8-yl hydrogen sulfate, mp 196.5-200°C

(50) (+-)-Trans-3-Butyl-3-ethyl-2,3,4,5-tetrahydro-1,1-dioxo-5-phenyl-1,4-benzothiazepin-8-yl dihydrogen phosphate

(51) 3,3-Diethyl-2,3,4,5-tetrahydro-1,1-dioxo-5-phenyl-1,4-benzothiazepin-8-ylhydrogen sulfate

(52) 3,3-Diethyl-2,3,4,5-tetrahydro-1,1-dioxo-5-phenyl-1,4-benzothiazepin-8-yldihydrogen phosphate

(53) (+-)-Trans-3-Butyl-3-ethyl-2,3,4,5-tetrahydro-1,1-dioxo-5-phenyl-1,4-benzothiazepin-8-yl aspartate

—

1. The compounds of the formula (I) :

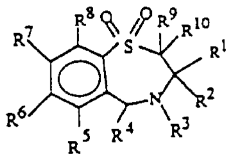

(I)

wherein $R^1$ is a straight chained $C_{1-6}$ alkyl group; $R^2$ is a straight chained $C_{1-6}$ alkyl group; $R^3$ is hydrogen or a group $OR^{11}$ in which $R^{11}$ is hydrogen, optionally substituted $C_{1-6}$ alkyl or a $C_{1-6}$ alkylcarbonyl group; $R^4$ is pyridyl or optionally substituted phenyl; $R^5$, $R^6$, $R^7$ and $R^8$ are the same or different and each is selected from hydrogen, halogen, cyano, $R^{15}$-acetylide, $OR^{15}$, optionally substituted $C_{1-6}$ alkyl, $COR^{15}$, $CH(OH)R^{15}$, $S(O)_nR^{15}$, $P(O)(OR^{15})_2$, $OCOR^{15}$, $OCF_3$, OCN, SCN, NHCN, $CH_2OR^{15}$, CHO, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2OR^{15}$, $OCH{=}CHR^{15}$, $O(CH_2CH_2O)_nR^{15}$, $O(CH_2)_pSO_3R^{15}$, $O(CH_2)_pNR^{12}R^{13}$ and $O(CH_2)_pN^+R^{12}R^{13}R^{14}$ wherein p is an integer from 1-4, n is an integer from 0-3 and $R^{12}$, $R^{13}$, $R^{14}$ and $R^{15}$ are independently selected from hydrogen and optionally substituted $C_{1-6}$ alkyl; or $R^6$ and $R^7$ are linked to form a group

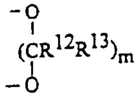

wherein $R^{12}$ and $R^{13}$ are as hereinbefore defined and m is 1 or 2; and $R^9$ and $R^{10}$ are the same or different and each is hydrogen or $C_{1-6}$ alkyl; with the proviso that when $R^3$ is hydrogen either $R^7$ is not hydrogen or at least two of $R^5$, $R^6$, $R^7$ and $R^8$ are not hydrogen; and salts, solvates and physiologically functional derivatives thereof.

2. The compounds as claimed in claim 1 which are of the formula (II)

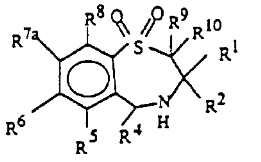

(II)

wherein $R^1$ to $R^{10}$ are as hereinbefore defined and $R^{7a}$ is selected from halogen, cyano, $R^{15}$-acetylide, $OR^{15}$, optionally substituted $C_{1-6}$ alkyl, $COR^{15}$, $CH(OH)R^{15}$, $S(O)_nR^{15}$, $P(O)(OR^{15})_2$, $OCOR^{15}$, $OCF_3$, OCN, SCN, HNCN, $CH_2OR^{15}$, CHO, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2OR^{15}$, $OCH{=}CHR^{15}$, $O(CH_2CH_2O)_nR^{15}$, $O(CH_2)_pSO_3R^{15}$, $O(CH_2)_pNR^{12}R^{13}$ and $O(CH_2)_pN^+R^{12}R^{13}R^{14}$ wherein n, p and $R^{12}$ to $R^{15}$ are as hereinbefore defined; and salts, solvates or physiologically functional derivatives thereof.

3. The compounds as claimed in claim 1 which are of the formula (III) :

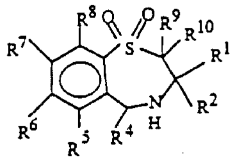

(III)

wherein $R^1$-$R^{10}$ are as defined in claim 1; and salts, solvates and physiologically functional derivatives thereof.

4. The compounds as claimed in claim 1 which are of the formula (IV)

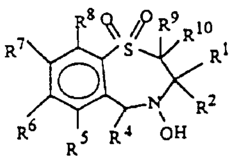

(IV)

wherein $R^1$-$R^{10}$ are as defined in claim 1; and salts, solvates and physiologically functional derivatives thereof.

5. The compounds as claimed in claim 1 which are of the formula (IVa)

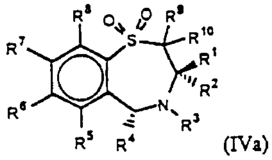

(IVa)

wherein $R^1$-$R^{10}$ are as defined in claim 1; and salts, solvates and physiologically functional derivatives thereof.

6. The compounds as claimed in claim 1 wherein:
$R^1$ and $R^2$ are straight chained $C_{1-6}$ alkyl;
$R^3$ is hydrogen or hydroxy;
$R^4$ is unsubstituted phenyl;
$R^5$ is hydrogen;
$R^9$ and $R^{10}$ are both hydrogen; and either
$R^7$ is selected from halogen, hydroxy, $C_{1-6}$ alkoxy, optionally substituted $C_{1-6}$ alkyl, $-S(O)_nR^{15}$, $-OC(O)R^{15}$, and $-CH_2OR^{15}$ wherein $R^{15}$ is hydrogen or $C_{1-6}$ alkyl; and
$R^6$ and $R^8$ are independently selected from hydrogen and those groups listed in the definition of $R^7$; or
$R^8$ is hydrogen and $R^6$ and $R^7$ are linked to form a group $-O-(CH_2)_m-O-$ wherein m is 1 or 2;
and salts, solvates, and physiologically functional derivatives thereof 7. A compound according to any of claims 1 to 6 wherein $R^6$ and $R^7$ are both methoxy.

8. A compound selected from the group consisting of:

(3R,5R)-3-Butyl-3-ethyl-2,3,4,5-tetrahydro-7,8-dimethoxy-5-phenyl-1,4-benzothiazepine 1,1-dioxide;

(3R,5R)-3-Butyl-3-ethyl-2,3,4,5-tetrahydro-7,8-dimethoxy-5-phenyl-1,4-benzothiazepin-4-ol 1,1-dioxide;

(+-)-Trans-3-butyl-3-ethyl-2,3,4,5-tetrahydro-7,8-dimethoxy-5-phenyl-1,4-benzothiazepine 1,1-dioxide;

(+-)-Trans-3-butyl-3-ethyl-2,3,4,5-tetrahydro-7,8-dimethoxy-5-phenyl-1,4,-benzothiazepin-4-ol 1,1-dioxide;

(3R,5R)-7-Bromo-3-butyl-3-ethyl-2,3,4,5-tetrahydro-8-methoxy-5-phenyl-1,4-benzothiazepine 1,1-dioxide;

(3R,5R)-7-Bromo-3-butyl-3-ethyl-2,3,4,5-tetrahydro-8-methoxy-5-phenyl-1,4-benzothiazepin-4-ol 1,1-dioxide;

(3R,5R)-3-Butyl-3-ethyl-2,3,4,5-tetrahydro-5-phenyl-1,4-benzothiazepine-7,8-diol 1,1-dioxide;

(3R,5R)-3-Butyl-3-ethyl-2,3,4,5-tetrahydro-8-methoxy-5-phenyl-1,4-benzothiazepin-7-ol 1,1-dioxide;

(3R,5R)-3-Butyl-3-ethyl-2,3,4,5-tetrahydro-7-methoxy-5-phenyl-1,4-benzothiazepin-8-ol 1,1-dioxide;

(+-)-Trans-3-butyl-3-ethyl-2,3,4,5-tetrahydro-8-methoxy-5-phenyl-1,4-benzothiazepine 1,1-dioxide;

(+-)-Trans-3-butyl-3-ethyl-2,3,4,5-tetrahydro-5-phenyl-1,4-benzothiazepin-8-ol 1,1-dioxide;

(+-)-Trans-3-butyl-3-ethyl-2,3,4,5-tetrahydro-5-phenyl-1,4-benzothiazepine-4,8-diol;

(+-)-Trans-3-butyl-3-ethyl-2,3,4,5-tetrahydro-8-methoxy-5-phenyl-1,4-benzothiazepine-7-carbaldehyde 1,1-dioxide;

(+-)-Trans-2-((3-butyl-3-ethyl-2,3,4,5-tetrahydro-8-methoxy-5-phenyl-1,4-benzothiazepin-7-yl)methoxy) ethanol S,S-dioxide;

(+-)-Trans-3-butyl-3-ethyl-2,3,4,5-tetrahydro-8-hydroxy-5-phenyl-1,4-benzothiazepine-7-carbaldehyde 1,1-dioxide;

(+-)-Trans-3-butyl-3-ethyl-2,3,4,5-tetrahydro-5-phenyl-1,4-benzothiazepin-8-thiol 1,1-dioxide;

(+-)-Trans-3-butyl-3-ethyl-2,3,4,5-tetrahydro-5-phenyl-1,4-benzothiazepin-8-sulfonic acid 1,1-dioxide;

(7R,9R)-7-Butyl-7-ethyl-6,7,8,9-tetrahydro-9-phenyl-1,3-dioxolo(4,5-H)(1,4)-benzothiazepine 5,5-dioxide;

(+-)-Trans-3-butyl-3-ethyl-2,3,4,5-tetrahydro-8,9-dimethoxy-5-phenyl-1,4-benzothiazepine 1,1-dioxide;

(3R,5R)-3-butyl-3-ethyl-5-(4-fluorophenyl)-2,3,4,5-tetrahydro-7,8-dimethoxy-1,4-benzothiazpin-4-ol 1,1-dioxide;

(+-)-Trans-3-butyl-3-ethyl-2,3,4,5-tetrahydro-8-methoxy-5-phenyl-1,4-benzothiazepine-7-methanol S,S-dioxide;

(3R,5R)-3-butyl-3-ethyl-2,3,4,5-tetrahydro-8-methoxy-7-nitro-5-phenyl-1,4-benzothiazepine 1,1-dioxide;

(+-)-Trans-3-butyl-3-ethyl-2,3,4,5-tetrahydro-8-methoxy-7-(methoxymethyl)-5-phenyl-1,4-benzothiazepine 1,1-dioxide;

(3R,5R)-3-butyl-3-ethyl-2,3,4,5-tetrahydro-5-phenyl-1,4-benzothiazepin-7,8-diyl diacetate 1,1-dioxide;

(8R,10R)-8-Butyl-8-ethyl-2,3,7,8,9,10-hexahydro-10-1,4-dioxono(2,3-H)(1,4)-benzothiazepine 6,6-dioxide;

(3R,5R)-3-butyl-7,8-diethoxy-2,3,4,5-tetrahydro-5-phenyl-1,4-benzothiazepine 1,1-dioxide;

(+-)-Trans-3-butyl-8-ethoxy-3-ethyl-2,3,4,5-tetrahydro-5-phenyl-1,4-benzothiazepine 1,1-dioxide;

(+-)-Trans-3-butyl-3-ethyl-2,3,4,5-tetrahydro-8-isopropoxy-5-phenyl-1,4-benzothiazepine 1,1-dioxide hydrochloride;

(+-)-Trans-3-butyl-3-ethyl-2,3,4,5-tetrahydro-5-phenyl-1,4-benzothiazepin-8-carbaldehyde 1,1-dioxide;

3,3-Diethyl-2,3,4,5-tetrahydro-7,8-dimethoxy-5-phenyl-1,4-benzothiazepine 1,1-dioxide;

3,3-Diethyl-5-(4-fluorophenyl)-2,3,4,5-tetrahydro-8-methoxy-1,4-benzothiazepine 1,1-dioxide;

3,3-Diethyl-2,3,4,5-tetrahydro-8-methoxy-5-phenyl-1,4-benzothiazepine 1,1-dioxide;

3,3-Diethyl-2,3,4,5-tetrahydro-5-phenyl-1,4-benzothiazpin-4,8-diol 1,1-dioxide;

(RS)-3,3-Diethyl-2,3,4,5-tetrahydro-4-hydroxy-7,8-dimethoxy-5-phenyl-1,4-benzothiazepine 1,1-dioxide;

(+-)-Trans-3-butyl-8-ethoxy-3-ethyl-2,3,4,5-tetrahydro-5-phenyl-1,4-benzothiazepin-4-ol1,1-dioxide;

(+-)-Trans-3-butyl-3-ethyl-2,3,4,5-tetrahydro-8-isopropoxy-5-phenyl-1,4-benzothiazepin-4-ol 1,1-dioxide;

(+-)-Trans-3-butyl-3-ethyl-2,3,4,5-tetrahydro-7,8,9-trimethoxy-5-phenyl-1,4-benzothiazepin-4-ol 1,1-dioxide;

(3R,5R)-3-butyl-3-ethyl-2,3,4,5-tetrahydro-5-phenyl-1,4-benzothiazpin-4,7,8-triol 1,1-dioxide;

(+-)-Trans-3-butyl-3-ethyl-2,3,4,5-tetrahydro-4,7,8-trimethoxy-5-phenyl-1,4-benzothiazepine 1,1-dioxide;

(+-)-Trans-3-butyl-3-ethyl-5-phenyl-2,3,4,5-tetrahydro-7,8-dimethoxy-1,4-benzothiazepin-4-yl acetate S,S-dioxide;

3,3-Diethyl-2,3,4,5-tetrahydro-5-phenyl-1,4-benzothiazepin-8-ol 1,1-dioxide;

3,3-Diethyl-2,3,4,5-tetrahydro-7-methoxy-5-phenyl-1,4-benzothiazepin-8-ol 1,1-dioxide;

3,3-Dibutyl-2,3,4,5-tetrahydro-5-phenyl-1,4-benzothiazepin-8-ol 1,1-dioxide;

(+-)-Trans-3-Butyl-3-ethyl-2,3,4,5-tetrahydro-1,1-dioxo-5-phenyl-1,4-benzothiazepin-8-yl hydrogen sulfate;

(+-)-Trans-3-Butyl-3-ethyl-2,3,4,5-tetrahydro-1,1-dioxo-5-phenyl-1,4-benzothiazepin-8-yl dihydrogen phosphate;

3,3-Diethyl-2,3,4,5-tetrahydro-1,1-dioxo-5-phenyl-1,4-benzothiazepin-8-yl hydrogen sulfate;

3,3-Diethyl-2,3,4,5-tetrahydro-1,1-dioxo-5-phenyl-1,4-benzothiazepin-8-yl dihydrogen phosphate;

(+-)-Trans-3-Butyl-3-ethyl-2,3,4,5-tetrahydro-1,1-dioxo-5-phenyl-1,4-benzothiazepin-8-yl aspartate; and 3,3-Diethyl-2,3,4,5-tetrahydro-1,1-dioxo-5-phenyl-1,4-benzothiazepin-8-yl aspartate.

9. (3R,5R)-3-Butyl-3-ethyl-2,3,4,5-tetrahydro-7, 8-dimethoxy-5-phenyl-1,4-benzothiazepine 1,1-dioxide, or a salt, solvate, or physiologically functional derivative thereof.

Compounds ) having exceptional hypolipidaemic properties include:-

(+-)-trans-3-ethyl-2,3,4,5-tetrahydro-3-((2R)-2-hydroxybutyl)-5-phenyl-1,4-benzothiazepine 1,1-dioxide;

(+-)-trans-1-(3-ethyl-2,3,4,5-tetrahydro-8-methoxy-5-phenyl-1,4-benzothiazepin-3-yl-2(R)-2-butanol S,S-dioxide;

(+-)-trans-1-(3-ethyl-2,3,4,5-tetrahydro-8-methoxy-5-phenyl-1,4-benzothiazepin-3-yl)-3-butanol S,S-dioxide;

(+-)-trans-1-(3-ethyl-2,3,4,5-tetrahydro-7-methoxy-5-phenyl-1,4-benzothiazepin-3-yl)-2(R)-2-butanol S,S-dioxide;

(+-)-trans-1-(3-ethyl-5-(4-fluorophenyl)-2,3,4,5-tetrahydro-7-methoxy-1,4-benzothiazepin-3-yl)-2(R)-2-butanol S,S-dioxide;

(+-)-trans-1-(3-ethyl-5-(4-hydroxyphenyl)-2,3,4,5-tetrahydro-1,4-benzothiazepin-3-yl)-2(R)-2-butanol S;S-dioxide 0.5 hydrate;

(+-)-trans-3-butyl-3-ethyl-2,3,4,5-tetrahydro-5-(4-hydroxyphenyl)-1,4-benzothiazepine 1,1-dioxide hydrochloride;
(+-)-cis-3-ethyl-2,3,4,5-tetrahydro-3-(4-hydroxybutyl)-5-phenyl-1,4-benzothiazepine 1,1-dioxide hydrochloride;
(+-)-trans-3-ethyl-2,3,4,5-tetrahydro-3-(4-hydroxybutyl)-5-phenyl-1,4-benzothiazepine 1,1-dioxide;
(+-)-trans-3-butyl-3-ethyl-2,3,4,5-tetrahydro-7-hydroxy-5-phenyl-1,4-benzothiazepine 1,1 dioxide;
(+-)-trans-1-(3-ethyl-2,3,4,5-tetrahydro-5-phenyl-1,4-benzothiazepin-3-yl)-4,4,4-trifluoro-(2S)-2-butanol- S,S-dioxide;
(+-)-trans-1-(3-ethyl-2,3,4,5-tetrahydro-7-methoxy-5-phenyl-1,4-benzothiazepin-3-yl)-4,4,4-trifluoro-(2S)-2-butanol-S,S-dioxide;
(+-)-trans-3-Ethyl-2,3,4,5-tetrahydro-3-(3-hydroxybutyl)-5-phenyl-1,4-benzothiazepine 1,1-dioxide;
(+-)-trans-3-Ethyl-2,3,4,5-tetrahydro-3-(2(R)-2-hydroxybutyl)-5-(4-hydroxyphenyl)-1,4-benzothiazepine 1,1-dioxide;
(+-)-trans-1-(3-Ethyl-5-(4-fluorophenyl)-2,3,4,5-tetrahydro-1,4-benzothiazepin-3-yl)-2(R)-2-butanol S,S-dioxide;
(+-)-trans-1-(3-Ethyl-2,3,4,5-tetrahydro-7-methoxy-5-phenyl-1,4 benzothiazepin-3-yl)-4,4,4-trifluoro-2(S)-2-butanol S,S-dioxide;
(+-)-trans-1-(3-Ethyl-2,3,4,5-tetrahydro-8-methoxy-5-phenyl-1,4-benzothiazepin-3-yl)-4,4,4-trifluoro-2(S)-butanol S,S-dioxide;
(+-)-trans-1-(3-ethyl-2,3,4,5-tetrahydro-7,8-dimethoxy-5-phenyl-1,4-benzothiazepin-3-yl-2(R)-2-butanol S,S dioxide;
(+-)-trans-1-(3-Ethyl-2,3,4,5-tetrahydro-7,8-dimethoxy-5-phenyl-1,4-benzothiazepin-3-yl)-4,4,4-trifluoro-2-butanol S,S-dioxide;
(+-)-trans-1-(3-Ethyl-2,3,4,5-tetrahydro-7,8-dimethoxy-5-phenyl-1,4-benzothiazepin-3-yl)-3,3,4,4,4-pentafluoro-2-butanol S,S-dioxide;
(+-)- trans-3-((3-ethyl-2,3,4,5-tetrahydro-5-phenyl-3-(4,4,4-trifluoro-2-hydroxybutyl)-1, 4-benzothiazepin-8-yl)oxy)propanesulfonic acid 1, 1-dioxide;
(+-)-trans-3-((3-ethyl-2,3,4,5-tetrahydro-3-(2-hydroxybutyl)-5-phenyl-1,4-benzothiazepin-8-yl)oxy)ethyltrimethylammonium iodide 1, 1-dioxide;
(+-)-trans-1-(3-Ethyl-2,3,4,5-tetrahydro-7,8-diethoxy-5-phenyl-1,4-benzothiazepin-3-yl)-4,4,4-trifluoro-2-butanol S,S-dioxide;
(+-)-trans-3-((3-ethyl-2,3,4,5-tetrahydro-5-phenyl-3(4,4,4-trifluoro-2-hydroxybutyl)-1,4-benzothiazepin-8-yl)oxy)ethyltrimethylammonium iodide 1,1-dioxide;

(+-)-trans-3-((3-ethyl-2,3,4,5-tetrahydro-3-(2-hydroxybutyl)-5-phenyl-1,4-benzothiazepin-8-yl)oxy)propanesulfonic acid 1,1-dioxide;

(+-)-trans-1-(3-ethyl-2,3,4,5-tetrahydro-7,8-diethoxy-5-phenyl-1,4-benzothiazepin-3-yl)-2-butanol S,S-dioxide;

(+-)-trans-1-(3-(2,2,2-trifluoroethyl)-2,3,4,5-tetrahydro-7,8-dimethoxy-5-phenyl-1,4-benzothiazepin-3-yl)-4,4,4-trifluoro-2-butanol S,S-dioxide;

(+-)-trans-1-(3-Ethyl-2,3,4,5-tetrahydro-7,8-dihydroxy-5-phenyl-1,4-benzothiazepin-3-yl)-4,4,4-trifluoro-2-butanol S,S-dioxide;

(+-)-trans-1-(3-ethyl-2,3,4,5-tetrahydro-7,8-dimethoxy-5-phenyl-1,4-benzothiazepin-3-yl)-1-butanol S,S-dioxide;

(+-)-trans-1-(3-Ethyl-2,3,4,5-tetrahydro-7,8-dihydroxy-5-phenyl-1,4-benzothiazepin-3-yl)-2-butanol S,S-dioxide;

(+-)-trans-1-(3-ethyl-2,3,4,5-tetrahydro-8-methoxy-5-phenyl-1,4-benzothiazepin-3-yl)-4,4,4-trifluoro-1-butanol S,S-dioxide;

(+-)-trans-1-(3-ethyl-2,3,4,5-tetrahydro-7,8-dihydroxy-5-phenyl-1,4-benzothiazepin-3-yl)-2-butanone S,S-dioxide;

Of the above the following compounds are most preferred:-

(+-)-trans-1-(3-ethyl-5-(4-fluorophenyl)-2,3,4,5-tetrahydro-7-methoxy-1,4-benzothiazepin-3-yl)-2(R)-2-butanol S,S-dioxide;

(+-)-trans-1-(3-ethyl-2,3,4,5-tetrahydro-5-phenyl-1,4-benzothiazepin-3-yl)-4,4,4-trifluoro-(2S)-2-butanol- S,S-dioxide;

(+-)-trans-1-(3-ethyl-2,3,4,5-tetrahydro-7-methoxy-5-phenyl-1,4-benzothiazepin-3-yl)-4,4,4-trifluoro-(2S)-2-butanol-S,S-dioxide;

(+-)-trans-1-(3-Ethyl-2,3,4,5-tetrahydro-8-methoxy-5-phenyl-1,4-benzothiazepin-3-yl)-4,4,4-trifluoro-2(S)-butanol S,S-dioxide;

(+-)-trans-1-(3-ethyl-2,3,4,5-tetrahydro-7,8-dimethoxy-5-phenyl-1,4-benzothiazepin-3-yl-2(R)-2-butanol S,S dioxide;

13) (+-)-Trans-2,3,4,5-Tetrahydro-3-methyl-5-phenyl-1,4-benzothiazepine-3-methanol 1,1-dioxide, mp 79-80°C;

14) (+-)-Cis-2,3,4,5-Tetrahydro-3-methyl-5-phenyl-1,4-benzothiazepine-3-methanol 1,1-dioxide hydrochloride 0.25 hydrate mp 222-224°C;

15) (+-)-Trans-4-(3-Butyl-3-ethyl-2,3,4,5-tetrahydro-1,4-benzothiazepin-5-yl)phenol hydrochloride, mp 234-235°cC(dec.);

16) (+-)-Trans-5-(4-Benzyloxyphenyl)-3-ethyl-2,3,4,5-tetrahydro-1,4-benzothiazepine-3-methanol, mp 138-143°C;

17) (+-)-Trans-3-Ethyl-2,3,4,5-tetrahydro-5-phenyl-1,4-benzothiapzepine-3-methanol 1.1-dioxide, mp 134-137°C;

18) (+-)-Trans-3-Ethyl-2,3,4,5-tetrahydro-3-(3-hydroxybutyl)-5-phenyl-1,4-benzothiazepine 1,1-dioxide, mp 151-155°C;

19) (+-)-Cis-3-Ethyl-2,3,4,5-tetrahydro-3-butyl-4-hydroxy-5-(3-pyridyl)-1,4-benzothiazepine 1,1-dioxide, mp 202-205°C;

20) (+-)-Cis-4-(3-Butyl-3-ethyl-2,3,4,5-tetrahydro-1,4-benzothiazepin-5-yl)phenol hydrochloride, mp 236-237°C(dec.);

21) (+-)-Cis-3-Butyl-3-ethyl-2,3,4,5-tetrahydro-5-(4-hydroxyphenyl)-1,4-benzothiazepine 1,1-dioxide, mp 163-165°C;

22) (+-)-Cis-3-Ethyl-2,3,4,5-tetrahydro-3-(3-hydroxybutyl))-5-phenyl-1,4-benzothiazepine 1.1-dioxide hydrochloride. mp 206-209°C;

23) (+-)-Trans-3-Ethyl-2,3,4,5-tetrahydro-3-(2(R)-2-hydroxybutyl)-5-(4-hydroxyphenyl)-1.4-benzothiazepine 1.1-dioxide, mp 197-198°C;

24) (+-)-Trans-3-Ethyl-2,3,4,5-tetrahydro-3-(2(S)-2-hydroxybutyl)-5-(4-hydroxyphenyl)-1,4-benzothiazepine 1,1-dioxide, mp 178-179°C;

25) (+-)-Trans-3-Ethyl-2,3,4,5-tetrahydro-5-phenyl-1,4-benzothiazepine-3-methanol, mp 104-106°C;

26) (+-)-Cis-5-(4-Benzyloxyphenyl)-3-ethyl-2,3,4,5-tetrahydro-1,4-benzothiazepine-3-methanol, mp 123-128°C;

27) (+-)-Trans-1-(3-Ethyl-5-(4-fluorophenyl)-2,3,4,5-tetrahydro-1,4-benzothiazepin-3-yl)-2(R)-2-butanol S,S-dioxide, mp 130-132°C;

28) (+-)-Trans-1-(3-Ethyl-2,3,4,5-tetrahydro-5-phenyl-1,4-benzothiazepin-3-yl)-4,4,4-trifluoro-2(R)-2-butanol S,S-dioxide, mp 140-145°C;

29) (+-)-Trans-1-(3-Ethyl-2,3,4,5-tetrahydro-5-phenyl-1,4-benzothiazepin-3-yl)-4-fluoro-2-(RS)-2-butanol S,S-dioxide 0.50 hydrate, mp 130-147°C;

30) (+-)-Trans-1-(3-Ethyl-2,3,4,5-tetrahydro-5-phenyl-1,4-benzothiazepin-3-yl)-4,4,4-trifluoro-2(S)-2-butanol S,oxide, mp 159-161°C;

31) (+-)-Trans-1-(3-Ethyl-2,3,4,5-tetrahydro-7-methoxy-5-phenyl-1,4-benzothiazepin-3-yl)-4,4,4-trifluoro-2(S)-2-butanol S,S-dioxide, mp 168-170°C;

32) (+-)-Trans-1-(3-Ethyl-2,3,4,5-tetrahydro-8-methoxy-5-phenyl-1,4-benzothiazepin-3-yl)-4,4,4-trifluoro-2(S)-2-butanol S,S-dioxide, mp 175-179°C;

33) (+-)-Trans-1-(3-ethyl-2,3,4,5-tetrahydro-7,8-dimethoxy-5-phenyl-1,4-benzothiazepin-3-yl-2(R)-2-butanol S,S-dioxide, mp 156-157°C;

34) (+-)-Trans-1-(3-Ethyl-2,3,4,5-tetrahydro-7,8-dimethoxy-5-phenyl-1,4-benzothiazepin-3-yl)-4,4,4-trifluoro-2-butanol S,S-dioxide;

35) (+-)-Trans-1-(3-Ethyl-2,3,4,5-tetrahydro-8-methoxy-5-phenyl-1,4-benzothiazepin-3-yl)-3,3,4,4,4-pentafluoro-2-butanol S,S-dioxide;

36) (+-)-Trans-1-(3-Ethyl-2,3,4,5-tetrahydro-7,8-dimethoxy-5-phenyl-1,4-benzothiazepin-3-yl)-3,3,4,4,4-pentafluoro-2-butanol S,S-dioxide;

37) (+-)-Trans-3-((3-ethyl-2,3,4,5-tetrahydro-5-phenyl-3-(4,4,4-trifluoro-2-hydroxybutyl)-1,4-benzothiazepin-7-yl)oxy)propanesulfonic acid 1,1-dioxide;

38) (+-)-Trans-3-((3-ethyl-2,3,4,5-tetrahydro-5-phenyl-3-(4,4,4-trifluoro-2- hydroxybutyl)-1,4-benzothiazepin-8-yl)oxy)propanesulfonic acid 1,1-dioxide;

39) (+-)-Trans-3-((3-ethyl-2,3,4,5-tetrahydro-3-(2-hydroxybutyl)-5-phenyl-1,4-benzothiazepin-7-yl)oxy)ethyltrimethylammonium iodide 1,1-dioxide;

40) (+-)-Trans-3-((3-ethyl-2,3,4,5-tetrahydro-3-(2-hydroxybutyl)-5-phenyl-1,4-benzothiazepin-8-yl)oxy)ethyltrimethylammonium iodide 1,1-dioxide;

41) (+-)-Trans-1-(3-Ethyl-2,3,4,5-tetrahydro-7,8-diethoxy-5-phenyl-1,4-benzothiazepin-3-yl)-4,4,4-trifluoro-2-butanol S,S-dioxide;

42) (+-)-Trans-3-((3-ethyl-2,3,4,5-tetrahydro-5-phenyl-3(4,4,4-trifluoro-2-hydroxybutyl)-1,4-benzothiazepin-7-yl)oxy)ethyltrimethylammonium iodide 1,1-dioxide 43) (+-)-Trans-3-((3-ethyl-2,3,4,5-tetrahydro-5-phenyl-3(4,4,4-trifluoro-2-hydroxybutyl)-1,4-benzothiazepin-8-yl)oxy)ethyltrimethylammonium iodide 1,1-dioxide;

44) (+-)-Trans-3-((3-ethyl-2,3,4,5-tetrahydro-3-(2-hydroxybutyl)-5-phenyl-1,4-benzothiazepin-8-yl)oxy)propanesulfonic acid 1,1-dioxide;

45) (+-)-Trans-3-((3-ethyl-2,3,4,5-tetrahydro-3-(2-hydroxybutyl)-5-phenyl-1,4-benzothiazepin-7-yl)oxy)propanesulfonic acid 1,1-dioxide;

46) (+-)-Trans-1-(3-ethyl-2,3,4,5-tetrahydro-7,8-diethoxy-5-phenyl-1,4-benzothiazepin-3-yl)-2-butanol S,S-dioxide;

47) (+-)-Trans-1-(3-(2,2,2-trifluoroethyl)-2,3,4,5-tetrahydro-7,8-dimethoxy-5-phenyl-1,4-benzothiazepin-3-yl)-4,4,4-trifluoro-2-butanol S,S-dioxide;

48) (+-)-Trans-1-(3-(2,2,2-trifluoroethyl)-2,3,4,5-tetrahydro-8-methoxy-5-phenyl-1,4-benzothiazepin-3-yl)-4,4,4-trifluoro-2-butanol S,S-dioxide;

49) (+-)-Trans-1-(3-Ethyl-2,3,4,5-tetrahydro-9-methoxy-5-phenyl-1,4-benzothiazepin-3-yl)-4,4,4-trifluoro-2-butanol S,S-dioxide;

50) (+-)-Trans-1-(3-ethyl-2,3,4,5-tetrahydro-9-methoxy-5-phenyl-1,4-benzothiazepin-3-yl)-2-butanol S,S-dioxide;

51) (+-)-Trans-1-(3-Ethyl-2,3,4,5-tetrahydro-7,8-dihydroxy-5-phenyl-1,4-benzothiazepin-3-yl)-4,4,4-trifluoro-2-butanol S,S-dioxide;

52) (+-)-Trans-1-(3-ethyl-2,3,4,5-tetrahydro-8-methoxy-5-phenyl-1,4-benzothiazepin-3-yl)-1-butanol S,S-dioxide;

53) (+-)-Trans-1-(3-ethyl-2,3,4,5-tetrahydro-7,8-dimethoxy-5-phenyl-1,4-benzothiazepin-3-yl)-1-butanol S,S-dioxide;

54) (+-)-Trans-1-(3-Ethyl-2,3,4,5-tetrahydro-7,8-dihydroxy-5-phenyl-1,4-benzothiazepin-3-yl)-2-butanol S,S-dioxide;

55) (+-)-Trans-1-(3-ethyl-2,3,4,5-tetrahydro-8-methoxy-5-phenyl-1,4-benzothiazepin-3-yl)-4,4,4-trifluoro-1-butanol S,S-dioxide;

56) (+-)-Trans-1-(3-ethyl-2,3,4,5-tetrahydro-7,8-dimethoxy-5-phenyl-1,4-benzothiazepin-3-yl)-4,4,4-trifluoro-1-butanol S,S-dioxide 57) (+-)-Trans-1-(3-Ethyl-2,3,4,5-tetrahydro-7,8-dihydroxy-5-phenyl-1,4-benzothiazepin-3-yl)-2-butanone S,S-dioxide 1. A compound of formula (I):

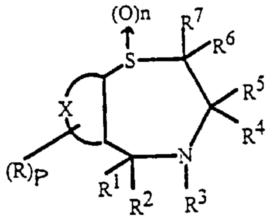

(I)

Wherein l is an integer of from 0 to 4;

n is an integer of from 0 to 2;

R is an atom or group selected from halogen, cyano, hydroxy, nitro, alkyl, alkoxy, aryl, heteroaryl, aryloxy, arylalkoxy, aralkyl, alkaryl, $-O(CH_2)_pSO_3R^{11}$, $-O(CH_2)_pNR^{11}R^{12}$, $-O(CH_2)_pN^+R^{11}R^{12}R^{14}$, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_2NR^{11}R^{12}$ and $-SO_3R^{11}$ or R is a group $-OCH_2O-$ which forms a further ring attached to X wherein p is an integer of from 1 to 4, $R^{11}$ $R^{12}$ are independently selected from hydrogen, $C_{1-6}$ alkyl and phenyl and $R^{14}$ is hydrogen or $C_{1-6}$ alkyl, wherein said alkyl, alkoxy, aryl, heteroaryl, aryloxy, arylalkoxy, aralkyl and alkaryl groups are optionally substituted by one or more atoms or groups selected from halogen, hydroxy, nitro, nitrile, alkyl, alkoxy, $-COR^{11}$, $-CO_2R^{11}$, $-SO_3R^{11}$ wherein $R^{11}$ is as hereinbefore defined and $-NR^{14}R^{15}$ wherein $R^{14}$ is as hereinbefore defined and $R^{15}$ is hydrogen or $C_{1-6}$ alkyl $R^1$ is hydrogen or $C_{1-6}$ alkyl;

$R^2$ is an atom or group selected from hydrogen, $C_{1-6}$ alkyl (including cycloalkyl and cycloalkylalkyl), $C_{1-4}$ alkoxy, pyrryl, thienyl, pyridyl, 1,3-benzodioxolo, phenyl and naphthyl, which groups are optionally substituted by one or more atoms or groups independently selected from halogen, cyano, hydroxy, nitro, carboxyl, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_3R^{11}$ (wherein $R^{11}$ and $R^{12}$ are as hereinbefore defined), $-OCH_2)_pNR^{11}R^{12}$, $-O(CH_2)_pN^+R^{11}R^{12}R^{13}$ and $-O(CH_2)_pSO_3R^{11}$ (wherein p, $R^{11}$ and $R^{12}$ are as hereinbefore defined and $R^{13}$ is hydrogen or $C_{1-6}$ alkyl);

$R^3$ is hydrogen, hydroxy $C_{1-6}$ alkyl, alkoxy or $-O-C_{1-6}$ Acyl;

$R^4$ is a group independently selected from $C_{1-6}$ alkyl (including cycloalkyl and cycloalkylalkyl), $C_{2-6}$ alkenyl, and $C_{2-6}$ alkynyl, which groups are optionally substituted by one or more atoms or groups independently selected from halogen, oxo, $-OR^{14}$, $-CO_2R^{14}$, $-NR^{14}R^{15}$, $-SR^{14}$, $-S(O)C_{1-6}$ alkyl, $-SO_2R^{14}$ and $-SO_3R^{14}$ (wherein $R^{14}$ and $R^{15}$ are as hereinbefore defined );

$R^5$ is a group independently selected from $C_{2-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, oxo, $-OR^{14}$, $-CO_2R^{14}$, $-NR^{14}R^{15}$, $-SR^{14}$, $-S(O)C_{1-6}$ alkyl, $-SO_2R^{14}$ and $-SO_3R^{14}$ (wherein $R^{14}$ and $R^{15}$ are as hereinbefore defined);

or $R^4$ and $R^5$, together with the carbon atom to which they are attached, form a $C_{3-7}$ spiro cycloalkyl group which is optionally substituted by one or more atoms or groups independently selected from halogen, $-OR^{14}$, $-CO_2R^{14}$, $-SO_3R^{14}$ and $-NR^{14}R^{15}$ (wherein $R^{14}$ and $R^{15}$ are as hereinbefore defined);

$R^6$ and $R^7$ are independently selected from hydrogen and $C_{1-6}$ alkyl; and X is an aromatic or non-aromatic monocyclic or bicyclic ring system having from 5 to 10 carbon atoms (including the two carbon atoms forming part of the thiazepine ring) wherein optionally one or more of the carbon atoms is/are replaced by heteroatom(s) independently selected from nitrogen, oxygen and sulphur;

with the proviso that at least one of R, $R^2$, $R^4$ and $R^5$ is hydroxy or a group containing hydroxy;

and salts, solvates and physiologically functional derivatives thereof.

2. A compound as claimed in Claim 1 wherein:

l is 0, 1, or 2;

n is 1 or 2; and $R^1$, $R^6$ and $R^7$ are all hydrogen; and $R^3$ is hydrogen or hydroxy 3. A compound as claimed in Claim 2 which is a trans isomer wherein:

(a) l is 0 or 1;

n is 2; and $R^4$ and $R^5$ are groups independently selected from $C_{1-6}$ alkyl (including cycloalkyl and cycloalkylalkyl), $C_{2-6}$ alkenyl and $C_{2-6}$ alkynyl, wherein said alkyl, alkenyl, or alkynyl group may be substituted by one or more hydroxy groups, or $R^4$ and $R^5$, together with the carbon atom to which they are attached, form a $C_{3-7}$ spiro cycloalkyl group which can be substituted by one or more hydroxy groups; or (b) l is 0 or 1;

n is 2;

$R^2$ is a phenyl group which may be substituted by one or more atoms or groups independently selected from halogen, cyano, hydroxy, nitro, carboxyl, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_3R^{11}$ (wherein $R^{11}$ and $R^{12}$ are independently selected from hydrogen, $C_{1-6}$ alkyl and phenyl), $-O(CH_2)_pNR^{11}R^{12}$, $-O(CH_2)_pNR^{+11}R^{12}R^{13}$ and $-O(CH_2)_pSO_3R^{11}$ (wherein p is an integer of from 1 to 4, $R^{11}$ and $R^{12}$ are as hereinbefore defined and $R^{13}$ is hydrogen or $C_{1-6}$ alkyl);

$R^4$ and $R^5$ are groups independently selected from $C_{1-6}$ alkyl (including cycloalkyl and cycloalkylalkyl), $C_{2-6}$ alkenyl and $C_{2-6}$ alkynyl, wherein said alkyl, alkenyl, or alkynyl group may be substituted by one or more hydroxy groups, or $R^4$ and $R^5$, together with the carbon atom to which they are attached, form a $C_{3-7}$ spiro cycloalkyl group which can be substituted by one or more hydroxy groups; or (c) l is 0 or 1:

n is 2;

$R^2$ is a phenyl group which may be substituted by one or more atoms or groups independently selected from halogen, cyano, hydroxy, nitro, carboxyl, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_3R^{11}$ (wherein $R^{11}$ and $R^{12}$ are independently selected from hydrogen, $C_{1-6}$ alkyl and phenyl), $-O(CH_2)_pNR^{11}R^{12}$, $-O(CH_2)_pNR^{+11}R^{12}R^{13}$ and $-O(CH_2)_pSO_3R^{11}$ (wherein p is an integer of from 1 to 4, $R^{11}$ and $R^{12}$ are as hereinbefore defined and $R^{13}$ is hydrogen or $C_{1-6}$ alkyl);

$R^4$ and $R^5$ are groups independently selected from $C_{1-6}$ alkyl (including cycloalkyl and cycloalkylalkyl), $C_{2-6}$ alkenyl and $C_{2-6}$ alkynyl, which groups can be substituted by one or more hydroxy groups; and X is a fused phenyl, naphthyl, pyrryl, thienyl, or pyridyl group;

4. A compound as claimed in Claim 1 which is:

(+-)-trans-3-ethyl-2,3,4,5-tetrahydro-3-((2R)-2-hydroxybutyl)-5-phenyl-1,4-benzothiazepine 1,1-dioxide;
(+-)-trans-1-(3-ethyl-2,3,4,5-tetrahydro-8-methoxy-5-phenyl-1,4-benzothiazepin-3-yl-2(R)-2-butanol S.S-dioxide;
(+-)-trans-1-(3-ethyl-2,3,4,5-tetrahydro-8-methoxy-5-phenyl-1,4-benzothiazepin-3-yl)-3-butanol S,S-dioxide;
(+-)-trans-1-(3-ethyl-2,3,4,5-tetrahydro-7-methoxy-5-phenyl-1,4-benzothiazepin-3-yl)-2(R)-2-butanol S,S-dioxide;
(+-)-trans-1-(3-ethyl-5-(4-fluorophenyl)-2,3,4,5-tetrahydro-7-methoxy-1,4-benzothiazepin-3-yl)-2(R)-2-butanol S,S-dioxide;
(+-)-trans-1-(3-ethyl-5-(4-hydroxyphenyl)-2,3,4,5-tetrahydro-1,4-benzothiazepin-3-yl)-2(R)-2-butanol S.S-dioxide 0.5 hydrate:

(+-)-trans-3-butyl-3-ethyl-2,3,4,5-tetrahydro-5-(4-hydroxyphenyl)-1,4-benzothiazepine 1,1-dioxide hydrochloride;

(+-)-cis-3-ethyl-2,3,4,5-tetrahydro-3-(4-hydroxybutyl)-5-phenyl-1,4-benzothiazepine 1,1-dioxide hydrochloride;

(+-)-trans-3-ethyl-2,3,4,5-tetrahydro-3-(4-hydroxybutyl)-5-phenyl-1,4-benzothiazepine 1,1-dioxide;

(+-)-trans-3-butyl-3-ethyl-2,3,4,5-tetrahydro-7-hydroxy-5-phenyl-1,4-benzothiazepine 1,1 dioxide;

(+-)-trans-1-(3-ethyl-2,3,4,5-tetrahydro-5-phenyl-1,4-benzothiazepin-3-yl)-4,4,4-trifluoro-(2S)-2-butanol- S,S-dioxide;

(+-)-trans-1-(3-ethyl-2,3,4,5-tetrahydro-7-methoxy-5-phenyl-1,4-benzothiazepin-3-yl)-4,4,4-trifluoro-(2S)-2-butanol-S,S-dioxide;

(+-)-trans-3-Ethyl-2,3,4,5-tetrahydro-3-(3-hydroxybutyl)-5-phenyl-1,4-benzothiazepine 1,1-dioxide;

(+-)-trans-3-Ethyl-2,3,4,5-tetrahydro-3-(2(R)-2-hydroxybutyl)-5-(4-hydroxyphenyl)-1,4-benzothiazepine 1,1-dioxide;

(+-)-trans-1-(3-Ethyl-5-(4-fluorophenyl)-2,3,4,5-tetrahydro-1,4-benzothiazepin-3-yl)-2(R)-2-butanol S,S-dioxide;

(+-)-trans-1-(3-Ethyl-2,3,4,5-tetrahydro-7-methoxy-5-phenyl-1,4 benzothiazepin-3-yl)-4,4,4-trifluoro-2(S)-2-butanol S,S-dioxide;

(+-)-trans-1-(3-Ethyl-2,3,4,5-tetrahydro-8-methoxy-5-phenyl-1,4-benzothiazepin-3-yl)-4,4,4-trifluoro-2(S)-butanol S,S-dioxide;

(+-)-trans-1-(3-ethyl-23,4,5-tetrahydro-7,8-dimethoxy-5-phenyl-1, 4-benzothiazepin-3-yl-2(R)-2-butanol S,S dioxide;

(+-)-trans-1-(3-Ethyl-2,3,4,5-tetrahydro-7,8-dimethoxy-5-phenyl-1,4-benzothiazepin-3-yl)-4,4,4-trifluoro-2-butanol S,S-dioxide;

(+-)-trans-1-(3-Ethyl-2,3,4,5-tetrahydro-7,8-dimethoxy-5-phenyl-1,4-benzothiazepin-3-yl)-3,3,4,4,4-pentafluoro-2-butanol S,S-dioxide;

(+-)- trans-3-((3-ethyl-2,3,4,5-tetrahydro-5-phenyl-3-(4,4,4-trifluoro-2-hydroxybutyl)-1, 4-benzothiazepin-8-yl)oxy)propanesulfonic acid 1, 1-dioxide;

(+-)-trans-3-((3-ethyl-2,3,4,5-tetrahydro-3-(2-hydroxybutyl)-5-phenyl-1,4-benzothiazepin-8-yl)oxy)ethyltrimethylammonium iodide 1, 1-dioxide;

(+-)-trans-1-(3-Ethyl-2,3,4,5-tetrahydro-7,8-diethoxy-5-phenyl-1,4-benzothiazepin-3-yl)-4,4,4-trifluoro-2-butanol S,S-dioxide;

(+-)-trans-3-((3-ethyl-2,3,4,5-tetrahydro-5-phenyl-3(4,4,4-trifluoro-2-hydroxybutyl)-1,4-benzothiazepin-8-yl)oxy)ethyltrimethylammonium iodide 1,1-dioxide;

(+-)-trans-3-((3-ethyl-2,3,4,5-tetrahydro-3-(2-hydroxybutyl)-5-phenyl-1,4-benzothiazepin-8-yl)oxy)propanesulfonic acid 1,1-dioxide;
(+-)-trans-1-(3-ethyl-2,3,4,5-tetrahydro-7,8-diethoxy-5-phenyl-1,4-benzothiazepin-3-yl)-2-butanol S,S-dioxide;
(+-)-trans-1-(3-(2,2,2-trifluoroethyl)-2,3,4,5-tetrahydro-7,8-dimethoxy-5-phenyl-1,4-benzothiazepin-3-yl)-4,4,4-trifluoro-2-butanol S,S-dioxide;
(+-)-trans-1-(3-Ethyl-2,3,4,5-tetrahydro-7,8-dihydroxy-5-phenyl-1,4-benzothiazepin-3-yl)-4,4,4-trifluoro-2-butanol S,S-dioxide;
(+-)-trans-1-(3-ethyl-2,3,4,5-tetrahydro-7,8-dimethoxy-5-phenyl-1,4-benzothiazepin-3-yl)-1-butanol S,S-dioxide;
(+-)-trans-1-(3-Ethyl-2,3,4,5-tetrahydro-7,8-dihydroxy-5-phenyl-1,4-benzothiazepin-3-yl)-2-butanol S,S-dioxide;
(+-)-trans-1-(3-ethyl-2,3,4,5-tetrahydro-8-methoxy-5-phenyl-1,4-benzothiazepin-3-yl)-4,4,4-trifluoro-1-butanol S,S-dioxide; or
(+-)-trans-1-(3-ethyl-2,3,4,5-tetrahydro-7,8-dihydroxy-5-phenyl-1,4-benzothiazepin-3-yl)-2-butanone S,S-dioxide 5. A compound as claimed in claim 1 of the formula (Ia)

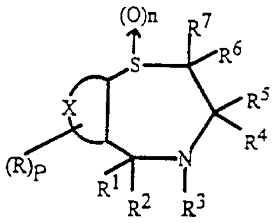

(Ia)

wherein
l is an integer of from 0 to 4;

n is an integer of from 0 to 2;

R is an atom or group selected from halogen, cyano, hydroxy, nitro, alkyl, alkoxy, aryl, heteroaryl, aryloxy, arylalkoxy, aralkyl, alkaryl, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$ and $-SO_3R^{11}$ wherein $R^{11}$ and $R^{12}$ are independently selected from hydrogen, $C_{1-6}$ alkyl and phenyl, wherein said alkyl, alkoxy, aryl, heteroaryl, aryloxy, arylalkoxy, aralkyl and alkaryl groups are optionally substituted by one or more atoms or groups selected from halogen, hydroxy, nitro, nitrile, alkyl, alkoxy, $-COR^{11}$, $-CO_2R^{11}$, -

$SO_3R^{11}$ wherein $R^{11}$ is as hereinbefore defined and $-NR^{14}R^{15}$ wherein $R^{14}$ and $R^{15}$ are as hereinbefore defined;

$R^1$ is hydrogen or $C_{1-6}$ alkyl;

$R^2$ is an atom or group selected from hydrogen, $C_{1-6}$ alkyl (including cycloalkyl and cycloalkylalkyl), $C_{1-4}$ alkoxy, pyrryl, thienyl, pyridyl, 1,3-benzodioxolo, phenyl and naphthyl, which groups are optionally substituted by one or more atoms or groups independently selected from halogen, cyano, hydroxy, nitro, carboxyl, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_3R^{11}$ (wherein $R^{11}$ and $R^{12}$ are independently selected from hydrogen, $C_{1-6}$ alkyl and phenyl), $-O(CH_2)_pNR^{11}R^{12}$, $-O(CH_2)_pN^+R^{11}R^{12}R^{13}$ and $-O(CH_2)_pSO_3R^{11}$ (wherein p is an integer of from 1 to 4, $R^{11}$ and $R^{12}$ are as hereinbefore defined and $R^{13}$ is hydrogen or $C_{1-6}$ alkyl);

$R^3$ is selected from hydrogen, hydroxy and $C_{1-6}$ alkyl;

$R^4$ is a group independently selected from $C_{1-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, $-OR^{14}$, $-CO_2R^{14}$, $-NR^{14}R^{15}$ and $-SO_3R^{14}$ (wherein $R^{14}$ and $R^{15}$ are independently selected from hydrogen and $C_{1-6}$ alkyl);

$R^5$ is a group independently selected from $C_{2-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, $-OR^{14}$, $-CO_2R^{14}$, $-NR^{14}R^{15}$ and $-SO_3R^{14}$ (wherein $R^{14}$ and $R^{15}$ are independently selected from hydrogen and $C_{1-6}$ alkyl);

or $R^4$ and $R^5$, together with the carbon atom to which they are attached, form a $C_{3-7}$ spiro cycloalkyl group which is optionally substituted by one or more atoms or groups independently selected from halogen, $-OR^{14}$, $-CO_2R^{14}$, $-SO_3R^{14}$ and $-NR^{14}R^{15}$ (where $R^{14}$ and $R^{15}$ are as hereinbefore defined;

$R^6$ and $R^7$ are independently selected from hydrogen and $C_{1-6}$ alkyl; and X is an aromatic or non-aromatic monocyclic or bicyclic ring system having from 5 to 10 carbon atoms (including the two carbon atoms forming part of the thiazepine ring) wherein optionally one or more of the carbon atoms is/are replaced by heteroatom(s) independently selected from nitrogen, oxygen and sulphur;

with the proviso that at least one of R, $R^2$, $R^4$ and $R^5$ is hydroxy or a group containing hydroxy;

and salts, solvates and physiologically functional derivatives thereof.

6. A compound of formula (I):

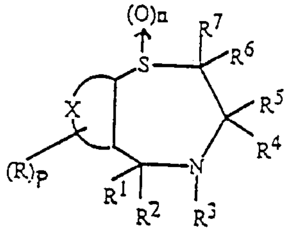

(I)

wherein l is an integer of from 0 to 4;

n is an integer of from 0 to 2;

R is an atom or group selected from halogen, cyano, hydroxy, nitro, alkyl, alkoxy, aryl, heteroaryl, aryloxy, arylalkoxy, aralkyl, alkaryl, $-O(CH_2)_pSO_3R^{11}$, $-O(CH_2)pNR^{11}R^{12}$, $-O(CH_2)_pN^+R^{11}R^{12}R^{14}$, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$ $-SO_2NR^{11}R^{12}$ and $-SO_3R^{11}$ or R is a group $-OCH_2O-$ which forms a further ring attached to X wherein p is an integer of from 1 to 4, $R^{11}$ and $R^{12}$ are independently selected from hydrogen, $C_{1-6}$ alkyl and phenyl and $R^{14}$ is hydrogen or $C_{1-6}$ alkyl, wherein said alkyl, alkoxy, aryl, heteroaryl, aryloxy, arylalkoxy, aralkyl and alkaryl groups are optionally substituted by one or more atoms or groups independently selected from halogen, hydroxy, nitro, nitrile, alkyl, alkoxy, $-COR^{11}$, $-CO_2R^{11}$, $-SO_3R^{11}$ wherein $R^{11}$ is as hereinbefore defined and $-NR^{14}R^{15}$ wherein $R^{14}$ is as hereinbefore defind and $R^{15}$ is hydrogen or $C_{1-6}$ alkyl;

$R^1$ is hydrogen or $C_{1-6}$ alkyl;

$R^2$ is an atom or group selected from hydrogen, $C_{1-6}$ alkyl (including cycloalkyl and cycloalkylalkyl), $C_{1-4}$ alkoxy, pyrryl, thienyl, pyridyl, 1,3-benzodioxolo, phenyl and naphthyl, which groups are optionally substituted by one or more atoms or groups independently selected from halogen, cyano, hydroxy, nitro, carboxyl, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_3R^{11}$ (wherein $R^{11}$ and $R^{12}$ are independently selected from hydrogen, $C_{1-6}$ alkyl and phenyl), $-O(CH_2)_pNR^{11}R^{12}$, $-O(CH_2)_pN^+R^{11}R^{12}R^{13}$ and $-O(CH_2)_pSO_3R^{11}$ (wherein p is an integer of from 1 to 4, $R^{11}$ and $R^{12}$ are as hereinbefore defined and $R^{13}$ is hydrogen or $C_{1-6}$ alkyl);

$R^3$ is hydrogen, hydroxy $C_{1-6}$ alkyl, alkoxy or $-O-C_{1-6}$ Acyl;

$R^4$ is a group independently selected from $C_{1-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, oxo, $-OR^{14}$, $-CO_2R^{14}$, $-NR^{14}R^{15}$, $-SR^{14}$, $-S(O)C_{1-6}$ alkyl, $-SO_2R^{14}$ and $-SO_3R^{14}$ (wherein $R^{14}$ and $R^{15}$ are as hereinbefore defined);

$R^5$ is a group independently selected from $C_{2-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, oxo, $-OR^{14}$, $-CO_2R^{14}$, $-NR^{14}R^{15}$, $-SR^{14}$,$-S(O)C_{1-6}$ alkyl, $-SO_2R^{14}$ and $-SO_3R^{14}$ (wherein $R^{14}$ and $R^{15}$ are as hereinbefore defined);

or $R^4$ and $R^5$, together with the carbon atom to which they are attached, form a $C_{3-7}$ spiro cycloalkyl group which is optionally substituted by one or more atoms or groups independently selected from halogen, $-OR^{14}$, $-CO_2R^{14}$, $-SO_3R^{14}$ and $-NR^{14}R^{15}$ (where $R^{14}$ and $R^{15}$ are as hereinbefore defined;

$R^6$ and $R^7$ are independently selected from hydrogen and $C_{1-6}$ alkyl; and X is an aromatic or non-aromatic monocyclic or bicyclic ring system having from 5 to 10 carbon atoms (including the two carbon atoms forming part of the thiazepine ring) wherein optionally one or more of the carbon atoms is/are replaced by heteroatom(s) independently selected from nitrogen, oxygen and sulphur;

with the proviso that at least one of R, $R^2$, $R^4$ and $R^5$ is hydroxy or a group containing hydroxy;

and salts, solvates and physiologically functional derivatives thereof, for use in the prophylaxis or treatment of clinical conditions for which a bile acid uptake inhibitor in indicated.

Compounds of formula (I) having exceptional hypolipidaemic properties include:-

(-)-(RR)-3-butyl-3-ethyl-2,3,4,5-tetrahydro-5-phenyl-1,4-benzothiazepine 1,1-dioxide;
(+-)-trans-3-((E)-2-butenyl)-3-ethyl-2,3,4,5-tetrahydro-5-phenyl-1,4-benzothiazepine1,1-dioxide;
(+-)-trans-3-ethyl-2,3,4,5-tetrahydro-3-(3-methoxypropyl)-5-phenyl-1,4-benzothiazepine 1,1-dioxide;
(+-)-trans-1-(3-ethyl-2,3,4,5-tetrahydro-5-phenyl-1,4-benzothiazepin-3-yl)-2-butanoneS,S-dioxide;
(+-)-trans-1-(3-ethyl-2,3,4,5-tetrahydro-8-methoxy-5-phenyl-1,4-benzothiazepin-3-yl)-2-butanone S,S-dioxide hydrochloride 1.1 hydrate;
(+-)-trans-3-(1-butenyl)-3-ethyl-2,3,4,5-tetrahydro-5-phenyl-1,4-benzothiazepine1,1-dioxide hydrochloride 0.4 hydrate;
(+-)-trans-3-(ethoxyethyl)-3-ethyl-2,3,4,5-tetrahydro-5-phenyl-1,4-benzothiazepine1,1-dioxide hydrochloride hemihydrate;
(+-)-trans-3-(ethoxymethyl)-3-ethyl-2,3,4,5-tetrahydro-5-phenyl-1,4-benzothiazepine1,1-dioxide hydrochloride;
(+-)-trans-ethyl 3-(3-ethyl-2,3,4,5-tetrahydro-5-phenyl-1,4-benzothiazepin-3-yl)propionate 1,1-dioxide;
(+-)-trans-(E)-4-(3-ethyl-2,3,4,5-tetrahydro-5-phenyl-1,4-benzothiazepin-3-yl)-3-buten-2-one 1,1-dioxide;
(+-)-2,3,4,5-tetrahydro-8-methoxy-5-phenylspiro(1,4-benzothiazepine-3,1-cyclohexane) 1,1-dioxide;
(+-)-trans-3-butyl-3-ethyl-2,3,4,5-tetrahydro-5-(4-pyridyl)-1,4-benzothiazepine 1,1-dioxide;
(+-)-trans-3-butyl-3-ethyl-2,3,4,5-tetrahydro-4-hydroxy-5-(4-pyridyl)-1,4-benzothiazepine 1,1-dioxide;
(+-)-trans-3-butyl-3-ethyl-2,3,4,5-tetrahydro-5-(2-thienyl)-1,4-benzothiazepine 1,1-dioxide;
(+-)-trans-3-butyl-3-ethyl-2,3,4,5-tetrahydro-5-(1H-pyrrol-1-yl)-1,4-benzothiazepine1,1-dioxide;
(+-)-trans-3-butyl-3-ethyl-2,3,4,5-tetrahydro-5-phenylpyrido(4,3-F)-1,4-benzothiazepine 1,1-dioxide;
(+-)-trans-3-butyl-3-ethyl-3,4,5,7-tetrahydro-5-phenyl-2H-pyrrolo(3,4-F)-1,4-benzothiazepine 1.1-dioxide 0.1 hydrate;
(+-)-trans-3-butyl-3-ethyl-2,3,4,5-tetrahydro-5-phenylthieno(2,3-F)-1,4-benzothiazepine1,1-dioxide;

(+-)-trans-3-ethyl-2,3,4,5-tetrahydro-5-phenyl-3-(4,4,4-trifluorobutyl)-1,4-benzothiazepine 1,1-dioxide;
(+-)-trans-2,3,4,5-tetrahydro-3-isopropyl-3-methyl-5-phenyl-1,4-benzothiazepine 1,1-dioxide 0.25 $H_2O$;
(+-)-trans-3-((E)-2-Butenyl)-3-ethyl-2,3,4,5-tetrahydro-5-phenyl-1,4-benzothiazepine;
(+-)-Cis-2,3,4,5-Tetrahydro-3-isopropyl-3-methyl-5-phenyl-1,4-benzothiazepine 1,1-dioxide 0.66 $H_2O$;
(+-)-trans-3-(3-Ethyl-2,3,4,5-tetrahydro-5-phenyl-1,4-benzothiazepin-3-yl)propanol 1,1 dioxide;
(+-)-trans-3-Ethyl-5-(4-Fluorophenyl)-2,3,4,5-tetrahydro-7-methoxy-3-(3-methoxypropyl)-1,4-benzothiazepine 1,1-dioxide hydrochloride;
(+-)-2,3,4,5-Tetrahydro-7-methoxy-5-phenylspiro(1,4-benzothiazepine-3,1-cyclohexane) 1,1-dioxide;
(+-)-trans-1-(3-Ethyl-2,3,4,5-tetrahydro-7-methoxy-5-phenyl-1,4-benzothiazepin-3-yl)-2-butanone S,S-dioxide hydrochloride;
(+-)- trans-3-butyl-3-ethyl-2,3,4,5-tetrahydro-5-phenylnaphtho(3,2-F)-1,4-benzothiazepine 1,1-dioxide;
(+-)-trans-1-(3-Ethyl-2,3,4,5-tetrahydro-7,8-dimethoxy-5-phenyl-1,4-benzothiazepin-3-yl)-2-butanone S,S-dioxide;
(+-)-trans-3-(1-butenyl)-3-ethyl-2,3,4,5-tetrahydro-7,8-dimethoxy-5-phenyl -1,4-benzothiazepine 1,1-dioxide;
(+-)-trans-1-(3-Ethyl-2,3,4,5-tetrahydro-7,8-dimethoxy-5-phenyl-1,4-benzothiazepin-3-yl)-3-butanone S,S-dioxide;
(+-)-trans-1-(3-Ethyl-2,3,4,5-tetrahydro-8-methoxy-5-phenyl-1,4-benzothiazepin-3-yl)-1-butanone S,S-dioxide;
(+-)-trans-1-(3-Ethyl-2,3,4,5-tetrahydro-7,8-dimethoxy-5-phenyl-1,4-benzothiazepin-3-yl)-1-butanone S,S-dioxide;
(+-)-trans-1-(3-ethyl-2,3,4,5-tetrahydro-7,8-dimethoxy-5-phenyl-1,4-benzothiazepin-3-yl)-4,4,4-trifluoro-1-butanone S,S-dioxide;
(+-)-trans-1-(3-ethyl-2,3,4,5-tetrahydro-7,8-dimethoxy-5-phenyl-1,4-benzothiazepin-3-yl)-3,3,4,4,4-pentafluoro-2-butanone S,S-dioxide;
(+-)-trans-1-(3-ethyl-2,3,4,5-tetrahydro-7,8-dimethoxy-5-phenyl-1,4-benzothiazepin-3-yl)-4,4,4-trifluoro-2-butanone S,S-dioxide;
(+-)-trans-3-ethyl-2,3,4,5-tetrahydro-7,8-dimethoxy-5-phenyl-3-(4,4,4-trifluorobutyl)-1,4-benzothiazepine 1,1-dioxide;
(+-)-trans-1-(3-(2,2,2-trifluoroethyl)-2,3,4,5-tetrahydro-7,8-dimethoxy-5-phenyl-1,4-benzothiazepin-3-yl)-2-butanone S,S-dioxide;

(+-)-trans-1-(3-Ethyl-2,3,4,5-tetrahydro-7,8-diethoxy-5-phenyl-1,4-benzothiazepin-3-yl)-2-butanone S,S-dioxide;

(+-)-trans-3-((3-ethyl-2,3,4,5-tetrahydro-3-(2-oxobutyl)-5-phenyl-1,4-benzothiazepin-8-yl)oxy)propanesulfonic acid 1,1-dioxide;

(+-)-trans-2-((3-ethyl-2,3,4,5-tetrahydro-3-(2-oxobutyl)-5-phenyl-1,4-benzothiazepin-8-yl)oxy)ethyltrimethylammonium iodide 1,1-dioxide;

(-)-(RR)-3-butyl-3-ethyl-2,3,4,5-tetrahydro-5-phenyl-1,4-benzothiazepine 1,1-dioxide;

(+-)-trans-1-(3-ethyl-2,3,4,5-tetrahydro-8-methoxy-5-phenyl-1,4-benzothiazepin-3-yl)-2-butanone S,S-dioxide hydrochloride 1.1 hydrate;

(+-)-Cis-2,3,4,5-Tetrahydro-3-isopropyl-3-methyl-5-phenyl-1,4-benzothiazepine 1,1-dioxide 0.66 $H_2O$;

(+-)-trans-1-(3-Ethyl-2,3,4,5-tetrahydro-7,8-dimethoxy-5-phenyl-1,4-benzothiazepin-3-yl)-2-butanone S,S-dioxide;

20) (+-)-2,3,4,5-Tetrahydro-5-phenylspiro(1,4-benzothiazepine-3,1'-cyclohexane) 1,1-dioxide, mp 177-179°C;

21) (+-)-Trans-2,3,4,5-tetrahydro-3-isopropyl-3-methyl-5-phenyl-1,4-benzothiazepine 1,1-dioxide 0.25 $H_2O$, mp 130-132°C;

22) (+)-(S)-2,3,4,5-Tetrahydro-5-phenylspiro(1,4-benzothiazepine-3,1'-cyclohexane) 1,1-dioxide, mp 210-211°C;

23) (-)-(R)-2,3,4,5-Tetrahydro-5-phenylspiro(1,4-benzothiazepine-3,1'-cyclohexane) 1,1-dioxide, mp 210-211°C;

24) (+-)-Trans-2,3,4,5-tetrahydro-3-isopropyl-3-methyl-5-phenyl-1,4-benzothiazepine hydrochloride, mp 211-213°C;

25) (+-)-Cis-2,3,4,5-tetrahydro-3-isopropyl-3-methyl-5-phenyl-1,4-benzothiazepine hydrochloride, mp 268-270°C;

26) (+-)-3-sec-Butyl-2,3,4,5-tetrahydro-3-methyl-5-phenyl-1,4-benzothiazepine hydrochloride, mp 202-205°C;

27) (+-)-4,5-Dihydro-5-phenylspiro(1,4-benzothiazepine-3-(2H),1'-cyclopentane) hydrochloride 0.25 $H_2O$, mp 224-226°C;

28) (+-)-2,3,4,5-Tetrahydro-5-phenylspiro(1,4-benzothiazepine-3,1'-cyclohexane) hydrochloride $H_2O$, mp 167-169°C (eff.);

29) (+-)-5-(2-Fluorophenyl)-2,3,4,5-tetrahydrospiro(1,4-benzothiazepine-3,1'-cyclohexane) 1,1-dioxide, mp 160-161°C;

30) (+-)-Cis-3-(2,3,4,5-tetrahydro-3-methyl-5-phenyl-1,4-benzothiazepin-3-yl)propionic acid 1,1-dioxide 0.5 $H_2O$, mp 132-133°C;

31) (±)-Trans-Ethyl 3-(2,3,4,5)-tetrahydro-3-methyl-5-phenyl-1,4-benzothiazepin-3-yl)propioniate 1,1-dioxide, mp 143-148°C;

32) (±)-Cis-Ethyl 5-(2,3,4,5-tetrahydro-3-methyl-5-phenyl-1,4-benzothiazepin-3-yl)valerate 1,1-dioxide, mp 121-122°C;

33) (±)-Trans-3-((E)-2-Butenyl)-3-ethyl-2,3,4,5-tetrahydro-5-phenyl-1,4-benzothiazepine, mp 69-74°C;

34) (±)-Trans-3-Ethyl-2,3,4,5-tetrahydro-3-isopropyl-5-phenyl-1,4-benzothiazepine 1,1-dioxide, mp 116-118°C;

35) (±)-Cis-3-iso-Butyl-3-ethyl-2,3,4,5-tetrahydro-5-phenyl-1,4-benzothiazepine 1-oxide, mp 91-93°C;

36) (±)-Cis-3-iso-Butyl-3-ethyl-2,3,4,5-tetrahydro-5-phenyl-1,4-benzothiazepine 1,1-dioxide, mp 149-151°C;

37) (±)-Trans-3-iso-Butyl-3-ethyl-2,3,4,5-tetrahydro-5-phenyl-1,4-benzothiazepine 1-oxide, mp 92-93°C;

38) (±)-Trans-3-iso-Butyl-3-ethyl-2,3,4,5-tetrahydro-5-phenyl-1,4-benzothiazepine 1,1-dioxide, mp 101-103°C;

39) (±)-Cis-3-Butyl-3-ethyl-2,3,4,5-tetrahydro-5-(3-pyridyl)-1,4-benzothiazepine 1,1-dioxide, mp 60-61°C;

40) (±)-Cis-Ethyl-2,3,4,5-tetrahydro-5-phenyl-1,4-benzothiazepine-3-carbaldehyde 1,1-dioxide, mp 162-164°C;

41) (±)-Cis-2,3,4,5-Tetrahydro-3-isopropyl-3-methyl-5-phenyl-1,4-benzothiazepine 1,1-dioxide 0.66 $H_2O$, mp 119-120°C;

42) (±)-Trans-3-Ethyl-2,3,4,5-tetrahydro-3-isopropyl-5-phenyl-1,4-benzothiazepine 1,1-dioxide, mp 121-124°C;

43) (±)-Cis-3-Ethyl-2,3,4,5-tetrahydro-3-isopropyl-5-phenyl-1,4-benzothiazepine 1,1-dioxide, mp 150-152°C;

44) (±)-Cis-3-Butyl-3-ethyl-2,3,4,5-tetrahydro-4-hydroxy-5-(3-pyridyl)-1,4-benzothiazepine 1,1-dioxide, mp 202-205°C;

45) (±)-Trans-3-(3-Ethyl-2,3,4,5-tetrahydro-5-phenyl-1,4-benzothiazepin-3-yl)propanol 1,1-dioxide mp 164-165°C;

46) (±)-Trans-3-Ethyl-5-(4-Fluorophenyl)-2,3,4,5-tetrahydro-7-methoxy-3-

(3-methoxypropyl)-1,4-benzothiazepine 1,1-dioxide hydrochloride, mp 179-181°C;

47) (+-)-Cis-3-Butyl-3-ethyl-2,3,4,5-tetrahydro-5-phenylpyrido(4,3-F)-1,4-thiazepine 1,1-dioxide 0.333 $H_2O$, mp 111-112°C;

48) (+-)-Cis-3-Butyl-3-ethyl-2,3,4,5-tetrahydro-5-(1H-pyrrol-1-yl)-1,4-benzothiazepine 1,1-dioxide, mp 50-52°C;

49) (+-)-Cis-3-Butyl-3-ethyl-2,3,4,5-tetrahydro-5-phenyl-7H-pyrrolo(3,4-F)-1,4-thiazepine 1,1-dioxide 0.125 $H_2O$, mp 75-77°C;

50) (+-)-2,3,4,5-Tetrahydro-7-methoxy-5-phenylspiro(1,4-benzothiazepine-3,1-cyclohexane) 1,1-dioxide, mp 142-143°C;

51) (+-)-Trans-1-(3-Ethyl-2,3,4,5-tetrahydro-7-methoxy-5-phenyl-1,4-benzothiazepin-3-yl)-2-butanone S,S-dioxide hydrochloride, mp 175-176°C;

52) (+-)- Trans-3-butyl-3-ethyl-2,3,4,5-tetrahydro-5-phenylnaphtho(3,2-F)-1,4-benzothiazepine 1,1-dioxide, mp 128-131°C;

53) (+-)-Trans-3-Butyl-3-ethyl-2,3,4,5-tetrahydro-5-(2-pyridyl)-1,4-benzothiazepine 1,1-dioxide, mp 50-53°C;

54) (+-)-Trans-3-Butyl-3-ethyl-2,3,4,5-tetrahydro-5-(3-pyridyl)-1,4-benzothiazepine 1,1-dioxide 0.25 hydrate, mp 153-155°C;

55) (+-)-Trans-1-(3-Ethyl-2,3,4,5-tetrahydro-7,8-dimethoxy-5-phenyl-1,4-benzothiazepin-3-yl)-2-butanone S,S-dioxide, mp 142-146° C;

56) (+-)-Trans-3-(1-butenyl)-3-ethyl-2,3,4,5-tetrahydro-8-methoxy-5-phenyl -1,4-benzothiazepine 1,1-dioxide 57) (+-)-Trans-3-(1-butenyl)-3-ethyl-2,3,4,5-tetrahydro-7,8-dimethoxy-5-phenyl -1,4-benzothiazepine 1,1-dioxide 58) (+-)-Trans-1-(3-Ethyl-2,3,4,5-tetrahydro-8-methoxy-5-phenyl-1,4-benzothiazepin-3-yl)-3-butanone S,S-dioxide 59) (+-)-Trans-1-(3-Ethyl-2,3,4,5-tetrahydro-7,8-dimethoxy-5-phenyl-1,4-benzothiazepin-3-yl)-3-butanone S,S-dioxide 60) (+-)-Trans-1-(3-Ethyl-2,3,4,5-tetrahydro-8-methoxy-5-phenyl-1,4-benzothiazepin-3-yl)-1-butanone S,S-dioxide 61) (+-)-Trans-1-(3-Ethyl-2,3,4,5-tetrahydro-7,8-dimethoxy-5-phenyl-1,4- benzothiazepin-3-yl)-1-butanone S.S-dioxide 62) (+-)-Trans-1-(3-ethyl-2,3,4,5-tetrahydro-8-methoxy-5-phenyl-1,4-benzothiazepin-3-yl)-4,4,4-trifluoro-1-butanone S,S-dioxide 63) (+-)-Trans-1-(3-ethyl-2,3,4,5-tetrahydro-7,8-dimethoxy-5-phenyl-1,4-benzothiazepin-3-yl)-4,4,4-trifluoro-1-butanone S,S-dioxide 64) (+-)-Trans-1-(3-ethyl-2,3,4,5-tetrahydro-7,8-dimethoxy-5-phenyl-1,4-benzothiazepin-3-yl)-3,3,4,4,4-pentafluoro-2-butanone S,S-dioxide 65) (+-)-Trans-1-(3-ethyl-2,3,4,5-tetrahydro-8-methoxy-5-phenyl-1,4-benzothiazepin-3-yl)-3,3,4,4,4-pentafluoro-2-butanone S,S-dioxide 66) (+-)-Trans-1-(3-ethyl-2,3,4,5-tetrahydro-7,8-dimethoxy-5-phenyl-1,4-benzothiazepin-3-yl)-4,4,4-trifluoro-2-butanone S,S-dioxide 67) (+-)-Trans-1-(3-ethyl-2,3,4,5-tetrahydro-8-methoxy-5-phenyl-1,4-benzothiazepin-3-yl)-4,4,4-trifluoro-2-butanone S,S-dioxide 68) (+-)-Trans-3-ethyl-2,3,4,5-tetrahydro-8-methoxy-5-phenyl-3-(4,4,4-trifluorobutyl)-1,4-benzothiazepine 1,1-dioxide 69) (+-)-Trans-3-ethyl-2,3,4,5-tetrahydro-7,8-dimethoxy-5-phenyl-3-(4,4,4-trifluorobutyl)-1,4-benzothiazepine 1,1-dioxide 70) (+-)-Trans-1-(3-(2,2,2-trifluoroethyl)-2,3,4,5-tetrahydro-8-methoxy-5-phenyl-1,4- benzothiazepin-3-yl)-2-butanone S,S-dioxide 71) (+-)-Trans-1-(3-(2,2,2-trifluoroethyl)-2,3,4,5-tetrahydro-7,8-dimethoxy-5-phenyl-1,4- benzothiazepin-3-yl)-2-butanone S,S-dioxide 72) (+-)-Trans-1-(3-Ethyl-2,3,4,5-tetrahydro-9-methoxy-5-phenyl-1,4-benzothiazepin-3-yl)-2-butanone S,S-dioxide 73) (+-)-Trans-3-((3-ethyl-2,3,4,5-tetrahydro-3-(2-oxobutyl)-5-phenyl-1,4-benzothiazepin-7-yl)oxy)propanesulfonic acid 1,1-dioxide 74) (+-)-Trans-1-(3-Ethyl-2,3,4,5-tetrahydro-7,8-diethoxy-5-phenyl-1,4-benzothiazepin-3-yl)-2-butanone S,S-dioxide 75) (+-)-Trans-1-(3-Ethyl-2,3,4,5-tetrahydro-7,8-dimethoxy-4-hydroxy-5-phenyl-1,4-benzothiazepin-3-yl)-2-butanone S,S-dioxide 76) (+-)-Trans-3-((3-ethyl-2,3,4,5-tetrahydro-3-(2-oxobutyl)-5-phenyl-1,4-benzothiazepin-8-yl)oxy)propanesulfonic acid 1,1-dioxide 77) (+-)-Trans-2-((3-ethyl-2,3,4,5-tetrahydro-3-(2-oxobutyl)-5-phenyl-1,4-benzothiazepin-7-yl)oxy)ethyltrimethylammonium iodide 1,1-dioxide 78) (+-)-Trans-2-((3-ethyl-2,3,4,5-tetrahydro-3-(2-oxobutyl)-5-phenyl-1,4-benzothiazepin-8-yl)oxy)ethyltrimethylammonium iodide 1,1-dioxide 1. A compound of formula (I) :

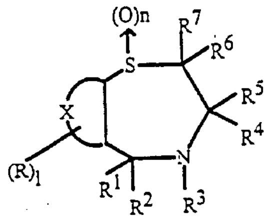

(I)

wherein l is an integer of from 0 to 4;

n is an integer of from 0 to 2;

R is an atom or group selected from halogen, cyano, nitro, alkyl, alkoxy, aryl, heteroaryl, aryloxy, arylalkoxy, aralkyl, alkaryl, $-O(CH_2)_pSO_3R^{11}$, $-O(CH_2)_pNR^{11}R^{12}$, $-O(CH_2)_pN^+R^{11}R^{12}R^{14}$, $COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_2NR^{11}R^{12}$, $-SO_3R^{11}$, wherein p is an integer from 1 to 4, $R^{11}$ and $R^{12}$ are independently selected from hydrogen, $C_{1-6}$ alkyl and phenyl, and $R^{14}$ is hydrogen or $C_{1-6}$ alkyl, or R is a group $-OCH_2O-$ which forms a further ring attached to X, wherein said alkyl, alkoxy, aryl, heteroaryl, aryloxy, arylalkoxy, aralkyl and alkaryl groups are optionally substituted by one or more atoms or groups selected from halogen, nitro, nitrile, alkyl, alkoxy, $-COR^{11}$, $-CO_2R^{11}$, $-SO_3R^{11}$ wherein $R^{11}$ is as hereinbefore defined and $-NR^{14}R^{15}$ wherein $R^{14}$ is as hereinbefore defined and $R^{15}$ is hydrogen or $C_{1-6}$ alkyl;

$R^1$ is hydrogen or $C_{1-6}$ alkyl;

$R^2$ is an atom or group selected from hydrogen, $C_{1-6}$ alkyl (including cycloalkyl and cycloalkylalkyl), $C_{1-4}$ alkoxy, pyrryl, thienyl, pyridyl, 1,3-benzodioxolo, phenyl and naphthyl, which groups are optionally substituted by one or more atoms or groups independently selected from halogen, cyano, nitro, carboxyl, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_3R^{11}$ (wherein $R^{11}$ and $R^{12}$ are as hereinbefore defined), $-O(CH_2)_pNR^{11}R^{12}$, $-O(CH_2)_pN^+R^{11}R^{12}R^{13}$ and $-O(CH_2)_pSO_3R^{11}$ (wherein p, $R^{11}$ and $R^{12}$ are as hereinbefore defined and $R^{13}$ is hydrogen or $C_{1-6}$ alkyl);

$R^3$ is hydrogen, OH, $C_{1-6}$ alkyl, $C_{1-6}$ alkoxy or $-OC_{1-6}$ acyl;

$R^4$ is a group independently selected from $C_{1-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, oxo, $C_{1-4}$ alkoxy, $-CO_2R^{14}$, $-NR^{14}R^{15}$, $-SR^{14}$, $-S(O)C_{1-6}$ alkyl, $-SO_2R^{14}$, $-SO_3R^{14}$ (wherein $R^{14}$ and $R^{15}$ are hereinbefore defined);

$R^5$ is a group independently selected from $C_{2-6}$ alkyl (including cycloalkyl and cycloalkylalkyl), $C_{2-6}$ alkenyl, and $C_{2-6}$ alkynyl, which groups are optionally substituted by one or more atoms or groups independently selected from halogen, oxo, $C_{1-4}$ alkoxy, $-CO_2R^{14}$, $-NR^{14}R^{15}$, $-SR^{14}$, $-S(O)$ $C_{1-6}$ alkyl, $-SO_2$ $R^{14}$, $-SO_3R^{14}$ (wherein $R^{14}$ and $R^{15}$ are hereinbefore defined);

or $R^4$ and $R^5$, together with the carbon atom to which they are attached, form a $C_{3-7}$ spiro cycloalkyl group which is optionally substituted by one or more atoms or groups independently selected from halogen, $C_{1-6}$ alkoxy, $-CO_2R^{14}$, $-SO_3R^{14}$ and $-NR^{14}R^{15}$ (where $R^{14}$ and $R^{15}$ are as hereinbefore defined);

$R^6$ and $R^7$ are independently selected from hydrogen and $C_{1-6}$ alkyl; and X is an aromatic or non-aromatic monocyclic or bicyclic ring system having from 5 to 10 carbon atoms (including the two carbon atoms forming part of the thiazepine ring) wherein optionally one or more of the carbon atoms is/are replaced by heteroatom(s) independently selected from nitrogen, oxygen and sulphur;

with the proviso that when l is an integer of from 0 to 4, $R^1 = R^6 = R^7 = H$, $R^3 = H$ or OH, $R^2$ = unsubstituted phenyl or phenyl substituted by one or more atoms or groups independently selected from halogen, nitro, phenylalkoxy, $C_{1-4}$ alkoxy, $C_{1-6}$ alkyl and $-O(CH_2)_pSO_3R^{11}$ wherein p and $R^{11}$ are as hereinbefore defined, wherein said phenylalkoxy, alkoxy and alkyl groups are optionally substituted by one or more halogen atoms, and X is a fused phenyl ring, then $R^4$ is other than a $C_{1-6}$ straight alkyl group and $R^5$ is other than a $C_{2-5}$ straight alkyl group, and salts, solvates and physiologically functional derivatives thereof.

2. A compound as claimed in claim 1 which is a trans isomer wherein l is 0, 1 or 2;

n is 1 or 2;

$R^1$, $R^6$ and $R^7$ are all hydrogen;

$R^3$ is hydrogen or hydroxy; and

X is a fused phenyl, naphthyl, pyrryl, thienyl or pyridyl, group.

3. A compound as claimed in claim 1 or claim 2 wherein l is 0 or 1;

n is 2; and $R^2$ is pyrryl, thienyl, pyridyl, phenyl or naphthyl, such groups being optionally substituted by one or more atoms or groups independently selected from halogen, cyano, nitro, carboxyl, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_3R^{11}$ (wherein $R^{11}$ and $R^{12}$ are independently selected from hydrogen, $C_{1-6}$ alkyl and phenyl), $-O(CH_2)_pNR^{11}R^{12}$, $-O(CH_2)N^+R^{11}R^{12}R^{13}$ and $-O(CH_2)_pSO_3R^{11}$ (wherein p is an integer of from 1 to 4, $R^{11}$ and $R^{12}$ are as hereinbefore defined and $R^{13}$ is hydrogen or $C_{1-6}$ alkyl).

4. A compound as claimed in Claim 1 which is :

(-)-(RR)-3-butyl-3-ethyl-2,3,4,5-tetrahydro-5-phenyl-1,4-benzothiazepine 1,1-dioxide;
(+-)-trans-3-((E)-2-butenyl)-3-ethyl-2,3,4,5-tetrahydro-5-phenyl-1,4-benzothiazepine1,1-dioxide;
(+-)-trans-3-ethyl-2,3,4,5-tetrahydro-3-(3-methoxypropyl)-5-phenyl-1,4-benzothiazepine 1,1-dioxide;
(+-)-trans-1-(3-ethyl-2,3,4,5-tetrahydro-5-phenyl-1,4-benzothiazepin-3-yl)-2-butanoneS,S-dioxide;
(+-)-trans-1-(3-ethyl-2,3,4,5-tetrahydro-8-methoxy-5-phenyl-1,4-benzothiazepin-3-yl)-2-butanone S,S-dioxide hydrochloride 1.1 hydrate;
(+-)-trans-3-(1-butenyl)-3-ethyl-2,3,4,5-tetrahydro-5-phenyl-1,4-benzothiazepine1,1-dioxide hydrochloride 0.4 hydrate;
(+-)-trans-3-(ethoxyethyl)-3-ethyl-2,3,4,5-tetrahydro-5-phenyl-1,4-benzothiazepine1,1-dioxide hydrochloride hemihydrate;
(+-)-trans-3-(ethoxymethyl)-3-ethyl-2,3,4,5-tetrahydro-5-phenyl-1,4-benzothiazepine1,1-dioxide hydrochloride;
(+-)-trans-ethyl 3-(3-ethyl-2,3,4,5-tetrahydro-5-phenyl-1,4-benzothiazepin-3-yl)propionate 1,1-dioxide;
(+-)-trans-(E)-4-(3-ethyl-2,3,4,5-tetrahydro-5-phenyl-1,4-benzothiazepin-3-yl)-3-buten-2-one 1,1-dioxide;
(+-)-2,3,4,5-tetrahydro-8-methoxy-5-phenylspiro(1,4-benzothiazepine-3,1-cyclohexane) 1,1-dioxide;
(+-)-trans-3-butyl-3-ethyl-2,3,4,5-tetrahydro-5-(4-pyridyl)-1,4-benzothiazepine 1,1-dioxide;
(+-)-trans-3-butyl-3-ethyl-2,3,4,5-tetrahydro-4-hydroxy-5-(4-pyridyl)-1,4-benzothiazepine 1,1-dioxide;
(+-)-trans-3-butyl-3-ethyl-2,3,4,5-tetrahydro-5-(2-thienyl)-1,4-benzothiazepine 1,1-dioxide;
(+-)-trans-3-butyl-3-ethyl-2,3,4,5-tetrahydro-5-(1H-pyrrol-1-yl)-1,4-benzothiazepine1,1-dioxide;
(+-)-trans-3-butyl-3-ethyl-2,3,4,5-tetrahydro-5-phenylpyrido(4,3-F)-1,4-benzothiazepine 1,1-dioxide;
(+-)-trans-3-butyl-3-ethyl-3,4,5,7-tetrahydro-5-phenyl-2H-pyrrolo(3,4-F)-1,4-benzothiazepine 1,1-dioxide 0.1 hydrate;

(+-)-trans-3-butyl-3-ethyl-2,3,4,5-tetrahydro-5-phenylthieno(2,3-F)-1,4-benzothiazepine1,1-dioxide;
(+-)-trans-3-ethyl-2,3,4,5-tetrahydro-5-phenyl-3-(4,4,4-trifluorobutyl)-1,4-benzothiazepine 1,1-dioxide;
(+-)-trans-2,3,4,5-tetrahydro-3-isopropyl-3-methyl-5-phenyl-1,4-benzothiazepine 1,1-dioxide 0.25 $H_2O$;
(+-)-trans-3-((E)-2-Butenyl)-3-ethyl-2,3,4,5-tetrahydro-5-phenyl-1,4-benzothiazepine;
(+-)-Cis-2,3,4,5-Tetrahydro-3-isopropyl-3-methyl-5-phenyl-1,4-benzothiazepine 1,1-dioxide 0.66 $H_2O$;
(+-)-trans-3-(3-Ethyl-2,3,4,5-tetrahydro-5-phenyl-1,4-benzothiazepin-3-yl)propanol 1,1 dioxide;
(+-)-trans-3-Ethyl-5-(4-Fluorophenyl)-2,3,4,5-tetrahydro-7-methoxy-3-(3-methoxypropyl)-1,4-benzothiazepine 1,1-dioxide hydrochloride;
(+-)-2,3,4,5-Tetrahydro-7-methoxy-5-phenylspiro(1,4-benzothiazepine-3,1-cyclohexane) 1,1-dioxide;
(+-)-trans-1-(3-Ethyl-2,3,4,5-tetrahydro-7-methoxy-5-phenyl-1,4-benzothiazepin-3-yl)-2-butanone S,S-dioxide hydrochloride;
(+-)- trans-3-butyl-3-ethyl-2,3,4,5-tetrahydro-5-phenylnaphtho(3,2-F)-1,4-benzothiazepine 1,1-dioxide;
(+-)-trans-1-(3-Ethyl-2,3,4,5-tetrahydro-7,8-dimethoxy-5-phenyl-1,4-benzothiazepin-3-yl)-2-butanone S,S-dioxide;
(+-)-trans-3-(1-butenyl)-3-ethyl-2,3,4,5-tetrahydro-7,8-dimethoxy-5-phenyl -1,4-benzothiazepine 1,1-dioxide;
(+-)-trans-1-(3-Ethyl-2,3,4,5-tetrahydro-7,8-dimethoxy-5-phenyl-1,4-benzothiazepin-3-yl)-3-butanone S,S-dioxide;
(+-)-trans-1-(3-Ethyl-2,3,4,5-tetrahydro-8-methoxy-5-phenyl-1,4-benzothiazepin-3-yl)-1-butanone S,S-dioxide;
(+-)-trans-1-(3-Ethyl-2,3,4,5-tetrahydro-7,8-dimethoxy-5-phenyl-1,4-benzothiazepin-3-yl)-1-butanone S,S-dioxide;
(+-)-trans-1-(3-ethyl-2,3,4,5-tetrahydro-7,8-dimethoxy-5-phenyl-1,4-benzothiazepin-3-yl)-4,4,4-trifluoro-1-butanone S,S-dioxide;
(+-)-trans-1-(3-ethyl-2,3,4,5-tetrahydro-7,8-dimethoxy-5-phenyl-1,4-benzothiazepin-3-yl)-3,3,4,4,4-pentafluoro-2-butanone S,S-dioxide;
(+-)-trans-1-(3-ethyl-2,3,4,5-tetrahydro-7,8-dimethoxy-5-phenyl-1,4-benzothiazepin-3-yl)-4,4,4-trifluoro-2-butanone S,S-dioxide;

(+-)-trans-3-ethyl-2,3,4,5-tetrahydro-7,8-dimethoxy-5-phenyl-3-(4,4,4-trifluorobutyl)-1,4-benzothiazepine 1,1-dioxide;

(+-)-trans-1-(3-(2,2,2-trifluoroethyl)-2,3,4,5-tetrahydro-7,8-dimethoxy-5-phenyl-1,4- benzothiazepin-3-yl)-2-butanone S,S-dioxide;

(+-)-trans-1-(3-Ethyl-2,3,4,5-tetrahydro-7,8-diethoxy-5-phenyl-1,4-benzothiazepin-3-yl)-2-butanone S,S-dioxide;

(+-)-trans-3-((3-ethyl-2,3,4,5-tetrahydro-3-(2-oxobutyl)-5-phenyl-1,4-benzothiazepin-8-yl)oxy)propanesulfonic acid 1,1-dioxide;

(+-)-trans-2-((3-ethyl-2,3,4,5-tetrahydro-3-(2-oxobutyl)-5-phenyl-1,4-benzothiazepin-8-yl)oxy)ethyltrimethylammonium iodide 1,1-dioxide;

5. A compound as claimed in claim 1 of the formula (Ia):

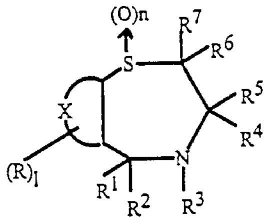

(Ia)

wherein l is an integer of from 0 to 4;

n is an integer of from 0 to 2;

R is an atom or group selected from halogen, cyano, nitro, alkyl, alkoxy, aryl, heteroaryl, aryloxy, arylalkoxy, aralkyl, alkaryl, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_3R^{11}$ wherein $R^{11}$ and $R^{12}$ are independently selected from hydrogen, $C_{1-6}$ alkyl and phenyl, wherein said alkyl, alkoxy, aryl, heteroaryl, aryloxy, arylalkoxy, aralyl and alkaryl groups are optionally substituted by one or more atoms or groups selected from halogen, nitro, nitrile. alkyl, alkoxy, $-COR^{11}$, $-CO_2R^{11}$, $-SO_3R^{11}$ wherein $R^{11}$ is as hereinbefore defined and $-NR^{14}R^{15}$ wherein $R^{14}$ and $R^{15}$ are as hereinbefore defined;

$R^1$ and $R^3$ are independently selected from hydrogen and $C_{1-6}$ alkyl;

$R^2$ is an atom or group selected from hydrogen, $C_{1-6}$ alkyl (including cycloalkyl and cycloalkylalkyl), $C_{1-4}$ alkoxy, pyrryl, thienyl, pyridyl, 1,3-benzodioxolo, phenyl and naphthyl, which groups are optionally substituted by one or more atoms or groups independently selected from halogen, cyano, nitro, carboxyl, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_3R^{11}$ (wherein $R^{11}$ and $R^{12}$ are independently selected from hydrogen, $C_{1-6}$ alkyl and phenyl), $-O(CH_2)_pNR^{11}R^{12}$, $-O(CH_2)_pN^+R^{11}R^{12}R^{13}$ and $-O(CH_2)_pSO_3R^{11}$ (wherein p is an integer of from 1 to 4, $R^{11}$ and $R^{12}$ are as hereinbefore defined and $R^{13}$ is hydrogen or $C_{1-6}$ alkyl);

$R^4$ is a group independently selected from $C_{1-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, $C_{1-4}$ alkoxy, $-CO_2R^{14}$, $-NR^{14}R^{15}$, $-SO_3R^{14}$ (wherein $R^{14}$ and $R^{15}$ are independently selected from hydrogen and $C_{1-6}$ alkyl) and $R^{16}COR^{17}$ where $R^{16}$ is a $C_{1-4}$ alkylene group and $R^{17}$ is a $C_{1-4}$ alkyl group;

$R^5$ is a group independently selected from $C_{2-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, $C_{1-4}$ alkoxy, $-CO_2R^{14}$, $-NR^{14}R^{15}$, $-SO_3R^{14}$ (wherein $R^{14}$ and $R^{15}$ are independently selected from hydrogen and $C_{1-6}$ alkyl) and $-R^{16}COR^{17}$ where $R^{16}$ is a $C_{1-4}$ alkylene group and $R^{17}$ is a $C_{1-4}$ alkyl group;

or $R^4$ and $R^5$, together with the carbon atom to which they are attached, form a $C_{3-7}$ spiro cycloalkyl group which is optionally substituted by one or more atoms or groups independently selected from halogen, $C_{1-6}$ alkoxy, $-CO_2R^{14}$, $-SO_3R^{14}$ and $-NR^{14}R^{15}$ (where $R^{14}$ and $R^{15}$ are as hereinbefore defined;

$R^6$ and $R^7$ are independently selected from hydrogen and $C_{1-6}$ alkyl; and X is an aromatic or non-aromatic monocyclic or bicyclic ring system having from 5 to 10 carbon atoms (including the two carbon atoms forming part of the thiazepine ring) wherein optionally one or more of the carbon atoms is/are replaced by heteroatom(s) independently selected from nitrogen, oxygen and sulphur;

with the proviso that when l is an integer of from 0 to 4, $R^1 = R^3 = R^6 = R^7 = H$, $R^2$ = unsubstituted phenyl or phenyl substituted by one or more atoms or groups independently selected from halogen, nitro, phenylalkoxy, $C_{1-4}$ alkoxy, $C_{1-6}$ alkyl and $-O(CH_2)_pSO_3R^{11}$ wherein p and $R^{11}$ are as hereinbefore defined, wherein said phenylalkoxy, alkoxy and alkyl groups are optionally substituted by one or more halogen atoms, and X is a fused phenyl ring, then $R^4$ is other than a $C_{1-6}$ straight alkyl group and $R^5$ is other than a $C_{2-5}$ straight alkyl group; and salts, solvates and physiologically functional derivatives thereof.

6. A compound of formula (I) :

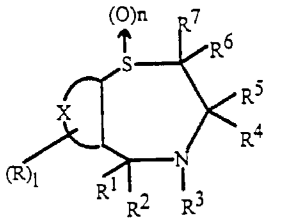

(I)

wherein l is an integer of from 0 to 4;

n is an integer of from 0 to 2;

R is an atom or group selected from halogen, cyano, nitro, alkyl, alkoxy, aryl, heteroaryl, aryloxy, arylalkoxy, aralkyl, alkaryl, $-O(CH_2)pSO_3R^{11}$, $-O(CH_2)pNR^{11}R^{12}$, $-O(CH_2)pN^+R^{11}R^{12}R^{14}$, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_2NR^{11}R^{12}$, $-SO_3R^{11}$ wherein p is an integer of from 1 to 4, $R^{11}$ and $R^{12}$ are independently selected from hydrogen, $C_{1-6}$ alkyl and phenyl, and $R^{14}$ is hydrogen or $C_{1-6}$ alkyl, or R is a group $-OCH_2O-$ which forms a further ring attached to X, wherein said alkyl, alkoxy, aryl, heteroaryl, aryloxy, arylalkoxy, aralkyl and alkaryl groups are optionally substituted by one or more atoms or groups selected from halogen, nitro, nitrile, alkyl, alkoxy, $-COR^{11}$, $-CO_2R^{11}$, $-SO_3R^{11}$ wherein $R^{11}$ is as hereinbefore defined and $-NR^{14}R^{15}$ wherein $R^{14}$ is as hereinbefore defined and $R^{15}$ is hydrogen or $C_{1-6}$ alkyl;

$R^1$ is hydrogen or $C_{1-6}$ alkyl;

$R^2$ is an atom or group selected from hydrogen, $C_{1-6}$ alkyl (including cycloalkyl and cycloalkylalkyl), $C_{1-4}$ alkoxy, pyrryl, thienyl, pyridyl, 1,3-benzodioxolo, phenyl and naphthyl, which groups are optionally substituted by one or more atoms or groups independently selected from halogen, cyano, nitro, carboxyl, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$ $-SO_3R^{11}$ (wherein $R^{11}$ and $R^{12}$ are as hereinbefore defined), $-O(CH_2)_pNR^{11}R^{12}$, $-O(CH_2)_pN^+R^{11}R^{12}R^{13}$ and $-O(CH_2)_pSO_3R^{11}$ (wherein p, $R^{11}$ and $R^{12}$ are as hereinbefore defined and $R^{13}$ is hydrogen or $C_{1-6}$ alkyl);

$R^3$ is hydrogen, OH, $C_{1-6}$ alkyl, $C_{1-6}$ alkoxy or $-OC_{1-6}$ acyl;

$R^4$ is a group independently selected from $C_{1-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, oxo, $C_{1-4}$ alkoxy, $-CO_2R^{14}$, $-NR^{14}R^{15}$, $-SR^{14}$, $-S(O)C_{1-6}$ alkyl, $-SO_2R^{14}$, $-SO_3R^{14}$ (wherein $R^{14}$ and $R^{15}$ are as hereinbefore described);

$R^5$ is a group independently selected from $C_{2-6}$ alkyl (including cycloalkyl and cycloalkylalkyl), $C_{2-6}$ alkenyl, and $C_{2-6}$ alkynyl, which groups are optionally substituted by one or more atoms or groups independently selected from halogen, oxo, $C_{1-4}$ alkoxy, $-CO_2R^{14}$, $-NR^{14}R^{15}$, $-SR^{14}$, $-S(O)C_{1-6}$ alkyl, $-SO_2R^{14}$ $-SO_3R^{14}$ (wherein $R^{14}$ and $R^{15}$ are as hereinbefore defined);

or $R^4$ and $R^5$, together with the carbon atom to which they are attached, form a $C_{3-7}$ spiro cycloalkyl group which is optionally substituted by one or more atoms or groups independently selected from halogen, $C_{1-6}$ alkoxy, $-CO_2R^{14}$, $-SO_3R^{14}$ and $-NR^{14}R^{15}$ (where $R^{14}$ and $R^{15}$ are as hereinbefore defined;

$R^6$ and $R^7$ are independently selected from hydrogen and $C_{1-6}$ alkyl; and X is an aromatic or non-aromatic monocyclic or bicyclic ring system having from 5 to 10 carbon atoms (including the two carbon atoms forming part of the thiazepine ring) wherein optionally one or more of the carbon atoms is/are replaced by heteroatom(s) independently selected from nitrogen, oxygen and sulphur;

with the proviso that when 1 is an integer of from 0 to 4, $R^1 = R^6 = R^7 = H$, $R^3 = H$ or OH, $R^2$ = unsubstituted phenyl or phenyl substituted by one or more atoms or groups independently selected from halogen, nitro, phenylalkoxy, $C_{1-4}$ alkoxy, $C_{1-6}$ alkyl and $-0(CH_2)_pSO_3R^{11}$ wherein p and $R^{11}$ are as hereinbefore defined, wherein said phenylalkoxy, alkoxy and alkyl groups are optionally substituted by one or more halogen atoms, and X is a fused phenyl ring, then $R^4$ is other than a $C_{1-6}$ straight alkyl group and $R^5$ is other than a $C_{2-5}$ straight alkyl group, and salts, solvates and physiologically functional derivatives thereof for use in therapy, 4) 3-Ethyl-3-methyl-2,3,4,5-tetrahydro-5-phenyl-1,4-benzothiazepine, mp 124-125°C;

5) (+)-3,3-Diethyl-2,3,4,5-tetrahydro-5-phenyl-1,4-benzothiazepine 1,1-dioxide, mp 100-102°C;

6) 3-Butyl-2,3,4,5-tetrahydro-3-methyl-5-phenyl-1,4-benzothiazepine 1,1-dioxide, mp 103-104°C;

7) 3-Methyl-3-propyl-2,3,4,5-tetrahydro-5-phenyl-1,4-benzothiazepine 1,1-dioxide, mp 120-121°C;

8) 3,3-Diethyl-2,3,4,5-tetrahydro-5-phenyl-1,4-benzothiazepine 1,1-dioxide, mp 115-116°C;

9) (+)-Trans-3-Butyl-3-ethyl-2,3,4,5-tetrahydro-5-phenyl-1,4-benzothiazepine 1,1-dioxide, mp 101°C;

10) (+)-Trans-2,3,4,5-Tetrahydro-3-methyl-5-phenyl-3-propyl-1,4-benzothiazepine 1,1-dioxide, mp 129-130°C;

11) (-)-3,3-Diethyl-2,3,4,5-tetrahydro-5-phenyl-1,4-benzothiazepine 1,1-dioxide, mp 101-103°C;

12) 3-Ethyl-2,3,4,5-tetrahydro-3-methyl-5-phenyl-1,4-benzothiazepine, mp 110-112°C;

13) 3-Ethyl-2,3,4,5-tetrahydro-3-methyl-5-phenyl-1,4-benzothiazepine hydrochloride $0.25H_2O$, mp 162-164°C (eff.);

14) 3-Ethyl-2,3,4,5-tetrahydro-3-methyl-5-phenyl-1,4-benzothiazepine 1,1-dioxide, mp 128-129°C;

15) 3,3-Diethyl-2,3,4,5-tetrahydro-5-phenyl-1,4-benzothiazepine hydrochloride, mp 211-214°C;

16) (+-)-2,3,4,5-Tetrahydro-3-methyl-5-phenyl-3-propyl-1,4-benzothiazepine, mp 101-103°C;

17) 2,3,4,5-Tetrahydro-3-methyl-5-phenyl-3-propyl-1,4-benzothiazepine, mp 72-74°C;

18) 3-Ethyl-2,3,4,5-tetrahydro-5-phenyl-3-propyl-1,4-benzothiazepine hydrochloride 0.25$H_2O$, mp 205-207°C;

19) 3-Ethyl-2,3,4,5-tetrahydro-5-phenyl-3-propyl-1,4-benzothiazepine 1,1-dioxide 0.25$H_2O$, mp 115-118°C;

20) 2,3,4,5-Tetrahydro-5-phenyl-3,3-dipropyl-1,4-benzothiazepine hydrochloride, 209-211°C;

21) 3-Ethyl-2,3,4,5-tetrahydro-5-phenyl-3-propyl-1,4-benzothiazepine 1,1-dioxide hydrochloride 0.33$H_2O$, 206-209°C;

22) 2,3,4,5-Tetrahydro-5-phenyl-3,3-dipropyl-1,4-benzothiazepine 1,1-dioxide, mp 104-106°C;

23) 3,3-Dibutyl-2,3,4,5-tetrahydro-5-phenyl-1,4-benzothiazepine hydrochloride, mp 209-212°C;

24) 3-Butyl-2,3,4,5-tetrahydro-3-methyl-5-phenyl-1,4-benzothiazepine hydrochloride, mp 203-205°C;

25) 3-Butyl-3-ethyl-2,3,4,5-tetrahydro-5-phenyl-1,4-benzothiazepine hydrochloride, mp 205-207°C;

26) 3-Butyl-3-ethyl-2,3,4,5-tetrahydro-5-phenyl-1,4-benzothiazepine 1,1-dioxide hydrochloride, mp 209-212°C;

27) 2,3,4,5-Tetrahydro-3-methyl-3-pentyl-5-phenyl-1,4-benzothiazepine maleate, mp 182-183°C;

28) 3-Ethyl-2,3,4,5-tetrahydro-5-phenyl-3-propyl-1,4-benzothiazepine hydrochloride, mp 198-200°C;

29) (+-)-Cis-3-Butyl-3-ethyl-2,3,4,5-tetrahydro-7-methyl-5-phenyl-1,4-benzothiazepine 1,1-dioxide, mp 138-140°C;

30) (+-)-Cis-3-Butyl-3-ethyl-2,3,4,5-tetrahydro-7-methoxy-5-phenyl-1,4-benzothiazepine, light yellow oil;

31) (+-)-Trans-3-Butyl-3-ethyl-2,3,4,5-tetrahydro-7-methoxy-5-phenyl-1,4-benzothiazepine, light yellow oil;

32) (+-)-Cis-3-Butyl-3-ethyl-2,3,4,5-tetrahydro-7-methoxy-5-phenyl-1,4-benzothiazepine 1,1-dioxide, mp 113-115°C;

33) (+-)-Cis-3-Butyl-3-ethyl-2,3,4,5-tetrahydro-7-methoxy-5-phenyl-1,4-benzothiazepine 1-oxide, mp 103-105°C;

34) (+-)-Trans-3-Butyl-3-ethyl-2,3,4,5-tetrahydro-7-methoxy-5-phenyl-1,4-benzothiazepine 1,1-dioxide hydrochloride, mp 199-201°C;

35) (+-)-Trans-3-Butyl-3-ethyl-5-phenyl-2,3,4,5-tetrahydro-1,4-benzothiazepine 1-oxide, mp 98-101°C;

36) (+-)-Trans-3-Butyl-3-ethyl-2,3,4,5-tetrahydro-5-phenyl-1,4-benzothiazepine 1-oxide, mp 133-136°C;

37) (+-)-Cis-7-Chloro-3-butyl-3-ethyl-2,3,4,5-tetrahydro-5-phenyl-1,4-benzothiazepine 0.4 toluene, light yellow oil;

38) (+-)-Trans-7-Chloro-3-butyl-3-ethyl-2,3,4,5-tetrahydro-5-phenyl-1,4-benzothiazepine 0.3 toluene, light yellow oil;

39) (+-)-Trans-3-Butyl-7-Chloro-3-ethyl-2,3,4,5-tetrahydro-5-phenyl-1,4-benzothiazepine 1,1-dioxide, mp 100-102°C;

40) (+-)-Trans-3-Butyl-3-ethyl-2,3,4,5-tetrahydro-5-(4-methoxyphenyl)-1,4-benzothiazepine 1,1-dioxide hydrochloride, mp 194-196°C;

41) (+-)-Trans-3-Butyl-3-ethyl-2,3,4,5-tetrahydro-5-(4-tolyl)-1,4-benzothiazepine 1,1-dioxide hydrochloride, mp 204-206°C;

42) (+-)-Cis-3-Butyl-3-ethyl-2,3,4,5-tetrahydro-5-(4-tolyl)-1,4-benzothiazepine 1,1-dioxide, mp 155-156C;

43) (+-)-Cis-3-Butyl-3-ethyl-2,3,4,5-tetrahydro-5-(4-methoxyphenyl)-1,4-benzothiazepine, mp 75-77°C;

44) (+-)-Cis-3-Butyl-3-ethyl-2,3,4,5-tetrahydro-5-(4-methoxyphenyl)-1,4-benzothiazepine 1,1-dioxide, mp 109-111°C;

45) (+-)-Cis-3-Butyl-3-ethyl-5-(4-fluorophenyl)-2,3,4,5-tetrahydro-1,4-benzothiazepine, mp 76-78°C;

46) (+-)-Trans-3-Butyl-5-(3,4-dichlorophenyl)-3-ethyl-2,3,4,5-tetrahydro-1,4-benzothiazepine, mp 98-100°C;

47) (+-)-Trans-3-Butyl-5-(4-chlorophenyl)-3-ethyl-2,3,4,5-tetrahydro-1,4-benzothiazepine 1,1-dioxide hydrochloride 0.3 $H_2O$, mp 178-180°C;

48) (+-)-Cis-3-Butyl-5-(4-chlorophenyl)-5-ethyl-2,3,4,5-tetrahydro-1,4-benzothiazepine 1,1-dioxide hydrochloride, mp 186-188°C;

49) Trans-3-Butyl-3-ethyl-2,3,4,5-tetrahydro-5-(3-nitrophenyl)-1,4-benzothiazepine 1,1-dioxide, mp 139-142°C;

50) Trans-3-Butyl-3-ethyl-2,3,4,5-tetrahydro-5-(4-nitrophenyl)-1,4-benzothiazepine 1,1-dioxide, mp 139-142°C;

51) (+-)-*Trans*-5-(4-Benzyloxyphenyl)-3-butyl-3-ethyl-2,3,4,5-tetrahydro-1,4-benzothiazepine 1,1-dioxide, mp 94-95°C;

52) (+-)-*Cis*-5-(4-Benzyloxyphenyl)-3-butyl-3-ethyl-2,3,4,5-tetrahydro-1,4-benzothiazepine 1,1-dioxide, mp 137-138°C;

53) (+-)-*Trans*-5-(4-Benzyloxyphenyl)-3-butyl-3-ethyl-2,3,4,5-tetrahydro-1,4-benzothiazepine, mp 97-98°C;

54) (+-)-*Trans*-3-[4-(3-Butyl-3-ethyl-2,3,4,5-tetrahydro-1,4-benzothiazepin-5-yl)phenoxy]propanesulphonic acid 1,1-dioxide, mp 270°C (dec.);

55) (+-)-*Trans*-3-Butyl-3-ethyl-2,3,4,5-tetrahydro-5-(2-fluorophenyl)-1,4-benzothiazepine 1,1-dioxide hydrochloride, mp 194-196°C;

56) (+-)-*Trans*-3-Butyl-3-ethyl-2,3,4,5-tetrahydro-5-(3-fluorophenyl)-1,4-benzothiazepine 1,1-dioxide, mp 143-145°C;

57) (+-)-*Cis*-3-Butyl-3-ethyl-2,3,4,5-tetrahydro-5-(4-pyridyl)-1,4-benzothiazepine 1,1-dioxide, mp 121-123°C;

58) (+-)-*Trans*-3-Butyl-3-ethyl-2,3,4,5-tetrahydro-5-(4-pyridyl)-1,4-benzothiazepine 1,1-dioxide, mp 110-111°C;

59) (+-)-*Cis*-3-Butyl-3-ethyl-2,3,4,5-tetrahydro-5-(4-trifluoromethylphenyl)-1,4-benzothiazepine 1,1-dioxide, mp 64-65°C;

60) (+-)-*Trans*-3-Butyl-3-ethyl-2,3,4,5-tetrahydro-5-(3-trifluoromethylphenyl)-1,4-benzothiazepine 1,1-dioxide, mp 110-112°C;

61) (+-)-*Trans*-3-Butyl-3-ethyl-2,3,4,5-tetrahydro-5-(3,4-difluorophenyl)-1,4-benzothiazepine 1,1-dioxide, mp 205-215°C;

62) (+-)-Trans-3-Butyl-3-ethyl-2,3,4,5-tetrahydro-5-(2,4-difluoro-phenyl)-1,4-benzothiazepine 1,1-dioxide, mp 97-99°C;

63) (+-)-Trans-3-isopentyl-3-ethyl-2,3,4,5-tetrahydro-5-phenyl-1,4-benzothiazepine 1,1-dioxide, mp 86-87°C; and 64) (+-)-Cis-3-isopentyl-3-ethyl-2,3,4,5-tetrahydro-5-phenyl-1,4-benzothiazepine 1,1-dioxide, mp 123-125°C.

(-)-(RR)-3-butyl-3-ethyl-2,3,4,5-tetrahydro-5-phenyl-1,4-benzothiazepine 1,1-dioxide hydrochloride 2) (+-)-Trans-3-Butyl-3-ethyl-2,3,4,5-tetrahydro-5-phenyl-1,4-benzothiazepine 1,1-dioxide, mp 98-100°C;

3) (-)-Trans-3-Methyl-3-propyl-2,3,4,5-tetrahydro-5-phenyl-1,4-benzothiazepine 1,1-dioxide, mp 129-130°C;

1. A compound of formula (I)

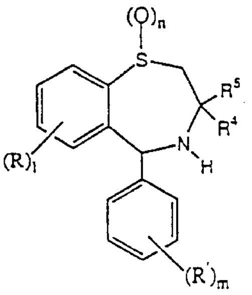

(I)

wherein l is an integer of from 0 to 4;

m is an integer of from 0 to 5;

n is an integer of from 0 to 2;

R and R' are atoms or groups independently selected from halogen, nitro, phenylalkoxy, $C_{1-4}$ alkoxy, $C_{1-6}$ alkyl and $-O(CH_2)_pSO_3R''$ wherein p is an integer of from 1 to 4 and R" is hydrogen or $C_{1-6}$ alkyl, wherein said phenylalkoxy, alkoxy and alkyl groups are optionally substituted by one or more halogen atoms;

$R^4$ is a $C_{1-6}$ straight alkyl group; and $R^5$ is a $C_{2-6}$ straight alkyl group;

and salts, solvates and physiologically functional derivatives thereof.

2. A compound of formula (I) as claimed in Claim 1, wherein n is 2;

$R^4$ is methyl, ethyl, n-propyl, or n-butyl; and $R^5$ is ethyl, n-propyl, or n-butyl;

and salts, solvates and physiologically functional derivatives thereof.

3. A compound of formula (I) as claimed in Claim 2, which compound is in the trans configuration as herein defined, or a salt, solvate, or physiologically functional derivative thereof.

4. A compound of formula (I) as claimed in Claim 3, which compound is trans-3-butyl-3-ethyl-2,3,4,5-tetrahydro-5-phenyl-1,4-benzothiazepine 1,1-dioxide, or a salt, solvate, or physiologically functional derivative thereof.

5. The compound of formula (I) claimed in Claim 4, which compound is in the (RR)-, (SS)-, or (RR,SS)-form, or is a salt, solvate, or physiologically functional derivative of any thereof.

6. (-)-(RR)-3-Butyl-3-ethyl-2,3,4,5-tetrahydro-5-phenyl-1,4-benzothiazepine 1,1-dioxide or a salt, solvate, or physiologically functional derivative thereof.

7. (-)-(RR)-3-Butyl-3-ethyl-2,3,4,5-tetrahydro-5-phenyl-1,4-benzothiazepine 1,1-dioxide 8. (+-)-(RR,SS)-3-Butyl-3-ethyl-2,3,4,5-tetrahydro-5-phenyl-1,4-benzothiazepine 1,1-dioxide or a salt, solvate, or physiologically functional thereof.

9. (+-)-(RR,SS)-3-Butyl-3-ethyl-2,3,4,5-tetrahydro-5-phenyl-1,4-benzothiazepine 1,1-dioxide 1. A polymeric or oligomeric bile acid, prepared by polymerization of a monomeric bile acid of the formula I

G—X—A (I)

in which

G is a free bile acid or its alkali metal salt or a bile acid having rings A, B, C, D esterified on ring D and which is bonded via its ring A, B or C, to the group X, X is a bridge group and A is a polymerizable, ethylenically unsaturated group, or by copolymerization with a monomer containing a polymerizable, ethylenically unsaturated double bond, or by copolymerization with N-vinylpyrrolidone or its derivatives, and/or by copolymerization with ethylenically unsaturated dicarboxylic anhydrides and ethylenically unsaturated dicarboxylic acids each having 2 to 6 carbon atoms; their esters or half esters, esters being understood as alkyl esters having 1-6 carbon atoms, cycloalkyl esters having 5 to 8 carbon atoms, benzyl esters or phenyl esters.

2. A polymer or oligomer as claimed in claim 1, wherein

G is a free bile acid or its alkali metal salt or a bile acid esterified on ring D and which is bonded via its ring A, B or C, to the group X, to which the formula II applies $(Y)_o-(Z)_p$ (II)

in which

Y is adjacent to G and is —O—, —NR'—,

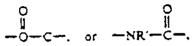

is $(C_1-C_{12})$-alkylene or $(C_7-C_{13})$-aralkylene, where individual methylene groups in the alkylene chain of the alkylene or aralkylene radical can be replaced by one or more groups selected from —O—, —NR'—,

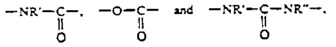

o and p independently of one another are zero or 1, where o and p are not simultaneously zero, A is an ethylenically unsaturated group of the formula

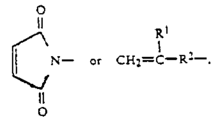

in which $R^1$ is hydrogen or $CH_3$ and $R^2$ is

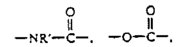

—O—, —NR'— or a single bond, where the carbonyl groups are adjacent to the C—C double bond, R' and R" independently of one another are hydrogen or $(C_1-C_6)$-alkyl.

3. A polymer or oligomer as claimed in claim 2, wherein

G corresponds to the formula III

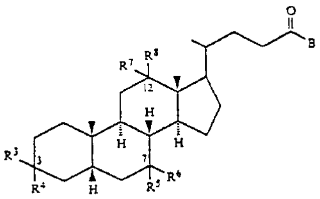

(III)

in which $R^3$ to $R^8$ independently of one another are hydrogen, OH, $NH_2$ or an OH group protected by an OH protective group and one of the radicals $R^3$ to $R^6$ is a bond to the group X, where this bond starts from the positions 3 ($R^3$ or $R^4$) or 7 ($R^5$ or $R_6$), and the other position 7 or 3 in each case carries an OH group or a protected OH group, B is —OH, —O-alkali metal, —O-alkaline earth metal, —O—$(C_1-C_{12})$-alkyl, —O-allyl or —O-benzyl where alkyl is either n-alkyl or iso-alkyl and where the ester group formed

is an ester which can be saponified both by acid and by base,

Y is —O—, —NR'—,

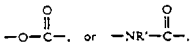

Z is $(C_1-C_{12})$-alkylene, $(C_7-C_{13})$-aralkylene, where 1 to 3 methylene groups in the alkylene chain are replaced by the groups —O—, —NR',

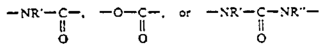

and o and p independently of one another are zero or 1, where o and p are not simultaneously zero, A is

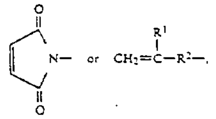

where $R^1$ is hydrogen or $CH_3$ and $R_2$ is

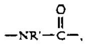

—NR'— or a single bond, in which R' and R" independently of one another are hydrogen or $(C_1-C_6)$-alkyl.

4. The polymeric or oligomeric bile acid of claim 1, wherein said monomer containing a polmerizable, ethylenically unsaturated double bond is a monomer of formula IV

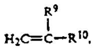
(IV)

in which
$R^9$ is hydrogen or methyl and
$R^{10}$ is

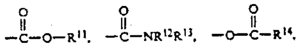

—CN, —O—$R^{15}$, hydrogen halogen —$SO_3H$, or —O—($CH_2$—$CH_2O$)$_n$$R^{16}$,
in which
$R^{11}$ is hydrogen, ($C_1$-$C_{10}$)-alkyl, ($C_1$-$C_{10}$)-monohydroxyalkyl or —($CH_2CH_2$—O—)$_n$$R^{16}$,
$R^{12}$, $R^{13}$, $R^{15}$, and $R^{16}$ are identical or different and are ($C_1$-$C_{10}$)-alkyl,
$R^{14}$ is ($C_1$-$C_{18}$)-alkyl and
n is 1 to 50.

5. A polymer or oligomer as claimed in claim 1, wherein the weight-average molecular weight is up 250,000 g/mol.

6. A polymer or oligomer as claimed in claim 1, wherein in the case of copolymers the molar ratio of bile acid units to copolymerized monomer units is between 300:1 and 1:300.

7. A polymer or oligomer as claimed in claim 1, wherein the crosslinking is carried out by means of copolymerization with ethylenically polyunsaturated monomers.

8. A polymer or oligomer as claimed in claim 7, wherein the crosslinking is carried out with ethylenically polyunsaturated acrylic acid and methacrylic acid derivatives.

9. A polymer or oligomer as claimed in claim 7, wherein the crosslinking is carried out with acid amides of the formula V

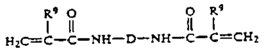
V in which
$R^9$ is hydrogen or methyl and
D is —(CHE)$_m$—,
where
m is 1 to 10 and
E is hydrogen or OH.

10. A pharmaceutical composition comprising a compound of claim 1 and a pharmaceutically acceptable carrier.

11. The polymer or oligomer as claimed in claim 5, wherein the weight-average molecular weight is between 2,000 and 100,000 g/mol.

12. The polymer or oligomer as claimed in claim 12, wherein the weight-average molecular weight is between 3,000 and 60,000 g/mol.

13. The polymer or oligomer as claimed in claim 3, wherein B is —OH, —O-alkali metal, —O—($C_1$-$C_6$)-alkyl, —O-allyl or —O-benzyl.

14. The polymer or oligomer as claimed in claim 3, wherein $R^3$ to $R^8$ independently of one another are hydrogen, OH, $NH_2$ or an OH group protected by an OH protective group and one of the radicals $R^3$ to $R^6$ is a bond to the group X, where this bond starts from the positions 3 ($R^3$ or $R^4$) or 7 ($R^5$ or $R^6$) in the $\beta$-position, and the other position 7 or 3 in each case carries an OH group or a protected OH group.

15. The polymer or oligomer as claimed in claim 2, wherein G is a free bile acid or its alkali metal salt or a bile acid esterfied on ring D which is bonded via its ring A to the group X.

16. A polymer or oligomer as claimed in claim 4, wherein the monomers are compounds according to the formula IV (meth)acrylic acid, (meth)acrylic acid esters, acrylamide and its derivatives, carboxylic acid vinyl esters having 3-20 carbon atoms or N-vinylpyrrolidone and its derivatives.

17. The polymeric or oligomeric bile acid of claim 4, wherein said halogen is chlorine, bromine, or iodine.

* * * * *

EXAMPLE 1

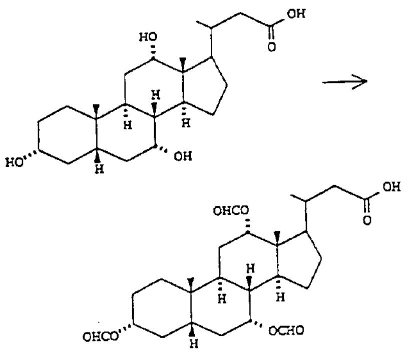

48 g (122 mmol) of 3α,7α,12α-trihydroxy-24-nor-23-cholanic acid (=norcholic acid), 200 ml of formic acid and 1 ml of perchloric acid (60%) are stirred at 50° C. for 1.5 hours, the mixture is cooled to room temperature, 160 ml of acetic anhydride are added and the mixture is stirred for a further 15 minutes. It is poured onto 1.5 l of water and the solid constituents are filtered off with suction and washed with 1l of water. The residue is dissolved in 700 ml of ether and washed three times with water. The organic phase is dried ($MgSO_4$) and concentrated. Yield 52 g (89%) of Example 1.

MS (FAB, 3-NBA/LiCl) $C_{26}H_{38}O_8$(478), 485 ($M+Li^+$)

EXAMPLE 2

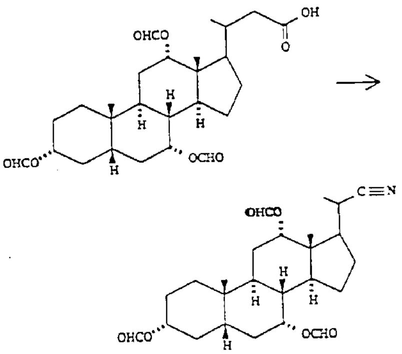

5 g (10.4 mmol) of Example 1 are dissolved in 20 ml of trifluoroacetic acid/5 ml of trifluoroacetic anhydride at 0° C. 840 mg (12 mmol) of sodium nitrite are added in portions in the course of one hour. The mixture is subsequently stirred at 0° C. for a further hour then at 40° C. for 2 hours. The solution is cooled to 0° C. again, neutralized with 5N NaOH and extracted with dichloromethane. The organic phase is dried ($MgSO_4$) and concentrated. Chromatography of the residue over silica gel (cyclohexane/ethyl acetate=2:1) gives 3.1 g (67%) of Example 2.

MS (FAB, 3-NBA/LiCl) $C_{25}H_{35}NO_6$ (445), 452 (M+Li$^+$)

EXAMPLE 3

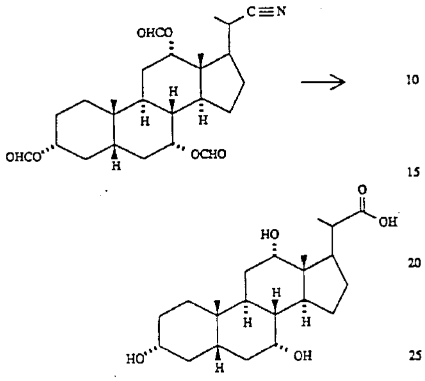

1.5 g (3.37 mmol) of Example 2 and 5 g of KOH are dissolved in 50 ml of ethanol/water (=1:1) and the solution is heated under reflux. When the reaction has ended (monitoring by thin layer chromatography), the ethanol is stripped off and the residue is washed with ether. The aqueous phase is acidified with 2N HCl and extracted three times with ethyl acetate. The combined organic phases are dried ($MgSO_4$) and concentrated. 1.25 g (97%) of Example 3 are obtained.

MS (FAB, 3-NBA/LiCl) $C_{22}H_{36}O_5$(380), 387 (M+Li$^+$)

EXAMPLE 4

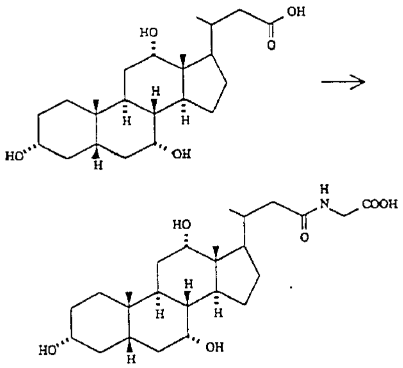

500 mg (12.87 mmol) of 3α,7α,12α-trihydroxy-24-nor-23-cholanic acid and 370 mg (36 mmol) of N-methylmorpholine are dissolved in 20 ml of THF. 0.34 ml (36 mmol) of ethyl chloroformate is added at 10° C. After 15 minutes, a solution of 270 mg (36 mmol) of glycine in 5 ml of 1N NaOH is added dropwise. The mixture is subsequently stirred at room temperature for 18 hours. The reaction mixture is concentrated and the residue is chromatographed over silica gel (dichloromethane/methanol= 8:2). 320 mg (56%) of Example 4 are obtained.

MS (FAB/3-NBA) $C_{25}H_{41}NO_6$ (451), 452 (M+H$^+$)

EXAMPLE 5

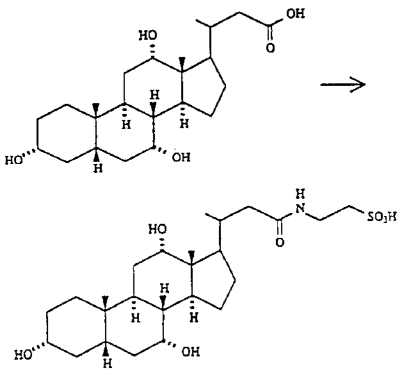

340 mg (53%) of Example 5 are obtained from 500 mg (12.67 mmol) of norcholic acid and 450 mg (836 mmol) of taurine by the process described for Example 4.

MS (FAB, 3-NBA) $C_{25}H_{43}NO_7S$ (501), 502 (M+H$^+$)

EXAMPLE 6

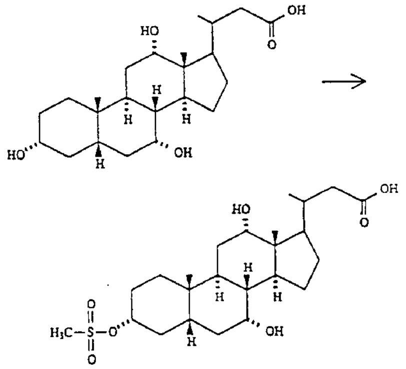

10 g (25.3 mmol) of norcholic acid are dissolved in 50 ml of pyridine. 2.6 ml of methanesulfonyl chloride are added dropwise at 0° C. The reaction mixture is then stirred at room temperature for 3 hours. It is poured onto ice-water and extracted three times with ethyl acetate. The organic phase is dried ($MgSO_4$) and concentrated. The crude product is crystallized from diisopropyl ether, filtered off with suction and then dried in vacuo. 11.2 g (93%) of Example 6 are obtained.

MS (FAB, 3-NBA/LiCl) $C_{24}H_{40}O_7S$ (472), 485 ($M+2Li^+-H^+$)

EXAMPLE 7

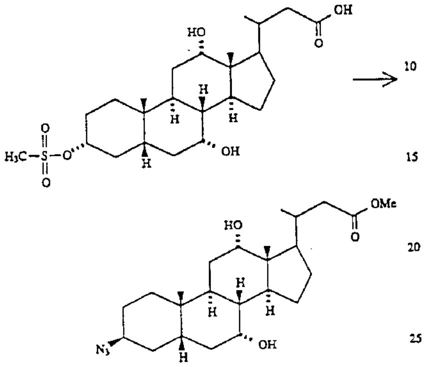

38.7 g (81.9 mmol) of Example 6 and 6.9 g (106 mmol) of sodium azide are stirred in 350 ml of dimethylformamide at 130° C. for 2.5 hours. After cooling, the mixture is poured onto 1.5 l of ice-water and extracted three times with ethyl acetate. The organic phase is dried ($MgSO_4$) and concentrated. The crude product is esterified in a methanolic hydrochloric acid solution, prepared from 100 ml of methanol and 14 ml of acetyl chloride, at room temperature for 2 hours. For working up, the mixture is partly concentrated and the product is poured onto 1 l of water and extracted three times with ethyl acetate. After drying and concentration of the organic phase, the crude product is chromatographed over silica gel (cyclohexane/ethyl acetate=6:4). 9.0 g (25%) of Example 7 are obtained.

MS (FAB, 3-NBA/LiCl) $C_{24}H_{39}N_3O_4$ (433), 440 ($M+Li^+$)

EXAMPLE 8

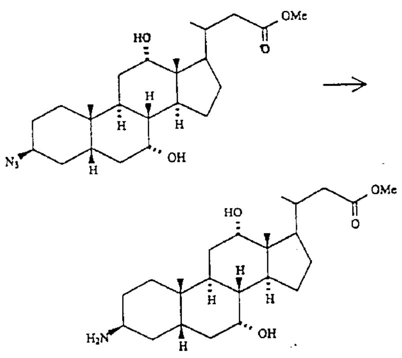

8.0 g (18.5 mmol) of Example 7 are hydrogenated with hydrogen in 220 ml of ethyl acetate in the presence of about 50 mg of 10% Pd/C. When the reaction has ended, the catalyst is filtered off and the filtrate is concentrated. Chromatography of the residue (methanol/triethylamine= 95:5) gives 6.0 g (80%) of Example 8.

MS (FAB, 3-NBA/LiCl) $C_{24}H_{41}NO_4$ (407), 414 ($M+Li^+$)

EXAMPLE 9

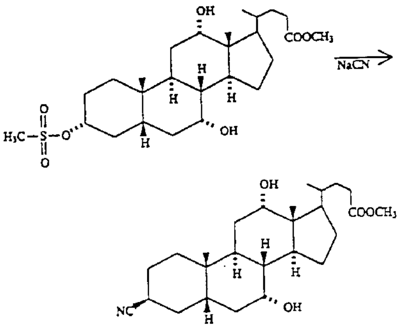

4.3 g (8.6 mmol) of the mesylate (cf. EP-A-0 489 423) are heated at 100 to 110° C. in 80 ml of dry DMF with 0.42 g (8.6 mmol) of sodium cyanide for 3 hours. The mixture is poured onto ice-water and extracted with ethyl acetate, and the residue from the organic phase is filtered over silica gel. (Ethyl acetate/heptane=2:1). 890 mg (25%) of nitrile are obtained.

MS (FAB, 3-NBA/LiCl) $C_{26}H_{41}NO_4$ (431), 438 ($M+Li^+$)

EXAMPLE 10

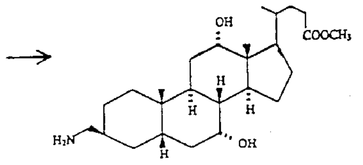

1.5 g (3.48 mmol) of the nitrile from Example 9 are hydrogenated in 100 ml of methanol with addition of 10 ml of concentrated ammonia solution and 1 g of 5% strength rhodium-on-$Al_2O_3$ under 140 bar at 50° C. for 24 hours. The catalyst is filtered off with suction, the filtrate is concentrated and the residue is purified over silica gel ($CH_2Cl_2$/MeOH/concentrated $NH_3$ solution=100:15:2). 1.1 g (73%) of amine (Example 10) are obtained.

MS (FAB, 3-NBA/LiCl) $C_{26}H_{45}NO_4$ (435), 442 ($M+Li^+$)

EXAMPLE 11A

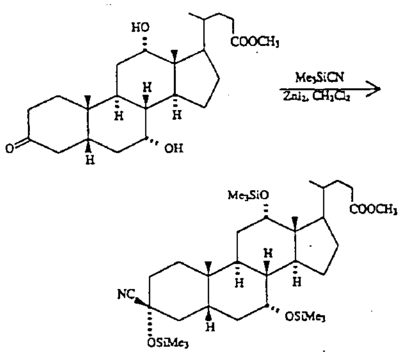

270 mg of dry zinc iodide are added to 9 g (21.4 mmol) of ketone (see equation 4) under argon in 50 ml of dry dichloromethane, and 10 ml (3.5 equivalents) of trimethylsilyl cyanide are added in portions, while cooling with ice. After about 1.5 hours, the reaction has ended. The residue which remains after concentration is purified with n-heptane/ethyl acetate=10:1 over silica gel. 12.1 g (85%) of the product are obtained as a colorless oil which predominantly (>9:1) comprises one stereoisomer.

MS (FAB, 3-NBA/LiCl) $C_{35}H_{65}NO_5Si_3$ (664), 671 $(M+Li^+)$

EXAMPLE 11B

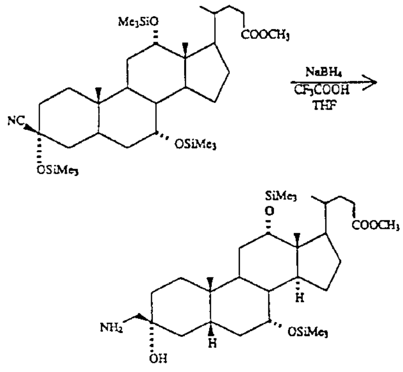

2.1 ml (27.4 mmol) of trifluoroacetic acid are first added to a suspension of 1.036 g (827.4 mmol) of sodium borohydride in dry THF, the mixture is stirred for 15 minutes and 12.1 g (18.2 mmol) of the nitrile from Example 11A in 40 ml of dry THF are then added, while cooling with ice. After 24 hours at room temperature, the mixture is worked up by addition of water and ether, the organic phase is extracted by shaking with hydrogen-carbonate solution and the residue is purified by chromatography with $CH_2Cl_2/CH_3OH$/concentrated $NH_3$ solution=100:10:1.5. 7.83 g (48%) of the amine are obtained.

MS (FAB, 3-NBA/LiCl) $C_{32}H_{61}NO_5Si_2$ (596), 603 $(M+Li^+)$

EXAMPLE 12A

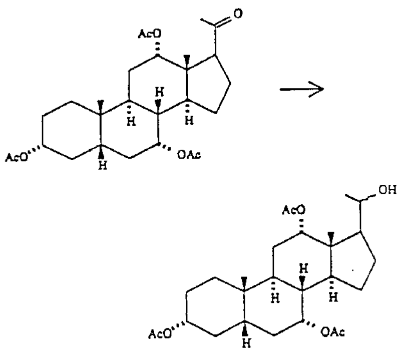

20 g (42 mmol) of methyl ketone (cf. equation 2) are dissolved in 400 ml of methanol, 2.48 g (64 mmol) of sodium borohydride are added and the mixture is stirred at room temperature for 45 minutes. After addition of 400 ml of water, 2N HCl is carefully added until the pH reaches 3. The mixture is concentrated, water is added again and the mixture is extracted with EA. The organic phase is dried and concentrated, and the residue is chromatographed over silica gel (cyclohexane/ethyl acetate 1:1).

Yield: 15.1 g (75%)

MS (FAB, 3-NBA/LiCl) $C_{27}H_{42}O_7$ (478), 485 $(M+Li^+)$

EXAMPLE 12B

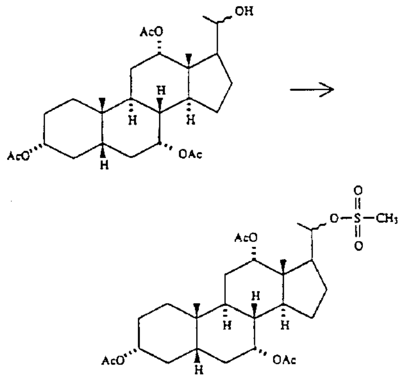

15.1 g (31.5 mol) of alcohol (Example 12A) are dissolved in 250 ml of dichloromethane/250 ml of pyridine, 4 g (35 mmol) of methanesulfonyl chloride are added at 0° C. and the mixture is stirred at room temperature for 2 hours. For working up, water is added and the mixture is extracted with ethyl acetate. After drying and concentration of the ethyl acetate phase, 17.5 g of (quaternary) mesyl compound, which can be reacted without further purification, are obtained.

MS (FAB, 3-NBA/LiCl) $C_{28}H_{44}O_9S$ (556), 563 (M+Li$^+$)

EXAMPLE 12C

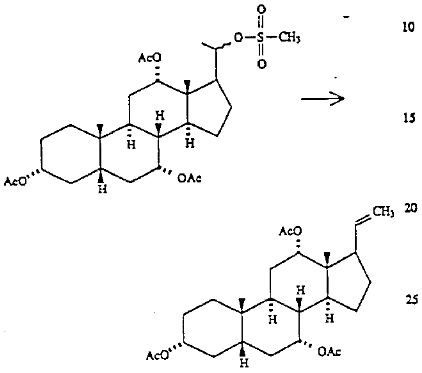

18 g (32.3 mmol) of Example 12B and 80 ml of diazabicycloundecene are dissolved in 400 ml of DMF. The mixture is stirred at 100° C. for 16 hours. After cooling, the reaction mixture is concentrated and the residue is chromatographed over silica gel (cyclohexane/ethyl acetate=7:3). The yield is 9.6 g (64%).

MS (FAB, 3-NBA/LiCl) $C_{27}H_{40}O_6$ (460), 467 (M+Li$^+$)

EXAMPLE 12D

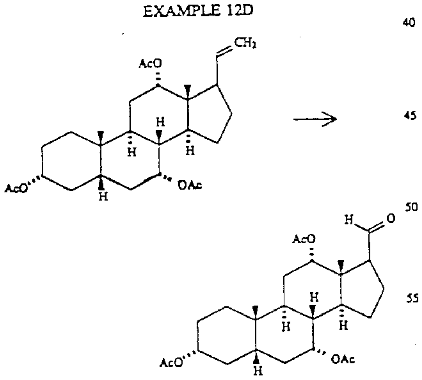

13 g (28.2 mmol) of Example 12C are dissolved in 100 ml of dichloromethane, 10 ml of pyridine are added and the mixture is cooled to −60° C. Ozone is passed in, while stirring, until a blue coloration is obtained. The mixture is then flushed with $N_2$ and warmed to room temperature, and dimethyl sulfide is added. The reaction mixture is concentrated and the residue is chromatographed over silica gel (cyclohexane/ethyl acetate=7.3). 5.8 g (44%) of aldehyde are obtained.

MS (FAB, 3-NBA/LiCl) $C_{26}H_{38}O_7$ (462), 469 (M+Li$^+$)

EXAMPLE 12E

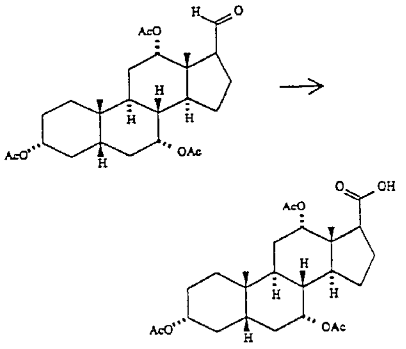

The aldehyde Example 12D is oxidized to the free C-20-carboxylic acid Example 12E by Jones oxidation (J. Chem. Soc. 1953, 2548).

MS (FAB, 3-NBA/LiCl) $C_{26}H_{38}O_8$ (478), 485 (M+Li$^+$)

EXAMPLE 12F

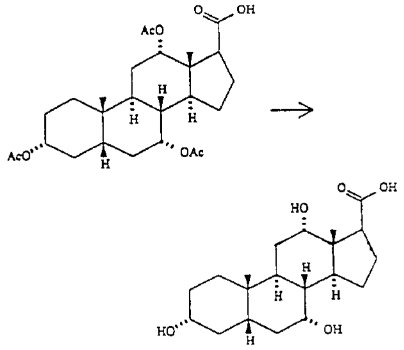

550 mg (1.15 mmol) of Example 12E are dissolved in 20 ml of ethanol, 10 ml of 2N NaOH are added and the mixture is stirred at room temperature for 24 hours. Water is added and the organic solvents are stripped off. The pH is brought to 3 to 4 with 2N HCl. Thereafter, the mixture is concentrated completely and the residue is chromatographed over silica gel ($CHCl_3$/MeOH=4:1). 270 mg (67%) of product are obtained.

MS (FAB, 3-NBA/LiCl) $C_{20}H_{32}O_5$ (352), 359 (M+Li$^+$)

EXAMPLE 13

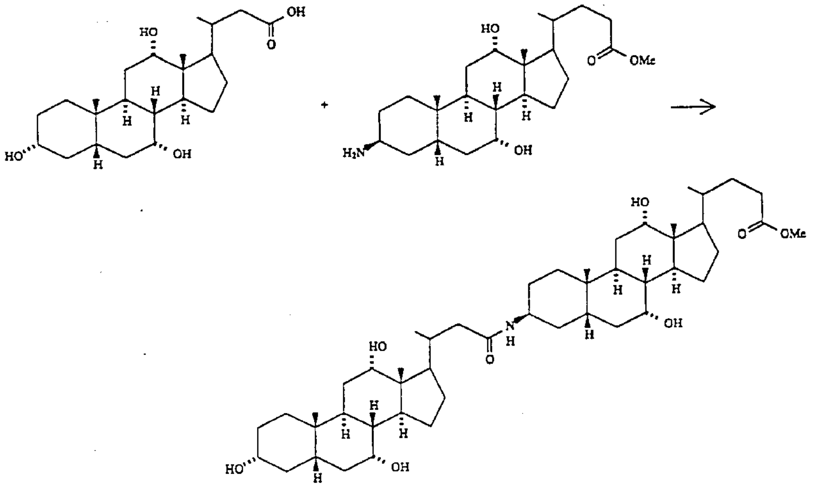

2.0 g (5.01 mmol) of 3α,7α,12α-trihydroxy-24-nor-23-cholanic acid, 2.1 g (4.98 mmol) of methyl 3β-amino-7α,12α-dihydroxy-24-cholanate (cf. EP-A-0 417 725), 1.36 g (10 mmol) of hydroxybenzotriazole and 1.04 g (5.4 mmol) of dicyclohexylcarbodiimide are stirred in 100 ml of dry tetrahydrofuran at room temperature for 24 hours. The reaction mixture is concentrated and the residue is chromatographed over silica gel (chloroform/methanol=85:15). 3.0 g (75%) of Example 13 are obtained.

MS (FAB, 3-NBA/LiCl) $C_{48}H_{79}NO_8$ (798), 805 ($M+Li^+$)

Examples 14 to 31 of Tables 1 to 3 are obtained analogously to Example 13 (reactive —X—G2 derivatives are described in EP-A-0 489 423 or EP-A-0 417 725).

TABLE 1

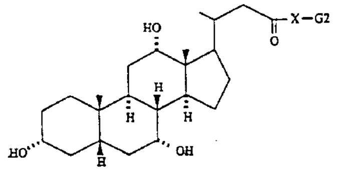

| Ex. | −X−G2 | MS (FAB, 3-NBA/LiCl) |
|---|---|---|
| 14 | 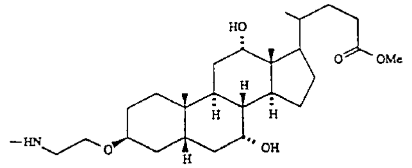 | $C_{50}H_{83}NO_9$ (842), 849 ($M+Li^+$) |

TABLE 1-continued
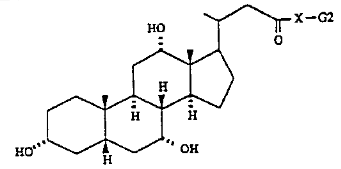
| Ex. | −X−G2 | MS (FAB, 3-NBA/LiCl) |
|---|---|---|
| 15 | 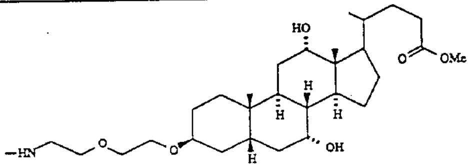 | $C_{52}H_{87}NO_{10}$ (886), 893 (M+Li$^+$) |
| 16 | 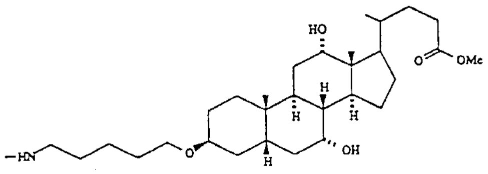 | $C_{54}H_{91}NO_9$ (898), 905 (M+Li$^+$) |
| 17 | 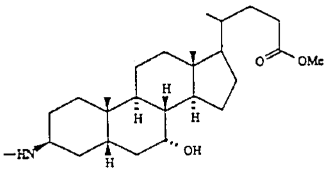 | $C_{48}H_{79}NO_7$ (782), 789 (M+Li$^+$) |
| 18 | 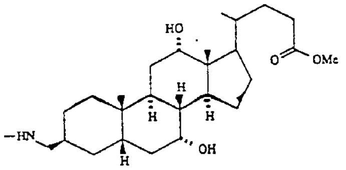 | $C_{49}H_{81}NO_8$ (812), 819 (M+Li$^+$) |
| 19 | 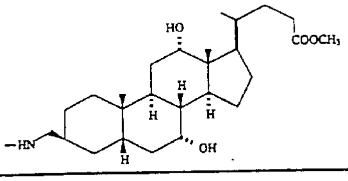 | $C_{55}H_{97}NO_9Si_2$ (972), 979 (M+Li$^+$) |

TABLE 2
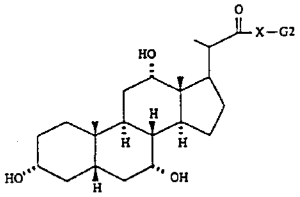
| Ex. | −X−G2 | MS (FAB, 3-NBA/LiCl) |
|---|---|---|
| 20 | 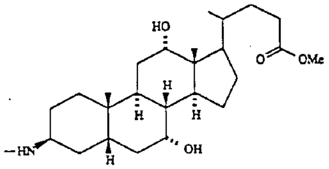 | $C_{47}H_{77}NO_8$ (784), 791 ($M+Li^+$) |
| 21 | 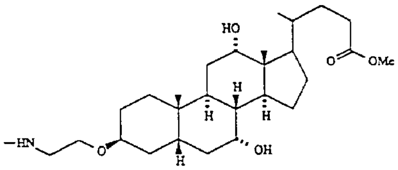 | $C_{49}H_{81}NO_9$ (828), 835 ($M+Li^+$) |
| 22 | 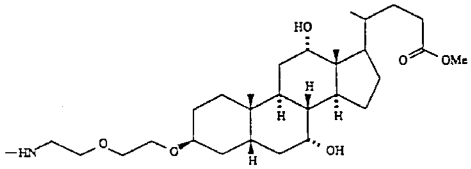 | $C_{51}H_{85}NO_{10}$ (872), 879 ($M+Li^+$) |
| 23 | 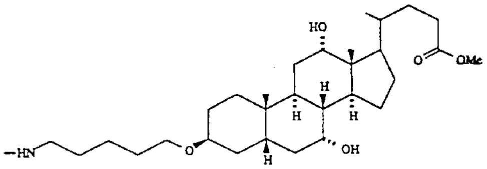 | $C_{53}H_{89}NO_9$ (884), 891 ($M+Li^+$) |
| 24 | 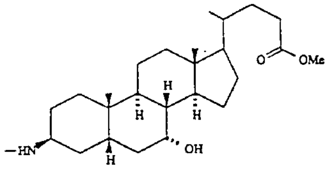 | $C_{47}H_{77}NO_7$ (768), 775 ($M+Li^+$) |

TABLE 2-continued
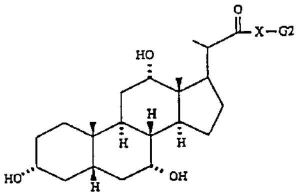
| Ex. | -X-G2 | MS (FAB, 3-NBA/LiCl) |
| --- | --- | --- |
| 25 | 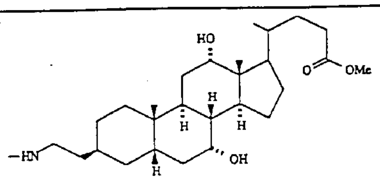 | $C_{49}H_{81}NO_8$ (812), 819 (M+Li$^+$) |
| 26 | 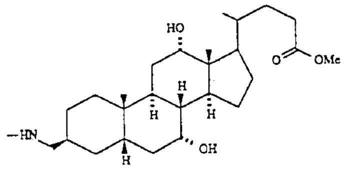 | $C_{48}H_{79}NO_9$ (814), 821 (M+Li$^+$) |
TABLE 3
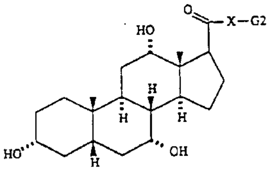
| Ex. | -X-G2 | MS (FAB, 3-NBA/LiCl) |
| --- | --- | --- |
| 27 | 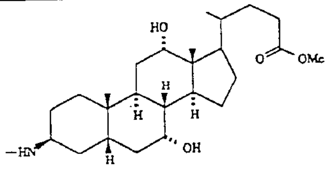 | $C_{45}H_{73}NO_8$ (756), 763 (M+Li$^+$) |

TABLE 3-continued
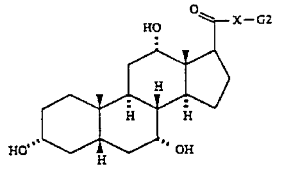
| Ex. | −X−G2 | MS (FAB, 3-NBA/LiCl) |
|---|---|---|
| 28 | 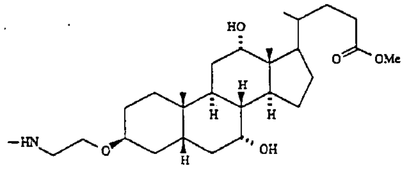 | $C_{47}H_{77}NO_9$ (800), 807 (M+Li$^+$) |
| 29 | 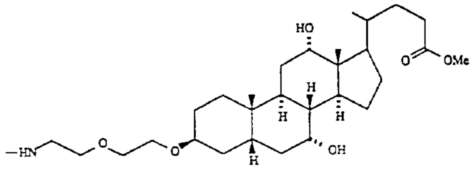 | $C_{49}H_{81}NO_{10}$ (844), 851 (M+Li$^+$) |
| 30 | 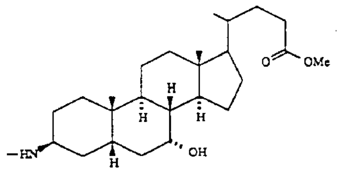 | $C_{45}H_{73}NO_7$ (740), 747 (M+Li$^+$) |
| 31 | 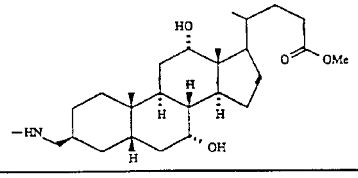 | $C_{46}H_{75}NO_7$ (754), 761 (M+Li$^+$) |

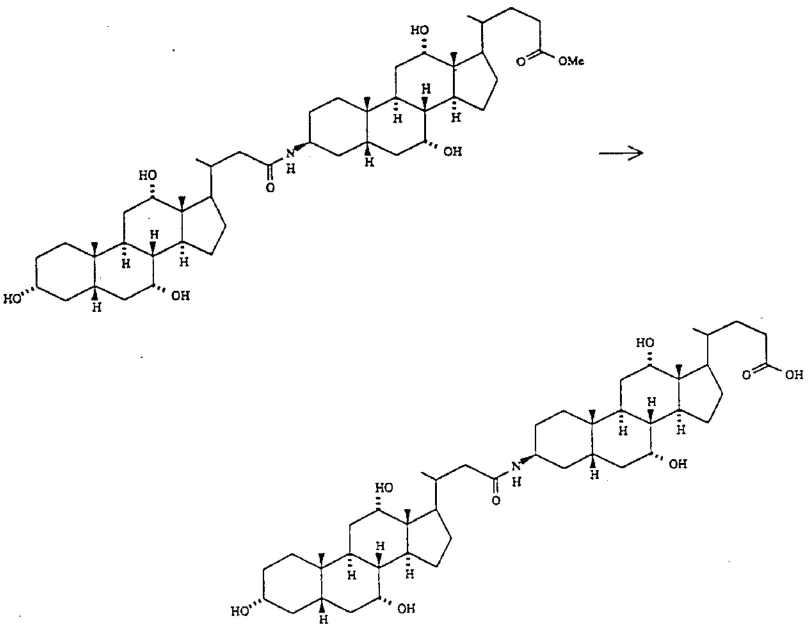

3.0 g (3.76mmol) of Example 13 are dissolved in 80 ml of ethanol, 30 mol of 1N aqueous NaOH are added and the mixture is stirred at room temperature for 16 hours. For working up, 30 ml of water are added and the alcohol is stripped off completely. After acidification with 1N HCl, the precipitate is filtered off with suction, washed with water and dried in vacuo. 2.5 g (85%) of Example 32 are obtained.

MS (FAB, 3-NBA/LiCl) $C_{47}H_{77}NO_8$ (784), 791 ($M+Li^+$)

Examples 33 to 50 of Tables 4 to 6 are obtained analogously to Example 32 from the methyl esters (Tables 1-3).

TABLE 4
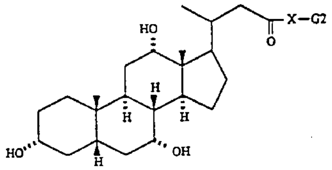
| Ex. | −X−G2 | MS (FAB, 3-NBA/LiCl) |
|---|---|---|
| 33 | 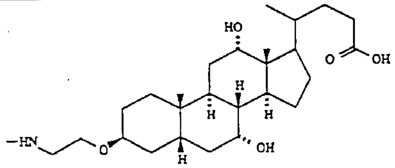 | $C_{49}H_{81}NO_9$ (828), 835 (M+Li$^+$) |
| 34 | 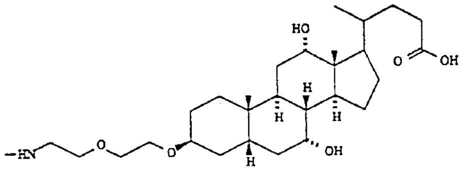 | $C_{51}H_{85}NO_{10}$ (872), 879 (M+Li$^+$) |
| 35 | 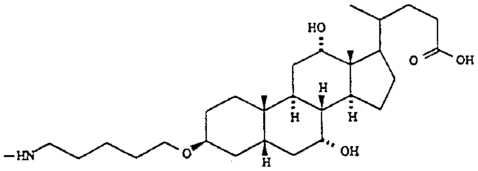 | $C_{53}H_{89}NO_9$ (884), 891 (M+Li$^+$) |
| 36 | 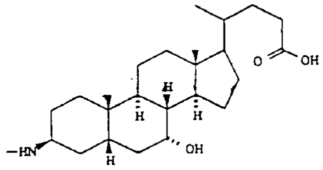 | $C_{47}H_{77}NO_7$ (768), 775 (M+Li$^+$) |
| 37 | 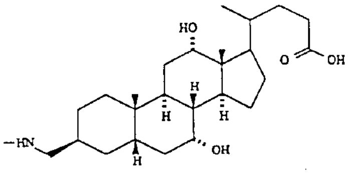 | $C_{48}H_{79}NO_8$ (798), 805 (M+Li$^+$) |

TABLE 4-continued
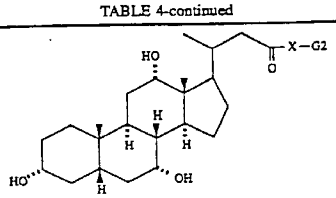
| Ex. | −X−G2 | MS (FAB, 3-NBA/LiCl) |
|---|---|---|
| 38 | 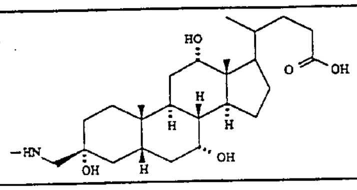 | $C_{48}H_{79}NO_9$ (814), 821 ($M+Li^+$) |
TABLE 5
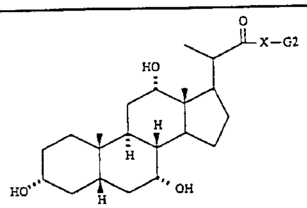
| Ex. | −X−G2 | MS (FAB, 3-NBA/LiCl) |
|---|---|---|
| 39 | 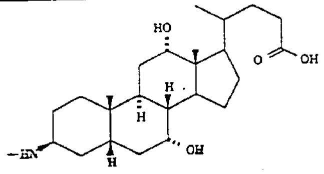 | $C_{46}H_{75}NO_8$ (770), 777 ($M+Li^+$) |
| 40 | 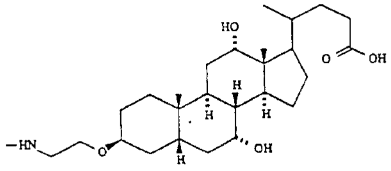 | $C_{48}H_{79}NO_9$ (814), 821 ($M+Li^+$) |

TABLE 5-continued
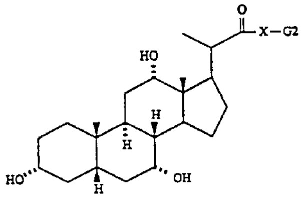
| Ex. | −X−G2 | MS (FAB, 3-NBA/LiCl) |
|---|---|---|
| 41 | 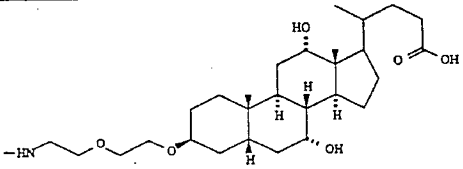 | $C_{50}H_{83}NO_{10}$ (858), 865 (M+Li⁺) |
| 42 | 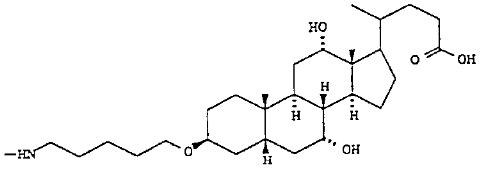 | $C_{52}H_{87}NO_9$ (870), 877 (M+Li⁺) |
| 43 | 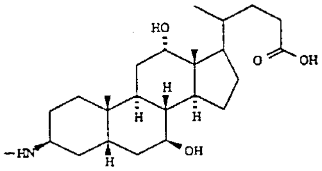 | $C_{46}H_{75}NO_7$ (754), 755 (M+Li⁺) |
| 44 | 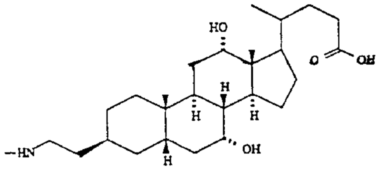 | $C_{48}H_{79}NO_8$ (798), 805 (M+Li⁺) |
| 45 | 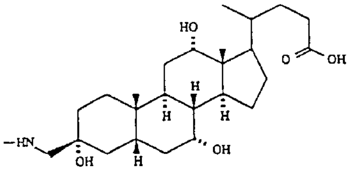 | $C_{47}H_{77}NO_9$ (800), 807 (M+Li⁺) |

TABLE 6
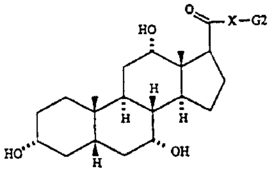
| Ex. | −X−G2 | MS (FAB, 3-NBA/LiCl) |
|---|---|---|
| 46 | 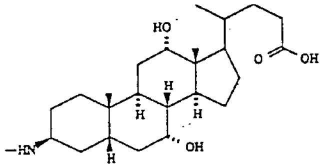 | $C_{44}H_{71}NO_8$ (742), 749 ($M+Li^+$) |
| 47 | 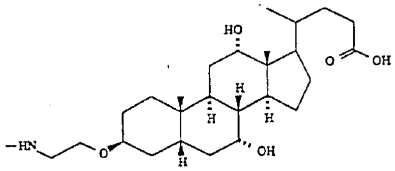 | $C_{46}H_{75}NO_9$ (786), 793 ($M+Li^+$) |
| 48 | 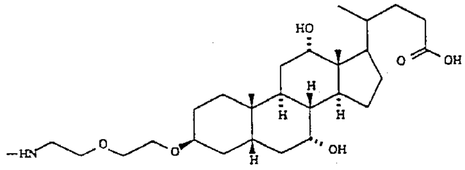 | $C_{48}H_{79}NO_{10}$ (830), 837 ($M+Li^+$) |
| 49 | 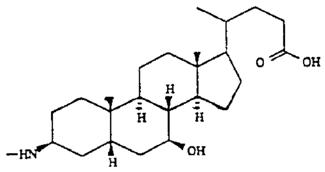 | $C_{44}H_{71}NO_7$ (726), 733 ($M+Li^+$) |
| 50 | 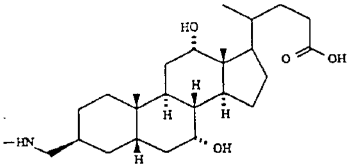 | $C_{45}H_{73}NO_7$ (740), 747 ($M+Li^+$) |
Examples 51 to 54 from Table 7 are obtained analogously to Example 5 from the acids described above.

TABLE 7
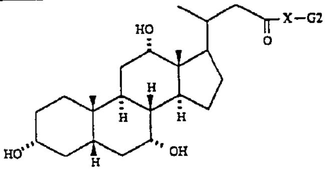
| Ex. | —X—G2 | MS (FAB, 3-NBA/LiCl) |
|---|---|---|
| 51 | 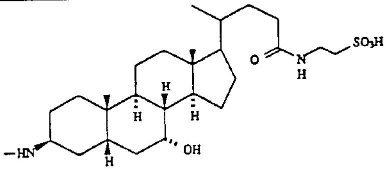 | $C_{49}H_{82}N_2O_{10}S$ (891), 892 (M+H⁺) |
| 52 | 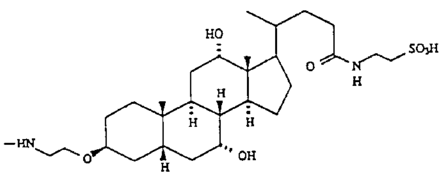 | $C_{51}H_{86}N_2O_{11}S$ (935), 942 (M+H⁺) |
| 53 | 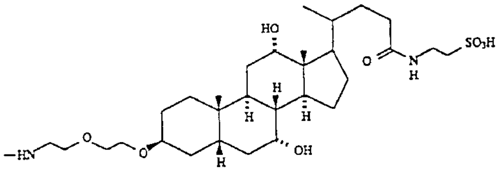 | $C_{53}H_{90}N_2O_{12}S$ (976), 1024 (M+H⁺) |
| 54 | 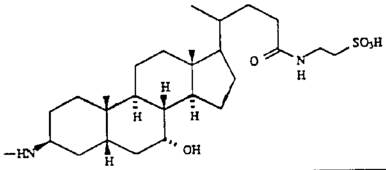 | $C_{49}H_{82}N_2O_9S$ (875), 920 (M+H⁺) |
Examples 55 to 57 of Table 8 are obtained analogously to Example 4.

TABLE 8
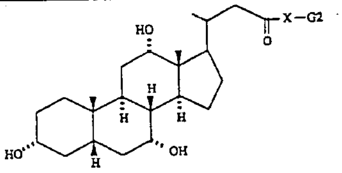
| Ex. | —X—G2 | MS (FAB, 3-NBA/LiCl) |
|---|---|---|
| 55 | 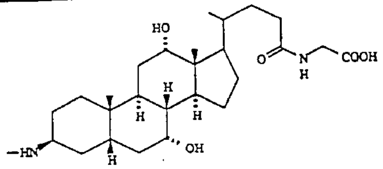 | $C_{48}H_{80}N_2O_9$ (841), 842 (M+H$^+$) |
| 56 | 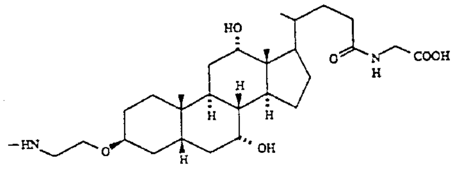 | $C_{51}H_{84}N_2O_{10}$ (885), 892 (M+Li$^+$) |
| 57 | 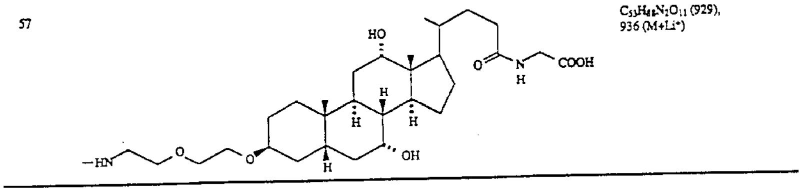 | $C_{53}H_{88}N_2O_{11}$ (929), 936 (M+Li$^+$) |
Examples 58 to 63 of Table 9 are obtained analogously to Example 13.

TABLE 9
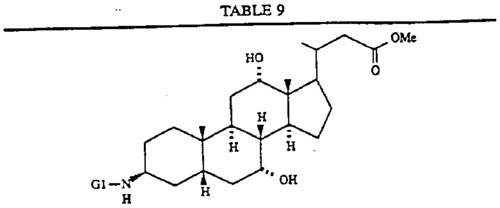
(in the following formulae, the free valency of G1 is not shown).
| Ex. | G1— | MS (FAB, 3-NBA/LiCl) |
|---|---|---|
| 58 | 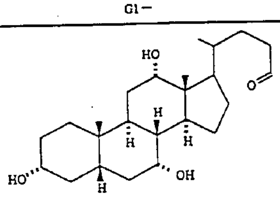 | $C_{48}H_{79}NO_8$ (798), 805 (M+Li$^+$) |
| 59 | 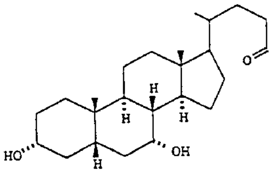 | $C_{48}H_{79}NO_7$ (782), 789 (M+Li$^+$) |
| 60 | 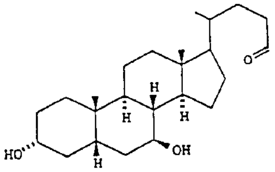 | $C_{48}H_{79}NO_7$ (782), 789 (M+Li$^+$) |
| 61 | 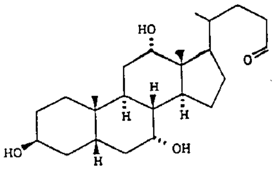 | $C_{48}H_{79}NO_8$ (798), 805 (M+Li$^+$) |
| 62 | 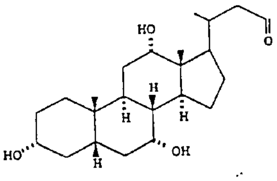 | $C_{47}H_{77}NO_8$ (784), 791 (M+Li$^+$) |

TABLE 9-continued
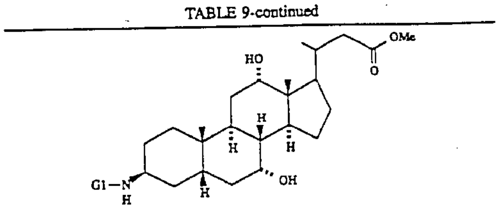
(in the following formulae, the free valency of G1 is not shown).
| Ex. | G1 — | MS (FAB, 3-NBA/LiCl) |
|---|---|---|
| 63 | 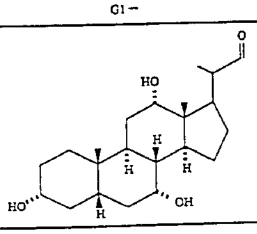 | $C_{46}H_{75}NO_8$ (770), 777 (M+Li$^+$) |
Examples 64 to 69 of Table 10 are obtained analogously to Example 32.
TABLE 10
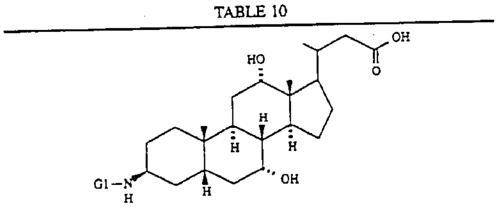
(The free valency of G1 is not shown in the following formulae)
| Ex. | G1 — | MS (FAB, 3-NBA/LiCl) |
|---|---|---|
| 64 | 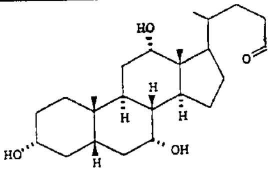 | $C_{47}H_{77}NO_8$ (784), 791 (M+Li$^+$) |
| 65 | 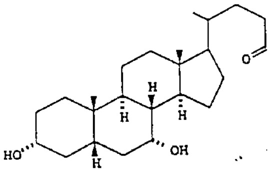 | $C_{47}H_{77}NO_7$ (768), 775 (M+Li$^+$) |

TABLE 10-continued

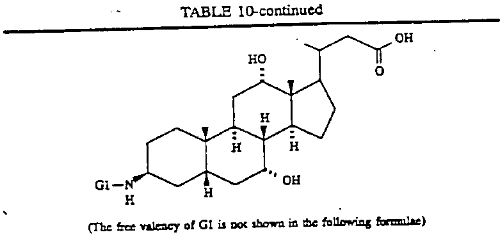

(The free valency of G1 is not shown in the following formulae)

| Ex. | G1 — | MS (FAB, 3-NBA/LiCl) |
|---|---|---|
| 66 | 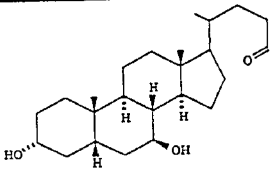 | $C_{47}H_{77}NO_7$ (768), 775 (M+Li$^+$) |
| 67 | 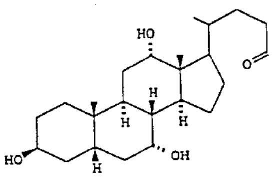 | $C_{47}H_{77}NO_8$ (784), 791 (M+Li$^+$) |
| 68 | 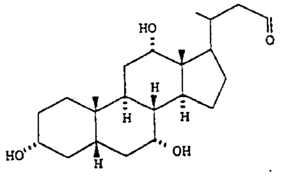 | $C_{46}H_{75}NO_8$ (770), 771 (M+Li$^+$) |
| 69 | 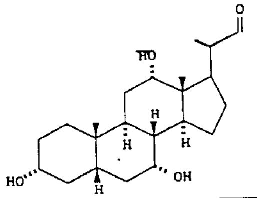 | $C_{45}H_{73}NO_8$ (756), 763 (M+Li$^+$) |

The sodium salts of Example 32 and all the examples of Tables 4 to 8 and 10 can be prepared. The compound is dissolved in methanol, an equimolar amount of 1N aqueous NaOH is added and the mixture is then evaporated in vacuo.

1. A bile acid derivative of the formula I $G_1—X—G_2$ wherein $G_1$ is linked via the side chain on atom No. 17 with the bonding member X to atom No. 3 of $G_2$, and $G_1$ is a radical of the formula II

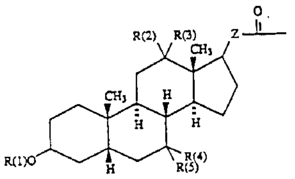

in which

Z is one of the following radicals

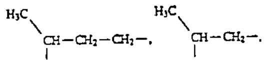

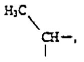

or a single bond,

R(1) is H, an alkyl radical having 1 to 10 carbon atoms or an alkenyl radical having 2 to 10 carbon atoms, R(2), R(3), R(4), R(5) are independently H, OH or R(2) and R(3), or R(4) and R(5) together form the oxygen of a carbonyl group, X is a single bond or a bridge member of the formula III

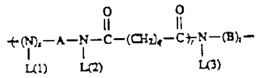

in which

A is an alkylene chain, which is branched or unbranched, and which is optionally interrupted by —O—, —S—, or phenylene, the linkage of the phenyl ring being in the ortho-, meta- or para-position and the chain comprising 2 to 12 chain members, B is an alkylene chain which is branched or unbranched, and which is optionally interrupted by —O—, —S—, or phenylene, the linkage of the phenyl ring being in the ortho-, meta- or para-position and the chain comprising 2 to 12 chain members, L(1), L(2) and L(3) are identical or different and are selected from H, an alkyl radical or alkenyl radical having up to 10 carbon atoms, a cycloalkyl radical having 3 to 8 carbon atoms, a phenyl radical, which is unsubstituted or mono- to trisubstituted by F, Cl, Br, $(C_1–C_4$-alkyl or $(C_1–C_4$-alkoxy, or a benzyl radical, which is unsubstituted or mono- to trisubstituted by F, Cl, Br, $(C_1–C_4)$-alkyl or $(C_1–C_4)$-alkoxy, q is 0 to 5;

r is 0 or 1;

s is 0 or 1; and t is 0 or 1, $G_2$ is a radical of the formula IV

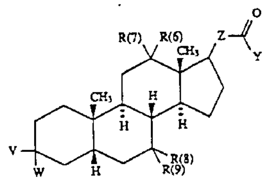

in which Z is one of the following radicals

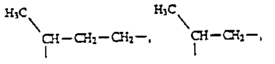

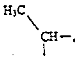

or a single bond, with the proviso that Z may be

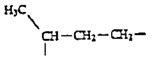

in only one of formulas II and IV;

V is —O— or

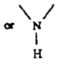

when

W is H or,

V is $—CH_2—$ or $—CH_2—CH_2—$ when W is H or OH,

Y is —OL, NHL,

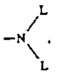

or an amino acid or amino-sulfonic acid bonded via the amino group, selected from the group consisting of $—NH—CH_2—COOH$, $—NH—CH_2—CH_2—$, $SO_3H$,

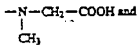 and 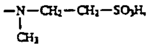

in which L is H, an alkyl radical or alkenyl radical having up to 10 carbon atoms, a cycloalkyl radical having 3 to 8 carbon atoms, a phenyl radical, which is unsubstituted or mono- to trisubstituted by F, Cl, Br, ($C_1$–$C_4$)-alkyl or ($C_1$–$C_4$)-alkoxy, or a benzyl radical, which is unsubstituted or mono- to trisubstituted by F, Cl, Br, ($C_1$–$C_4$)-alkyl or ($C_1$–$C_4$)-alkoxy, and R(6), R(7), R(8), R(9) are independently H, OH or R(6) and R(7) or R(8) and R(9) together form the oxygen of a carbonyl group.

2. The bile acid derivative of the formula I, as claimed in claim 1, wherein L is an alkenyl radical having 2 to 10 carbon atoms.

3. The bile acid derivative of formula I, as claimed in claim 1, wherein one or more of L(1), L(2) or L(3) is an alkenyl radical having 2 to 10 carbon atoms.

Description

Bile acid derivatives, processes for their preparation and the use of these compounds as medicaments The invention relates to novel bile acid derivatives, processes for their preparation, pharmaceutical preparations based on these compounds and the use of the bile acid derivatives as medicaments.

Bile acids have an important physiological function in lipolysis, for example as cofactors of pancreatic lipases and as natural detergents for solubilizing fats and fat-soluble vitamins. As the end product of cholesterol metabolism, they are synthesized in the liver, stored in the gall bladder and secreted from this by contraction into the small intestine, where they display their physiological action. The greatest proportion of the bile acids secreted is recovered via the enterohepatic circulation. They return to the liver via the mesenterial veins of the small intestine and the portal vein system. Both active and passive transportation processes play a role in reabsorption in the intestine. Most of the bile acids is reabsorbed at the end of the small intestine, the terminal ileum, by a specific $Na^+$-dependent transportation system, and returns to the liver with the mesenterial vein blood via the portal vein, to ' secreted by the liver cells again into the bile. The bile acids appear in the enterohepatic circulation both as free acids and in the form of glycine conjugates and taurine conjugates.

Non-absorbable, insoluble, basic, crosslinked polymers have been used for many years for binding bile acids and utilized therapeutically on the basis of these properties. Bile acid derivatives described in Patent Application EP-A-0 489 423 have a high affinity for the intestinal bile acid transportation system and therefore allow specific inhibition of the enterohepatic circulation. All diseases in which inhibition of bile acid resorption in the intestine, in particular in the small intestine, seems desirable are regarded as the therapeutic object. For example, the biligenic diarrhea following ileum resection or increased blood cholesterol levels are treated in this manner. In the case of increased blood cholesterol level, a reduction in this level can be achieved by intervention in the enterohepatic circulation. The corresponding new synthesis of bile acids from cholesterol in the liver is caused by lowering the bile acid pool in the enterohepatic circulation. The LDL-cholesterol in the blood circulation is resorted to in order to meet the cholesterol requirement in the liver, the hepatic LDL receptors increasingly being used. The acceleration of LDL metabolism which has thus occurred takes effect by reducing the atherogenic cholesterol content in the blood.

The object was to discover novel medicaments which are capable of reducing the atherogenic cholesterol content in the blood or of influencing the enterohepatic circulation in respect of increased excretion of bile acid and consequent reduction in the cholesterol level.

This object is achieved by the bile acid derivatives according to the invention.

EP-A-0 489 423 relates to dimeric bile acid derivatives of the formula

G1-X-G2 in which G1 and G2 are linked in positions 3, 7 or 12 or by the side chain via the linker X. Bile acid derivatives in which G1 is bonded to X via positions 7 or 12 and G2 is bonded to X via positions 3, 7 or 12 or the side chain are not described in the examples of the European Patent Application cited.

The invention therefore relates to bile acid derivatives of the formula I

G1 - X - G2 I in which G1 is a radical of the formula II

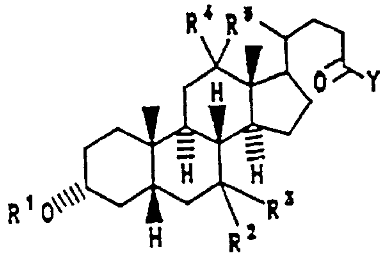

(II)

in which

Y has the following meaning: OKa, in which Ka is an alkali metal, alkaline earth metal or quaternary ammonium ion, -OL, -NHL, $-NL_2$, an amino acid or aminosulfonic acid bonded via the amino group, such as, for example

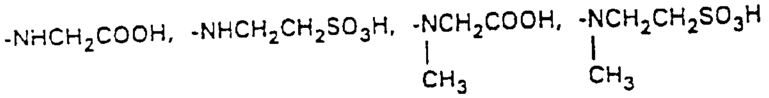

and $(C_1-C_4)$-alkyl esters, alkali metal and alkaline earth metal salts and quaternary ammonium salts thereof, and in which L is H, an alkyl or alkenyl radical having up to 10 carbon atoms, which is branched or unbranched, a cycloalkyl radical having 3 to 8 carbon atoms or a phenyl or benzyl radical, which are unsubstituted or mono- to trisubstituted by F, Cl, Br, $(C_1-C_4)$-alkyl or $(C_1-C_4)$-alkoxy, $R^1$ is H, an alkyl or alkenyl radical having up to 10 carbon atoms, which is branched or unbranched, a cycloalkyl radical having 3 to 8 carbon atoms, a benzyl radical, a biphenylmethyl or a triphenylmethyl radical, in which the nuclei are unsubstituted or mono- to trisubstituted by F, Cl, Br, $(C_1-C_4)$-alkyl or $(C_1-C_4)$-alkoxy, or a radical

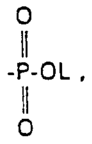, 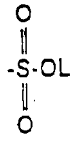 or 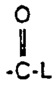

in which L has the abovementioned meaning, $R^2$ to $R^5$, $R^2$ and $R^3$ or $R^4$ and $R^5$ in each case together being the oxygen of a carbonyl group, or individually and in each case independently of one another being H, -OT, -ST, -NHT, 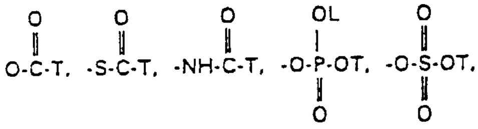, -T in which T has the meaning of L or is a free valency for bonding the group X, and in which in total only one free valency starts from G1 for bonding the group X, X is a single bond or a group of the formula III

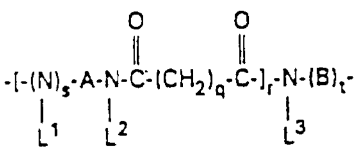 (III), in which

A and B are alkylene chains, which are branched or unbranched, it being possible for the chains to be optionally interrupted by -O- or -S-, $L^1$, $L^2$ and $L^3$ are identical or different and have the meaning of L and q is zero to 5, r is zero or 1, s is zero or 1 and t is zero or 1 and G2 is a radical of the formula IV

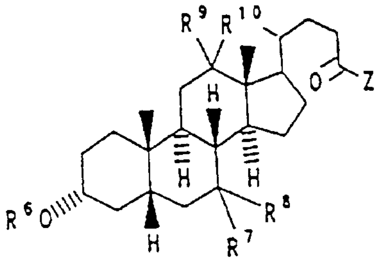

(IV)

in which

Z is a free valency to the group X or has the meaning given under Y, $R^6$ is a free valency to the group X or has the meaning given under $R^1$ and $R^7$ to $R^{10}$ have the meaning given under $R^2$ to $R^5$, and in which in total only one free valency starts from G2 to the group X.

The compounds according to the invention have a high affinity for the specific bile acid transportation system of the small intestine and inhibit bile acid absorption in a concentration-dependent and competitive manner. The compounds according to the invention furthermore are not themselves absorbed and thus do not enter the blood circulation. The enterohepatic circulation can be interrupted very specifically and efficiently by application of this principle of action.

By using the compounds according to the invention, it is possible to reduce the amount of bile acids in the enterohepatic circulation such that a reduction of the cholesterol level in the serum occurs. Avitaminoses are just as unlikely during their use as effects on the absorption of other medicaments or an adverse effect on the intestinal flora. Furthermore, the side-effects known of polymers (constipation, steratorrhea) are not found, i.e. lipolysis is not adversely influenced. Because of the high affinity for the specific bile acid transportation system of the small intestine, low daily doses are sufficient, so that acceptance of such medicaments by the doctor and patient will be very high.

Particularly preferred compounds of the formula I are those in which G1 is a radical of the formula II

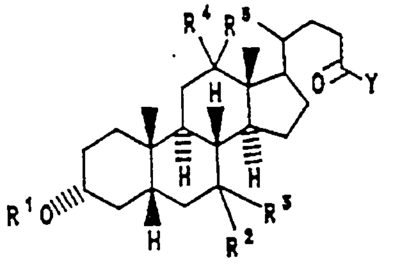

(II)

in which

Y OH, O-($C_1$-$C_4$)-Alkyl, $-NHCH_2COOH$,
$-NCH_2COOH$, $-NHCH_2CH_2SO_3H$, $-NCH_2CH_2SO_3H$
| |
$CH_3$ $CH_3$ $R^1$ is H, benzyl, biphenylmethyl, formyl or acetyl, $R^2$ to $R^5$, $R^2$ and $R^3$ or $R^4$ and $R^5$ in each case together being the oxygen of a carbonyl group, or individually and in each case independently of one another being

O O
‖ ‖
H, -OT, -NHT, -O-C-T, -NH-C-T, -T in which T is

H, a branched or unbranched ($C_1$-$C_4$)-alkyl radical or a free valency to bridge group X, and in which a total of one free valency starts from G1 for bonding the group X, X is a bond,

-N- ,
H $-CH_2CH_2NH-$ $-CH_2CH_2CH_2NH-$

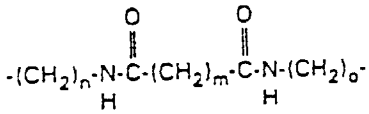

where n is 2 or 3, m is 1 to 4 and o is 2 or 3, and

G2 is a radical of the formula IV

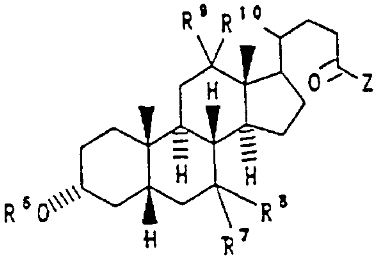

(IV)

in which

Z is a free valency to group X or has the meaning given above under Y, $R^6$ is a free valency to group X or has the meaning given above under $R^1$ and $R^7$ to $R^{10}$ have the meaning given above under $R^2$ to $R^5$, and in which only one free valency starts from G2 to the group X.

The invention furthermore relates to a process for the preparation of compounds of the formula I, which comprises a) in the case where X is a single bond, reacting suitable forms of G1 and G2 with one another by processes which are known in principle, or b) in the case where X is a bridge group, reacting
α) reactive forms of G1-X with G2 or
β) reactive forms of G2-X with G1
by processes which are known in principle, or c) preparing compounds of the formula I (G1-X-G2) from G1-X1 and X2-G2 by processes which are known or, where they are not known, by the processes described below in more detail, X being formed from X1 and X2 by formation of a covalent bond, in particular within a condensation or substitution reaction.

a) X is a single bond
The bile acids G1 are employed either in the free form or in protected form. After linking with G2, which is likewise present in a free or protected form, the protective groups are split off, if appropriate, and the C-24 carboxyl function is converted into a derivative, if appropriate. Suitable protective groups for the alcohol groups are expediently formyl, acetyl, tetrahydropyranyl or t-butyldimethylsilyl. Various alkyl or benzyl esters, and also, for example, orthoesters, are suitable protective groups for the C-24 carboxyl group.

For example, bile acid preferentially reacts at position 3, but also at position 7, with activated forms of carboxylic acids, such as acid chlorides or mixed anhydrides, with addition of bases, such as trialkylamine or pyridine, but also NaOH, at room temperature in suitable solvents, such as tetrahydrofuran, methylene chloride or ethyl acetate, but also dimethylformamide (DMF) or dimethoxyethane (DME).

The various isomers can be separated, for example by chromatography. The reaction can be carried out selectively by using suitable protective groups.

The corresponding amino-bile acids can be converted into corresponding amides analogously. Here also, the reaction can be carried out either with protected or with free bile acids.

Other compounds according to the invention can be linked analogously by known standard processes.

b) X is a bridge group
The processes specified under a) are also used to carry out the linking of G1-X with G2 or G1 with X-G2. Here also, the bile acid portion is expediently employed either in protected or in unprotected form.

A preferred preparation process comprises reacting reactive forms of G1 with reactive forms of X-G2. If appropriate, the linking reaction is followed by splitting-off of protective groups and conversion of C-24 carboxyl into derivatives.

The preparation of reactive bile acid units G1-X and X-G2 is shown in the following equation.

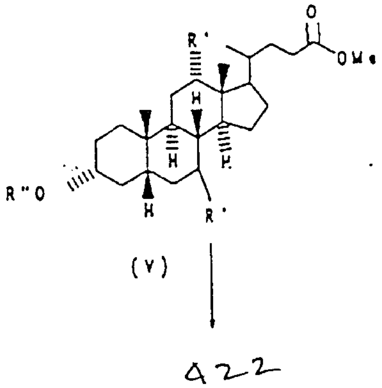

(V)

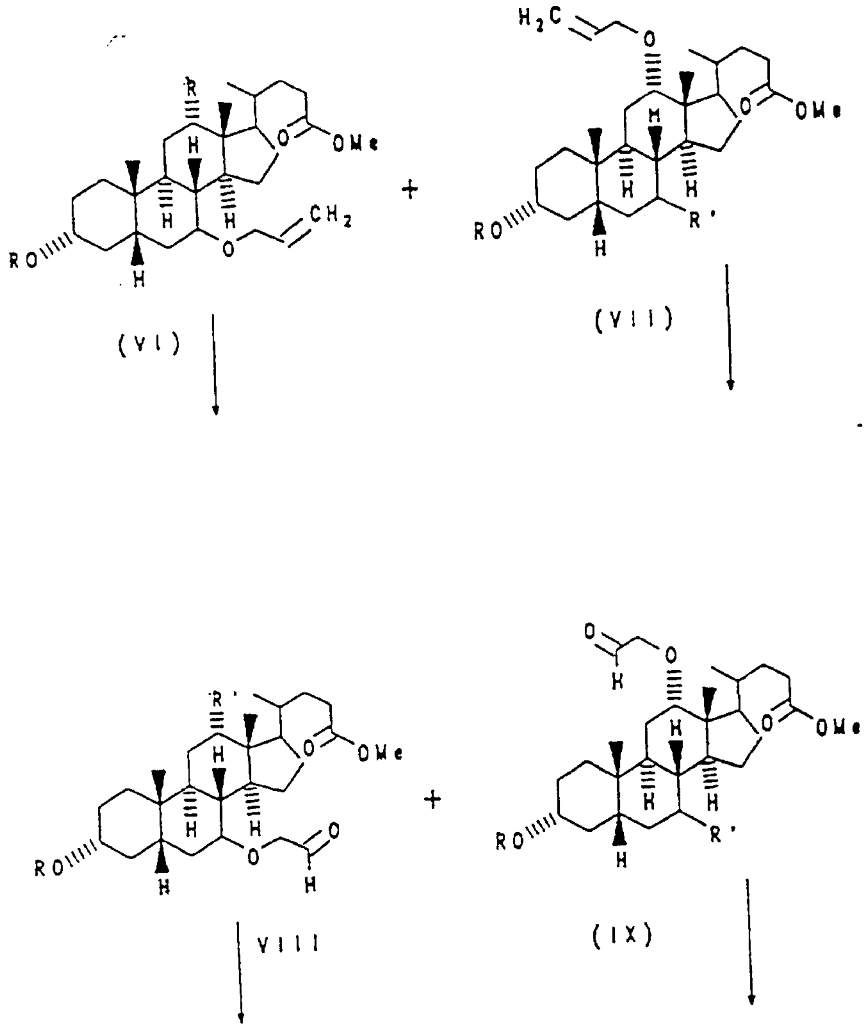
(VI)
(VII)
VIII
(IX)

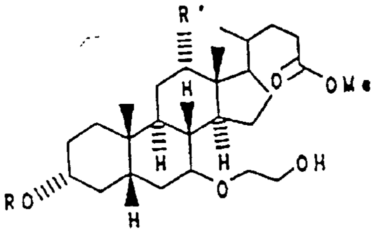
(X)
+
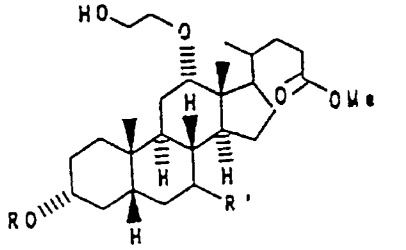
(XI)
R = H, formyl or acetyl, R' = H or OH, R" = formyl or acetyl
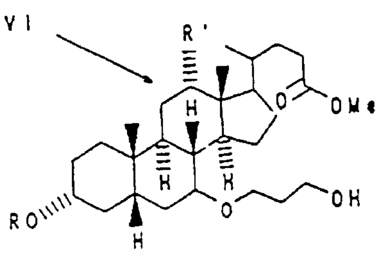
(XII)
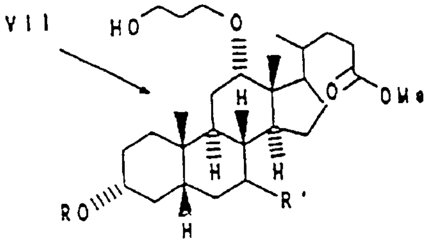
(XIII)

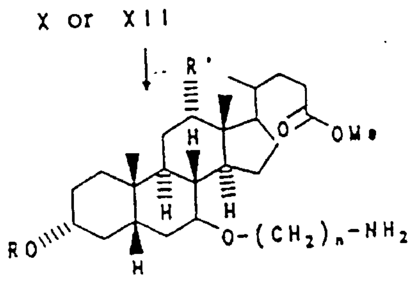

(XIV)

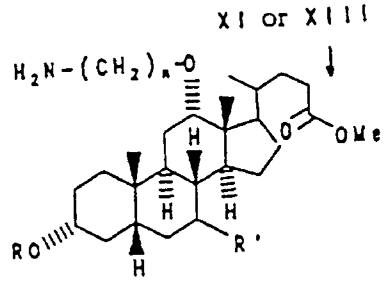

(XV)

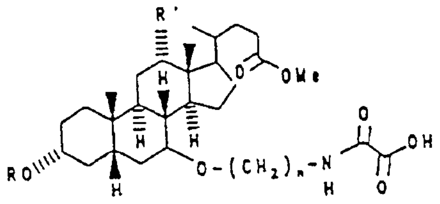

(XVI)

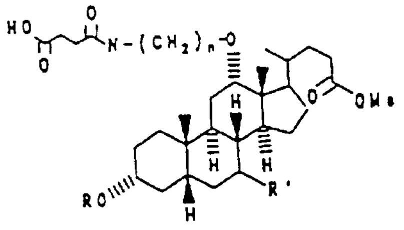

(XVII)

R = H, formyl or acetyl, R′ = H or OH, n = 2 or 3

Compounds of the type V in which the 3-position is protected are reacted with allyl bromide/Hünig base or triethylamine. If the compound V has one OH group, the alkylation is unambiguous; if two free OH groups are present, monoalkylation takes place at positions 7 and 12 in approximately equal proportions and only traces of the dialkylated product are formed. The protective group in the 3-position can either be split off with sodium methylate or retained for further reactions. The monoalkylated compounds VI and VII can be split with ozone or with $OsO_4/NaIO_4$ to give the aldehydes VIII and IX. The 7-and 12-hydroxyethyl compounds X and XI are readily accessible from these by simple reduction, for example with $NaBH_4$. The corresponding 7- and 12-hydroxypropyl derivatives XII and XIII can be synthesized from the allyl compounds VI and VII by hydroboration. The aminoalkyl derivatives XIV and XV can be prepared from the hydroxyalkyl compounds of the type X to XIII by a reaction sequence which is known in principle (mesylation of the primary OH group with methanesulfonyl chloride/ pyridine, azide exchange with $NaN_3$ in dimethylformamide, reduction of the azide function with hydrogen under catalytic conditions). Further reaction of the amino functions of these compounds with succinic anhydride gives bile acid units of the type XVI and XVII. Suitable bile acid units furthermore are described in EP-A-0 489 423.

The invention furthermore relates to the use of the compounds according to the invention for the preparation of a medicine. For this, the compounds of the formula I are dissolved or suspended in pharmacologically acceptable organic solvents, such as mono- or polyhydric alcohols, such as, for example, ethanol or glycerol, or in triacetin, oils, such as, for example, sunflower oil or cod-liver oil, ethers, such as, for example, diethylene glycol dimethyl ether, or also polyethers, such as, for example, polyethylene glycol, or also in the presence of other pharmacologically acceptable polymeric carriers, such as, for example, polyvinylpyrrolidone, or other pharmaceutically acceptable additives, such as starch, cyclodextrin or polysaccharides. The compounds according to the invention furthermore can be administered in combination with other medicaments.

The compounds of the formula I are administered in various dosage forms, preferably orally in the form of tablets, capsules or liquids. The daily dose varies in the range from 3 mg to 5000 mg, but preferably in the dose range from 10 to 1000 mg, depending on the body weight and constitution of the patient.

On the basis of their pharmacological properties, the compounds are particularly suitable as hypolipidemic agents.

The invention therefore also relates to medicaments based on the compounds of the formula (I) and to the use of the compounds as medicaments, in particular for lowering the cholesterol level.

The compounds according to the invention were tested biologically by determination of the inhibition of [$^3$H]-taurocholate uptake in brush border membrane vesicles of the ileum in rabbits. The inhibition test was carried out as follows:

1. Preparation of brush border membrane vesicles from the ileum of rabbits

The brush border membrane vesicles from the intestinal cells of the small intestine were prepared by the so-called $Mg^{2+}$ precipitation method. Male New Zealand rabbits (2 to 2.5 kg body weight) were sacrificed by intravenous injection of 0.5 ml of an aqueous solution of 2.5 mg of tetracaine HCl, 100 T 61® and 25 mg of mebezonium iodide. The small intestine was removed and flushed with ice-cold physiological saline solution. The terminal 7/10 of the small intestine (measured in the oral-rectal direction, i.e. the terminal ileum which contains the active $Na^+$-dependent bile acid transportation system) was used for preparation of the brush border membrane vesicles. The intestines were frozen in plastic bags under nitrogen at -80°C. To prepare the membrane vesicles, the frozen intestines were thawed at 30°C in a water-bath. The mucosa was scraped off and suspended in 60 ml of ice-cold 12 mM Tris/HCl buffer (pH 7.1)/300 mM mannitol, 5 mM EGTA/10 mg/l of phenylmethylsulfonyl fluoride/1 mg/l of trypsin inhibitor from soybeans (32 U/mg)/0.5 mg/l of trypsin inhibitor from bovine lung (193 U/mg)/5 mg/l of bacitracin. After dilution to 300 ml with ice-cold distilled water, the mixture was homogenized with an Ultraturrax (18-rod, IKA Werk Staufen, FRG) for 3 minutes at 75% of the maximum output, while cooling with ice. After addition of 3 ml of 1 M $MgCl_2$ solution (final concentration 10 mM), the mixture was left to stand at 0°C for exactly 1 minute. By addition of $Mg^{2+}$, the cell membranes aggregate and precipitate with the exception of the brush border membranes. After centrifugation at 3000 × g (5000 rpm, SS-34 rotor) for 15 minutes, the precipitate is discarded and the supernatant, which contains the brush border membranes, is centrifuged at 267000 × g (15000 rpm, SS-34 rotor) for 30 minutes. The supernatant was discarded and the precipitate was rehomogenized in 60 ml of 12 mM Tris/HCl buffer (pH 7.1)/60 mM mannitol, 5 mM EGTA using a Potter Elvejhem homogenizer (Braun, Melsungen, 900 rpm, 10 strokes). After addition of 0.1 ml of 1 M $MgCl_2$ solution and an incubation time of 15 minutes at 0°C, the mixture was centrifuged again at 3000 × g for 15 minutes. The supernatant was then centrifuged again at 46000 × g (15000 rpm, SS-34 rotor) for 30 minutes. The precipitate was taken up in 30 ml of 10 mM Tris/Hepes buffer (pH 7.4)/300 mM mannitol and resuspended homogeneously by 20 strokes in a Potter Elvejhem homogenizer at 1000 rpm. After centrifugation at 48000 × g (20000 rpm, SS-34 rotor) for 30 minutes, the precipitate was taken up in 0.5 to 2 ml of Tris/Hepes buffer (pH 7.4)/280 mM mannitol (final concentration 20 mg/ml) and resuspended with the aid of a tuberculin syringe with a 27 gauge needle. The vesicles were either used for transportation studies immediately after preparation or stored in 4 mg portions in liquid nitrogen at -196°C.

2. Inhibition of $Na^+$-dependent uptake of [$^3H$]-taurocholate in the brush border membrane vesicles of the ileum The uptake of substrates in the brush border membrane vesicles described above was determined by means of the so-called membrane filtration technique. 10 µl of the vesicle suspension (100 µg of protein) were pipetted as drops onto the wall of a polystyrene incubation tube (11 × 70 mm) which contained the incubation medium with the corresponding ligands (90 µl). The incubation medium contained 0.75 µl = 0.75 µCi [$^3$H(G)]-taurocholate (specific activity: 2.1 Ci/mmol)/0.5 µl of 10 mM taurocholate/8.75 µl of sodium transportation buffer (10 mM Tris/Hepes (pH 7.4)/100 mM mannitol/100 mM NaCl) (Na-T-P) or 8.75 µl of potassium transportation buffer (10 mM Tris/Hepes (pH 7.4)/100 mM mannitol/100 mM KCl) (K-T-P) and 80 µl of the inhibitor solution in question as a solution in Na-T buffer or K-T buffer, depending on the experiment. The incubation medium was filtered through a polyvinylidene fluoride membrane filter (SYHV LO 4NS, 0.45 µm, 4 mm Ø, Millipore, Eschborn, FRG). The transportion measurement was started by mixing the vesicles with the incubation medium. The concentration of taurocholate in the incubation batch was 50 µM. After the desired incubation time (usually 1 minute), the transportation was stopped by addition of 1 ml of ice-cold stopping solution (10 mM Tris/Hepes (pH 7.4)/150 mM KCl).

The mixture formed was immediately filtered off with suction over a membrane filter of cellulose nitrate (ME 25, 0.45 µm, 25 mm diameter, Schleicher & Schuell, Dassell, FRG) under a vacuum of 25 to 35 mbar. The filter was rinsed with 5 ml of ice-cold stopping solution.

To measure the uptake of radioactively labeled taurocholate, the membrane filter was dissolved with 4 ml of the scintillator Quickszint 361 (Zinssér Analytik GmbH, Frankfurt, FRG) and the radioactivity was measured by liquid scintillation measurement in a TriCarb 2500 measuring instrument (Canberra Packard GmbH, Frankfurt, FRG). After calibration of the instrument with the aid of standard samples and after correction for any chemiluminescence present, the values measured were obtained as dpm (decompositions per minute).

The control values were determined in each case in Na-T-P and K-T-P. The difference between the uptake in Na-T-P and K-T-P gave the $Na^+$-dependent transportation content. The concentration of inhibitor at which the $Na^+$-dependent transportation content was inhibited by 50% - based on the control - was designated the $IC_{50}$ $Na^+$.

The pharmacological data include a test series in which the interaction of the compounds according to the invention with the intestinal bile acid transportation system in the terminal small intestine was investigated. The results are summarized in Table 11.

Examples 1 and 2

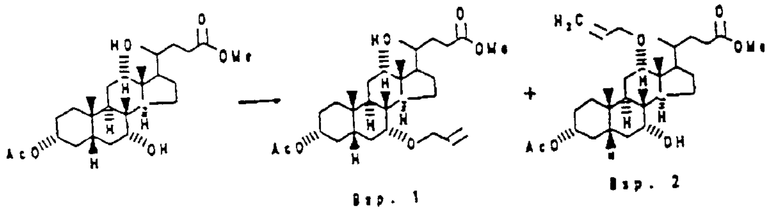

150 g (0.32 mol) of methyl 3-acetyl-cholate, 500 ml of dimethylformamide, 125 ml of N-ethyl-diisopropylamine and 70 ml of allyl bromide are heated under reflux for 16 hours. New allyl bromide (25 ml) is added every 2 hours. The reaction solution is evaporated on a rotary evaporator. The residue is partitioned between water/methylene chloride and the organic phase is separated off and dried with magnesium sulfate. After column chromatography (ethyl acetate/cyclohexane 1:2, silica gel 70-200 μm), the product fractions are evaporated on a rotary evaporator.

Yield = 92.2 g of 7-/12-allyl mixture.

$C_{30}H_{48}O_6$ (504), MS 511 (M + $Li^+$)
The mixture was separated by fractional crystallization with n-heptane.

Example 3

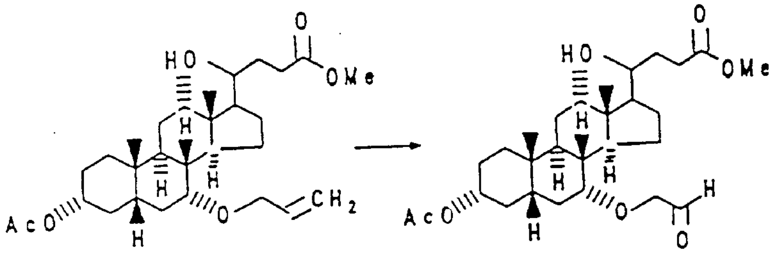

50 g (0.1 mol) of Example 1, 250 ml of diethyl ether and 250 ml of water are initially introduced into the reaction vessel, while stirring vigorously. 503 mg (0.002 mol) of osmium tetroxide are added. The mixture is stirred at room temperature for 15 minutes. 53 g (0.25 mol) of sodium periodate are added in portions over the course of 1 hour, and the mixture is subsequently stirred for 8 hours, while stirring vigorously. The ether phase is separated off, dried with magnesium sulfate and evaporated on a rotary evaporator.
Yield: 47 g of crude $C_{29}H_{46}O_7$ (506), MS 513 (M + $Li^+$)
Example 3 is further reacted without additional purification.

Example 4

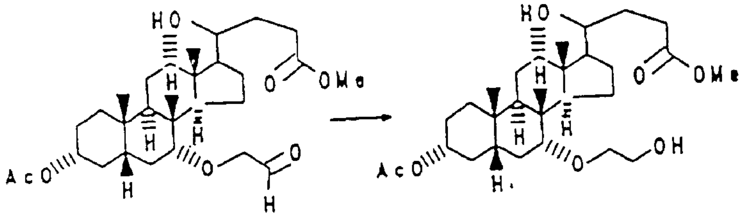

4.2 g (0.11 mol) of sodium borohydride are added in portions to 47 g (0.093 mol) of Example 3 and 250 ml of methanol at 0°C. After 2 hours at 0°C, the reaction solution is poured onto saturated ammonium chloride solution, the mixture is extracted 3 times with ethyl acetate and the combined organic phases are dried with magnesium sulfate and evaporated on a rotary evaporator. After column chromatography (ethyl acetate/cyclohexane 1.5:1, silica gel 35 - 70 μm), the product fractions are evaporated on a rotary evaporator and the residue is crystallized with diisopropyl ether. Yield: 25 g of $C_{29}H_{48}O_7$ (508), MS 515 (M + $Li^+$)

Example 5

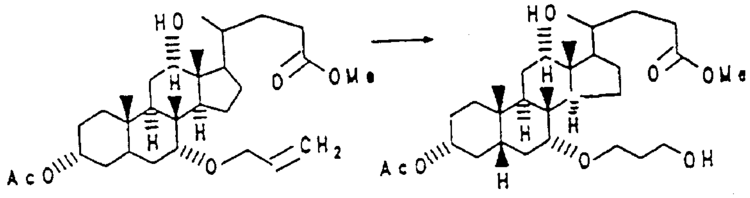

10 g (0.02 mol) of Example 1 and 250 ml of tetrahydrofuran were initially introduced into a reaction vessel at room temperature, and 40 ml (0.04 mol) of borane-tetrahydrofuran complex (1 molar) were added dropwise at room temperature. The mixture was subsequently stirred at room temperature for 2 hours, and 25 ml of water, 25 ml of 2 N sodium hydroxide solution and 25 ml of 35% strength hydrogen peroxide solution were added dropwise in succession. The mixture was subsequently stirred at room temperature for a further 15 minutes. The reaction solution was poured onto water, the mixture was extracted 3 times with diethyl ether and the combined organic phases were dried with magnesium sulfate and evaporated on a rotary evaporator.

Yield: 8.5 g of $C_{30}H_{50}O_7$ (522), MS 529 (M + $Li^+$)

Example 5 was further reacted without additional purification.

Example 6

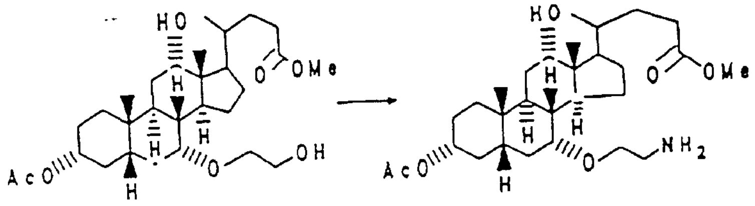

10 g (0.02 mol) of Example 4 and 100 ml of pyridine are initially introduced into a reaction vessel at 0°C. 1.7 ml (0.022 mol) of methanesulfonyl chloride are added dropwise at 0°C and the mixture is subsequently stirred at 0°C for a further 30 minutes and at room temperature for 2 hours. The reaction solution is poured onto water, the mixture is extracted 3 times with ethyl acetate, and the combined organic phases are dried with magnesium sulfate and evaporated on a rotary evaporator. The residue is dissolved in 100 ml of dimethylformamide, 1.4 g (0.022 mol) of sodium azide are added and the mixture is stirred at 80°C for 2 hours. The reaction solution is poured onto water and the mixture is worked up as described above. The residue is dissolved in 100 ml of methanol, 100 mg of palladium-on-charcoal (10%) are added and hydrogenation is carried out under normal pressure for 2 hours. The catalyst is filtered off and the filtrate is evaporated on a rotary evaporator. After column chromatography (ethyl acetate/ MeOH/$Et_3N$ 10:1:1, silica gel 70-200 μm), Example 6 is obtained.
Yield = 7.3 g of $C_{29}H_{49}NO_6$ (507), MS 514 (M + $Li^+$)

Example 7

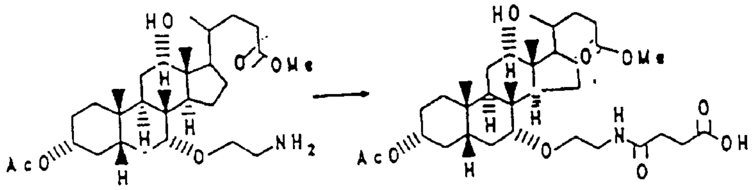

98.6 mg (0.001 mol) of succinic anhydride are added to 500 mg (0.001 mol) of amino compound, 20 ml of tetrahydrofuran and 4 ml of triethylamine at room temperature. The mixture is subsequently stirred at room temperature for 1 hour. The reaction solution is poured onto 25% strength sodium dihydrogen phosphate solution, the mixture is extracted 3 times with ethyl acetate and the organic phase is dried with magnesium sulfate and evaporated on a rotary evaporator.

Yield: 580 mg of $C_{33}H_{53}NO_9$ (607), MS 614 $(M + Li^+)$

Example 7 was further reacted without additional purification.

Examples 8 to 12 were prepared analogously to Examples 3 to 7.

Examples 8-12

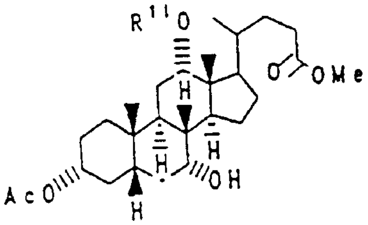

| Example | $R^{11}$ | MS |
|---|---|---|
| 8 | $-CH_2CHO$ | 513 $(M + Li^+)$ |
| 9 | $-CH_2CH_2OH$ | 515 $(M + Li^+)$ |
| 10 | $-CH_2CH_2CH_2OH$ | 529 $(M + Li^+)$ |
| 11 | $-CH_2CH_2NH_2$ | 514 $(M + Li^+)$ |
| 12 | $-CH_2CH_2NHCOCH_2CH_2COOH$ | 614 $(M + Li^+)$ |

Example 13

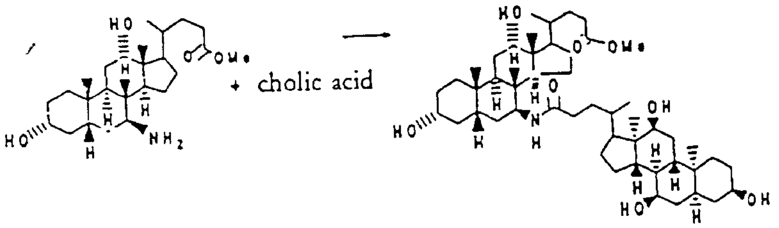

300 mg (0.73 mmol) of cholic acid, 330 mg (0.78 mmol) of methyl 7β-amino-3α,12α-dihydroxy-5β-cholanate (Redel, Bull. Soc. Chim. Fr., page 877, 1949), 240 mg (0.97 mmol) of EEDQ and 0.25 ml of diisopropylethylamine are stirred in 20 ml of DMF at 90°C for 4 hours. After cooling, the reaction mixture is concentrated and the residue is chromatographed over silica gel ($CH_2Cl_2$/MeOH 8.2). $C_{49}H_{81}NO_8$ (812) 819 (M + $Li^+$). The two bile acid derivatives can also be linked with triethylamine in methylene chloride or with dicyclohexylcarbodiimide, hydroxybenzotriazole or triethylamine in tetrahydrofuran.

The compounds of Table 1 were prepared analogously to Example 13.

Table 1

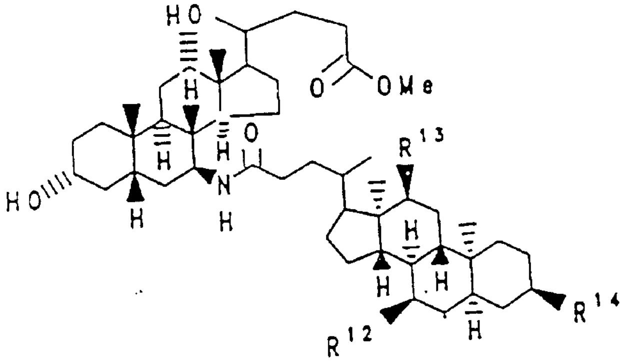

| Example | $R^{12}$ | $R^{13}$ | $R^{14}$ | MS (FAB, 3-NBA/Licl) |
|---|---|---|---|---|
| 14 | α-OH | H | -OH | $C_{49}H_{81}NO_7$ (796) 803 (M + $Li^+$) |
| 15 | β-OH | H | -OH | $C_{49}H_{81}NO_7$ (796) 803 (M + $Li^+$) |
| 16 | H | H | -OCHO | $C_{50}H_{81}NO_7$ (808.5) 809.5 (M+$H^+$) |

The examples of Table 2 were obtained analogously to Example 13 from Examples 7 and 8.

Table 2
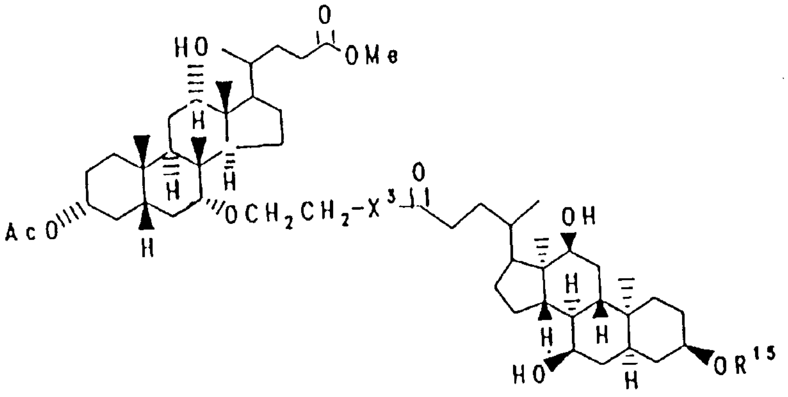
| Example | $X^3$ | $R^{15}$ | MS (FAB, 3-NBA/LiCl) |
|---|---|---|---|
| 17 | -NH- | H | $C_{53}H_{87}NO_{10}$ (898) 905 (M + $Li^+$) |
| 18 | -NH- | diphenylmethyl | $C_{66}H_{97}NO_{10}$ (1064) 1071 (M + $Li^+$) |
| 19 | $-NHCO(CH_2)_2CONH(CH_2)_3NH-$ | H | $C_{60}H_{99}N_3O_{12}$ (1054) 1061 (M + $Li^+$) |
| 20 | $-NHCO(CH_2)_2CONH(CH_2)_3NH-$ | diphenylmethyl | $C_{73}H_{109}N_3O_{12}$ (1220) 1227 (M + $Li^+$) |
437

The examples of Tables 3 and 4 were likewise obtained analogously to Example 13.
Table 3
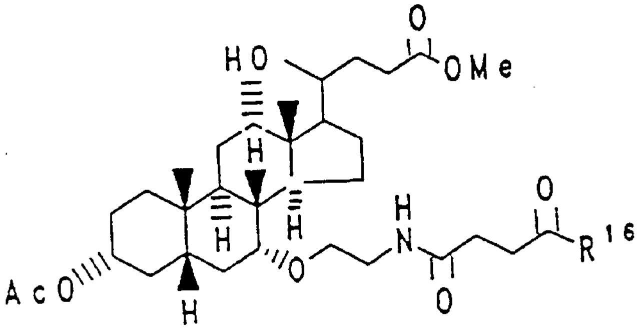
| Example | $R^{16}$ | MS (FAB, 3-NBA/LiCl) |
| --- | --- | --- |
| 21 | 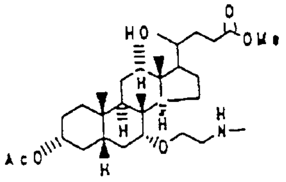 | $C_{62}H_{100}N_2O_{14}$ (1097) 1104 (M+L$^+$) |
| 22 | 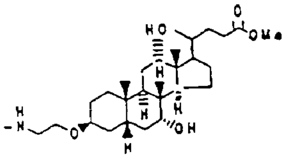 | $C_{60}H_{98}N_2O_{13}$ (1055) 1104 (M+L$^+$) |

Table 4
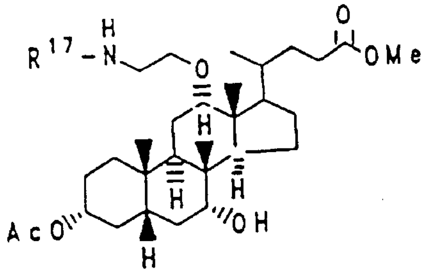
| Example | $R^{17}$ | MS (FAB, 3-NBA/LiCl) |
|---|---|---|
| 23 | 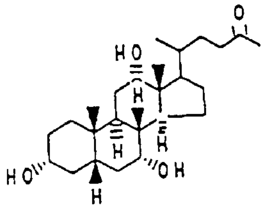 | $C_{53}H_{87}NO_{10}$ (898) 905 (M+L$^{+}$) |
| 24 | 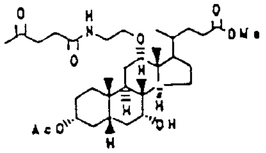 | $C_{62}H_{100}N_2O_{14}$(1097)1104 (M+L$^{+}$) |
| 25 | 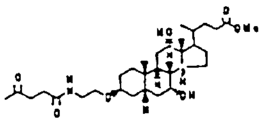 | $C_{60}H_{98}NO_{13}$(1055) 1062 (M+L$^{+}$) |

Example 26

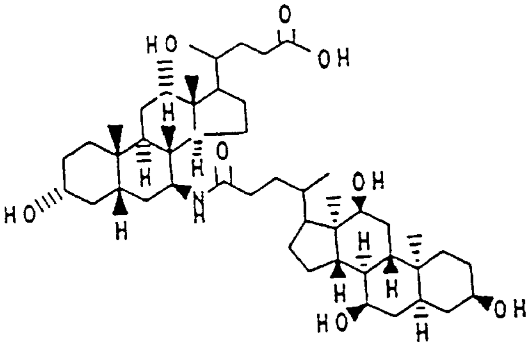

250 mg (0.31 mmol) of Example 13 are dissolved in 20 ml of ethanol, 2 ml of 1N NaOH solution are added and the mixture is stirred at room temperature for 16 hours. For working up, the mixture is concentrated, the residue is dissolved in $H_2O$, the pH is brought to 1-2 with 2N HCl and the mixture is concentrated again. The residue is chromatographed over silica gel ($CHCl_3$/MeOH 8:2). 220 mg of free acid are obtained (90%).

MS (FAB, 3-NBA/LiCl) $C_{48}H_{79}NO_8$ (798) 805 (M + $Li^+$)

The examples of Tables 5 to 8 are obtained analogously to Example 26.

Table 5

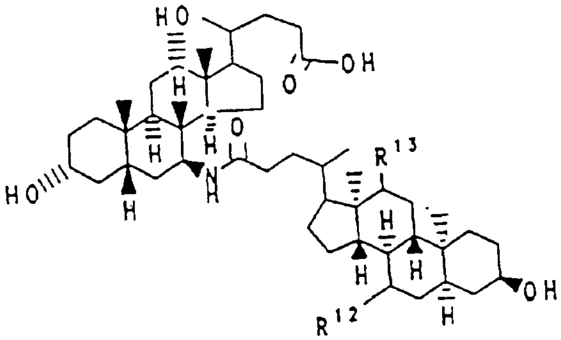

| Example | $R^{12}$ | $R^{13}$ | MS |
|---|---|---|---|
| 27 | α-OH | H | $C_{48}H_{79}NO_7$ (782) 789 ($M+Li^+$) |
| 28 | β-OH | H | $C_{48}H_{79}NO_7$ (782) 789 ($M+Li^+$) |
| 29 | H | H | $C_{48}H_{79}NO_7$ (766) 773 ($M+Li^+$) |

Table 6
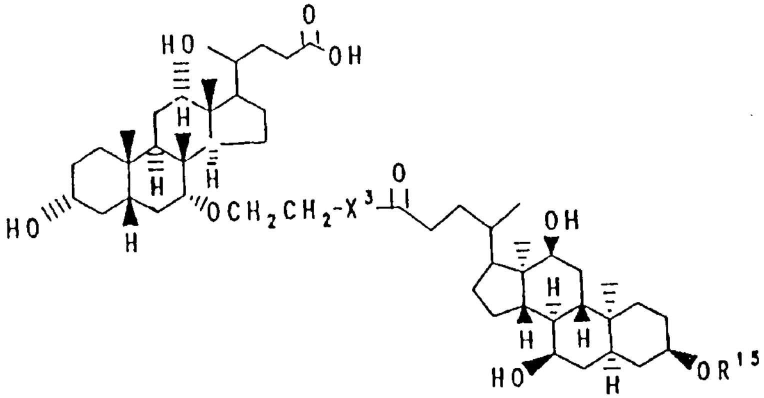
| Example | $X^3$ | $R^{15}$ | MS |
|---|---|---|---|
| 30 | -NH- | H | $C_{50}H_{85}NO_{10}$ (860) 867 (M + $Li^+$) |
| 31 | -NH- | diphenylmethyl | $C_{63}H_{95}NO_{10}$ (1026) 1033 (M + $Li^+$) |
| 32 | $-NHCO(CH_2)_2CONH(CH_2)_3NH-$ | H | $C_{57}H_{97}N_3O_{12}$ (1016) 1023 (M + $Li^+$) |
| 33 | $-NHCO(CH_2)_2CONH(CH_2)_3NH-$ | diphenylmethyl | $C_{70}H_{107}N_3O_{12}$ (1182) 1189 (M + $Li^+$) |

Table 7
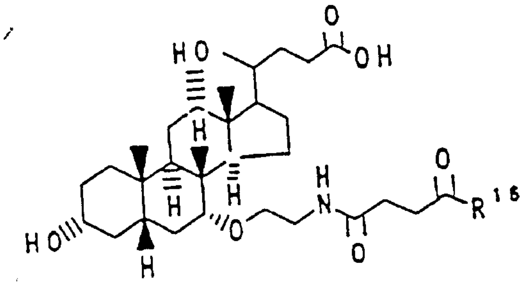
| Example | $R^{16}$ | MS |
|---|---|---|
| 34 | 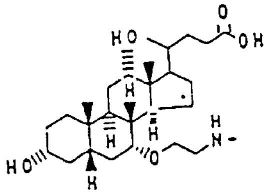 | $C_{56}H_{92}N_2O_{12}$(985) 992 ($M+Li^+$) |
| 35 | 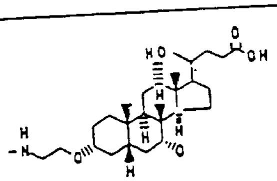 | $C_{58}H_{96}N_2O_{12}$(985) 992 ($M+Li^+$) |

Table 8
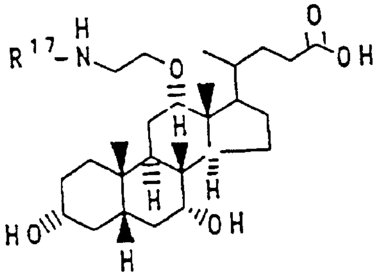
| Example | $R^{17}$ | MS (FAB, 3-NBA/LiCl) |
|---|---|---|
| 36 | 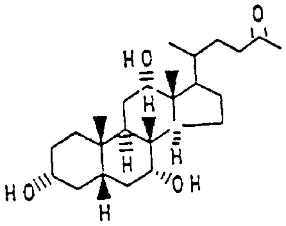 | $C_{50}H_{83}NO_9$ (842) 849 $(M+Li^+)$ |
| 37 | 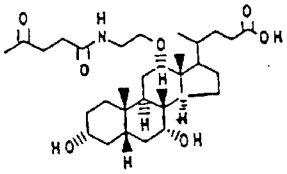 | $C_{56}H_{92}N_2O_{12}$ (985) 992 $(M+Li^+)$ |
| 38 | 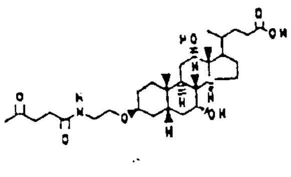 | $C_{56}H_{92}N_2O_{12}$ (985) 992 $(M+Li^+)$ |
The following glycine conjugates and taurine conjugates were obtained analogously to synthesis processes which have already been described (EP 489 423).

Table 9
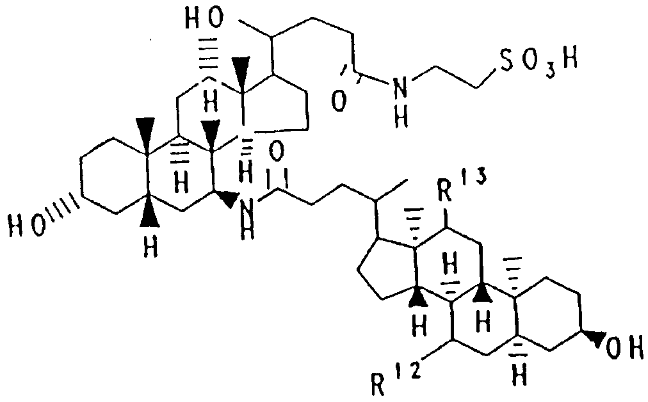
| Example | $R^{12}$ | $R^{13}$ | MS (FAB, 3-NBA/LiCl |
|---|---|---|---|
| 39 | α-OH | α-OH | $C_{50}H_{84}N_2O_{10}S$ (905) 918 (M + $2Li^+$-$H^+$) |
| 40 | α-OH | H | $C_{50}H_{84}N_2O_9S$ (889) 890 (M + $H^+$) |
| 41 | β-OH | H | $C_{50}H_{84}N_2O_9S$ (889) 912 (M + $Na^+$) |
| 42 | H | H | $C_{50}H_{84}N_2O_8S$ (872.5) 895.5 (M + $Na^+$) |
445

Table 10
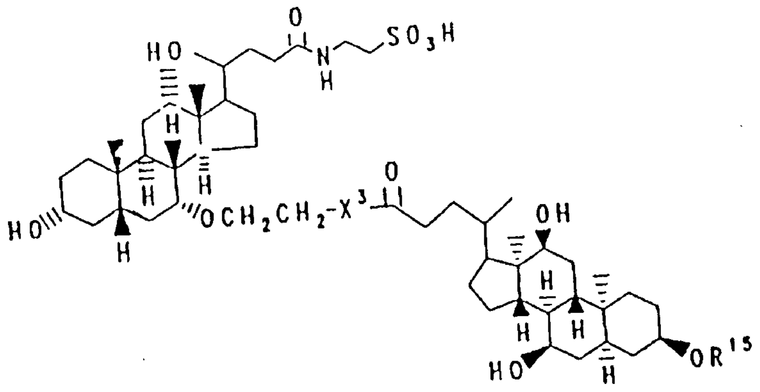
| Example | $X^3$ | $R^{15}$ | MS |
|---|---|---|---|
| 43 | -NH- | H | $C_{52}H_{90}N_2O_{12}S$ (967) 974 (M + $Li^+$) |
| 44 | -NH- | diphenylmethyl | $C_{65}H_{100}N_2O_{12}S$ (1133) 1140 (M + $Li^+$) |
| 45 | $-NHCO(CH_2)_2CONH(CH_2)_3NH-$ | H | $C_{55}H_{102}N_4O_{14}S$ (1123) 1130 (M + $Li^+$) |
| 46 | $-NHCO(CH_2)_2CONH(CH_2)_3NH-$ | diphenylmethyl | $C_{72}H_{102}N_4O_{14}S$ (1289) 1296 (M + $Li^+$) |
446

Example 47

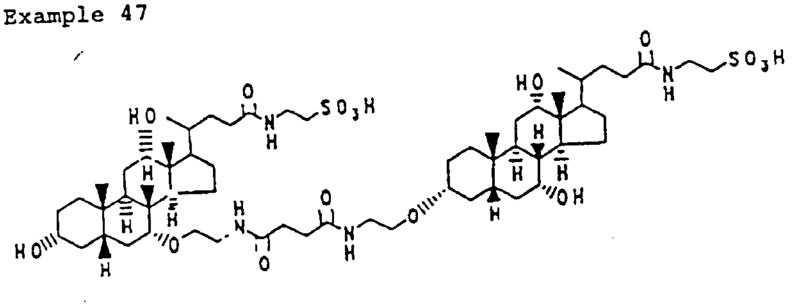

MS (FAB, 3-NBA/LiCl) $C_{60}H_{101}N_3O_{14}S$ (1092) 1099 (M + $Li^+$)

Example 48

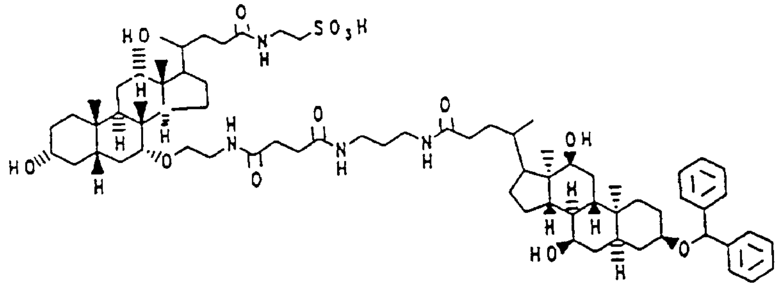

MS (FAB, 3-NBA/LiCl) $C_{72}H_{110}N_4O_{13}$ (1239) 1246 (M + $Li^+$)

Table 11 shows measurement values for the inhibition of the uptake of [$^3$H]-taurocholate in brush border membrane vesicles from the ileum of rabbits. The quotients of the $IC_{50}$ and $IC_{50}$ Na values of the reference substance taurochenodeoxycholate (TCDC) and of the particular test substance are stated.

Table 11

| Compound from Example | $IC_{50}$-TCDC[μmol] / $IC_{50}$-substance[μmol] | $IC_{50NA}$-TCDC[μmol] / $IC_{50NA}$-substance[μmol] |
|---|---|---|
| 20 | 0.00 | 0.12 |
| 26 | 0.00 | 0.29 |
| 27 | 0.64 | 0.44 |
| 28 | 0.54 | 0.43 |
| 29 | 0.23 | 0.17 |
| 30 | 0.93 | 0.85 |
| 32 | 1.00 | 0.80 |
| 39 | 0.92 | 1.05 |
| 40 | 0.54 | 0.52 |
| 43 | 1.18 | 0.96 |
| 47 | 0.35 | 0.26 |
| 48 | 0.75 | 0.71 |

1. A bile acid derivative of the formula I

G1 - X - G2 I in which G1 is a radical of the formula II

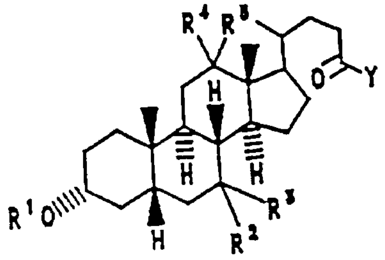

(II)

in which

Y has the following meaning: OKa, in which Ka is an alkali metal, alkaline earth metal or quaternary ammonium ion,
-OL, -NHL, $-NL_2$,
an amino acid or aminosulfonic acid bonded via the amino group, such as, for example
$-NHCH_2COOH$, $-NHCH_2CH_2SO_3H$, 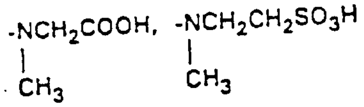

and $(C_1-C_4)$-alkyl esters, alkali metal and alkaline earth metal salts and quaternary ammonium salts thereof, and in which L is
H, an alkyl or alkenyl radical having up to 10 carbon atoms, which is branched or unbranched, a cycloalkyl radical having 3 to 8 carbon atoms or a phenyl or benzyl radical, which are unsubstituted or mono- to trisubstituted by F, Cl, Br, $(C_1-C_4)$-alkyl or $(C_1-C_4)$-alkoxy, $R^1$ is H, an alkyl or alkenyl radical having up to 10 carbon atoms, which is branched or unbranched, a cycloalkyl radical having 3 to 8 carbon atoms, a benzyl radical, a biphenylmethyl or a triphenylmethyl radical, in which the nuclei are unsubstituted or mono-to trisubstituted by F, Cl, Br, $(C_1-C_4)$-alkyl or $(C_1-C_4)$-alkoxy, or a radical

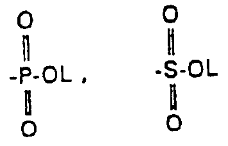

or

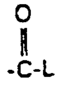

in which L has the abovementioned meaning, $R^2$ to $R^5$, $R^2$ and $R^3$ or $R^4$ and $R^5$ in each case together being the oxygen of a carbonyl group, or individually and in each case independently of one another being H, -OT, -ST, -NHT, 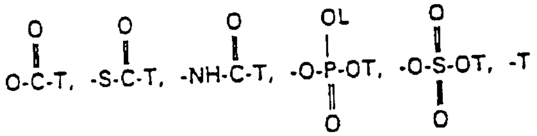

in which T has the meaning of L or is a free valency for bonding the group X, and in which in total only one free valency starts from G1 for bonding the group X, X is a single bond or a group of the formula III

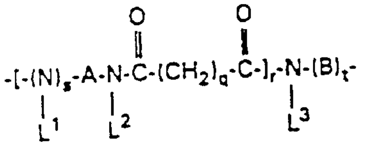

(III), in which

A and B are alkylene chains, which are branched or unbranched, it being possible for the chains to be optionally interrupted by -O- or -S-, $L^1$, $L^2$ and $L^3$ are identical or different and

450 have the meaning of L and q is zero to 5, r is zero or 1, s is zero or 1 and t is zero or 1 and G2 is a radical of the formula IV

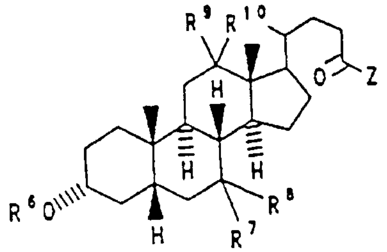

(IV)

in which

Z is a free valency to the group X or has the meaning given under Y, $R^6$ is a free valency to the group X or has the meaning given under $R^1$ and $R^7$ to $R^{10}$ have the meaning given under $R^2$ to $R^5$, and in which in total only one free valency starts from G2 to the group X.

2. A bile acid derivative of the formula I as claimed in claim 1, in which G1 is a radical of the formula II

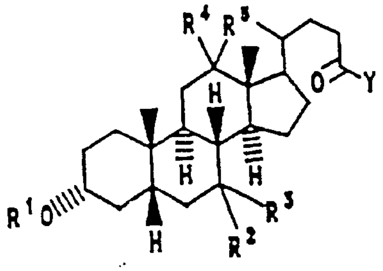

(II)

in which

Y is OH, O-$(C_1$-$C_4)$-Alkyl, -$NHCH_2COOH$,

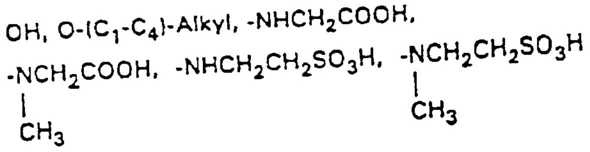

$R^1$ is H, benzyl, biphenylmethyl, formyl or acetyl, $R^2$ to $R^5$, $R^2$ and $R^3$ or $R^4$ and $R^5$ in each case together being the oxygen of a carbonyl group, or individually and in each case independently of one another being

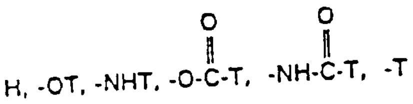

in which T is H, a branched or unbranched $(C_1$-$C_4)$-alkyl radical or a free valency to bridge group X, and in which a total of one free valency starts from G1 for bonding the group X, X is a bond,

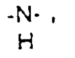

-$CH_2CH_2NH$-

-$CH_2CH_2CH_2NH$-

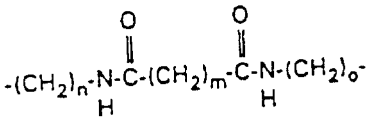

where n is 2 or 3, m is 1 to 4 and o is 2 or 3, and

G2 is a radical of the formula IV

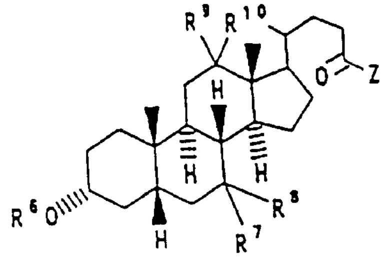

(IV)

in which

Z is a free valency to group X or has the meaning given above under Y, $R^6$ is a free valency to group X or has the meaning given above under $R^1$ and $R^7$ to $R^{10}$ have the meaning given above under $R^2$ to $R^5$, and in which only one free valency starts from G2 to the group X.

3. Process for the preparation of a bile acid derivative of the formula I as claimed in claim 1, which comprises a) in the case where X is a single bond, reacting suitable forms of G1 and G2 with one another by processes which are known in principle, or b) in the case where X is a bridge group, reacting α) reactive forms of G1-X with G2 or β) reactive forms of G2-X with G1 by processes which are known in principle, or c) preparing compounds of the formula I (G1-X-G2) from G1-X1 and X2-G2 by processes which are known or, where they are not known, by the processes described below in more detail, X being formed from X1 and X2 by formation of a covalent bond, in particular within a condensation or substitution reaction.

4. A medicament comprising a bile acid derivative as claimed in claim 1.

5. A hypolipidemic agent comprising a bile acid

MONOMERIC BILE ACID DERIVATIVES, PROCESSES FOR THEIR PREPARATION AND THE USE OF THESE COMPOUNDS AS MEDICAMENTS

Bile acids are synthesized in the liver from cholesterol in several enzymatic steps. They are stored in the gall bladder, from which they are secreted with the bile into the small intestine. They fulfill important physiological functions there during the digestion process, for example as cofactors or pancreatic lipases and as natural detergents for absorption of fats and fat-soluble vitamins. The greatest proportion of bile acids returns to the liver from the small intestine via the portal vein blood by active and passive transportation processes.

Polymers which bind bile acids have been employed as therapeutics for a relatively long time. They are used for diseases where inhibition of the absorption of bile acid is desirable. In cases of an increased blood cholesterol level, increased synthesis of bile acids from cholesterol can be induced in the liver by reducing the amount of bile acids in the enterohepatic circulation. This leads to an increased LDL cholesterol uptake from the blood into the liver and an accelerated LDL catabolism. The effect achieved is a reduction in the atherogenic LDL cholesterol in the blood.

The polymers used as medicaments for this purpose, for example cholestyramine or colestipol, must be administered in very high daily doses of 12 to 30 g. In addition to the high dosage, the taste and smell make acceptance by patient and doctor more difficult.

The polymers mentioned display side-effects because their selectivity is too low and their binding of vitamins is too high, and because of interactions with drugs administered at the same time. Furthermore they can modify the composition of bile acid in the bile. These properties manifest themselves in various gastrointestinal disturbances (for example constipation, steatorrhea), avitaminoses and an increased risk of cholelithiasis.

Surprisingly, novel monomeric bile acid derivatives have now been found which can interrupt the enterohepatic circulation of bile acids and do not have the disadvantages mentioned.

The invention therefore relates to monomeric bile acid derivatives of the formula I

Z—X—GS    I.

in which

GS is a bile acid radical having an acid function in the side chain or a salt thereof, X is a covalent bond or a bridge group of the formula $(CH_2)_n$, where n=1 to 10, in which the alkylene chain can contain 1 to 3 oxygen atoms, NH or

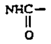

groups, and in which GS is bonded via X as desired, and

Z is

HO—, $CH_3$—O—, HO—$CH_2$—CH=CH—$CH_2$—,

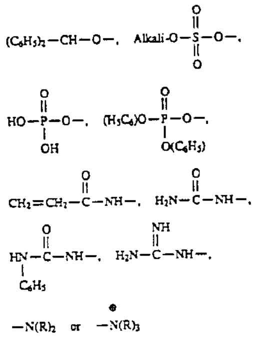

where R is in each case $C_1$–$C_7$ alkyl, or $H_2$—N—$(CH_2)_6$—,

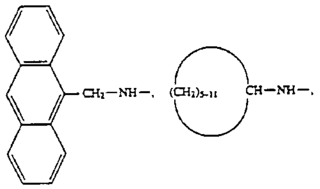

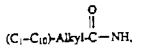

where the alkyl moiety is optionally substituted by a COOH group,

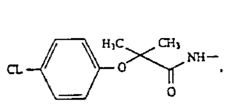,

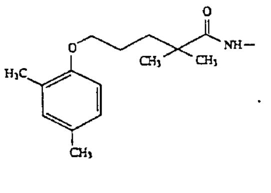.

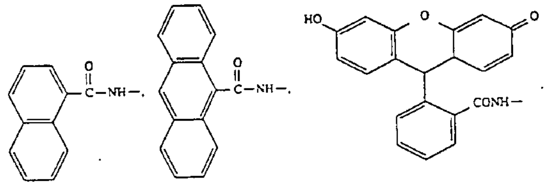

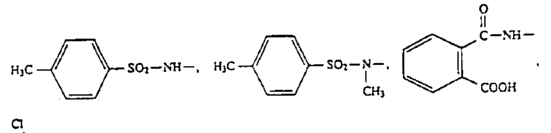

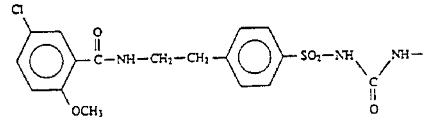

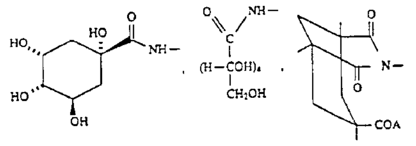

oder

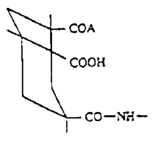

where A is in each case OH or $NH(C_1-C_{10})$alkyl.

Preferred compounds of the formula I are those in which GS is linked to X in the 3-position, linking taking place in the α- or β-position.

An acid function is understood as meaning, in particular, the COOH group or the sulfonic acid group.

Alkyl radicals are straight-chain or branched.

The compounds of the formula (I) according to the invention have a high affinity for the specific bile acid transportation system of the small intestine and inhibit bile acid absorption in a concentration-dependent and competitive manner.

By competitive inhibition, intervention in the enterohepatic circulation can be considerably more selective. Avitaminoses are not to be expected, and a qualitative change in the bile acid composition in the bile is just as unlikely. A controlled reduction in the serum cholesterol level can be achieved with compounds according to the invention, without the known side effects being observed. Because of their high affinity for the bile acid transportation system, very much lower daily doses than with the commercially available polymers are sufficient; this also leads to a high acceptance by patient and doctor.

The compounds have valuable pharmacological properties and are therefore particularly suitable as hypolipidemic agents.

The invention thus also relates to medicaments based on the compounds of the formula (I) and to the use of the compounds as medicaments, in particular for reducing the cholesterol level.

The compounds according to the invention were tested biologically by determination of the inhibition of $[^3H]$ taurocholate uptake in the brush border membrane vesicles from the ileum of rabbits. The inhibition test was carried out as follows:

1. Preparation of brush border membrane vesicles from the ileum of rabbits

Brush border membrane vesicles were prepared from the intestinal cells of the small intestine by the so-called $Mg^{2+}$ precipitation method. Male New Zealand rabbits (2 to 2.5 kg body weight) were sacrificed by intravenous injection of 0.5 ml of an aqueous solution of 2.5 mg of tetracaine HCl, 100 T 61® and 25 mg of mebezonium iodide. The small intestine was removed and rinsed with ice-cold physiological saline solution. The terminal 7/10 of the small intestine (measured in the oral-rectal direction, i.e. the terminal ileum, which contains the active $Na^+$-dependent bile acid transportation system) was used for preparation of the brush border membrane vesicle. The intestines were frozen in plastic bags under nitrogen at −80° C. For preparation of the membrane vesicles, the frozen intestines were thawed at 30° C. in a water bath. The mucosa was scraped off and suspended in 60 ml of ice-cold 12 mM Tris/HCl buffer (pH 7.1)/300 mM mannitol, 5 mM EGTA/10 mg/l of phenylmethylsulfonyl fluoride/1 mg/l of trypsin inhibitor from soybeans (32 U/mg)/0.5 mg/l of trypsin inhibitor from bovine lung (193 U/mg)/5 mg/l of bacitracin. After dilution to 300 ml with ice-cold distilled water, the mixture was homogenized with an Ultraturrax (18-rod, IKA Werk Staufen, FRG) for 3 minutes at 75% of the maximum output, while cooling with ice. After addition of 3 ml of 1M $MgCl_2$ solution (final concentration 10 mM), the mixture was left to stand at 0° C. for exactly 1 minute. The cell membranes aggregate by addition of $Mg^{2+}$ and precipitate, with the exception of the brush border membranes. After centrifugation at 3000× g (5000 rpm, SS-34 rotor) for 15 minutes, the precipitate was discarded, and the supernatant, which contained the brush border membranes, was centrifuged at 267000× g (15000 rpm, SS-34 rotor) for 30 minutes. The supernatant was discarded and the precipitate was rehomogenized in 60 ml of 12 mM Tris/HCl buffer (pH 7.1)/60 mM mannitol, 5 mM EGTA using a Potter Elvejhem homogenizer (Braun, Melsungen, 900 rpm, 10 strokes). After addition of 0.1 ml of 1 M $MgCl_2$ solution and an incubation time of 15 minutes at 0° C., the mixture was centrifuged again at 3000× g for 15 minutes. The supernatant was then centrifuged again at 46000× g (15000 rpm, SS-34 rotor) for 30 minutes. The precipitate was taken up in 30 ml of 10 mM Tris/Hepes buffer (pH 7.4)/300 mM mannitol and resuspended homogeneously by 20 strokes in a Potter Elvejhem homogenizer at 1000 rpm. After centrifugation at 48000× g (20000 rpm, SS-34 rotor) for 30 minutes, the precipitate was taken up in 0.5 to 2 ml of Tris/Hepes buffer (pH 7.4)/280 mM mannitol (final concentration 20 mg/ml) and resuspended with the aid of a tuberculin syringe with a 27 gauge needle. The vesicles were either used immediately for transportation studies after preparation, or stored at −196° C. in portions of 4 mg in liquid nitrogen.

2. Inhibition of $Na^+$-dependent [$^3H$]-taurocholate uptake in the brush border membrane vesicles of the ileum The uptake of substrates into the brush border membrane vesicles described above was determined by means of the so-called membrane filtration technique. 10 μl of the vesicle suspension (100 μg of protein) were pipetted as drops onto the wall of a polystyrene incubation tube (11×70 mm) which contained the incubation medium with the corresponding ligands (90 μl). The incubation medium contained 0.75 μl=0.75 μCi of [$^3H$(G)]-taurocholate (specific activity: 2.1 Ci/mmol)/0.5 μl of 10 mM taurocholate/8.75 μl of sodium transportation buffer (10 mM Tris/Hepes (pH 7.4)/100 mM mannitol/100 mM NaCl) (Na—T—P) or 8.75 μl of potassium transportation buffer (10 mM Tris/Hepes (pH 7.4)/100 mM mannitol/100 mM KCl) (K—T—P) and 80 μl of the inhibitor solution in question, dissolved in Na-T buffer or K-T buffer, depending on the experiment. The incubation medium was filtered through a polyvinylidene fluoride membrane filter (SYHV LO 4NS, 0.45 μm, 4 mm ϕ, Millipore, Eschborn, FRG). The transportation measurement was started by mixing the vesicles with the incubation medium. The concentration of taurocholate in the incubation batch was 50 μM. After the desired incubation time (usually 1 minute), the transportation was stopped by addition of 1 ml of ice-cold stopping solution (10 mM Tris/Hepes (pH 7.4)/ 150 mM KCl).

The mixture formed was immediately filtered off with suction over a membrane filter of cellulose nitrate (ME 25, 0.45 μm, 25 mm diameter, Schleicher & Schuell, Dassell, FRG) under a vacuum of 25 to 35 mbar. The filter was rinsed with 5 ml of ice-cold stopping solution.

To measure the uptake of the radioactively labeled taurocholate, the membrane filter was dissolved with 4 ml of the scintillator Quickszint 361 (Zinsser Analytik GmbH, Frankfurt, FRG) and the radioactivity was measured by liquid scintillation measurement in a TriCarb 2500 measuring instrument (Canberra Packard GmbH, Frankfurt, FRG). After calibration of the instrument with the aid of standard samples and after correction for any chemiluminescence present, the values measured were obtained as dpm (decompositions per minute).

The control values were in each case determined in Na—T—P and K—T—P. The difference between the uptake in Na—T—P and K—T—P was the $Na^+$-dependent transportation content. The concentration of inhibitor at which the $Na^+$-dependent transportation content was inhibited by 50%—based on the control—was designated as the $IC_{50}Na^+$.

The table shows the measurement values of the inhibition of the [$^3H$]-taurocholate uptake in brush border membrane vesicles from the ileum of rabbits. The quotients of the $IC_{50}$ and $IC_{50Na}$ values of the taurochenodesoxycholate (TCDC) investigated as the standard in each vesicle preparation and the particular substance are stated.

| Substance from Example: | $IC_{50}$ (TCDC) / $IC_{50}$ (Substance) | $IC_{50Na}$ (TCDC) / $IC_{50Na}$ (Substance) |
|---|---|---|
| 3 | 0.4 | 0.35 |
| 4 | 0.77 | 0.69 |
| 18 | 0.47 | 0.42 |
| 21 | 0.34 | 0.33 |
| 33 | 0.33 | 0.35 |
| 35 | 1.0 | 1.02 |
| 36 | 0.19 | 0.20 |
| 38 | 0.49 | 0.41 |
| 40 | 0.52 | 0.50 |
| 43 | 0.78 | 0.73 |

The invention furthermore relates to the use of the compounds according to the invention for the preparation of a medicine.

For this, the compounds of the formula I are dissolved or suspended in pharmacologically acceptable organic solvents, such as mono- or polyhydric alcohols, such as, for example, ethanol or glycerol, or in triacetin, oils, for example sunflower oil or cod-liver oil, ethers, such as, for example, diethylene glycol dimethyl ether, or also polyethers, for example polyethylene glycol, or also in the presence of other pharmacologically acceptable polymeric carriers, such as, for example, polyvinylpyrrolidone, or other pharmaceutically acceptable additives, such as starch, cyclodextrin or polysaccharides. The compounds according to the invention furthermore can be administered in combination with other medicaments.

The compounds of the formula I are administered in various dosage forms, preferably orally in the form of tablets, capsules or liquids. The daily dose varies in the range from 3 mg to 5000 mg, but preferably in the dose range of 10 to 1000 mg, depending on the body weight and constitution of the patient.

The particular monoisotopic molecular weights calculated are stated in the following examples.

Unless stated otherwise, mass spectra were recorded by the FAB technique with addition of LiCl and 3-nitrobenzaldehyde[3-NBA].

Starting compounds which have the bile acid structure have already been described in some cases (cf., for example, EP-A-0 417 725, EP-A-0 489 423 and EP-A-0 548 793.

$R^1$ is defined in Example 6.

EXAMPLE 1

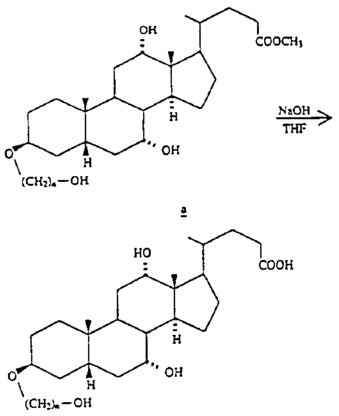

a n = 5

1 g (1.96 mmol) of the methyl ester a is dissolved in 15 ml of tetrahydrofuran (THF) or 1,4-dioxane and the solution is stirred intensively with 10 ml of 2N NaOH overnight at room temperature. It is then diluted with a large quantity of water and acidified with half-concentrated hydrochloric acid, while cooling with ice. Precipitation is brought to completion by subsequent stirring for 1 hour, while cooling with ice, and the precipitate formed is filtered off with suction and rinsed with cold water. Recrystallization from ethanol/water and drying in vacuo give 940 mg (96%) of Example 1.

$C_{29}H_{50}O_6$(494) MS: 501 (M+Li$^+$).

The following Examples 2 to 7 are prepared analogously to "Example 1" from the corresponding bile acid esters:

| Example No. | as "Example 1" where n = | Empirical formula | MW | MS |
|---|---|---|---|---|
| 2 | 6 | $C_{30}H_{52}O_6$ | 508 | 515 (M + Li$^+$) |
| 3 | 8 | $C_{32}H_{56}O_6$ | 536 | 543 (M + Li$^+$) |
| 4 | 9 | $C_{33}H_{58}O_6$ | 550 | 557 (M + Li$^+$) |
| 5 | 10 | $C_{34}H_{60}O_6$ | 564 | 571 (M + Li$^+$) |

EXAMPLE 6

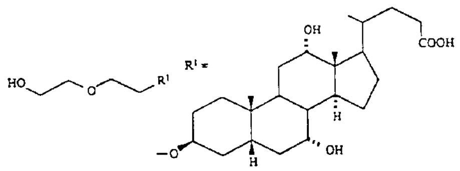

$C_{28}H_{48}O_7$ (496) MS: 503 (M + Li$^+$)

EXAMPLE 7

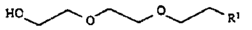

$C_{30}H_{52}O_7$ (540) MS: 547 (M + Li$^+$)

457

EXAMPLE 8

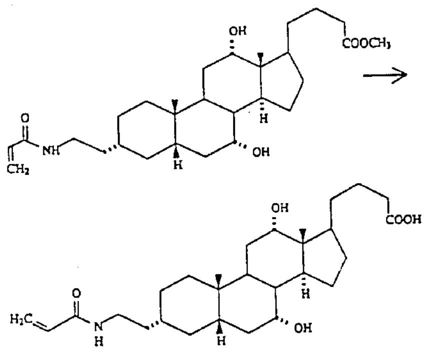

100 mg (0.2 mmol) of the methyl ester are dissolved in 10 ml of dioxane and the solution is stirred with 3 ml of half-concentrated sodium hydroxide solution at room temperature for 6 hours. The mixture is diluted with water and acidified with half-concentrated hydrochloric acid to give, after filtration with suction and washing, the acid "Example 8" (50 mg, 51%).

$C_{29}H_{47}NO_5$ (489) MS: 496 ($M+Li^+$)

The following substance examples were prepared as for "Example 8":

EXAMPLE 9

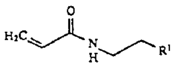

$C_{29}H_{47}NO_6$(505) MS: 512 ($M + Li^+$)

EXAMPLE 10

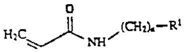

n = 5

$C_{32}H_{53}NO_6$ (547) MS: 554 ($M + Li^+$)

EXAMPLE 11

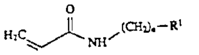

n = 6

$C_{33}H_{55}NO_6$ (561) MS: 568 ($M + Li^+$)

EXAMPLE 12

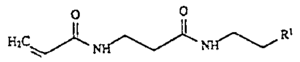

$C_{32}H_{52}N_2O_7$ (576) MS: 583 ($M + Li^+$)

EXAMPLE 13

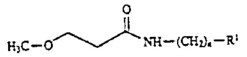

n = 6

$C_{34}H_{59}NO_7$ (593) MS: 600 ($M + Li^+$)

EXAMPLE 14

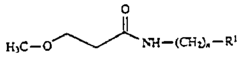

n = 5

$C_{33}H_{57}NO_7$ (579) MS: 586 ($M + Li^+$)

EXAMPLE 15

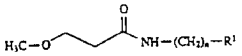

n = 2

$C_{30}H_{51}NO_7$ (537) MS: 544 ($M + Li^+$)

EXAMPLE 16

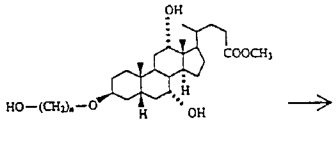

-continued

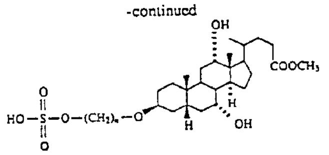

n = 6

0.84 ml of triethylamine is added to 3.14 g (6 mmol) of the primary alcohol a (n =6) in 100 ml of dry methylene chloride and the mixture is cooled to −10° C. 0.4 ml (6 mmol) of chlorosulfonic acid in 20 ml of dry methylene chloride is added to the solution at this temperature. After 1 hour at 0° C. and 1 hour at room temperature, water is added, the organic phase is separated off, the aqueous phase is extracted several times with ethyl acetate and the combined organic phases are dried and concentrated. The residue is purified by chromatography ($SiO_2$, ethyl acetate/methanol=3:1). 1.45 g (40%) of "Example 16" are obtained.

$C_{31}H_{54}O_9S$ (602) MS: 631 (M−H$^+$+Li$^+$+Na$^+$) 615 (M−H$^+$ 2Li$^+$)

EXAMPLE 17

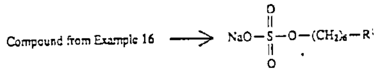

0.5 g (0.83 mmol) of "Example 16" is stirred in 20 ml of dioxane with 7 ml of half-concentrated sodium hydroxide solution at room temperature for 6 hours. The mixture is then acidified with half-concentrated hydrochloric acid, while cooling, and is concentrated in vacuo. The residue is purified by column filtration ($SiO_2$, ethyl acetate/methanol=3:1). 254 mg (52%) of "Example 17" are obtained.

$C_{30}H_{51}O_9S$ (610) MS=617 (M+Li$^+$) 601 (M−Na$^+$+2Li$^+$)

EXAMPLE 18

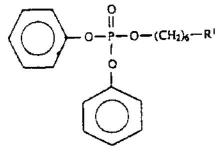

15 ml of phosphoric acid diphenyl ester chloride are added dropwise to a solution of 2.6 g (5.12 mmol) of "Example 2" in 20 ml of pyridine at 0 to 5° C. and the mixture is subsequently stirred at room temperature for 2 hours. It is poured onto 200 ml of ice-water, about 15 ml of concentrated sulfuric acid are added, while stirring and cooling, and the mixture is extracted several times with ethyl acetate. The organic phase is dried and concentrated and the residue is purified by chromatography ($SiO_2$, $CH_2Cl_2$/$CH_3OH$=10:1). 1.78 g (47%) of "Example 18" are obtained.

$C_{42}H_{61}O_9P$ (740) MS: 747 (M+Li$^+$)

EXAMPLE 19

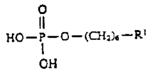

1 g (1.35 mmol) of "Example 18" is hydrogenated in 50 ml of glacial acetic acid with a spatula-tip of platinum-on-charcoal in a shaking vessel. When the reaction has ended (about 4 hours), the catalyst is filtered off with suction and the filtrate is concentrated. The residue is purified by column filtration ($SiO_2$, ethyl acetate/$CH_3OH$=2:1). 270 mg (34%) of "Example 19" are obtained.

$C_{30}H_{53}O_9P$ (588) MS: 601 (M−H$^+$+2Li$^+$) 595 (M+Li$^+$)

EXAMPLE 20

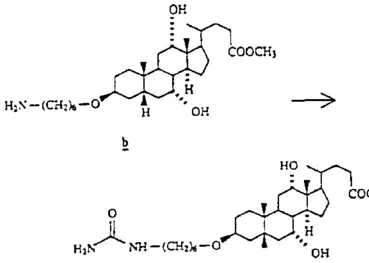

2.24 g (4 mmol) of amine b and 324 mg (4 mmol) of potassium cyanate are suspended in 60 ml of water and the suspension is heated to boiling point. A solution is formed, from which a solid precipitates after a short time. The mixture is stirred at boiling point for 30 minutes and cooled, about 40 ml of water are added and the mixture is acidified with dilute hydrochloric acid. It is extracted several times with ethyl acetate, the organic phase is dried and concentrated in vacuo and the residue is purified by chromatography ($SiO_2$, EtOAc/$CH_3OH$=10:1). 520 mg (23%) of "Example 20" are obtained.

$C_{32}H_{56}N_2O_6$ (564 ) MS: 571 (M+Li$^+$)

EXAMPLE 21

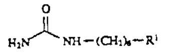

450 mg (0.mmol) of "Example 20" are stirred in 10 ml of dioxane with 5 ml of half-concentrated sodium hydroxide solution at room temperature for 6 hours. When the reaction has ended, the mixture is diluted with water, acidified with hydrochloric acid and subsequently stirred in an ice-bath for 1 hour. The precipitate is filtered off with suction and rinsed with water to give, after drying in vacuo, 430 mg (97%) of "Example 21".

$C_{31}H_{54}N_2O_6$ (550) MS: 557 (M+Li$^+$)

EXAMPLE 22

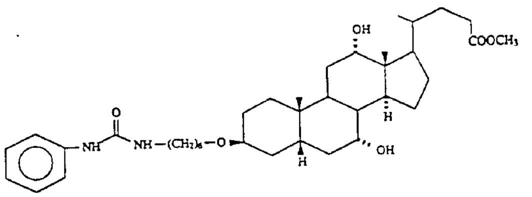

2 mmol of phenyl isocyanate in 5 ml of methylene chloride are added to 1.04 g (2 mmol) of amine b (Example 20) in 50 ml of dry methylene chloride and 28 ml of triethylamine at 0° C. The mixture is subsequently stirred at room temperature for 6 hours and worked up as described under "Example 16", the aqueous phase being acidified. After column filtration ($CH_2Cl_2/CH_3OH$=10:1), 6540 mg (51%) of "Example 22" are obtained.

$C_{38}H_{60}N_2O_6$ (640) MS: 647 ($M+Li^+$)

EXAMPLE 23

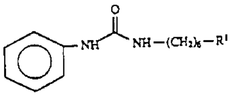

$C_{37}H_{58}N_2O_6$ MS: 633 ($M+Li^+$)

EXAMPLE 24

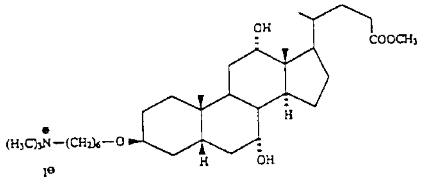

2.08 g (4 mmol) of amine b, 10 ml of triisobutylamine and 5 ml of iodomethane are heated at boiling point in 50 ml of acetonitrile for 2 hours. All the volatile constituents are removed in vacuo and the residue is purified by chromatography ($SiO_2$, $CH_2Cl_2/CH_3OH$=10: 1). 1.2 g (43%) of "Example 24" are obtained.

$C_{34}H_{62}INO_5$ (691) MS (FAB, 3-NBA): 564 ($M-I^{\ominus}$)

EXAMPLE 25

$(H_3C)_3\overset{\oplus}{N}-(CH_2)_6-R^1$ $Cl^{\ominus}$

Compound Example 25 is prepared from Example 24 analogously to "Example 21". The crude product is purified by medium pressure chromatography over RP-8 silica gel ($CH_3OH/H_2O$=7:3).

$C_{33}H_{60}ClNO_5$ (585) MS (FAB, 3-NBA): 550 ($M-Cl^{\ominus}$)

EXAMPLE 26

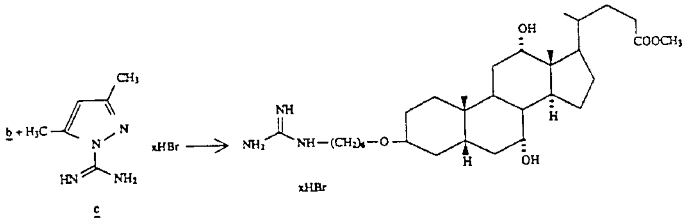

1.04 g (2 mmol) of amine b and 276 mg (2 mmol) of pyrazole c are heated under reflux in 40 ml of dry acetonitrile for 10 hours. After cooling and addition of ether, a precipitate is formed, and is filtered off with suction and rinsed with dry ether. After drying, 450 mg of "Example 26" are obtained.

$C_{32}H_{58}BrN_3O_5$ (643) MS: 570 (M-HBr+Li$^+$) 564 (M-Br$^\ominus$)

EXAMPLE 27

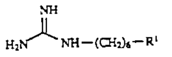

xHCl is prepared analogously to "Example 21".

$C_{31}H_{56}ClN_3O_5$ (585) MS: 556 (M-HCl+Li$^+$) 550 (M-Cl$^\ominus$)

EXAMPLE 28

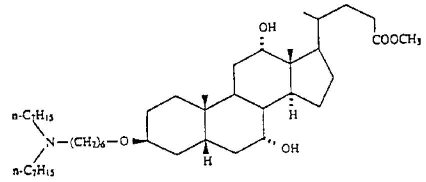

1.0 g (1.9 mmol) of amine b, 265 mg of $NaBH_3CN$ and 610 mg of heptanal are stirred in 10 ml of dry methanol at room temperature for 48 hours. The mixture is concentrated in vacuo, the residue is partitioned between ethyl acetate and saturated bicarbonate solution and the residue of the organic phase is purified by chromatography. In addition to a small amount of monoheptylamino derivative, 650 mg (49%) of "Example 28" are obtained.

$C_{45}H_{83}NO_5$ (718) MS: 725 (M+Li$^+$)

EXAMPLE 29

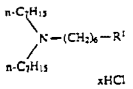

xHCl is prepared analogously to "Example 21". The aqueous phase is decanted off from the oily crude product after acidification, and the residue is extracted by stirring with ethyl acetate and then filtered off with suction and dried.

$C_{44}H_{82}ClNO_5$ (740) MS: 711 (M-HCl+Li$^+$) 705 (M-Cl$^\ominus$)

EXAMPLE 30

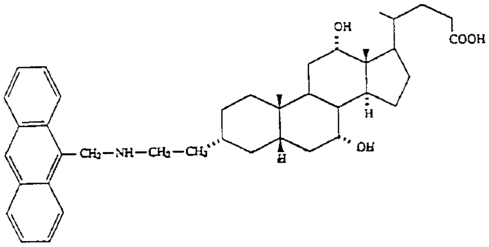

is prepared analogously to "Example 28" and "Example 29" by reductive amination of anthracene-9-carbaldehyde with methyl 3α-(aminoethyl)-7α, 12α-dihydroxy-24-cholanate (d) and subsequent alkaline hydrolysis.

$C_{41}H_{55}NO_4$ (625) MS: 632 (M+Li$^+$)

EXAMPLE 31

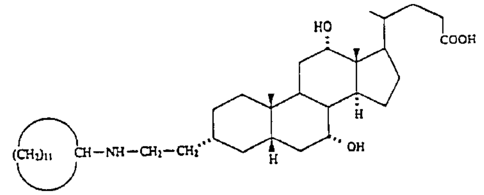

is prepared analogously to "Example 30" using cyclododecanone as the carbonyl component.

$C_{38}H_{87}NO_4$ (602) MS: 609 ($M+Li^+$)

EXAMPLE 32

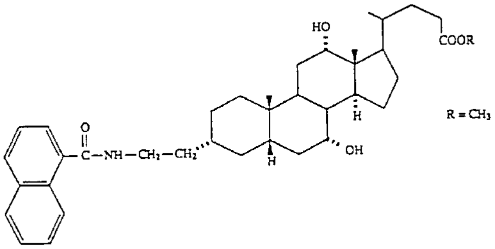

0.38 g (2 mmol) of naphthoyl chloride in 5 ml of $CH_2Cl_2$ is added to 0.9 g (2 mmol) of amine d and 0.6 ml of triethylamine in 20 ml of dry $CH_2Cl_2$, while cooling with ice. The mixture is subsequently stirred at 0° C. for 1 hour and left to stand overnight. Water is added, and the mixture is acidified and extracted several times with $CH_2Cl_2$. The residue from the organic phase is purified by chromatography ($SiO_2$, EtOAc/cyclohexane=3:1). 1 g (83%) of "Example 32" is obtained.

$C_{38}H_{53}NO_5$ (603) MS: 610 ($M+Li^+$)

EXAMPLE 33

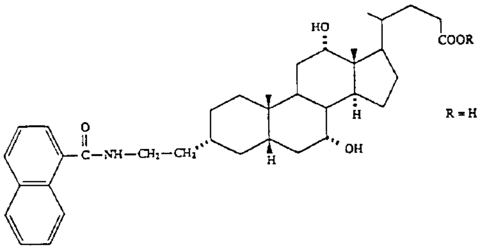

is prepared analogously to "Example 21".

$C_{37}H_{51}NO_5$ (589) MS: 596 ($M+Li^+$)

EXAMPLE 34

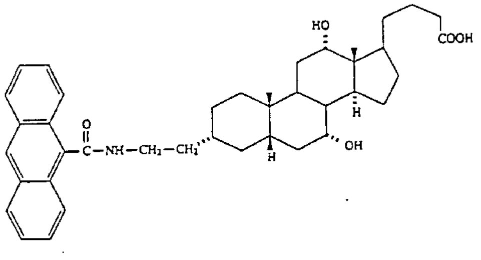

is prepared analogously to "Example 32" and "Example 33" using anthracene-9-carbonyl chloride.

$C_{41}H_{53}NO_5$ (639) MS: 646 (M+Li$^+$)

EXAMPLE 35

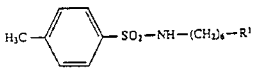

is prepared analogously to "Example 34" using p-toluenesulfonyl chloride and amine b.

$C_{37}H_{59}NO_7S$ (661) MS: 668 (M+Li$^+$)

EXAMPLE 36

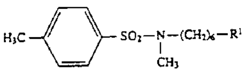

is prepared analogously to "Example 35". The methyl ester obtained as an intermediate product is methylated in dimethylformamide, after deprotonation by sodium hydride, with iodomethane at room temperature. The product is then subjected to alkaline hydrolysis analogously to "Example 35".

$C_{38}H_{61}NO_7S$ (675) MS: 688 (M-H$^+$+2Li$^+$) 682 (M+Li$^+$)

EXAMPLE 37

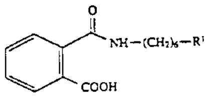

is prepared analogously to "Example 34" using o-phthalic anhydride and amine b.

$C_{38}H_{57}NO_8$ (655) MS: 668 (M-H$^+$+2Li$^+$) 662 M+Li$^+$)

EXAMPLE 38

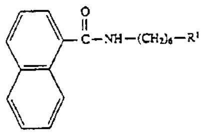

is prepared analogously to "Example 32"/"Example 33" using amine b.

$C_{41}H_{59}NO_6$ (661) MS: 668 (M+Li$^+$)

EXAMPLE 39

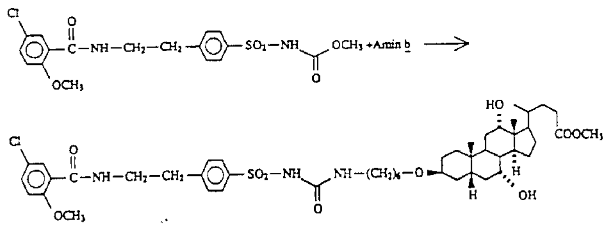

426 mg (1 mmol) of urethane and 782 mg (15 mmol) of amine b are heated under reflux in 50 ml of dioxane for 4 hours. The mixture is then concentrated and the residue is purified by chromatography ($SiO_2$, $CH_2Cl_2/CH_3OH$=10:1). 540 g (59%) of "Example 39" are obtained.

$C_{48}H_{70}ClN_3O_{10}S$ (915) MS: 922 ($M+Li^+$)

EXAMPLE 40

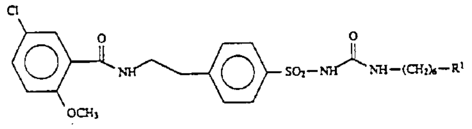

is prepared analogously to "Example 21".

$C_{47}H_{68}ClN_3O_{10}S$ (901) MS (electrospray): 902 ($M+H^+$)

EXAMPLE 41

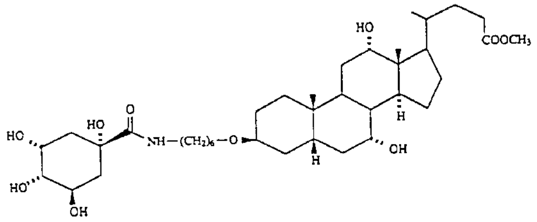

750 mg (3.6 mmol) of dicyclohexylcarbodiimide are added to a solution of 1.56 g (3 mmol) of amine b, 576 mg (3 mmol) of China acid and 490 mg (83.6 mmol) of hydroxybenzotriazole in 100 ml of THF. The mixture is stirred at room temperature for 40 hours. The urea formed is filtered off, the solution is concentrated and the residue is taken up in ethyl acetate. The solution is washed with saturated $NaHCO_3$ solution, 2N citric acid, saturated $NaHCO_3$ solution and water. The residue from the organic phase is purified by chromatography ($SiO_2$, ethyl acetate/$CH_3OH$= 5:1). 1.2 g (58%) of "Example 41" are obtained.

$C_{38}H_{65}NO_{10}$ (695) MS: 702 ($M+Li^+$)

EXAMPLE 42

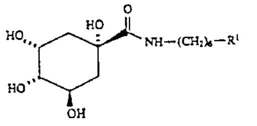

is prepared analogously to "Example 21".

$C_{37}H_{63}NO_{10}$ (681) MS (FAB, 3-NBA): 682 ($M+H^+$)

EXAMPLE 43

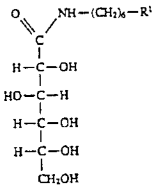

is prepared analogously to "Example 41"/"Example 42" using gluconic acid.

$C_{36}H_{63}NO_{11}$ (685) MS: 714 ($M-H^++Li^++Na^+$)

EXAMPLE 44

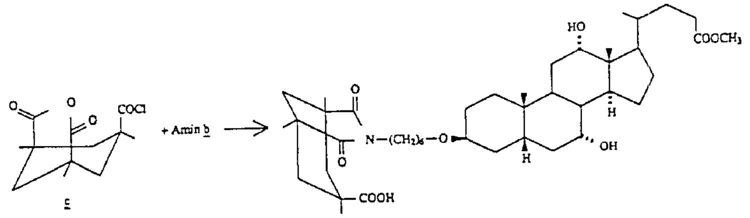

1.04 g (4 mmol) of acid chloride e, 2.1 g (4 mmol) of amine b and a spatula-tip of 4-dimethylaminopyridine are stirred in 40 ml of dry pyridine at room temperature for 6 hours. After standing overnight at room temperature, the mixture is concentrated in vacuo. "Example 44" is isolated after purification by chromatography ($SiO_2$, $CH_2Cl_2/CH_3OH$=20:1).

$C_{43}H_{69}NO_9$ (743) MS: 750 ($M+Li^+$)

EXAMPLE 45

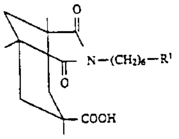

is prepared analogously to "Example 21".

$C_{42}H_{67}NO_9$ (729) MS: 742 ($M-H^++2Li^+$) 736 ($M+Li^+$)

EXAMPLE 46

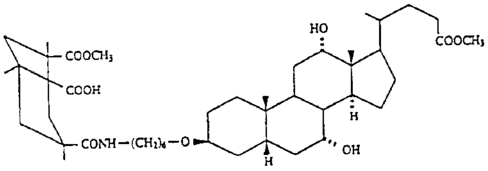

2.6 g (5 mmol) of amine b in $CH_2Cl_2$ are added to 1.3 g (5 mmol) of acid chloride e and 0.8 ml of triethylamine in 50 ml of dry $CH_2Cl_2$, while cooling with ice, and the mixture is stirred at 0° C. for 1 hour. An excess of methanol is then added, the mixture is allowed to come to room temperature, water is added and the mixture is acidified with dilute hydrochloric acid. The aqueous phase is extracted several times by shaking with $CH_2Cl_2$. After purification of the residue from the organic phase by chromatography ($SiO_2$, $CH_2Cl_2/CH_3OH$=10:1), "Example 46" is obtained.

$C_{44}H_{73}NO_{10}$ (775) MS: 783 ($M+Li^+$)

EXAMPLE 47

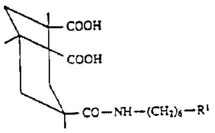

is prepared analogously to "Example 21".

$C_{42}H_{69}NO_{10}$ (747) MS: 760 ($M-H^++2Li^+$) 754 (($M+Li^+$)

EXAMPLE 48

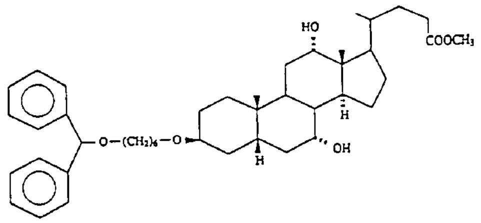

3.14 g (6 mmol) of alcohol a (n=6) are heated at 100° C. with 3 ml of ethyldiisopropylamine and 1.5 g of diphenylmethyl bromide in 50 ml of DMF for 8 hours. After aqueous working up and purification by chromatography ($SiO_2$, $CH_2Cl_2/CH_3OH$=10:1), "Example 48" is obtained.

$C_{44}H_{64}O_6$ (688) MS: 695 ($M+Li^+$)

EXAMPLE 49

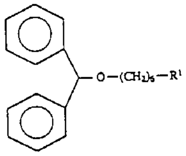

is prepared analogously to "Example 21".

$C_{43}H_{62}O_6$ (674) MS: 681 ($M+Li^+$)

The following compounds are prepared analogously to Example 1 from the corresponding bile acid esters by alkaline ester hydrolysis:

EXAMPLE 50

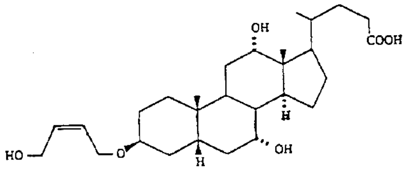

$C_{28}H_{46}O_6$ MW: 478 MS: 485 ($M+Li^+$)

EXAMPLE 51

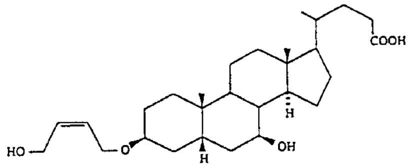

$C_{28}H_{46}O_5$ MW: 462 MS: 469 ($M+Li^+$)

EXAMPLE 52

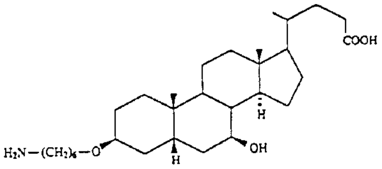

$C_{30}H_{53}NO_{44}$ MW: 491 MS: 498 ($M+H^+$)

EXAMPLE 53

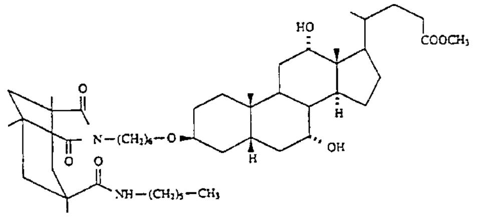

is prepared from Example 44 and n-hexylamine analogously to Example 41 with a reaction time of 25 hours.

$C_{49}H_{82}N_2O_8$ (827) MS: 834 ($M+Li^+$)

EXAMPLE 54

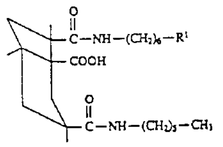

170 mg of "Example 53" are dissolved in 5 ml of dioxane, 1.5 ml of half-concentrated sodium hydroxide and 25 ml of water are added, and the mixture is stirred at room temperature for 12 hours.

A suspended solid is filtered off and the filtrate is acidified with dilute hydrochloric acid, stirring is continued for 1 hour, and the precipitate formed is filtered off with suction. After drying, 154 mg of "Example 54" are obtained.

$C_{48}H_{82}N_2O_9$ (831) MS: 838 ($M+Li^+$)

EXAMPLE 55

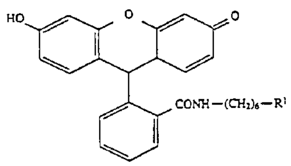

Prepared analogously to "Example 53" and "Example 54" from fluoresceine and amine b.

$C_{50}H_{63}NO_9$ (821) MS: 828 ($M+Li^+$)

EXAMPLE 56

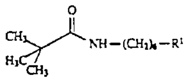

Prepared analogously to "Example 55" from pivalic acid and amine b.

$C_{35}H_{61}NO_6$ (591) MS: 598 ($M+Li^+$)

EXAMPLE 57

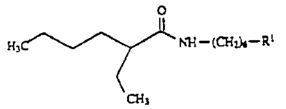

is prepared analogously to "Example 55" from 2-ethylhexanoic acid and amine b.

$C_{38}H_{67}NO_6$ (633) MS: 640 $(M+Li^+)$

EXAMPLE 58

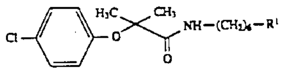

is prepared analogously to "Example 55" from clofibric acid and amine b.

$C_{40}H_{62}ClNO_7$ (703) MS: 710 $(M+Li^+)$

EXAMPLE 59

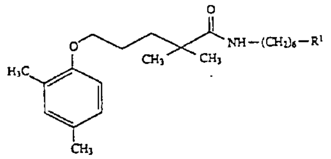

is prepared analogously to "Example 55" from gemfibrocil and amine b.

$C_{45}H_{73}NO_7$ (740) MS: 747 $(M+Li^+)$

EXAMPLE 60

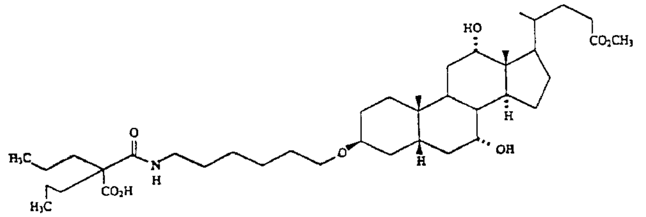

Prepared from 522 mg of amine b and 94.1 mg of di-n-propylmalonic acid in THF in the presence of DCC/HOBT. Isolated after 54 h. The yield is 69%.

$C_{40}H_{69}NO_8$ (690) MS: 697 $(M+Li^+)$

EXAMPLE 61

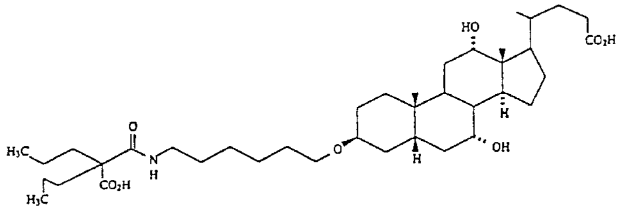

250 mg of "Example 60" are hydrolyzed in dioxane using 2N NaOH. After aqueous work-up and purification by column chromatography (EtOAc/$CH_3OH$ 10:1), 160 mg of compound 61 are obtained.

$C_{39}H_{67}NO_8$ (676) MS: 677 (M+1)

We claim:

1. A monomeric bile acid derivative of the formula IA

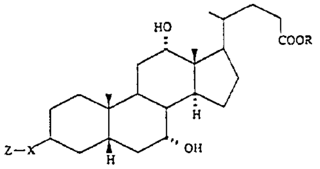

IA wherein

R is H, $CH_3$ or M and M is a metal capable of forming a salt,

X is a bridge group of the formula $(CH_2)_n$, where n=1 to 3, in which 1 to 3 $(CH_2)$-groups can be replaced by NH or

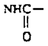

groups, or a bridge group of the formula $(CH_2)_n$ where n=4 to 10, in which 1 to 3 $(CH_2)$-groups can be replaced by oxygen atoms, NH or

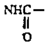

groups with the proviso that no neighboring $(CH_2)$-groups are replaced by oxygen atoms and in which GS is bonded via X as desired; and Z is

HO—, $CH_3$—O—, HO—$CH_2$—CH=CH—$CH_2$—, $(C_6H_5)_2$—CH—O—, 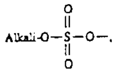

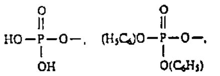

-continued

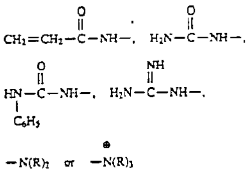

or —$N(R)_3$ where

R is in each case $C_1$–$C_7$ alkyl, or $H_2$—N—$(CH_2)_6$;

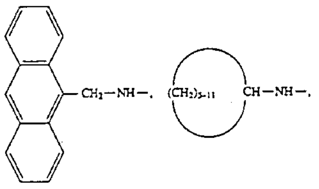

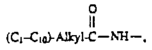

where the alkyl moiety is optionally substituted by a COOH group,

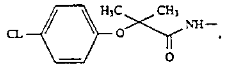

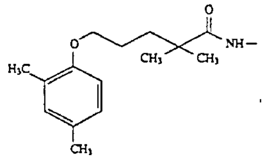

-continued
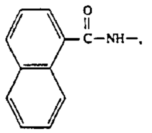
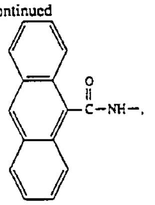
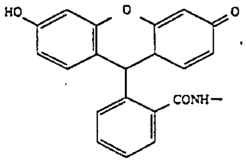
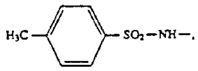
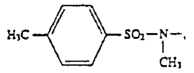
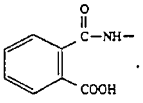
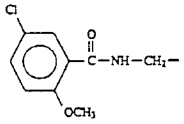
-continued
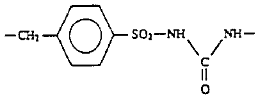
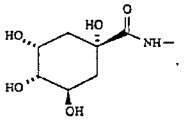
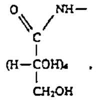
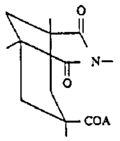
or
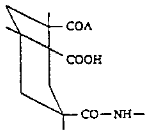
where A is in each case OH or NH ($C_1$–$C_{10}$) alkyl.
2. A bile acid derivative of the formula I as claimed in claim 1, in which GS is linked to X in the 3-position, linking taking place in the α- or β-position.
3. A medicament comprising a bile acid derivative as claimed in claim 1.
4. A hypolipidemic agent comprising a bile acid derivative as claimed in claim 1.
* * * * *

APPENDIX B

HMG CoA Reductase Inhibitors

| COMPOUNDS and COMPOUND CLASSES | CAS NUMBERS for SPECIFIC and REPRESENTATIVE COMPOUNDS | REFERENCE |
|---|---|---|
| Benfluorex | 23602-78-0 | ES 474498 |
| Fluvastatin | 93957-54-1 | EP 244364 |
| Lovastatin | 75330-75-5 | EP 22478 |
| Pravastatin | 81093-37-0 | DE 3122499 |
| Simvastatin | 79902-63-9 | EP 33538 |
| Atorvastatin | 134523-00-5 | EP 409281 |
| Cerivastatin | 145599-86-6 | JP 08073432 |
| Bervastatin and related benzopyrans | 132017-01-7 | EP 380392 |
| BMS 180431 | 129829-03-4 | Sit, Parker, Motoc, Han, Balasubramanian, Catt, Brown, Harte, Thompson, and Wright, J.Med. Che (1990), 33(11), 2982-99. |
| NK-104 | 141750-63-2 | Takano, Kamikubo, Sugihara, Suzu: Ogasawara, Tetrahedron:Assymetry (1993), 4(2), 201-4 |
| (Carboxydihydroxyheptenyl)sulfonylpyrroles including S-4522 | 148966-78-3, 139993-44-5, 139993-45-6, 139993-46-7, 139993-47-8, 139993-48-9, 139993-49-0, 139993-50-3, 139993-51-4, 139993-52-5, 139993-53-6, 139993-54-7, 139993-55-8, 139993-56-9, 139993-57-0, 139993-58-1, 139993-59-2, 139993-60-5, 139993-61-6, 139993-62-7, 139993-63-8, 139993-64-9, 139993-65-0, 139993-66-1, 139993-67-2, 139993-68-3, 139993-69-4, 139993-70-7, 139993-71-8, 139993-72-9, 139993-73-0, 139993-74-1, 139993-75-2, 139993-76-3, 139993-77-4, 139993-78-5, 139993-79-6, 139993-80-9, 140110-63-0, 140128-98-9, 140128-99-0, 140157-62-6 | EP 464845 |
| Boron Analogs of di- and tripeptides | 125894-01-1, 125894-02-2, 125894-03-3, 125894-04-4, 125894-05-5, 125894-08-8, 125894-09-9, 125914-96-7 | Sood, Sood, Spielvogel, Hall, Eur Med. Chem. (1990), 25(4), 301-8. |
| Zaragozic acids | 157058-13-4, 157058-14-5, 157058- | GB 2270312 |

| | | |
|---|---|---|
| | 15-6, 157058-16-7, 157058-17-8, 157058-18-9, 157058-19-0 | |
| Seco-oxysterol analogs including U-88156 | 157555-28-7, 157555-29-8 | Larsen, Spilman, Yagi, Dinh, Hart, and Hess, J. Med. Chem. (1994), 37(15), 2343-51. |
| Pyridopyrimidines including acitemate | 64405-40-9, 101197-99-3 | Hermecz, Meszaros, Vasvari-Debreczy, Horvath, Virag, and Sipos, Hung. Arzneim-Forsch. (1979), 29(12), 1833-5 |
| BMY 22566 | 129829-03-4 | Sit, Parker, Motoc, Han, Balasubramanian, Catt, Brown, Harte, Thompson, and Wright, J.Med. Chem. (1990), 33(11), 2982-99. |
| Colestolone | 50673-97-7 | Raulston, Mishaw, Parish and Schroepfer, Biochem. Biophys. Res. Commun. (1976), 71(4), 984-9. |
| CP-83101 | 130746-82-6, 130778-27-7 | Wint and McCarthy, J. Labelled Compd. Radiopharm. (1988), 25(11), 1289-97. |
| Dalvastatin | 132100-55-1 | Kumar, Windisch, Trivedi and Golebiowski, J. Chromatogr., A (1994), 678(2), 259-63. |
| Dihydromevinolin | 77517-29-4 | Falck and Yang, Tetrahedron Lett. (1984), 25(33), 3563-66. |
| DMP-565 | | Ko, Trzaskos, Chen, Hausner, Brosz, and Srivastava, Abstr. Papers Am. Chem. Soc. (207th National Meeting, Part 1, MEDI 10, 1994) |
| Pyridyl and Pyrimidinylethenyldesmethyl-mevalonates including glenvastin | 122254-45-9 | Beck, Kesseler, Baader, Bartmann, Bergmann, Granzer, Jendralla, Von Kerekjarto, Krause, et al, J. Med. Chem. (1990), 33(1), 52-60. |
| GR 95030 | 157243-22-6 | US 5316765 |
| Isoxazolopyridylmevalonates, carboxylic acids and esters | 130581-42-9, 130581-43-0, 130581-44-1, 130581-45-2, 130581-46-3, 130581-47-4, 130581-48-5, 130581-49-6, 130581-50-9, 130581-51-0, 130581-52-1, 130619-07-7, 130619-08-8, 130619-09-9 | EP 369323 |
| Lactones of 6-phenoxy-3,5-dihydroxy-hexanoic acids | 127502-48-1, 136006-66-1, 136034-04-3 | Jendralla, Granzer, Von Kerekjarto, Krause, Schacht, Baader, Bartmann, Beck, Bergmann, et al., J. Med. Chem |

| | | |
|---|---|---|
| | | (1991), 34(10), 2962-83. |
| L 659699 | 29066-42-0 | Chiang, Yang, Heck, Chabala, and Chang, J. Org. Chem. (1989), 54(24), 5708-12. |
| L 669262 | 130468-11-0 | Stokker, J. Org. Chem. (1994), 59(20), 5983-6. |
| Mevastatin | 73573-88-3 | JP 56051992 |
| Pannorin | 137023-81-5 | Ogawa, Hasumi, Sakai, Murakawa and Endo, J. Antibiot. (1991), 44(7), 762-7 |
| Rawsonol | 125111-69-5 | Carte, Troupe, Chan, Westley and Faulkner, Phytochemistry (1989), 28(11), 2917-19 |
| RP 61969 | 126059-69-6 | EP 326386 |
| Bile acid derived HMG CoA reductase inhibitors including Na S-2467 and S-2468 | | Kramer, Wess, Enhsen, Bock, Falk, Hoffmann, Neckermann, Gantz, Schulz et al., Biochim. Biophys. Acta D (1994), 1227(3), 137-54. |
| SC 32561 | 76752-41-5 | US 4230626 |
| SC 45355 | 125793-76-2 | EP 329124 |
| Phosphorus containing HMG CoA reductase inhibitors including SQ 33600 | 133983-25-2 | US 5274155 |
| 6-Aryloxymethyl-4-hydroxytetrahydro-pyran-2-ones, carboxylic acids and salts | 135054-71-6, 136215-82-2, 136215-83-3, 136215-84-4, 136215-85-5, 136315-18-9, 136315-19-0, 136315-20-3, 136315-21-4, 136316-20-6 | EP 418648 |
| Atorvastatin calcium (CI 981) | 134523-03-8 | Baumann, Butler, Deering, Mennen, Millar, Nanninga, Palmer and Roth, Tetrahedron Lett. (1992), 33(17), 2283-4 |
| Fenofibrate | 49562-28-9 | DE 2250327 |
| Benzafibrate | 41859-67-0 | DE 2149070 |
| Etofibrate | 31637-97-5 | US 3723446 |
| Mevinolin analogs | | EP 245003 |
| Pyranone derivatives | | US 4937259 |
| 1,2,4-Triazolidine-3,5-diones | 16044-43-2 | WO 9000897 |

| | | |
|---|---|---|
| Isoazolidine-3,5-diones | 124756-24-7 | EP 321090 |
| CS-514 | 81181-70-6 | DE 3122499 |
| 1,10-bis(carboxymethylthio)decane | 32827-49-9 | DE 2038835 |
| α-, β-, and γ-alkylaminophenone analogs including N-phenylpiperazinopropiophenone | | Huang and Hall, Eur. J. Med. Chem. (1996), 31(4), 281-90. |
| 3-Amino-1-(2,3,4-mononitro-, mono-, or dihalophenyl)propan-1-ones including 3-morpholino- or piperidino-1-(3-nitrophenyl)propan-1-ones | | Huang and Hall, Arch. Pharm. (1996), 329(7), 339-346. |
| Substituted isoxazolo pyridinones | 64769-68-2 | US 4049813 |
| Biphenyl derivatives | | JP 07089898 |
| 4-[1-(Substituted phenyl)-2-oxo-pyrrolidin-4-yl]methoxybenzoic acids | | Watanabe, Ogawa, Ohno, Yano, Yamada and Shirasaka, Eur. J. Med. Chem. (1994), 29(9), 675-86. |
| Dihydroxy(tetrahydroindazolyl, tetrahydrocyclopentapyrazolyl, or hexahydrocycloheptapyrazole)heptenoate derivatives | | US 5134155 |

| | |
|---|---|
| benfluorex | Servier |
| fluvastatin | Sandoz |
| lovastatin | Merck & Co |
| pravastatin | Sankyo |
| simvastatin | Merck & Co |
| atorvastatin | Warner-Lambert |
| cerivastatin | Bayer |
| bervastatin | Merck KGaA |
| BMS-180431 | Bristol-Myers Squibb |
| NK-104 | Nissan Chemical |
| S-4522 | Shionogi |
| Boron Analogs | Boron Biologicals |
| HMG-CoA Reductase Inhibitors | British Biotech & Japan Tobacco |
| HMG-CoA Reductase Inhibitors | Merck & Co |
| U-88156 | Pharmacia & Upjohn |
| A-1233 | Kitasato University |
| acitemate | Mitsubishi Chemical |
| BAY-w-9533 | Bayer |
| BB-476 | British Biotech |
| BMS-180436 | Bristol-Myers Squibb |
| BMY-22566 | |
| colestolone | American Home Products |
| CP-83101 | Pfizer |
| dalvastatin | Rhone-Poulenc Rorer |
| dihydromevinolin | Merck & Co |
| DMP-565 | DuPont Merck |
| glenvastatin | Hoechst Marion Roussel |
| GR-95030 | Glaxo Wellcome |
| HMG-CoA Reductase Inhibitors | Bristol-Myers Squibb |
| HMG-CoA Reductase Inhibitors | Ono |
| HMG-CoA Reductase Inhibitors, Chiral | Chiroscience |
| HMG-CoA Reductase Inhibitors, isoxazolo-pyridine | Nissan Chemical |
| HMG-CoA Reductase Inhibitors, seco-oxysterol | Pharmacia & Upjohn |
| HMG-CoA Reductase Inhibitors, thiophene | Sandoz |
| HMG-CoA Reductase Inhibitors, 6-phenoxy-3,5-dihydoxyhexanoic acids | Hoechst Marion Roussel |
| hypolipaemics, Warner-Lambert | Warner-Lambert |
| L-659699 | Merck & Co |
| L-669262 | Merck & Co |
| mevastatin | Sankyo |
| N-((1-methylpropyl)carbonyl)-8-(2-(tetrahydro-4-hydroxy-6-oxo-2H-pyran-2-yl)ethyl)-perhydro-isoquinoline | Sandoz |

| | |
|---|---|
| N-(1-oxododecyl)-4alpha,10-dimethyl-8-aza-trans-decal-3beta-ol | Hoechst Marion Roussel |
| P-882222 | Nissan Chemical |
| pannorin | Tokyo Noko University |
| rawsonol | SmithKline Beecham |
| RP 61969 | Rhone-Poulenc Rorer |
| S-2468 | Hoechst Marion Roussel |
| S-853758A | Hoechst Marion Roussel |
| (S)-4-((2-(4-(4-fluorophenyl)-5-methyl-2-(1-methylethyl)-6-phenyl-3-pyridinyl) ethenyl)hydroxyphosphinyl)-3-hydroxybutanoic acid, disodium salt | Bristol-Myers Squibb |
| SC-32561 | Monsanto |
| sc-45355 | Non-industrial source |
| SDZ-265859 | Sandoz |
| SQ-33600 | Bristol-Myers Squibb |
| (4R-(4alpha,6beta(E)))-6-(2-(5-(4-fluorophenyl)-3-(1-methyl-ethyl)-1-(2-pyridinyH-pyrazol-4-yl)ethenyl) tetrahydro-4-hydroxy-2H-pyran-2-one | Warner Lambert |
| 5-beta-amino-ethylthiopentanoic acid derivatives | Boehringer Mannheim |
| 6-amino-2-mercapto-5-methylpyrimidine-4-carboxylic acid | North Carolina Universi |
| 6-phenoxymethyl- & 6-phenylethylen-(4-hydroxy-tetrahydropyran-2-one) analogues | Hoechst Marion Roussel |
| atorvastatin | |
| (4R-(4alpha,6beta(E)))-6-(2-(5-(4-fluorophenyl)-3-(1-methyl-ethyl)-1-(2-pyridinyH-pyrazol-4-yl)ethenyl) tetrahydro-4-hydroxy-2H-pyran-2-one | |

What is claimed is:

1. A composition comprising an ileal bile acid transport inhibitor and an HMG Co-A reductase inhibitor, wherein said ileal bile acid transport inhibitor is a compound of formula (I):

(I)

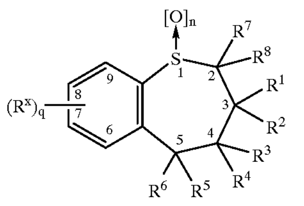

wherein:

q is an integer from 1 to 4;

n is an integer from 0 to 2;

$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more, substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene, wherein $R^9$, $R^{10}$, and $R^w$ are independently selected from the group consisting of H, alkyl, alkenyl, alkynyl, cycloalkyl, aryl, acyl, heterocycle, heteroaryl, ammoniumalkyl, alkylammoniumalkyl, and arylalkyl; or $R^1$ and $R^2$ taken together with the carbon to which they are attached form $C_3$–$C_{10}$ cycloalkylidene;

$R^3$ and $R^4$ are independently selected from the group consisting of H, alkyl, alkenyl, alkynyl, acyloxy, aryl, heterocycle, heteroaryl, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together form $=O$, $=NOR^{11}$, $=S$, $=NNR^{11}R^{12}$, $=NR^9$, or $=CR^{11}R^{12}$, wherein $R^{11}$ and $R^{12}$ are independently selected from the group consisting of H, alkyl, alkenyl, alkynyl, aryl, arylalkyl, alkenylalkyl alkynylalkyl, heterocycle, heteroaryl, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, or SH, or $R^{11}$ and $R^{12}$ together with the nitrogen or carbon atom to which they are attached form a cyclic ring;

$R^5$ and $R^6$ are independently selected from the group consisting of H, alkyl, alkenyl, alkynyl, aryl, cycloalkyl, heterocycle, heteroaryl, quaternary heterocycle, quaternary heteraryl, $SR^9$, $S(O)R^9$, $SO_2R^9$, and $SO_3R^9$, wherein alkyl, alkenyl, alkynyl, aryl, cycloalkyl, heterocycle, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, heteroaryl, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}$, $NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P+R^{13}R^{14}R^{15}A^-$, $P(OR^{13})OR^{14}$, $S^+R^{13}R^{14}A^-$, and $N^+R^9R^{11}R^{12}A^-$, wherein:

$A^-$ is a pharmaceutically acceptable anion and M is a pharmaceutically acceptable cation, said alkyl, alkenyl, alkynyl, polyalkyl, polyether aryl, haloalkyl, cycloalkyl, heterocycle and heteroaryl can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, heteroaryl, arylalkyl, quaternary heterocycle, quaternary heteroaryl, $P(O)R^7R^8$, $P^+R^7R^8R^9A^-$, and $P(O)(OR^7)OR^8$, and wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl, wherein alkyl, alkenyl, alkynyl, arylalkyl, heterocycle, heteroaryl and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and $R^{13}$, $R^{14}$, and $R^{15}$ are optionally substituted with one or more groups selected from the group consisting of sulfoalkyl, heterocycle, heteroaryl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring;

$R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}$, $R^{14}$, $NR^{14}C(O)R^{13}$, C(O)OM, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, heteroaryl, acyloxy, arylalkyl, haloalkyl, polyether, quaternary heterocycle, and quaternary heteroaryl can be further substituted with $OR^9$, $NR^9R^{10}$, $N^{30}R^9R^{11}R^{12}A^-$, $SR^9$, $S(O)R^9$, $SO_2R$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein $R^{18}$ is selected from the group consisting of acyl, arylalkoxycarbonyl, arylalkyl, heterocycle, heteroaryl, alkyl, quaternary heterocycle and quaternary heteroaryl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}$, $R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^{+R13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, provided that both $R^5$ and $R^6$ cannot be hydrogen, OH or SH, and when $R^5$ is OH, $R^1$, $R^2$, $R^3$, $R^4$, $R^7$ and $R^8$ cannot be all hydrogen;

provided that when $R^5$ or $R^6$ is phenyl, only one of $R^1$ or $R^2$ is H;

provided that when q=1 and $R^x$ is styryl, anilido, or anilinocarbonyl, only one of $R^5$ or $R^6$ is alkyl; or a pharmaceutically acceptable salt, solvate, or prodrug thereof.

2. The composition of claim 1, wherein said HMG Co-A reductase inhibitor is selected from the group consisting of pitavastatin, rosuvastatin, mevastatin and cerivastatin.

3. The composition of claim 2, wherein said HMG Co-A reductase inhibitor comprises pitavastatin.

4. The composition of claim 2, wherein said HMG Co-A reductase inhibitor comprises rosuvastatin.

5. The composition of claim 2, wherein said HMG Co-A reductase inhibitor comprises mevastatin.

6. The composition of claim 2, wherein said HMG Co-A reductase inhibitor comprises cerivastatin.

7. A pharmaceutical composition, comprising:

a first amount of an ileal bile acid transport inhibitor, a second amount of an HMG Co-A reductase inhibitor, and a pharmaceutically acceptable carrier, wherein said first and second amounts of said inhibitors together comprise an anti-hyperlipidemic condition effective amount of said inhibitors, and wherein the ileal bile acid transport inhibitor is a compound of formula (I):

(I)

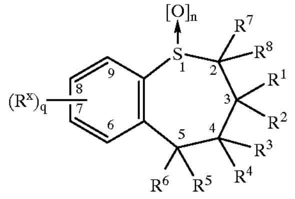

wherein:

q is an integer from 1 to 4;

n is an integer from 0 to 2;

$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^WA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene, wherein $R^9$, $R^{10}$, and $R^W$ are independently selected from the group consisting of H, alkyl, alkynyl, alkynyl, cycloalkyl, aryl, acyl, heterocycle, heteroaryl, ammoniumalkyl, alkylammoniumalkyl, and arylalkyl; or $R^1$ and $R^2$ taken together with the carbon to which they are attached form $C_3$–$C_{10}$ cycloalkylidene;

$R^3$ and $R^4$ are independently selected from the group consisting of H, alkyl, alkenyl, alkynyl, acyloxy, aryl, heterocycle, heteroaryl, $OR^9$, $NR^9$, $R^{10}$, $SR^9$, $S(O)R^9$, $SO_2R^9$, and $SO_3R^9$, wherein $R^9$ and $R^{10}$ are as defined above; or $R^3$ and $R^4$ together form =O, $=NOR^{11}$, =S, $=NNR^{11}R^{12}$, $=NR^9$, or $=CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, heteroaryl, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, or SH, or $R^{11}$ and $R^{12}$ together with the nitrogen or carbon atom to which they are attached form a cyclic ring;

$R^5$ and $R^6$ are independently selected from the group consisting of H, alkyl, alkenyl, alkynyl, aryl, cycloalkyl, heterocycle, heteroaryl, quaternary heterocycle, quaternary heteraryl, $SR^9$, $S(O)R^9$, $SO_2R^9$, and $S_3R^9$, wherein alkyl, alkenyl, alkynyl, aryl, cycloalkyl, heterocycle, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, heteroaryl, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}$, $R^{14}R^{15}A^-$, $P(OR^{13})OR^{14}$, $S^+R^{13}R^{14}A^-$, and $N^+R^9R^{11}R^{12}A^-$, wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, heterocycle and heteroaryl can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, heteroaryl, arylalkyl, quaternary heterocycle, quaternary heteroaryl, $P(O)R^7R^8$, $P^+R^7R^8R^9A^-$, and $P(O)(OR^7)OR^8$, and wherein said all, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl, wherein alkyl, alkenyl, alkynyl, arylalkyl, heterocycle, heteroaryl and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and $R^{13}$, $R^{14}$, and $R^{15}$ are optionally substituted with one or more groups selected from the group consisting of sulfoalkyl, heterocycle, heteroaryl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring;

$R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}$, $OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkyl, cycloalkyl, aryl, polyalkyl, heterocycle, heteroaryl, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O) OM, and wherein $R^{18}$ is selected from the group consisting of acyl, arylalkoxycarbonyl, arylalkyl, heterocycle, heteroaryl, alkyl, quaternary heterocycle and quaternary heteroaryl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}$, $A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, provided that both $R^5$ and $R^6$ cannot be hydrogen, OH or SH, and when $R^5$ is OH, $R^1$, $R^2$, $R^3$, $R^4$, $R^7$ and $R^8$ cannot be all hydrogen;

provided that when $R^5$ or $R^6$ is phenyl, only one of $R^1$ or $R^2$ is H;

provided that when q=1 and $R^x$ is styryl, anilido, or anilinocarbonyl, only one of $R^5$ or $R^6$ is alkyl; or a pharmaceutically acceptable salt, solvate, or prodrug thereof.

8. The composition of claim 7, wherein said HMG Co-A reductase inhibitor is selected from the group consisting of pitavastatin, rosuvastatin, mevastatin and cerivastatin.

9. The composition of claim 8, wherein said HMG Co-A reductase inhibitor comprises pitavastatin.

10. The composition of claim 8, wherein said HMG Co-A reductase inhibitor comprises rosuvastatin.

11. The composition of claim 8, wherein said HMG Co-A reductase inhibitor comprises mevastatin.

12. The composition of claim 8, wherein said HMG Co-A reductase inhibitor comprises cerivastatin.

13. A combination therapy method for the treatment of a hyperlipidemic condition in a mammal in need thereof, comprising:

administering to said mammal a first amount of an ileal bile acid transport inhibitor, and administering to said mammal a second amount of an HMG Co-A reductase inhibitor, wherein said first and second amounts of said inhibitors together comprise an anti-hyperlipidemic condition effective amount of said inhibitors, and wherein the ileal bile acid transport inhibitor is a compound of formula (I):

(I)

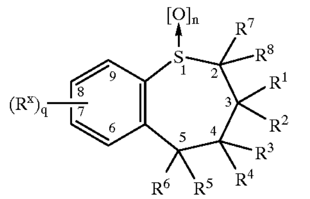

wherein:

q is an integer from 1 to 4;

n is an integer from 0 to 2;

$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene, wherein $R^9$, $R^{10}$, and Rw are independently selected from the group consisting of H, alkyl, alkenyl, alkynyl, cycloalkyl, aryl, acyl, heterocycle, heteroaryl, ammoniumalkyl, alkylammoniumalkyl, and arylalkyl; or $R^1$ and $R^2$ taken together with the carbon to which they are attached form $C_3$–$C_{10}$ cycloalkylidene;

$R^3$ and $R^4$ are independently selected from the group consisting of H, alkyl, alkenyl, alkynyl, acyloxy, aryl, heterocycle, heteroaryl, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together form $=O$, $=NOR^{11}$, $=S$, $=NNR^{11}R^{12}$, $=NR^9$, or $=CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, heteroaryl, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, or SH, or $R^{11}$ and $R^{12}$ together with the nitrogen or carbon atom to which they are attached form a cyclic ring;

$R^5$ and $R^6$ are independently selected from the group consisting of H, alkyl, alkenyl, alkynyl, aryl, cycloalkyl, heterocycle, heteroaryl, quaternary heterocycle, quaternary heteraryl, $SR^9$, $S(O)R^9$, $SO_2R^9$, and $SO_3R^9$, wherein alkyl, alkenyl, alkynyl, aryl, cycloalkyl, heterocycle, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, heteroaryl, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}$, $R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein:

A− is a pharmaceutically acceptable anion and M is a pharmaceutically acceptable cation, said alkyl, alkenyl, alkynyl, polyalkyl, polyether, aryl, haloalkyl, cycloalkyl, heterocycle and heteroaryl can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, heteroaryl, arylalkyl, quaternary heterocycle, quaternary heteroaryl, $P(O)R^7R^8$, $P^+R^7R^8R^9A^-$, and $P(O)(OR^7)OR^8$, and wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R_{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl, wherein alkyl, alkenyl, alkynyl, arylalkyl, heterocycle, heteroaryl and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and $R^{13}$, $R^{14}$, and $R^{15}$ are optionally substituted with one or more groups selected from the group consisting of sulfoalkyl, heterocycle, heteroaryl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^9)OR^9$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring;

$R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, heteroaryl, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein $R^{18}$ is selected from the group consisting of acyl, arylalkoxycarbonyl, arylalkyl, heterocycle, heteroaryl, alkyl, quaternary heterocycle and quaternary heteroaryl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, provided that both $R^5$ and $R^6$ cannot be hydrogen, OH or SH, and when $R^5$ is OH, $R^1$, $R^2$, $R^3$, $R^4$, $R^7$ and $R^8$ cannot be all hydrogen;

provided that when $R^5$ or $R^6$ is phenyl, only one of $R^1$ or $R^2$ is H;

provided that when q=1 and $R^x$ is styryl, anilido, or anilinocarbonyl, only one of $R^5$ or $R^6$ is alkyl; or a pharmaceutically acceptable salt, solvate, or prodrug thereof.

14. The composition of claim 13, wherein said HMG Co-A reductase inhibitor is selected from the group consisting of pitavastatin, rosuvastatin, mevastatin and cerivastatin.

15. The combination therapy method of claim 14, wherein said HMG Co-A reductase inhibitor comprises pitavastatin.

16. The combination therapy method of claim 14, wherein said HMG Co-A reductase inhibitor comprises rosuvastatin.

17. The combination therapy method of claim 14, wherein said HMG Co-A reductase inhibitor comprises mevastatin.

18. The combination therapy method of claim 14, wherein said HMG Co-A reductase inhibitor comprises cerivastatin.

19. The composition of claim 4, wherein $R^5$ and $R^6$ are independently selected from the group consisting of H, aryl, heterocycle, heteroaryl, quaternary heterocycle, and quaternary heteroaryl, wherein said aryl, heterocycle, heteroaryl, quaternary heterocycle, and quaternary heteroaryl can be substituted with one or more substituent groups independent selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}NR^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A^-$, S, SO, $SO_2$, $S^-R^7A^-$, $PR^7$, $P(O)R^7$, $P^+R^7R^8A^-$, or phenylene, wherein said alkyl, alkenyl, alkynyl, polyalkyl, polyether, aryl, haloalkyl, cycloalkyl, heterocycle and heteroaryl can be further substituted with one or more substituent groups selected from the group consisting of $OR^7$, $NR^7R^8$, $SR^7$, $S(O)R^7$, $SO_2R^7$, $CO_2R^7$, CN, oxo, $CONR^7R^8$, $N^+R^7R^8R^9A^-$, alkyl, alkenyl, alkynyl, aryl, cycloalkyl, heterocycle, heteroaryl, arylalkyl, quaternary heterocycle, quaternary heteroaryl, $P(O)R^7R^8$, $P^+R^7R^8R^9A^-$ and $P(O)(OR^7)OR^8$.

20. The composition of claim 19, wherein $R^5$ or $R^6$ has the formula:

$$—Ar—(R^y)_t$$

wherein t is an integer from 0 to 5,

Ar is selected from the group consisting of phenyl, thiophenyl, pyridyl, piperazinyl, piperonyl, pyrolyl, naphthyl, furanyl, anthracenyl, quinolinyl, isoquinolinyl, quinoxalinyl, imidazolyl, pyrazolyl, oxazolyl, isoxazolyl, pyrimidinyl, thiazolyl, triazolyl, isothiazolyl, indolyl, benzoimidazolyl, benzoxazolyl, benzothiazolyl, and benzoisothiazolyl; and one or more $R^y$ are independent selected from the group consisting of H, alkyl, alkenyl, alkynyl, aryl, cycloalkyl, heterocycle, heteroaryl, quaternary heterocycle, quaternary heteroaryl, $OR^9$, $SR^9$, $S(O)R^9$, $SO^2R^9$ and $SO_3R^9$, wherein said alkyl, alkenyl, alkynyl, aryl, cycloalkyl, heterocycle, heteroaryl can be substituted with one or more substituent groups independently selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein said alkyl, alkenyl, alkynyl, polyalkyl, polyether, aryl, haloalkyl, cycloalkyl, heterocycle and heteroaryl can be further substituted with one or more substituent groups independently selected from the group consisting of $OR^7$ $NR^7R^8$, $SR^7$, $S(O)R^7$, $SO_2R^7$ $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, heteroaryl, arylalkyl, quaternary heterocycle, and quaternary heteroaryl, $P(O)R^7R^8$, $P^+R^7R^8R^9A^-$, and $P(O)(OR^7)OR^8$; and wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A^-$, S, SO, $SO_2$, $S^-R^7A^-$, $PR^7$, $P(O)R^7$, $P^+R^7R^8A^-$, or phenylene.

21. The composition of claim 20, wherein $R^5$ or $R^6$ has the formula (II):

II

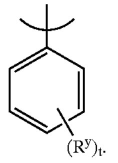

22. The combination therapy method of claim 14, wherein $R^5$ and $R^6$ are independently selected from the group consisting of H, aryl, heterocycle, heteroaryl, quaternary heterocycle, and quaternary heteroaryl, wherein said aryl, heterocycle, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}OR^{14}R^{15}$, $NO_2$, $CO_2R^{13}$, CN, OM, $SO_2OM$, $SO_2NR^{13}NR^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, $N^+R^9R^{11}R^{12}A^-$, wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$ or phenylene, wherein said alkyl, alkenyl, alkynyl, polyalkyl, polyether, aryl, haloalkyl, cycloalkyl, heterocycle and heteroaryl can be further substituted with one or more substituent groups independently selected from the group consisting of $OR^7$, $NR^7R^8$, $SR^7$, $S(O)R^7$, $SO_2R^7SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, heteroaryl, arylalkyl, quaternary heterocycle, and quaternary heteroaryl, $P(O)R^7R^8$, $P^+R^7R^8R^9A^-$, and $P(O)(OR^7)OR^8$.

23. The combination therapy method of claim 22, wherein $R^5$ or $R^6$ has the formula:

$$—Ar—(R^y)_t$$

wherein:

t is an integer from 0 to 5,

Ar is selected from the group consisting of phenyl, thiophenyl, pyridyl, piperazinyl, piperonyl, pyrolyl, naphthyl, furanyl, anthracenyl, quinolinyl, isoquinolinyl, quinoxalinyl, imidazolyl, pyrazolyl, oxazolyl, isoxazolyl, pyridinyl, thiazolyl, triazolyl, isothiazolyl, indolyl, benzoimidazolyl, benzoxazolyl, benzothiazolyl, and benzoisothiazolyl; and one or more $R^y$ are independently selected from the group consisting of H, alkyl, alkenyl, alkynyl, aryl, cycloalkyl, heterocycle, heteroaryl, quaternary heterocycle, quaternary heteroaryl, $OR^9$, $SR^9$, $S(O)R^9$, $SO_2R^9$ and $SO_3R^9$, wherein said alkyl, alkenyl, alkynyl, aryl, cycloalkyl, heterocycle, heteroaryl can be substituted with one or more substituent groups independently selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{14}R^{14}A^-$, wherein said alkyl, alkenyl, alkynyl, polyalkyl, polyether, aryl, haloalkyl, cycloalkyl, heterocycle and heteroaryl can be further substituted with one or more substituent groups independently selected from the group consisting of $OR^7$, $N^7R^8$, $SR^7$, $S(O)R^7$, $SO_2R^7$ $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, heteroaryl, arylalkyl, quaternary heterocycle, and quaternary heteroaryl, $P(O)R^7R^8$, $P^+R^7R^8R^9A^-$, and $P(O)(OR^7)OR^8$; and wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A^-$, S, SO, $SO_2$, $S^-R^7A^-$, $PR^7$, $P(O)R^7$, $P^+R^7R^8A^-$, or phenylene.

24. The combination therapy method of claim 23, wherein $R^5$ or $R^6$ has the formula (II):

II

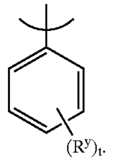

25. A combination therapy method for the prophylaxis of a hyperlipidemic condition in a mammal in need thereof, comprising:

administering to said mammal a first amount of an ileal bile acid transport inhibitor, and administering to said mammal a second amount of an HMG Co-A reductase inhibitor, wherein said first and second amounts of said inhibitors together comprise an anti-hyperlipidemic condition effective amount of said inhibitors, and wherein said ileal bile acid transport inhibitor is a compound of formula (I):

(I)

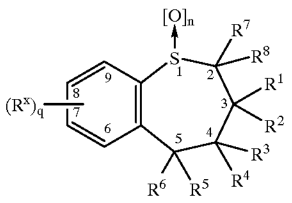

wherein:

q is an integer from 1 to 4;

n is an integer from 0 to 2;

$R^1$ and $R^2$ are independently selected from the group consisting of H, alkyl, alkenyl, alkynyl, haloalkyl, alkylaryl, arylalkyl, alkoxyl, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, polyalkyl)aryl, and cycloalkyl optionally are substituted with one or more substituents selected from the group consisting of $OR^9$, $NR^9NR^{10}$, $N^+R^9R^{10}R^WA^-$, $SR^9$, $SR^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have on or more carbons replace by O, $NR^9$, $N^+R^9R^{10}A^-$, S, SO, $SO_2$, $S^+R^9A^-$, $P^+R^9R^{10}A^-$, or phenylene, wherein $R^9$, $R^{10}$, $R^w$ are independently selected from the group consisting of H, alkyl, alkenyl, alkynyl, cycloalkyl, aryl, acyl, heterocycle, heteroaryl, ammoniumalkyl, alkylammoniumalkyl, and arylalkyl; or $R^1$ and $R^2$ taken together with the carbon to which they are attached form $C_3$–$C_{10}$ cycloalkylidene;

$R^3$ and $R^4$ are independently selected from the group consisting of H, alkyl, alkenyl, alkynyl, acyloxy, aryl, heterocycle, heteroaryl, $OR^9$, $NR^9R^{10}$, $SR^9$, $S(O)R^9$, $SO_2R^9$, and $SO_3R^9$, wherein $R^9$ and $R^{10}$ are as defined above, or $R^3$ and $R^4$ together form $=O$, $=NOR^{11}$, $=S$, $NNR^{11}R^{12}$, $=NR^9$, or $=CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, heteroaryl, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo and $CONR^9R^{10}$, wherein $R^9$ and $R^{10}$ are as defined above, provided that both $R^3$ and $R^4$ cannot be OH, $NH_2$, or SH, or $R^{11}$ and $R^{12}$ together with the nitrogen or carbon atom to which they are attached form a cyclic ring;

$R^5$ and $R^6$ are independently selected from the group consisting of H, alkyl, alkenyl, alkynyl, aryl, cycloalkyl, heterocycle, heteroaryl, quaternary heterocycle, quaternary heteroaryl, $SR^9$, $S(O)R^9$, $SO_2R^9$, and $SO_3R^9$, wherein alkyl, alkenyl, alkynyl, aryl, cycloalkyl, heterocycle, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, heteroaryl, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, heterocycle; and heteroaryl can be further substituted with one or more substituent groups selected from the group consisting of $OR^7$, $NR^7R^8$, $SR^7$, $S(O)R^7$, $SO_2R^7$ $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, heteroaryl, arylalkyl, quaternary heterocycle, quaternary heteroaryl, $P(O)R^7R^8$, $P^+R^7R^8R^9A^-$, and $P(O)(OR^7)OR^8$; and wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A^-$, S, SO, $SO_2$, $S^-R^7A^-$, $PR^7$, $P(O)R^7$, $P^+R^7R^8A^-$, or phenylene, a $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl, wherein alkyl, alkenyl, alkynyl, arylalkyl, heterocycle, heteroaryl and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and $R^{13}$, $R^{14}$, and $R^{15}$ are optionally substituted with one ore more groups selected from the group consisting of sulfoalkyl, heterocycle, heteroaryl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2$, OM, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents consisting $R^9$ and M; or $R^{14}$ and $R^{15}$, together with the nitrogen atom to which they are attached, form a cyclic ring;

$R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $SR^{13}R^{14}$, $A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}$, $R^{18}$, $NR^{18}$, $OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, heteroaryl, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$' oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein $R^{18}$ is selected from the group consisting of acyl, arylalkoxycarbonyl, arylalkyl, heterocycle, heteroaryl, alkyl, quaternary heterocycle and quaternary heteroaryl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo $CO_2R^9$, CN, halogen $CONR^9R^{10}$, $SO_3R^9$, $SO_2OM$, $SO_2NR^9R^{10}$, $PO(OR^{16})OR^{17}$ and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}OR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, provided that both $R^5$ and $R^6$ cannot be hydrogen, OH or SH, and when $R^5$ is OH, $R^1$, $R^2$, $R^3$, $R^4$, $R^7$ and $R^8$ cannot be all hydrogen;

provided that when $R^5$ or $R^6$ is phenyl only one of $R^1$ or $R^2$ is H;

provided that when q=1 and $R^x$ is styryl, anilido, or anilinocarbonyl, only one of $R^5$ or $R^6$ is alkyl; or a pharmaceutically acceptable salt, solvate, or prodrug thereof.

26. The combination therapy method of claim 25, wherein said HMG Co-A reductase inhibitor is selected from the group consisting of pitavastatin, rosuvastatin, mevastatin and cerivastatin.

27. The combination therapy method of claim 26, wherein said HMG Co-A reductase inhibitor comprises pitavastatin.

28. The combination therapy method of claim 26, wherein said HMG Co-A reductase inhibitor comprises rosuvastatin.

29. The combination therapy method of claim 26, wherein said HMG Co-A reductase inhibitor comprises mevastatin.

30. The combination therapy method of claim 26, wherein said HMG Co-A reductase inhibitor comprises cerivastatin.

31. The combination therapy method of claim 26, wherein $R^5$ and $R^6$ are independently selected from the group consisting of H, aryl, heterocycle, heteroaryl, quaternary heterocycle, and quaternary heteroaryl, wherein said aryl, heterocycle, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^{31}$ and $N^+R^9R^{11}R^{12}A^-$, wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, wherein said alkyl, alkenyl, alkynyl, polyalkyl, polyether, aryl, haloalkyl, cycloalkly, heterocycle and heteroaryl can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, heteroaryl, arylalkyl, quaternary heterocycle, quaternary heteroaryl, $P(O)R^7R^8$, $P^+R^7R^8R^9A^-$, and $P(O)(OR^7)OR^8$.

32. The combination therapy method of claim 31, wherein $R^5$ and $R^6$ has the formula $$—Ar—(R^y)_t$$

wherein t is an integer from 0 to 5,

Ar is selected from the group consisting of phenyl, thiophenyl, pyridyl, piperazinyl, piperonyl, pyrrolyl, naphthyl, furanyl, anthracenyl, quinolinyl, isoquinolinyl, quinoxalinyl, imidazolyl, pyrazolyl, oxazolyl, isoxazolyl, pyrimidinyl, thiazolyl, triazolyl, isothiazolyl, indolyl, benzoimdazolyl, benzoxazolyl, benzothiazolyl, and benzoisothiazolyl; and one or more $R^y$ are independently selected from the group consisting of H, alkyl, alkenyl, alkynyl, aryl, cycloalkyl, heterocycle, heteroaryl, quaternary heterocycle, quaternary heteroaryl, $OR^9$, $SR^9$, $S(O)R^9$, $SO_2R^9$ and $SO_3R^9$, wherein said alkyl, alkenyl, alkynyl, aryl, cycloalkyl, heterocycle, heteroaryl can be substituted with one or more substituent groups independently selected from tie group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$; $P(OR^{13})OR^{14}$, $S^+R^{13}R^{14}A^-$, and $N^+R^9R^{11}R^{12}A^-$, wherein said alkyl, alkenyl, alkynyl, polyalkyl, polyether, aryl, haloalkyl, cycloalkyl, heterocycle and heteroaryl can be further substituted with one or more substituent groups independent selected from the group consisting of $OR^7$ $NR^7NR^8$, $SR^7$, $S(O)R^7$, $SO_2R^7$ $SO_3R^7$, $CO_2R^7$, CN, oxo, $C(O)NR^7R^8$, $N^+R^7R^8R^9A^-$, alkyl, alkenyl, alkynyl, aryl, cycloalkyl, heterocycle, heteroaryl, arylalkyl, quaternary heterocycle, quaternary heteroaryl, $P(O)R^7R^8$, $P^+R^7R^8R^9A^-$, and $P(O)(OR^7)OR^8$; and wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A^-$, S, SO, $SO_2$, $S^-R^7A^-$, $PR^7$, $P(O)R^7$, $P^+R^7R^8A^-$; or phenylene.

33. The combination therapy method of claim 32, wherein $R^5$ or $R^6$ has the formula (II):

II

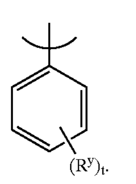

34. A pharmaceutical composition, comprising:

a first amount of an ileal bile acid transport inhibitor, and a second amount of an HMG Co-A reductase inhibitor, and a pharmaceutically acceptable carrier, wherein said first and second amounts of said inhibitors together comprise an anti-hyperlipidemic condition effective amount of said inhibitors, and wherein said ileal bile acid transport inhibitor is a compound of formula (LX):

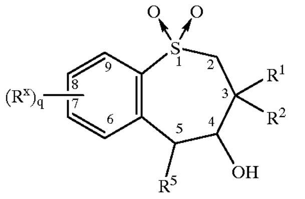

wherein:

$R^1$ and $R^2$ are independently selected from alkyl;

$R^5$ is substituted phenyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}OR^{14}$, $N^+R^9R^{11}R^{12}A^-$; $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, heteroaryl, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A$–, or C(O)OM, and wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$; and wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^{31}$; and $N^+R^9R^{11}R^{12}A^-$, and wherein $R^9$ and $R^{10}$ are independently selected from the group consisting of H, alkyl, alkenyl, alkynyl, cycloalkyl, aryl, acyl, heterocycle, heteroaryl, ammoniumalkyl, alkylammoniumalkyl, and arylalkyl; and wherein $R^{11}$ and $R^{12}$ are independently selected from the group consisting of H, alkyl, alkenyl, alkynyl, aryl, arylalkyl, alkenylalkyl, alkynylalkyl, heterocycle, heteroaryl, carboxyalkyl, carboalkoxyalkyl, cycloalkyl, cyanoalkyl , $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, or $R^{11}$ and $R^{12}$ together with the nitrogen or carbon atom to which they are attached form a cyclic ring;

wherein $R^{13}$, $R^{14}$, and $R^{15}$ are independently selected from the group consisting of hydrogen, alkyl, alkenyl, alkenyl, polyalkyl, aryl, arylalkyl, cycloalkyl, heterocycle, heteroaryl, quaternary heterocycle, quaternary heteroaryl, and quaternary heteroarylalkyl, wherein alkyl, alkenyl, alkynyl, arylalkyl, heterocycle, heteroaryl and polyalkyl optionally have one or more carbons replaced by O, $NR^9$, $N^{+/R9}R^{10}A^-$, S, SO, $SO_2$, $S^{+R9}A^-$, $PR^9$, $P^+R^9R^{10}A^-$, $P(O)R^9$, phenylene, carbohydrate, amino acid, peptide, or polypeptide, and wherein $R^{13}$, $R^{14}$, and $R^{15}$ are optionally substituted with one or more groups selected from the group consisting of sulfoalkyl, heterocycle, heteroaryl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, or $R^{14}$ and $R^{15}$, together with the nitrogen atom to which they are attached, form a cyclic ring; and wherein $R^{16}$ and $R^{17}$ are independently selected from the substituents constituting $R^9$ and M; and wherein $R^{18}$ is selected from the group consisting of acyl, arylalkoxycarbonyl, arylalkyl, heterocycle, heteroaryl, alkyl, quaternary heterocycle and quaternary heteroaryl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM; and wherein $A^-$ is a pharmaceutically acceptable anion and M is a pharmaceutically acceptable cation, or a pharmaceutically acceptable salt, solvate, or prodrug thereof.

35. The composition of claim 34, wherein said HMG Co-A reductase inhibitor is selected from the group consisting of pitavastatin, rosuvastatin, mevastatin and cerivastatin.

36. The composition of claim 35, wherein said HMG Co-A reductase inhibitor comprises pitavastatin.

37. The composition of claim 35, wherein said HMG Co-A reductase inhibitor comprises rosuvastatin.

38. The composition of claim 35, wherein said HMG Co-A reductase inhibitor comprises mevastatin.

39. The composition of claim 35, wherein said HMG Co-A reductase inhibitor comprises cerivastatin.

40. The composition of claim 35, wherein $R^1$ and $R^2$ are independently selected from the group consisting of ethyl, n-propyl, n-butyl and isobutyl.

41. The composition of claim 40, wherein one or more $R^x$ are independently selected from the group consisting of methyl, ethyl, isopropyl, t-butyl, hydroxy, methoxy, ethoxy, isopropoxy, methylthio, iodo, bromo, fluoro, methylsulfinyl, methylsulfonyl, ethylthio, amino, hydroxyalamine, N-methylamino, N,N-dimethylamino, N,N-diethylamino, (N)-benzyloxycarbomoyl, trimethylammonium $A^-$, —$NHC(=O)CH_3$, —$NHC(=O)C_5H_{11}$, —$NHC(=O)C_6H_{13}$, carboxyethylamino, (N)—morpholinyl, (N)—azetidinyl, (N)-N-methylazetidinium $A^-$, (N)-pyrrolidinyl, pyrrolyl, (N)—N—methylpyridinium $A^-$, (N)-N-methylmorpholinium $A^-$,N-N'-methylpiperazinyl, (N)-bromomethylamido, (N)-N-hexylamino, thiophene, —$N^+(CH_3)_2CO_2HI^-$, —$NCH_3CH_2CO_2H$, -(N)-N'-dimethylpiperazinium $I^-$, N-t-butyloxycarbamoyl, (N)-methylsulfonamido, (N)N'-methylpyrrolidinium and —$OCH_2CH_2)_3I$, wherein $A^-$ is a pharmaceutically acceptable anion.

42. A combination therapy method for the treatment or prophylaxis of a hyperlipidemic condition in a mammal in need thereof, comprising:

administering to said mammal a first amount of an ileal bile acid transport inhibitor, and administering to said mammal a second amount of an HMG Co-A reductase inhibitor, wherein said first and second amounts of said inhibitors together comprise an anti-hyperlipidemic condition effective amount of said inhibitors, and wherein said ileal bile acid transport inhibitor is a compound of formula (LX):

wherein:

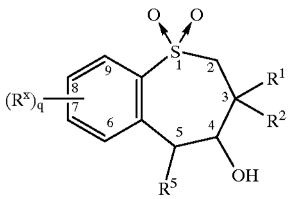

$R^1$ and $R^2$ are independently selected from alkyl;

$R^5$ is substituted phenyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, heteroaryl, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$; $S^+R^9R^{10}A^-$, or C(O)OM, and wherein in $R^x$, one or more carbons are optionally replaced by O, $NR^{13}$, $N^+R^{13}R^{14}A^-$; S, SO, $SO_2$, $S^+R^{13}A^-$, $PR^{13}$, $P(O)R^{13}$, $P^+R^{13}$, $R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$; and wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$; and $N^+R^9R^{11}R^{12}A^-$, and wherein $R^9$ and $R^{10}$ are independently selected from the group consisting of H, alkyl, alkenyl, alkynyl, cycloalkyl, aryl, acyl, heterocycle, heteroaryl, ammoniumalkyl, alkylammoniumalkyl, and arylalkyl; and wherein $R^{11}$ and $R^{12}$ are independently selected from the group consisting of H, alkyl, alkenyl, alkynyl, aryl, arylalkyl, alkenylalkyl, alkynylalkyl, heterocycle, heteroaryl, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, or $R^{11}$ and $R^{12}$ together with the nitrogen or carbon atom to which they are attached form a cyclic ring;

wherein $R^{13}$, $R^{14}$ and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl, wherein alkyl, alkenyl, alkynyl, arylalkyl, heterocycle, heteroaryl and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and wherein $R^{13}$, $R^{14}$, and $R^{15}$ are optionally substituted with one or more groups selected from the group consisting of sulfoalkyl, heterocycle, heteroaryl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$; $S^{30}$ $R^9R^{10}A^-$, and C(O)OM, or $R^{14}$ and $R^{15}$, together with the nitrogen atom to which they are attached, form a cyclic ring; and wherein $R^{16}$ and $R^{17}$ are independently selected from the substituents constituting $R^9$ and M; and wherein $R^{18}$ is selected from the group consisting of acyl, arylalkoxycarbonyl, arylalkyl, heterocycle, heteroaryl, alkyl, quaternary heterocycle and quaternary heteroaryl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^{30}R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM; and wherein $A^-$ is a pharmaceutically acceptable anion and M is a pharmaceutically acceptable cation, or a pharmaceutically acceptable salt, solvate, or prodrug thereof.

43. The combination therapy method of claim 42, wherein said HMG Co-A reductase inhibitor is selected from the group consisting of pitavastatin, rosuvastatin, mevastatin and cerivastatin.

44. The combination therapy method of claim 43, wherein $R^1$ and $R^2$ are independently selected from the group consisting of ethyl, n-propyl, n-butyl, and isobutyl.

45. The combination therapy method of claim 43, wherein said HMG Co-A reductase inhibitor comprises pitavastatin.

46. The combination therapy method of claim 43, wherein said HMG Co-A reductase inhibitor comprises rosuvastatin.

47. The combination therapy method of claim 43, wherein said HMG Co-A reductase inhibitor comprises mevastatin.

48. The combination therapy method of claim 43, wherein said HMG Co-A reductase inhibitor comprises cerivastatin.

49. The combination therapy method of claim 43, wherein one or more $R^x$ are independently selected from the group consisting of methyl, ethyl, isopropyl, t-butyl, hydroxy, methoxy, ethoxy, isopropoxy, methylthio, iodo, bromo, fluoro, methylsulfinyl, methylsufonyl, ethylthio, amino, hydroxylamine, N-methylamino, N,N-dimethylamino, N,N-diethylamino, (N)-benzyloxycarbomoyl, trimethylammonium $A^-$, N-N'-methylpiperazinyl, (N)-bromomethtylamido, (N)-N-hexylamino, thiophene, —$N^+(CH_3)_2CO_2H$ $I^-$, —$NCH_3CH_2CO_2H$, -(N)-N'-dimethylpiperazinium $I^-$, N-t-butyloxycarbamoyl, (N)-methylsulfonamido, -(N)-N'-methylpyrrolidinium and —$(OCH_2CH_2)_3I$, wherein $A^-$ is a pharmaceutically acceptable ion.

50. The combination therapy method of claim 32, wherein $R^5$ and $R^6$ has the formula $$—Ar—(R^y)_t$$

wherein t is an integer from 0 to 5,

Ar is selected from the group consisting of phenyl, thiophenyl, pyridyl, piperazinyl, piperonyl, pyrolyl, naphthyl, furanyl, anthracenyl, quinolinyl, isoquinolinyl, quinoxalinyl, imidazolyl, pyrazolyl, oxazolyl, isoxazolyl, pyrimidinyl, thiazolyl, triazolyl, isothiazolyl, indolyl, benzoimidazolyl, benzoxazolyl, benzothiazolyl, and benzoisothiazolyl; and one or more $R^y$ are independent selected from the group consisting of H, alkyl, alkenyl, alkynyl, aryl, cycloalkyl, heterocycle, heteroaryl, quaternary heterocycle, quaternary heteroaryl, $OR^9$, $SR^9$, $S(O)R^9$, $SO_2R^9$ and $SO_3R^9$, wherein said alkyl, alkenyl, alkynyl, aryl, cycloalkyl, heterocycle, heteroaryl can be substituted with one or more substituent groups independently selected from the group consisting of alkyl, alkenyl, alkyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $C(O)NR^{13}R^{14}$, C(O)OM, $COR^{13}$, $P(O)R^{13}R^{14}$, $P^+R^{13}R^{14}R^{15}A^{31}$, $P(OR^{13})OR^{14}$, $S^+R^{14}R^{14}A^-$, and $N^+R^9R^{11}R^{12}A^-$, wherein said alkyl, alkenyl, alkynyl, polyalkyl, polyether, aryl, haloalkyl, cycloalkyl, heterocycle and heteroaryl can be further substituted with one or more substituent groups independent selected from the group consisting of $OR^7$ $NR^7NR^8$, $SR^7$, $S(O)R^7$, $SO_2R^7$ $SO_3R^7$, $CO_2R^7$, CN, oxo, $C(O)NR^7R^8$, $N^+R^7R^8R^9A^-$, alkyl, alkenyl, alkynyl, aryl, cycloalkyl, heterocycle heteroaryl, arylalkyl, quaternary heterocycle, and quaternary heteroaryl, $P(O)R^7R^8$, $P^+R^7R^8R^9A^-$, and $P(O)(OR^7)OR^8$; and wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A^-$; S, SO, $SO_2$, $S^-R^7A^-$, $PR^7$, $P(O)R^7$, $P^+R^7R^8A^-$, or phenylene.

* * * * *